US010345593B2

(12) United States Patent
Samec et al.

(10) Patent No.: US 10,345,593 B2
(45) Date of Patent: Jul. 9, 2019

(54) METHODS AND SYSTEMS FOR PROVIDING AUGMENTED REALITY CONTENT FOR TREATING COLOR BLINDNESS

(71) Applicant: MAGIC LEAP, INC., Dania Beach, FL (US)

(72) Inventors: Nicole Elizabeth Samec, Fort Lauderdale, FL (US); John Graham Macnamara, Plantation, FL (US); Christopher M. Harrises, Nashua, NH (US); Brian T. Schowengerdt, Seattle, WA (US); Rony Abovitz, Hollywood, FL (US); Mark Baerenrodt, Fort Lauderdale, FL (US)

(73) Assignee: Magic Leap, Inc., Plantation, FL (US)

( * ) Notice: Subject to any disclaimer, the term of this patent is extended or adjusted under 35 U.S.C. 154(b) by 0 days.

(21) Appl. No.: 15/269,785

(22) Filed: Sep. 19, 2016

(65) Prior Publication Data
US 2017/0017083 A1 Jan. 19, 2017

Related U.S. Application Data

(63) Continuation of application No. 15/072,290, filed on Mar. 16, 2016.
(Continued)

(51) Int. Cl.
*G09G 5/00* (2006.01)
*G02B 27/01* (2006.01)
(Continued)

(52) U.S. Cl.
CPC ........ *G02B 27/0172* (2013.01); *A61B 3/0008* (2013.01); *A61B 3/022* (2013.01);
(Continued)

(58) Field of Classification Search
CPC . G02B 27/0172; A61B 3/0008; A61B 3/0025; A61B 3/0033; A61B 3/005;
(Continued)

(56) References Cited

U.S. PATENT DOCUMENTS 3,724,938 A * 4/1973 Nepela ............... G02B 27/28
353/122
4,065,208 A 12/1977 Currey
(Continued)

FOREIGN PATENT DOCUMENTS

CA 2385849 3/2001
CN 101359098 2/2009
(Continued)

OTHER PUBLICATIONS

Invitation to Pay Additional Fees and, Where Applicable, Protest Fee for PCT Application No. PCT/US16/22710, dated Jun. 8, 2016.
(Continued)

*Primary Examiner* — Sarah Lhymn
(74) *Attorney, Agent, or Firm* — Knobbe, Martens, Olson & Bear, LLP

(57) ABSTRACT

Configurations are disclosed for a health system to be used in various healthcare applications, e.g., for patient diagnostics, monitoring, and/or therapy. The health system may comprise a light generation module to transmit light or an image to a user, one or more sensors to detect a physiological parameter of the user's body, including their eyes, and processing circuitry to analyze an input received in response to the presented images to determine one or more health conditions or defects.

18 Claims, 49 Drawing Sheets

Related U.S. Application Data

(60) Provisional application No. 62/133,870, filed on Mar. 16, 2015.

(51) Int. Cl.

| | | |
|---|---|---|
| *A61B 3/14* | (2006.01) | |
| *A61B 3/113* | (2006.01) | |
| *A61B 3/16* | (2006.01) | |
| *A61B 5/0476* | (2006.01) | |
| *A61B 5/145* | (2006.01) | |
| *A61M 21/02* | (2006.01) | |
| *G06T 19/00* | (2011.01) | |
| *A61B 5/1455* | (2006.01) | |
| *A61B 5/00* | (2006.01) | |
| *A61B 3/12* | (2006.01) | |
| *A61B 8/10* | (2006.01) | |
| *A61B 8/00* | (2006.01) | |
| *A61B 3/08* | (2006.01) | |
| *A61B 3/00* | (2006.01) | |
| *A61B 3/10* | (2006.01) | |
| *A61B 3/103* | (2006.01) | |
| *A61F 9/00* | (2006.01) | |
| *G02B 27/00* | (2006.01) | |
| *A61B 3/028* | (2006.01) | |
| *A61B 3/06* | (2006.01) | |
| *A61B 3/02* | (2006.01) | |
| *A61B 5/0496* | (2006.01) | |
| *A61B 3/13* | (2006.01) | |
| *G02B 21/00* | (2006.01) | |
| *A61B 3/024* | (2006.01) | |
| *G16H 40/63* | (2018.01) | |
| *G16H 40/67* | (2018.01) | |
| *A61B 5/01* | (2006.01) | |
| *A61M 21/00* | (2006.01) | |
| *A61F 7/00* | (2006.01) | |
| *A61N 5/06* | (2006.01) | |
| *A61F 9/008* | (2006.01) | |

(52) U.S. Cl.
CPC .............. *A61B 3/024* (2013.01); *A61B 3/028* (2013.01); *A61B 3/063* (2013.01); *A61B 3/066* (2013.01); *A61B 3/08* (2013.01); *A61B 3/085* (2013.01); *A61B 3/10* (2013.01); *A61B 3/102* (2013.01); *A61B 3/1015* (2013.01); *A61B 3/1035* (2013.01); *A61B 3/113* (2013.01); *A61B 3/12* (2013.01); *A61B 3/1216* (2013.01); *A61B 3/13* (2013.01); *A61B 3/14* (2013.01); *A61B 3/165* (2013.01); *A61B 5/0059* (2013.01); *A61B 5/0476* (2013.01); *A61B 5/0496* (2013.01); *A61B 5/1455* (2013.01); *A61B 5/14532* (2013.01); *A61B 5/14555* (2013.01); *A61B 5/6803* (2013.01); *A61B 8/10* (2013.01); *A61B 8/461* (2013.01); *A61F 9/0026* (2013.01); *A61M 21/02* (2013.01); *G02B 21/0032* (2013.01); *G02B 27/0093* (2013.01); *G02B 27/0179* (2013.01); *G06T 19/006* (2013.01); *G16H 40/63* (2018.01); *G16H 40/67* (2018.01); *A61B 5/0066* (2013.01); *A61B 5/0077* (2013.01); *A61B 5/01* (2013.01); *A61B 2562/0204* (2013.01); *A61B 2562/0219* (2013.01); *A61B 2562/0247* (2013.01); *A61F 2007/0004* (2013.01); *A61F 2009/00863* (2013.01); *A61H 2201/165* (2013.01); *A61M 2021/0022* (2013.01); *A61M 2021/0027* (2013.01); *A61M 2021/0066* (2013.01); *A61M 2205/3375* (2013.01); *A61M 2205/507* (2013.01); *A61N 2005/0648* (2013.01); *G02B 2027/014* (2013.01); *G02B 2027/0138* (2013.01); *G02B 2027/0185* (2013.01); *G06T 2207/10024* (2013.01); *G06T 2207/10148* (2013.01); *G06T 2207/10152* (2013.01); *G06T 2207/30041* (2013.01)

(58) Field of Classification Search
CPC ..... A61B 3/0058; A61B 3/0091; A61B 3/022; A61B 3/024; A61B 3/032; A61B 3/063; A61B 3/066; A61B 3/08
USPC ................................ 345/418, 619, 632, 633
See application file for complete search history.

(56) References Cited

U.S. PATENT DOCUMENTS

| | | |
|---|---|---|
| 4,573,982 A | 3/1986 | Forbes et al. |
| 4,669,836 A | 6/1987 | Richardson et al. |
| 4,826,308 A | 5/1989 | Sadun |
| 4,848,898 A | 7/1989 | Massof |
| 5,166,778 A | 11/1992 | Beamon, III |
| 5,223,971 A | 6/1993 | Magel |
| 5,491,492 A | 2/1996 | Knapp et al. |
| 5,537,162 A | 7/1996 | Hellmuth et al. |
| 5,776,068 A | 7/1998 | Silverman et al. |
| 5,997,141 A | 12/1999 | Heacock |
| 6,003,991 A | 12/1999 | Viirre |
| 6,045,515 A | 4/2000 | Lawton |
| 6,151,167 A | 11/2000 | Melville |
| 6,235,014 B1 | 5/2001 | Abe et al. |
| 6,251,101 B1 | 6/2001 | Glockler |
| 6,386,706 B1 | 5/2002 | McClure et al. |
| 6,447,119 B1 | 9/2002 | Stewart et al. |
| 6,490,319 B1 | 12/2002 | Yang |
| 6,579,235 B1 | 6/2003 | Abita et al. |
| 6,736,510 B1 | 5/2004 | Heugten |
| 6,975,898 B2 | 12/2005 | Seibel |
| 7,036,931 B2 | 5/2006 | Lindacher |
| 7,425,067 B2 | 9/2008 | Warden et al. |
| 7,883,505 B2 | 2/2011 | Heugten et al. |
| 8,128,606 B2 | 3/2012 | Anderson et al. |
| 8,279,544 B1 | 10/2012 | O'Neill |
| 8,348,429 B2 | 1/2013 | Walsh et al. |
| 8,721,572 B1 | 5/2014 | Linder et al. |
| 8,820,931 B2 | 9/2014 | Walsh et al. |
| 8,824,779 B1 | 9/2014 | Smyth |
| 8,909,327 B1 | 12/2014 | Bosworth |
| 8,950,867 B2 | 2/2015 | MacNamara |
| 8,956,396 B1 | 2/2015 | Friend et al. |
| 9,125,724 B2 | 9/2015 | Berdahl et al. |
| 9,215,293 B2 | 12/2015 | Miller |
| 9,295,388 B2 | 3/2016 | Lawson et al. |
| 9,310,559 B2 | 4/2016 | MacNamara |
| 9,348,143 B2 | 5/2016 | Gao et al. |
| D758,367 S | 6/2016 | Natsume |
| 9,417,452 B2 | 8/2016 | Schowengerdt et al. |
| 9,462,262 B1 | 10/2016 | Worley, III et al. |
| 9,462,945 B1 | 10/2016 | Barriga et al. |
| 9,489,044 B2 | 11/2016 | Fateh |
| 9,671,566 B2 | 6/2017 | Abovitz et al. |
| 9,720,238 B2 * | 8/2017 | Munger ............ G02B 27/0172 |
| 9,791,700 B2 | 10/2017 | Schowengerdt et al. |
| 9,874,749 B2 | 1/2018 | Bradski |
| 2001/0009973 A1 | 7/2001 | Miwa |
| 2002/0036750 A1 | 3/2002 | Eberl et al. |
| 2002/0064341 A1 | 5/2002 | Fauver et al. |
| 2002/0072658 A1 | 6/2002 | Rice et al. |
| 2002/0109819 A1 * | 8/2002 | Tuval .................... A61B 3/032 351/206 |
| 2002/0124843 A1 | 9/2002 | Skiba et al. |
| 2003/0007124 A1 | 1/2003 | Levine |
| 2003/0009156 A1 | 1/2003 | Levine |
| 2003/0071969 A1 | 4/2003 | Levine et al. |
| 2003/0081170 A1 | 5/2003 | Zolten |
| 2003/0187503 A1 | 10/2003 | Lipshitz et al. |

(56) References Cited

U.S. PATENT DOCUMENTS

| | | |
|---|---|---|
| 2003/0210378 A1 | 11/2003 | Riza |
| 2004/0085648 A1 | 5/2004 | Tomono |
| 2004/0114242 A1* | 6/2004 | Sharp .............. G02B 5/3041 351/159.6 |
| 2004/0129949 A1 | 7/2004 | Deliwala et al. |
| 2004/0130783 A1 | 7/2004 | Solomon |
| 2004/0136570 A1 | 7/2004 | Ullman et al. |
| 2004/0151466 A1 | 8/2004 | Crossman-Bosworth et al. |
| 2004/0254438 A1 | 12/2004 | Chuck et al. |
| 2004/0257958 A1 | 12/2004 | Kimura et al. |
| 2005/0015120 A1 | 1/2005 | Seibel et al. |
| 2005/0122475 A1 | 6/2005 | Vilser et al. |
| 2005/0159662 A1 | 7/2005 | Imanishi et al. |
| 2005/0244476 A1 | 11/2005 | Burke et al. |
| 2005/0246783 A1 | 11/2005 | Christmann |
| 2005/0280777 A1 | 12/2005 | Dai |
| 2005/0286019 A1 | 12/2005 | Wiltberger et al. |
| 2006/0033992 A1* | 2/2006 | Solomon .............. G02B 27/017 359/462 |
| 2006/0114411 A1 | 6/2006 | Wei et al. |
| 2006/0114585 A1 | 6/2006 | Ho |
| 2006/0152525 A1 | 7/2006 | Woog |
| 2006/0159395 A1 | 7/2006 | Hnatiw et al. |
| 2006/0186325 A1 | 8/2006 | Johnston et al. |
| 2007/0010748 A1 | 1/2007 | Rauch et al. |
| 2007/0027442 A1 | 2/2007 | Campin et al. |
| 2007/0121120 A1 | 5/2007 | Schachar |
| 2007/0139613 A1 | 6/2007 | Tanifuji et al. |
| 2007/0200927 A1 | 8/2007 | Krenik |
| 2007/0236661 A1 | 10/2007 | Fukuma |
| 2008/0091250 A1 | 4/2008 | Powell |
| 2008/0117289 A1 | 5/2008 | Schowengerdt et al. |
| 2008/0117384 A1 | 5/2008 | Inakagata et al. |
| 2008/0124787 A1 | 5/2008 | Christmann |
| 2008/0137031 A1 | 6/2008 | Hillis et al. |
| 2008/0212738 A1 | 9/2008 | Gertner et al. |
| 2008/0213904 A1 | 9/2008 | Sliwa et al. |
| 2008/0218685 A1 | 9/2008 | Ribak |
| 2008/0277601 A1 | 11/2008 | Phinney et al. |
| 2008/0309879 A1 | 12/2008 | Hirji |
| 2009/0024191 A1 | 1/2009 | Seibel et al. |
| 2009/0030299 A1 | 1/2009 | Naito et al. |
| 2009/0036955 A1 | 2/2009 | Han |
| 2009/0073428 A1 | 3/2009 | Magnus et al. |
| 2009/0082829 A1 | 3/2009 | Panken et al. |
| 2009/0153796 A1* | 6/2009 | Rabner .............. A61B 3/0091 351/201 |
| 2009/0182291 A1 | 7/2009 | Eilat |
| 2009/0219486 A1 | 9/2009 | Bonnin et al. |
| 2009/0231545 A1 | 9/2009 | Peyman |
| 2009/0268162 A1 | 10/2009 | Stetson et al. |
| 2010/0004537 A1 | 1/2010 | Eilers et al. |
| 2010/0033676 A1 | 2/2010 | De Vries et al. |
| 2010/0069775 A1 | 3/2010 | Milgramm et al. |
| 2010/0149073 A1 | 6/2010 | Chaum et al. |
| 2010/0201944 A1 | 8/2010 | Lewis et al. |
| 2010/0214635 A1 | 8/2010 | Sasaki et al. |
| 2010/0220914 A1 | 9/2010 | Iwase et al. |
| 2010/0283969 A1 | 11/2010 | Cooperstock et al. |
| 2011/0007277 A1 | 1/2011 | Solomon |
| 2011/0018903 A1 | 1/2011 | Lapstun et al. |
| 2011/0063571 A1 | 3/2011 | Duffy |
| 2011/0109877 A1 | 5/2011 | Ramo et al. |
| 2011/0118556 A1 | 5/2011 | Siegel et al. |
| 2011/0178815 A1 | 7/2011 | Levett |
| 2011/0218456 A1 | 9/2011 | Graham et al. |
| 2011/0242306 A1 | 10/2011 | Bressler et al. |
| 2011/0267663 A1 | 11/2011 | Murayama |
| 2011/0276312 A1 | 11/2011 | Shalon et al. |
| 2011/0299027 A1 | 12/2011 | Shantha et al. |
| 2012/0019703 A1 | 1/2012 | Thorn |
| 2012/0069413 A1 | 3/2012 | Schultz |
| 2012/0083718 A1 | 4/2012 | Alleman et al. |
| 2012/0113092 A1 | 5/2012 | Bar-Zeev et al. |
| 2012/0127062 A1 | 5/2012 | Bar-Zeev et al. |
| 2012/0127426 A1 | 5/2012 | Backus et al. |
| 2012/0133890 A1 | 5/2012 | Rathjen |
| 2012/0147038 A1* | 6/2012 | Perez .............. G02B 27/0172 345/632 |
| 2012/0147163 A1 | 6/2012 | Kaminsky |
| 2012/0172854 A1 | 7/2012 | Raymond et al. |
| 2012/0188637 A1 | 7/2012 | Joseph et al. |
| 2012/0194781 A1 | 8/2012 | Agurok |
| 2012/0206485 A1 | 8/2012 | Osterhout et al. |
| 2012/0212399 A1 | 8/2012 | Border et al. |
| 2012/0226267 A1 | 9/2012 | Hauger |
| 2012/0236257 A1 | 9/2012 | Hillis et al. |
| 2012/0249956 A1 | 10/2012 | Narashimha-Iyer et al. |
| 2012/0274897 A1 | 11/2012 | Narasimha-Iyar et al. |
| 2012/0293773 A1 | 11/2012 | Publicover et al. |
| 2012/0307203 A1 | 12/2012 | Vendel et al. |
| 2012/0330387 A1 | 12/2012 | Ferraz Rigo et al. |
| 2013/0004485 A1 | 1/2013 | Bansal |
| 2013/0016292 A1 | 1/2013 | Miao et al. |
| 2013/0023966 A1 | 1/2013 | Depfenhart et al. |
| 2013/0070338 A1 | 3/2013 | Gupta et al. |
| 2013/0072916 A1 | 3/2013 | Bischoff et al. |
| 2013/0082922 A1 | 4/2013 | Miller |
| 2013/0100401 A1 | 4/2013 | Tabor |
| 2013/0125027 A1 | 5/2013 | Abovitz |
| 2013/0144137 A1 | 6/2013 | Zalevsky et al. |
| 2013/0169930 A1 | 7/2013 | Calderia et al. |
| 2013/0177883 A1 | 7/2013 | Barnehama et al. |
| 2013/0184554 A1 | 7/2013 | Elsheikh et al. |
| 2013/0245505 A1 | 9/2013 | Khuri-Yakub et al. |
| 2013/0250207 A1 | 9/2013 | Bohn |
| 2013/0250430 A1 | 9/2013 | Robbins et al. |
| 2013/0250431 A1 | 9/2013 | Robbins et al. |
| 2013/0253330 A1 | 9/2013 | Demos |
| 2013/0257312 A1 | 10/2013 | Maxik et al. |
| 2013/0285885 A1 | 10/2013 | Nowatzyk et al. |
| 2013/0286053 A1 | 10/2013 | Fleck et al. |
| 2013/0296710 A1 | 11/2013 | Zuzak et al. |
| 2013/0308094 A1 | 11/2013 | Mohan et al. |
| 2013/0314793 A1 | 11/2013 | Robbins et al. |
| 2013/0321265 A1 | 12/2013 | Bychkov et al. |
| 2013/0322810 A1 | 12/2013 | Robbins |
| 2014/0003762 A1 | 1/2014 | Macnamara |
| 2014/0009741 A1 | 1/2014 | Levien et al. |
| 2014/0016093 A1 | 1/2014 | Korb et al. |
| 2014/0039309 A1 | 2/2014 | Harris et al. |
| 2014/0043320 A1 | 2/2014 | Tosaya et al. |
| 2014/0046291 A1 | 2/2014 | Harris et al. |
| 2014/0055746 A1 | 2/2014 | Nistico et al. |
| 2014/0058483 A1 | 2/2014 | Zao et al. |
| 2014/0063005 A1 | 3/2014 | Ahn et al. |
| 2014/0068513 A1 | 3/2014 | Sakagawa |
| 2014/0071539 A1 | 3/2014 | Gao |
| 2014/0098010 A1 | 4/2014 | Travis et al. |
| 2014/0129259 A1 | 5/2014 | Seriani |
| 2014/0152531 A1 | 6/2014 | Murray et al. |
| 2014/0160283 A1 | 6/2014 | Hofman et al. |
| 2014/0168783 A1 | 6/2014 | Luebke et al. |
| 2014/0177023 A1 | 6/2014 | Gao et al. |
| 2014/0178861 A1 | 6/2014 | Duer |
| 2014/0186348 A1 | 7/2014 | Bansal et al. |
| 2014/0194702 A1 | 7/2014 | Tran |
| 2014/0194740 A1 | 7/2014 | Stein et al. |
| 2014/0198017 A1 | 7/2014 | Lamb et al. |
| 2014/0218468 A1 | 8/2014 | Gao et al. |
| 2014/0240842 A1* | 8/2014 | Nguyen .............. G02B 6/0076 359/630 |
| 2014/0267420 A1 | 9/2014 | Schowengerdt |
| 2014/0275935 A1 | 9/2014 | Walsh et al. |
| 2014/0285429 A1 | 9/2014 | Simmons |
| 2014/0285769 A1 | 9/2014 | Palanker et al. |
| 2014/0306866 A1 | 10/2014 | Miller et al. |
| 2014/0306874 A1 | 10/2014 | Finocchio et al. |
| 2014/0313484 A1 | 10/2014 | Bogaert |
| 2014/0340390 A1 | 11/2014 | Lanman et al. |
| 2014/0354514 A1 | 12/2014 | Aronsson |
| 2014/0368793 A1 | 12/2014 | Friedman et al. |
| 2014/0372944 A1 | 12/2014 | Mulcahy et al. |

(56) References Cited

U.S. PATENT DOCUMENTS

| | | | |
|---|---|---|---|
| 2014/0375790 A1* | 12/2014 | Robbins | G02B 27/0172 348/78 |
| 2015/0016777 A1 | 1/2015 | Abovitz et al. | |
| 2015/0018781 A1 | 1/2015 | Rinderknect et al. | |
| 2015/0035744 A1* | 2/2015 | Robbins | G02B 27/017 345/156 |
| 2015/0038869 A1 | 2/2015 | Simon et al. | |
| 2015/0088546 A1 | 3/2015 | Balram et al. | |
| 2015/0103306 A1 | 4/2015 | Kaji et al. | |
| 2015/0124073 A1 | 5/2015 | Fujishima et al. | |
| 2015/0146301 A1 | 5/2015 | Wong et al. | |
| 2015/0150444 A1 | 6/2015 | Bex et al. | |
| 2015/0178923 A1 | 6/2015 | Liang et al. | |
| 2015/0178939 A1 | 6/2015 | Bradski et al. | |
| 2015/0182118 A1 | 7/2015 | Bradbury et al. | |
| 2015/0185503 A1 | 7/2015 | Tate et al. | |
| 2015/0205126 A1 | 7/2015 | Schowengerdt | |
| 2015/0222883 A1 | 8/2015 | Welch | |
| 2015/0222884 A1 | 8/2015 | Cheng | |
| 2015/0234188 A1 | 8/2015 | Lee | |
| 2015/0238362 A1 | 8/2015 | Chayet et al. | |
| 2015/0241614 A1 | 8/2015 | Ide et al. | |
| 2015/0248169 A1 | 9/2015 | Abovitz et al. | |
| 2015/0248170 A1 | 9/2015 | Abovitz et al. | |
| 2015/0248788 A1 | 9/2015 | Abovitz et al. | |
| 2015/0248793 A1 | 9/2015 | Abovitz et al. | |
| 2015/0257735 A1 | 9/2015 | Ball et al. | |
| 2015/0262424 A1 | 9/2015 | Tabaka et al. | |
| 2015/0265146 A1 | 9/2015 | Bloom et al. | |
| 2015/0268415 A1 | 9/2015 | Schowengerdt et al. | |
| 2015/0277121 A1 | 10/2015 | Fridental | |
| 2015/0281630 A1 | 10/2015 | Melville et al. | |
| 2015/0289762 A1 | 10/2015 | Popovich et al. | |
| 2015/0302652 A1 | 10/2015 | Miller et al. | |
| 2015/0313949 A1 | 11/2015 | Cutillo | |
| 2015/0326570 A1 | 11/2015 | Publicover et al. | |
| 2015/0346490 A1 | 12/2015 | TeKolste et al. | |
| 2015/0346495 A1 | 12/2015 | Welch et al. | |
| 2015/0351690 A1 | 12/2015 | Toth et al. | |
| 2015/0356781 A1 | 12/2015 | Miller | |
| 2015/0356782 A1 | 12/2015 | Miller et al. | |
| 2016/0008169 A1 | 1/2016 | Yu | |
| 2016/0011375 A1 | 1/2016 | Anderson et al. | |
| 2016/0011419 A1 | 1/2016 | Gao | |
| 2016/0026253 A1 | 1/2016 | Bradski et al. | |
| 2016/0033771 A1 | 2/2016 | Tremblay et al. | |
| 2016/0066780 A1 | 3/2016 | Pamplona et al. | |
| 2016/0067087 A1 | 3/2016 | Tedford et al. | |
| 2016/0077338 A1 | 3/2016 | Robbins et al. | |
| 2016/0089023 A1 | 3/2016 | Takeno et al. | |
| 2016/0104453 A1* | 4/2016 | Borenstein | G09G 5/02 348/62 |
| 2016/0106591 A1 | 4/2016 | McArdle | |
| 2016/0116979 A1 | 4/2016 | Border | |
| 2016/0159276 A1 | 5/2016 | Thomas et al. | |
| 2016/0216515 A1 | 7/2016 | Bouchier et al. | |
| 2016/0256086 A1 | 9/2016 | Byrd et al. | |
| 2016/0270648 A1 | 9/2016 | Freeman et al. | |
| 2016/0270656 A1 | 9/2016 | Samec et al. | |
| 2016/0287153 A1 | 10/2016 | Samec et al. | |
| 2016/0324403 A1 | 11/2016 | Yeoh et al. | |
| 2016/0324416 A1 | 11/2016 | Fateh | |
| 2016/0379593 A1 | 12/2016 | Borenstein et al. | |
| 2017/0000324 A1 | 1/2017 | Samec et al. | |
| 2017/0000325 A1 | 1/2017 | Samec et al. | |
| 2017/0000326 A1 | 1/2017 | Samec et al. | |
| 2017/0000329 A1 | 1/2017 | Samec et al. | |
| 2017/0000330 A1 | 1/2017 | Samec et al. | |
| 2017/0000331 A1 | 1/2017 | Samec et al. | |
| 2017/0000332 A1 | 1/2017 | Samec et al. | |
| 2017/0000333 A1 | 1/2017 | Samec et al. | |
| 2017/0000334 A1 | 1/2017 | Samec et al. | |
| 2017/0000335 A1 | 1/2017 | Samec et al. | |
| 2017/0000337 A1 | 1/2017 | Samec et al. | |
| 2017/0000340 A1 | 1/2017 | Samec et al. | |
| 2017/0000341 A1 | 1/2017 | Samec et al. | |
| 2017/0000342 A1 | 1/2017 | Samec et al. | |
| 2017/0000343 A1 | 1/2017 | Samec et al. | |
| 2017/0000345 A1 | 1/2017 | Samec et al. | |
| 2017/0000454 A1 | 1/2017 | Samec et al. | |
| 2017/0000683 A1 | 1/2017 | Samec et al. | |
| 2017/0001032 A1 | 1/2017 | Samec et al. | |
| 2017/0007111 A1 | 1/2017 | Samec et al. | |
| 2017/0007115 A1 | 1/2017 | Samec et al. | |
| 2017/0007116 A1 | 1/2017 | Samec et al. | |
| 2017/0007122 A1 | 1/2017 | Samec et al. | |
| 2017/0007123 A1 | 1/2017 | Samec et al. | |
| 2017/0007182 A1 | 1/2017 | Samec et al. | |
| 2017/0007450 A1 | 1/2017 | Samec et al. | |
| 2017/0007799 A1 | 1/2017 | Samec et al. | |
| 2017/0007843 A1 | 1/2017 | Samec et al. | |
| 2017/0010469 A1 | 1/2017 | Samec et al. | |
| 2017/0010470 A1 | 1/2017 | Samec et al. | |
| 2017/0078652 A1 | 3/2017 | Hua et al. | |
| 2017/0112666 A1 | 4/2017 | Fateh | |
| 2017/0127932 A1 | 5/2017 | Walsh et al. | |
| 2017/0135896 A1 | 5/2017 | Snow | |
| 2017/0205618 A1 | 7/2017 | Basset et al. | |
| 2017/0299869 A1 | 10/2017 | Urey et al. | |
| 2018/0011324 A1 | 1/2018 | Popovich et al. | |
| 2018/0136471 A1 | 5/2018 | Miller et al. | |
| 2018/0136486 A1 | 5/2018 | MacNamara et al. | |
| 2018/0279870 A1 | 10/2018 | Walsh et al. | |

FOREIGN PATENT DOCUMENTS

| | | |
|---|---|---|
| CN | 103207458 | 7/2013 |
| WO | WO 2001/022741 | 3/2001 |
| WO | WO 2001/47463 | 7/2001 |
| WO | WO 2013/123461 | 8/2013 |
| WO | WO 2014/015378 | 1/2014 |
| WO | WO 2014/031961 | 2/2014 |
| WO | WO 2014/144940 | 9/2014 |
| WO | WO 2014/182769 | 11/2014 |
| WO | WO 2015/025251 | 2/2015 |
| WO | WO 2016/070188 | 5/2016 |
| WO | WO 2016/149416 | 9/2016 |
| WO | WO 2016/182974 | 11/2016 |
| WO | WO 2018/022521 | 2/2018 |

OTHER PUBLICATIONS

International Search Report and Written Opinion for PCT Application No. PCT/US16/22710, dated Aug. 19, 2016.

"Eye Chromatism", Telescope-Optics.net, retrieved Sep. 6, 2016, in 6 pages. URL: http://www.telescopeoptics.net/eye_chromatism.htm.

Abdulhalim, I., "Liquid crystal devices tailored for specific imaging applications", SPIE Newsroom, published Sep. 5, 2014, in 4 pages. URL: http://spie.org/newsroom/5605-liquid-crystal-devices-tailored-for-specific-imaging-applications.

Chan, E. et al., "Pulse oximetry: Understanding its basic principles facilitates appreciation of its limitations", Respiratory Medicine, Mar. 13, 2013, vol. 107, in 11 pages. URL: http://www.sciencedirect.com/science/article/pii/S095461111300053X.

Creel, D., "The Electroretinogram and Electro-oculogram: Clinical Applications", Webvision, updated Jul. 14, 2015, in 25 pages. URL: http://webvision.med.utah.edu/book/electrophysiology/the-electroretinogram-clinical-applications/.

EnChroma, "Technology", retrieved Sep. 6, 2016, in 10 pages. URL: http://enchroma.com/technology/.

Felleman et al., "Distributed Hierarchical Processing in the Primate Cerebral Cortex", Cerebral Cortex, Jan./Feb. 1991, in 47 pages. URL: http://cercor.oxfordjournals.org/content/1/1/1.1.full.pdf+html.

Goldman-Rakic, P. et al., "Preface: Cerebral Cortex Has Come of Age", Cerebral Cortex, vol. 1, Jan. 1991, in 2 pages. URL: http://cercor.oxfordjournals.org/content/1/1/1.1.full.pdf+html.

Haller et al., Better Imaging, Better Detection and Treatment, Medscape, Dec. 28, 2015, in 3 pages. URL: http://www.medscape.com/viewarticle/856387_print.

(56) References Cited

OTHER PUBLICATIONS

Hayes, T., "EyeSelfie Gives Patients Control Over Retinal Imaging", Optics.org, Jul. 8, 2015, in 2 pages. URL: http://optics.org/news/6/7/5.

Heiting, G., "Contrast Sensitivity Testing", All About Vision, updated Jan. 2016, in 4 pages. URL: http://www.allaboutvision.com/eye-exam/contrast-sensitivity.htm.

Jacques, S.L., "Optical properties of biological tissues: a review", Phys. Med. Biol., published May 10, 2013, vol. 58, R37, in 28 pages. URL: http://iopscience.iop.org/article/10.1088/0031-9155/58/11/R37.

Kirkpatrick, C. et al., "How to Perform a Basic Cover Test in Ocular Misalignment or Strabismus", Apr. 24, 2015, in 4 pages. URL: http://www.eyerounds.org/video/basic-cover-test.htm, Apr. 24, 2015.

Kovacs et al., "When the brain changes its mind: Interocular grouping during binocular rivalry", Proc. Natl. Acad. Sci., Dec. 1996, vol. 93, in 4 pages. URL: http://www.pnas.org/content/93/26/15508.full.pdf.

La Trobe University, "Maddox Rod Test (Tutorial)", published Sep. 24, 2014, in 1 page. URL: https://www.youtube.com/watch?v=Y4GmXGErosw.

Mansurov, N., "What is Chromatic Aberration?", Photography Life, Nov. 8, 2011, in 14 pages. URL: https://photographylife.com/what-is-chromatic-aberration.

Martin, B., "In-Depth: Cognitive Behavioral Therapy", Psych Central, published on May 17, 2016, retrieved on Oct. 13, 2016, in 8 pages. URL: http://psychcentral.com/lib/in-depth-cognitive-behavioral-therapy/.

MIT Media Lab Camera Culture, "Snapshots—Camera Culture News", Aug. 18, 2015, in 5 pages.

National Instruments, "Electrooculogram Measurement", published Jul. 29, 2010, in 2 pages. URL: http://www.ni.com/white-paper/11958/en/.

Paton, J. et al., "The primate amygdala represents the positive and negative value of stimuli during learning", Nature, Feb. 16, 2006, vol. 439, in 6 pages. URL: http://www.nature.com/nature/journal/v439/n7078/full/nature04490.html.

Robertson et al., "Reduced GABAergic Action in the Autistic Brain", Current Biology, 2016, in 7 pages. URL: http://www.cell.com/current-biology/abstract/S0960-9822(15)01413-X.

Salomon, R. et al., "The Insula Mediates Access to Awareness of Visual Stimuli Presented Synchronously to the Heartbeat", Journal of Neuroscience, May 6, 2016, vol. 36(18), in 13 pages. URL: http://www.jneurosci.org/content/36/18/5115.short.

Tan, J., "Eye Clinic Tests New Myopia Treatment Using Vitamin B2 and Ultraviolet Light", The New Paper, published Dec. 28, 2015, in 5 pages. URL: http://www.tnp.sg/news/singaporenews/eyeclinictestsnewmyopiatreatmentusingvitaminb2andultravioletlight.

Yim et al., "On the Modeling of Light Interactions with Human Blood", Natural Phenomena Simulation Group, D.R. Cheriton School of Computer Science, University of Waterloo Technical Report CS-2011-30, Dec. 2011, in 19 pages. URL: https://cs.uwaterloo.ca/research/tr/2011/CS-2011-30.pdf.

International Preliminary Report on Patentability for PCT Application No. PCT/US2016/022710, dated Sep. 28, 2017.

U.S. Office Action for U.S. Appl. No. 15/072,290, dated May 17, 2018.

U.S. Office Action (Restriction Requirement) for U.S. Appl. No. 15/269,521, dated Dec. 4, 2017.

U.S. Office Action for U.S. Appl. No. 15/269,521, dated Jan. 24, 2018.

U.S. Office Action for U.S. Appl. No. 15/269,627, dated Mar. 2, 2018.

U.S. Office Action for U.S. Appl. No. 15/269,667, dated Nov. 29, 2017.

U.S. Notice of Allowance for U.S. Appl. No. 15/269,521, dated Jun. 11, 2018.

U.S. Final Office Action for U.S. Appl. No. 15/269,764, dated Jul. 18, 2018.

U.S. Notice of Allowance for U.S. Appl. No. 15/269,667, dated Jul. 13, 2018.

U.S. Final Office Action for U.S. Appl. No. 15/269,376, dated Jul. 30, 2018.

U.S. Final Office Action for U.S. Appl. No. 15/269,627, dated Aug. 16, 2018.

U.S. Office Final Action for U.S. Appl. No. 15/269,762, dated Aug. 15, 2018.

U.S. Notice of Allowance for U.S. Appl. No. 15/269,667, dated Sep. 12, 2018.

Bartsch, D. et al., "Confocal Scanning Infrared Laser Ophthalmoscopy for Indocyanine Green Angiography", Americal Journal of Ophthalmology, vol. 120, Nov. 1995, in 10 pages.

Black J.M. et al., "The Measurement and Treatment of Suppression in Amblyopia", J. Vis. Exp. (JoVE) Dec. 14, 2012; 70:e3927 in 7 pages.

U.S. Appl. No. 15/072,290, Methods and Systems for Diagnosing and Treating Health Ailments, filed Mar. 16, 2016.

U.S. Appl. No. 15/269,376, Methods and Systems for Determining Intraocular Pressure, filed Sep. 19, 2016.

U.S. Appl. No. 15/269,521, Methods and Systems for Diagnosing Color Blindness, filed Sep. 19, 2016.

U.S. Appl. No. 15/269,627, Methods and Systems for Diagnosing and Treating Eyes Using Light Therapy, filed Sep. 19, 2016.

U.S. Appl. No. 15/269,764, Methods and Systems for Diagnosing Contrast Sensitivity, filed Sep. 19, 2016.

U.S. Appl. No. 15/269,762, Augmented and Virtual Reality Display Systems and Methods for Diagnosing Health Conditions Based on Visual, filed Sep. 19, 2016.

U.S. Appl. No. 15/269,676, Augmented and Virtual Reality Display Platforms and Methods for Delivering Health Treatments to a User, filed Sep. 19, 2016.

U.S. Appl. No. 15/269,667, Augmented Reality Display Systems and Methods for Re-Rendering the World, filed Sep. 19, 2016.

U.S. Notice of Allowance for U.S. Appl. No. 15/269,627, dated Feb. 7, 2019.

U.S. Final Office Action for U.S. Appl. No. 15/072,290, dated Oct. 16, 2018.

U.S. Notice of Allowance for U.S. Appl. No. 15/269,521, dated Oct. 4, 2018.

U.S. Notice of Allowance for U.S. Appl. No. 15/269,521, dated Feb. 5, 2019.

U.S. Notice of Allowance for U.S. Appl. No. 15/269,627, dated Oct. 22, 2018.

U.S. Final Office Action for U.S. Appl. No. 15/269,676, dated Oct. 4, 2018.

U.S. Advisory Action for U.S. Appl. No. 15/269,676, dated Jan. 14, 2019.

U.S. Notice of Allowance for U.S. Appl. No. 15/269,667, dated Jan. 18, 2019.

Childs, et al.: "Retinal imaging: a first report of the retinal microvasculature in acute mild traumatic brain injury," Eur J Emerg Med., vol. 2, No. 5, Aug. 28, 2014, in 2 pages.

Flusberg, et al., "Fiber-optic fluorescence imaging," Nat Methods. Dec. 2005; 2(12): 941-950.

Hoerauf, et al., "Slit-lamp-adapted optical coherence tomography of the anterior segment," 2000, Graefe's Arch Clin Exp Opthalmol, Springer-Verlag, pp. 238-218 (Year: 2000).

Patil, et al., "Slit-lamp adapted, video-correlated real-time optical coherence tomorgraphy of the anterior segment," 2002, OSA/BoSD, AOIMP, TLA 2002, pp. 322-324 (Year: 2002).

Radhakrishnan, et al., "Real-time optical coherence tomography of the anterior segment using hand-held and slit-lapm adapted systems," 2002, Proc. SPIE vol. 4619, pp. 227-229 (Year: 2002).

Eyenetra, NETRA Refraction for Anyone Anywhere, https://web.archive.org/web/20150617231941/http://eyenetra.com/product-netra.html as archived Jun. 17, 2015, including an embedded video which is understood to be: "The Blink Process", https://web.archive.org/web/20160328164326/https://vimeo.com/117414944 as archived Mar. 28, 2016.

Karp, Andrew, "How wearables and eye tracking are adding new dimensions to ocular health", Vision Monday, http://visionmonday.com/article/from-eye2-to-eyecare/, published Jul. 20, 2015.

(56) References Cited

OTHER PUBLICATIONS

Wikipedia, Pinhole Glasses, https://web.archive.org/web/20151211100505/https://en.wikipedia.org/wiki/Pinhole_glasses as archived Dec. 11, 2015.

The Free Dictionary by Farlex, Scheiner's Experiment, https://web.archive.org/web/20150923200056/http://nedical-dictionary.thefreedictionary.com/Scheiner's+experiment as archived Sep. 23, 2015.

All About Vision, Wavefront Technology in Eye Exams, https://web.archive.org/web/20160314205244/https://www.allaboutvision.com/eye-exam/wavefront.htm as archived Mar. 14, 2016.

Wikipedia, Retinal Scan, https://web.archive.org/web/20160108023330/https://en.wikipedia.org/wiki/Retinal_scan as archived Jan. 8, 2016.

Wikipedia, Accommodation Reflex, https://web.archive.org/web/20160312224519/https://en.wikipedia.org/wiki/Accomodation_reflex as archived Mar. 12, 2016.

Wikipedia, Optical Coherence Tomography, https://web.archive.org/web/2016030923843/https://en.wikipedia.org/wiki/Optical_coherence_tomography as archived Mar. 9, 2016.

Tavakoli M, Hossain P, Malik RA. Clinical applications of corneal confocal microscopy. Clin Ophthalmol. Jun. 2008;2(2):435-45.

Wikipedia, Two-Photon Excitation Microscopy, https://web.archive.org/web/20160124131037/https://en.wikipedia.org/wiki/Two-photon_excitation_microscopy as archived Jan. 24, 2016.

So, Peter TC, "Two-photon Fluorescence Light Microscopy" Massachusetts Institute of Technology, Encyclopedia of Life Sciences. Published 2002.

Wikipedia, Optogenetics, https://web.archive.org/web/20160304035328/https://en.wikipedia.org/wiki/Optogenetics as archived Mar. 4, 2016.

Wikipedia, Scanning laser ophthalmoscopy, https://web.archive.org/web/20150603044310/https://en.wikipedia.org/wiki/Scanning_laser_opthalmoscopy as archived Jun. 3, 2015.

Tonometry Presentation published Apr. 22, 2015 available at http://www.slideshare.net/mandakini000/tonometry-47300598.

Reichert Technologies, Tonometry, http://web.archive.org/web/20160716015310/http://www.reichert.com/product_details.ofm?pcid=3048skuld=4376&skuTk=1286486472 as archived Jul. 16, 2016, including understood to be: a. Reichert—Eye Care, "The Role of Corneal Hysteresis Response Analyzer", YouTube, published Jul. 17, 2015, in 7 pages https://www.youtube.com/watch?v=UnUmXoS3h54 b. Reichert—Eyecare, "Corneal Hysteresis: Clinical Relevance in Glaucoma in 90 Seconds", YouTube, published May 13, 2015, in 4 pages (with video transcription). https://www.youtube.com/watch?v=4h_0G0vIVxU c. Reichert—Eye Care, "Corneal Hysteresis and IOPcc: Clinical Applications in Glaucoma", YouTube, published Mar. 12, 2015, in 14 pages. (with video transciption). https://www.youtube.com/watch?v=qOLcpWB2MbM d. Reichert—Eye Care, "Understanding Corneal Hysteresis in Glaucoma", YouTube, published Apr. 23, 2010, in 13 pages (with video transcription). https://www.youtube.com/watch?v=2v9w8ATbIgU.

BiomedEngg, "How does ocular response analyser works", YouTube, published Mar. 14, 2014, in 15 pages. (with video transcription). URL: https://www.youtube.com/watch?v=gfHr_XC0cYI.

Willekens et al., Ophthalmic Research, Review on Dynamic Contour Tonometry and Ocular Pulse Amplitude, Published Dec. 10, 2015.

Retinal Oximetry, http://web.archive.org/web/20170703083202/http://eyewiki.org/Retinal_Oximetry as archived Jul. 3, 2017.

Introduction to Ultrasound, https://web.archive.org/web/20160124030833/http://www.brooksidepress.org/Products/OBGYN_101/MyDocuments4/Ultrasound/basic_ultrasound.htm as archived Jan. 24, 2016.

Lee et al., "Scanning Fiber Endoscopy with Highly Flexible, 1-mm Catheterscopes for Wide-Field, Full-Color Imaging", J Biophotonics: Jun. 2010 3(5-6): 385-407.

Ibrahim et al., "Assessment of oxygen saturation in retinal vessels of normal subjects and diabetic patients with and without retinopathy using Flow Oximetry System" Quantitative Imaging in Medicine and Surgery, vol. 5, No. 1, Feb. 2015. https://web.archive.org/web/20151019073656/http://www.amepc.org/glma/article/view/5359/6245 as archived Oct. 19, 2015.

Wikipedia, Electroretinography, http://web.archive.org/web/20160117075807/https://en.wikipedia.org/wiki/Electroretinography as archived Jan. 17, 2016.

Wikipedia, Binocular Rivalry, https://web.archive.org/web/20160112024410/https://en.wikipedia.org/wiki/Binocular_rivalry as archived Jan. 12, 2016.

Cedars-Sinai, "Keith Black, MD & The First Eye Test for Alzheimer's | Cedars-Sinai", YouTube, published Nov. 23, 2015, in 8 pages. (with video transcription). https://www.youtube.com/watch?v=XpzkZlo3YQk.

Koronyo-Hamaoui et al., "Identification of amyloid plaques in retinas from Alzheimer's patients and noninvasive in vivo optical imaging of retinal plaques in a mouse model". Neuroimage; Jan. 2011; 54 Suppl 1:S204-17. doi: 10.1016/j.neuroimage.2010.06.020.

Johnsen, M. "Contact lens with built-in sensor can measure risk of glaucoma progression, study finds" dated Feb. 4, 2016 https://web.archive.org/web/20160205100510/http://www.drugstorenews.comarticle/contact-lens-built-sensor-can-measure-risk-glaucoma-progression-study-finds as archived Feb. 5, 2016.

Wikipedia, Cover Test, https://web.archive.org/web/20151204195654/https://en.wikipedia.org/wiki/Cover_test as archived Dec. 4, 2015.

Wikipedia, Red-eye effect, https://web.archive.org/web/20160113194839/https://en.wikipedia.org/wiki/Red-eye_Effect as archived Jan. 13, 2016.

Mukamal, R. "Photos Can Help Diagnose Children's Eye Problems and Save Sight" dated Jul. 28, 2014, https://web.archive.org/web/20160307060813/http://www.aao.org/eye-health/tips-prevention/diagnosing-children-from-photographs as archived Mar. 7, 2016.

Ophthalmoscope, https://web.archive.org/web/20150826030102/http://www.yorku.ca/eye/opthal.htm as archived Aug. 26, 2015.

Medical Device Depot, Inc. Welch Allyn Binocular Indirect Ophthalmoscopes, https://web.archive.org/web/20150909051129/https://www.medicaldevicedepot.com/Welch-Allyn-Binocular-Indirect-Opthamoscopes-p/wabio.htm?1=1&CartID=0 as archived Sep. 9, 2015.

Roux, P. Ophthalmoscopy for the general practitioner, South African Family Practice, Published Aug. 15, 2014 available at https://doi.org/10.1080/20786204.2004.10873079.

Wikipedia, Electrooculography, https://web.archive.org/web/20160118002107/https://en.wikipedia.org/wiki/Electrooculography as archived Jan. 18, 2016.

Plainis et al. CRSTEurope, "The Physiologic Mechanism of Accommodation" Apr. 2014, http://crstodayeurope.com/2014/04/the-physiologic-mechanism-of-accomodation.

Tyson, J., "Lasik Surgery" https://web.archive.org/web/20150906190835/http://health.howstuffworks.com/medicine/surgeries-procedures/lasik6.htm as archived Sep. 6, 2015.

Carleton Optical, "Vision Screening | PlusoptiX A09 Paediatric Binocular Autorefractor", https://web.archive.org/web/20170323175824/http://carletonitd.com/products/sight-testing-and-refraction/vision-screening/plusoptix-paedeactric-binocular-autorefractor as archived Mar. 26, 2017.

Wikipedia, Confocal Microscopy, https://web.archive.org/web/20151121002858/https://en.wikipedia.org/wiki/Confocal_microscopy as archived Nov. 21, 2015.

Bennett, T., "Scanning Laser Ophthalmoscopy" https://web.archive.org/web/20151107054433/http://www.opsweb.org/?page=SLO as archived Nov. 7, 2015.

Browne, J. "Direct Ophthalmoscope: The Ultimate Pediatric Screening Tool" dated Jul. 9, 2013 https://web.archive.org/web/20150709202404/http://www.optometrystudents.com/direct-opthalmoscope-the-ultimate-pediactric-screening-tool/#sthash.O3Ed3a58.dpuf as archived Jul. 9, 2015.

Pietrangelo, A., "Eye and Orbit Ultrasound" https://web.archive.org/web/20160216123839/http://www.healthline.com/eye-and-orbit-ultrasound as archived Feb. 16, 2016.

Wikipedia, Non-Contact Ultrasound, https://web.archive.org/web/20151126014623/https://en.wikipedia.org/wiki/Non-contact_ultrasound as archived Nov. 26, 2015.

Eye Tech Care, Unique Technology for Non-Invasive Treatment, https://web.archive.org/web/201601212001/https://www.eyetechcare.com/en/treatment/the-medical-device/ as archived Jan. 21, 2016.

(56) References Cited

OTHER PUBLICATIONS

Schwartz, et al. "Therapeutic ultrasound for glaucoma: clinical use of a low-frequency low-power ultrasound device for lowering intraocular pressure" Published Online Sep. 26, 2014, Journal of Therapeutic Ultrasound available at https://www.ncbi.nlm.gov/pmc/articles/PMC4266006/.

EyeSonix, Therapeutic Ultrasound for Glaucoma "TUG" https://web.archive.org/web/20160305124153/http://eyesonix.com as archived Mar. 5, 2016.

Fyola, "Ultrasound Therapy With Fyola Facial Machine", http://www.fyola.com/facialtreatment/ultrasound-facial.shtml printed Feb. 6, 2019.

Arterial Ultrasound Scan, https://web.archive.org/web/20160301083227/http://hyperphysics.phy-astr.gsu.edu/hbase/sound/usound2.html as archived Mar. 1, 2016.

NTNU, Cardiac Ultrasound, https://web.archive.org/web/20150915045624/https://www.ntnu.edu/isb/echocardiography as archived Sep. 15, 2015.

Convex Lens http://web.archive.org/web/20160426123327/http://cbakken.net/obookshelf/cvreal.html as archived Apr. 26, 2016.

Wikipedia, Optical coherence tomography, https://web.archive.org/web/20160309023843/https://en.wikipedia.org/wiki/Optical_coherence_tomography as archived Mar. 9, 2016.

The Free Dictionary, Accommodation, https://web.archive.org/web/20150906042456/http://medical-dictionary.thefreedictionary.com/accomodation as archived Sep. 6, 2015.

Wikipedia, Bagolini Striated Glasses Test, https://web.archive.org/web/20151201023513/https://en.wikipedia.org/wiki/Bagolini_Striated_Glasss_Test as archived Dec. 1, 2015.

Worth 4-dot test, https://www.aao.org/bcscsnippetdetail.aspx?id=8200e4a2-f7ee-47f4-b8b7-985b30b52f67 printed Feb. 11, 2019.

Lam, Steven, "Orthoptical Clinical Skills—Assessment of Binocular", YouTube, published Sep. 2, 2013, in 14 pages (with video transcription). https://www.youtube.com/watch?v=IZYB3UON0HM.

American Academy of Ophthalmology, EyeWiki, Worth 4 dot, https://web.archive.org/web/20160305174751/http://eyewiki.aao.org/Worth_4_dot as archived Mar. 5, 2016.

Wikipedia, Worth 4 dot test, https://web.archive.org/web/20150114111313/https://en.wikipedia.org/wiki/Worth_4_dot_test as archived Jan. 14, 2015.

GuldenOpthalmics, "Trial Frame Multi-Pinhole Occluder", http://web.archive.org/web/20160118002107/https://en.wikipedia.org/wiki/Electrooculaography as archived Mar. 21, 2018.

MedlinePlus, U.S. National Library for Medicine, "Fluorescein eye stain", https://web.archive.org/web/20160105060436/https://www.nim.nih.gov/medlineplus/ency/article/003845.htm as archived Jan. 5, 2016.

Labrigger, "Fast Z-Galvo for 3D Two-Photon Imaging", https://web.archive.org/web/20151031101132/http://labrigger.com/blog/2012/02/17fast-z-galvo-for-3d-two-photon-imaging/ as archived Oct. 31, 2015.

Rosen et al., "Multidimensional en-Face OCT imaging of the retina," Opt. Express 17, 4112-4133 (2009).

Laboratory for Functional Optical Imaging, "Imaging Technology", https://web.archive.org/web/20151224023624/http://orion.bme.columbia.edu/~hillman/Instrumentation.html, Hillman Lab 2012, Columbia University Department of Biomedical Engineering, New York, as archived Dec. 24, 2015 in 6 pages.

Vision-Systems, "Leading Edge Views: 3-D Imaging Advances Capabilities of Machine Vision: Part I", http://www.vision-systems.com/articles/print/volume-17/issue-4/departments/leading-edge-views/3-d-imaging-advances-capabilities-of-machin-vision-part-i.html, Apr. 1, 2012.

bsigroup.com, "Ophthalmic Devices", https://web.archive.org/web/2016118063943/http://www.bsigroup.com/en-GB/medical-devices/technologies/opthalmic/ as archived Jan. 18, 2016 in 10 pages.

WebMD, "Laser Photocoagulation for Diabetic Retinopathy", https://web.archive.org/web/20160104133456/http://www.webmd.com/diabetes/laser-photocoagulation-for-diabetic-retinopathy, as archived Jan. 4, 2016 in 4 pages.

Women's and Children's Hospital, "Electro-retinography & Electro-oculography", https://web.archive.org/web/20160304171451/http://www.wch.sa.gov.au/services/az/divisions/paedm/neurology/electro.html as archived Mar. 4, 2016 in 5 pages.

Telescope-optics.net, "Eye Chromatism", https://web.archive.org/web/20160310131809/http://www.telescope-optics.net/eye_chromatism.htm as archived Mar. 10, 2016 in 5 pages.

Wikipedia, "Slit lamp", https://web.archive.org/web/201602241772608/https://en.wikipedia.org/wiki/Slit_lamp as archived Feb. 24, 2016 in 5 pages.

Mordant et al., "Spectral imaging of the retina", Eye (2011) 25, pp. 309-320.

Mordant et al., "Validation of Human Whole Blood Oximetry, Using a Hyperspectral Fundus Camera with a Model Eye", Investigative Opthalmology & Visual Science, Apr. 2011, vol. 52, No. 5, pp. 2851-2859.

Villanueva et al., "A Novel Gaze Estimation System With One Calibration Point", IEEE Transactions on Systems, Man, and Cybernetics—Part B: Cybernetics, vol. 38, No. 4, Aug. 2008, pp. 1123-1138.

Levoy et al., "Light Field Microscopy", ACM Transaction on Graphics 25(3), Proc. SIGGRAPH 2006 in 11 pages.

Malara, Marilyn, "Simple eye test may detect autism in children sooner", http://www.upi.com/Health_News/2016/04/02/Simple-eye-test-ma . . . , UPI.com in 3 pages printed Apr. 4, 2016.

Wikipedia, "Hirschberg test", https://web.archive.org/web/20151220061524/https://en.wikipedia.org/wiki/hirschberg_test archived Dec. 20, 2015 in 2 pages.

Christensen, Dana, "V-Beam Laser", https://web.archive.org/web/20160130091016/presstelegraph.com/2016/01/23/v-beam-laser.html archived Jan. 30, 2016 in 5 pages.

Telescope-optics.net, "Notes on Amateur Telescope Optics", http://www.telescope.optics.net/index.htm web-published on Jul. 14, 2006, updated Mar.-Jun. 2015 in 3 pages.

Telescope-optics.net., "Eye Spectral Response", http://www.telescope-optics.net/eye-spectral_response.htm accessed on Dec. 8, 2015 in 9 pages.

Levoy, Marc, "Optical recipes for light field microscopes", Stanford Computer Graphics Laboratory Technical Memo 2006-001, Computer Science Department, Stanford University, Jun. 20, 2006 (revised Jun. 28 and Aug. 9) in 5 pages.

Wikipedia, "Red reflex", https://en.wikipedia.org/wiki/Red_reflex accessed on Feb. 25, 2016 in 2 pages.

Wikipedia, "Ganzfeld effect", https://web.archive.org/web/20160305082958/https://en.wikipedia.org/wiki/Ganzfeld_effect as archived Mar. 5, 2016 in 2 pages.

Lumus, "The Lumus Solution", https://web.archive.org/web/20150212093731/http://www.lumus-optical.com/index.php?option=com_content&task=view&id=5&itemid=8 as archived Feb. 12, 2015 in 2 pages.

Wikipedia, "Myopia", https://web.archive.org/web/20150527122730/https://en.wikipedia.org/wiki/Near-sightedness as archived May 27, 2015 in 21 pages.

Wikipedia, "Astigmatism", https://web.archive.org/web/20160223084059/https://en.wikipedia.org/wiki/Astigmatism as archived Feb. 23, 2016 in 5 pages.

Hutton et al., "Undestanding Electric Viewing", RNIB, Sep. 5, 2014 in 4 pages.

Dunaief, MD, PhD, Joshua, "Low-Vision Therapy for Macular Degeneration: How It Can Help", BrightFocus Foundation, published Nov. 30, 2016 in 5 pages.

Wikipedia, "Phoropter", https://web.archive.org/web/20160122152227/https://en.wikipedia.org/wiki/Phoropter as archived Jan. 22, 2016 in 5 pages.

Wikipedia, "Retinoscopy", https://web.archive.org/web/20151019024742/https://en.wikipedia.org/wiki/Retinoscopy as archived Oct. 19, 2015 in 2 pages.

Wikipedia, "Ishihara test", https://web.archive.org/web/20160302073646/https://en.wikipedia.org/wiki/Ishihara_test as archived Mar. 2, 2016 in 4 pages.

Memim Encyclopedia, "Anomaloscope", https://memim.com/anomaloscope.html in 3 pages printed Feb. 11, 2019.

(56) References Cited

OTHER PUBLICATIONS

Vessel, Madeleine, "Wavefront Technology in Eye Exams", https://web.archive.org/web/20160314205244/https://www.allaboutvision.com/eye_exam/wavefront.htm as archived Mar. 14, 2016 in 5 pages.

Wikipedia, "Stereoscopy", https://web.archive.org/web/20160309170108/https://en.wikipedia.org/wiki/Stereoscopy as archived Mar. 9, 2016 in 8 pages.

Wikipedia, "Haploscope", https://web.archive.org/web/20151023085410/https://en.wikipedia.org/wiki/Haploscope as archived Oct. 23, 2015 in 2 pages.

Sunnex Technologies, "The Role of Blue Light in the Pathogenesis of AMD", https://web.archive.org/web/20151212232525/http://www.sunnexbiotech.com/therapist/blue%20light%20and%20amd.html as archived Dec. 12, 2015 in 13 pages.

Kodak, "In-Vivo Multispectral System Fx", http://clab.aiums.ac.ir/_clab/documents/Multispectral_In-Vivo_Imaging.pdf, Carestream Health, Inc., 2008 in 8 pages.

\* cited by examiner

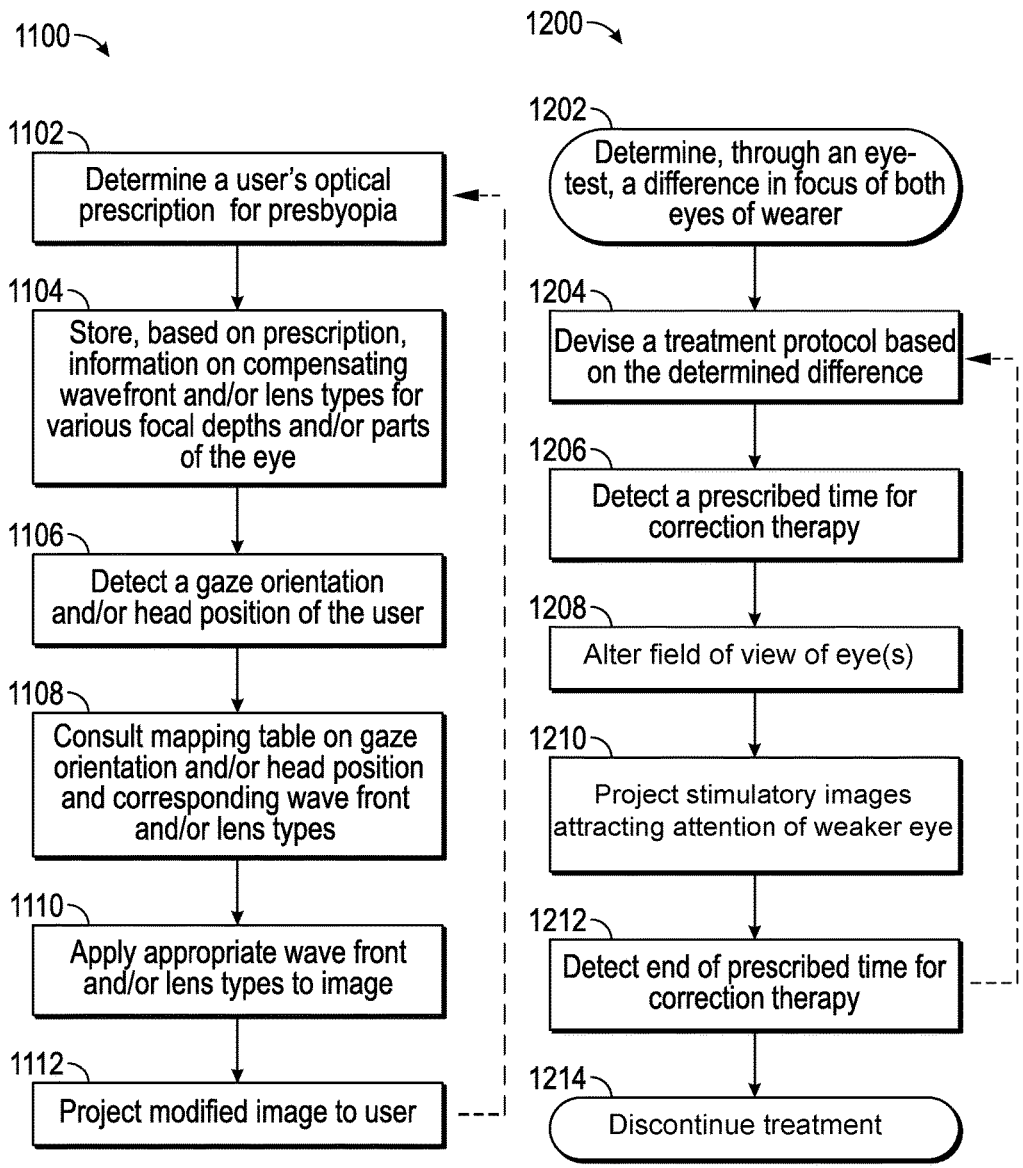

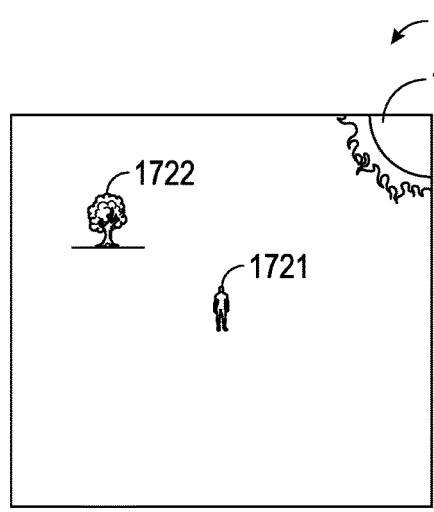
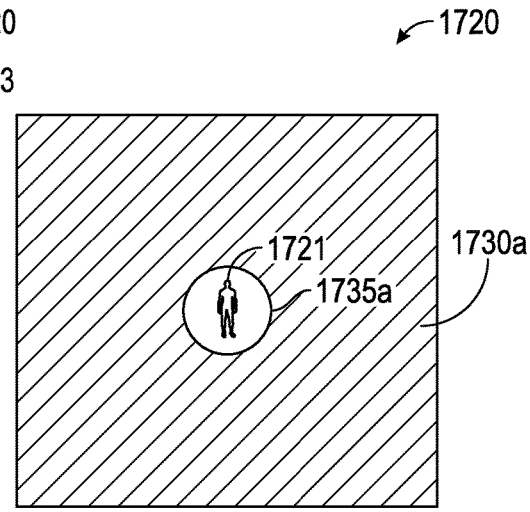
FIG. 17A    FIG. 17B
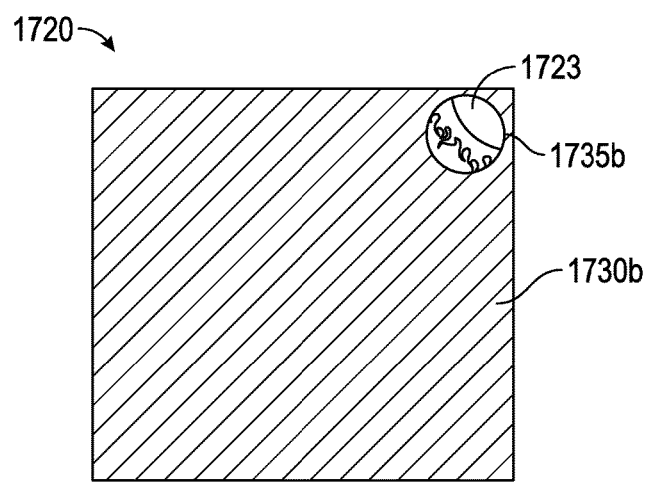
FIG. 17C

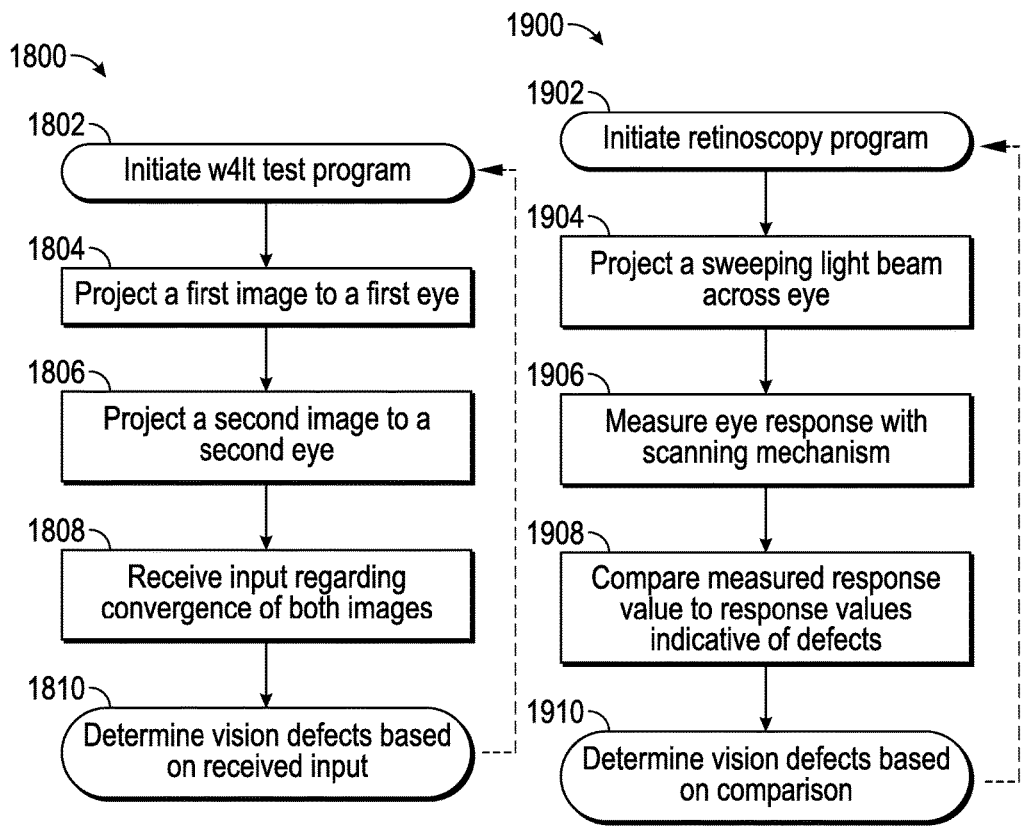

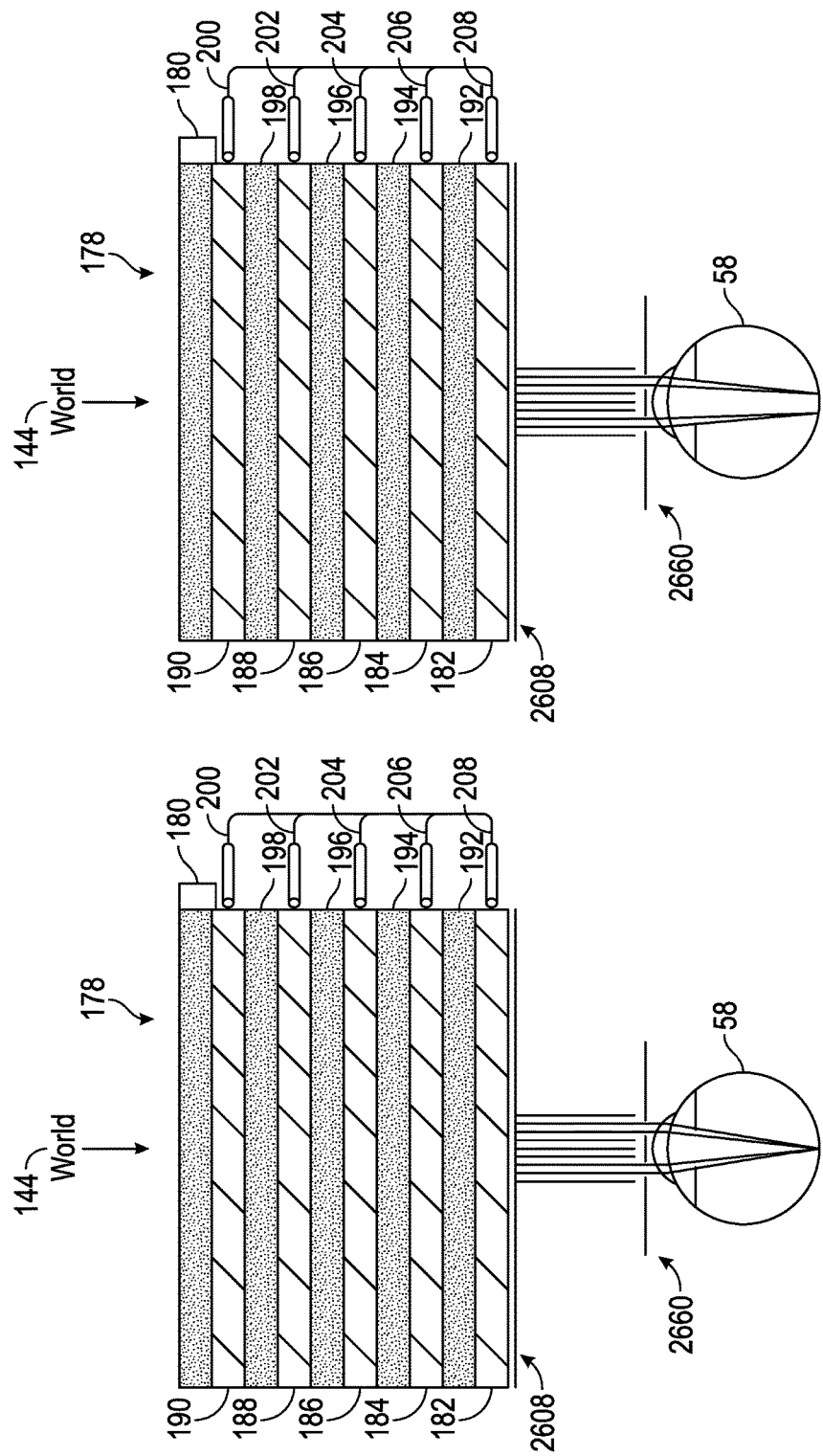

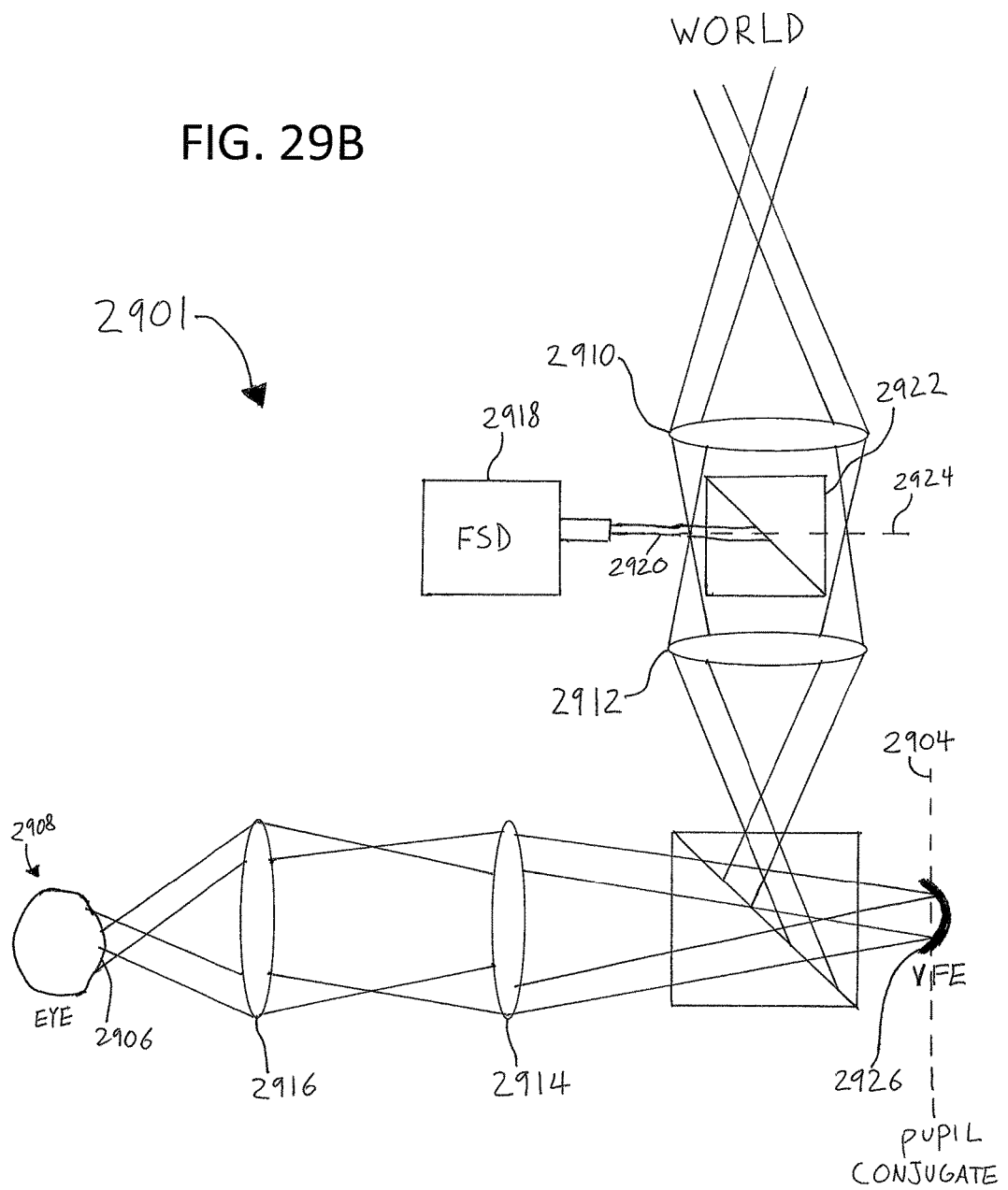

METHODS AND SYSTEMS FOR PROVIDING AUGMENTED REALITY CONTENT FOR TREATING COLOR BLINDNESS

RELATED APPLICATIONS

This non-provisional patent application claims priority under 35 U.S.C. 120 from U.S. application Ser. No. 15/072,290 filed on Mar. 16, 2016 titled "METHODS AND SYSTEMS FOR DIAGNOSING AND TREATING HEALTH AILMENTS" which is hereby incorporated by reference in its entirety. U.S. application Ser. No. 15/072,290 claims priority under 35 U.S.C. 119(e) from U.S. Provisional Application Ser. No. 62/133,870 filed on Mar. 16, 2015 titled "METHODS AND SYSTEM FOR DIAGNOSING AND TREATING HEALTH AILMENTS" which is hereby incorporated by reference herein in its entirety.

The aforementioned patent applications as well as U.S. application Ser. No. 14/555,585 titled "VIRTUAL AND AUGMENTED REALITY SYSTEMS AND METHODS", and U.S. Prov. Application Ser. No. 62/005,834, titled "METHODS AND SYSTEM FOR CREATING FOCAL PLANES IN VIRTUAL AND AUGMENTED REALITY" are each hereby expressly incorporated by reference herein in their entirety for all purposes. Any and all applications for which a foreign or domestic priority claim is identified in the Application Data Sheet as filed with the present application are hereby incorporated by reference in their entirety under 37 CFR 1.57.

FIELD

The present disclosure relates to various methods and systems for diagnosing, monitoring, and treating health conditions and ailments, including ophthalmic as well as other conditions and ailments.

BACKGROUND

Ophthalmic instruments and techniques are routinely used by clinicians to diagnose and treat eye-related ailments. An example of a traditional ophthalmic device is shown in FIG. 1. As illustrated, the patient may be positioned in a specific, seated position for the entire duration of the procedure, which may last anywhere between a few seconds to a few minutes. This positioning has been considered necessary to properly align the patient's eye with the ophthalmic device, to perform measurements and/or therapeutic procedures on the patient's eyes.

Undesirably, ophthalmic devices tend to be large, bulky and expensive devices, and are typically used exclusively in doctor's offices. Thus, patients may be required to make an appointment with an optometrist and visit the doctor for any diagnoses or treatment to take place. This can be a deterring factor for many patients, who may delay the trip to the doctor's office for long periods of time, possibly until a condition has worsened. The worsened condition may require even more drastic therapies or procedures to address, when it could have been more easily alleviated had the patient been timely diagnosed or treated. Furthermore, the large and bulky nature of most ophthalmic devices forces patients to be placed in an uncomfortable position for a large amount of time, which in turn may actually increase risks of mis-diagnoses and patient error.

Accordingly, there is a need for health systems that address one or more of the difficulties above.

SUMMARY

Example embodiments described herein have innovative features, no single one of which is indispensable or solely responsible for their desirable attributes. Without limiting the scope of the claims, some of the advantageous features will now be summarized.

An innovative aspect of the subject matter described herein can be implemented in a user-wearable diagnostic health system comprising a frame, an augmented reality display attached to the frame, a light detector attached to the frame and a processor configured to conduct a health analysis of the user based on light detected by the light detector. The frame is configured to mount on the user. The augmented reality display is configured to direct images to an eye of the user. The light detector is configured to detect light reflected from an eye of the user.

Another innovative aspect of the subject matter described herein can be implemented in a user-wearable diagnostic health system comprising a frame, an augmented reality display attached to the frame, a sound emitter configured to emit sound waves toward the user, a sound detector attached to the frame and configured to detect sound waves reflected from the user, and a processor configured to conduct a health analysis of the user based on information detected by the sound detector. The frame is configured to mount on the user. The augmented reality display is configured to direct images to an eye of the user.

Yet another innovative aspect of the subject matter described herein can be implemented in a user-wearable therapeutic health system comprising a frame configured to mount on the user, an augmented reality display attached to the frame and a processor configured to direct the augmented reality display to conduct a health therapy protocol on the user. The augmented reality display is further configured to direct images to an eye of the user.

An innovative aspect of the subject matter described herein can be implemented in a wearable diagnostic health system comprising a frame configured to mount on a clinician, an augmented reality display attached to the frame and configured to direct images to an eye of the clinician, an outward-facing image capture device configured to image an eye of a patient and a processor configured to conduct a health analysis of the patient based on the image of the eye captured by the image capture device.

Additional example embodiments are provided below. Note that structures for various health analyses and/or therapies may coexist in the same health system. Moreover, as disclosed herein, the same feature may be applied to facilitate multiple health analyses and/or therapies. For example, structures used for delivering medication may also be utilized for various diagnostics, as disclosed herein. Consequently, health systems according to some embodiments may include various combinations of the structural features disclosed herein, including combinations of features disclosed under different headings. In addition, the health system may be configured to perform various combinations of the health analyses and therapies disclosed herein, including those disclosed under different headings. Accordingly, a variety of example embodiments are set for below.

Myopia/Hyperopia/Astigmatism

1. A wearable ophthalmic device, comprising:
    a head-mounted display system; and
    a light source configured to direct light into an eye of
        a person to form an image in the eye; and a waveguide stack comprising one or more waveguides, wherein each of the one or more waveguides is configured to project the light at one of the one or more focal planes, wherein the image is modified by a wavefront correction based on an optical prescription for the eye.

2. The device of embodiment 1, wherein the waveguide stack further comprises one or more lenses.

3. The device of embodiment 1, wherein the head-mounted display system comprises an augmented reality head-mounted ophthalmic system configured to pass light from the world into the eye of the person wearing the head-mounted system.

4. The device of embodiment 1, wherein the optical prescription comprises a prescription for myopia.

5. The device of embodiment 1, wherein the optical prescription comprises a prescription for hyperopia.

6. The device of embodiment 1, wherein the optical prescription comprises a prescription for astigmatism.

7. A wearable ophthalmic device, comprising:
an augmented reality head-mounted display system configured to pass light from the world into an eye of a person wearing the head-mounted system;
a light source configured to direct light into an eye of the person to form an image in the eye; and
an adaptable optics element configured to apply a wavefront correction to the image based on an optical prescription for the eye.

8. The device of embodiment 7, wherein the adaptable optics element comprises a variable focus element.

9. The device of embodiment 8, wherein the variable focus element comprises a membrane mirror.

10. The device of embodiment 9, further comprising:
one or more electrodes coupled to the membrane mirror; and
a control system configured to selectively control the one or more electrodes to modify a shape of the membrane mirror based on a corneal shape of the eye.

11. The device of embodiment 7, wherein the optical prescription comprises a prescription for myopia.

12. The device of embodiment 7, wherein the optical prescription comprises a prescription for hyperopia.

13. The device of embodiment 7, wherein the optical prescription comprises a prescription for astigmatism.

14. A wearable ophthalmic device, comprising:
a head-mounted ophthalmic system;
a light source configured to direct light into an eye of a person to form an image in the eye; and
an adaptable optics element configured to apply a wavefront correction to the image based on an optical prescription for the eye, wherein the adaptable optics comprises a membrane mirror.

15. The device of embodiment 14, further comprising:
one or more electrodes coupled to the membrane mirror; and
a control system configured to selectively control the one or more electrodes to modify a shape of the membrane mirror based on a corneal shape of the eye.

16. The device of embodiment 14, wherein the optical prescription comprises a prescription for myopia.

17. The device of embodiment 14, wherein the optical prescription comprises a prescription for hyperopia.

18. The device of embodiment 14, wherein the optical prescription comprises a prescription for astigmatism.

19. A wearable ophthalmic device, comprising:
a head-mounted display system; and
a light source configured to direct light into an eye of a person to form an image in the eye, the light source comprising a fiber scanning projector,
wherein the image is modified by a wavefront correction based on an optical prescription for the eye.

20. The device of embodiment 19, wherein the optical prescription comprises a prescription for myopia.

21. The device of embodiment 19, wherein the optical prescription comprises a prescription for hyperopia.

22. The device of embodiment 19, wherein the optical prescription comprises a prescription for astigmatism.

23. A wearable augmented reality ophthalmic device, comprising:
an augmented reality head-mounted ophthalmic system configured to pass light from the world into an eye of a person wearing the head-mounted system; and
a light source configured to project light into the eye of the person to form an image in the eye, the image being modified by a wavefront correction based on an optical prescription for the eye.

24. The device of embodiment 23, wherein the optical prescription comprises a prescription for myopia.

25. The device of embodiment 23, wherein the optical prescription comprises a prescription for hyperopia.

26. The device of embodiment 23, wherein the optical prescription comprises a prescription for astigmatism.

27. A method for addressing vision defects of a person wearing a head mounted display system, comprising:
identifying an optical prescription of said person;
producing an image using a display in the head mounted display system;
applying wavefront correction to said image based on said prescription to yield a corrected image; and
displaying the corrected image to the person wearing the head mounted display.

28. The method of embodiment 27, wherein identifying an optical prescription of the person comprises receiving input from the person specifying the prescription.

29. The method of embodiment 27, wherein identifying an optical prescription of the person comprises presenting the person with different wavefront corrections.

30. The method of embodiment 29, further comprising receiving input from the person specifying the preferred correction.

31. The method of embodiment 27, wherein the wavefront correction is implemented by adjusting adaptive optics in the head mounted display.

32. The method of embodiment 31, wherein the adaptive optics comprises a variable focus element.

33. The method of embodiment 31, wherein the adaptive optics comprises a deformable optical element.

34. The method of embodiment 38, wherein the deformable optical element comprises a deformable mirror.

35. The method of embodiment 27, wherein the wavefront correction is implemented by using a waveguide stack comprising a plurality of waveguides configured to provide different focal planes.

36. The method of embodiment 35, wherein the wavefront correction is implemented by directing said image through the combination of waveguides that provide the desired optical power to provide the wavefront correction.

37. The method of embodiment 27, further comprising providing different image content at different depth planes.

38. The method of embodiment 37, wherein said providing different image content at different depth planes comprising providing different image content through different waveguides in a waveguide stack thereby providing different optical power to different image content.
39. The method of embodiment 38, wherein different image content propagates through a different number of waveguides thereby providing different optical power to different image content.
40. The method of embodiment 39, wherein said waveguides include static optical elements having optical power.
41. The method of embodiment 27, wherein the wavefront correction is implemented by directing said image through at least one waveguide.
42. The method of embodiment 41, wherein said at least one waveguide includes a dynamic optical element having variable optical power.
43. The method of embodiment 27, wherein said optical correction is configured to correct for myopia.
44. The method of embodiment 27, wherein said optical correction is configured to correct for hyperopia.
45. The method of embodiment 27, wherein said optical correction is configured to correct for astigmatism.
46. The method of embodiment 27, wherein applying the wavefront correction comprises accessing processing electronics.
47. The method of embodiment 27, wherein said wavefront correction is applied to a virtual reality image.
48. The method of embodiment 27, wherein said wavefront correction is applied to an augmented reality image.
49. The method of embodiment 27, wherein said wavefront correction is applied to said image from said display and in imaging objects in front of said head mounted display and said person wearing said head mounted display.
50. A wearable ophthalmic device, comprising:
    a light source and wearable optics configured to direct light into the eye of the person wearing said wearable optics to form an image in said eye, said wearable optics configured to provide prescription refractive correction to said image based on an optical prescription for said person's eye.
51. The device of embodiment 50, further comprising user interface controls configured to receive input from the person specifying the person's optical prescription.
52. The device of embodiment 50, configured to present the person with different wavefront corrections to identify an optical prescription of the person.
53. The device of embodiment 52, further comprising a user interface configured to receive input from the person specifying the preferred correction.
54. The device of embodiment 50, wherein said wearable optics comprise adaptive optics in the wearable optics configured to be adjusted to implement the correction.
55. The device of embodiment 54, wherein the adaptive optics comprises a variable focus element.
56. The device of embodiment 54, wherein the adaptive optics comprises a deformable optical element.
57. The device of embodiment 56, wherein the deformable optical element comprises a deformable mirror.
58. The device of embodiment 50, wherein said wearable optics comprise a waveguide stack comprising a plurality of waveguides configured to provide different focal planes, said waveguide stack configured to provide the prescription correction.
59. The device of embodiment 58, wherein the waveguide stack comprises a combination of waveguides that provide the desired optical power to provide the prescription correction, said prescription correction being implemented by directing said light through the combination of waveguides.
60. The device of embodiment 50, wherein the wearable optic comprise different depth planes, said wearable optics configured to provide different image content at said different depth planes.
61. The device of embodiment 60, wherein said wearable optics comprise a waveguide stack comprising a plurality of waveguides, said providing different image content at different depth planes comprising providing different image content through different waveguides in a waveguide stack thereby providing different optical power to different image content.
62. The device of embodiment 61, wherein different image content propagates through a different number of waveguides thereby providing different optical power to different image content.
63. The device of embodiment 58, wherein said waveguides include static optical elements having optical power.
64. The device of embodiment 50, wherein said wearable optics comprises at least one waveguide, wherein the prescription correction is implemented by directing said light through at least one waveguide.
65. The device of embodiment 64, wherein said at least one waveguide includes a dynamic optical element having variable optical power.
66. The device of embodiment 50, wherein said prescription correction is configured to correct for myopia.
67. The device of embodiment 50, wherein said prescription correction is configured to correct for hyperopia.
68. The method of embodiment 50, wherein said prescription correction is configured to correct for astigmatism.
69. The method of embodiment 50, further comprising processing electronics configured to be accessed to provide the prescription correction.
70. The device of embodiment 69, further comprising a sensor to determine orientation of said person's head.
71. The device of embodiment 70, wherein said sensor comprises a gyroscopic sensor.
72. The device of embodiment 70, wherein said wearable optics is configured to alter the focus of said image based on said head position.
73. The device of embodiment 69, wherein said wearable optics comprises a variable focus element configured to vary a focus of said image to provide said correction.
74. The device of embodiment 69, further comprising an eye tracking system configured to determine a person's convergence point.
75. The device of embodiment 74, wherein said wearable optics is configured to alter the focus of said image based on said determined convergence point.
76. The device of any of embodiments 50, wherein said device comprises a virtual reality device configured to provide said prescription correction to virtual reality image content.
77. The device of any of embodiments 50, wherein said device comprises an augmented reality system configured to provide said prescription correction to augmented reality image content.

78. The device of embodiment 77, wherein said wearable optics are configured such that said prescription correction is applied to an image formed from light from said light source and to images formed from objects in front of said device and said person wearing said wearable optics.
79. The method of embodiment 27, wherein identifying the optical prescription of the person comprises identifying a plurality of optical prescriptions at a plurality of intervals, wherein each optical prescription corresponds to an interval.
80. The method of embodiment 79, wherein the wavefront correction is dynamically adjusted based on the each optical prescription.
81. The device of embodiment 52, configured to identify a plurality of optical prescriptions at plurality of intervals, wherein each optical prescription corresponds to an interval, wherein the refractive correction is dynamically adjusted based on each optical prescription.
82. The device of embodiment 7, wherein the augmented reality head-mounted display system comprises a display lens configured to pass light from the world into an eye of a person wearing the head-mounted system, and wherein the adaptable optics element is positioned between the display lens and a source of the light from the world.
83. The device of embodiment 7, wherein the augmented reality head-mounted display system comprises a display lens configured to pass light from the world into an eye of a person wearing the head-mounted system, and wherein the adaptable optics element is positioned between the display lens and the eye of the user.
84. The device of embodiment 7, wherein the adaptable optics element are positioned between the light source and the eye of the user.
85. The device of embodiment 7, wherein the adaptable optics element are integrated into the light source.
86. The device of any of embodiments 50, wherein said device comprises an augmented reality system configured pass ambient light from in front of the person to the eye of the person to provide, wherein said device is further configured to provide said prescription correction to the ambient light.
87. The device of embodiment 58, wherein said wearable optics comprise adaptive optics in the wearable optics configured to be adjusted to implement the correction.
88. The device of embodiment 87, wherein the adaptive optics is positioned in at least one of:
between the light source and the waveguide stack;
between at least one of the plurality of waveguides and another one of the plurality of waveguides;
between the waveguide stack and the eye of the person; and
between the waveguide stack and an ambient light source from in front of said device.
89. The device of embodiment 87, wherein the adaptive optics is integrated in at least one of the waveguide stack and the light source.
90. The method of embodiment 27, further comprising:
passing ambient light from the world in front of the person and in front of the head mounted display device;
applying wavefront correction to said ambient light based on said prescription;
displaying the corrected ambient light to the person, wherein the corrected ambient light is displayed with the corrected image.

The additional numbered embodiments below in the section titled "ADDITIONAL NUMBERED EMBODIMENTS" are to be repeated, added to, and concatenated to the list of numbered embodiments here as if the list of additional numbered embodiments below in the section titled "ADDITIONAL NUMBERED EMBODIMENTS" immediately followed the list of numbered embodiments here.

Presbyopia

1. A wearable ophthalmic device for addressing presbyopia, comprising:
a head-mounted ophthalmic system;
a sensor configured to determine an orientation of a gaze of a person;
a light source configured to direct a light form into an eye of the person to form an image in the eye; and
an adaptive optics element through which the light form is projected, wherein the adaptive optics element is configured to modify a focus of the image based on the orientation of the gaze of the person.
2. The device of embodiment 1, wherein the orientation of the gaze of the person is based on a position of a head of the person.
3. The device of embodiment 1, further comprising gyroscopic sensors to determine a position of a head of the person.
4. The device of embodiment 1, wherein the orientation of the gaze of the person is determined by tracking a position of the eye.
5. A wearable ophthalmic device, comprising:
a light source and wearable optics configured to direct light into the eye of the person wearing said wearable optics to form an image in said eye, said wearable optics configured to correct for presbyopia based on an optical prescription for said person's eye.
6. The device of embodiment 5, further comprising user interface controls configured to receive input from the person specifying the person's optical prescription.
7. The device of embodiment 5, configured to present the person with different wavefront corrections to identify an optical prescription of the person.
8. The device of embodiment 7, further comprising a user interface configured to receive input from the person specifying the preferred correction.
9. The device of embodiment 5, wherein said wearable optics comprise adaptive optics in the wearable optics configured to be adjusted to implement the correction.
10. The device of embodiment 9, wherein the adaptive optics comprises a variable focus element.
11. The device of embodiment 9, wherein the adaptive optics comprises a deformable optical element.
12. The device of embodiment 11, wherein the deformable optical element comprises a deformable mirror.
13. The device of embodiment 5, wherein said wearable optics comprise a waveguide stack comprising a plurality of waveguides configured to provide different focal planes, said waveguide stack configured to provide the prescription correction.
14. The device of embodiment 13, wherein the waveguide stack comprises a combination of waveguides that provide the desired optical power to provide the prescription correction, said prescription correction being implemented by directing said light through the combination of waveguides.
15. The device of embodiment 5, wherein the wearable optics provide different depth planes, said wearable optics configured to provide different image content at said different depth planes.
16. The device of embodiment 15, wherein said wearable optics comprise a waveguide stack comprising a plurality of waveguides, said providing different image content at different depth planes comprising providing different image content through different waveguides in a waveguide stack thereby providing different optical power to different image content.
17. The device of embodiment 16, wherein different image content propagates through a different number of waveguides thereby providing different optical power to different image content.
18. The device of embodiment 13, wherein said waveguides include static optical elements having optical power.
19. The device of embodiment 5, wherein said wearable optics comprises at least one waveguide, wherein the prescription correction is implemented by directing said light through at least one waveguide.
20. The device of embodiment 19, wherein said at least one waveguide includes a dynamic optical element having variable optical power.
21. The device of embodiment 5, further comprising processing electronics configured to be accessed to provide the prescription correction.
22. The device of embodiment 21, further comprising a sensor to determine orientation of said person's head.
23. The device of embodiment 22, wherein said sensor comprises a gyroscopic sensor.
24. The device of embodiment 22, wherein said wearable optics is configured to alter the focus of said image based on said head position.
25. The device of embodiment 21, wherein said wearable optics comprises a variable focus element configured to vary a focus of said image to provide said correction.
26. The device of embodiment 21, further comprising an eye tracking system configured to determine a person's convergence point.
27. The device of embodiment 26, wherein said wearable optics is configured to alter the focus of said image based on said determined convergence point.
28. The device of embodiment 5, wherein said device comprises a virtual reality device configured to provide said prescription correction to virtual reality image content.
29. The device of embodiment 5, wherein said device comprises an augmented reality system configured to provide said prescription correction to augmented reality image content.
30. The device of embodiment 29, wherein said wearable optics are configured such that said prescription correction is applied to an image formed from light from said light source and to images formed from objects in front of said device and said person wearing said wearable optics.
31. The device of embodiment 5, further comprising electronics configured to determine the person's gaze based on movement of one or more of the person's eyes.
32. The device of embodiment 31, wherein the said wearable optics is configured to alter the focus of said image based on said determined gaze.
33. The device of embodiment 31, wherein a downward movement of one or more of the person's eyes is indicative of the person focusing at a near-field focal depth.
34. The device of embodiment 33, wherein the said wearable optics is configured to increase the optical power of a portion of the said wearable optics based on the optical prescription for said person's eye.
35. The device of embodiment 16, further comprising an electronics configured to determine the person's gaze based on movement of one or more of the person's eyes.
36. The device of embodiment 1, wherein the sensor comprises an eye-tracking system configured to determine the convergence point of the eye of the person.
37. The device of embodiment 4, wherein an angle of convergence is determined based on the position of the eye, wherein the focus is modified based on the angle of convergence.
38. The device of embodiment 31, wherein a downward movement of one or more of the person's eyes is indicative of an increase in an angle of the convergence of the eyes, wherein an increase in the angle of the convergence of the eye is indicative of the person focusing at a near-field focal depth.
39. The device of embodiment 5, further comprising a biofeedback system configured to determine the wavefront correction based on monitoring one or more properties of the eye while viewing the image.
40. The device of embodiment 40, wherein the biofeedback system receives inputs from at least one of a phoropter, an autorefractor, and an eye tracking system.
41. The device of embodiment 40, wherein the properties of the eye is at least one of: changes in a convergence point of the eye, changes in a position of a head of the person, change in a size of a pupil of the eye.
42. The device of embodiment 5, further comprising electronics configured to determine the person's gaze based on glint detection.

The additional numbered embodiments below in the section titled "ADDITIONAL NUMBERED EMBODIMENTS" are to be repeated, added to, and concatenated to the list of numbered embodiments here as if the list of additional numbered embodiments below in the section titled "ADDITIONAL NUMBERED EMBODIMENTS" immediately followed the list of numbered embodiments here.

Strabismus/Amblyopia
1. A wearable augmented reality device configured to be used by a wearer having eyes having an inability to align at a single convergence point, said device comprising:
   an augmented reality head-mounted ophthalmic system comprising a wearable augmented reality display platform, said augmented reality head-mounted ophthalmic system configured to pass light from the world into an eye of a wearer wearing the head-mounted system;
   a light source configured to project light into the eye of the wearer to form an image in the eye; and
   an eye tracking system configured to determine gaze of said eye,
   wherein the image is modified to add compensating prism correction to bring the convergence point of both eyes together.
2. A wearable virtual reality device configured to be used by a wearer having eyes having an inability to align at a single convergence point, said device comprising:

a virtual reality head-mounted ophthalmic system comprising a wearable virtual reality display platform comprising a display for providing images to an eye of the wearer;

a light source configured to project light into the eye of the wearer to form an image in the eye; and an eye tracking system configured to determine gaze of said eye, wherein the image is modified to add compensating prism correction to bring the convergence point of both eyes together.

3. A wearable augmented reality device configured to be used by a wearer having eyes having an inability to align at a single convergence point, said device comprising:

an augmented reality head-mounted ophthalmic system comprising a wearable augmented reality display platform, said augmented reality head-mounted ophthalmic system configured to pass light from the world into an eye of a wearer wearing the head-mounted system;

a light source configured to project light into the eye of the wearer to form an image in the eye;

an eye tracking system configured to determine gaze of said eye; and an adaptable optics element configured to add compensating prism correction to bring the convergence point of both eyes together.

4. The device of embodiment 3, wherein the adaptable optics element comprises a variable focus element.

5. The device of embodiment 4, wherein the variable focus element comprises a membrane mirror.

6. The device of embodiment 5, further comprising:
one or more electrodes coupled to the membrane mirror; and
a control system configured to selectively control the one or more electrodes to modify a shape of the membrane mirror based on a corneal shape of the eye.

7. A wearable virtual reality device configured to be used by a wearer having eyes having an inability to align at a single convergence point, said device comprising:

a virtual reality head-mounted ophthalmic system comprising a wearable virtual reality display platform comprising a display for providing images to an eye of the wearer;

a light source configured to project light into the eye of the wearer to form an image in the eye;

an eye tracking system configured to determine gaze of said eye; and an adaptable optics element configured to add compensating prism correction to bring the convergence point of both eyes together.

8. The device of embodiment 7, wherein the adaptable optics element comprises a variable focus element.

9. The device of embodiment 8, wherein the variable focus element comprises a membrane mirror.

10. The device of embodiment 9, further comprising:
one or more electrodes coupled to the membrane mirror; and
a control system configured to selectively control the one or more electrodes to modify a shape of the membrane mirror based on a corneal shape of the eye.

11. A wearable display device configured to be used by a wearer having eyes having an inability to align at a single convergence point, said display device comprising:

a wearable head-mounted ophthalmic system;

a light source configured to direct light into an eye of said wearer to form an image in the eye, the light source comprising a fiber scanning projector; and an eye tracking system configured to determine gaze of said eye, wherein the light source is configured to add compensating prism correction to bring the convergence point of both eyes together.

12. A wearable display device configured to be used by a wearer having eyes having an inability to align at a single convergence point, said display device comprising:

a wearable head-mounted ophthalmic system;

a light source configured to direct light into an eye of said wearer to form an image in the eye;

a waveguide stack comprising a plurality of waveguides, wherein different waveguides are configured to project light from different depth planes; and an eye tracking system configured to determine gaze of said eye, wherein the image is modified to add compensating prism correction to bring the convergence point of both eyes together.

13. The device of embodiment 12, wherein the waveguide stack further comprises one or more lenses.

14. The device of embodiment 12, wherein the head-mounted ophthalmic system comprises an augmented reality display platform, said head-mounted ophthalmic system configured to pass light from the world into the eye of the wearer wearing the head-mounted display system.

15. A wearable augmented reality device configured to be used by a wearer having eyes having an inability to align at a single convergence point, said device comprising:

an augmented reality head-mounted ophthalmic system comprising an augmented reality display platform, said augmented reality head-mounted ophthalmic system configured to pass light from the world into an eye of a wearer wearing the head-mounted system;

a light source configured to direct light into the eye of the wearer to form an image in the eye; and an eye tracking system configured to determine gaze of said eye, wherein the wearable augmented reality device is configured to re-train to gradually align the convergence point of both eyes.

16. The device of embodiment 15, wherein the wearable augmented reality device is configured to re-train by occluding one eye.

17. The device of embodiment 15, wherein the wearable augmented reality device is configured to re-train by reducing intensity of light into one eye.

18. The device of embodiment 15, wherein the wearable augmented reality device is configured to re-train by defocusing the light directed into one eye.

19. A wearable virtual reality device configured to be used by a wearer having eyes having an inability to align at a single convergence point, said device comprising:

a virtual reality head-mounted ophthalmic system comprising a virtual reality display platform comprising a display for providing images to an eye of the wearer;
a light source configured to direct light into the eye of the wearer to form an image in the eye; and
an eye tracking system configured to determine gaze of said eye,
wherein the wearable virtual reality device is configured to re-train to gradually align the convergence point of both eyes.
20. The device of embodiment 19, wherein the wearable virtual reality device is configured to re-train by occluding one eye.
21. The device of embodiment 19, wherein the wearable virtual reality device is configured to re-train by reducing intensity of light into one eye.
22. The device of embodiment 19, wherein the wearable virtual reality device is configured to re-train by defocusing the light directed into one eye.
23. A wearable display device configured to be used by a wearer having eyes having an inability to align at a single convergence point, said device comprising:
an augmented reality head-mounted ophthalmic system comprising an augmented reality display platform, said augmented reality head-mounted ophthalmic system configured to pass light from the world into an eye of a wearer wearing the head-mounted ophthalmic system;
a light source configured to direct light into the eye of the wearer to form an image in the eye;
an adaptable optics element configured to modify said image; and
an eye tracking system configured to determine gaze of said eye,
wherein the wearable display device is configured to re-train to gradually align the convergence point of both eyes.
24. The device of embodiment 23, wherein the adaptable optics element comprises a variable focus element.
25. The device of embodiment 24, wherein the variable focus element comprises a membrane mirror.
26. The device of embodiment 25, further comprising:
one or more electrodes coupled to the membrane mirror; and
a control system configured to selectively control the one or more electrodes to modify a shape of the membrane mirror based on a corneal shape of the eye.
27. A wearable display device configured to be used by a wearer having eyes having an inability to align at a single convergence point, said device comprising:
a head-mounted ophthalmic system;
a light source configured to direct light into an eye of the wearer to form an image in the eye;
an adaptable optics element configured to modify said image; and
an eye tracking system configured to determine gaze of said eye,
wherein the wearable display device is configured to re-train to gradually align the convergence point of both eyes.
28. The device of embodiment 27, wherein the adaptable optics element comprises a variable focus element.
29. The device of embodiment 28, wherein the variable focus element comprises a membrane mirror.
30. The device of embodiment 29, further comprising:
one or more electrodes coupled to the membrane mirror; and
a control system configured to selectively control the one or more electrodes to modify a shape of the membrane mirror based on a corneal shape of the eye.
31. A wearable display device configured to be used by a wearer having eyes having an inability to align at a single convergence point, said device comprising:
a head-mounted ophthalmic system;
a light source configured to direct light into an eye of the wearer to form an image in the eye, the light source comprising a fiber scanning projector; and
an eye tracking system configured to determine gaze of said eye,
wherein the wearable display device is configured to re-train to gradually align the convergence point of both eyes.
32. A wearable display device configured to be used by a wearer having eyes having an inability to align at a single convergence point, said device comprising:
a head-mounted ophthalmic system;
a light source configured to direct light into an eye of the wearer to form an image in the eye;
a waveguide stack comprising a plurality of waveguides, wherein different waveguides are configured to project light from different depth planes; and
an eye tracking system configured to determine gaze of said eye,
wherein the wearable display device is configured to re-train to gradually align the convergence point of both eyes.
33. The device of embodiment 32, wherein the waveguide stack further comprises one or more lenses.
34. The device of embodiment 32, wherein the head-mounted ophthalmic system comprises an augmented reality display platform, said head-mounted ophthalmic system configured to pass light from the world into the eye of the wearer wearing the head-mounted display system.

The additional numbered embodiments below in the section titled "ADDITIONAL NUMBERED EMBODIMENTS" are to be repeated, added to, and concatenated to the list of numbered embodiments here as if the list of additional numbered embodiments below in the section titled "ADDITIONAL NUMBERED EMBODIMENTS" immediately followed the list of numbered embodiments here.

Higher Order Aberrations

1. A wearable augmented reality device configured to be used by a person, said device comprising:
an augmented reality head-mounted ophthalmic system comprising an augmented reality display platform, said augmented reality head-mounted ophthalmic system configured to pass light from the world into an eye of the person wearing the head-mounted system; and
at least one light source and wearable optics configured to project light into the eye of the person to form an image in the eye, said at least one light source and wearable optics configured to provide refractive correction for higher order refractive errors.
2. The device of embodiment 1, wherein said at least one light source comprises a fiber scanning display.
3. The device of embodiment 1, further comprising user interface controls configured to receive an input specifying the person's optical prescription.

4. The device of embodiment 1, wherein said wearable optics comprise adaptive optics in the wearable optics configured to be adjusted to implement the refractive correction.
5. The device of embodiment 4, wherein the adaptive optics comprises a variable focus element.
6. The device of embodiment 4, wherein the adaptive optics comprises a deformable optical element.
7. The device of embodiment 6, wherein the deformable optical element comprises a deformable mirror.
8. The device of embodiment 1, wherein said wearable optics comprise a waveguide stack comprising a plurality of waveguides configured to provide different focal planes.
9. The device of embodiment 1, wherein the wearable optics comprise different depth planes, said wearable optics configured to provide different image content at said different depth planes.
10. The device of embodiment 9, wherein said wearable optics comprise a waveguide stack comprising a plurality of waveguides, said providing different image content at different depth planes comprising providing different image content through different waveguides in a waveguide stack thereby providing different optical power to different image content.
11. The device of embodiment 10, wherein different image content propagates through a different number of waveguides thereby providing different optical power to different image content.
12. The device of embodiment 8, wherein said waveguides include static optical elements having optical power.
13. The device of embodiment 1, wherein said wearable optics comprises at least one waveguide.
14. The device of embodiment 13, wherein said at least one waveguide includes a dynamic optical element having variable optical power.
15. The device of embodiment 1, further comprising processing electronics configured to be accessed to provide the refractive correction.
16. The device of embodiment 1, wherein said wearable optics are configured such that said refractive correction is applied to an image formed from light from said light source and to images formed from objects in front of said device and said person wearing said wearable optics.
17. A wearable virtual reality device configured to be used by a person, said device comprising:
a virtual reality head-mounted ophthalmic system comprising an virtual reality display platform comprising a display for providing images to the eye of the person; and
at least one light source and wearable optics configured to project light into the eye of the person to form an image in the eye, said at least one light source and wearable optics configured to provide refractive correction for higher order refractive errors.
18. The device of embodiment 1, further comprising a receiver circuit configured to receive input from a remote source specifying the person's optical prescription.
19. The device of embodiment 1, further comprising a receiver configured to receive, from a memory circuit external to the wearable augmented reality device, an optical prescription stored on the memory circuit, wherein the wearable augmented reality device provides refractive correction based on the received optical prescription.
20. The device of embodiment 17, further comprising an outward facing camera configured to obtain images of light formed from objects in front of said device, wherein the image provided to the eye of the person comprises the obtained images.
21. The device of embodiment 3, wherein the user interface controls are configured to receive the input from at least one of the person, a third party, and a doctor.
22. The device of embodiment 15, wherein the wearable optics are configured to provide refractive correction in real-time as the light forming the image is projected into the eye of the person.

The additional numbered embodiments below in the section titled "ADDITIONAL NUMBERED EMBODIMENTS" are to be repeated, added to, and concatenated to the list of numbered embodiments here as if the list of additional numbered embodiments below in the section titled "ADDITIONAL NUMBERED EMBODIMENTS" immediately followed the list of numbered embodiments here.

Chromatic Aberrations

1. A wearable augmented reality device configured to be used by a person, said device comprising:
an augmented reality head-mounted ophthalmic system comprising a wearable augmented reality display platform, said augmented reality head-mounted ophthalmic system configured to pass light from the world into an eye of a person wearing the head-mounted system, said augmented reality display platform comprising optics configured to project an image in said eye,
wherein said augmented reality display is configured to project a first color component of the image at a first depth plane and a second color component of the image at a second depth plane different than the first depth plane to compensate for longitudinal chromatic aberration of the person's eye.
2. The device of embodiment 1, wherein said augmented reality display is configured to output a third color component of the image at a third depth plane different than the first and second depth planes to compensate for longitudinal chromatic aberration of the person's eye.
3. The device of embodiment 1, wherein said first color component is red.
4. The device of embodiment 1, wherein said second color component is green.
5. The device of embodiment 2, wherein said third color component is blue.
6. The device of embodiment 1, further comprising a user interface for receiving a prescription for said longitudinal chromatic aberration.
7. The device of embodiment 1, wherein said augmented reality head-mounted ophthalmic system is configured to vary the focus of the image automatically to provide incremental change in optical prescription thereby conducting eye exams.
8. The device of embodiment 7, wherein said augmented reality head-mounted ophthalmic system is configured to vary the focus of the first color component of the image automatically to provide incremental change in optical prescription thereby conducting eye exams.
9. The device of embodiment 8, wherein said augmented reality head-mounted ophthalmic system is configured to vary the focus of a monochromatic image of said second color component automatically to provide incremental change in optical prescription thereby conducting eye exams.
10. The device of embodiment 9, wherein said augmented reality head-mounted ophthalmic system is configured to vary the focus of a monochromatic image of a third color component of the image automatically to provide incremental change in optical prescription thereby conducting eye exams.
11. The device of embodiment 10, wherein said images comprise letters.
12. The device of embodiment 10, wherein said images comprise graphic symbols, pictures, or drawings.
13. The device of embodiment 7, further comprising a user interface configured to receive input from the wear regarding the image.
14. The device of embodiment 7, wherein said augmented reality head-mounted ophthalmic system is configured to assess whether the person can view the image comfortably and incrementally increase the prescription, positive or negative, by changing focus if not.
15. The device of any of embodiments any of embodiment 7, wherein said augmented reality head-mounted ophthalmic system is configured to assess whether the person can view the image comfortably and determine the prescription of the person if so.
16. The device of embodiment 1, wherein said wearable augmented reality display platform comprises a fiber scanning device.
17. The device of embodiment 1, wherein said wearable augmented reality device system is configured such that the angle at which light of different color is projected may be varied based lateral chromatic aberration.
18. The device of embodiment 1, wherein said optics comprises an adaptable optics element configured to project the light.
19. The device of embodiment 18, wherein the adaptable optics element comprises a variable focus element.
20. The device of any of embodiments any of embodiment 1, further comprising a waveguide stack comprising a plurality of waveguides, wherein different waveguides are configured to project light from different depth planes.
21. The device of embodiment 20, wherein the waveguide stack further comprises one or more lenses.
22. A wearable augmented reality device configured to be used by a person, said device comprising:
an augmented reality head-mounted ophthalmic system comprising a wearable augmented reality display platform, said augmented reality head-mounted ophthalmic system configured to pass light from the world into an eye of a person wearing the head-mounted system, said augmented reality display platform comprising optics configured to project an image in said eye,
wherein said augmented reality display is configured to project a first color component of the image at a first angle and a second color component of the image at a second angle different than the first angle to compensate for lateral chromatic aberration of the person's eye.
23. The device of embodiment 22, further comprising a user interface for receiving a prescription for said lateral chromatic aberration.
24. The device of any of embodiments 22, wherein said augmented reality head-mounted ophthalmic system is configured to vary the angle of the image automatically to provide incremental change in optical prescription thereby conducting eye exams.
25. A wearable virtual reality device configured to be used by a person, said device comprising:
a virtual reality head-mounted ophthalmic system comprising a wearable virtual reality display platform, said virtual reality display platform comprising optics configured to project an image in an eye of the person,
wherein said virtual reality display is configured to project a first color image at a first depth plane and a second color image at a second depth plane different than the first depth plane to compensate for longitudinal chromatic aberration of the person's eye.
26. A wearable virtual reality device configured to be used by a person, said device comprising:
a virtual reality head-mounted ophthalmic system comprising a wearable virtual reality display platform, said virtual reality platform comprising optics configured to project an image in an eye of the person,
wherein said virtual reality display is configured to project a first color image at a first angle and a second color image at a second angle different than the first angle to compensate for lateral chromatic aberration of the person's eye.
27. The device of any of embodiments 1, further comprising one or more outwardly facing cameras configured to obtain an image, wherein said image projected into said eye comprises the obtained image.
28. The device of embodiment 17, wherein varying said angle at which light of different color is projected displaces an image formed by said light of different color along the focal plane of said optics.
29. The device of embodiment 17, wherein said optics comprises an adaptable optics configured to receive an input and vary the angle at which light of the first color component is projected based on lateral chromatic aberration.
30. A wearable device configured to be used by a person, said device comprising:
a head-mounted ophthalmic system comprising:
a display platform comprising optics configured to project an image in said eye, and
a processor circuit configured to drive the optics based on an image modification program, wherein said image modification program is configured to compensate for chromatic aberration imparted on to said image by an optical surface.
31. The device of embodiment 30, wherein said head-mounted ophthalmic system further comprises a memory circuit operatively connected to the processor circuit and configured to store said image modification program.
32. The device of embodiment 30, wherein said image modification program is based on an optical prescription of the person, wherein said optical surface comprises a surface of said eye.
33. The device of embodiment 30, wherein said image modification program is based on chromatic aberrations imparted on to said image by said optics, wherein said optical surface comprises a surface of said optics.
34. The device of embodiment 30, wherein said optics comprises a variable focus element, wherein the image modification program is configured to drive the variable focus element by selectively projecting a first color component of the image at a first depth plane and a second color component of the image at a second depth plane different than the first depth plane to compensate for longitudinal chromatic aberrations.

35. A wearable device configured to be used by a person, said device comprising:
   a head-mounted ophthalmic system comprising:
      a memory circuit configured to store an image,
      a display platform comprising optics configured to project said image in an eye of the person, and
      a processor circuit operatively coupled to the memory circuit and configured to modify said image to compensate for chromatic aberration in the person's eye.

36. The device of embodiment 35, wherein the processor is configured to apply an image modification program based on an optical prescription of the person.

37. A wearable device configured to be used by a person, said device comprising:
   a head-mounted ophthalmic system comprising a display platform, said display platform comprising optics configured to project an image in an eye of the person,
   wherein said display platform is configured to project a first color component of the image at a first intensity and a second color component of the image at a second intensity different than the first intensity to compensate for chromatic aberration of the person's eye.

38. The device of embodiment 37, wherein said chromatic aberrations of the person's eye causes said first color component to focus before a retina of said eye, wherein said first intensity is greater than said second intensity.

39. The device of embodiment 37, wherein said chromatic aberrations of the person's eye causes said first color component to focus after a retina of said eye, wherein said first intensity is less than said second intensity.

40. The device of embodiment 7, further comprising a biofeedback system configured to provide an input to the augmented reality head-mounted ophthalmic system, wherein the incremental change in the optical prescription is based on the input.

41. The device of embodiment 7, further comprising a biofeedback system configured to objectively monitor one or more properties of said eye, wherein the optical prescription is based on the monitored one or more properties.

42. The device of embodiment 41, wherein the biofeedback system receives inputs from at least one of a phoropter, an auto-refractor, and an eye tracking system.

43. The device of embodiment 41, wherein the one or more properties of said eye is at least one of: changes in a convergence point of the eye, changes in a position of a head of the person, change in a size of a pupil of the eye.

44. The device of embodiment 24, further comprising a biofeedback system configured to objectively monitor one or more properties of said eye, wherein the prescription is based on the monitored one or more properties of the eye.

45. The device of embodiment 32, further comprising a biofeedback system configured to objectively monitor one or more properties of said eye, wherein the optical prescription is based on the monitored one or more properties of the eye.

The additional numbered embodiments below in the section titled "ADDITIONAL NUMBERED EMBODIMENTS" are to be repeated, added to, and concatenated to the list of numbered embodiments here as if the list of additional numbered embodiments below in the section titled "ADDITIONAL NUMBERED EMBODIMENTS" immediately followed the list of numbered embodiments here.

Phoropter

1. A wearable augmented reality device configured to be used by a wearer having left and right eyes, said device comprising:
   an augmented reality head-mounted ophthalmic system comprising a wearable augmented reality display platform, said augmented reality head-mounted ophthalmic system configured to pass light from the world into an eye of a wearer wearing the head-mounted system, said augmented reality display platform optics configured to project an image in said eye,
   wherein said augmented reality head-mounted ophthalmic system is configured to vary the focus of the image automatically to provide incremental changes in optical prescription thereby conducting eye exams.

2. The device of embodiment 1, wherein said wearable augmented reality display platform comprises a fiber scanning display.

3. The device of any of embodiments 1-2, wherein said optics comprises an adaptable optics element configured to project the light.

4. The device of embodiment 3, wherein the adaptable optics element comprises a variable focus element.

5. The device of any of embodiments any of embodiments 1-4, further comprising a waveguide stack comprising a plurality of waveguides, wherein different waveguides are configured to project light from different depth planes.

6. The device of embodiment 5, wherein the waveguide stack further comprises one or more lenses.

7. The device of any of embodiments any of embodiments 1-6, wherein said augmented reality head-mounted ophthalmic system is configured to project a variety of images of varying sizes and/or intensity.

8. The device of embodiments 7, wherein said images comprise letters.

9. The device of any of embodiments any of embodiments 1-8, further comprising a user interface configured to receive input from the wear regarding the image.

10. The device of any of embodiments any of embodiments 1-9, wherein said augmented reality head-mounted ophthalmic system is configured to assess whether the patient can view the image with normal visual acuity and to incrementally change the prescription, positive or negative, by changing focus based on the assessment.

11. The device of any of embodiments any of embodiments 1-10, wherein said augmented reality head-mounted ophthalmic system is configured to assess whether the patient can view the image with normal visual acuity and to determine the prescription of the wearer based on the assessment.

12. The device of any of embodiments any of embodiments 1-11, wherein said augmented reality head-mounted ophthalmic system is configured to automatically perform adjustments to the prescription based on physical changes of the eye.

13. The device of embodiment 12, wherein said augmented reality head-mounted ophthalmic system is configured to track eye behavior such that adjustments may be automatically made by the ophthalmic system.

14. The device of any of embodiments 1-12, further comprising a fiber light source, wherein said augmented reality head-mounted ophthalmic system varies the focus of the image by varying fiber length or position.

15. The device of any of embodiments 1-12, further comprising a microelectromechanical systems (MEMS) device, wherein said augmented reality head-mounted ophthalmic system varies the focus of the image by varying said MEMS device.

16. The device of any of embodiments 1-15, wherein the eye exams include visual acuity exams, brightness tests, and/or glare tests.

17. The device of any of embodiments 1-16, wherein said augmented reality head-mounted ophthalmic system is configured to automatically determine a focus quality of the projected image.

18. The device of embodiment 17, wherein the focus quality of the projected image is determined through analysis of accommodation, vergence, and/or pupil size of the eye of the wearer.

19. The device of any of embodiments any of embodiments 1-18, wherein said augmented reality head-mounted ophthalmic system is configured to measure accommodation reflex by measuring accommodation, vergence, and/or pupil size.

20. A wearable virtual reality device configured to be used by a wearer having left and right eyes, said device comprising:
a virtual reality head-mounted ophthalmic system comprising a wearable virtual reality display platform, said virtual reality display platform optics configured to project an image in said eye, wearable augmented reality display platform comprises a fiber scanning display,
wherein said virtual reality head-mounted ophthalmic system is configured to vary the focus of the image automatically to provide incremental change in optical prescription thereby conducting eye exams.

21. A wearable virtual reality device configured to be used by a wearer having left and right eyes, said device comprising:
a virtual reality head-mounted ophthalmic system comprising a wearable virtual reality display platform, said virtual reality display platform optics configured to project an image in said eye, wearable augmented reality display platform comprises a waveguide stack comprising a plurality of waveguides, wherein different waveguides are configured to project light from different depth planes,
wherein said virtual reality head-mounted ophthalmic system is configured to vary the focus of the image automatically to provide incremental change in optical prescription thereby conducting eye exams.

The additional numbered embodiments below in the section titled "ADDITIONAL NUMBERED EMBODIMENTS" are to be repeated, added to, and concatenated to the list of numbered embodiments here as if the list of additional numbered embodiments below in the section titled "ADDITIONAL NUMBERED EMBODIMENTS" immediately followed the list of numbered embodiments here.

Red Reflex

1. A wearable augmented reality device configured to be used by a wearer, said device comprising:
an augmented reality head-mounted ophthalmic system comprising an augmented reality display platform, said augmented reality head-mounted ophthalmic system configured to pass light from the world into an eye of a wearer wearing the head-mounted system, said eye comprising a retina and a cornea;
a light source configured to project light into the eye of the wearer, at least a portion of said light reflecting from at least a portion of said eye so as to produce a reflection; and
a camera configured to capture an image of the reflection, said device being configured to perform a diagnostic test of the wearer's eye to detect abnormalities of the eye.

2. A wearable virtual reality device configured to be used by a wearer, said device comprising:
a virtual reality head-mounted ophthalmic system comprising a virtual reality display platform comprising a display for providing images to the eye of the wearer, said eye comprising a retina and a cornea;
a light source configured to project light into the eye of the wearer, at least a portion of said light reflecting from at least a portion of said eye so as to produce a reflection; and
a camera configured to capture an image of the reflection, said device being configured to perform a diagnostic test of the wearer's eye to detect abnormalities of the eye.

3. The device of embodiment 1 or 2, wherein said light source is configured to direct said light into said eye along the normal line of sight of said eye.

4. The device of embodiment 1 or 2, wherein said light source is configured to direct said light into said eye at a first angle at a first time and at a second different angle at a second time.

5. The device of embodiment 1 or 2, wherein said light source is configured to project said light to a first portion of the wearer's eye at a first time and to project said light to a second different portion of the wearer's eye at a second time.

6. The device of embodiment 1 or 2, wherein the light source is configured to project light into two eyes of the wearer, each of the two eyes comprising a retina and a cornea.

7. The device of embodiment 1 or 2, further comprising a second light source configured to project light into a second eye of the wearer, said second eye comprising a second retina and a second cornea, at least a portion of said light reflecting from at least a portion of said second eye so as to produce a reflection.

8. The device of any of embodiments 1-6, wherein said light source comprises a display.

9. The device of embodiment 8, wherein said display comprises a fiber scanning display.

10. The device of embodiment 1 or 2, wherein said camera comprises an eye tracking camera.

11. The device of embodiment 1 or 2, further comprising an eye tracking camera.

12. The device of embodiment 1 or 2, wherein said abnormality of the eye comprises glaucoma, a cataract, cancer of the eye, retinoblastoma, a detached retina, aberrations of the eye, or corneal scarring.

13. The device of any of embodiments 1-12, wherein said light source is configured to project light into wearer's left and right eye.

14. The device of any of embodiments 1-13, wherein said camera is configured to capture an image of the reflection and to perform a red reflex test of the wearer's left and right eye.
15. The device of embodiment 13 or 14, wherein said abnormality of the eye comprises eye misalignment, strabismus, or asymmetry.
16. The device of embodiment 1 or 2, further comprising an adaptable optics element.
17. The device of embodiment 16, wherein the adaptable optics element comprises a variable focus element.
18. The device of embodiment 16 or 17, wherein said adaptable optics element is configured to direct said light into said eye at a first angle at a first time and at a second different angle at a second time.
19. The device of embodiment 16 or 17, wherein said adaptable optics element is configured to project said light to a first portion of the wearer's eye at a first time and to project said light to a second different portion of the wearer's eye at a second time.
20. The device of any of embodiments 1-19, further comprising a waveguide stack comprising a plurality of waveguides, wherein different waveguides are configured to project light as if from different depth planes.
21. The device of embodiment 20, wherein the waveguide stack further comprises one or more lenses.
22. The device of embodiment 20 or 21, wherein the waveguide stack is configured to provide a fixation target for the wearer at different depth planes.
23. The device of any of embodiments 19-21, wherein the waveguide stack is configured to vary the depth plane of said fixation target thereby causing the wearer's eye to accommodate.
24. The device of any of embodiments 19-23, wherein said fixation target is located away from the center of the wearer's field of view.
25. The device of embodiment 1 or 2, wherein at least one of said waveguides is configured to capture said image of the reflection.
26. The device of embodiment 25, wherein a plurality of said waveguides are configured to capture a plurality of images of the reflection at different depth planes.
27. The device of embodiment 26, wherein said at least one of said waveguides includes an optical element having optical power, said optical power corresponding to a depth plane of between 8 inches to 4 feet from said eye.
28. The device of embodiment 1 or 2, wherein said display platform is configured to provide a first fixation target at a first location at a first time and a second fixation target at a second different location at a second time that causes the eye to move.
29. The device of any of embodiments 1-28, wherein said camera comprises a light pipe.
30. The device of any of embodiments 1-29, wherein said light source comprises a light pipe.
31. The device of any of embodiments 1-30, wherein said light comprises visible light.
32. The device of embodiment 31, wherein said light comprises white light.
33. The device of embodiment 32, further comprising at least one mechanical filter configured to limit the spectrum of reflected light detected at the camera.
34. The device of embodiment 32, wherein the device is configured to digitally filter images captured by the camera to remove light of at least one wavelength range from the images.
35. The device of any of embodiments 1-32, wherein said light comprises infrared light.
36. The device of any of embodiments 1-33, wherein said at least a portion of said light reflects from said retina, and wherein said diagnostic test comprises a red reflex test.
37. The device of any of embodiments 1-313 wherein said at least a portion of said light reflects from said cornea, and wherein said diagnostic test comprises a Hirschberg corneal reflex test.
38. The device of any of embodiments 1-35, wherein said device is further configured to compare the results of said diagnostic test with a database of normal or abnormal results.

The additional numbered embodiments below in the section titled "ADDITIONAL NUMBERED EMBODIMENTS" are to be repeated, added to, and concatenated to the list of numbered embodiments here as if the list of additional numbered embodiments below in the section titled "ADDITIONAL NUMBERED EMBODIMENTS" immediately followed the list of numbered embodiments here.

Intraocular Pressure

1. A wearable augmented reality device configured to be used by a wearer, said device comprising:
    an augmented reality head-mounted ophthalmic system comprising a wearable augmented reality display platform, said augmented reality head-mounted ophthalmic system configured to pass light from the world into an eye of a wearer wearing the head-mounted system, said eye comprising a cornea, said augmented reality head-mounted ophthalmic system configured to apply a force to the cornea of said eye; and
    a sensor configured to determine applanation of said cornea to determine intraocular pressure of the eye.
2. A wearable virtual reality device configured to be used by a wearer, said device comprising:
    a virtual reality head-mounted ophthalmic system comprising a wearable virtual reality display platform comprising a display for providing images to the eye of the wearer, said eye comprising a cornea, said virtual reality head-mounted ophthalmic system configured to apply a force to the cornea of said eye; and
    a sensor configured to determine applanation of said cornea to determine intraocular pressure of the eye.
3. The device of embodiment 1 or 2, wherein said head-mounted ophthalmic system is configured to apply a pulse of air to flatten the cornea.
4. The device of embodiment 1 or 2, wherein said head-mounted ophthalmic system is configured to apply mechanical force to the cornea of said eye through an eyelid of the wearer.
5. The device of embodiment 4, wherein said head-mounted ophthalmic system comprises a transducer.
6. The device of any of embodiments 1-4, wherein said sensor utilizes ultrasonic range imaging.
7. The device of any of embodiments 1-4, wherein said sensor utilizes photoacoustic imaging.
8. The device of any of embodiments 1-4, wherein said sensor comprises an imaging head.
9. The device of embodiment 8, wherein said imaging head comprises an interferometry 3D imaging head.
10. The device of any of embodiments 1-9, further comprising a light source configured to project beams of light into the wearer's eyes.

11. The device of any of embodiments 1-9, further comprising a fiber scanning display configured to project beams of light into the wearer's eyes.
12. The device of embodiment 10, further comprising an adaptable optics element.
13. The device of embodiment 12, wherein the adaptable optics element is configured to project the light.
14. The device of embodiment 13, wherein the adaptable optics element comprises a variable focus element.
15. The device of any of embodiments 1-14, further comprising a waveguide stack comprising a plurality of waveguides, wherein different waveguides are configured to project light from different depth planes.
16. The device of embodiment 15, wherein the waveguide stack further comprises one or more lenses.
17. A wearable augmented reality device configured to be used by a wearer, said device comprising:
    an augmented reality head-mounted ophthalmic system comprising a wearable augmented reality display platform, said augmented reality head-mounted ophthalmic system configured to pass light from the world into an eye of a wearer wearing the head-mounted system;
    a light source configured to project light into the eye of the wearer; and
    a light-monitoring device configured to measure reflected light,
    wherein said augmented reality head-mounted ophthalmic system is configured to determine intraocular pressure from said measured reflected light.
18. A wearable virtual reality device configured to be used by a wearer, said device comprising:
    a virtual reality head-mounted ophthalmic system comprising a wearable virtual reality display platform comprising a display for providing images to the eye of the wearer,
    a light source configured to project light into the eye of the wearer; and
    a light-monitoring device configured to measure reflected light,
    wherein said virtual reality head-mounted ophthalmic system is configured to determine intraocular pressure from said measured reflected light.
19. The device of embodiment 17 or 18, wherein said light source comprises a fiber scanning display configured to project beams of light into the wearer's eyes.
20. The device of embodiment 19, wherein the fiber length of the fiber scanning display can be varied.
21. The device of embodiment 19, wherein said light-monitoring device comprises said fiber scanning display.
22. The device of embodiment 17 or 17, wherein said light-monitoring device comprises a fiber scanning display or photo-detectors.
23. The device of embodiment 17 or 18, wherein the wavelength of said light projected into said eye can be changed.
24. The device of embodiment 17 or 18, further comprising an adaptable optics element configured to project the light into the wearer's eye.
25. The device of embodiment 24, wherein the adaptable optics element comprises a variable focus element.
26. The device of embodiment 17 or 18, further comprising a waveguide stack comprising a plurality of waveguides, wherein different waveguides are configured to project light from different depth planes.
27. The device of embodiment 26, wherein the waveguide stack further comprises one or more lenses.
28. The device of any of embodiments 17-27, wherein the light-monitoring device is configured to measure back-scattered light.
29. The device of any of embodiments 17-27, wherein the light-monitoring device is configured to detect on or more Purkinje images of the wearer's eye.
30. The device of embodiment 29, wherein the head-mounted ophthalmic system is configured to determine intraocular pressure at least in part based on the shape or location of said one or more Purkinje images.
31. The device of embodiment 29 or 30, wherein said one or more Purkinje images comprises a glint.
32. The device of any of embodiments 1-31, wherein said ophthalmic system is further configured to detect the presence of ocular hypertension at least in part based on said determined intraocular pressure.
33. The device of any of embodiments 1-31, wherein said ophthalmic system is further configured to determine an ocular pulse rate at least in part based on comparing a plurality of intraocular pressures determined from measurements taken at a regular time interval.

The additional numbered embodiments below in the section titled "ADDITIONAL NUMBERED EMBODIMENTS" are to be repeated, added to, and concatenated to the list of numbered embodiments here as if the list of additional numbered embodiments below in the section titled "ADDITIONAL NUMBERED EMBODIMENTS" immediately followed the list of numbered embodiments here.

Pinhole Occluder

1. A wearable augmented reality device configured to be used by a person, said display device comprising:
    an augmented reality head-mounted ophthalmic system comprising a augmented reality display platform, said augmented reality head-mounted ophthalmic system configured to pass light from the world into at least one eye of a person wearing the head-mounted system;
    a light source configured to project light into the eye of the person to form an image in the eye; and
    a user interface configured to receive input from a person,
    wherein the wearable augmented reality device is configured to occlude a particular portion of the person's eye and to receive input from the person regarding the wear's vision through the user interface.
2. The device of embodiment 1, wherein the wearable augmented reality device is configured to occlude a central region.
3. The device of embodiment 1, wherein the wearable augmented reality device is configured to occlude a peripheral region.
4. The device of embodiment 1, wherein the wearable augmented reality device is configured to occlude the particular portion of the person's eye digitally.
5. The device of embodiment 1, wherein the wearable augmented reality device is configured to occlude the particular portion of the person's eye manually.
6. A wearable virtual reality device configured to be used by a person, said display device comprising:
    a head-mounted display comprising a virtual reality display platform; and
    a light source configured to project light into the eye of the person to form an image in the eye, and a user interface configured to receive input from a person, wherein the wearable virtual reality device is configured to occlude a particular portion of the person's eye and to receive input from the person regarding the wear's vision through the user interface.

7. The device of embodiment 6 wherein the wearable augmented reality device is configured to occlude a central region.

8. The device of embodiment 6, wherein the wearable augmented reality device is configured to occlude a peripheral region.

9. The device of embodiment 6, wherein an image is presented to the person and the wearable virtual reality device is configured to receive input from the person regarding the image through the user interface.

10. A wearable display device configured to be used by a person, said display device comprising:

a head-mounted ophthalmic system;

a light source configured to direct light into an eye of said person to form an image in the eye;

a user interface configured to receive input from a person, and an adaptable optics element configured to project the image to a particular portion of the person's eye, wherein the wearable display device is configured to occlude a particular portion of the person's eye and to receive input from the person regarding the wear's vision through the user interface.

11. The device of embodiment 10, wherein the adaptable optics element comprises a variable focus element.

12. The device of embodiment 11, wherein the variable focus element comprises a membrane mirror.

13. The device of embodiment 12, further comprising:

one or more electrodes coupled to the membrane mirror; and a control system configured to selectively control the one or more electrodes to modify a shape of the membrane mirror based on a corneal shape of the eye.

14. A wearable display device configured to be used by a person, said display device comprising:

a head-mounted display system; and a light source configured to direct light into an eye of a person to form an image in the eye, the light source comprising a fiber scanning projector; and a user interface configured to receive input from a person, wherein the wearable display device is configured to occlude a particular portion of the person's eye and to receive input from the person regarding the wear's vision through the user interface.

15. A wearable display device configured to be used by a person, said display device comprising:

a head-mounted display system; and a light source configured to direct light into one eye of said person to form an image in the eye;

a waveguide stack comprising a plurality of waveguides, wherein different waveguides are configured to project the light at different focal planes; and a user interface configured to receive input from a person, wherein the wearable display device is configured to occlude a particular portion of the person's eye and to receive input from the person regarding the wear's vision through the user interface.

16. The device of embodiment 15, wherein the waveguide stack further comprises one or more lenses.

17. The device of embodiment 15, wherein the head-mounted display system comprises an augmented reality head-mounted ophthalmic system configured to pass light from the world into an eye of a person wearing the head-mounted system.

18. A wearable augmented reality device configured to be used by a person, said display device comprising:

an augmented reality head-mounted ophthalmic system comprising a augmented reality display platform, said augmented reality head-mounted ophthalmic system configured to pass light from the world into an eye of a person wearing the head-mounted system; and a light source configured to project light into the eye of the person to form an image in the eye, wherein the wearable augmented reality device is configured to occlude a particular portion of the person's eye.

19. The device of embodiment 18, wherein the wearable augmented reality device is configured to occlude a central region.

20. The device of embodiment 18, wherein the wearable augmented reality device is configured to occlude a peripheral region.

21. The device of embodiment 18, wherein the wearable augmented reality device is configured to occlude the particular portion of the person's eye digitally.

22. The device of embodiment 18, wherein the wearable augmented reality device is configured to occlude the particular portion of the person's eye manually.

23. The device of embodiment 1, wherein the augmented reality device is configured to obstruct a portion of the light corresponding to the particular portion of the person's eye.

24. The device of embodiment 2, wherein occluding the central region improves the person's vision of the image, being indicative of a visual defect in the eye of the person.

25. The device of embodiment 18, wherein the wearable augmented reality device is configured to occlude a particular portion of the person's eye based on an optical prescription of the person.

26. The device of embodiment 18, wherein the wearable augmented reality device is configured to occlude a particular portion of the person's eye by stopping down a peripheral portion of the light forming the image 27. The device of embodiment 18, wherein the wearable augmented reality device is configured to adjust intensity of ambient light from the world surrounding the person.

28. The device of embodiment 18, wherein the wearable augmented reality device is configured to occlude the particular portion of the eye based on inputs from the world surrounding of the person.

29. The device of embodiment 28, wherein inputs from surroundings includes at least one of changes in gaze orientation, ambient light from the surroundings, and accommodation.

30. The device of embodiment 21, further comprising a waveguide stack comprising a plurality of waveguides, wherein different waveguides are configured to project the light at different focal plane, wherein digitally occluding the particular portion of the eye comprises selectively projecting light at different focal planes, wherein the particular portion of the eye corresponds to a selected focal plane.

31. The device of embodiment 18, wherein the wearable augmented reality device is configured to modify a color of a portion of the image corresponding to the particular portion of the eye.

32. The device of embodiment 18, wherein the wearable augmented reality device is configured to modify an intensity of a portion of the image corresponding to the particular portion of the eye.

33. The device of embodiment 9, further comprising a camera configured to receive a reflected image based on the image presented to the person having passed through the particular portion of the person's eye and reflected by the retina of said eye, wherein the received input is based on a comparison of the reflected image and an expected reflected image, the expected reflected image being based on a healthy eye.

34. The device of embodiment 14, wherein an image is presented to the person and the wearable virtual reality device is configured to receive input from the person regarding the image through the user interface.

35. The device of embodiment 34, further comprising a camera configured to receive a reflected image based on the image presented to the person having passed through the particular portion of the person's eye and reflected by the retina of said eye, wherein the received input is based on a comparison of the reflected image and an expected reflected image, the expected reflected image being based on a healthy eye.

36. The device of embodiment 21, wherein the wearable augmented reality device is configured to modify a focus of a portion of the image corresponding to the particular portion of the eye.

37. The device of embodiment 21, wherein the wearable augmented reality device is configured to modify a contrast of a portion of the image corresponding to the particular portion of the eye relative to another portion of the image that does not correspond to the particular portion of the eye.

38. A wearable virtual reality device configured to be used by a person, said display device comprising:
a virtual reality head-mounted ophthalmic system comprising a virtual reality display platform; and
a light source configured to project light into the eye of the person to form an image in the eye,
wherein the wearable virtual reality device is configured to occlude a particular portion of the person's eye.

The additional numbered embodiments below in the section titled "ADDITIONAL NUMBERED EMBODIMENTS" are to be repeated, added to, and concatenated to the list of numbered embodiments here as if the list of additional numbered embodiments below in the section titled "ADDITIONAL NUMBERED EMBODIMENTS" immediately followed the list of numbered embodiments here.

Initial W4LT Test

1. A wearable augmented reality device configured to be used by a wearer having left and right eyes, said device comprising:
an augmented reality head-mounted ophthalmic system comprising a wearable augmented reality display platform, said augmented reality head-mounted ophthalmic system configured to pass light from the world into an eye of a wearer wearing the head-mounted system; and
first and second displays included in said augmented reality display platform for said left and right eyes respectively,
wherein said augmented reality head-mounted ophthalmic system is configured to project independent first and second images into said left and right eyes respectively and to identify a vision defect.

2. The device of embodiment 1, wherein said augmented reality head-mounted ophthalmic system is configured to assess the wearer's degree of binocular vision and binocular single vision.

3. The device of embodiment 1, wherein said augmented reality head-mounted ophthalmic system is configured to administer a Worth Four Light Test or a Worth Four Dot Test.

4. The device of embodiment 1, wherein said images comprise colored dots.

5. The device of embodiment 1, wherein said augmented reality head-mounted ophthalmic system is configured to detect suppression of either the right eye or the left eye.

6. The device of embodiment 1, wherein said augmented reality head-mounted ophthalmic system is configured to receive input from the wearer, to analyze the received input, and to identify said vision defect of the wearer.

7. The device of embodiment 1, wherein said augmented reality head-mounted ophthalmic system is configured to project said independent first and second images from different depth planes.

8. The device of any of embodiments 1-7, further comprising a fiber scanning display configured to project light into the wearer's eyes.

9. The device of any of embodiments 1-8, further comprising an adaptable optics element configured to project the independent first and second images.

10. The device of embodiment 9, wherein the adaptable optics element comprises a variable focus element.

11. The device of any of embodiments 1-10, further comprising a waveguide stack comprising a plurality of waveguides, wherein different waveguides are configured to project light from different depth planes.

12. The device of embodiment 11, wherein the waveguide stack further comprises one or more lenses.

13. The device of any of embodiments 1-12, wherein said augmented reality head-mounted ophthalmic system is configured to automatically determine said vision defect of the wearer through analysis of the independent first and second images as imaged on corresponding retinas of the wearer.

14. A wearable virtual reality device configured to be used by a wearer having left and right eyes, said device comprising:
a virtual reality head-mounted ophthalmic system comprising a wearable virtual reality display platform comprising a display for providing images to an eye of the wearer; and
first and second displays included in said virtual reality display platform for said left and right eyes respectively,
wherein said virtual reality head-mounted ophthalmic system is configured to project independent first and second images into said left and right eyes respectively and to identify a vision defect.

15. The device of embodiment 14, wherein said virtual reality head-mounted ophthalmic system is configured to assess the wearer's degree of binocular vision and binocular single vision.
16. The device of embodiment 14, wherein said virtual reality head-mounted ophthalmic system is configured to administer a Worth Four Light Test or a Worth Four Dot Test.
17. The device of embodiment 14, wherein said images comprise colored dots.
18. The device of embodiment 14, wherein said virtual reality head-mounted ophthalmic system is configured to detect suppression of either the right eye or the left eye.
19. The device of embodiment 14, wherein said virtual reality head-mounted ophthalmic system is configured to receive input from the wearer, to analyze the received input, and to identify said vision defect of the wearer.
20. The device of embodiment 14, wherein said virtual reality head-mounted ophthalmic system is configured to project said independent first and second images from different depth planes.
21. The device of any of embodiments 14-20, further comprising a fiber scanning display configured to project light into the wearer's eyes.
22. The device of any of embodiments 14-21, further comprising an adaptable optics element configured to project the independent first and second images.
23. The device of embodiment 22, wherein the adaptable optics element comprises a variable focus element.
24. The device of any of embodiments 14-23, further comprising a waveguide stack comprising a plurality of waveguides, wherein different waveguides are configured to project light from different depth planes.
25. The device of embodiment 24, wherein the waveguide stack further comprises one or more lenses.
26. The device of any of embodiments 14-25, wherein said augmented reality head-mounted ophthalmic system is configured to automatically determine said vision defect of the wearer through analysis of the independent first and second images as imaged on corresponding retinas of the wearer.

The additional numbered embodiments below in the section titled "ADDITIONAL NUMBERED EMBODIMENTS" are to be repeated, added to, and concatenated to the list of numbered embodiments here as if the list of additional numbered embodiments below in the section titled "ADDITIONAL NUMBERED EMBODIMENTS" immediately followed the list of numbered embodiments here.

Retinoscopy

1. A wearable augmented reality device configured to be used by a wearer, said device comprising:
    an augmented reality head-mounted ophthalmic system comprising an augmented reality display platform, said augmented reality head-mounted ophthalmic system configured to pass light from the world into an eye of a wearer wearing the head-mounted system, said eye having a retina;
    at least one light source configured to project light into the eye of the wearer to form an image in the eye, said at least one light source configured to sweep light across the retina of the eye of the wearer producing a reflex of the retina; and
    a sensor configured to measure a response of the retina to the swept light such that said augmented reality head-mounted ophthalmic system can perform retinoscopy to measure refractive error of said eye.
2. The device of embodiment 1, wherein said image can be dynamically modified to provide dynamic retinoscopy.
3. The device of any of embodiments 1-2, wherein said at least one light source comprises a fiber scanning display.
4. The device of any of embodiments 1-3, wherein said at least one light source comprises a fiber scanning display and a light generating source.
5. The device of any of embodiments 1-4, further comprising an adaptable optics element configured to project the image to a targeted portion of the wearer's eye.
6. The device of embodiment 5, wherein the adaptable optics element comprises a variable focus element.
7. The device of embodiment 6, wherein the variable focus element comprises a membrane mirror.
8. The device of embodiment 7 further comprising:
    one or more electrodes coupled to the membrane mirror; and
    a control system configured to selectively control the one or more electrodes to modify a shape of the membrane mirror based on a corneal shape of the eye.
9. The device of any of embodiments any of embodiments 1-8, further comprising a waveguide stack comprising a plurality of waveguides, wherein different waveguides are configured to project light from different depth planes.
10. The device of embodiment 9, wherein the waveguide stack further comprises one or more lenses.
11. The device of any of embodiments any of embodiments 1-10, wherein the wearable augmented reality device is configured to determine whether the measured refractive error has improved in response to a change in optical power.
12. The device of embodiment any of embodiments 11, wherein the wearable augmented reality device is configured to modify an applied optical power to reduce the measured refractive error.
13. A wearable augmented reality device configured to be used by a wearer, said device comprising:
    an augmented reality head-mounted ophthalmic system comprising an augmented reality display platform, said augmented reality head-mounted ophthalmic system configured to pass light from the world into an eye of a wearer wearing the head-mounted system,
    wherein said augmented reality head-mounted ophthalmic system is configured to perform retinoscopy to measure refractive error of said eye.
14. A wearable virtual reality device configured to be used by a wearer, said device comprising:
    a virtual reality head-mounted ophthalmic system comprising a virtual reality display platform comprising a display for providing images to an eye of the wearer, said eye having a retina;
    at least one light source configured to project light into the eye of the wearer to form an image in the eye, said at least one light source configured to sweep light across the retina of the eye of the wearer producing a reflex of the retina; and
    a sensor configured to measure a response of the retina to the swept light such that said virtual reality head-mounted ophthalmic system can perform retinoscopy to measure refractive error of said eye.

15. A wearable virtual reality device configured to be used by a wearer, said device comprising:
    a virtual reality head-mounted ophthalmic system comprising a virtual reality display platform comprising a display for providing images to an eye of the wearer, said eye having a retina;
    wherein said virtual reality head-mounted ophthalmic system is configured to perform retinoscopy to measure refractive error of said eye.

The additional numbered embodiments below in the section titled "ADDITIONAL NUMBERED EMBODIMENTS" are to be repeated, added to, and concatenated to the list of numbered embodiments here as if the list of additional numbered embodiments below in the section titled "ADDITIONAL NUMBERED EMBODIMENTS" immediately followed the list of numbered embodiments here.

Slit Lamp

1. A wearable augmented reality device configured to be used by a wearer, said device comprising:
    an augmented reality head-mounted ophthalmic system comprising an augmented reality display platform, said augmented reality head-mounted ophthalmic system configured to pass light from the world into an eye of a wearer wearing the head-mounted system;
    an optical source configured to project an illumination beam of light into the eye of the wearer to illuminate an anterior or posterior portion of the eye, a cross-sectional beam shape of the illumination beam configured such that a dimension of the cross-sectional beam shape along a superior-inferior direction of the eye is greater than a dimension of the cross-sectional beam shape along a nasal-temporal direction of the eye; and
    an imaging system configured to capture an image of the illuminated portion of the wearer's eye so as to perform a slit lamp examination to determine health of said eye.
2. The device of embodiment 1, wherein the illumination beam from said optical source is incident on a location on the surface of the eye at an angle with respect to a normal to the surface of the eye at the location.
3. The device of embodiment 2, wherein the illumination beam from said optical source is incident on the location on the surface of the eye at an angle between about ±10-degrees and about ±90-degrees with respect to the normal to the surface of the eye at the location.
4. The device of embodiment 2, wherein the illumination beam from said optical source is incident along an axis intersecting the eye and passing through the pupil.
5. The device of embodiment 1, wherein the illumination beam from said optical source has a width along a temporal-nasal axis of the wearer's eye, wherein the width is between about 25 microns and about 1.0 mm
6. The device of embodiment 1, wherein the imaging system comprises a camera configured to track the wearer's eye.
7. The device of embodiment 1, wherein said device is further configured to determine the health of the eye by matching a known pattern with the image captured by the imaging system.
8. The device of embodiment 1, wherein said device is further configured to compare the image captured by the imaging system with a previously obtained image of the eye.
9. The device of embodiment 1, wherein said light source comprises a fiber scanning device.
10. The device of embodiment 1, further comprising an adaptable optics element configured to project the illumination beam to a particular portion of the wearer's eye.
11. The device of embodiment 10, wherein the adaptable optics element comprises a variable focus element.
12. The device of embodiment 11, wherein the variable focus element comprises a membrane mirror.
13. The device of embodiment 12, further comprising:
    one or more electrodes coupled to the membrane mirror; and
    a control system configured to selectively control the one or more electrodes to modify a shape of the membrane mirror.
14. The device of embodiment 10, wherein the adaptable optics element is configured to change the angle of incidence of the illumination beam at the particular portion of the wearer's eye.
15. The device of embodiment 10, wherein the adaptable optics element is configured to change the width of the illumination beam.
16. The device of embodiment 10, wherein the adaptable optics element is configured to change the depth in the wearer's eye at which the illumination beam is focused.
17. The device of any of embodiments 1 to 17, further comprising a waveguide stack comprising a plurality of waveguides, wherein different waveguides are configured to project light from different focal planes.
18. The device of embodiment 17, wherein the waveguide stack further comprises one or more lenses.
19. The device of embodiment 1, wherein the illumination beam comprises a thin sheet of light.
20. A wearable augmented reality device configured to be used by a wearer, said device comprising:
    an augmented reality head-mounted ophthalmic system comprising an augmented reality display platform, said augmented reality head-mounted ophthalmic system configured to pass light from the world into an eye of a wearer wearing the head-mounted system;
    a scanning fiber device configured to project light into the eye of the wearer to illuminate the eye to perform a slit lamp examination of the eye; and
    a camera configured to capture an image of the illuminated portion of the wearer's eye so as to determine health of said eye.
21. The device of embodiment 20, wherein said fiber scanning device is configured to project an illumination beam into the eye of the wearer.
22. The device of embodiment 20, wherein the illumination beam has a width along a nasal-temporal direction of the eye of the wearer, wherein the width is between about 25 microns and about 1.0 mm
23. The device of embodiment 20, wherein the illumination beam has a rectangular cross-sectional shape.
24. The device of embodiment 23, wherein a dimension of the rectangular cross-sectional shape along a superior-inferior direction of the eye is greater than a dimension of the rectangular cross-sectional beam shape along a nasal-temporal direction of the eye.
25. The device of embodiment 20, wherein said scanning fiber device is configured to project light into the eye of the wearer at a non-normal angle to the surface of the eye at the incidence location.

26. The device of embodiment 20, wherein said device is further configured to determine the health of the eye by matching a known pattern with the image captured by the camera.
27. The device of embodiment 20, wherein said device is further configured to compare the image captured by the imaging system with a previously obtained image of the eye.
28. The device of any of the embodiments, wherein said device is configured to detect changes in the wearer's eye at least twice a year.
29. A wearable virtual reality device configured to be used by a wearer, said device comprising:
   a virtual reality head-mounted ophthalmic system comprising a virtual reality display platform comprising a display for providing images to the eye of the wearer;
   an optical source configured to project an illumination beam of light into the eye of the wearer to illuminate an anterior or posterior portion of the eye, a cross-sectional beam shape of the illumination beam configured such that a dimension of the cross-sectional beam shape along a superior-inferior direction of the eye is greater than a dimension of the cross-sectional beam shape along a nasal-temporal direction of the eye; and
   an imaging system configured to capture an image of the illuminated portion of the wearer's eye so as to perform a slit lamp examination to determine health of said eye.
30. A wearable virtual reality device configured to be used by a wearer, said device comprising:
   a virtual reality head-mounted ophthalmic system comprising an virtual reality display platform comprising a display for providing images to the eye of the wearer;
   at scanning fiber device configured to project light into the eye of the wearer to illuminate the eye to perform a slit lamp examination of the eye; and
   a camera configured to obtain an image of the illuminated portion of the wearer's eye so as to determine health of said eye.
31. A wearable augmented reality device configured to be used by a wearer, said device comprising:
   an augmented reality head-mounted ophthalmic system comprising an augmented reality display platform, said augmented reality head-mounted ophthalmic system configured to pass light from the world into an eye of a wearer wearing the head-mounted system;
   a light source configured to project a thin sheet of light into the eye of the wearer to illuminate an anterior or posterior portion of the eye; and
   a camera configured to capture an image of the illuminated portion of the wearer's eye so as to perform a slit lamp examination to determine health of said eye.
32. The device of embodiment 21, wherein the sheet of light from said optical source is incident on a location on the surface of the eye at an angle with respect to a normal to the surface of the eye at the location.
33. The device of embodiment 21, wherein the sheet of light from said optical source has a width along a temporal-nasal axis of the wearer's eye, wherein the width is between about 25 microns and about 1.0 mm
34. The device of embodiment 21, wherein the camera is further configured to track the wearer's eye.
35. The device of embodiment 31, wherein said device is further configured to determine the health of the eye by matching a known pattern with the image captured by the imaging system.
36. The device of embodiment 31, wherein said device is further configured to compare the image captured by the imaging system with a previously obtained image of the eye.
37. The device of embodiment 31, wherein said light source comprises a fiber scanning device.
38. The device of embodiment 31, further comprising an adaptable optics element configured to project the thin sheet of light to a particular portion of the wearer's eye.
39. The device of embodiment 38, wherein the adaptable optics element comprises a variable focus element.
40. The device of embodiment 39, wherein the variable focus element comprises a membrane mirror.
41. The device of embodiment 31, further comprising:
   one or more electrodes coupled to the membrane mirror; and
   a control system configured to selectively control the one or more electrodes to modify a shape of the membrane mirror.
42. The device of any of the embodiments above, wherein said camera comprises a visible camera.
43. The device of any of the embodiments above, wherein said camera comprises an infrared camera.
44. The device of any of the embodiments above, wherein said device is configured to detect changes in the wearer's eye at least twice a year.
45. The device any of the embodiments above, further comprising a frame, said display supported by said frame.
46. The device of Embodiment 45, wherein the optical source is disposed on the frame.
47. The device of Embodiments 45-46, wherein the imaging system is disposed on the frame.
48. The device of Embodiments 45-47, wherein the frame includes one or more ear stems.

The additional numbered embodiments below in the section titled "ADDITIONAL NUMBERED EMBODIMENTS" are to be repeated, added to, and concatenated to the list of numbered embodiments here as if the list of additional numbered embodiments below in the section titled "ADDITIONAL NUMBERED EMBODIMENTS" immediately followed the list of numbered embodiments here.

Color Blindness

1. A wearable augmented reality device configured to be used by a wearer, said device comprising:
   an augmented reality head-mounted ophthalmic system comprising a wearable augmented reality display platform comprising a display, said augmented reality head-mounted ophthalmic system configured to pass light from the world into an eye of a wearer wearing the head-mounted system, said wearable augmented reality display platform comprising a display comprising at least one light source,
   wherein said wearable augmented reality device is configured to administer a color test to test for deficiencies of the wearer in detecting specific colors.
2. A wearable virtual reality device configured to be used by a wearer, said device comprising:
   a virtual reality head-mounted ophthalmic system comprising a wearable virtual reality display platform comprising a display, said wearable virtual reality display platform comprising a display comprising at least one light source,
    wherein said wearable virtual reality device is configured to administer a color test to test for deficiencies of the wearer in detecting specific colors.
3. The device of embodiment 1 or 2, wherein said head-mounted ophthalmic system is configured such that said display provides images of Ishihara color plates.
4. The device of embodiment 1 or 2, wherein said head-mounted ophthalmic system is configured such that said display provides virtual images of Ishihara color plates.
5. The device of any of embodiments 1-4, wherein said head-mounted ophthalmic system is configured to receive user input regarding said color plates or color image.
6. The device of any of embodiments 1-5, wherein said head-mounted ophthalmic system is configured to determine whether the wearer has defects based on the color test.
7. The device of embodiment 1 or 2, wherein said head-mounted ophthalmic system is configured to administer an anomaloscope test, said head-mounted ophthalmic system being configured to project light of a control color onto a first portion of said retina, and to project light of variable color onto a second portion of said retina, said variable color being controllable by the wearer.
8. The device of any of embodiments 1-7, where said at least one light source comprises a fiber scanning display configured to project light into the wearer's eyes.
9. The device of any of embodiments 1-7, where said at least one light source comprises multiple fiber scanning displays configured to project different color light into the wearer's eyes.
10. The device of any of the above embodiments, where said head-mounted ophthalmic system is configured to provide a background to enhance the visibility of said color test.
11. The device of embodiment 10, wherein said background is provided using one or more spatial light modulators configured to selectively attenuate light.
12. The device of any of the above embodiments, further comprising an adaptable optics element.
13. The device of embodiment 12, wherein the adaptable optics element comprises a variable focus element.
14. The device of any of the above embodiments, wherein said display comprises a waveguide stack comprising a plurality of waveguides, wherein the waveguide stack is configured to project light from different depth planes.
15. The device of embodiment 14, wherein said display is configured to project Ishihara color plates at a plurality of depth planes.
16. The device of embodiment 14, wherein said display is configured to project anomaloscope images at a plurality of depth planes.
17. The device of embodiment 14, wherein the waveguide stack further comprises one or more lenses.
18. A wearable augmented reality device configured to be used by a wearer, said device comprising:
    an augmented reality head-mounted ophthalmic system comprising a wearable augmented reality display platform and at least one outward-facing camera configured to image light from the world, said augmented reality head-mounted ophthalmic system configured to pass said light from the world into an eye of a wearer wearing the head-mounted system, said wearable augmented reality display platform comprising a display comprising at least one light source, said eye comprising a retina,
    wherein said wearable augmented reality device is configured to selectively modify said light from the world based on a color detection deficiency of the wearer.
19. A wearable virtual reality device configured to be used by a wearer, said device comprising:
    a virtual reality head-mounted ophthalmic system comprising a wearable virtual reality display platform and at least one outward-facing camera configured to image light from the world and project said light from the world into an eye of a wearer wearing the head-mounted system, said virtual reality head-mounted virtual reality display platform comprising a display comprising at least one light source, said eye comprising a retina,
    wherein said wearable virtual reality device is configured to selectively modify said light from the world projected to the eye based on a color detection deficiency of the wearer.
20. The device of embodiment 18 or 19, wherein said outward-facing camera is configured to detect the presence in said light from the world of a color for which the wearer has a detection deficiency.
21. The device of embodiment 20, wherein said selective modification comprises projecting light from the light source to increase the amplitude of said light in a region of the display comprising a color for which the wearer has a detection deficiency.
22. The device of embodiment 20, wherein said selective modification comprises changing the color of light in a region of the display.
23. The device of embodiment 22, wherein changing the color of light in a region of the display comprises using an optical filter to remove spectral overlap between a plurality of photopigments.
24. A wearable augmented reality device configured to be used by a wearer, said device comprising:
    an augmented reality head-mounted ophthalmic system comprising a wearable augmented reality display platform, said augmented reality head-mounted ophthalmic system configured to pass said light from the world into an eye of a wearer wearing the head-mounted system, said wearable augmented reality display platform comprising a display comprising at least one light source,
    wherein said wearable augmented reality device is configured to selectively modify said light projected from the display based on a color detection deficiency of the wearer.
25. A wearable virtual reality device configured to be used by a wearer, said device comprising:
    a virtual reality head-mounted ophthalmic system comprising a wearable virtual reality display platform system, said virtual reality head-mounted virtual reality display platform comprising a display comprising at least one light source,
    wherein said wearable virtual reality device is configured to selectively modify said light projected from the display to the eye based on a color detection deficiency of the wearer.

26. The device of embodiment 24 or 25, wherein said selective modification comprises projecting light from the light source to increase the amplitude of said light in a region of the display comprising a color for which the wearer has a detection deficiency.
27. The device of embodiment 24 or 25, wherein said selective modification comprises changing the color of light in a region of the display.
28. The device of embodiment 24 or 25, wherein said selective modification comprises enhancing the color of light projected from at least a portion of the display.
29. The device of embodiment 24, wherein said selective modification comprises decreasing the visibility of at least a portion of said light from the world through destructive interference.

The additional numbered embodiments below in the section titled "ADDITIONAL NUMBERED EMBODIMENTS" are to be repeated, added to, and concatenated to the list of numbered embodiments here as if the list of additional numbered embodiments below in the section titled "ADDITIONAL NUMBERED EMBODIMENTS" immediately followed the list of numbered embodiments here.

Ophthalmoscope/Funduscope

1. A wearable augmented reality device configured to be used by a wearer, said device comprising:
    an augmented reality head-mounted ophthalmic system comprising an augmented reality display platform, said augmented reality head-mounted ophthalmic system configured to pass light from the world into an eye of a wearer wearing the head-mounted system,
    wherein said augmented reality head-mounted ophthalmic system is configured to capture an image of an illuminated portion of the wearer's eye for analysis to monitor health of the wearer's eye, detect abnormalities of the eye or other health problems.
2. The device of embodiment 1, further comprising a fiber scanning display configured to project a beam of light of a particular focus to at least one portion of the wearer's eye.
3. The device of embodiment 1, further comprising an eye tracking cameras for capturing said image of the illuminated portion of the wearer's eye.
4. The device of embodiment 2, wherein said fiber scanning display is configured to capture said image of the illuminated portion of the wearer's eye.
5. The device of embodiment 1, further comprising a specialized camera for capturing said image of the illuminated portion of the wearer's eye.
6. The device of any one of embodiments 1-5, further comprising an electronic hardware processor configured to analyze the captured image to detect abnormalities of the eye or health problems.
7. The device of embodiment 6 wherein the electronic processor is configured to detect the abnormality of the eye by matching a known pattern with the image.
8. The device of embodiment 6 wherein the electronic processor is pre-loaded with patterns indicative of health problems.
9. The device of any one of embodiments 1-8 wherein the electronic hardware processor is remote from the augmented reality head-mounted ophthalmic system.
10. The device of embodiment 1-10, further comprising an adaptable optics element.
11. The device of embodiment 11, wherein the adaptable optics element is configured to project the beam of light to a particular portion of the wearer's eye.
12. The device of embodiment 11, wherein the adaptable optics element comprises a variable focus element.
13. The device of any of embodiments 1 to 13, further comprising a waveguide stack comprising a plurality of waveguides, wherein different waveguides are configured to project light as if originating from different focal planes.
14. The device of embodiment 13 wherein the waveguide stack further comprises one or more lenses.
15. The device of embodiment 1, wherein the fiber scanning is configured to project the beam of light on a fundus of the wearer's eye.
16. The device of embodiment 1, wherein the projected beam of light comprises a white light.
17. The device of embodiment 1, wherein the projected beam of light comprises a colored light.
18. The device of embodiment 17, wherein the projected beam of light has a wavelength in red, green or blue spectral region of the visible spectrum of light.
19. The device of embodiment 1, wherein the projected beam of light is in a range of wavelengths in the infrared spectrum of light.
20. The device of embodiment 1, wherein the projected beam of light is configured to be focused at different depths in the wearer's eye.
21. The device of embodiment 1, wherein said augmented reality head-mounted ophthalmic system is configured to capture an image of at least a portion of the fundus of the wearer's eye.
22. The device of embodiment 21, wherein said augmented reality head-mounted ophthalmic system is configured to capture an image of at least a portion of the retina of the wearer's eye.
23. The device of embodiment 1, wherein said augmented reality head-mounted ophthalmic system is configured to capture an image from different depths in the wearer's eye.
24. A wearable augmented reality device configured to be used by a wearer, said device comprising:
    an augmented reality head-mounted ophthalmic system comprising an augmented reality display platform, said augmented reality head-mounted ophthalmic system configured to pass light from the world into an eye of a wearer wearing the head-mounted system;
    a light source configured to project a beam of light to at least one portion of the wearer's eye; and
    a camera configured to capture an image of an illuminated portion of the wearer's eye for analysis to monitor health of the wearer's eye, detect abnormalities of the eye or other health problems.
25. The device of embodiment 24, wherein said light source comprises a fiber scanning device.
26. The device of embodiment 24, wherein said camera comprises eye tracking cameras.
27. The device of embodiment 24, wherein said camera comprises said fiber scanning device.
28. The device of embodiment 24, further comprising an electronic hardware processor configured to analyze the captured image to monitor health of the wearer's eye or detect the abnormality of the eye.
29. The device of embodiment 28, wherein the electronic hardware processor is configured to analyze the captured image by matching a known pattern, color, shape or size with the captured image.
30. The device of embodiment 29, wherein the electronic hardware processor is pre-loaded with patterns indicative of health problems.
31. The device of embodiment 28, wherein the electronic hardware processor is configured to compare the captured image with one or more images stored in an information store accessible by the electronic hardware processor.
32. The device of embodiment 24 further comprising an adaptable optics element.
33. The device of embodiment 32, wherein the adaptable optics element is configured to project the beam of light to a particular portion of the wearer's eye.
34. The device of embodiment 32, wherein the adaptable optics element comprises a variable focus element.
35. The device of any of embodiments 24 to 34, further comprising a waveguide stack comprising a plurality of waveguides, wherein different waveguides are configured to project light as if originating from different focal planes.
36. The device of embodiment 35, wherein the waveguide stack further comprises one or more lenses.
37. The device of embodiment 24, wherein the light source is configured to project the beam of light on a fundus of the wearer's eye.
38. The device of embodiment 24, wherein the projected beam of light comprises a white light.
39. The device of embodiment 24, wherein the projected beam of light comprises a colored light.
40. The device of embodiment 39, wherein the projected beam of light has a wavelength in red, green or blue spectral region of the visible spectrum of light.
41. The device of embodiment 24, wherein the projected beam of light includes a range of wavelengths in the infrared spectrum of light.
42. The device of embodiment 24, wherein the projected beam of light is configured to be focused at different depths in the wearer's eye.
43. The device of embodiment 24, wherein said camera is configured to capture an image of at least a portion of the fundus of the wearer's eye.
44. The device of embodiment 24, wherein said camera is configured to capture an image from different depths in the wearer's eye.
45. A wearable virtual reality device configured to be used by a wearer, said device comprising:
   a virtual reality head-mounted ophthalmic system comprising a virtual reality display platform comprising a display for providing images to the eye of the wearer; and
   a fiber scanning display configured to project a beam of light of a particular focus to at least one portion of the wearer's eye,
   wherein said virtual reality head-mounted ophthalmic system is configured to capture an image of an illuminated portion of the wearer's eye for analysis to monitor health of the wearer's eye, detect abnormalities of the eye or other health problems.
46. A wearable virtual reality device configured to be used by a wearer, said device comprising:
   a virtual reality head-mounted ophthalmic system comprising a virtual reality display platform comprising a display for providing images to the eye of the wearer;
   a light source configured to project a beam of light of a particular focus to at least one portion of the wearer's eye; and
   an imaging system configured to capture an image of an illuminated portion of the wearer's eye for analysis to monitor health of the wearer's eye, detect abnormalities of the eye or other health problems.
47. The device of any of the embodiments above, wherein the portion of the eye for which an image is captured by the device comprises the fundus.
48. The device of any of the embodiments above, wherein the portion of the eye for which an image is captured by the device comprises the retina.

The additional numbered embodiments below in the section titled "ADDITIONAL NUMBERED EMBODIMENTS" are to be repeated, added to, and concatenated to the list of numbered embodiments here as if the list of additional numbered embodiments below in the section titled "ADDITIONAL NUMBERED EMBODIMENTS" immediately followed the list of numbered embodiments here.

Confocal Microscopy/SLO

1. A wearable augmented reality device configured to be used by a wearer, said device comprising:
   an augmented reality head-mounted ophthalmic system comprising a wearable augmented reality display platform, said augmented reality head-mounted ophthalmic system configured to pass light from the world into an eye of a wearer wearing the head-mounted system, said augmented reality head-mounted ophthalmic system comprising a confocal microscope configured to image the eye.
2. The device of embodiment 1, wherein said confocal microscope comprises a light source.
3. The device of embodiment 2, wherein said light source comprises a point source.
4. The device of embodiment 3, wherein the light source further comprises an aperture to form a point source.
5. The device of any of embodiments 2-4, wherein said light source is configured to project light beams of different wavelengths at different times.
6. The device of embodiment 5, wherein said wavelengths include visible wavelengths.
7. The device of embodiment 5, wherein said wavelengths include infrared wavelengths.
8. The device of any of embodiments 1-7, where said confocal microscope is configured such that the angle at which light is projected by a light source onto the eye may be varied based on the portions of the eye space to be imaged.
9. The device of any of embodiments 1-8, wherein said confocal microscope comprises at least one pinhole aperture configured to pass light reflected from the eye.
10. The device of embodiment 9, wherein said confocal microscope comprises at least one imaging optical element with optical power to focus light reflected from said eye.
11. The device of embodiment 10, wherein said pinhole aperture is disposed in an optical path between said imaging optical element and said optical detector.
12. The device of any of embodiments 9-11, wherein said pinhole aperture is disposed at the focus of said light reflected from said eye.
13. The device of any of embodiments 9-11, wherein said pinhole aperture is disposed at the focus of said imaging optical element.

14. The device of any of embodiments 1-13, wherein said confocal microscope comprises an optical detector.
15. The device of any of embodiments 1-14, wherein said confocal microscope comprises a fiber scanning device.
16. The device of embodiment 15, wherein said fiber scanning device is configured to project a light beam.
17. The device of any of embodiments 15-16, wherein said fiber scanning device is configured to receive light reflected from said eye.
18. The device of embodiment 17, wherein said fiber scanning device include an optical detector.
19. The device of any of embodiments 1-18, wherein said optics comprises an adaptable optics element configured to project the light.
20. The device of embodiment 19, wherein the adaptable optics element comprises a variable focus element.
21. The device of any of embodiments any of embodiments 1-20, further comprising a waveguide stack comprising a plurality of waveguides, wherein different waveguides are configured to project light from different depth planes.
22. The device of embodiment 21, wherein the waveguide stack further comprises one or more lenses.
23. A wearable virtual reality device configured to be used by a wearer, said device comprising:
   a virtual reality head-mounted ophthalmic system comprising a wearable virtual reality display platform, said virtual reality display platform configured to project an image into an eye of the wearer, said virtual reality head-mounted ophthalmic system comprising a confocal microscope configured to image the eye.
24. The device of any of embodiments 1 and 3-23, wherein said confocal microscope comprises a scanning laser ophthalmoscope comprising a light source comprising a laser.
25. The device of any of the embodiments above, further comprising a fluid delivery system configured to deliver a fluorescent dye.
26. The device of any of embodiments above, configured to visualize in real time an image projected onto retina of the eye.

The additional numbered embodiments below in the section titled "ADDITIONAL NUMBERED EMBODIMENTS" are to be repeated, added to, and concatenated to the list of numbered embodiments here as if the list of additional numbered embodiments below in the section titled "ADDITIONAL NUMBERED EMBODIMENTS" immediately followed the list of numbered embodiments here.

Two-Photon Microscopy
1. A wearable augmented reality device configured to be used by a wearer, said device comprising:
   an augmented reality head-mounted ophthalmic system comprising a wearable augmented reality display platform, said augmented reality head-mounted ophthalmic system configured to pass light from the world into an eye of a wearer wearing the head-mounted system, said augmented reality head-mounted ophthalmic system comprising a two-photon absorption microscope configured to image the eye by producing two-photon absorption to generate fluorescence.
2. The device of embodiment 1, wherein said two-photon absorption microscope comprises a light source.
3. The device of embodiment 2, wherein said light source comprises a laser.
4. The device of embodiment 3, wherein said laser comprises a pico-second laser configured to output pico-second pulses.
5. The device of embodiment 3, wherein said laser comprises a femto-second laser configured to output femto-second pulses.
6. The device of embodiment 3, wherein said laser comprises a mode-locked laser.
7. The device of embodiment 3, wherein said laser comprises a fiber laser.
8. The device of embodiment 2, wherein light source is configured to output infrared wavelengths.
9. The device of embodiment 8, wherein light source is configured to output infrared light having a wavelength between 700-1000 nm.
10. The device of any of embodiments 1-9, further comprising an optical element with optical power configured to focus the light onto the eye.
11. The device of any of embodiments 1-10, where said two-photon absorption microscope is configured such that the angle at which light is projected by a light source onto the eye may be varied based on the portions of the eye to be imaged.
12. The device of any of embodiments 1-11, further comprising a scanner configured to scan a beam of light onto said eye.
13. The device of any of embodiments 1-12, wherein said two-photon absorption microscope comprises an optical detector.
14. The device of any of embodiments 1-13, wherein said two-photon absorption microscope comprises a fiber scanning device.
15. The device of embodiment 14, wherein said fiber scanning device is configured to project a light beam.
16. The device of any of embodiments 14-15, wherein said fiber scanning device is configured to receive light reflected from said eye.
17. The device of embodiment 16, wherein said fiber scanning device include an optical detector.
18. The device of any of embodiments 1-17, further comprising an adaptable optics element configured to project the light.
19. The device of embodiment 18, wherein the adaptable optics element comprises a variable focus element.
20. The device of any of embodiments any of embodiments 1-19, further comprising a waveguide stack comprising a plurality of waveguides, wherein different waveguides are configured to project light from different depth planes.
21. The device of embodiment 20, wherein the waveguide stack further comprises one or more lenses.
22. A wearable augmented reality device configured to be used by a wearer, said device comprising:
   an augmented reality head-mounted ophthalmic system comprising a wearable augmented reality display platform, said augmented reality head-mounted ophthalmic system configured to pass light from the world into an eye of a wearer wearing the head-mounted system, said augmented reality head-mounted ophthalmic system comprising a multi-photon absorption microscope configured to image the eye by producing multi-photon absorption to generate fluorescence.
23. A wearable virtual reality device configured to be used by a wearer, said device comprising:
   a virtual reality head-mounted ophthalmic system comprising a wearable virtual reality display platform, said virtual reality display platform configured to project an image into an eye of the wearer, said virtual reality head-mounted ophthalmic system comprising a two-photon absorption microscope configured to image the eye.
24. A wearable virtual reality device configured to be used by a wearer, said device comprising:
a virtual reality head-mounted ophthalmic system comprising a wearable virtual reality display platform, said virtual reality display platform configured to project an image into an eye of the wearer, said virtual reality head-mounted ophthalmic system comprising a multi-photon absorption microscope configured to image the eye.

The additional numbered embodiments below in the section titled "ADDITIONAL NUMBERED EMBODIMENTS" are to be repeated, added to, and concatenated to the list of numbered embodiments here as if the list of additional numbered embodiments below in the section titled "ADDITIONAL NUMBERED EMBODIMENTS" immediately followed the list of numbered embodiments here.

Autorefractor

1. A wearable augmented reality device configured to be used by a wearer, said device comprising:
   an augmented reality head-mounted ophthalmic system comprising an augmented reality display platform, said augmented reality head-mounted ophthalmic system configured to pass light from the world into an eye of a wearer wearing the head-mounted system, said eye having a retina,
   wherein said augmented reality head-mounted ophthalmic system is configured to capture images of the retina and determine when the one or more images formed by said fiber scanning display is on the retina to determine an optical prescription for the wearer.
2. The device of embodiment 1, further comprising a fiber scanning display configured to provide the one or more images at varying depth.
3. The device of embodiment 2, further comprising an adaptable optics element configured to provide the one or more images at varying depth.
4. The device of embodiment 3, wherein the adaptable optics element comprises a variable focus element.
5. The device of embodiment 4, wherein the variable focus element comprises a membrane mirror.
6. The device of embodiment 5, further comprising:
   one or more electrodes coupled to the membrane mirror; and
   a control system configured to selectively control the one or more electrodes to modify a shape of the membrane mirror.
7. The device of any of embodiments 1 to 6, further comprising a waveguide stack comprising a plurality of waveguides, wherein different waveguides are configured to project light from different focal planes.
8. The device of embodiment 7, wherein the waveguide stack further comprises one or more lenses.
9. A wearable virtual reality device configured to be used by a wearer, said device comprising:
   a virtual reality head-mounted ophthalmic system comprising a virtual reality display platform comprising a display for providing images to the eye of the wearer, said eye having a retina; and
   a fiber scanning display configured to provide one or more images at varying depth, wherein said virtual reality head-mounted ophthalmic system is configured to capture images of the retina and determine when the one or more images formed by said fiber scanning display is on the retina to determine an optical prescription for the wearer.

The additional numbered embodiments below in the section titled "ADDITIONAL NUMBERED EMBODIMENTS" are to be repeated, added to, and concatenated to the list of numbered embodiments here as if the list of additional numbered embodiments below in the section titled "ADDITIONAL NUMBERED EMBODIMENTS" immediately followed the list of numbered embodiments here.

OCT

1. A wearable augmented reality device configured to be used by a wearer, said device comprising:
   an augmented reality head-mounted ophthalmic system comprising a wearable augmented reality display platform, said augmented reality head-mounted ophthalmic system configured to pass light from the world into an eye of a wearer wearing the head-mounted system, said augmented reality display comprising an optical coherence tomography system configured to image the eye.
2. The device of embodiment 1, wherein said optical coherence tomography system is configured to project light beams of varying wavelengths.
3. The device of embodiment 2, wherein said wavelengths include visible wavelengths.
4. The device of embodiment 2, wherein said wavelengths include infrared wavelengths.
5. The device of any of embodiments 1-4, wherein said wearable augmented reality display platform comprises a 3D scanning head comprising a fiber scanning device.
6. The device of embodiment 5, wherein said fiber scanning device is configured to project light beams into the eye.
7. The device of embodiment 5, wherein said fiber scanning device is configured to receive light from the eye.
8. The device of any of embodiments 1-7, further comprising an eye tracking system configured to measure eye movement to de-noise the optical coherence tomography images.
9. The device of any of embodiments 1-7, further comprising ERG.
10. The device of any of embodiments 1-9, where said optical coherence tomography system is configured such that the angle at which light is projected by a light source may be varied based on the regions of the eye space to be imaged.
11. The device of any of embodiments 1-10, further comprising one or more inward facing cameras configured to receive light from the eye.
12. The device of embodiment 11, wherein the one or more inward facing cameras comprise at least one CMOS sensor.
13. The device of any of embodiments 1-10, further comprising a plurality of photodetectors positioned at different parts of the system.
14. The device of embodiment 12, wherein said photodetectors may be positioned around a rim of the head-mounted ophthalmic system.
15. The device of embodiment 12, wherein said photodetectors may be positioned around the periphery of a frame of the head-mounted ophthalmic system.
16. The device of any of embodiments 1-14, wherein said optics comprises an adaptable optics element configured to project light.

17. The device of embodiment 15, wherein the adaptable optics element comprises a variable focus element.
18. The device of any of embodiments any of embodiments 1-16, further comprising a waveguide stack comprising a plurality of waveguides, wherein different waveguides are configured to project light from different depth planes.
19. The device of embodiment 17, wherein the waveguide stack further comprises one or more lenses.
20. A wearable virtual reality device configured to be used by a wearer, said device comprising:
   a virtual reality head-mounted ophthalmic system comprising a wearable virtual reality display platform, said virtual reality display platform configured to project an image into an eye of the wearer, said virtual reality display comprising a optical coherence tomography system configured to image the eye,
   wherein wearable virtual reality display platform comprises a fiber scanning device.
21. A wearable virtual reality device configured to be used by a wearer, said device comprising:
   a virtual reality head-mounted ophthalmic system comprising a wearable augmented reality display platform, said virtual reality display platform configured to project an image into an eye of the wearer, said virtual reality display comprising an optical coherence tomography system configured to image the eye,
   wherein said wearable virtual reality display platform comprises a waveguide stack comprising a plurality of waveguides, wherein different waveguides are configured to project light from different depth planes.

The additional numbered embodiments below in the section titled "ADDITIONAL NUMBERED EMBODIMENTS" are to be repeated, added to, and concatenated to the list of numbered embodiments here as if the list of additional numbered embodiments below in the section titled "ADDITIONAL NUMBERED EMBODIMENTS" immediately followed the list of numbered embodiments here.

Aberrometer
1. A wearable augmented reality device configured to be used by a wearer, said device comprising:
   an augmented reality head-mounted ophthalmic system comprising an augmented reality display platform, said augmented reality head-mounted ophthalmic system configured to pass light from the world into an eye of a wearer wearing the head-mounted system, said eye having a cornea, lens, and retina;
   at least one light source and wearable optics configured to produce a wavefront and project the wavefront into the eye of the wearer so as to pass through the cornea and lens of the eye and be reflected back by the retina of the eye; and
   an aberrometer configured to measure the wavefront that passes through the eye to determine abnormalities of the eye.
2. The device of embodiment 1, wherein said at least one light source comprises a fiber scanning display.
3. The device of embodiment 1, wherein said at least one light source is configured to produce a desired wavefront.
4. The device of embodiment 1, wherein said at least one light source is configured to produce wavefronts of different wavelengths.
5. The device of embodiment 4, wherein said at least one light source is configured to produce visible wavefronts that are projected into the eye.
6. The device of embodiment 4, wherein said at least one light source is configured to produce invisible wavefronts that are projected into the eye.
7. The device of embodiment 1, wherein said wearable optics comprise adaptive optics configured to be adjusted to implement the correction.
8. The device of embodiment 7, wherein the adaptive optics comprises a variable focus element.
9. The device of embodiment 7, wherein the adaptive optics comprises a deformable optical element.
10. The device of embodiment 9, wherein the deformable optical element comprises a deformable mirror.
11. The device of embodiment 1, wherein said wearable optics comprise a waveguide stack comprising a plurality of waveguides configured to provide different focal planes.
12. The device of embodiment 11, wherein the waveguide stack is configured to configured to produce a desired wavefront.
13. A wearable virtual reality device configured to be used by a wearer, said device comprising:
   a virtual reality head-mounted ophthalmic system comprising a virtual reality display platform comprising a display for providing images to the eye of the wearer, said eye having a cornea, lens, and retina;
   at least one light source and wearable optics configured to produce a wavefront and project the wavefront into the eye of the wearer so as to pass through the cornea and lens of the eye and be reflected back by the retina of the eye; and
   an aberrometer configured to measure the wavefront that passes through the eye to determine abnormalities of the eye.

The additional numbered embodiments below in the section titled "ADDITIONAL NUMBERED EMBODIMENTS" are to be repeated, added to, and concatenated to the list of numbered embodiments here as if the list of additional numbered embodiments below in the section titled "ADDITIONAL NUMBERED EMBODIMENTS" immediately followed the list of numbered embodiments here.

Ultrasound
1. A wearable augmented reality device configured to be used by a wearer, said device comprising:
   an augmented reality head-mounted ophthalmic system comprising an augmented reality display platform comprising a display configured for forming an image viewable by said wearer, said augmented reality head-mounted ophthalmic system configured to pass light from the world into an eye of a wearer wearing the head-mounted system; and
   an ultrasound producing component comprising an ultrasound transducer included with said augmented reality head-mounted ophthalmic system so as to deliver ultrasound to the user's eye so as to create an ultrasound image.
2. The device of embodiment 1, wherein said wearable augmented reality system is configured to detect eye abnormalities or monitor health of the user's eye from the created ultrasound image.
3. The device of embodiment 2, further comprising a processor configured with a pattern match algorithm to detect eye abnormalities.

4. The device of embodiment 1, wherein said ultrasound producing component is configured to deliver ultrasound based on a protocol for said user.
5. The device of embodiment 1, further comprising an adaptable optics element configured to project the image to a particular portion of the wearer's eye.
6. The device of embodiment 5, wherein the adaptable optics element comprises a variable focus element.
7. The device of embodiment 6, wherein the variable focus element comprises a membrane mirror.
8. The device of embodiment 7, further comprising:
one or more electrodes coupled to the membrane mirror; and
a control system configured to selectively control the one or more electrodes to modify a shape of the membrane mirror.
9. The device of embodiment 1, further comprising a light source for forming said images in said eye of the wearer, said light source comprising a fiber scanning projector.
10. The device of embodiment 1, wherein said display comprising a waveguide stack comprising a plurality of waveguides, wherein different waveguides are configured to project light at different focal planes.
11. The device of embodiment 10, wherein the waveguide stack further comprises one or more lenses.
12. The device of embodiments 1-11, wherein the ultrasound producing component comprises a probe configured to deliver ultrasound energy to the eye and receive ultrasound energy from the eye.
13. A wearable augmented reality device configured to be used by a wearer, said device comprising:
an augmented reality head-mounted ophthalmic system comprising an augmented reality display platform comprising a display configured for forming an image viewable by said wearer, said augmented reality head-mounted ophthalmic system configured to pass light from the world into an eye of a wearer wearing the head-mounted system; and
an ultrasound producing component comprising an ultrasound transducer coupled to said augmented reality head-mounted ophthalmic system so as to deliver ultrasound to the user's eye so as to create an ultrasound image so that abnormalities of the eye can be detected,
wherein said wearable augmented reality device is configured to measure a response of the user's eye to said ultrasound to detect eye abnormalities.
14. The device of embodiment 13, wherein said abnormality includes a detached retina.
15. The device of embodiment 13, further comprising an adaptable optics element configured to project the image to a particular portion of the wearer's eye.
16. The device of embodiment 13, wherein the adaptable optics element comprises a variable focus element.
17. The device of embodiment 16, wherein the variable focus element comprises a membrane mirror.
18. The device of embodiment 17, further comprising:
one or more electrodes coupled to the membrane mirror; and
a control system configured to selectively control the one or more electrodes to modify a shape of the membrane mirror.
19. The device of embodiment 13, further comprising a light source for forming said images in said eye of the wearer, said light source comprising a fiber scanning projector.
20. The device of embodiment 13, wherein said display comprising a waveguide stack comprising a plurality of waveguides, wherein different waveguides are configured to project light at different focal planes.
21. The device of embodiment 20, wherein the waveguide stack further comprises one or more lenses.
22. The device of embodiments 13-21, wherein the ultrasound producing component comprises a probe configured to deliver ultrasound energy to the eye and receive ultrasound energy from the eye.
23. A wearable virtual reality device configured to be used by a wearer, said device comprising:
a virtual reality head-mounted ophthalmic system comprising a virtual reality display platform comprising a display for providing images to the eye of the wearer; and
an ultrasound producing component comprising an ultrasound transducer coupled to said virtual reality head-mounted ophthalmic system so as to deliver ultrasound to the user's eye so as to create an ultrasound image.
24. The device of Embodiments 21, configured to detect abnormalities of the eye from the created ultrasound image.
25. A wearable virtual reality device configured to be used by a wearer, said device comprising:
a virtual reality head-mounted ophthalmic system comprising a virtual reality display platform comprising a display for providing images to the eye of the wearer; and
an ultrasound producing component comprising an ultrasound transducer coupled to said virtual reality head-mounted ophthalmic system so as to deliver ultrasound to the user's eye so as to create an ultrasound image so that abnormalities of the eye can be detected,
wherein said wearable virtual reality device is configured measure a response of the user's eye to said ultrasound.
26. The device of Embodiments 22, configured to detect abnormalities of the eye from the measured response.
27. The device of any of the embodiments above, wherein the device is configured to auscultation.
28. The device of any of the embodiments above, wherein the device is configured to transmit or receive ultrasound energy to or from the eye in audible frequency range.

The additional numbered embodiments below in the section titled "ADDITIONAL NUMBERED EMBODIMENTS" are to be repeated, added to, and concatenated to the list of numbered embodiments here as if the list of additional numbered embodiments below in the section titled "ADDITIONAL NUMBERED EMBODIMENTS" immediately followed the list of numbered embodiments here.

Electrooculography (EOG), Electroencephalography (EEG), and Electroretinography (ERG)

1. A wearable augmented reality device configured to be used by a wearer, said device comprising:
an augmented reality head-mounted ophthalmic system comprising an augmented reality display platform comprising a display, said augmented reality head-mounted ophthalmic system configured to pass light from the world into an eye of a wearer wearing the head-mounted system;
a plurality of electrodes configured to be placed around the eye, wherein said wearable augmented reality device is configured to measure and compare resting electrical potentials of the retina.
2. The device of embodiment 1, wherein the electrodes comprise electrooculography (EOG) sensors.
3. The device of embodiment 2, further comprising electroencephalography (EEG) sensors.
4. The device of embodiment 1, further comprising a camera configured to optically image the eye.
5. The device of embodiment 1, further comprising an adaptable optics element configured to project the image to a particular portion of the wearer's eye.
6. The device of embodiment 6, wherein the adaptable optics element comprises a variable focus element.
7. The device of embodiment 7, wherein the variable focus element comprises a membrane mirror.
8. The device of embodiment 8, further comprising:
one or more electrodes coupled to the membrane mirror; and
a control system configured to selectively control the one or more electrodes to modify a shape of the membrane mirror based on a corneal shape of the eye.
9. The device of embodiment embodiment1, wherein the light source comprising a fiber scanning projector.
10. The device of embodiment embodiment1, further comprising a waveguide stack comprising a plurality of waveguides, wherein different waveguides are configured to project light at different focal planes.
11. The device of embodiment embodiment11, wherein the waveguide stack further comprises one or more lenses.
12. A wearable augmented reality device configured to be used by a wearer, said device comprising:
an augmented reality head-mounted ophthalmic system comprising an augmented reality display platform comprising a display, said augmented reality head-mounted ophthalmic system configured to pass light from the world into an eye of a wearer wearing the head-mounted system; and
a plurality of electroencephalography (EEG) sensors configured to map brain activity,
wherein said wearable augmented reality device is configured detect abnormal activity or pattern in the brain of the wearer.
13. The device of embodiment embodiment12, further comprising an adaptable optics element configured to project the image to a particular portion of the wearer's eye.
14. The device of embodiment embodiment13, wherein the adaptable optics element comprises a variable focus element.
15. The device of embodiment embodiment14, wherein the variable focus element comprises a membrane mirror.
16. The device of embodiment embodiment15, further comprising:
one or more electrodes coupled to the membrane mirror; and
a control system configured to selectively control the one or more electrodes to modify a shape of the membrane mirror based on a corneal shape of the eye.
17. The device of embodiment embodiment12, wherein the light source comprising a fiber scanning projector.
18. The device of embodiment embodiment12, further comprising a waveguide stack comprising a plurality of waveguides, wherein different waveguides are configured to project light at different focal planes.
19. The device of embodiment embodiment18, wherein the waveguide stack further comprises one or more lenses.
20. A wearable virtual reality device configured to be used by a wearer, said device comprising:
a virtual reality head-mounted ophthalmic system comprising an virtual reality display platform comprising a display for providing images to the eye of the wearer; and
a plurality of electrodes configured to be placed around the eye,
wherein said wearable virtual reality device is configured to measure and compare resting electrical potentials of the retina.
21. A wearable virtual reality device configured to be used by a wearer, said device comprising:
a virtual reality head-mounted ophthalmic system comprising an virtual reality display platform comprising a display for providing images to the eye of the wearer; and
a plurality of electroencephalography (EEG) sensors configured to map brain activity, wherein said wearable virtual reality device is configured detect abnormal activity or pattern in the brain of the wearer.
22. The device of embodiment embodiment1, wherein said electrodes are disposed on said augmented reality head-mounted ophthalmic system around the wear's eye.
23. The device of embodiment 1 or 20, wherein the electrodes comprise electroretinography (ERG) sensors.

The additional numbered embodiments below in the section titled "ADDITIONAL NUMBERED EMBODIMENTS" are to be repeated, added to, and concatenated to the list of numbered embodiments here as if the list of additional numbered embodiments below in the section titled "ADDITIONAL NUMBERED EMBODIMENTS" immediately followed the list of numbered embodiments here.

Light Therapy
1. A wearable augmented reality device configured to be used by a wearer, the device comprising:
an augmented reality head-mounted ophthalmic system comprising an augmented reality display platform, the augmented reality head-mounted ophthalmic system configured to pass light from the world into an eye of a wearer wearing the head-mounted system; and
a light source configured to project light into the eye of the wearer to form an image in the eye,
wherein the wearable augmented reality device is configured to detect an amount of one or more wavelengths of light directed towards the eye and to modify the amount of the one or wavelengths of light reaching the eye based on the detected amount.
2. The device of embodiment 1, wherein the head-mounted system is configured to actively reduce the amount of light of one or more wavelengths reaching the eye.
3. The device of embodiment 2, wherein the head-mounted system is configured to actively reduce the amount of light of one or more wavelengths by reducing the amount of light of one or more wavelengths projected by the light source to the eye.
4. The device of embodiment 3, wherein the head-mounted system is configured to:

provide instructions for the amount of light of the one or more wavelengths to be outputted by the light source; and subsequently modify the instructions to reduce an output of the light of the one or more wavelengths by the light source.

5. The device of embodiment 2, wherein the head-mounted system is configured to:

block at least a portion of the wearer's view of the world, thereby reducing the amount of the one or more wavelengths of light reaching the eye from the world, wherein a size and location of the portion of the wearer's view of the world that is blocked is determined based on the detected amount of the one or more wavelengths of the light.

6. The device of embodiment 1, further comprising one or more sensors configured to detect an amount of the one or more wavelengths of light incident on the head-mounted system.

7. The device of embodiment 6, wherein the one or more sensors is a camera attached to the head-mounted system.

8. The device of embodiment 6, wherein the one or more sensors is configured to detect an overexposure of light of a particular color, wherein the head-mounted system is configured to reduce an mount of the light of the particular color reaching the eye.

9. The device of embodiment 1, wherein the wearable augmented reality device is configured to selectively reduce blue light reaching the eye.

10. The device of embodiment 1, wherein the wearable augmented reality device is configured to modify the amount of the one or wavelengths of light reaching the eye based on the detected amount and based on a time of day.

11. The device of embodiment 1, wherein the wearable augmented reality device is configured to modify the amount of the one or wavelengths of light reaching the eye based on the detected amount and based on a calendar date.

12. The device of embodiment 1, wherein the wearable augmented reality device is configured to modify the amount of the one or wavelengths of light reaching the eye based on the detected amount and based on a current season and location of the wearer.

13. The device of embodiment 1, further comprising an adaptable optics element configured to project the image to a particular portion of the wearer's eye.

14. The device of embodiment 13, wherein the adaptable optics element comprises a variable focus element.

15. The device of embodiment 14, wherein the variable focus element comprises a membrane mirror.

16. The device of embodiment 15, further comprising:
one or more electrodes coupled to the membrane mirror; and
a control system configured to selectively control the one or more electrodes to modify a shape of the membrane mirror.

17. The device of embodiment 14, wherein the light source comprising a fiber scanning projector.

18. The device of embodiment 1, further comprising a waveguide stack comprising a plurality of waveguides, wherein different waveguides are configured to project light at different focal planes.

19. The device of embodiment 18, wherein the waveguide stack further comprises one or more lenses.

20. A wearable augmented reality device configured to be used by a wearer, the device comprising:
an augmented reality head-mounted ophthalmic system comprising an augmented reality display platform, the augmented reality head-mounted ophthalmic system configured to pass light from the world into an eye of a wearer wearing the head-mounted system; and
a light source configured to project light into the eye of the wearer to form an image in the eye,
wherein the wearable augmented reality device is configured to selectively administer light of a portion of a light spectrum into the wearer's eyes.

21. The device of embodiment 20, further comprising one or more sensors configured to detect the under exposure of light of the portion of the light spectrum, wherein the wearable augmented reality device is configured to selectively augment the light based on the detected under exposure.

22. The device of embodiment 20, further comprising one or more sensors configured to detect an underexposure of blue light.

23. The device of embodiment 22, wherein the wearable augmented reality device is configured to selectively administer blue light.

24. The device of embodiment 20, wherein the light comprises a range of wavelengths corresponding to daylight.

25. The device of embodiment 20, wherein the light comprises a range of wavelengths corresponding to full spectrum light.

26. The device of embodiment 20, further comprising a second light source configured to provide the light to be selectively administered to the wearer's eyes.

27. A wearable augmented reality device configured to be used by a wearer, the device comprising:
an augmented reality head-mounted ophthalmic system comprising an augmented reality display platform, the augmented reality head-mounted ophthalmic system configured to pass light from the world into an eye of a wearer wearing the head-mounted system; and
a light source configured to project light into the eye of the wearer to form an image in the eye,
wherein the wearable augmented reality device is configured to selectively administer light of a predefined range of wavelengths into the wearer's eyes based on a treatment protocol.

28. The device of embodiment 27, wherein the treatment protocol is to administer a prescribed amount of the light periodically.

29. The device of embodiment 27, wherein the treatment protocol is to administer a prescribed amount of the light continuously.

30. The device of embodiment 27, wherein the wearable augmented reality device is configured to modify the predefined range of wavelengths based on a time of day.

31. The device of embodiment 27, wherein the wearable augmented reality device is configured to modify the predefined range of wavelengths based on a calendar date.

32. The device of embodiment 27, wherein the wearable augmented reality device is configured to modify the predefined range of wavelengths based on a current season and/or location of the wearer.

33. The device of embodiment 27, wherein the wearable augmented reality device is configured to determine a treatment protocol for selectively administering the light of the certain portion of the spectrum into the wearer's eyes.

34. The device of embodiment 33, wherein the wearable augmented reality device is configured to determine the treatment protocol based on one or more of the following: a physiological state of the wearer, a mood of the wearer, and an ambient environment around the wearer.

35. The device of embodiment 33, wherein the wearable augmented reality device is configured to determine the treatment protocol based on input from the wearer.

36. The device of embodiment 33, wherein the wearable augmented reality device is configured to determine the treatment protocol based on a sign of depression or other abnormality of the wearer.

37. A wearable virtual reality device configured to be used by a wearer, the device comprising:
 a reality head-mounted ophthalmic system comprising a virtual reality display platform; and
 a light source configured to project light into the eye of the wearer to form an image in the eye,
 wherein the wearable virtual reality device is configured to selectively remove light of a particular color.

38. A wearable virtual reality device configured to be used by a wearer, the device comprising:
 a virtual reality head-mounted ophthalmic system comprising an virtual reality display platform; and
 a light source configured to project light into the eye of the wearer to form an image in the eye,
 wherein the wearable virtual reality device is configured to detect an underexposure of light within a certain portion of the spectrum and to selectively administer light of the certain portion of the spectrum into the wearer's eyes.

39. A wearable virtual reality device configured to be used by a wearer, the device comprising:
 a virtual reality head-mounted ophthalmic system comprising a virtual reality display platform; and
 a light source configured to project light into the eye of the wearer to form an image in the eye,
wherein the wearable virtual reality device is configured to selectively administer light of the certain portion of the spectrum into the wearer's eyes based on a treatment protocol.

The additional numbered embodiments below in the section titled "ADDITIONAL NUMBERED EMBODIMENTS" are to be repeated, added to, and concatenated to the list of numbered embodiments here as if the list of additional numbered embodiments below in the section titled "ADDITIONAL NUMBERED EMBODIMENTS" immediately followed the list of numbered embodiments here.

Macular Degeneration

1. A wearable augmented reality device configured to be used by a wearer, said display device comprising:
 an augmented reality head-mounted ophthalmic system comprising an augmented reality display platform, said augmented reality head-mounted ophthalmic system configured to pass light from the world into an eye of a wearer wearing the head-mounted system;
 a light source configured to project light into the eye of the wearer to form an image in the eye; and
 a user interface configured to receive input from a user,
 wherein the wearable augmented reality device is configured to project the image to a particular portion of the wearer's eye and to detect a response regarding the image to determine the health of that portion of the eye.

2. A wearable virtual reality device configured to be used by a wearer, said display device comprising:
 a head-mounted display comprising a virtual reality display platform; and
 a light source configured to project light into the eye of the wearer to form an image in the eye, and
 a user interface configured to receive input from a user,
 wherein the wearable virtual reality device is configured to project the image to a particular portion of the wearer's eye and to detect a response regarding the image to determine the health of that portion of the eye.

3. A wearable display device configured to be used by a wearer, said display device comprising:
 a head-mounted ophthalmic system;
 a light source configured to direct light into an eye of said wearer to form an image in the eye;
 a user interface configured to receive input from a user, and
 an adaptable optics element configured to receive, from the light source, light that is directed to the eye;
 wherein said wearable augmented reality device is configured to detect a response regarding the image to determine the health of that portion of the eye.

4. The device of embodiment 3, wherein the adaptable optics element comprises a variable focus element.

5. The device of embodiment 4, wherein the variable focus element comprises a membrane mirror.

6. The device of embodiment 5, further comprising:
one or more electrodes coupled to the membrane mirror; and
a control system configured to selectively control the one or more electrodes to modify a shape of the membrane mirror.

7. A wearable display device configured to be used by a wearer, said display device comprising:
a head-mounted display system; and
a light source configured to direct light into an eye of a wearer to form an image in the eye, the light source comprising a fiber scanning projector; and
a user interface configured to receive input from a user,
 wherein the wearable display device is configured to project the image to a particular portion of the wearer's eye and to detect a response regarding the image to determine the health of that portion of the eye.

8. A wearable display device configured to be used by a wearer, said display device comprising:
a head-mounted display system; and
a light source configured to direct light into one eye of said wearer to form an image in the eye;
a waveguide stack comprising a plurality of waveguides; and
a user interface configured to receive input from a user,
wherein the wearable display device is configured to project the image to a particular portion of the wearer's eye and to detect a response regarding the image to determine the health of that portion of the eye.

9. The device of embodiment 8, wherein the waveguide stack further comprises one or more lenses.

10. The device of embodiment 8, wherein the head-mounted display system comprises an augmented reality head-mounted ophthalmic system configured to pass light from the world into an eye of a wearer wearing the head-mounted system.

11. The device of any of embodiments 1-10, wherein the wearable device is configured to project the image to another portion of the wearer's eye and to detect a response regarding the image to determine the health of that portion of the eye.

12. The device of any of embodiments 1-10, wherein the wearable device is configured to project a first image and a second image to the same portion of the wearer's eye, to detect a response regarding each image, and to compare the first response to the second response to determine the health of that portion of the eye.

13. The device of embodiment 12, wherein at least one hue present in the first image is different from at least one hue present in the second image.

14. The device of embodiment 13, wherein said wearable augmented reality device is configured to identify areas of reduced color sensitivity based on the portions of the eye tested.

15. The device of embodiment 11, wherein said wearable augmented reality device is configured to determine the location of macular degeneration based on the portions of the eye tested.

16. The device of embodiment 15, wherein determining the location of macular degeneration is further based on imaging of a retina of the eye of the wearer.

17. The device of embodiment 11, wherein said wearable augmented reality device is configured to identify anomalies in the wearer's eye based on the portions of the eye tested.

18. The device of embodiment 11, wherein said determining the health of a portion of the eye is performed in real time.

19. The device of embodiment 11, wherein said wearable augmented reality device is further configured to store data regarding the projected images and the detected responses, and wherein said determining the health of a portion of the eye is performed at a later time based on the stored data.

20. The device of embodiment 19, wherein said wearable augmented reality device is further configured to transmit the stored data, and wherein said determining the health of a portion of the eye is performed remotely based on the transmitted data.

21. The device of any of embodiments 1-10, wherein detecting a response comprises receiving an input from the user through the user interface.

22. The device of any of embodiments 1-10, wherein detecting a response comprises detecting a movement of the eye of the wearer.

23. The device of embodiment 22, wherein said movement of the eye of the wearer is a voluntary response to the image.

24. The device of embodiment 23, wherein said movement of the eye of the wearer is an involuntary response to the image.

25. The device of any of embodiments 1-10, further comprising a display for forming the image in the eye of the wearer.

26. The device of embodiment 25, wherein the display comprises a fiber scanning display.

27. The device of any of embodiments 25 or 26, wherein the display further comprises a waveguide stack.

28. The device of any of embodiments 25, 26, or 27, wherein the display is configured to produce images at multiple depth planes.

29. A wearable augmented reality device configured to be used by a wearer, said display device comprising:
an augmented reality head-mounted ophthalmic system comprising a augmented reality display platform, said augmented reality head-mounted ophthalmic system configured to pass light from the world into an eye of a wearer wearing the head-mounted system; and
a light source configured to project light into the eye of the wearer to form an image in the eye,
wherein the wearable device is configured to selectively project pixels of an image to healthy cells.

30. A wearable display device configured to be used by a wearer, said display device comprising:
a head-mounted display system; and
a light source configured to direct light into an eye of a wearer to form an image in the eye, the light source comprising a fiber scanning projector,
wherein the light source is configured to selectively project pixels of an image to healthy cells.

31. A wearable display device configured to be used by a wearer, said display device comprising:
a head-mounted display system; and
a light source configured to direct light into one eye of said wearer to form an image in the eye; and
a waveguide stack comprising a plurality of waveguides,
wherein the wearable display device is configured to selectively project pixels of an image to healthy cells.

32. The device of embodiment 31, wherein the waveguide stack further comprises one or more lenses.

33. The device of embodiment 31, wherein the head-mounted display system comprises an augmented reality head-mounted ophthalmic system configured to pass light from the world into an eye of a wearer wearing the head-mounted system.

34. The device of any of Embodiments 29-33, wherein the wearable device is configured to selectively project pixels of an image to healthy cells at the periphery of the retina.

35. The device of any of Embodiments 29-33, wherein the wearable device is configured to selectively project a portion of the image to healthy cells.

36. The device of any of Embodiments 29-33, wherein the wearable device is configured to alter the light projected to the eye.

37. The device of Embodiment 36, wherein the wearable device is configured to magnify or brighten pixels of the image projected to damaged areas of the eye.

38. A wearable virtual reality device configured to be used by a wearer, said display device comprising:
a head-mounted display comprising a virtual reality display platform; and
a light source configured to project light into the eye of the wearer to form an image in the eye,
wherein the wearable device is configured to selectively project pixels of an image to healthy cells.

39. The device of Embodiment 38, wherein the wearable device is configured to selectively project pixels of an image to healthy cells at the periphery of the periphery of the retina.

40. The device of Embodiment 38, wherein the wearable device is configured to selectively project a portion of the image to healthy cells.

41. A wearable virtual reality device configured to be used by a wearer, said display device comprising:
a head-mounted display comprising a virtual reality display platform; and a light source configured to project light into the eye of the wearer to form an image in the eye;

wherein the wearable device is configured to alter the light projected to damaged areas of the eye.

42. The device of embodiment 41, wherein the wearable device is configured to magnify pixels of the image projected to damaged areas of the eye.

43. The device of embodiment 41, wherein the wearable device is configured to increase or decrease the intensity of the pixels of the image projected to damaged areas of the eye.

44. The device of embodiment 41, wherein the wearable device is configured to increase or decrease the contrast of the pixels of the image projected to damaged areas of the eye.

45. The device of embodiment 41, wherein the wearable device is configured to alter the hue of the pixels of the image projected to damaged areas of the eye.

46. The device of embodiment 41, wherein the wearable device is configured to alter the light projected for specific wavelengths determined to have reduced sensitivity when projected on said damaged areas of the eye.

47. The device of embodiment 46, wherein the wearable device is configured to magnify pixels of the image projected to damaged areas of the eye.

48. The device of embodiment 46, wherein the wearable device is configured to increase the intensity of the pixels of the image projected to damaged areas of the eye.

49. The device of embodiment 46, wherein the wearable device is configured to increase the contrast of the pixels of the image projected to damaged areas of the eye.

50. A wearable display device configured to be used by a wearer, said display device comprising:
a head-mounted ophthalmic system;
a light source configured to direct light into an eye of said wearer to form an image in the eye; and
an adaptable optics element configured to receive light from the light source,
wherein the wearable device is configured to selectively project pixels of an image to healthy cells.

51. The device of embodiment 50, wherein the adaptable optics element comprises a variable focus element.

52. The device of embodiment 50, wherein the variable focus element comprises a membrane mirror.

53. The device of embodiment 52, further comprising:
one or more electrodes coupled to the membrane mirror; and
a control system configured to selectively control the one or more electrodes to modify a shape of the membrane mirror.

54. The device of any of Embodiments 1-28, wherein the wearable device is configured to selectively project pixels of an image to healthy cells.

55. The device of Embodiment 53, wherein the wearable device is configured to selectively project pixels of an image to healthy cells at the periphery of the retina.

56. The device of Embodiment 53, wherein the light source is configured to selectively project a portion of the image to healthy cells.

57. The device of any of Embodiment 1-23, wherein the wearable device is configured to alter the light projected to the eye.

58. The device of Embodiment 56, wherein the wearable device is configured to magnify pixels of the image projected to damaged areas of the eye.

59. The device of embodiment 56, wherein the wearable device is configured to increase the contrast of the pixels of the image projected to damaged areas of the eye.

60. The device of embodiment 56, wherein the wearable device is configured to alter the light projected for specific wavelengths determined to have reduced sensitivity when projected on said damaged areas of the eye.

61. The device of embodiment 59, wherein the wearable device is configured to magnify pixels of the image projected to damaged areas of the eye.

62. The device of embodiment 59, wherein the wearable device is configured to increase the intensity of the pixels of the image projected to damaged areas of the eye.

63. The device of embodiment 59, wherein the wearable device is configured to increase the contrast of the pixels of the image projected to damaged areas of the eye.

64. The device of embodiment 28, wherein the multiple depth planes are separated by at least 10 centimeters.

65. The device of any of embodiments 28 or 63, wherein the multiple depth planes comprises at least 3 depth planes.

66. The device of embodiment 37, wherein the wearable device is configured to increase or decrease the spatial frequency of a periodic image projected to damaged areas of the eye.

The additional numbered embodiments below in the section titled "ADDITIONAL NUMBERED EMBODIMENTS" are to be repeated, added to, and concatenated to the list of numbered embodiments here as if the list of additional numbered embodiments below in the section titled "ADDITIONAL NUMBERED EMBODIMENTS" immediately followed the list of numbered embodiments here.

Contrast Testing

1. A wearable augmented reality device configured to be used by a wearer, said display device comprising:
an augmented reality head-mounted ophthalmic system comprising an augmented reality display platform, said augmented reality head-mounted ophthalmic system configured to pass light from the world into an eye of a wearer wearing the head-mounted system;
a light source configured to project light into the eye of the wearer to form an image in the eye; and
a user interface configured to receive input from a user,
wherein the wearable augmented reality device is configured to project the image to the wearer and to detect a response regarding the image to determine a contrast sensitivity of the wearer.

2. A wearable virtual reality device configured to be used by a wearer, said display device comprising:
a head-mounted display comprising a virtual reality display platform; and
a light source configured to project light into the eye of the wearer to form an image in the eye, and
a user interface configured to receive input from a user,
wherein the wearable virtual reality device is configured to project the image to the wearer and to detect a response regarding the image to determine a contrast sensitivity of the wearer.

3. The device of embodiment 1 or 2, wherein said image comprises a plurality of regions having different contrast levels.
4. The device of embodiment 3, wherein said image comprises a sine-wave grating.
5. The device of embodiment 3, wherein said image comprises a plurality of letters or numbers projected at different contrast levels.
6. The device of embodiment 5, wherein said image comprises a Pelli-Robson chart.
7. The device of embodiment 5, wherein the wearable device is configured to detect a response from the wearer indicating the letters, numbers, or shapes that are visible to the wearer.
8. The device of embodiment 1 or 2, wherein the light source is configured to consecutively project a plurality of images to the wearer.
9. The device of embodiment 8, wherein each of the plurality of images differs from at least one other of the plurality of images in contrast.
10. The device of embodiment 9, wherein the wearable device is configured to detect a response from the wearer indicating the wearer's ability to detect a contrast feature within the image.
11. The device of embodiment 1 or 2, wherein the light source is configured to decrease the contrast of said image over time.
12. The device of embodiment 11, wherein the wearable device is configured to detect a response from the wearer indicating a time at which the wearer cannot discern contrasting features of the image.
13. The device of any of embodiments 1-12, further comprising a display for forming the image in the eye of the wearer.
14. The device of embodiment 13, wherein the display comprises a fiber scanning display.
15. The device of embodiment 13 or 14, wherein the display further comprises a waveguide stack.
16. The device of any of embodiments 10-12, wherein the display is configured to produce images at multiple depth planes.
17. The device of any of embodiments 1-16, wherein the wearable device is configured to perform a plurality of contrast sensitivity measurements and perform a comparative analysis of the results.

The additional numbered embodiments below in the section titled "ADDITIONAL NUMBERED EMBODIMENTS" are to be repeated, added to, and concatenated to the list of numbered embodiments here as if the list of additional numbered embodiments below in the section titled "ADDITIONAL NUMBERED EMBODIMENTS" immediately followed the list of numbered embodiments here.

Visual Fields
1. A wearable augmented reality device configured to be used by a wearer, said display device comprising:
an augmented reality head-mounted ophthalmic system comprising an augmented reality display platform, said augmented reality head-mounted ophthalmic system configured to pass light from the world into an eye of a wearer wearing the head-mounted system;
a light source configured to project light into the eye of the wearer to form a moving image in the eye; and
a user interface configured to receive input from a user, wherein the wearable augmented reality device is configured to project the image at a particular portion of the periphery of the wearer's visual field and to detect a response regarding the image to determine the health of that portion of the visual field.
2. A wearable virtual reality device configured to be used by a wearer, said display device comprising:
a head-mounted display comprising a virtual reality display platform; and
a light source configured to project light into the eye of the wearer to form a moving image in the eye, and
a user interface configured to receive input from a user, wherein the wearable virtual reality device is configured to project the image at a particular portion of the periphery of the wearer's visual and to detect a response regarding the image to determine the health of that portion of the visual field.
3. The device of embodiment 1 or 2, wherein said moving image moves inward from the periphery of the wearer's visual field toward the center of the wearer's visual field.
4. The device of embodiment 3, wherein the wearable device is configured to detect a response from the wearer indicating the time at which the image becomes visible to the wearer.
5. The device of embodiment 3, wherein the wearable device is configured to detect a response from the wearer regarding an observed characteristic of the image.
6. The device of embodiment 3, wherein the light source is further configured to project an image of an object approaching the eye of the wearer.
7. The device of any of embodiments 1-6, further comprising a display for forming the image in the eye of the wearer.
8. The device of embodiment 7, wherein the display comprises a fiber scanning display.
9. The device of embodiment 7 or 8, wherein the display further comprises a waveguide stack.
10. The device of any of embodiments 7-9, wherein the display is configured to produce images at multiple depth planes.
11. The device of any of embodiments 1-10, wherein the device is configured to provide a visual, audio, or tactile notification to the wearer based on detecting a hazard in an unhealthy portion of the wearer's visual field.

The additional numbered embodiments below in the section titled "ADDITIONAL NUMBERED EMBODIMENTS" are to be repeated, added to, and concatenated to the list of numbered embodiments here as if the list of additional numbered embodiments below in the section titled "ADDITIONAL NUMBERED EMBODIMENTS" immediately followed the list of numbered embodiments here.

Laser Therapy
1. A wearable augmented reality device configured to be used by a wearer, the device comprising:
an augmented reality head-mounted ophthalmic system comprising an augmented reality display platform, the augmented reality head-mounted ophthalmic system configured to pass light from the world into an eye of a wearer wearing the head-mounted ophthalmic system; and
a laser configured to administer laser therapy to the eye of the wearer.
2. The device of embodiment 1, wherein the device is configured to direct laser light to the eye at an intensity, wavelength, and duration to alter eye tissue.

3. The device of embodiment 1, wherein the laser is configured to reduce a growth of abnormal blood vessels or to close abnormal blood vessels.
4. The device of embodiment 3, wherein the laser is configured to perform full laser photocoagulation.
5. The device of embodiment 3, wherein the laser is configured to treat wet age-related macular degeneration.
6. The device of embodiment 1, further comprising a module configured to inject a photosensitizer into the eye, the laser configured to activate the photosensitizer.
7. The device of embodiment 1, wherein the wearable augmented reality device is configured to determine an area for exposure to light from the laser.
8. The device of embodiment 7, wherein the wearable augmented reality device is configured to determine the area for exposure by imaging a retina and surrounding tissue of the eye and determining a presence of choroidal neurovascularization.
9. The device of embodiment 1, wherein the augmented reality head-mounted ophthalmic system is configured to provide instructions to the wearer before exposing the wearer to light from the laser.
10. The device of embodiment 9, wherein the augmented reality head-mounted ophthalmic system is configured to display images to the wearer as part of the laser therapy.
11. The device of embodiment 10, wherein the augmented reality head-mounted ophthalmic system is configured to display the instructions to the wearer before exposing the wearer to light from the laser.
12. The device of embodiment 9, wherein the augmented reality head-mounted ophthalmic system is configured to orient the eye of the wearer in a desired direction during exposing the wearer to light from the laser, wherein the augmented reality head-mounted ophthalmic system is configured to orient the eye by displaying an object for the eye of the wearer to focus on.
13. The device of embodiment 9, wherein the augmented reality head-mounted ophthalmic system is configured to display a moving object as part of the laser therapy.
14. The device of embodiment 9, wherein the augmented reality head-mounted ophthalmic system is configured to provide instructions to the wearer after exposing the wearer to light from the laser.
15. The device of embodiment 14, wherein the instructions comprise one or more of shutting the eyelids for a set duration and blinking a set number of times.
16. The device of embodiment 1, wherein the laser is mounted to a frame of the ophthalmic system.
17. The device of embodiment 1, further comprising an adaptable optics element configured to project an image to a particular portion of the wearer's eye.
18. The device of embodiment 17, wherein the adaptable optics element comprises a variable focus element.
19. The device of embodiment 18, wherein the variable focus element comprises a membrane mirror.
20. The device of embodiment 19, further comprising:
one or more electrodes coupled to the membrane mirror; and
a control system configured to selectively control the one or more electrodes to modify a shape of the membrane mirror.
21. The device of embodiment 1, further comprising a fiber scanning projector for outputting light to form images in the eye of the wearer.
22. The device of embodiment 1, further comprising a waveguide stack comprising a plurality of waveguides, wherein different waveguides are configured to project light at different focal planes.
23. The device of embodiment 22, wherein the waveguide stack further comprises one or more lenses.
24. A wearable virtual reality device configured to be used by a wearer, the device comprising:
a virtual reality head-mounted ophthalmic system comprising a virtual reality display platform comprising a display for providing images to the eye of the wearer; and
a laser configured to selectively administer laser therapy to the eye of the wearer.
25. The device of embodiment 24, wherein the virtual reality head-mounted ophthalmic system is configured to not pass light from the world in front of the head-mounted ophthalmic system into the eye of the wearer wearing the head-mounted ophthalmic system that would form an image of the world in the eye of the wearer.

The additional numbered embodiments below in the section titled "ADDITIONAL NUMBERED EMBODIMENTS" are to be repeated, added to, and concatenated to the list of numbered embodiments here as if the list of additional numbered embodiments below in the section titled "ADDITIONAL NUMBERED EMBODIMENTS" immediately followed the list of numbered embodiments here.

Delivery of Medication

1. A wearable augmented reality device configured to be used by a wearer, the device comprising:
an augmented reality head-mounted ophthalmic system comprising an augmented reality display platform, the augmented reality head-mounted ophthalmic system configured to pass light from the world into an eye of a wearer wearing the head-mounted ophthalmic system,
wherein the augmented reality head-mounted ophthalmic system is configured to deliver medication to the eye of the wearer.
2. The device of embodiment 1, wherein the augmented reality head-mounted ophthalmic system is configured to deliver the medication to the eye of the wearer based on a treatment protocol.
3. The device of embodiment 1, wherein the augmented reality head-mounted ophthalmic system is configured to provide an alert to the wearer while the medication is delivered.
4. The device of embodiment 1, wherein the augmented reality head-mounted ophthalmic system is configured to provide an alert to the wearer to keep the eye open while the medication is delivered.
5. The device of embodiment 1, wherein the augmented reality head-mounted ophthalmic system is configured to provide an alert to the wearer to focus on a visual cue while the medication is delivered.
6. The device of embodiment 1, wherein the augmented reality head-mounted ophthalmic system is configured to deliver the medication as part of a light or laser therapy.
7. The device of embodiment 6, wherein the medication is photosensitive to wavelengths of light used for the light or laser therapy.
8. A wearable augmented reality device configured to be used by a wearer, the device comprising:
an augmented reality head-mounted ophthalmic system comprising an augmented reality display platform, the augmented reality head-mounted ophthalmic system configured to pass light from the world into an eye of a wearer wearing the head-mounted ophthalmic system, wherein the augmented reality head-mounted ophthalmic system is configured to deliver a liquid to the eye of the wearer.

9. The device of embodiment 8, wherein the augmented reality head-mounted ophthalmic system is configured to deliver a spray or mist of the liquid to the eye.

10. The device of embodiment 8, wherein the augmented reality head-mounted ophthalmic system is configured to deliver drops of the liquid to the eye.

11. The device of embodiment 8, wherein the augmented reality head-mounted ophthalmic system is configured to deliver a stream of the liquid to the eye.

12. The device of embodiment 8, wherein the augmented reality head-mounted ophthalmic system is configured to deliver a saline solution to the eye of the wearer.

13. The device of embodiment 12, wherein the augmented reality head-mounted ophthalmic system is configured to detect that the eye is dry and to deliver the saline solution when the eye is dry.

14. The device of embodiment 12, wherein the augmented reality head-mounted ophthalmic system is configured to detect that red or bloodshot eyes, and to deliver the saline solution upon detection of the red or bloodshot eyes.

15. The device of embodiment 8, wherein the augmented reality head-mounted ophthalmic system further comprises one or more sensors to measure one or more of a temperature of the wearer, a duration since an immediately previous delivery of liquid or powdered medication to the eye, an ambient humidity, a presence of foreign objects on the eye, a presence of chemical irritants in the eyes, and/or a pollen or particulate count.

16. The device of embodiment 15, wherein the augmented reality head-mounted ophthalmic system is configured to deliver the liquid to the eye based upon one or more measurements of the one or more sensors exceeding a threshold.

17. The device of embodiment 15, wherein the augmented reality head-mounted ophthalmic system is configured to deliver sufficient liquid to flush the eye.

18. A wearable virtual reality device configured to be used by a wearer, the device comprising:
a virtual reality head-mounted ophthalmic system comprising a virtual reality display platform comprising a display for providing images to the eye of the wearer,
wherein the virtual reality head-mounted ophthalmic system is configured to deliver medication to the eye of the wearer.

19. The device of embodiment 18, wherein the virtual reality head-mounted ophthalmic system is configured to not pass light from the world in front of the head-mounted ophthalmic system into the eye of the wearer wearing the head-mounted ophthalmic system that would form an image of the world in the eye of the wearer.

20. A wearable virtual reality device configured to be used by a wearer, the device comprising:
a virtual reality head-mounted ophthalmic system comprising a virtual reality display platform comprising a display for providing images to the eye of the wearer,
wherein the virtual reality head-mounted ophthalmic system is configured to deliver saline to the eye of the wearer.

21. The device of embodiment 20, wherein the virtual reality head-mounted ophthalmic system is configured to not pass light from the world in front of the head-mounted ophthalmic system into the eye of the wearer wearing the head-mounted ophthalmic system that would form an image of the world in the eye of the wearer.

The additional numbered embodiments below in the section titled "ADDITIONAL NUMBERED EMBODIMENTS" are to be repeated, added to, and concatenated to the list of numbered embodiments here as if the list of additional numbered embodiments below in the section titled "ADDITIONAL NUMBERED EMBODIMENTS" immediately followed the list of numbered embodiments here.

Platform for other Treatments

1. A wearable augmented reality device configured to be used by a wearer, the device comprising:
an augmented reality head-mounted ophthalmic system comprising an augmented reality display platform, the augmented reality head-mounted ophthalmic system configured to pass light from the world into an eye of a wearer wearing the head-mounted system,
wherein the augmented reality head-mounted ophthalmic system is configured to deliver therapy other than light therapy to the wearer.

2. The device of embodiment 1, wherein the augmented reality head-mounted ophthalmic system is configured to deliver vibration therapy.

3. The device of embodiment 2, wherein the augmented reality head-mounted ophthalmic system is configured to massage the face or skull of the wearer.

4. The device of embodiment 3, wherein the augmented reality head-mounted ophthalmic system further comprises an actuator having a contact surface configured to contact the wearer during the massage.

5. The device of embodiment 5, wherein the actuator selected from the group consisting of piezoelectric actuators, eccentric cams, Eccentric Rotating Mass (ERM) vibration motors, and Linear Resonant Actuators (LNAs).

6. The device of embodiment 2, wherein the augmented reality head-mounted ophthalmic system further comprises speakers configured to deliver sound therapy.

7. The device of embodiment 6, wherein the augmented reality head-mounted ophthalmic system is configured to output binaural beats.

8. The device of embodiment 6, wherein the augmented reality head-mounted ophthalmic system is configured to direct sound waves to the eye.

9. The device of embodiment 1, wherein the augmented reality head-mounted ophthalmic system is configured to deliver temperature therapy to the wearer.

10. The device of embodiment 9, wherein the augmented reality head-mounted ophthalmic system further comprises a cooler.

11. The device of embodiment 9, wherein the augmented reality head-mounted ophthalmic system is configured to deliver cool air cooled by the cooler to the wearer.

12. The device of embodiment 9, wherein the augmented reality head-mounted ophthalmic system further comprises a heater.

13. The device of embodiment 9, wherein the augmented reality head-mounted ophthalmic system is configured to deliver heated air heated by the heater to the eye.
14. The device of embodiment 1, further comprising an EEG sensor, wherein the augmented reality head-mounted ophthalmic system is configured to deliver the therapy based upon a physiological state of the wearer measured by the EEG sensor.
15. The device of embodiment 1, wherein the augmented reality head-mounted ophthalmic system is configured to provide an alert to the wearer while the therapy is delivered.
16. The device of embodiment 15, wherein the augmented reality head-mounted ophthalmic system is configured to provide an alert to the wearer to keep the eye open while the therapy is delivered.
17. The device of embodiment 15, wherein the augmented reality head-mounted ophthalmic system is configured to provide an alert to the wearer to focus on a visual cue while the therapy is delivered.
18. The device of embodiment 15, wherein the augmented reality head-mounted ophthalmic system is configured to direct air to the eye during the therapy.
19. A wearable virtual reality device configured to be used by a wearer, the device comprising:
    a virtual reality head-mounted ophthalmic system comprising a virtual reality display platform comprising a display for providing images to the eye of the wearer,
    wherein the virtual reality head-mounted ophthalmic system is configured to deliver therapy other than light therapy to the eye of the wearer.
20. The device of embodiment 19, wherein the virtual reality head-mounted ophthalmic system is configured to not pass light from the world in front of the head-mounted system into the eye of the wearer wearing the head-mounted system that would form an image of the world in the eye of the wearer.

The additional numbered embodiments below in the section titled "ADDITIONAL NUMBERED EMBODIMENTS" are to be repeated, added to, and concatenated to the list of numbered embodiments here as if the list of additional numbered embodiments below in the section titled "ADDITIONAL NUMBERED EMBODIMENTS" immediately followed the list of numbered embodiments here.

Outward Looking Camera

1. A wearable display system, the display system comprising:
    a head-mounted display; and
    at least one outward looking camera configured to capture an image of the world around a wearer of the head-mounted display,
    wherein the display system is configured to process the image of the world, re-render the image of the world, and project the re-rendered image from the head-mounted display to an eye of the wearer.
2. The wearable display system of embodiment 1, wherein the display system is configured to re-render the image of the world is at least in part based on a known ophthalmic condition of the wearer.
3. The wearable display system of embodiment 1, wherein the display system is configured to re-render the image of the world by modifying a hue of at least a portion of the image.
4. The wearable display system of embodiment 3, wherein the display system is configured to re-render the image of the world by shifting a color of at least a portion of the image.
5. The wearable display system of embodiment 1, wherein the display system is configured to re-render the image of the world by modifying an intensity of at least a portion of the image.
6. The wearable display system of embodiment 1, wherein the display system is configured to re-render the image of the world by altering portions of the imagebased on a distribution of health and unhealthy cells in a retina of the wearer.
7. The wearable display system of embodiment 1, wherein the display system is configured to re-render the image of the world by modifying a wavefront of at least a portion of the image.
8. The wearable display system of embodiment 1, wherein the display system is configured to re-render the image of the world by magnifying at least a portion of the image.
9. The wearable display system of embodiment 1, wherein the display system is configured to re-render the image of the world by modifying the saturation of at least a portion of the image.
10. The wearable display system of embodiment 1, wherein the display system is configured to re-render the image of the world by modifying a spatial frequency of at least a portion of the image.
11. The wearable display system of embodiment 1, wherein the head-mounted display comprises a virtual reality display.
12. The wearable display system of embodiment 1, wherein the head-mounted display comprises an augmented reality display device configured to pass light from the world into an eye of the wearer.
13. The wearable display system of any of embodiments 1-12, wherein the head-mounted display comprises a light field display.

The additional numbered embodiments below in the section titled "ADDITIONAL NUMBERED EMBODIMENTS" are to be repeated, added to, and concatenated to the list of numbered embodiments here as if the list of additional numbered embodiments below in the section titled "ADDITIONAL NUMBERED EMBODIMENTS" immediately followed the list of numbered embodiments here.

Additional Numbered Embodiments

These additional embodiments are to be added to the list of embodiments provided in the different sections above including without limitation the sections titled: Myopia/Hyperopia/Astigmatism; Presbyopia; Strabismus/Amblyopia; Higher Order Aberrations; Chromatic Aberration; Phoropter; Red Reflex; Intraocular Pressure; Pinhole Occluder; Initial W4LT Test; Retinoscopy; Slit Lamp; Color Blindness; Ophthalmoscope/Funduscope; Confocal Microscopy/Two-Photon Microscopy/SLO; Two-Photon Microscopy; Autorefractor; OCT; Aberrometer; Ultrasound; Electrooculography (EOG), Electroencenphalography (EEG), and Electroretinography (ERG); Light Therapy; Macular Degeneration; Contrast Testing; Visual Fields; Laser Therapy; Delivery of Medication; Platform for Other Treatments; and Outward Looking Camera.

These additional embodiments are to be repeated and concatenated to the list of embodiments provided in each of the different sections above as if the list below immediately followed the list of embodiments in a particular section. In addition, the additional numbered embodiments below will be understood to apply to any of the claims of this application, and, in determining the subject matter encompassed by these embodiments, the references to the "device of any of the above embodiments" will be understood to also be a reference to any of the claims below.

1. The device of any of the above embodiments, wherein the device comprises a light field display.
2. The device of any of the above embodiments, wherein the device is configured to project images to the eye of the wearer from different depth planes.
3. The device of any of the above embodiments, wherein the device comprises a plurality of optical elements having optical power to project images from different depth planes.
4. The device of any of the above embodiments, wherein the device comprises a plurality of lenses having optical power to project images from different depth planes.
5. The device of any of the above embodiments, wherein the device is configured to project images from different depth planes into an eye using time multiplexing such that images for different depth planes are projected at different times.
6. The device of any of the above embodiments, wherein the device is configured to project at least one beam of light in a scanning pattern in the eye of the wearer.
7. The device of any of the above embodiments, wherein the device is configured to project at least one beam of light in a scanning pattern in the eye of the wearer to form an image.
8. The device of any of the above embodiments, wherein the display device is configured to project at least one beam of light having a lateral dimension of between 1 and 25 microns in the eye of the wearer.
9. The device of any of the above embodiments, further comprising a transmissive adaptive optics element.
10. The device of any of the above embodiments, further comprising a transmissive adaptive optics element, wherein the transmissive adaptive optics element comprises an adaptive optics lens or a spatial light modulator that modulates phase.
11. The device of any of the above embodiments, further comprising a transmissive adaptive optics element comprising a deformable lens.
12. The device of any of the above embodiments, further comprising a transmissive adaptive optics element comprising a deformable lens that comprises a deformable elastomeric lens.
13. The device of any of the above embodiments, wherein the device is configured to track data on the user obtained by the device over a period of time.
14. The device of any of the above embodiments, wherein the device is further configured to account for results in previous tests, examinations, or procedures performed by the device when providing output or controlling light reaching the user.
15. The device of any of the above embodiments, wherein the device is further configured to modify providing output or controlling light reaching the user based at least in part on results of one or more previous test, examinations or procedures performed by the device.
16. The device of any of the above embodiments, wherein the test, examination, or procedure performed by the device is initialized based at least in part on results from previous tests, examinations, or procedures performed by the device.
17. The device of any of the above embodiments, wherein the device comprises a gaming system.
18. The device of any of the above embodiments, wherein the device comprises an entertainment system.
19. The device of any of the above embodiments, wherein the device comprises a personal display system.
20. The device of any of the above embodiments, wherein the device comprises an occupational display system.
21. The device of any of the above embodiments, wherein the device is configured to perform tests, examinations or procedures while presenting a movie.
22. The device of any of the above embodiments, wherein the device is configured to perform tests, examinations, or procedures while the wearer is playing a video game.
23. The device of any of the above embodiments, wherein the device is configured to acquire test results based at least in part on measurements of the eye of the wearer while presenting a movie.
24. The device of any of the above embodiments, wherein the device is configured to acquire test results based at least in part on measurements of the eye of the wearer while playing a video game.
25. The device of any of the above embodiments, wherein the device is configured to project a movie wherein portions of the movie are projected from a variety of depth planes and to perform tests, examinations, or procedures on the eye of the wearer based on measurements of the eye when viewing the portions of the movie projected from the variety of depth planes.
26. The device of any of the above embodiments, wherein the device is configured to present a video game wherein portions of the video game are presented from a variety of depth planes and to perform tests, examinations, or procedures on the eye of the wearer based on measurements of the eye when playing the video game presented from the variety of depth planes.
27. The device of any of the above embodiments, wherein the device is a medical system configured for use by an optometrist, clinician, or doctor.
28. The device of any of the above embodiments, wherein the test, examination, or procedure is administered from an office of the optometrist, clinician, or doctor or from a hospital, clinic, or medical facility.
29. The device of any of the above embodiments, wherein the device is primarily configured as an ophthalmic system configured to perform ophthalmic diagnostics or perform ophthalmic treatments.
30. The device of any of the above embodiments, wherein the device is primarily configured as an ophthalmic system configured to determine refractive errors or administer eye exams.
31. The device of any of the above embodiments, wherein the tests, examinations, or procedures are performed by the device multiple times per year.
32. The device of any of the above embodiments, wherein the tests, examinations, procedures are performed by the device multiple times per week.
33. The device of any of the above embodiments, wherein the tests, examinations, procedures are performed by the device multiple times per day.
34. The device of any of the above embodiments, wherein the tests, examinations, or procedures are performed by the device at a wearer's discretion.
35. The device of any of the above embodiments, wherein the tests, examinations, or procedures are dynamically scheduled or suggested based at least in part on results obtained by the device of monitoring performance of the eye of the wearer.

36. The device of any of the above embodiments, wherein a scheduled time for a test, examination, or procedure is modified based at least in part on results of the device monitoring performance of the eye of the wearer.

37. The device of any of the above embodiments, wherein device is configured to generate an alert that the device will be performing a test, examination or procedure on the wearer.

38. The device of any of the above embodiments, wherein device is configured to generate an alert that the device has completed a test, examination or procedure on the wearer.

39. The device of any of the above embodiments, wherein the device is configured to generate an alert to the wearer when performance of the eye of the wearer is outside a targeted performance range.

40. The device of any of the above embodiments, wherein device is configured to generate an alert comprising a suggested test based on performance characteristics of the eye that are outside the targeted performance range.

41. The device of any of the above embodiments, wherein device is configured to generate an alert comprising information on performance characteristics of the eye that are outside the targeted performance range.

42. The device of any of the above embodiments, wherein device is configured to generate an alert comprising a sound or visual notification presented to the wearer to indicate a suggested test.

43. The device of any of the above embodiments, wherein device is configured to generate an alert comprising a sound or visual notification presented to the wearer to indicate which performance characteristics are outside the targeted performance range.

44. The device of any of the above embodiments, wherein the device is configured to:
   obtain information regarding an ambient environment of the eyewear;
   measure biological characteristics of the wearer; and
   determine a relationship between the information and the measured biological characteristics.

45. The device of the embodiment 44, wherein the device is configured to obtain the information regarding the ambient environment by using an outward facing camera to acquire images of objects in the environment outside of the eyewear; and wherein the device is configured to determine a relationship between the objects in the acquired images and the measured biological characteristics.

46. The device of embodiment 45, wherein the objects in the acquired images comprise food.

47. The device of any of embodiments 44-46, wherein the biological characteristics comprise at least one of a heart rate or a trend in blood pressure.

48. The device of any of embodiments 44-47, wherein the relationship is stored to accrue historical records of the determined relationships.

49. The device of any of embodiments 44-48, wherein the device is configured to obtain the information regarding the ambient environment by determining a location of the wearer, wherein the information characterizes one or more conditions of the ambient environment at the location.

50. The device of the any of embodiments 44-49, wherein the device is configured to obtain the information regarding the ambient environment by accessing a remote data repository.

51. The device of any of embodiments 44-50, wherein the information describes one or more of pollen count, pollution, demographics, environmental toxins, interior climate and air quality conditions, lifestyle statistics, and proximity to health-care providers.

BRIEF DESCRIPTION OF THE DRAWINGS

The drawings illustrate some examples of embodiments disclosed herein and do not limit the invention. It should be noted that the figures are not drawn to scale and that elements of similar structures or functions are represented by like reference numerals throughout the figures.

FIG. 11 illustrates an example process flow for correcting presbyopia according to some embodiments.

FIG. 12 illustrates an example method for treating convergence deficiencies, such as those caused by strabismus and/or amblyopia, by occluding an eye of the wearer.

FIG. 17A-C illustrates embodiments of example pinhole occluder devices according to some embodiments.

FIG. 18 illustrates an example method of administering a Worth Four Light Test or Worth Four Dot Test to assess the wearer's degree of binocular single vision.

FIG. 19 illustrates an example method for measuring refractive error of a wearer of an augmented reality device configured to perform retinoscopy.

FIG. 23A-1 is a partial schematic illustration of an example of an augmented reality/virtual reality eyewear comprising a fiber scanning device and a plurality of waveguides that are configured to perform optical coherence tomography (OCT) examination.

FIG. 24D-1 is a partial schematic illustration of an embodiment of an augmented reality/virtual reality eyewear comprising a fiber scanning device and a plurality of waveguides that are configured to perform confocal microscopy, scanning laser ophthalmoscopy or two-photon microscopy.

FIG. 24D-2 is a schematic partial illustration of an embodiment of an eyewear comprising an optical source, one or more imaging devices, a beam splitter, a lensing system and a scanning mirror.

FIG. 26A-G illustrates example embodiments of an augmented and/or virtual reality system configured as an autorefractor.

FIG. 29B schematically illustrates an example embodiment of a system with reflective adaptive optics.

DETAILED DESCRIPTION

Figure 1:
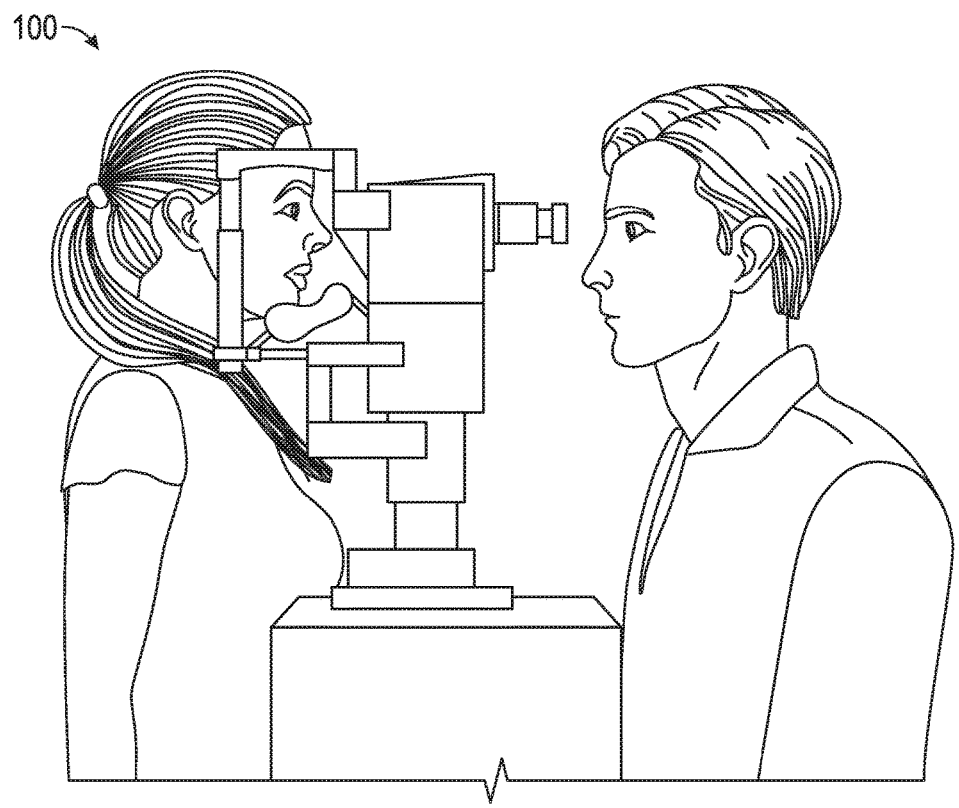
FIG. 1 illustrates a traditional ophthalmic instrument being used at a clinician's office.

Various embodiments of the invention are directed to methods, systems, and articles of manufacture for implementing a user-wearable health system, which may be used for performing health-related diagnostics, monitoring, and therapeutics on the user. Various objects, features, and advantages of the invention are described in the detailed description, figures, and claims.

Various embodiments will be described in detail with reference to the drawings, which are provided as illustrative examples of the invention so as to enable those skilled in the art to practice the invention. Notably, the figures and the examples below are not meant to limit the scope of the present invention. Where certain elements of the present invention may be partially or fully implemented using known components (or methods or processes), only those portions of such known components (or methods or processes) that are necessary for an understanding of the present invention will be described, and the detailed descriptions of other portions of such known components (or methods or processes) will be omitted so as not to obscure the invention. Further, various embodiments encompass present and future known equivalents to the components referred to herein by way of illustration.

Disclosed are methods and systems for diagnosing and/or treating health ailments of patients through a user-wearable health system, e.g., a user-wearable ophthalmic device that interacts with the user's eyes. In one or more embodiments, the device may be a head-mounted system capable of performing one or more diagnostic or treatment regimens. In some other embodiments, the device may be stationary (e.g., stationary at a physician's office). In one or more embodiments, the device may be an augmented reality system that advantageously combines many augmented reality (AR) and/or virtual reality (VR) techniques for health or ophthalmic purposes. In some other embodiments, the clinician may wear the device for the purpose of diagnosis and/or simulation and training. Various embodiments described below discuss a new paradigm of health systems in relation to AR systems, but it should be appreciated that the techniques disclosed here may be used independently of any existing and/or known AR systems. Thus, the examples discussed below are for example purposes only and should not be read to be limited to AR systems.

As noted above, embodiments of the present inventions present a new paradigm in which user-wearable diagnostic health or health therapy systems (generally referred to herein as health systems), e.g., ophthalmic instruments, are worn by the patient, and may be programmed with one or more applications specific to various health-related, e.g., eye-related, ailments. In some embodiments, diagnoses and/or treatment may be provided by optical, mechanical structures, processing algorithms or any combination of the above. In some other embodiments, the patient worn health system may further entail sensing and/or stimulating capabilities, for enhanced treatment or diagnostic purposes. In some embodiments, a head-worn augmented reality system may be used to provide various health-related, e.g., ophthalmic, measurements, assessments, diagnoses or treatments.

Given that the head-mounted augmented reality display system interacts with the user's eyes, many applications may be envisioned for eye-related diagnostics and therapeutics. Further, many other applications in non-eye diagnostics and therapeutics may be similarly envisioned. Accordingly, the disclosure presented herein is not limited diagnosing, monitoring, and treating the eye. Embodiments disclosed herein may also be applied to diagnose, monitor, and treat other areas of the user's health, including but not limited to the user's cardiovascular and neurological health.

Many embodiments of the health system will be discussed in relation to various eye-related and other ailments. Prior to delving into various embodiments of the health system, the biological mechanisms of the human eye will be briefly discussed below to provide context to common ailments that may affect patients.

Figure 2:
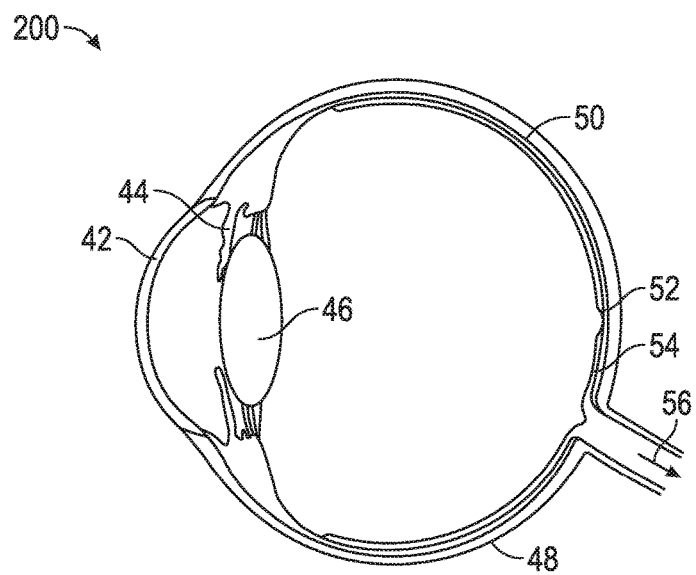
FIG. 2 illustrates a cross-section of a human eye.

Referring to FIG. 2, a simplified cross-sectional view of a human eye is depicted featuring a cornea (42), iris (44), lens—or "crystalline lens" (46), sclera (48), choroid layer (50), macula (52), retina (54), and optic nerve pathway (56) to the brain. The macula is the center of the retina, which is utilized to see moderate detail; at the center of the macula is a portion of the retina that is referred to as the "fovea", which is utilized for seeing the finest details, and which contains more photoreceptors (approximately 120 cones per visual degree) than any other portion of the retina. The human visual system is not a passive sensor type of system; it is configured to actively scan the environment. In a manner somewhat akin to use of a flatbed scanner to capture an image, or use of a finger to read Braille from a paper, the photoreceptors of the eye fire in response to changes in stimulation, rather than constantly responding to a constant state of stimulation.

Thus, motion is required to present photoreceptor information to the brain (as is motion of the linear scanner array across a piece of paper in a flatbed scanner, or motion of a finger across a word of Braille imprinted into a paper). Indeed, experiments with substances such as cobra venom, which has been utilized to paralyze the muscles of the eye, have shown that a human subject will experience blindness if positioned with his eyes open, viewing a static scene with venom-induced paralysis of the eyes. In other words, without changes in stimulation, the photoreceptors do not provide input to the brain and blindness is experienced. It is believed that this is at least one reason that the eyes of normal humans have been observed to move back and forth, or dither, in side-to-side motion in what are called "micro-saccades".

As noted above, the fovea of the retina contains the greatest density of photoreceptors, and while humans typically have the perception that they have high-resolution visualization capabilities throughout their field of view, they generally actually have only a small high-resolution center that they are mechanically sweeping around a lot, along with a persistent memory of the high-resolution information recently captured with the fovea. In a somewhat similar manner, the focal distance control mechanism of the eye (ciliary muscles operatively coupled to the crystalline lens in a manner wherein ciliary relaxation causes taut ciliary connective fibers to flatten out the lens for more distant focal lengths; ciliary contraction causes loose ciliary connective fibers, which allow the lens to assume a more rounded geometry for more close-in focal lengths) dithers back and forth by approximately ¼ to ½ diopter to cyclically induce a small amount of what is called "dioptric blur" on both the close side and far side of the targeted focal length; this is utilized by the accommodation control circuits of the brain as cyclical negative feedback that helps to constantly correct course and keep the retinal image of a fixated object approximately in focus.

The visualization center of the brain also gains valuable perception information from the motion of both eyes and components thereof relative to each other. Vergence movements (i.e., rolling movements of the pupils toward or away from each other to converge the lines of sight of the eyes to fixate upon an object) of the two eyes relative to each other are closely associated with focusing (or "accommodation") of the lenses of the eyes. Under normal conditions, changing the focus of the lenses of the eyes, or accommodating the eyes, to focus upon an object at a different distance will automatically cause a matching change in vergence to the same distance, under a relationship known as the "accommodation-vergence reflex." Likewise, a change in vergence will trigger a matching change in accommodation, under normal conditions. Working against this reflex, as do most conventional stereoscopic AR or VR configurations, is known to produce eye fatigue, headaches, or other forms of discomfort in users.

Movement of the head, which houses the eyes, also has a key impact upon visualization of objects. Humans move their heads to visualize the world around them; they often are in a fairly constant state of repositioning and reorienting the head relative to an object of interest. Further, most people prefer to move their heads when their eye gaze needs to move more than about 20 degrees off center to focus on a particular object (i.e., people do not typically like to look at things "from the corner of the eye"). Humans also typically scan or move their heads in relation to sounds—to improve audio signal capture and utilize the geometry of the ears relative to the head. The human visual system gains powerful depth cues from what is called "head motion parallax", which is related to the relative motion of objects at different distances as a function of head motion and eye vergence distance (i.e., if a person moves his head from side to side and maintains fixation on an object, items farther out from that object will move in the same direction as the head; items in front of that object will move opposite the head motion; these are very salient cues for where things are spatially in the environment relative to the person—perhaps as powerful as stereopsis). Head motion also is utilized to look around objects, of course.

Further, head and eye motion are coordinated with something called the "vestibulo-ocular reflex", which stabilizes image information relative to the retina during head rotations, thus keeping the object image information approximately centered on the retina. In response to a head rotation, the eyes are reflexively and proportionately rotated in the opposite direction to maintain stable fixation on an object. As a result of this compensatory relationship, many humans can read a book while shaking their head back and forth (interestingly, if the book is panned back and forth at the same speed with the head approximately stationary, the same generally is not true—the person is not likely to be able to read the moving book; the vestibulo-ocular reflex is one of head and eye motion coordination, generally not developed for hand motion). This paradigm may be significant for patient-worn health systems, because head motions of the user may be associated relatively directly with eye motions, and the system preferably will be ready to work with this relationship. Thus, when designing a patient-worn or stationary display-based health system, characteristics and sometimes, limitations, of the human eye are preferably taken into account to provide meaningful virtual reality content that works with eye's natural mechanisms rather than stressing it. Furthermore, in the context of health-related applications of augmented reality display systems, this can provide a variety of advantages, as disclosed herein. As discussed above, the display of the health system may be implemented independently of augmented reality (AR) systems, but many embodiments below are described in relation to AR systems for illustrative purposes only.

Referring now to FIGS. 3A-3D, some general componentry options are illustrated. It should be appreciated that although the embodiments of FIGS. 3A-3D illustrate head-mounted displays, the same components may be incorporated in stationary health systems as well, in some embodiments.

Figure 3A:
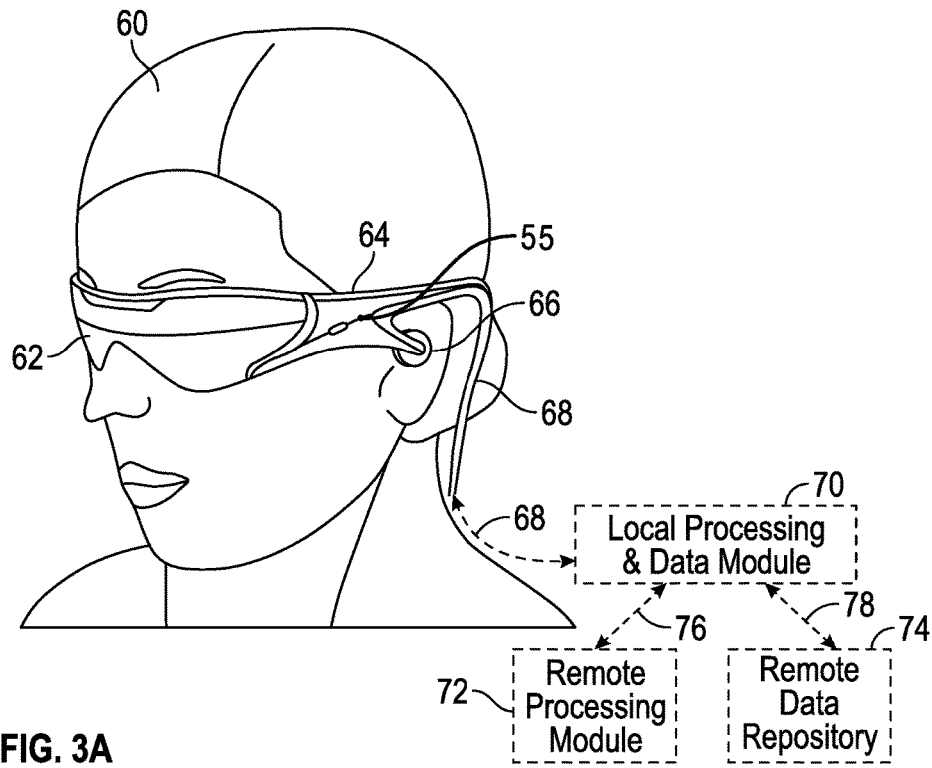
FIG. 3A-3D illustrates various configurations of an example ophthalmic device.

As shown in FIG. 3A, a user (60) is depicted wearing a patient-worn ophthalmic device that includes a frame (64) structure coupled to a display system (62) positioned in front of the eyes of the user. The frame 64 may be coupled to a number of ophthalmic-specific measurement subsystems depending on the application of the health system. Some embodiments may be built for one or more ophthalmic applications, and other embodiments may be general AR systems that are also capable of ophthalmic applications. In either case, the following paragraph describes possible components of the health system or an AR system used for ophthalmic instrumentation and/or treatment.

In one or more embodiments, the health system is patient, or user, worn. In some other embodiments, the health system may be worn by another person, e.g., a physician or clinician, and may be used to perform a set of diagnostics tests and/or treatment protocols on a patient that is not the wearer of the system. It should be appreciated that any of the applications below may be used for health systems worn other persons as well for conducting diagnostics tests and/or treatment protocols on a patient.

Figure 3B:
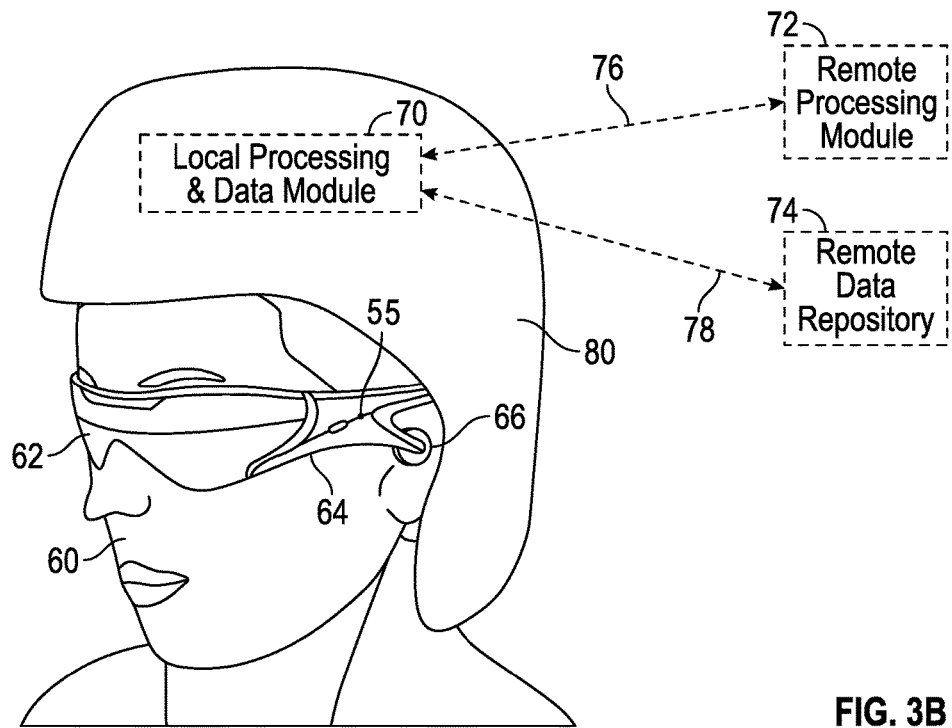
Figure 3C:
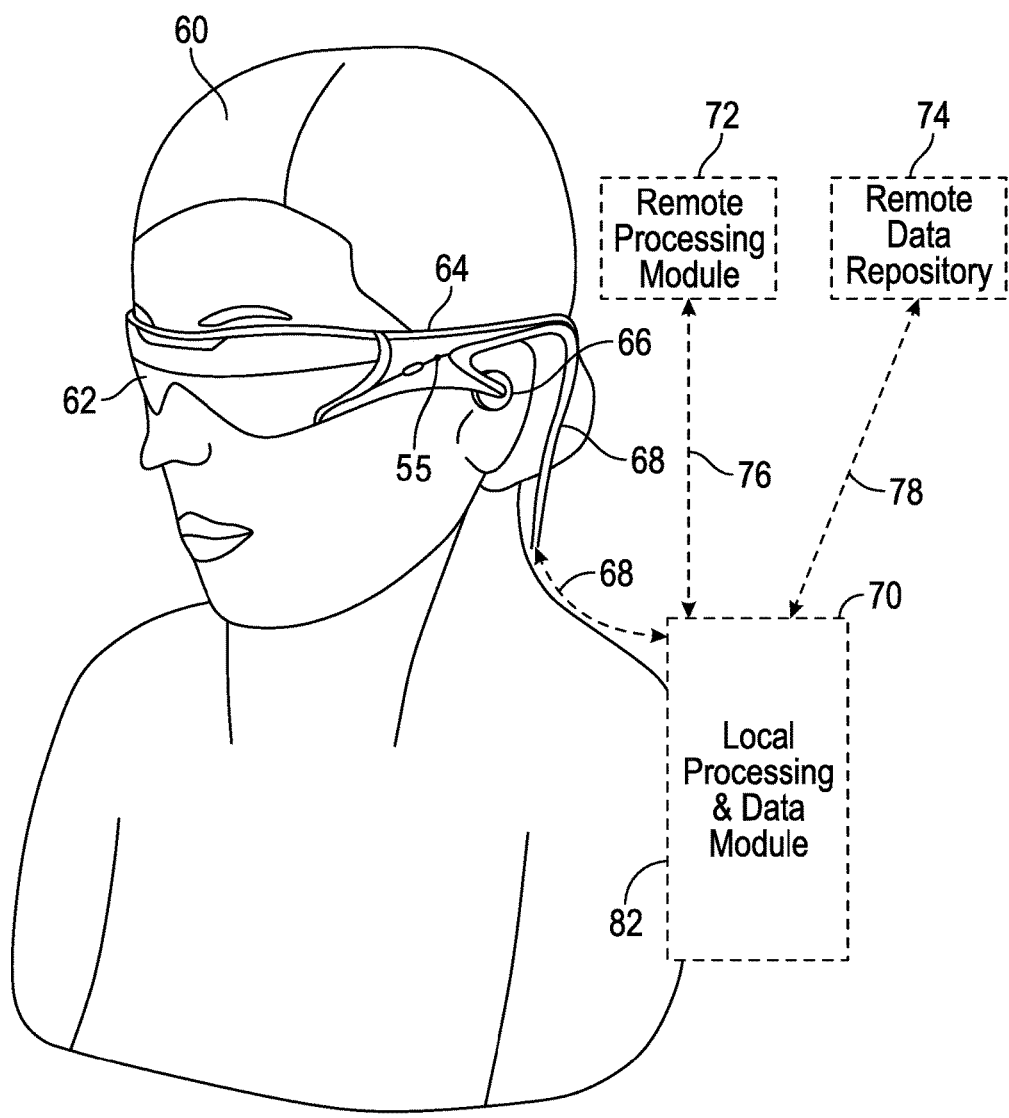
Figure 3D:
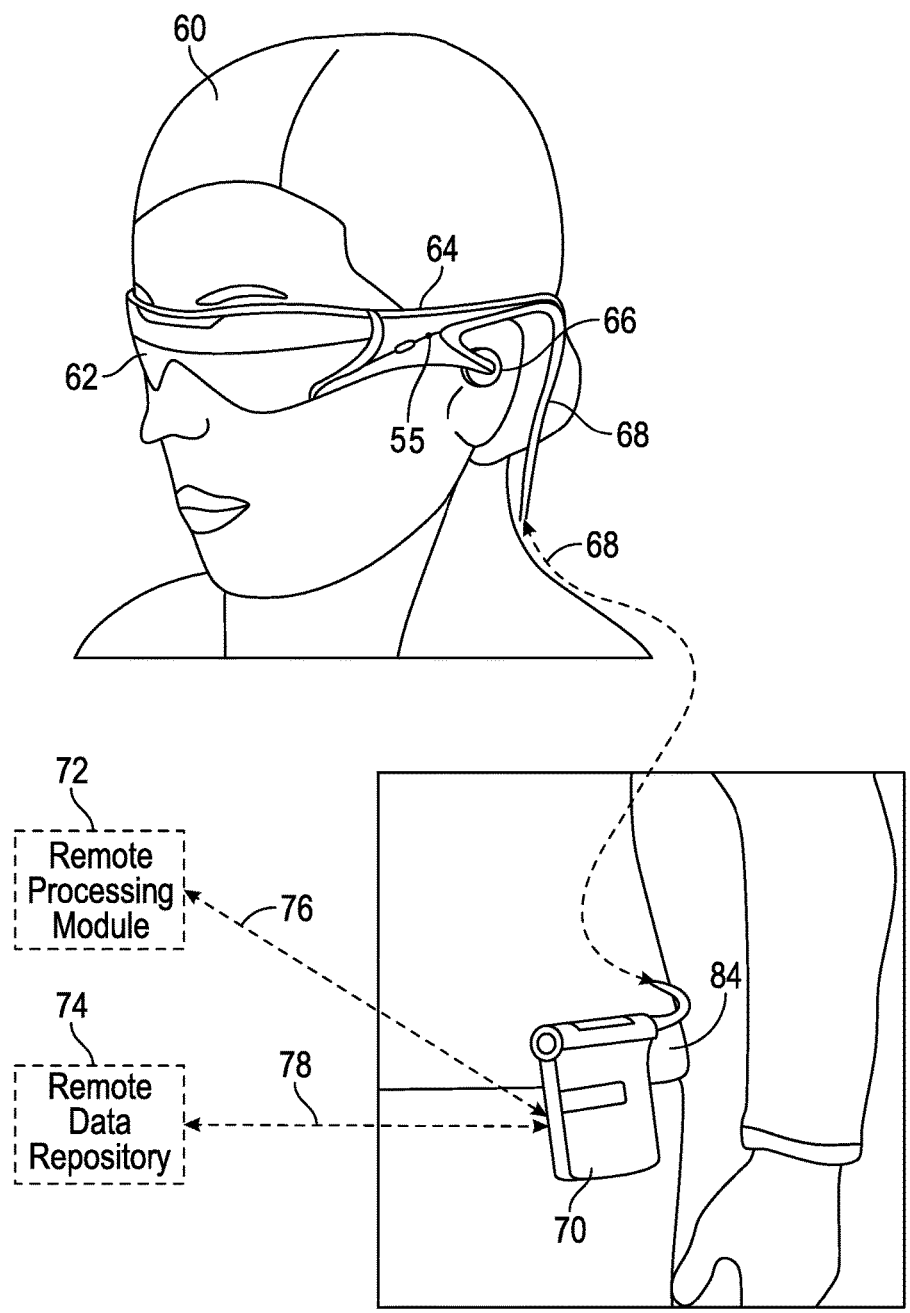

A speaker (66) may be coupled to the frame (64) in the depicted configuration and positioned adjacent the ear canal of the user (in one embodiment, another speaker, not shown, is positioned adjacent the other ear canal of the user to provide for stereo/shapeable sound control). A microphone (55) may also be coupled to the frame, to detect sound from the user or the ambient environment. In some embodiments, another microphone (not illustrated) may be provided, e.g., coupled the frame (64) on the right hand side of the user. In one or more embodiments, the health system may have a display (62) that is operatively coupled (68), such as by a wired lead or wireless connectivity, to a local processing and data module (70) which may be mounted in a variety of configurations, such as fixedly attached to the frame (64), fixedly attached to a helmet or hat (80) as shown in the embodiment of FIG. 3B, embedded in headphones, removably attached to the torso (82) of the user (60) in a backpack-style configuration as shown in the embodiment of FIG. 3C, or removably attached to the hip (84) of the user (60) in a belt-coupling style configuration as shown in the embodiment of FIG. 3D.

The local processing and data module (70) may comprise a power-efficient processor or controller, as well as digital memory, such as flash memory, both of which may be utilized to assist in the processing, caching, and storage of data a) captured from sensors which may be operatively coupled to the frame (64), such as image capture devices (such as cameras), microphones, inertial measurement units, accelerometers, compasses, GPS units, radio devices, and/or gyros; and/or b) acquired and/or processed using the remote processing module (72) and/or remote data repository (74), possibly for passage to the display (62) after such processing or retrieval. The local processing and data module (70) may be operatively coupled (76, 78), such as via a wired or wireless communication links, to the remote processing module (72) and remote data repository (74) such that these remote modules (72, 74) are operatively coupled to each other and available as resources to the local processing and data module (70).

In some embodiments, the remote processing module (72) may comprise one or more relatively powerful processors or controllers configured to analyze and process data and/or image information. In some embodiments, the remote data repository (74) may comprise a relatively large-scale digital data storage facility, which may be available through the internet or other networking configuration in a "cloud" resource configuration. In some embodiments, all data is stored and all computation is performed in the local processing and data module, allowing fully autonomous use from any remote modules.

Advantageously, health systems (or AR systems having ophthalmic applications) similar to those described in FIGS. 3A-3D provide unique access to a user's eyes and head. Given that the health system interacts with the user's eye to allow the user to perceive 3D virtual content, and in many embodiments, tracks various biometrics related to the user's eyes (e.g., eye vergence, eye motion, retinal structures, anterior and posterior eye geometry, patterns of eye movements, etc.), the resultant tracked data may be advantageously used in health-related applications, as described in further detail herein. This unprecedented access to the user's eyes the implementation of various health applications. Depending on the type of health ailment, the health system may be configured to provide imaging of, sensing of (including measurements), and/or stimulation to the user's eyes to diagnose and/or treat the ailment.

In one or more embodiments, the augmented reality display system may be used as a patient-worn, or user-worn, ophthalmic device. Ophthalmic instrumentation is used by clinicians to view into and a patient's eye, to execute a medical procedure and/or to perform tests on the user's eyes. Traditionally, ophthalmic devices have been large and bulky stationary devices, and often require a patient to go to a doctor's office, wherein a clinician or the doctor performs eye-related tests on the patient. Typically, the patient is confined to the ophthalmic instrumentation device (e.g., chin on chin-resting component of ophthalmic device, head forward, etc.) until the clinician has completed the series of tests. Thus, the current approach has a number of limitations.

In addition to using a heavy and bulky device for the tests, the traditional approach requires doctor supervision, and the patient may need to return to the clinician's office repeatedly for further tests/progress evaluations and may need to be in uncomfortable or restriction positions for extended periods of time. Further, given the short duration of time during which the patient is exposed to the ophthalmic device, there are limitations on the amount of data the clinician is able to collect in order to diagnose or treat the patient. In addition, the traditional approach does not take into account the user's behavior and dynamic changes in the orientation of the user. Many tests performed under the traditional approach require that the user be constrained in a particular, usually static position. However, if the user is taking a visual fields test and has limited attention span, they may move their head and eyes, thereby creating noise and possibly causing inaccurate test results.

In one or more embodiments, a head-worn health (e.g., ophthalmic) device similar to the ones shown in FIG. 3A-3D may be used by a patient to track data, identify and correct one or more eye-related ailments, and/or help prevent other health issues. In one or more embodiments, an AR display system may be used as a head-worn health (e.g., ophthalmic) device. It should be appreciated that a number of the embodiments described below may be implemented in head-worn embodiments, while other embodiments may be implemented in stationary devices. Further, some embodiments may utilize AR technology to implement systems and methods for diagnosis, monitoring, and/or treatments with doctor supervision (e.g., for medical safety concerns, regulatory concerns, etc.), while other embodiments may be implemented for self-diagnosis and/or monitoring through the head-worn health devices or AR devices, or be implemented as part of a treatment protocol for a particular ailment, as described herein. For illustrative purposes, the disclosure will mainly focus on head-worn health devices, e.g., health systems, and particularly AR devices, but it should be appreciated that the same principles may be applied to non-head-worn embodiments as well.

In one or more embodiments, the AR display device may be used as a patient-worn health device, e.g., a patient-worn health system. The device may be typically fitted for a particular user's head, and the optical components are aligned to the user's eyes. These configuration steps may be used in order to help ensure that the user is provided with an optimum augmented reality experience without causing any physiological side-effects, such as headaches, nausea, discomfort, etc. Thus, in one or more embodiments, the patient-worn health system is configured (both physically and digitally) for each individual user, and a set of programs may be calibrated specifically for the user. In other scenarios, a loose fitting AR device may be used comfortably by a variety of users. For example, in some embodiments, the patient worn health system knows one or more of the distance between the user's eyes, the distance from the head worn display and the user's eyes, a curvature of the user's forehead, the distance to the ears, or the height of the bridge of the nose for correct fitting purposes. All of these measurements may be used to provide the right head-worn display system for a given user. In some other embodiments, such measurements may not be necessary in order to perform the ophthalmic functions.

Figure 4A:
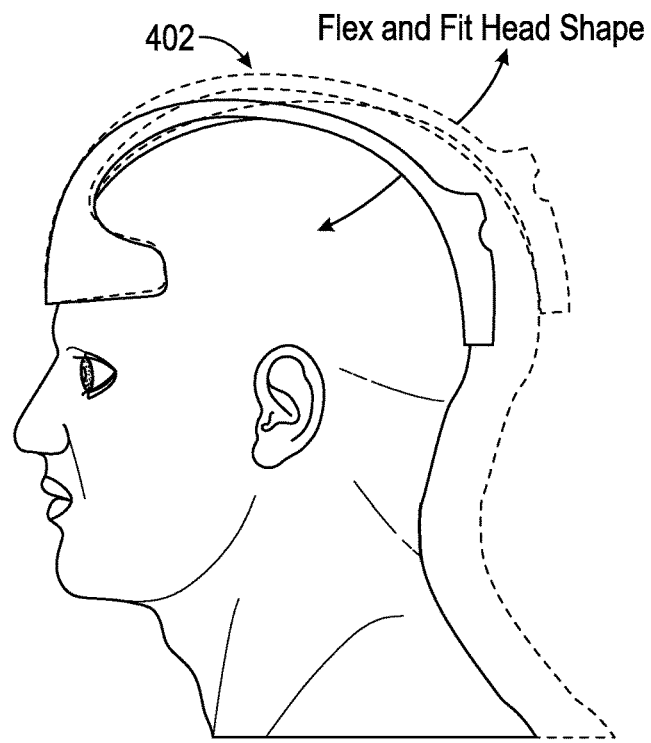
FIG. 4A-4D illustrates various eye and head measurements taken in order to configure the ophthalmic device for a particular user.
Figure 4B:
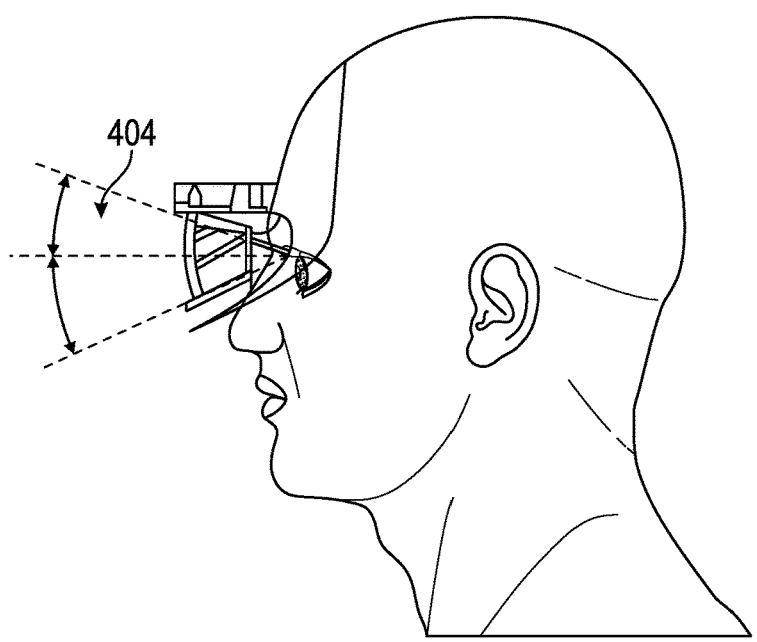
Figure 4C:
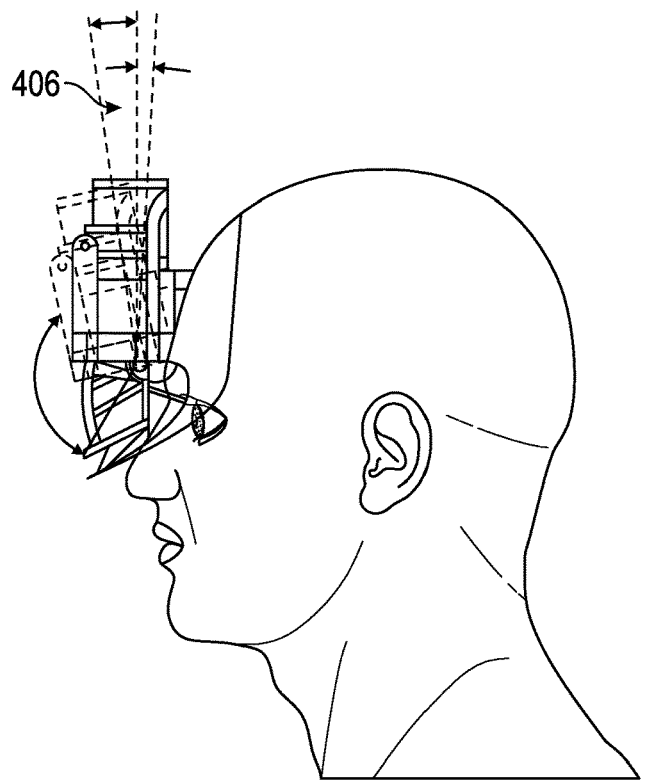
Figure 4D:
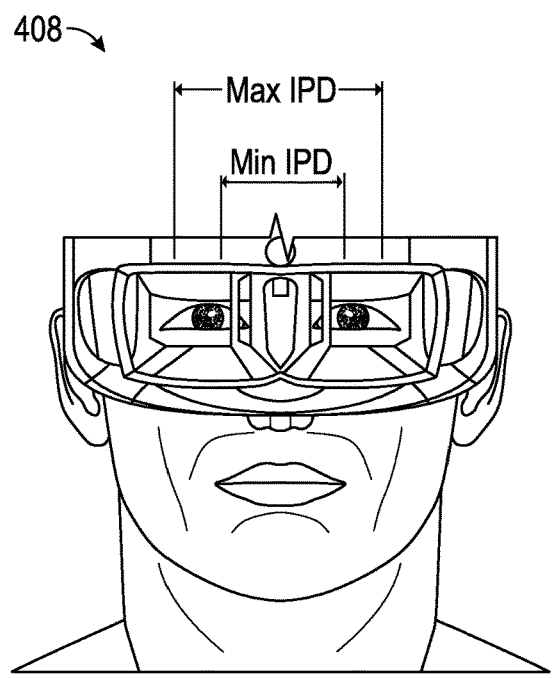

For example, referring to FIG. 4A-4D, the health system may be customized for each user. The user's head shape 402 may be taken into account when fitting the head-mounted patient-worn health system, in one or more embodiments, as shown in FIG. 4A. Similarly, the eye components 404 (e.g., optics, structure for the optics, etc.) may be rotated or adjusted for the user's comfort both horizontally and vertically, or rotated for the user's comfort, as shown in FIG. 4B. In one or more embodiments, as shown FIG. 4C, a rotation point of the head set with respect to the user's head may be adjusted based on the structure of the user's head. Similarly, the inter-pupillary distance (IPD) (i.e., the distance between the user's eyes) may be compensated for, as shown in FIG. 4D.

In the context of patient-worn health systems, this aspect of the head-worn devices may be advantageous because the system already has a set of measurements about the user's physical features (e.g., eye size, head size, distance between eyes, etc.), and other data that may be used in therapy and diagnosis of the patient.

In addition to the various measurements and calibrations performed on the user, the patient-worn health system may be configured to track a set of biometric data about the user for patient identification and secure communications. For example, the system may perform iris recognition and/or retinal matching for patient identification, track eye movements, eye movement patterns, blinking patterns, eye vergence, fatigue parameters, changes in eye color, changes in focal distance, and many other parameters, that may be used in providing an optical augmented reality experience to the user. In the case of AR devices used for healthcare applications, it should be appreciated that some of the above-mentioned aspects may be part of generically-available AR devices, and other features may be incorporated for particular health-related applications.

Figure 5:
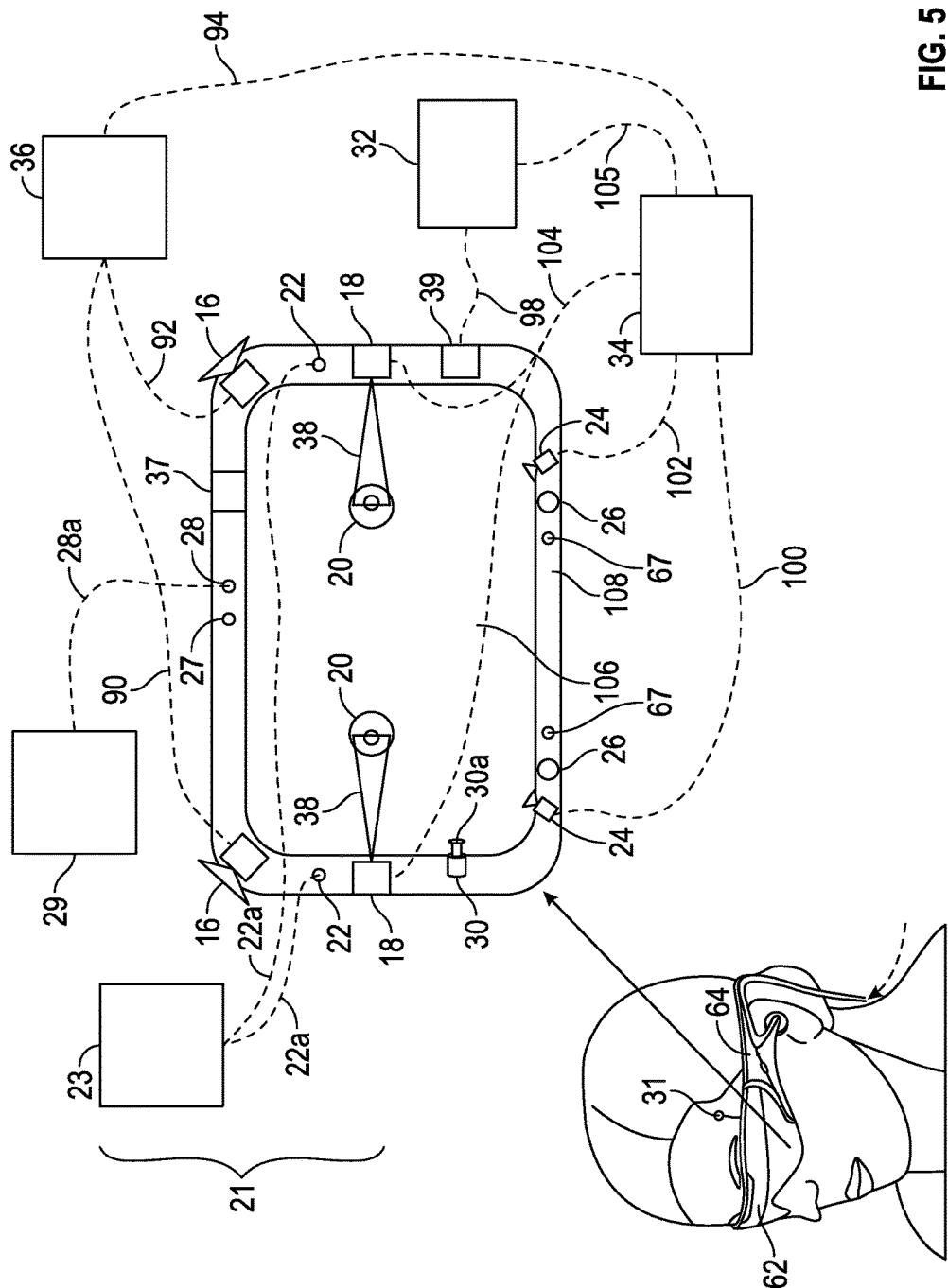
FIG. 5 shows a schematic view of various components of an ophthalmic device according to some embodiments.

Referring now to FIG. 5, the various components of an example patient-worn health display device will be described. It should be appreciated that other embodiments may have additional or fewer components depending on the application (e.g., a particular diagnostic tool) for which the system is used. Nevertheless, FIG. 5 provides a basic idea of some of the various components and types of biometric data that may be collected and stored through the patient-worn health system or AR device. FIG. 5 shows a simplified version of the head-mounted health system 62 in the block diagram to the right for illustrative purposes.

Referring to FIG. 5, one embodiment of a suitable user display device (62) is shown, comprising a display lens (106) that may be mounted to a user's head or eyes by a housing or frame (108), which corresponds to the frame (64) (FIGS. 3A-3D). The display lens (106) may comprise one or more transparent mirrors positioned by the housing (108) in front of the user's eyes (20) and configured to bounce projected light (38) into the eyes (20) and facilitate beam shaping, while also allowing for transmission of at least some light from the local environment. As illustrated, two wide-field-of-view machine vision cameras (16) are coupled to the housing (108) to image the environment around the user; in one embodiment these cameras (16) are dual capture visible light/non-visible (e.g., infrared) light cameras.

With continued reference to FIG. 5, a pair of scanned-laser shaped-wavefront (i.e., for depth) light projector modules with display mirrors and optics configured to project light (38) into the eyes (20) as shown. The depicted embodiment also comprises two miniature infrared cameras (24) paired with infrared light sources (26, such as light emitting diodes "LED"s), which are configured to be able to track the eyes (20) of the user to support rendering and user input. The system (62) further features a sensor assembly (39), which may comprise X, Y, and Z axis accelerometer capability as well as a magnetic compass and X, Y, and Z axis gyro capability, preferably providing data at a relatively high frequency, such as 200 Hz. The depicted system also comprises a head pose processor (36), such as an ASIC (application specific integrated circuit), FPGA (field programmable gate array), and/or ARM processor (advanced reduced-instruction-set machine), which may be configured to calculate real or near-real time user head pose from wide field of view image information output from the capture devices (16).

Also shown is a processor (32) configured to execute digital and/or analog processing to derive pose from the gyro, compass, and/or accelerometer data from the sensor assembly (39). The depicted embodiment also features a GPS (37, global positioning satellite) subsystem to assist with pose and positioning analyses. In addition, the GPS may further provide remotely-based (e.g., cloud-based) information about the user's environment. This information may be used for diagnostic purposes. For example, if the user is situated in an area having high pollen in the surrounding air, this information may be useful to diagnose and/or treat a particular ailment. Or, in another example, information about air pollution in a particular air may be advantageously used when considering treatment options for a particular user. Other types of information (e.g., pollen count, pollution, demographics, environmental toxins, interior climate and air quality conditions, lifestyle statistics, proximity to health-care providers, etc.) may be similarly used in one or more applications.

The depicted embodiment may also comprise a rendering engine (34) that may feature hardware running a software program configured to provide rendering information local to the user to facilitate operation of the scanners and imaging into the eyes of the user, for the user's view of the world. The rendering engine (34) is operatively coupled (105, 94, 100/102, 104; i.e., via wired or wireless connectivity) to the sensor pose processor (32), the image pose processor (36), the eye tracking cameras (24), and the projecting subsystem (18) such that rendered light is projected using a scanned laser arrangement (18) in a manner similar to a retinal scanning display. The wavefront of the projected light beam (38) may be bent or focused to coincide with a desired focal distance of the projected light.

The cameras (24) (e.g., mini infrared cameras) may be utilized to track the eyes to support rendering and user input (i.e., where the user is looking, at what depth he or she is focusing; as discussed below, eye verge may be utilized to estimate depth of focus). The GPS (37), gyros, compass, and accelerometers (39) may be utilized to provide coarse and/or fast pose estimates. The camera (16) images and pose, in conjunction with data from an associated cloud computing resource, may be utilized to map the local world and share user views with others and/or a virtual or augmented reality community and/or healthcare providers. In one or more embodiments, the cameras (16) may be used to analyze food, drug, nutrients and toxins that the user intakes as part of a comprehensive health-care and/or wellness system or health-care surveillance system.

With continued reference to FIG. 5, the display device (62) may include a medication dispensing module (21) to deliver medication to the user. The medication dispensing module (21) may include one or more outlets (22) and at least one medication container (23), which may be a reservoir storing the medication to be dispensed out through the outlets (22). The outlet (22) may be connected to the container (23) by one or more channels (22a), which convey the medication (e.g., a liquid or gas) from the container (23) to the outlets (22). In some embodiments, the outlets (22) may simply be openings in the frame (108), or may be nozzles attached to or integral with the frame (108). In some embodiments, the nozzles may be atomizers. In some embodiments, the channels (22a) are formed by openings in the frame (108) and/or tubing.

In one or more embodiments, the display device may comprise a light emitting module (27) to selectively administer light to the wearer, such as for treatment of the wearer's eyes based on a treatment protocol. The light emitting module (27) may comprise a light source, which may include a light emitter emitting polychromatic polarized light, a laser, a light-emitting diode, a fluorescent lamp, a dichroic lamp, a full spectrum light source, etc. In some embodiments, one light emitting module (27) may be provided for both eyes. In some other embodiments, the display device may include multiple light emitting modules (27), and each eye may have at least one light emitting module configured to direct light to that eye.

While much of the hardware in the display system (62) featured in FIG. 5 is depicted directly coupled to the housing (108) which is adjacent the display (106) and eyes (20) of the user, the hardware components depicted may be mounted to or housed within other components, such as a belt-mounted component, as shown, for example, in FIG. 3D. In addition, as noted herein, multiple sensors and other functional modules are shown together for ease of illustration and description. It will be appreciated, however, that some embodiments may include only one or a subset of these sensors and/or modules.

In one embodiment, all of the components of the system (62) featured in FIG. 5 are directly coupled to the display housing (108) except for the image pose processor (36), sensor pose processor (32), and rendering engine (34), and communication between the latter three and the remaining components of the system may be by wireless communication, such as ultra-wideband, or by wired communication. The depicted housing (108) preferably is head-mountable and wearable by the user. It may also feature speakers (e.g., speakers (66), FIGS. 3A-3D), such as those which may be inserted into the ears of a user and utilized to provide sound to the user.

Regarding the projection of light (38) into the eyes (20) of the user, in some embodiment, the cameras (24) may be utilized to measure where the centers of a user's eyes (20) are geometrically verged to, which, in general, coincides with a position of focus, or "depth of focus", of the eyes (20). A 3-dimensional surface of all points the eyes verge to is called the "horopter". The focal distance may take on a finite number of depths, or may be infinitely varying. Light projected from the vergence distance appears to be focused to the subject eye (20), while light in front of or behind the vergence distance is blurred.

Further, without being limited by theory, it has been discovered that spatially coherent light with a beam diameter of less than about 0.7 millimeters is correctly resolved by the human eye regardless of where the eye focuses; given this understanding, to create an illusion of proper focal depth, the eye vergence may be tracked with the cameras (24), and the rendering engine (34) and projection subsystem (18) may be utilized to render all objects on or close to the horopter in focus, and all other objects at varying degrees of defocus (i.e., using intentionally-created blurring). Preferably the system (62) renders to the user at a frame rate of about 60 frames per second or greater. As described above, preferably the cameras (24) may be utilized for eye tracking, and software may be configured to pick up not only vergence geometry but also focus location cues to serve as user inputs. Preferably, such a display system is configured with brightness and contrast suitable for day or night use.

In some embodiments, the display system preferably has latency of less than about 20 milliseconds for visual object alignment, less than about 0.1 degree of angular alignment, and about 1 arc minute of resolution, which, without being limited by theory, is believed to be approximately the limit of the human eye. The display system (62) may be integrated with a localization system, which may involve GPS elements, optical tracking, compass, accelerometers, and/or other data sources, to assist with position and pose determination; localization information may be utilized to facilitate accurate rendering in the user's view of the pertinent world (e.g., such information would facilitate the glasses to know where they are with respect to the real world). Having described the general components of some embodiments of a user-worn heath system, e.g., an ophthalmic system, additional components and/or features pertinent to healthcare and diagnostics will be discussed below. It should be appreciated that some of the features described below will be common to various embodiments of the user-worn health system or many embodiments of AR systems used for health purposes, while others will require additional or fewer components for health diagnostics and treatment purposes.

In some embodiments, the user-worn health system is configured to display one or more virtual images based on the accommodation of the user's eyes. Unlike prior 3D display approaches that force the user to focus where the images are being projected, in some embodiments, the user-worn health system is configured to automatically vary the focus of projected virtual content to allow for a more comfortable viewing of one or more images presented to the user. For example, if the user's eyes have a current focus of 1 m, the image may be projected to coincide with the user's focus. Or, if the user shifts focus to 3 m, the image is projected to coincide with the new focus. Thus, rather than forcing the user to a predetermined focus, the user-worn health system or AR display system of some embodiments allows the user's eye to a function in a more natural manner.

Such a user-worn health system may eliminate or reduce the incidences of eye strain, headaches, and other physiological symptoms typically observed with respect to virtual reality devices. To achieve this, various embodiments of the patient-worn health system are configured to project virtual images at varying focal distances, through one or more variable focus elements (VFEs). In one or more embodiments, 3D perception may be achieved through a multi-plane focus system that projects images at fixed focal planes away from the user. Other embodiments employ variable plane focus, wherein the focal plane is moved back and forth in the z-direction to coincide with the user's present state of focus.

In both the multi-plane focus systems and variable plane focus systems, the patient-worn health system may employ eye tracking to determine a vergence of the user's eyes, determine the user's current focus, and project the virtual image at the determined focus. In other embodiments, the user-worn health system comprises a light modulator that variably projects, through a fiber scanner, or other light generating source, light beams of varying focus in a raster pattern across the retina. Thus, the ability of the display of the health system to project images at varying focal distances not only eases accommodation for the patient to view objects in 3D, but may also be used to compensate for patient ocular anomalies, as will be described in further detail below. In some other embodiments, a spatial light modulator may project the images to the user through various optical components. For example, as described further below, the spatial light modulator may project the images onto one or more waveguides, which then transmit the images to the user.

Figure 6:
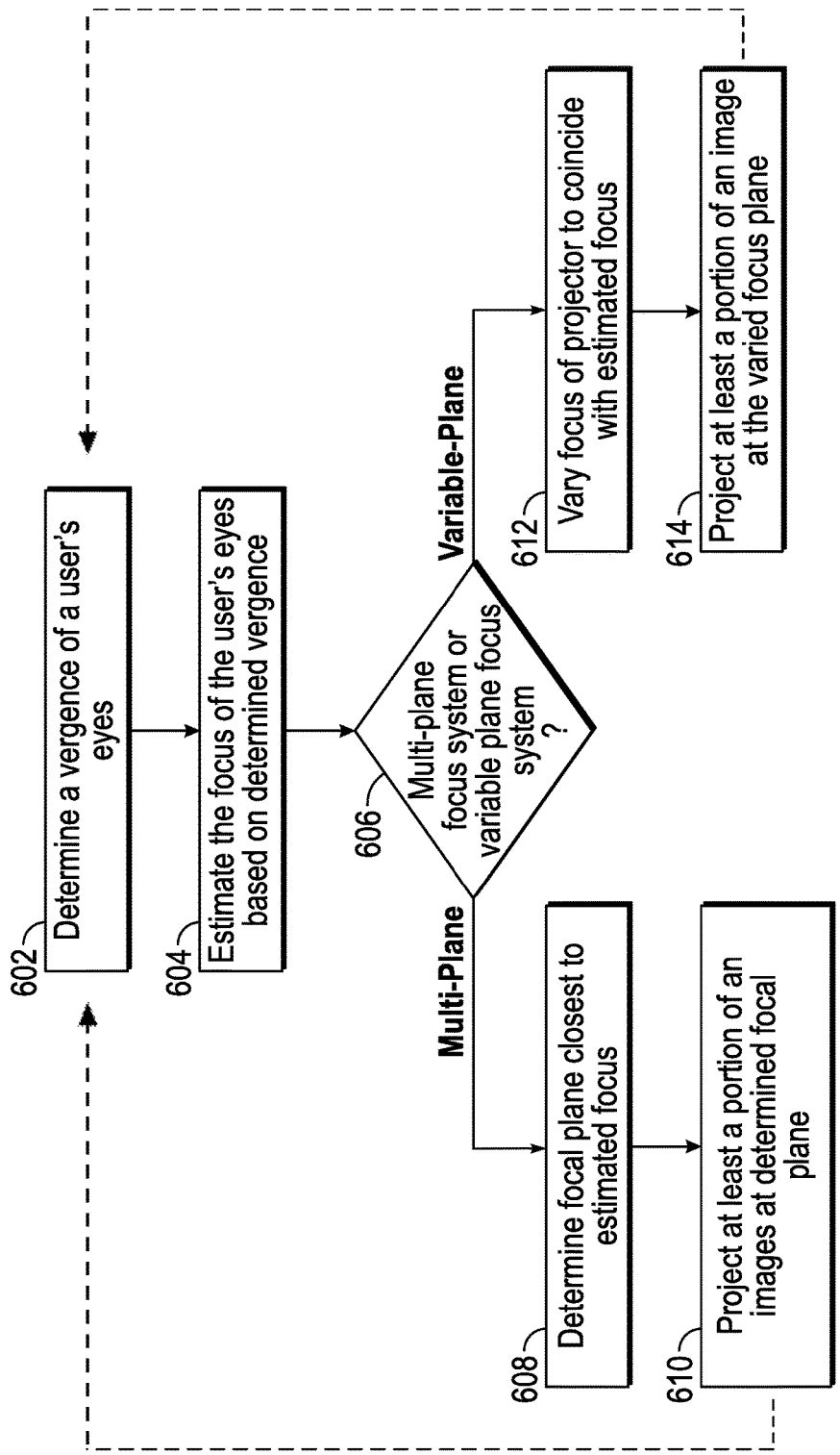
FIG. 6 is an example process flow for varying the focus of the health system according to some embodiments.

Referring now to FIG. 6, an example process flow for projecting one or more virtual images based on the user's accommodative reflex will be briefly described. At 602, the system may determine a vergence of the user's eyes through an eye tracking system. At 604, the system may estimate a current focus of the user's eyes based on the determined vergence. It should be appreciated that other embodiments of the AR system (or health system) may not necessarily utilize eye tracking, and images may be sequentially displayed at a rapid pace to give a perception of 3D. Thus, the process flow of FIG. 6 should not be seen as limiting, and is only provided for illustrative purposes.

If the health system utilizes a multi-depth plane display system (i.e., light is projected at multiple fixed depth planes), the system may at 608 determine a focal plane closest to the estimated focus based on eye vergence and accommodation. It will be appreciated that accommodation may be measured by, e.g., use of an autorefractor, or other devices compatible with the display system. At 610, the health system may project at least a portion of an image at the determined focal plane.

If the health system utilizes a variable-depth plane display system (i.e., one or more focal planes at which virtual content is projected may be moved back and forth in the z direction), at 612, the focus of the system, through a VFE, is varied to coincide with the estimated focus. At 614, the health system may project at least a portion of an image at the focal plane. Similarly, other embodiments of health systems may use other 3D image generating techniques to provide a comfortable, accommodative reflex-friendly projection of virtual objects to the user.

Although, in some embodiments, images are displayed based on the projection of light associated with virtual images into the user's eye, light of any wavelength may be similarly projected into the user's eye. In addition to visible light, infrared light, or other light forms may be similarly projected through the patient-worn health system. This aspect of the patient-worn health system may also be similarly used for compensating health anomalies, as will be described below.

It should also be appreciated that although various embodiments are described in which light is projected into the user's eyes, in one or more embodiments, the health system may also receive light emitted from the user's eyes. In one or more embodiments, the light source for the health system may be a fiber scanning device (FSD) that projects light in various patterns (e.g., raster scan, spiral scan, Lissajous, etc.) into the user's eye. Similarly, other light sources (e.g., OLED, DLP, LCD, etc.) may be similarly used in other embodiments of the health system. In addition to projecting light, the FSD, in one or more embodiments, may receive emitted light. The same fibers that project light may be used to receive light. In this mode, the health system may function as a multi-depth scanner that multiplexes outputted modulated light waves with sensed or captured light waves. In some embodiments, the fiber scanner may be used in conjunction with, or in place of, the camera (24) (FIG. 5) to, e.g., track or image the user's eyes. In one or more embodiments, rather than the FSD being configured to receive light, the health system may have a separate light-receiving device to receive light emitted from the user's eyes, and to collect data associated with the emitted light. Thus, in one or more embodiments, this emitted light, and corresponding data may be analyzed to diagnose or treat anomalies, as will be discussed below.

Figure 28A:
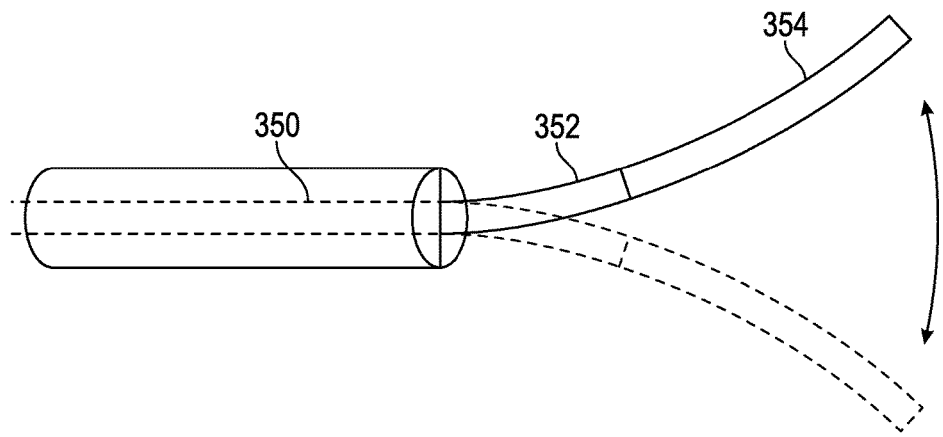
FIG. 28A schematically illustrates an example of a scanning fiber.

Various details of a fiber scanning display device will now be discussed with reference to FIGS. 28A-28C. Referring to FIG. 28A, a gradient refractive index, or "GRIN", lens 354 is shown fused to the end of a single mode optical fiber. An actuator 350 (such as a piezoelectric actuator) is coupled to a fiber 352 and may be used to scan the fiber tip.

Figure 28B:
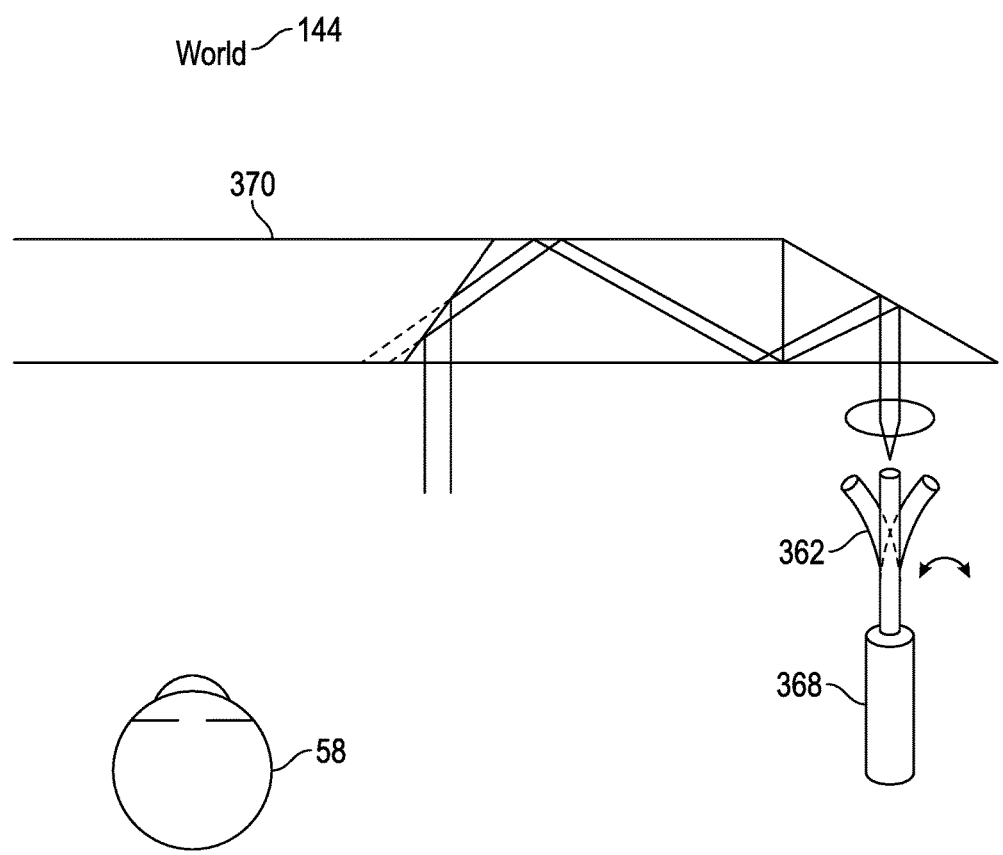
FIG. 28B schematically illustrates an example of a display using a scanning fiber.
Figure 28C:
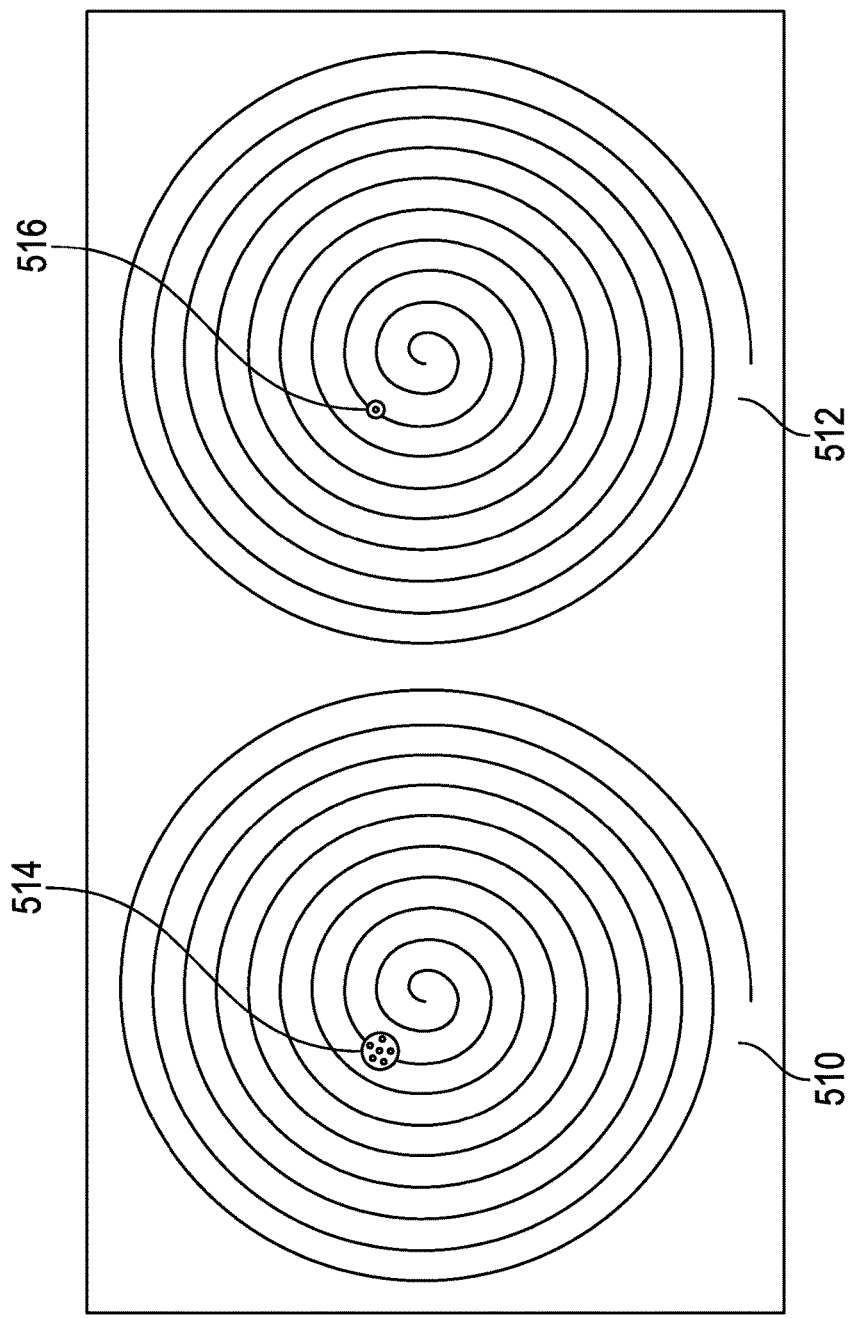
FIG. 28C schematically illustrates an example spiral pattern formed by a moving scanning fiber of a fiber scanning display.

Referring to FIG. 28B, a multicore fiber 362 may be scanned (such as by a piezoelectric actuator 368) to create a set of beamlets with a multiplicity of angles of incidence and points of intersection which may be relayed to the eye 58 by a waveguide (370). Thus in one embodiment a collimated lightfield image may be injected into a waveguide, and without any additional refocusing elements, and that lightfield display may be translated directly to the human eye.

Display systems have been created in the past that use eye or gaze tracking as an input, and to save computation resources by only creating high resolution rendering for where the person is gazing at the time, while lower resolution rendering is presented to the rest of the retina; the locations of the high versus low resolution portions may be dynamically slaved to the tracked gaze location in such a configuration, which may be termed a "foveated display".

An improvement on such configurations may comprise a scanning fiber display with pattern spacing that may be dynamically slaved to tracked eye gaze. For example, with a typical scanning fiber display operating in a spiral pattern, as shown in FIG. 28C (the leftmost portion 510 of the image in FIG. 28C illustrates a spiral motion pattern of a scanned multicore fiber 514; the rightmost portion 512 of the image in FIG. 28C illustrates a spiral motion pattern of a scanned single fiber 516 for comparison), a constant pattern pitch provides for a uniform display resolution.

It will be appreciated that, in addition to displaying images or acting as an imager, the display system may provide illumination for imaging the eye or its surrounding tissue. In one or more embodiments, the health system may comprise an optical scanning or optical sensing module to allow the device to scan an anterior and interior portion of the eye using known visible and non-visible light spectrum techniques including visible imagery, photo-refraction, optical coherence tomography (OCT) and light field microscopy (LFM). In one or more embodiments, the ophthalmic system may further comprise a light field imaging module to capture multiple images of the eye at different focal lengths simultaneously. It should be appreciated that the display, e.g., a FSD, may be advantageously configured such that the multiple frequencies of light may be simultaneously emitted by the display. For example, the FSD may include a single core fiber or may include multicore fibers, which may advantageously emit multiple frequencies of light simultaneously.

In the context of health-care and diagnostics, the type, frequency, color-scheme, placement, etc. of one or more images presented to the user may be advantageously manipulated for diagnoses and treatment of one or more disorders. For example, certain ailments may require strengthening of one eye in relation to the other. To this end, a treatment protocol may be devised in order to "train" the weak eye, by providing increased stimulation to the weak eye in comparison to the strong eye, for example. Or, in another example, a particular portion of the retina may have decreased sensitivity due to macular degeneration; to counter this, images may be modulated, or re-formatted and projected to the peripheries of the retina, thereby compensating for the user's decreased field of vision. Thus, as will be described in further detail below, the ability of the health system to modulate a number of parameters related to virtual image projection may be used to diagnose and/or treat certain health anomalies.

Additionally, using the various principles outlined above, the health system may be designed to provide diagnosis using a stimulus-response-measurement analysis process. Devices such as these may either be used by a clinician, or in other embodiments, certain ailments may simply be "diagnosed" or have symptoms acknowledged by the patient (e.g., eye fatigue, dry eye, hypertension, onset of stroke or seizures etc.). This may crucially help the user to actively take control of his/her health and prevent the onset of diseases by proactively taking care of them at the onset of certain symptoms. Such diagnoses may be made by analyzing contemporaneous data with historical data related to one or more tracked biometric parameters and environmental changes. In one or more embodiments, the health system may also be configured to provide informational cues, to send alerts to the user and/or doctor or others, or assisting in other response means.

It should be appreciated that the health system may be configured to be autonomous (i.e., provide results directly to the user or other person or entity without input or control from a clinician or other person) or semi-autonomous (i.e., some degree of input or control from the clinician or other person. In other embodiments, the health system may be completely controlled by the clinician or other person, e.g., in a networked or an all remotely based (e.g., cloud-based) implementation (e.g., software-controlled implementation of the health system for diagnosing, monitoring, or treating the user, or in an implementation in which the health system is worn by the clinician to examine a patient.

As discussed in relation to FIG. 5, the health system may be designed with a number of additional health-related sensors, in one or more embodiments. The health system may include many sensors (e.g., accelerometers, gyroscopes, temperature sensors, pressure sensors, light sensors, non-invasive blood glucose sensors, ETCO2, EEG, and/or other physiological sensors, etc.) to monitor one or more physiological responses of the user.

As described herein, the health system comprises an eye-tracking module, in one or more embodiments. The eye tracking module may be configured to determine the vergence of the user's eyes in order to determine what the appropriate normal accommodation would be (through the direct relationship between vergence and accommodation) for the projection of one or more virtual images, and may also be configured to track one or more eye-related parameters (e.g., position of the eye, eye movements, eye patterns, etc.). This data may be used for several health-related diagnoses and treatment applications as will be described below.

As is apparent from the description herein, the health system may be used for diagnosis, monitoring, and therapy, which can include eye-related diagnosis, monitoring, and therapy. In such eye-related applications, the health system may be referred to as an ophthalmic system. As is also apparent from the description herein, the user (or wearer) of the device may be referred to as the patient where the diagnosis, monitoring, and therapy are conducted on that user by the device. In some other embodiments, the user may be a clinician and the patient is a third party, who may be evaluated are treated by the user. It will also be appreciated that the diagnosis and monitoring may be referred to generally as health analysis.

Myopia/Hyperopia/Astigmatism

Having described the various components of the ophthalmic system in the context of healthcare diagnoses and treatments, embodiments of using the ophthalmic system to compensate for common eye-related ailments will be described below. It should be appreciated that the embodiments below are for illustrative purposes only, and should not be seen in a limiting light. For example, the embodiments described herein may also be applicable to other non-ophthalmic systems as well.

Vision defects such as short-sightedness (e.g., myopia) and far-sightedness (e.g., hyperopia), astigmatisms, etc. are very common in the general population. Often, these defects are corrected through corrective lenses. In one or more embodiments, the optics of the ophthalmic system may be modulated in order to naturally compensate for a user's vision defects. In one or more embodiments, the ophthalmic system may be configured to automatically or interactively determine (e.g., during a setup process or later) an optical prescription of a user and incorporate the optical prescription in the optical sub-parts of the ophthalmic system. The optical prescription may be determined during initialization of the ophthalmic system, calibration of the system, as part of an eye-prescription configurator program (e.g., phoropter or other visual acuity examination as described herein), or at any time during use of the ophthalmic system. Biometric data may be used to identify a user and associated optical prescription. In various embodiments, the wavefront of the light projected into the user's eye may be modified based on the determined prescription. In other embodiments, alternatively or in combination, the wavefront of ambient light in front of the user, for example, light that is passed from the surrounding world in front of the user through the ophthalmic system to the user's eye, is modified to provide optical correction. Accordingly, the user's optical prescription, and changes therein, may be used to make real-time changes to the user's incoming lightfield, and may be configured to correct for one or more optical defects or aberrations. One non-limiting advantage of the embodiments described herein, is that the ophthalmic system may be configured to dynamically correct vision defects as a user's vision changes over time, for example, 2, 3, 4, 6, or more times a year without requiring replacement or substitution of parts into the system. Rather, the parts can be dynamically reconfigured electrically during use of the ophthalmic device in a real-time based on changes to the user's vision (e.g., the optical prescription).

Figure 7A:
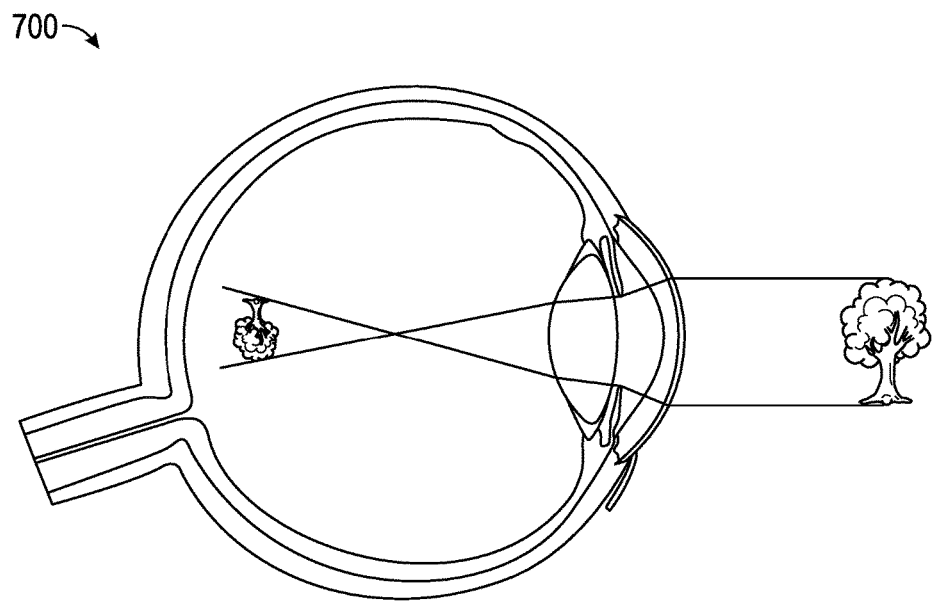
FIG. 7A-7B illustrates a schematic, cross-sectional view of a user's eye suffering from myopia.
Figure 7B:
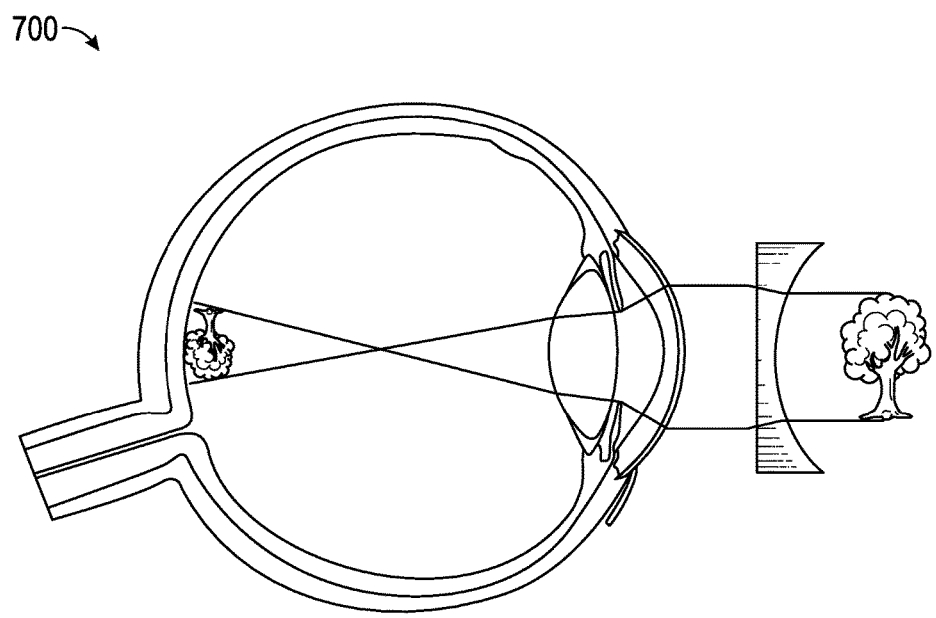

For example, in the case of myopia, light associated with one or more objects is focused in front of the retina, as shown in FIG. 7A, rather than onto the retina. This causes the objects to appear out of focus. Referring now to FIG. 7B, a concave lens can be used to compensate for the disorder, changing the nature of the incoming light, and causing the light to be focused on the retina.

In one or more embodiments, once an optical prescription of the user has been determined, a desired power spherical wavefront curvature (e.g., a negative power spherical wavefront curvature) may be encoded into the optics of the ophthalmic system to correct for the user's optical prescription. For example, the phrase "encode into the optics" may refer to applying a voltage to an electrode of an adaptable optic (e.g., in the embodiment employing adaptable optics), where the voltage to be applied to the electrode and the voltage applied thereto is determined based on the desired compensating wavefront to correct for refractive errors in the eye. Or, in the embodiment of a waveguide stack, the phrase "encode into the optics" may refer to selectively addressing a waveguide to direct light to a proper focal depth for a certain portion of the eye to generate a compensating wavefront to correct for refractive errors in the eye. In some embodiments, a negative power spherical wavefront is encoded into the optics of the ophthalmic system to correct for a user's lower order aberration (e.g., defocus), such as for correcting myopia. In an augmented reality display system, such correction may be applied to ambient light from the surrounding world, e.g., in front of the user, similar to a pair of glasses. Or, in some embodiments, either in combination or alternatively, the correction may be applied by modifying an image projected by a display in the ophthalmic system to the eye of the user (e.g., by the processor of the ophthalmic system) with the appropriate negative spherical wavefront. The phase of the projected image may thus be modified such that the projected image appears to be in focus and corrected based on the optical prescription.

Figure 8A:
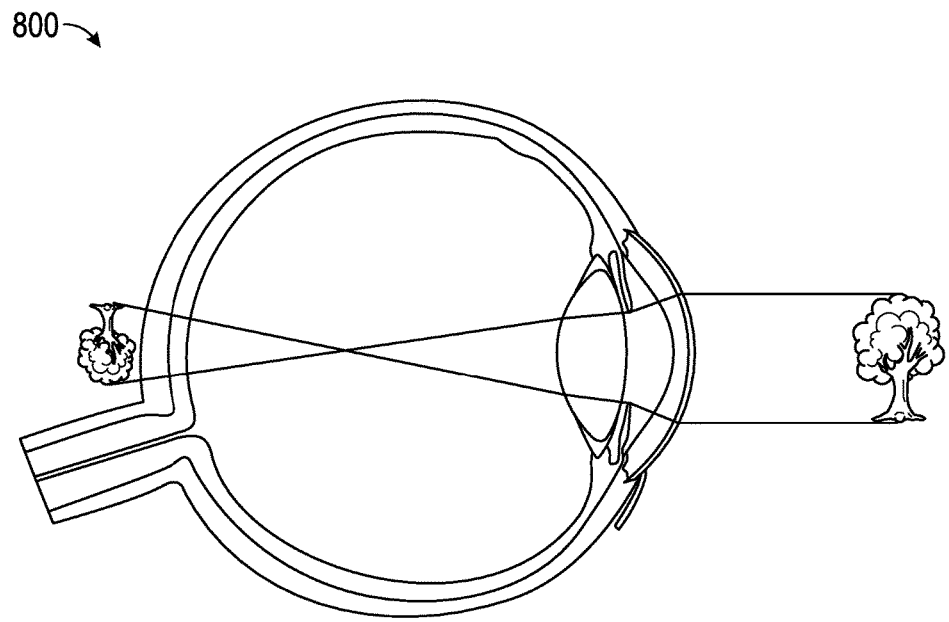
FIG. 8A-8B illustrates a schematic, cross-sectional view of a user's eye suffering from hyperopia.
Figure 8B:
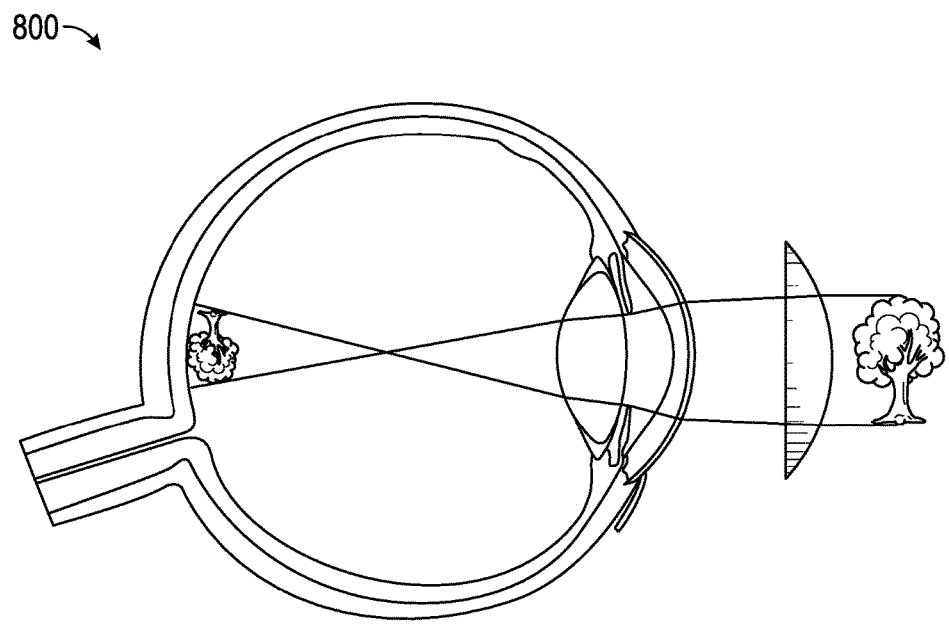

In the case of hyperopia, light associated with one or more objects is focused behind the retina, as shown in FIG. 8A, rather than on the retina. This causes the objects to appear out of focus. Referring now to FIG. 8B, a convex lens can be used to compensate for the disorder.

In one or more embodiments, once the optical prescription has been determined, a compensating spherical wavefront (e.g., a positive power spherical wavefront) may be encoded into the optics of the ophthalmic system. In some embodiments, a positive power spherical wavefront is encoded into the optics of the ophthalmic system to correct for a user's lower order aberration (e.g., defocus), such as for correcting hyperopia. Such correction may be applied to modify ambient light from the world surrounding the user, e.g., in front of the user. Or, as described above, the processor may apply the corrected wavefront to modify the image projected by the ophthalmic system based on the determined prescription such that the projected image appears to be in focus and corrected based on the optical prescription. Again, a combination of both may be used in an augmented reality system.

Figure 9A:
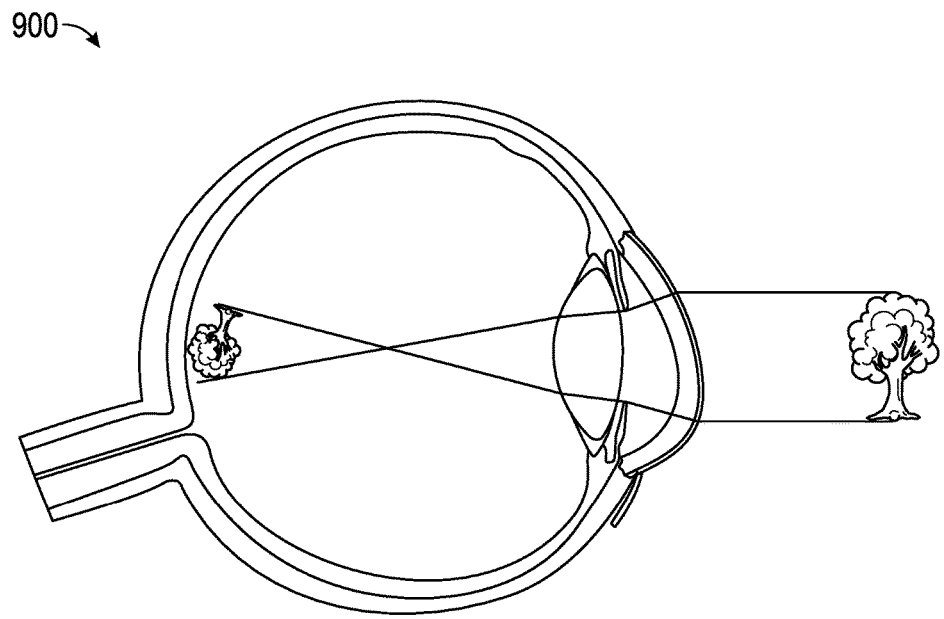
FIG. 9A-9B illustrates a schematic, cross-sectional view of a user's eye suffering from astigmatism.
Figure 9B:
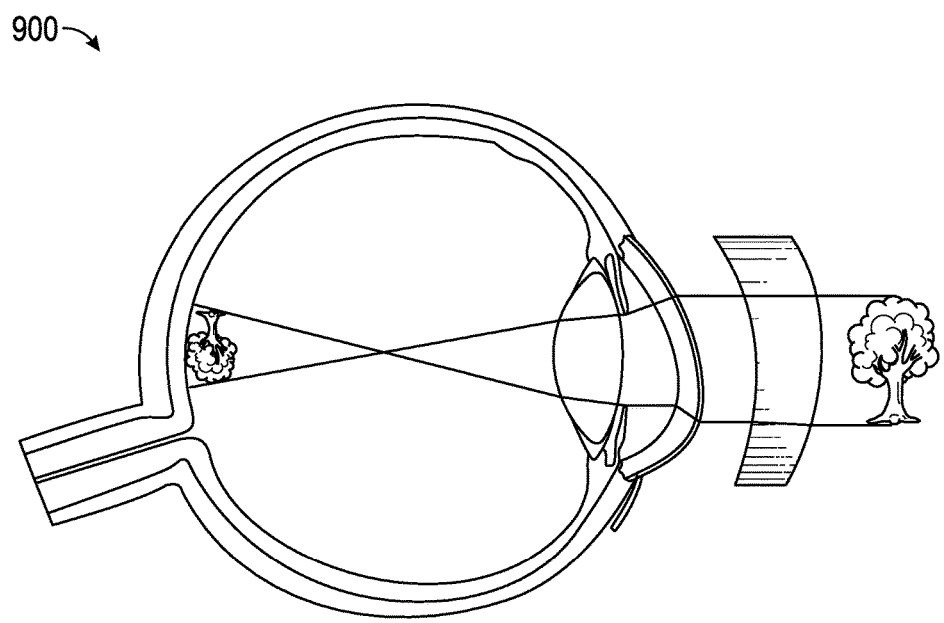

Astigmatism is a condition wherein light coming into the eye is improperly or partially focused onto the retina. As is schematically illustrated in FIG. 9A, the shape of the eye may be misshaped (usually caused by an irregularly shaped cornea) which causes the resulting image to be both out of focus and distorted. For example, the curvature along a meridian may be different than the curvature along a perpendicular meridian. Referring now to FIG. 9B, the ophthalmic device may correct astigmatism by applying an appropriate level of compensating wavefront curvature correction, e.g., along the appropriate transverse axis of the meridian.

More particularly, in various embodiments, once the appropriate optical prescription has been determined, the appropriate compensating wavefront correction may be encoded into the optics of the ophthalmic. A wavefront (e.g., a 4D wavefront) that is incident on the optics of the ophthalmic system may be modified (e.g., modify the phase of the incident wavefront) by the optics to generate a compensating wavefront that is incident on the eye of the user to correct for defects in the eye. In other words, the optics of the ophthalmic system (e.g., an adaptable optics as described below) may be configured to vary the focus and/or wavefront of the light reaching the user's eye based on, for example, the refractive error of the eye, the shape of the user's eye, e.g., the shape of the cornea and/or the lens in the eye, the length of the user's eye (e.g., the length of the eye's natural optics transmission to the retina), etc. In some embodiments, the compensating wavefront may modify the phase of the wavefront incident on the optics of the ophthalmic device.

In some embodiments, higher order aberrations may be difficult to compensate for by spherical wavefront correction as described above. Thus, in some embodiments, multiple, independently controllable lenses may be controlled by the ophthalmic system to form a complex lens that may correct for higher order aberrations, as described below. In other embodiments, alternatively or in combination, the ophthalmic system may be configured to retrieve a known aberration pattern based on the prescription of a user and apply this pattern to an image stored in the ophthalmic system to be presented to the eye of the user.

For example, the ophthalmic system may store one or more images that may be retrieved by the ophthalmic system. In some embodiments, the images may be pre-loaded or generated by the ophthalmic system. In some embodiments, the images may be part of a moving image (e.g., a video). In other embodiments, the images may be feed from another source external to the ophthalmic system (e.g., remote data repository (72)). In other embodiments, alternatively or in combination, the images may be obtained based on ambient light in front of the ophthalmic system, as described herein. The image may be projected by the ophthalmic system to the user, and may be modified by the software included in the ophthalmic system. The ophthalmic system may generate one or more 2D images to be presented to the eye of a user, and the system may be configured to modify these images prior to projecting the images based on the optical prescription of the user. In some embodiments, as described below for an embodiment of the ophthalmic system comprising a waveguide stack, different image content projected at different focal depths provides the user a 3D perception of images. Thus, each image may be a 2D representation of an image at a different focal depth. Each image may be modified individually by software included in the ophthalmic system. For example, the pattern or collection of pixels that form each image can be modified to counter, offset, or reduce effects of errors introduced by the eye.

For example, defects in the retina of a user's eye may result in errors as to the intensity, shape, magnification, or color viewed by the user. In various embodiments, the wavelength of light or intensity of light of an image projected by the ophthalmic system may be modified to account for color blindness in the eye of the user. For example, the wavelength of the light presented to the user may be changed based on the color blindness prescription to compensate for the color blindness. In some embodiments, modification of the 2D images (e.g., each of which may be a 2D representation of an image at different focal depths) may be employed to correct for dead spots or weak spots in the eye. For example, by mapping the eye to determine dead/weak spots, the intensity of light of a projected image may be increased for identified areas of the eye or retina having dead or weak spots. Thus, in some embodiments, modification of the image may be performed by modifying the intensity of one or more portions of the image to be presented. For example, a fiber scanning display or a spatial light modulator included in the ophthalmic system may vary intensity while generating the image.

Another example of modifying an image comprises modification of the intensity pattern of the image. For example, if it is known that the image viewed by the user will exhibit radial distortions (e.g., barrel, pincushion, or mustache distortions) a compensating distortion may be applied to the image to correct for such distortions. The distortions sought to be corrected may be a result of either refractive errors in the eye or by the optics of the ophthalmic system, thus would be known by the optical prescription, or the ophthalmic system. Thus, the ophthalmic system may modify the intensity pattern of a projected image to compensate for the refractive errors. For example, if a user's eye were to introduce pincushion distortion to the image, the ophthalmic system may be configured to modify the intensity pattern of the image projected to the user via the display to include barrel distortion in an amount so as to cancel out or reduce the amount of pincushion distortion in the image on the retina, which is the opposite of pincushion distortion. Similarly, the ophthalmic system may be configured modify the image by adding pincushion distortion to the intensity pattern making up the image on the display if the user's eye introduced barrel distortion. In some embodiments, the modification of the image may be done to correct for fisheye distortions by altering the image presented by the display by applying a distortion of opposite angle and amount.

In various applications, a combination of wavefront correction and modification of an image generated by the ophthalmic system (e.g., modification of the intensity pattern comprising the image) may be used to compensate for the astigmatism or any other defect in the user's eye.

In some embodiments, the ophthalmic system may be a patient-worn ophthalmic device as illustrated in FIGS. 3A-3D and 5 that may be implemented for correcting vision defects like myopia, hyperopia, and astigmatism. The ophthalmic device includes a display device (62) that includes a light source (18) configured to project light (38) that is directed into the eyes of a user in a display lens (106) of the display device (62). The ophthalmic device may also direct ambient light from the surrounding world, e.g., in front of the user, to the eyes of the user through display lens (106). The display device (62) also comprises one or more adaptable optics (e.g., variable focus elements or VFEs, electrically reconfigurable reflective or refractive optical elements, etc.). Such adaptable optics may be included in the display lens (106) or located between the display lens (106) and the light source (18) or between the display lens (106) and the eye or elsewhere in the path of light to the eye. The adaptable optics or VFE is an optical element that can be dynamically altered, for example, by applying an electrical signal thereto to change the shape of a wavefront that is incident thereon. The adaptable optics may be a reflective optical element such as a deformable mirror or a transmissive optical element such as a dynamic lens (e.g., a liquid crystal lens, an electro-active lens, a conventional refractive lens with moving elements, a mechanical-deformation-based lens, an electrowetting lens, an elastomeric lens, or a plurality of fluids with different refractive indices). By altering the adaptable optics' shape or other characteristics, the wavefront incident thereon can be changed, for example, to alter the focus of the wavefront as described herein to provide optical correction.

In various embodiments, the ophthalmic device includes outward facing cameras configured to capture ambient light from the environment surrounding the user. For example, the ophthalmic device may include one or more wide-field-of-view machine vision cameras (16) operatively coupled to local processing module (70). These cameras may be configured to image the environment around the user. In one embodiment these cameras (16) are dual capture visible light/infrared light cameras. Images taken by cameras (16) may be stored in a digital memory of the ophthalmic device and retrieved for subsequent processing. The images may then be retrieved by the ophthalmic device, which may then re-render the obtained images to the user by projecting the images through display device (62).

In various embodiments, the ophthalmic device may comprise a biofeedback system configured to determine a comfort level of the user in viewing an object or image. For example, if a user's eyes are shifting, changing accommodation, changing pupil size, changing vergence, etc., these may be indicators that the user is unable to comfortably view an object or image. In some embodiments, changes in accommodation or behavior associated with accommodation may be represented as an unsteady, random fluctuation, instability and/or oscillation in the accommodation or behavior of the eye. Instability or oscillation in accommodation or behaviors associated with accommodation may be a sign that the user is struggling with focusing on or accommodating on an object or image. Accordingly, the biofeedback system may receive real-time inputs relating to the state or properties of the user's eye.

In various embodiments, the ophthalmic device includes one or more eye tracking cameras or other cameras or imaging systems to track one or more eyes of the user. For example, some embodiments may utilize cameras (24) (e.g., infrared cameras) paired with light sources (26) (e.g., infrared light sources) configured to monitor and track the eyes of the user. These cameras and sources can be operatively coupled to the local processing module (70). Such cameras and/or imaging systems can monitor the orientation of the eyes, pupil size of the eyes, vergence of the eyes, and the corresponding direction of the line of sight of the respective eyes. As described below in connection with phoropter technology, the cameras (24) may be configured to determine accommodation of the eyes of the user. In some embodiments, the cameras (24) may be configured to determine the convergence point of the eyes, as described above in reference to FIGS. 5 and 6.

In some embodiments, the ophthalmic device comprises gyroscopic sensors, accelerometers, other sensors, or a combination thereof to monitor changes in the head position, head pose or orientation. In some embodiments, the display device (62) may comprise a sensor assembly (39) configured to detect movement imparted onto and orientation of the display device (62) due to movement of the user's head. The biofeedback system may be configured to receive the detected head movement, and if the frequency and/or magnitude of movement is beyond a threshold, the system may be configured to determine that the user is unable to comfortably view the image. For example, constant head movement may be indicative of a searching for a comfortable viewing position of the image. If such signs are present that the person may not be focusing well, then the ophthalmic system may be configured to alert the user of such, perform a phoropter test or other vision test, or may objectively and automatically evaluate the user's prescription to improve vision quality.

In some embodiments, the adaptable optics may be operatively coupled to a local processing module (70) and configured to compensate for vision defects of the wearer as shown in FIG. 3C. The local processing module (70) may store the one or more optical prescriptions of the user. Or, in some embodiments, the local processing module (70) may store one or more image modification programs (e.g., programs configured to modify an image presented to the wearer) that correspond to one or more optical prescriptions. The local processing module (70) may be configured to encode the appropriate compensating wavefront into the adaptable optics of the display device (62) and/or modify the image generated by the ophthalmic system based on an optical prescription and/or an image modification program. For example, as will be described in greater detail below with reference to FIGS. 10A and 11, the local processing module (70) may execute logic devices configured to modify the VFE or adaptable optics to generate a corrected wavefront, based on the optical prescription, of an image generated by the ophthalmic device and/or ambient light presented to the eye of the use.

In some embodiments, the ophthalmic device may include one or more transmitters and receivers to allow transmission and reception of data between the ophthalmic device and the remote processing module (72) and/or remote data repository (74). In some embodiments, any of the processing steps executed by the local processing module (70) and digital memory therein may be performed remote from the user by remote processing module (72) operatively coupled to remote data repository (74).

In some embodiments, the display device (62) includes one or more VFE or adaptable optics included with the display lens (106). For example, the VFE or adaptable optics may be included with a waveguide stack, as described in connection with FIG. 10E. For example, the VFE or adaptable optics (316a, 316b) may be disposed between the surrounding world and the waveguide stack or between the user and the waveguide stack. Thus, the VFE or adaptable optics may be configured to modify the wavefront of projected light (38) that produces the image generated by the display device (62) of FIG. 5 and/or the ambient light surrounding the user, e.g., in front of the user. In another embodiment, in the alternative or in combination, the VFE or adaptable optics may be disposed between the light source, for example, the plurality of displays (200, 202, 204, 206, 208), and the with the waveguide stack shown in FIG. 10E. In this case, the wavefront of the image generated by the ophthalmic system may be modified without also modifying the wavefront of ambient light passed to the eye of the user.

The VFE or adaptable optics may be any optical element implemented to modify the wavefront of the image. In various embodiments, the light (38) projected by the display is incident on one or more VFE or adaptable optics, and the VFE or adaptable optics may modify the phase of the wavefront incident thereon. The modified wavefront may propagate to the user who perceives an image based on the modified wavefront. In another embodiment, the VFE or adaptable optics modify the ambient light in front of the user to correct for vision defects experienced when viewing the outside world. As described below, FIGS. 10B-10D illustrate example configurations where VFE or adaptable optics as used in the ophthalmic system as disclosed herein to correct for vision defects. However, it will be understood that other VFE or adaptable optics may be used.

The VFE or adaptable optics may achieve a variable focus and resultant wavefront modification by utilizing transmissive, refractive, diffractive, or reflective techniques. For example, the VFE or adaptable optics may be a refractive element, such as a liquid crystal lens, an electro-active lens, a conventional refractive lens with moving elements, a mechanical-deformation-based lens (such as a fluid-filled membrane lens, or a lens akin to the human crystalline lens wherein a flexible element is flexed and relaxed by actuators), an electrowetting lens, or a plurality of fluids with different refractive indices. The VFE or adaptable optic may comprise one or more lenses formed using flexible and deformable elastomers (e.g., elastomeric lenses). Such elastomeric lenses may be configured to receive a voltage applied to electrodes disposed at different axes of the lens, the voltage may impart a strain along the axes thereby modifying the shape of the lenses and varying the optical power. The VFE or adaptable optics may also comprise a switchable diffractive optical element (such as one featuring a polymer dispersed liquid crystal approach wherein a host medium, such as a polymeric material, has microdroplets of liquid crystal dispersed within the material; when a voltage is applied, the molecules reorient so that their refractive indices no longer match that of the host medium, thereby creating a high-frequency switchable diffraction pattern). Other arrangements are possible, as described below in connection with FIGS. 10B-10E.

FIGS. 10B and 10C illustrate an example embodiment of adaptable optics. For example, the adaptable optics may comprise a variable focus element (VFE) (1020) (e.g., a deformable mirror membrane, any mirror-based VFE, deformable lens, elastomeric lens, phase modulator, etc., as described above). In some embodiments, the VFE (1020) may be integrated with or embedded in the display lens (106). In some embodiments, for example, one or more adaptable optical elements or VFEs (1020) may be integrated with a stacked waveguide assembly and/or disposed on one or more sides thereof.

FIG. 10B illustrates an example embodiment of modifying a shape of a VFE (1020) based on a shape of a cornea (1026) is illustrated. In order to compensate for astigmatism, or any other corneal defect, the phase and/or focus of the light displayed to the user may be modified based on the shape of the cornea (1026). For example, where the displayed image includes ambient light from the surroundings, e.g., in front of the user, the focus of the light transmitted through the lens to the wearer (e.g., the focal depth) is modified in real-time, as the user moves about the surroundings and light is transmitted through the lens to the wearer. In another embodiment, where the displayed image is an image generated by the ophthalmic system to be displayed by the ophthalmic system as the user moves, the modification of the phase and/or focus of the light can be done on a per frame or per pixel basis, as the user moves about the surroundings, based on the shape of the cornea (1026). For example, a wavefront correction may be applied to each frame of an image, and may be different between frames, and/or the wavefront may be corrected for each pixel of a display, which may be different between the pixels. In one or more embodiments, the ophthalmic system may determine the refractive errors caused by the eye of the user, for example, the shape of the user's cornea (1026), and modify a shape of the VFE (1020) based on the shape of the cornea. See, for example, the description below in connection with aberrometry and retinoscopy technology. Although reference in this example is made to the shape of the cornea as the cause of the vision defect, correction can be performed for other causes of refractive error.

Some VFEs such as deformable membrane (e.g., lens or mirror) VFEs (1020) are coupled to a set of electrodes (1022) that are then selectively controlled in order to modify the shape of the membrane (e.g., lens or mirror), and consequently change the phase, wavefront shape, and possibly the focus of the light. As shown in FIG. 10B, the electrodes (1022) may be controlled in a manner such that the shape of the VFE (1020) complements the shape of the cornea (1026) (or other refractive error) such that the image may be appropriately viewed by the user's eye as shown in FIG. 10C. It should be appreciated that such techniques of changing the shape of the VFE (1020) for every frame (or every pixel) may be used for other applications such as other types of causes of refractive errors as detailed below as well, and the astigmatism example of FIG. 10C is an example only.

With reference to FIG. 10D, the VFE or adaptable optics can be included with a waveguide stack (178) and can be driven to compensate for the shape of a user's cornea or address any other refractive condition of the user. The optics illustrated in FIG. 10D comprises a stacked waveguide assembly of transmissive beamsplitter substrates, each of which is configured to project light at a different focal plane or as if originating from a different focal plane. For example, a first waveguide may be configured to modify the wavefront of incident light by a first optical power while a second waveguide may modify the wavefront by a second optical power. The first and second optical powers may be spherical wavefront corrections and they may be positive or negative corrections. The first and second optical powers need not be the same degree of correction or same direction of curvature correction. The VFE or adaptable optics of FIGS. 10D and 10E may be integrated with the display lens (106) of FIG. 5 and configured to both project an image generated by the ophthalmic system and permit ambient light to pass through the waveguide stack to the user's eye.

The stacked waveguide assembly (178) may be utilized to provide three-dimensional perception to the eye/brain by having a plurality of waveguides (182, 184, 186, 188, 190) and a plurality of lenses (198, 196, 194, 192) configured together to send image information to the eye with various levels of wavefront curvature for each waveguide level indicative of focal distance to be perceived for that waveguide level. In some embodiments, the plurality of lenses (198, 196, 194, 192) are weak lenses, however, it will be understood that lenses (198, 196, 194, 192) are not to be limited to such and may be any lens suitable for providing the desired properties of the waveguide stack (178). A plurality of displays (200, 202, 204, 206, 208), or in another embodiment a single multiplexed display or reduced number of multiplexed displays, may be utilized to inject light, e.g., collimated light with image information into the waveguides (182, 184, 186, 188, 190), each of which may be configured to distribute incoming light substantially equally across the length of each waveguide, for exit down toward the eye.

In some embodiments, one or more of the plurality of lenses (198, 196, 194, and 192) may be adaptable optics, as described above, configured to provide for prescription correction in accordance with the embodiments described herein. In this case, the lenses (198, 196, 194, and 192) may be adaptable optics that are dynamic, adaptable, or switchable, such that the shape and/or characteristics of these lenses may be altered to provide refractive correction based on the prescription of the use. For example, the lenses (198, 196, 194, and 192) may comprise switchable adaptable optical elements, deformable lens such as an elastomeric lens with electrodes as described herein, or VFEs of FIGS. 10B and 10C and or any of the transmissive lenses described herein.

The waveguide (182) nearest the eye may be configured to deliver collimated light, as injected into such waveguide (182), to the eye, which may be representative of the optical infinity focal plane. The other waveguides may be configured to represent focal planes closer than infinity at a range of diopters, giving the user 3D perception of images generated by the ophthalmic system as different image content from different waveguides will appear to originate from different depths or distances from the user.

For example, the next waveguide up (184) is configured to send out collimated light which passes through the first lens (192; e.g., a weak lens, for example, a weak negative lens) before it can reach the eye (58); such first lens (192) may be configured to create a slight convex wavefront curvature so that the eye/brain interprets light coming from that next waveguide (184) as coming from a first focal plane closer inward toward the person from optical infinity. Similarly, the third waveguide (186) passes its output light through both the first (192) and second (194) lenses before reaching the eye (58); the combined optical power of the first (192) and second (194) lenses may be configured to create another incremental amount of wavefront divergence so that the eye/brain interprets light coming from that third waveguide (186) as coming from a second focal plane even closer inward toward the person from optical infinity than was light from the next waveguide (184).

The other waveguide layers (188, 190) and lenses (196, 198) are similarly configured, with the highest or furthest waveguide (190) in the stack sending its output through all of the lenses between it and the eye for an aggregate focal power representative of the closest focal plane to the person. To compensate for the stack of lenses (198, 196, 194, 192) when viewing/interpreting light coming from the world (144) on the other side of the stacked waveguide assembly (178), a compensating lens layer (180) is disposed at the top or in front of the stack to compensate for the aggregate power of the lens stack (198, 196, 194, 192) below. Such a configuration provides as many perceived focal planes as there are available waveguide/lens pairings. Both the reflective aspects of the waveguides and the focusing aspects of the lenses may be static (i.e., not dynamic or electro-active or electrically switchable). In an alternative embodiment they may be dynamic using, for example, electro-active or electrically driven changes of features as described above. Such dynamic configurations can enable a small number of waveguides to be multiplexed in a time sequential fashion to produce a larger number of effective focal planes. In addition, such dynamic configurations can enable the dynamic correction of refractive errors of the user's eye.

As shown in 1050, the eye 58 is a normal eye having a normal cornea. In this case, the different waveguides interact with the eye/cornea providing images at various focal planes. In the case of an abnormal cornea, as shown in 1060, the adaptable optics of each of the waveguides may be selectively addressed in order to complement the irregular shape of the cornea. The adaptable optics of each waveguide may comprise a reflective optical element such as a deformable membrane mirror or a partially or fully transmissive optical element such as a dynamic lens (e.g., a liquid crystal lens, an electro-active lens, a conventional refractive lens with moving elements, a mechanical-deformation-based lens, an electrowetting lens, an elastomeric lens, or a plurality of fluids with different refractive indices). For example, lenses of a first waveguide may be identified to receive light of the wavefront of an image from one of the plurality of displays. The lenses of an identified waveguide may be selectively deformed or addressed to reflect or pass the light while modifying the incident wavefront and generating a desired wavefront curvature indicative of focal distance to correct for the irregular shape of the cornea. Thus, the focus and/or the wavefront of the image may be carefully distorted/changed by selecting the configuration of the lenses for each of the waveguides to produce an appropriate wavefront curvature to the user, thereby correcting for any irregular shape of the cornea, length of the eye, irregular lens shape or the refractive error of the eye or combination of those.

Figure 10A:
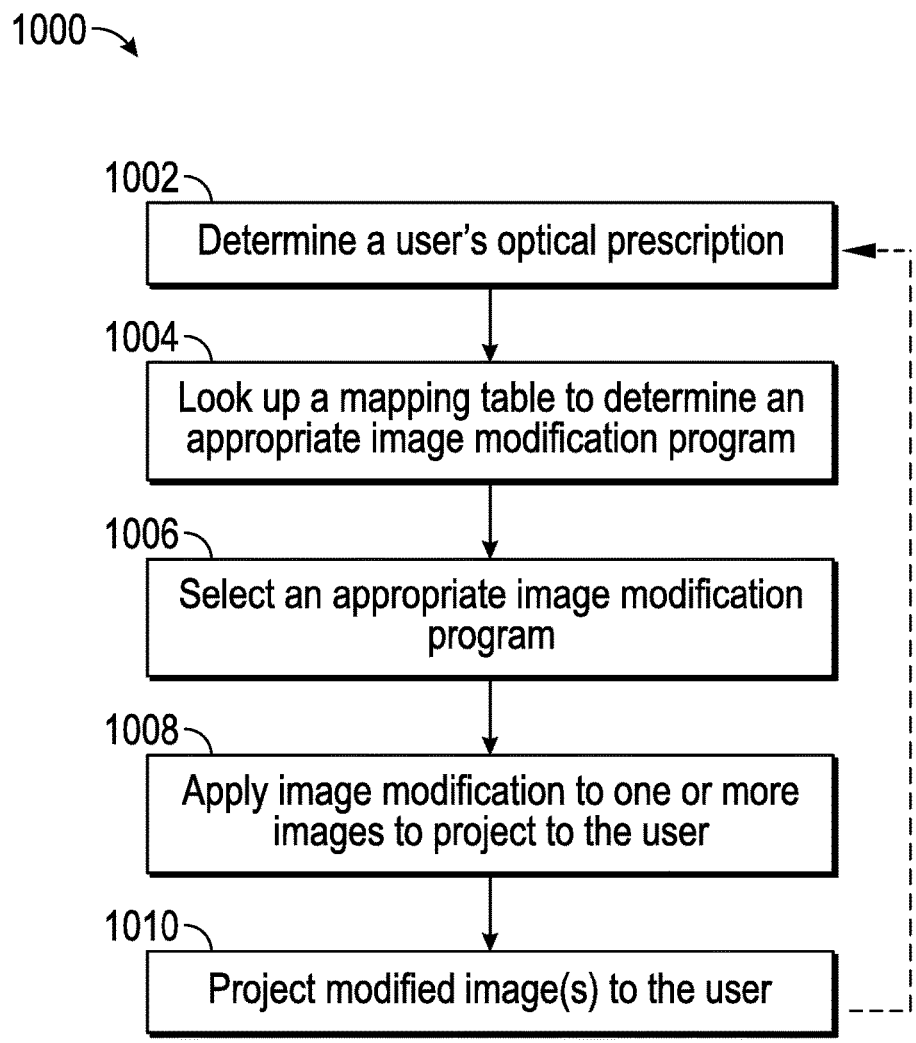
FIG. 10A illustrates an example process flow for correcting for vision defects according to some embodiments.
Figure 10B:
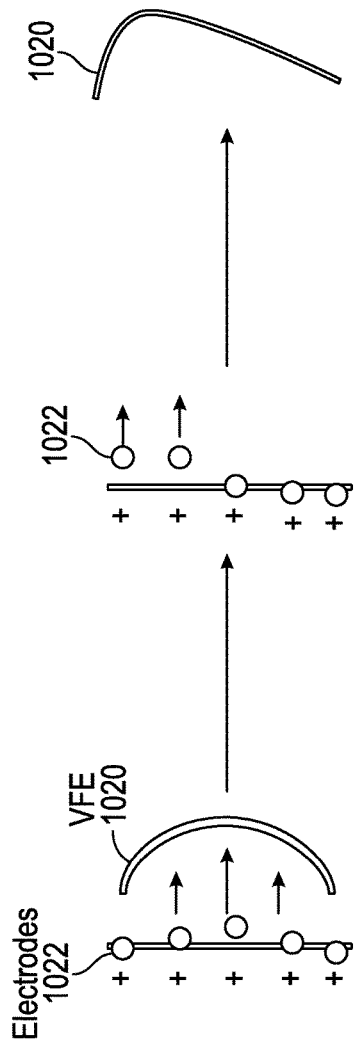
FIG. 10B-10E illustrates examples of structures for correcting optical prescriptions according to some embodiments.
Figure 10C:
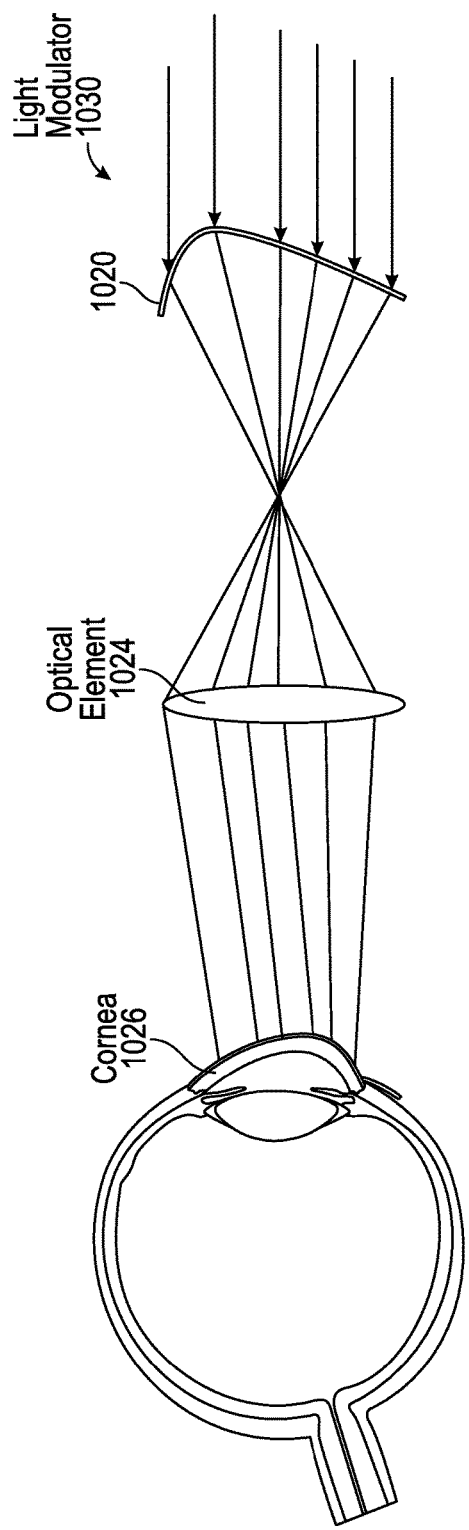
Figure 10D:
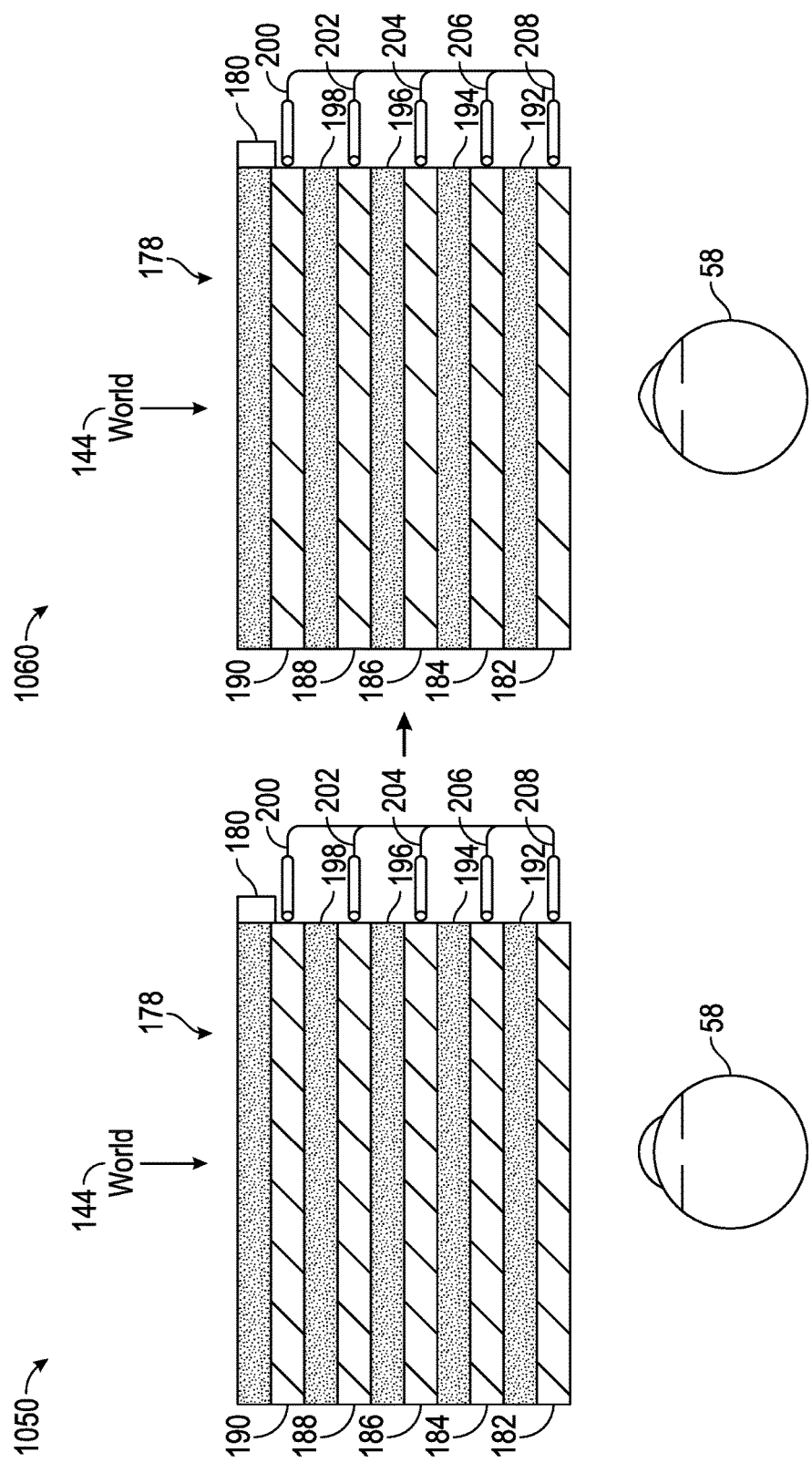
Figure 10E:
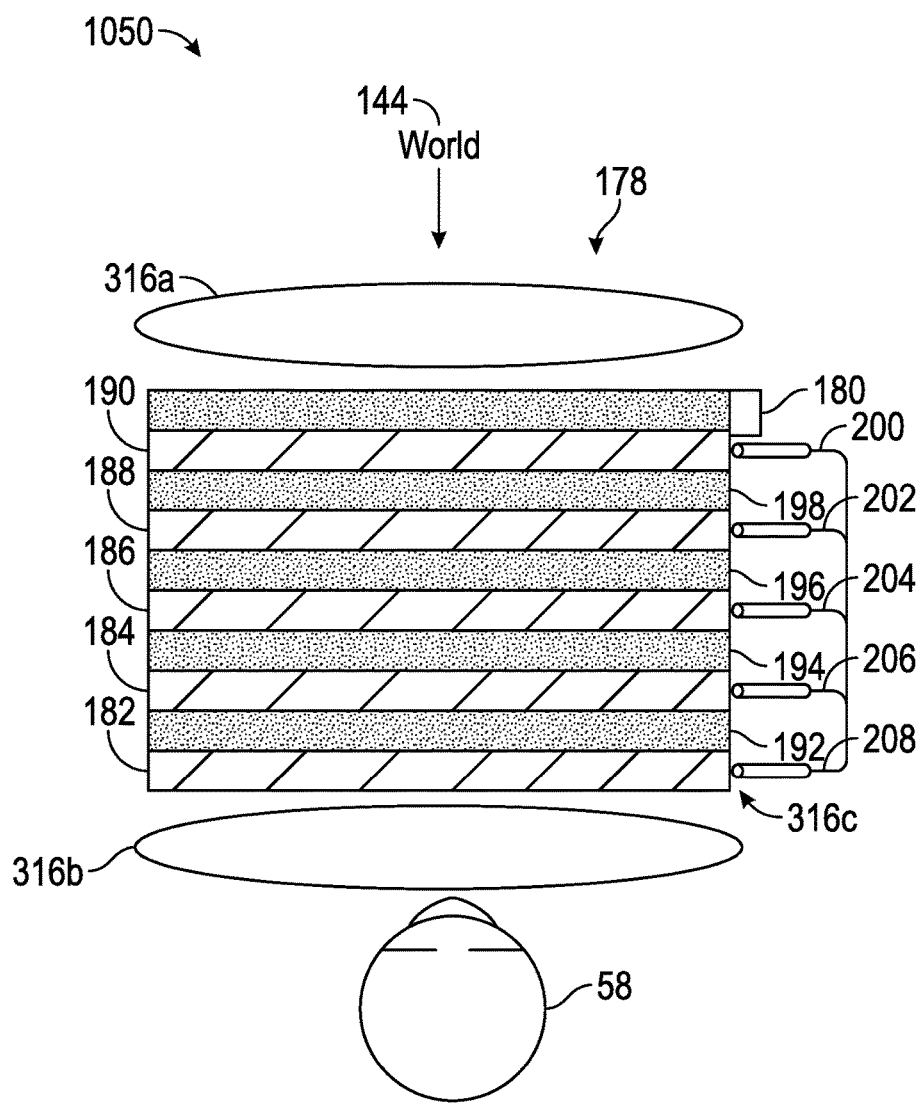

FIG. 10E illustrates example embodiments of arrangements of VFE or adaptable optics. In some embodiments, the ophthalmic system may include both the stacked waveguide assembly (178) of FIG. 10D and one or more VFE or adaptable optics (1020) of FIGS. 10B and 10C as shown in FIG. 10E. For example, the stacked waveguide assembly (178) may be embedded in or integrated with the display lens (106). In some embodiments, a VFE or adaptable optics (1020) may also be embedded in or integrated with the display lens (106). In one implementation, the VFE or adaptable optics (1020) may be positioned between the stacked waveguide assembly (178) and the surrounding world (e.g., adaptable optics 316*a*). In another implementation, the VFE or adaptable optics (1020) may be positioned between the stacked waveguide assembly (178) and the user (e.g., adaptable optics 316*b*). In yet another embodiment, one or more VFEs or adaptable optics (1020) may be positioned between the stacked waveguide assembly (178) and the plurality of displays (200, 202, 204, 206, and 208). There may be a single VFE or adaptable optic (1020) between the stacked waveguide assembly (178) and all of the plurality of displays (200, 202, 204, 206, and 208). Or, there may be multiple VFEs or adaptable optics (1020), for example, a VFE or adaptable optics (1020) for each of displays (200, 202, 204, 206, and 208) (e.g., adaptable optics 316*d*). The VFE or adaptable optics (1020) may be positioned between the light source (18) and the waveguide stack (178) or may be integrated into the light source (18). The VFE (1020) or adaptable optics may be integrated in the waveguide stack (178). In another embodiment, the VFE or adaptable optics (1020) may be disposed between the one or more of the plurality of waveguides (182, 184, 186, 188, 190) and configured to be altered so as to provide vision correction based on the optical prescription.

Accordingly, various embodiments of an ophthalmic system may include a light modulator configured to variably project light beams of varying focal depth, through a fiber scanner, or other light generating source, in a raster pattern across the retina. In this embodiment, the ophthalmic system may be able to project images at varying focal distances to compensate of vision defects, in a manner similar to the stacked waveguide assembly (178). Similarly, the light source may be configured to provide refractive correction to correct for myopia, hyperopia, or astigmatism based on the optical prescription of the user. In various embodiments, the ophthalmic system includes one or more spatial light modulators configured to modulate the phase of the light and alter the shape of the wavefront to provide suitable optical correction based on the user's prescription. Such phase modulator may receive light from the light source mounted on the ophthalmic system. In some embodiments, the spatial light modulators are included in addition to the adaptable optics or VFEs described herein.

In some embodiments, the ophthalmic system may be an augmented reality system that uses AR and/or VR techniques to compensate for the shape of a user's cornea and/or otherwise correct for vision defects. For example, the ophthalmic system may be an augmented reality head mounted display system configured to pass light from the world in front of the user of the augmented reality system into an eye of a person wearing the ophthalmic system. In such embodiments, the ophthalmic system also corrects or modifies the wavefront of the lighted passed from the world based on an optical prescription of the person wearing the ophthalmic system. Such an ophthalmic device can also be configured to provide wavefront correction to AR image content generated by the ophthalmic system and projected to the eye of the user. In this way, the ophthalmic system modifies the images content presented to the wearer to correct for myopia, hyperopia, astigmatism, etc.

In another embodiment, in the alternative, the ophthalmic system is a VR head mounted display system that is opaque and blocks the transmission of ambient light formed in front of the user and the VR head mounted display. The VR head mounted display may be configured to display only virtual image content to the wearer or user. In some embodiments, where ambient light is formed in front of the user and thus is blocked by the VR head mounted display system, the VR head mounted display system may, however, include outward facing cameras (e.g., wide-field-of-view machine vision cameras (16)), which provide a view of the world in front of the user. These cameras may capture the ambient light in front of the user, reproduce images containing views of the world in front of the user on the display, and project these images onto the eyes of the user. The virtual image content may be modified by a wavefront correction based on the optical prescription in a manner similar to the AR image content of the augmented reality head mounted display system. Such as described above, for example, one or more adaptable optics, such as shown in FIG. 10E, may be adjusted to provide suitable refractive correction. Such ophthalmic systems can be configured to provide wavefront correction to the virtual reality image content. While the VR system is opaque to ambient light, VR image content may be any image content stored in the memory or generated by the ophthalmic system, including images of ambient light in front of the user obtained by the outward facing cameras.

Referring now to FIG. 10A, an example process flow of correcting vision defects like myopia, hyperopia, and astigmatism is briefly discussed. The process flow 1000 is directed to modifying an image presented to the user based on a prescription of the user. In some embodiments, process flow 1000 may be performed by patient-worn ophthalmic devices, such as those described in connection with FIGS. 3A-3D. The process flow 1000 can be implemented by the local processing module (70) configured to execute logic devices in the local processing module (70). In another embodiment, local processing module (70) may implement process flow 1000 via the remote processing module (72) executed by logic devices in the local processing module (70) operably connected to the remote data repository (74). Adaptive optics such as electrically reconfigurable mirrors or lenses such as lenses located as shown in FIGS. 10B-10E may be used to provide refractive correction based on the user's optical prescription.

Referring now to process flow 1000, at 1002, the ophthalmic system may determine a prescription of the user. In one or more embodiments, the user may simply provide the ophthalmic system with the information. For example, the user may input a prescription into a user interface. Or, in other embodiments, the ophthalmic system may go through an eye-prescription configurator program to manually and interactively determine the user's prescription, as will be described further below. For example, the ophthalmic device may be pre-programmed with discrete granular steps in adjusting focus or altered wavefronts. Adjusting the focus many include adjusting the focus on a first meridian and/or a second meridian, where adjustment to one meridian may be independent of adjustments to the other. The user may then specify a desired wavefront, which may define an optical prescription, to the ophthalmic system through an appropriate feedback mechanism (e.g., a user interface). Or, in another embodiment, the user may have the option of incrementally increasing or decreasing a prescription (e.g., changing the focus and/or wavefront) until the user arrives at a comfortable viewing prescription. See, for example, the description below in connection with phoropter technology.

In another embodiment, the ophthalmic system may automatically and incrementally change the user's prescription in real-time, without requiring user input, based tracking and monitoring the eyes via the eye-tracking system or other systems as described herein. In some embodiments, the ophthalmic system may utilize the biofeedback system to automatically change the user's prescription. For example, if a user's eyes are shifting, unstable, oscillating, changing (e.g., in an unsteady or random manner) accommodation, etc., these may be indicators that the user is unable to comfortably view the object. Accordingly, the biofeedback system may receive real-time inputs relating to the state of the user's eye. If a determination is made that the user is unable to comfortably view the virtual reality content, augmented reality content, or real content from ambient light from in front of the user and displayed through the display device (62), then the ophthalmic system may automatically initiate an eye-prescription configurator program (e.g., phoropter, autorefractor, or other visual acuity examinations as described herein).

In some embodiments, as described above, the biofeedback system may utilize the eye-tracking system to provide real-time inputs related to the eye of the user. For example, as described below in connection with phoropter technology, the eye tracking system may monitor the accommodation state. The eye tracking system may detect a fluctuation (e.g., changes) in the accommodation of the eyes, for example, by comparing multiple measurements. In some embodiments, the accommodation may be monitored by monitoring the shape of the lens of one or more eyes, vergence of the eyes, pupil size of one or more eyes, etc. In some embodiments, monitoring the accommodation state may comprise projecting a small image into the eye (e.g., a dot or multiple dots) and, using inward facing cameras, monitor whether the image is focused on the fovea of the retina or changes position. For example, as described herein in connection with autorefractor, phoropter, and SLO technologies. Fluctuations in accommodation may indicate an uncomfortable focal depth or blurred image. Thus, the ophthalmic system may increase or decrease the prescription until the fluctuations cease or lessen, thereby arriving at a comfortable viewing prescription.

Similarly, the biofeedback system may also receive inputs concerning changes in eye position or gaze orientation, and/or changes in the head position of the user. In some embodiments, where these inputs are constantly changing within determined threshold (e.g., a determined frequency of change), the biofeedback system may be configured to determine that the user is unable to view the object or image conformably. Accordingly, the ophthalmic system may be able to change the optical prescription of the user in real-time without requiring user input indicating the comfort level of viewing an image by, for example, alerting the user of the need for a new optical prescription or initiate a test to update the prescription.

In some embodiments, the ophthalmic system may be configured to receive an optical prescription from a third party. For example, a doctor may be able to send a user optical prescription wirelessly (e.g., over the internet, Bluetooth connection, etc.), which is received by a receiver and stored in the digital memory of the local processing module (70).

At 1004, the system may look up a mapping table to determine an appropriate image modification program (e.g., a program with an appropriate set of parameters) to modify one or more images to be presented to the user. In some embodiments, the mapping table may comprise an association of different optical prescriptions to different image modification programs. For example, for a given optical prescription of the user, the mapping table may list an image modification program configured to compensate for the vision defects as defined by the optical prescription.

In one embodiment, the image modification program defines modifications to the incident wavefront to generate a compensating wavefront. In another embodiment, the image modification program defines modification to the 2D image generated by the ophthalmic system and presented to the eye of the user. In one or more embodiments, the ophthalmic system may be pre-coded with such programs, or these programs may be downloaded in order to perform image modulation based on the prescription. See, for example, the description below in connection with phoropter technology. In some embodiments, the remote processing module (72) may be executed to retrieve or look up the mapping stored in the remote data repository (74).

In some embodiments, each image modification program may comprise a set of parameters to be applied to the VFE or adaptable optics of display device (62) based on the desired wavefront correction. Such parameters may be a set of signals (e.g., electrical signals) that define the modifications to be applied to the shape and/or characteristics of the adaptable optics, thereby altering the wavefront. For example, for the VFE or adaptable optics, which may comprise one or more VFEs or adaptable optics (e.g., as described above, for example, in connection with FIGS. 10B-10E), the parameters may define the modification to the shape of the VFE or adaptable optics such that the wavefront presented to the user is similarly modified. In another embodiment, where the VFE or adaptable optics is included in a waveguide stack (e.g., as described above in connection with FIG. 10D), the parameters may define changes to be applied to adaptable optics integrated into the waveguides, so as to alter the phase, focal length, and wavefront of incident light based on the optical prescription. In yet another embodiment, where the ophthalmic device comprises a light modulator such as a phase modulator configured to variably project light beams of varying phase and possibly focus in a raster pattern, the parameters may define the phase and/or focus of the raster pattern. By modulating the phase, the wavefront projected by the light beams may be controlled to correct for vision defects.

In another embodiment, each image modification program may comprise a set of parameters to be applied to the image generated by the ophthalmic system based on the desired modification to the image. For example, as described above, the ophthalmic system may modify the color, magnification, shape, intensity, and/or distortion to correct for defects in the eye. In some applications, the image modification program may include parameters to modify the wavefront (e.g., phase) and the image in combination.

The parameters of the image modification program and corresponding set of signals may be based on the optical prescription. For example, in the case of myopia, the image modification program may have a set of parameters configured to encode a negative power spherical wavefront curvature into the optics of the ophthalmic system (e.g., the VFE or adaptable optics of display device (62)). In the case of hyperopia, the image modification program may have a set of parameters configured to encode a positive power spherical wavefront curvature into the optics of the ophthalmic system. In the case of astigmatism, the image modification program may have a set of parameters configured to define different focal depths for the optics of ophthalmic system based on the on the shape of the user's cornea. For example, the eye of a user suffering from astigmatism may comprise different optical powers along different axes or meridians of the cornea of the eye. Thus, the image modification program may include a set of parameters that define different focal lengths, depth planes, optical powers or other optical corrections based on the optical prescription and shape of the eye.

In some embodiments, encoding a corrected wavefront comprises modifying the wavefronts of ambient light passed to the user from the surrounding world, e.g., in front of the user and ophthalmic system. Similarly, encoding a corrected wavefront may comprise modifying the wavefront the image generated by the ophthalmic device and projected by the display device to the user. For example, an electrical signal may be applied to electrodes coupled to the adaptable optics that alters the shape or optical characteristics of the adaptable optics. This in turn may alter any wavefront incident on the adaptable optics. In some embodiments, the wavefront of the ambient light and any projected images may be both modified by either a single VFE or adaptable optics or independently by different VFE or adaptable optics.

At 1006, an appropriate program may be selected. In one or more embodiments, the mapping table may employ one to one association, many to one association, or many to many association. For example, the mapping table may associate one or more optical prescriptions with a corresponding one or more image modification program (e.g., that provide parameters that define alterations to be applied to the adaptable optics) to be applied to the VFE or adaptable optics to modify the wavefronts. For example, in a case where the user suffers from one or more vision defects, one optical prescription may correspond to multiple image modification programs, or vice versa. Accordingly, in some embodiments, the ophthalmic system may utilize the local processing module (70) in communication with the remote processing module (72) to select the appropriate program based on the optical prescription from the remote data repository (74). In another embodiment, 1006, or any aspect of process flow 1000, may be performed locally on the local processing module (70).

At 1008, the appropriate image modification program may be applied to one or more images to be projected to the user's eyes. In some embodiments, the digital memory or remote data repository (74) may be configured to store image content (e.g., AR and/or VR image content). The local processing module (70), either independently or in communication with remote processing module (72), may be configured to retrieve this image content and execute instructions based on the parameters of the appropriate program to modify the image projected to the user. In some embodiments, the local processing module (70) may execute instructions based on the parameters and corresponding set of signals to modify the ambient light. In another embodiment, the remote processing module (72) may execute instructions based on the parameters of the appropriate program to modify ambient light passed to the user.

The appropriate image modification program may be applied so as to modify the wavefront of the image. In some embodiments, the wavefront compensation is performed by adjusting the shape of an adaptable optic. In some embodiments, the compensation may be implemented by altering characteristics of adaptable optics integrated with a waveguide stack, thereby altering the focus depth, phase, and/or wavefront of incident light. In other embodiments, the appropriate image modification program may be applied so as to modify one or more 2D images presented by the ophthalmic display. For example, where each 2D image is a representation of the image at different focal depths, a 3D perception of the combined image can be provided to the user. In various embodiments, the local processing module (70) may be executed to encode the VFE or adaptable optics of the display device (62) to modify the wavefront based on the optical prescription in accordance with process flow 1000.

At 1010, the modified images are projected to the user such that the user views the images comfortably. For example, the ophthalmic system may project light (38) to the user to form an image in the eye of the user. The image may be a modified image based on the wavefront correction applied by the VFE or adaptable optics of the display device (62) to an unmodified image. In another embodiment, alternatively or in combination, each 2D image (e.g., of different focal depths providing the perception of a 3D image) generated by the ophthalmic system may be modified based on software executed in the local processing module (70) and then displayed through display device (62). In some embodiments, where the ophthalmic device is an augmented reality head-mounted display system, wavefront correction may be applied to an image to be presented to the wearer while imaging objects located in front of the head mounted display and the user. For example, AR image content presented by the ophthalmic system may be modified and projected in combination with ambient light. In some embodiments, the ambient light passing from the outside world through the lens 106 may also be modified by the appropriate program to provide optical correction for a wearer viewing the outside world through the lens 106. In another embodiment, in the case of a VR head mounted display system that is opaque to the world in front of the user, the modified image may be a modification of a VR image provided by the ophthalmic system and the display therein for visual representation, for example, a VR image content.

Accordingly, the process flow 1000 may be implemented as a dynamic vision correction system. For example, the adaptable optics can be driven by electrical signals that change the shape and/or characteristics of the adaptable optics, thus changing the optical power of the adaptable optics. The altered characteristics of the adaptable optics may then change the shape of a wavefront incident on the adaptable optics to produce a corrected wavefront. This wavefront correction by the ophthalmic system may be changed in real-time as the optical prescription of the user changes over time. For example, the vision correction may be adjusted at intervals in time (e.g., daily or at least two times a year, three times a year, or for four times a year, possibly monthly, etc.). The interval may be predetermined and based on an expected rate or occurrence of vision defects, deterioration, or changes. For example, the vision of a user may change as the user ages.

In some embodiments, at 1010 the ophthalmic system may implement dynamic vision correction by initiating an eye-prescription configurator program. At 1010, the ophthalmic system can be configured to return to block 1002 and manually and interactively determine the user's prescription at each interval, in some embodiments, without user activation. Thus, the ophthalmic system may dynamically identify a first optical prescription at a first time and adjust the vision correction based on that prescription, and identify a second optical prescription at a second time and adjust the vision correction based on that second prescription. In another embodiment, at any point during the use of the ophthalmic system, the biofeedback system may monitor movements and changes in the eye of the user (e.g., via camera 24), as described above. If the eye is constantly moving or the properties of the eyes are constantly changing, the biofeedback system may determine that the user is struggling to focus or accommodate. Thus, the ophthalmic system may then initiate an eye-prescription configuration program to determine a new optical prescription and/or adjust the image modification program.

The techniques shown in FIG. 10A-10E are example techniques of modifying the optics of the ophthalmic system or software algorithms to correct for certain eye defects. It should be appreciated that any of the healthcare defects described in further detail below may use either the optical techniques or programming techniques, or a combination of both to correct for one or more irregularities.

Presbyopia

In one or more embodiments, the ophthalmic system may be used to compensate for presbyopia. Presbyopia is a reduction in an amplitude of accommodation of the crystalline lens of the eye, and is typically associated with aging. For close objects, the crystalline lens of the eye changes shape and accommodates to focus the light received by the eye onto the retina to form an image thereon. With age, the ability of the crystalline lens of the eye to change shape and accommodate for near distance viewing is diminished. Often, presbyopia is treated by using a multi-focal corrective lens system that comprises a divided lens (e.g., bifocals, trifocals, etc.), or lenses with a continuous focal length gradient (e.g., progressive lenses) or variable focus mechanically deformable or liquid crystal lenses.

In one or more embodiments, the ophthalmic system may be configured to assist with presbyopia. In various embodiments, the ophthalmic device can function as a solid state variable focus lens with an adjustable focus (e.g., adaptable optics or variable focus element (VFE)). As described above, for example, in correcting for myopia, hyperopia, or astigmatism, the ophthalmic system may be equipped with one or more adaptable optics or VFEs. The adaptable optic may be dynamically altered, for example by applying electrical signals thereto to change the shape of a wavefront that is incident thereon. By altering the adaptable optic's shape or other characteristics, the wavefront is changed, for example to focus of the wavefront on the retina for near distance viewing as described herein in order to provide presbyopia correction.

As described above and shown in FIG. 5, the ophthalmic device may include an augmented (or virtual) reality display device (62) that includes a display lens (106) and a light source configured to project light (38) that is directed into the eyes of a user to form images in the eye of the user for the user's viewing. In various embodiments, this display device comprises a waveguide stack that received light from a fiber scanning display disposed at the edge of the waveguide and couples the light out of the waveguide from the backside thereof to the wearer's eyes. In the case where the display device is an augmented reality display device, the ophthalmic device may also direct ambient light from the surrounding world, e.g., light from in front of the user, to the eyes of the user through display lens (106). This light may, for example, be transmitted through the waveguide stack to the wearer's eye. As discussed above, the display device (62) may also comprise one or more adaptable optics or variable focus elements (VFEs). As described above, the adaptable optics may be an optical element that can be dynamically altered so as to alter the wavefront incident thereon. For example, the adaptable optic may be a reflective optical element such as a deformable mirror or a transmissive optical element such as a dynamic lens, such as described above in FIGS. 10B-10E.

In some embodiments, the user may be able to manually adjust the focus of the variable focus lenses by providing input to the system. For example, in one or more embodiments, the ophthalmic device may have a feedback mechanism (e.g., user interface controls) to increase or decrease a power of the optics, or the focus of the images being presented to the user. The user input may cause the one or more adaptable optics to change shape thereby altering the focus of the wavefront to cause the associated light and image to focus on the retina.

In one or more embodiments, the ophthalmic system may be configured to automatically (e.g., based on a biofeedback system described below) or interactively determine an optical prescription of a user (e.g., by employing phoropter technology as described below) and incorporate the optical prescription in the optical sub-parts of the ophthalmic system. In some embodiments, the wavefront of an image projected into the user's eye may be modified based on the determined prescription. For example, the wavefront of ambient light in front of the user may be incident on adaptable optics of the ophthalmic system and, may be corrected based on the prescription. In another embodiment, alternatively or in combination, the wavefront of an image generated by a display of the ophthalmic system and presented to the user by the display of the system may be corrected based on the prescription. For example, the phase and/or focus of the wavefront of the projected image may be modified such that the projected image appears to be in focus and corrected based on the optical prescription.

In some embodiments, an ophthalmic system configured to correct for presbyopia may be similar to the ophthalmic system described above for correcting for myopia, hyperopia, and/or astigmatism. In some embodiments, the ophthalmic system may be configured to correct for presbyopia along with myopia, hyperopia, and/or astigmatism.

In some embodiments, the ophthalmic system may be an augmented reality system that combines AR and VR techniques to correct for presbyopia. As described above, the ophthalmic system may be an augmented reality head mounted display system configured to provide wavefront correction to ambient light from the world in front of the user, as well as providing wavefront correction to AR image content generated by the ophthalmic system. Alternatively, the ophthalmic system may be a VR head mounted display system configured to produce VR image content generated by the ophthalmic system having a corrected wavefront and provided to the user while the user's eyes are covered from ambient light in front of the user by the VR head mounted display system. As described previously, a VR head mounted display system may include outward facing cameras configured to capture ambient light from the world in front of the user, and generate and project corrected wavefronts of these images into the eye of the wearer.

For example, the ophthalmic system may be a patient-worn ophthalmic device as illustrated in FIGS. 3A-3D and 5 that may be implemented to compensate for presbyopia. The ophthalmic device includes a display device (62) that includes a light source configured to project light (38) that is directed into the eyes of a user in a display lens (106) and displayed by a rendering engine (34) of the display device (62). The ophthalmic device may also direct ambient light from the surrounding world to the eyes of the user through display lens (106), e.g., light from in front of the user. The display device (62) also comprises one or more VFEs or adaptable optics. As described above, the VFE or adaptable optics may comprise an optical element that can be dynamically altered so as to alter the wavefront incident thereon. For example, the adaptable optic may be a reflective optical element such as a deformable mirror or a transmissive optical element such as a dynamic lens, such as described above in FIGS. 10B-10D. As described above in FIG. 10E, the VFEs or adaptable optics may be included in the display lens (106) or located between the display lens (106) and the light source. The VFEs or adaptable optics may also be integrated into a waveguide stack or light source (18). Furthermore, the VFEs or adaptable optics may be positioned between the waveguide stack and the world in front of the ophthalmic device and user. The VFEs or adaptable optics may also be positioned between the waveguide stack and the eye of the user. In another embodiment, the adaptable optic may be positioned between waveguides of the waveguide stack.

In some embodiments, the VFEs or adaptable optics may be altered as to modify the phase and/or focus of the wavefront incident thereon.

In some embodiments, alternatively or in combination, adaptable optics comprises a spatial light modular configure to modify phase on a pixel by pixel basis. Optical correction can therefore be imparted on the wavefronts. In various embodiment therefore, the ophthalmic device may be configured to drive the light modulator to compensate for presbyopia.

In various embodiments, the ophthalmic device includes one or more eye tracking camera or other cameras or imaging systems to track the eye. Such cameras and/or imaging systems can monitor the orientation of the eyes and the corresponding direction of the line of sight of the respective eyes. These cameras and imaging systems may also be part of a biofeedback system configured to monitor the user's comfort in viewing images and provide feedback for monitoring or modifying an optical prescription.

In one or more embodiments, the ophthalmic system may comprise one or more sensors configured to detect an orientation of a user's gaze. These sensors may also be part of the biofeedback system. For example, if the wearer's eyes are tilted forward and downward, the wearer may be looking at a closer object such as a book or may be looking at projected image content corresponding to images placed in a location (lower part of field of view) typically associate with nearby objects. The gaze may also be determined based with the vergence of the eyes, (see e.g., the description above in connection with FIG. 6), for example, how the lines of sight of the pair of eyes converge on a location and how far that location is with respect to the wearer. Accordingly, by monitoring the vergence, the distance at which the viewer is intending to view an object may be determined.

In another embodiment, the one or more sensors may be configured to detect a head position. In one embodiment, the distance at which the viewer is intending to view an object may be estimated or detected based on a user's head position (e.g., head pose, or orientation), e.g., forward tilt. For example, if the wearer's head is tilted forward and downward the wearer may be looking at a closer object such as a book or may be looking at projected image content corresponding to images placed in a location (lower part of field of view) typically associate with nearby objects.

In some embodiments, the ophthalmic device of FIGS. 3A-3D may comprise gyroscopic sensors configured to determine a head positions, (e.g., head pose or head orientation), or head movement of the user (e.g., straight, tilted down, looking up, etc.). In some embodiments, the display device (62) may comprise a sensor assembly (39) having accelerometer, gyroscope, and/or other types of orientation and/or movement sensors several of which are discussed elsewhere herein. The sensor assembly (39) may be configured to detect movement imparted onto and orientation of the display device (62) due to movement of the user's head. The display device (62) may also include processor (32) (e.g., a head pose processor) operably coupled to the sensor assembly (39) and configured to execute digital and/or analog processing to derive head positions, head pose, and/or orientation from movement detected by the sensor assembly (39). In one embodiment, sensor assembly (39) may generate movement data stored in a digital memory. In some embodiments, the movement data may be used to reduce noise while diagnosing visual defects (e.g., detecting a head movement during a test may be indicative of a faulty test and result). The processor (32) may retrieve this movement data and execute processing logic to determine head positions (e.g., head pose or orientation).

In one or more embodiments, gaze orientation may also be based on tracking eye movement through an eye tracking system. In one embodiment, the prescription may be correlated with a set of user eye convergence points that are indicative of a focus depth of the eye. For example, while the user's head position may be unchanged, the user's eyes may be tracked to a convergence point that is below the horizon. Such movement may be indicative of the eye focusing on an object located at a near-field focal depth. Also, as discussed above, the vergence of the eyes can assist in determining the distance at which the viewer is direction attention (e.g., focusing). This distance may be ascertained from the convergence of the lines of sights of the eyes. Accordingly, in various embodiments, the user's eyes may be tracked to a convergence point at a particular distance from the wearer.

Likewise, in various embodiments, the ophthalmic system may be configured to determine a focal depth at which the eyes are focused or accommodated. In some embodiments, eye-tracking system may be used to triangulate the user's convergence point and adjust the focus of the images to be presented to the user accordingly. For example, the eye-tracking system may determine a direction that each eye is viewing along (e.g., a line extending from each eye) and determine a convergence angle where the directions intersect. The convergence point may be determined from the determined angle of convergence. In some embodiments, the eye-tracking system may be included as part of the biofeedback system. As described above, in various embodiments, the ophthalmic system may utilize cameras (24) paired with light sources (26) (e.g., an infrared light source and infrared camera) to track the position of each eye, which can be operatively coupled to the local processing module (70). The local processing module (70) may include software that, when executed, may be configured to determine the convergence point of the eyes, as described above in reference to FIG. 6 and/or the direction of the eyes. From this determination, the ophthalmic system may also execute logic device to determine a focus location or depth based on the orientation or direction of the user's gaze.

In another embodiment, gaze orientation may be determined through glint detection. The eye tracking system may be configured to discern one or more glints or reflections from the eye and determine a position of the one or more glints on the eye relative to the features of the eye (e.g., pupil, cornea, etc.). As the eye is moved, the relative position of the glint on the eye may change. For example, if a glint is located at the top of an eye and the space between the glint and the pupil increases, this may be indicative that the gaze orientation has tilted downward, the eyes may be accommodating at a near-field focal depth.

In some embodiments, the ophthalmic device may include one or more transmitters and receivers to allow transmission and reception of data between the ophthalmic device and the remote processing module (72) and/or remote data repository (74). In some embodiments, any of the processing steps executed by the local processing module (70) and digital memory therein may be performed remote from the user by remote processing module (72) operatively coupled to remote data repository (74).

In one embodiment, the ophthalmic system may include a rendering engine (34) operatively coupled (105, 94, 100/102, 104) to processor (32), the head pose processor (36), cameras (24), light source (18), local processing module (70), and remote processing module (72). The rendering engine (34) may be configured to render an image to be projected to the user via projected light (38) having a wavefront that is modified, bent, or focused at selected focal depths based on the optical prescription and/or gaze orientation.

Referring to FIG. 11, an example process flow of such a system is briefly described. The process flow 1100 is directed to modifying an image presented to the user based on a prescription of the user. In some embodiments, process flow 1100 may be performed by patient-worn ophthalmic devices, such as those described in connection with FIGS. 3A-3D. In various embodiments, the VFEs or adaptable optics described in FIGS. 10B-10E may be used to provide correction for presbyopia based on the user's optical prescription. The process flow 1100 can be implemented by the local processing module (70), possibly for example, by the remote processing module (72) executed by logic devices in the local processing module (70) operably connected to the remote date repository (74). In other embodiments, process flow 1100 may be implemented by processor (32), head pose processor (36), and/or sensor assembly (39). Other configurations are possible. Any combination of local and/or remote processing may be employed.

At 1102, a presbyopia prescription is determined for the user. As was the case in the previous discussion in reference block 1002 of FIG. 10A, the prescription may be determined by receiving information from the user, or may be determined by the ophthalmic system itself by adjusting the wavefront presented to the user and the user selecting a desired prescription. For example, the ophthalmic system may be configured to test for an optical prescription for different focal planes of accommodation. In some embodiments, the ophthalmic system may be pre-programmed with discrete granular steps in altering wavefronts of an image presented to the user through the display device (62) for a plurality of focal depths. For example, the ophthalmic system may employ phoropter technology, as described herein. In some embodiments, the wavefront incident on a given waveguide of the waveguide stack (178) (e.g., associated with a selected focal depth) may be altered to correct for refractive errors in order to define the optical prescription. The prescription may be entered by the user through a user interface and may be stored in the remote data repository (74). The prescription may be retrieved by one or more processors of the ophthalmic system, for example, remote processing module (72).

In another embodiment, the ophthalmic system may automatically and possibly incrementally change the user's prescription via the biofeedback system. The biofeedback system may be configured to determine a comfort level of the user in viewing an object or image. For example, as described above in connection with FIG. 10A, if a user's eyes are unstable, shifting, oscillating, changing accommodation (e.g., in an unsteady or random manner), etc., these may be indicators that the user is unable to comfortably view the object. Accordingly, the accommodation, vergence, pupil size, etc., may be monitored and/or an autorefractor may be used to see if an image is focused on the fovea of the retina.

In some embodiments, the ophthalmic system may be configured to receive an optical prescription for presbyopia (e.g., the added optical power) from a third party. For example, a doctor may be able to send a user optical prescription wirelessly (e.g., over the internet, Blue-tooth connection, etc.), which is received by a receiver or transceiver and stored in the digital memory of the local processing module (70).

At 1104, the system may store information on compensating wavefronts and/or lens types. The wavefronts and/or lens types may be based on the optical prescription of the user for various focal depths of accommodation (e.g., which may also include different focal depths for different parts of the eye). In some embodiments, the information may be input parameters for varying the focal depth, altering the shape, or altering other optical characteristics the VFEs or adaptable optics, to provide refractive correction to the eye. In some embodiments, the different lens types may refer to the modified or altered VFEs or adaptable optics as defined by the input parameters.

In some embodiments, each corrective function comprises a set of input parameters that define adjustments to shape and/or characteristics of the adaptable optic to achieve the desired wavefront correction. The input parameters may be similar to the parameters of the image modification programs of block 1004 of FIG. 10A, but are based on the optical prescription for correcting a user's presbyopia when the wearer is focusing at a near-field focal depth. For example, in the case where the adaptable optic is VFE (1020) of FIG. 10B, the input parameters may define a plurality of voltages to be applied to electrodes (1022) so as to modify the VFE (1020) to compensate for the presbyopia based on the prescription when the wearer is focusing at a near-field focal depth. In the case of a stacked waveguide assembly (178), the input parameters may define changes to be applied to VFEs or adaptable optics integrated into the waveguides, so as to alter the phase, focal length, and wavefront of incident light based on the optical prescription when viewing close objects and/or images presented at near depth planes, as described above with reference to FIG. 10D. In some embodiments, each waveguide may be associated with a given focal depth, thus the waveguide may be selectively addressed to correct the wavefront for a given focal depth of accommodation.

In one embodiment, local processing module (70) may execute instructions to retrieve the prescription from a digital memory, determine input parameters defining the alternations for the VFEs or adaptable optics, and store the input parameters in the digital memory. In some embodiments, remote processing module (72) and remote data repository (74) may also be used.

Without subscribing to any scientific theory, the eye of a user may experience different refractive errors and/or need for optical correction based on the focal depth that the eyes are accommodating. Accordingly, in one or more embodiments the system may create a map of the distances of the eyes for a plurality of different depth planes (e.g., 2 or more, 3 or more, 4 or more, 5 or more, 6 or more, or more depth planes) and corresponding corrective functions to compensate for refractive errors associated with accommodating at varying focal depths. For example, the ophthalmic system may determine at least one of the user's eyes has a positive spherical wavefront while accommodating at one focal depth and areas of the user's eye need a negative spherical wavefront for another focal depth (or a different amount of prescription correction). Accordingly, different convergence points, and thereof focal depths of accommodation, are also correlated with different prescription correction.

In one or more embodiments, this information may further be correlated with a set of head positions (e.g. head poses, orientations), and/or gaze directions. For example, if the user's head is tilted downward, the eyes may be accommodating at a certain (e.g., closer) focal depth. Or if the user's head is tilted to the right, the eyes may be accommodating at another focal depth. Accordingly, in various embodiments, programs specific for presbyopia may be pre-programmed into the ophthalmic system (or downloaded) such that the right head position (e.g., head pose, orientation) and/or gaze orientation and focal depth at which the eye experiences optical shortcoming can be matched correctly. Different gaze directions and head orientations are thereof correlated with different prescription correction for different focal depths associated with accommodation. The ophthalmic system thus is configured to provide a different optical correction depending on a measured gaze direction and/or head position, head pose, or orientation.

At 1106, the system may detect, through gyroscopes, accelerometers, IMUs, other sensors, or combinations thereof, an orientation of the user's gaze and/or head position, head pose, or orientation. The gaze orientation (e.g., including the convergence point of the eyes) and/or head position, head pose, or orientation may be indicative of whether the wearer is viewing near or far and thus whether the wearer need to accommodate, as described above. Accordingly, different corrective functions may be used for different focal depths of accommodation.

In some embodiments, as described above, the head position, head pose, or orientation of the user may be detected by a gyroscope, accelerometer, IMUs, other sensors, or a combination thereof. For example, a described above, the ophthalmic device comprises sensor assembly (39), processor (32), and head pose processor (36) which may be configured to detect movement, tilt, and orientation of the user's head. In some embodiments, sensors may be operably coupled to local processing module (70) and which may execute logic devices to retrieve the detected head movement and/or determined head position, head pose, or orientation. A downward movement of the user's head may be indicative of focusing on an object in the near-field.

In some embodiment, the gaze orientation may be based on tracking the eye movement, as described above. For example, downward movement of one or more eyes of the user may be indicative of focusing on an object in the near-field (e.g., shifting view from the horizon to a book held below the horizon). Thus, if the eye tracking system determines that the user's eyes have shifted downward, an appropriate corrective function may be determined based on the presbyopia prescription. In another embodiment, the eye tracking system may be configured to determine the angle of convergence is increasing (e.g., the convergence point is becoming closer to the user). Such determination may be indicative of focusing on an object in the near-field. From this determination, the ophthalmic system may determine that a convergence point is below the horizon, which may also be indicative of focusing at a near-field focal depth. Thus, the ophthalmic system may be able to determine focal depth of accommodation.

In some embodiments, the system may utilize cameras (24) to track the position of each eye, which can be operatively coupled to the local processing module (70). In another embodiment, the system may utilize cameras (24) to perform glint detection and monitoring, for example, the camera (24) tracks the position of a glint with respect to features of the eye (e.g., edge of the eye, intersection of the eye with an eye lid, pupil, etc.). The local processing module (70) may include software that, when executed, may be configured to track eye movement, glint movement, and/or determine the convergence point of the eyes. In some embodiments, the gaze orientation may be stored in the remote data repository (74).

For example, in some embodiments, the remote processing module (72) may be configured to correlate gaze orientation, angle of convergence, and/or head position information with the optical prescription, both being stored in the remote data repository (74).

At 1108, based on the detected gaze orientation and/or head position, the system consults the mapping table (e.g., the information stored at 1104) to determine an appropriate corrective function to apply to the adaptable optic to produce a compensating wavefront and/or lens type. For example, based on the gaze orientation or direction and/or head position (e.g., head poses, orientation), the system may determine a focal depth that the eye is accommodating. In various embodiments, the optical prescriptions may be correlated with one or more focal depths associated with accommodation. For example, different convergence points, and therefore focal depths associated with different amounts of accommodation, may be correlated with a different optical prescriptions and corrective functions.

In various embodiments, at 1108, the system may retrieve the detected focal depth of accommodation and may consult the mapping stored at 1104. Based on the mapping, the system may determine the appropriate corrective function for that identified focal depth. The appropriate corrective function includes the parameters for applying to the VFEs or adaptable optics to produce the appropriate compensating wavefront. For example, the compensating may be defined by parameters of the selected corrective function.

In some embodiments, the local processing module (70) may retrieve the detected gaze orientation stored in a digital memory at 1106. Or, the local processing module (70) may receive the detected gaze orientation directly from the eye tracking system, sensor assembly (39), and/or head pose processor (36). The local processing memory (70) may execute logic devices to access the mapping table stored at 1106 and, based on the gaze orientation, angle of convergence, and/or head position (e.g., head pose, orientation), select an appropriate corresponding corrective function to be applied to the adaptable optic to compensate for the presbyopia.

At 1110, the appropriate compensating wavefront and/or lens type, e.g., an amount of optical power (e.g., positive spherical power) is applied to one or more images. In some embodiments, the appropriate corrective function is applied to the VFEs or adaptable optics so as to alter the shape and/or characteristics of the VFEs or adaptable optics. This, in turn, may modify a wavefront incident thereon to correct for refractive errors, e.g., presbyopia.

In some embodiments, where the adaptable optic is a variable focus element (VFE), the shape of a VFE is adjusted based on voltages applied to electrodes to alter the shape and/or optical characteristics of the VFE. In some embodiments, the local and/or remote processing module (70, 72) may be configured to encode the appropriate compensating wavefront into the VFEs or adaptable optics of the display device (62) based on an appropriate corrective function, as selected based on the optical prescription and gaze orientation. For example, the local and/or remote processing module (70, 72) may execute logic devices configured to alter the VFEs or adaptable optics to change to wavefront incident thereon and pass a corrected wavefront to the eye of the user based on the optical prescription. For example, the local processing module (70) may be operatively coupled to electrodes connected to the adaptable optic and cause the electrodes to apply an electrical signal thereto to alter adaptable optic thereby changing the shape of a wavefront incident thereon.

At 1112, the modified image is presented to the user. For example, the ophthalmic system may include rendering engine (34) operatively coupled (105, 94, 100/102, 104) to the processor (32) local processing module (70), and/or remote processing module (72). The rendering engine (34) may be configured to render an image to be projected to the user via projected light (38) having a wavefront that is modified, bent, or focused at selected focal depths based on the selected corrective functions as applied to the compensating lens at block 1110.

In some embodiments, the image may be a modified image based on the wavefront correction applied by the VFEs or adaptable optics of the display device (62) to an unmodified image. In some embodiments, where the ophthalmic device is an augmented reality head-mounted display system, wavefront correction may be applied to an image to be projected to the wearer, while also passing ambient light located in front of the head mounted display to the eye of the user. For example, AR image content presented by the ophthalmic system may be modified and projected in combination with ambient light. In some embodiments, the ambient light may also be modified and optically corrected by the appropriate program. In another embodiment, in the case of a VR head mounted display system that is opaque to the world in front of the user, the modified image may be a modification of a VR image provided by the ophthalmic system for visual representation, for example, VR image content.

Accordingly, the process flow 1100 may be implemented to dynamically correct a user presbyopia. For example, the VFEs or adaptable optics can be driven by electrical signals that change the shape and/or characteristics of the VFEs or adaptable optics, thus correcting for a user's presbyopia as it changes over time. The components can thus be dynamically reconfigured, for example, reconfigured electrically in real-time as the optical prescription of the user changes and hence repeatedly updated during use of the ophthalmic system. For example, the presbyopia prescription correction may be adjusted at a variety of intervals in time (e.g., every day, once a month, three times, a year etc.) periodic or non-periodic. The ophthalmic system may therefore be configured to dynamically correct for changes in a user's presbyopia prescription over time, for example, 2, 3, 4, 6, or more times a year without requiring replacement or substitution of parts into the system. The interval may be predetermined and based on an expected rate or occurrence of vision defects, deterioration, or changes. For example, the presbyopia of a user may change as the user ages.

In some embodiments, at 1010 the ophthalmic system may implement an eye-prescription configuration program. At 1010, the ophthalmic system can be configured to return to block 1002 to update or adjust the prescription based on inputs from the biofeedback system, as described above, to manually and interactively determine the user's prescription at each interval, without user activation. Such procedures can be scheduled by a protocol (e.g., configured to check once a month, a couple times a year, etc.) or when determined that vision, for example, near vision, is deteriorating. In another embodiment, as described above, the biofeedback system may monitor movements and changes in the eye of the user (e.g., via camera 24 and light source 26) to determine that the user is struggling to accommodate. For example, the ophthalmic system may monitor vergence, pupil dilation, and/or movement and/or shape of the natural lens of the eye. The ophthalmic system may also use an autorefractor, or other technology as described herein, to monitor an image formed on the fovea of the retina. The ophthalmic system may then initiate an eye-prescription configuration program to determine a new optical prescription and/or adjust the corrective function (e.g., update the mapping table of focal depths and lens types).

In one or more embodiments, the ophthalmic system may allow the user to manually adjust the focus of one or more images presented to the user. For example, the system may be pre-programed with discrete steps in adjusting focus. The user may then specify the desired focus to the ophthalmic system through a user interface. In some embodiments, the user may have the option of incrementally increasing or decreasing a prescription (e.g., changing the focus) until the user arrives at a comfortable viewing focus. Or, the ophthalmic system may possibly incrementally increase or decrease a prescription automatically by utilizing the biofeedback system and other diagnostic technologies (see for example, the description of phoropter and autorefractor technology herein). In some embodiments, such user input prescriptions may be associated with a particular gaze or head orientation and provided when the wear has such gaze or head orientation. In some embodiments, such user input prescription is applied independent of the gaze or head orientation and is not changed with change in gaze, line of sight, and/or head orientation.

Strabismus/Amblyopia

Another common visual ailment is strabismus, which is an inability of both eyes to align at a single convergence point in order to produce a fused stereo image. This typically results from an eye with weakened ocular muscles being unable to coordinate its motions with that of its normal counterpart. Similarly, amblyopia is a visual ailment where there is decreased vision in one or both eyes. This decreased vision may be caused by abnormal development of vision in infancy or during childhood. Amblyopia is sometimes referred to as a "lazy eye."

In some embodiments, an ophthalmic system comprising a wearable augmented reality head-mounted device, similar to the devices described herein, may be used to treat or correct convergence deficiencies, such as deficiencies resulting from strabismus or amblyopia. As an example, if the convergence is offset in an angular fashion, a compensating prism correction may be applied to bring the convergence point of both eyes together. The compensating prism correction may be applied by the processor, adaptable optics elements, or a combination of both. This process generally follows the method described herein with reference to FIG. 10*a*.

Where the convergence of both eyes is offset angularly, one or more of the following techniques may be used. In one or more embodiments, an eye tracking system may determine a gaze vector and/or a point of focus of a healthy eye. This information may be extrapolated to determine a targeted convergence point for both eyes. In certain embodiments, an eye tracking system and a depth sensing system may be used in conjunction to determine the convergence point of both eyes. In certain implementations, muscles of one or more eyes may be "re-trained" through a treatment protocol to gradually align the focus and/or convergence point of both eyes. The treatment protocol can include the methods described herein, including methods that are designed to strengthen muscles of a weaker eye and/or to stimulate neural responses to optic signals from a weaker eye.

In some embodiments, a wearable augmented reality (or virtual reality) device can be used as an ophthalmic system to identify, treat, and/or correct convergence deficiencies, such as those resulting from strabismus and/or amblyopia. The augmented reality device can be configured to correct or compensate for vergence deficiencies by applying a compensating prism correction, as described herein. The augmented reality device can be configured to re-train eyes of the wearer to gradually align the convergence point of both eyes. It should be appreciated that such a system may be used to test and/or treat the eyes of the wearer, and this may or may not occur at a doctor's or clinician's office. In one or more embodiments, the patient's individual ophthalmic system may be used, possibly with doctor supervision, or the doctor's office may have its own version of the ophthalmic system that may be used for testing and/or treatment.

In various embodiments, the wearable augmented reality device includes an augmented reality display platform configured to pass light from the world or environment beyond the eyewear through the display platform (e.g., a lens and/or adaptive optics elements in the front thereof) to the eye of the wearer. The display platform can be configured similarly to the display lens 106, as described herein, for example, with reference to FIG. 5. Accordingly, the wearer can see images projected with the display platform superimposed with what the wearer can see in the world.

In some embodiments, the wearable augmented reality device includes the display platform described above and at least one light source configured to project light into the eye of the wearer. The at least one light source can be configured to project light into the eye of the wearer to form an image in the eye. In some embodiments, the at least one light source includes a fiber scanning display, such as described herein. The fiber scanning display can be configured to display or transmit light from one or more depth planes.

In some embodiments, the display platform includes a waveguide stack, such as described herein. The waveguide stack can be configured to project light from different focal planes. In certain implementations, the waveguide stack includes one or more lenses in the stack, as described herein. The waveguide stack can be configured to apply a compensating prism correction, for example, through configuration of lenses, mirrors, reflective elements, refractive elements, or the combination of any of these components. In various implementations, the waveguide stack can be configured to vary its mechanical configuration to provide a compensating prism correction.

In some embodiments, the display platform includes adaptable optics elements configured to project light to different or targeted portions of the eye of the wearer. In certain implementations, the adaptable optics elements include variable focus elements (VFEs), as described herein. In some embodiments, the variable focus elements include a membrane mirror. The membrane mirror can include one or more electrodes on the mirror and a control system that is configured to control the one or more electrodes to modify a shape of the membrane mirror. The adaptable optics can be used to provide a compensating prism correction for correction and/or treatment of convergence deficiencies. In certain implementations, the augmented reality device is configured to vary the focus and/or position of the projected image by varying a microelectromechanical system (MEMS). For example, the augmented reality device can include micro-optics implemented using MEMS that include reflective, refractive, and/or diffractive optics elements that can be used to vary the focus and/or position of the projected image. In some embodiments, the augmented reality device includes an array of micro-mirrors that are configured to respond to signals to alter their orientation. This can be done, for example, to provide an image shift (e.g., a compensating prism correction) and/or to occlude an eye of the wearer. Other types of adaptive optics may be used to provide prism. For example, transmissive elastomeric material (such as used in an adaptive optics lens) that is affected by electric field may be driven by electrode to change shape so as to introduce prism. Phase modulators, including transmissive or reflective phase modulators, may also be used. Such phase modulators may alter the phase on a pixel by pixel based. Possible phase modulators include liquid crystal phase modulators. In some embodiments, the augmented reality device includes one or more spatial light modulators configured to control intensity, for example, attenuate or occlude, on a pixel by pixel basis. For example, liquid crystals configured to selectively occlude an eye or eyes of the wearer or a portion of the eye or eyes of the wearer or attenuation intensity to said eye or eyes. The liquid crystals may also be configured to selectively turn on or off the effects of a diffraction grating (e.g., a holographic diffraction grating). This can be done, for example, to selectively apply a prismatic effect. Such adaptive optics can be in the optical path from the display to the eye to provide correction for the user when viewing image content on the display. These adaptive optics can also be included in the optical path from the world in front of the eyewear and the eye to provide correction for the user when viewing the world in front of the eyewear.

The augmented reality device can be configured to selectively introduce a prismatic effect or an angular shift in images provided to the wearer. This can be done in a number of ways and for different purposes. For example, a compensating prism correction can be applied as an optical correction for the wearer, e.g., to compensate for convergence deficiencies in one or both eyes of the wearer. This correction can be applied to account for the deficiencies of the wearer so that the wearer can achieve or approximate binocular single vision even where the wearer suffers from strabismus and/or amblyopia.

The compensating prism correction can be achieved by shifting, e.g., laterally (e.g., orthogonal to the normal line of sight or normal to the optical axis), a location of an image provided to the wearer. In some embodiments, the shift in location can be provided in image processing. For example, the augmented reality device can be configured to adjust via software relative location of the images presented in the display or the relative locations of an image being projected in one or both eyes of the wearer compared to the relative locations of the image being projected to a wearer that does not suffer from convergence deficiencies or to the other eye. The augmented reality device can be configured to detect the focal point or the alignment of the eyes of the wearer and to adjust the positions of the respective left and right images to be at a targeted point within the field of view of each eye. For example, the augmented reality device can include eye tracking to determine the gaze of each eye. When the gaze is determined, the augmented reality device can be configured to position respective left and right images centered within the field of view of the respective left and right eyes. In some embodiments, to re-train a weaker eye, the augmented reality device can gradually move the image presented to the weaker eye towards a desired or targeted convergence point. In this way, the weaker eye can be re-trained to verge at the same point as the strong eye. In some embodiments, the shift in location can be provided optically. For example, the augmented reality device can include adaptable optics elements configured to optically shift the location of an image to one or both eyes of a wearer (e.g., laterally) or shift the image on the display. Similarly, the augmented reality device can include adaptable optics elements to add a prism to shift light arriving to the wearer from the world or environment outside of or beyond the eyewear. In some embodiments, the lateral shift in location can be provided optically in combination with image processing.

To determine the amount of prism correction to apply, the augmented reality device can be configured to monitor where the image and light were being projected on the retina of the weak eye of the wearer. If the prism correction allows the light to shine on the retina, then it is correct. If not, more or less is needed. As described herein, W4LT, SLO, autorefractor, photo-refractor, etc. can be used to determine if the compensating prism correction has reduced or corrected the misaligned vision of the wearer. In some embodiments, the augmented reality device is configured to determine (or receive input indicating) whether the user has an exotropic or esotropic deviation. Once this deviation is known by the device, prism corrections can be applied until the vision defect is substantially corrected. This may be determined automatically or it can be determined based on user input. In some embodiments, to determine a correct or suitable prism correction automatically, the augmented reality device can include one or more inward-facing cameras to measure angular deviation (e.g., a shift in fixation) and use the display to occlude one eye while changing the prism prescription in the other. In some embodiments, to determine a correct or suitable prism correction using user input, the augmented reality device can be configured to implement a test similar to a Maddox rod test. For example, the augmented reality device can provide a mechanical filter to filter light for the test. As another example, the augmented reality device can provide image sources from two different depth planes. Based on user input, the augmented reality device can adjust the prism correction until satisfactory conditions are met (e.g., a first image is aligned with a second image).

As another example, a compensating prism correction can be applied for a therapeutic purpose, e.g., to gradually re-train the eyes to arrive at a targeted convergence point. Disclosed herein are also methods for re-training eyes that emphasize the presentation of images of differing characteristics to respective eyes of the wearer.

In some embodiments, the wearable augmented reality device includes an eye tracking system. The eye tracking system can be configured to determine gaze of the wearer's eyes. The eye tracking system can include one or more sensors configured to sense properties of the eyes of the wearer. In some embodiments, the one or more sensors include cameras, as described herein. In various embodiments, the one or more sensors including cameras can be configured to image the glint and/or Purkinje fringes to determine a gaze. The eye tracking system can include an analysis module configured to determine a direction of gaze of the wearer's eyes based at least in part on the information acquired with the one or more sensors.

In some embodiments, the wearable augmented reality device includes one or more outward facing cameras. In certain implementations, the one or more outward facing cameras can be similar to the cameras 16 described herein with reference to FIG. 5.

The wearable augmented reality device can include one or more user interface features configured to allow a wearer or other person to provide input to the device. The user interface features can be integrated with the device. In some implementations, the user interface features are provided by a device or component that is not physically integrated with the device. For example, the user interface features can be provided by a device or system that is in communication with the device. This can be a smartphone, computer, tablet, or other computational device that is in wired or wireless communication with the device. In some embodiments, the user interface features can be provided by a combination of different devices and systems linked to the device, e.g., through wired or wireless communication networks or through components that are physically linked to the device or integrated with the device. The user interface features can be presented on a device with a touch screen wherein interaction with the touch screen provides input to the wearable augmented reality device. Voice recognition and/or virtual touch screen technology can also be employed. The user interface features can include capacitive features sensitive to touch, keyboards, buttons, microphones, photodetectors, or a variety of software-implemented features provided by a graphical user interface. In some embodiments, the user interface features include gesture detection components to allow a wearer to provide user input through gestures. In some embodiments, the user interface features include gaze detection components to allow a wearer to provide user input through gaze of the eyes (e.g., this can include selecting a button or other element when the wearer fixates on the button for a time or when the wearer blinks when fixated on the button). Such systems can be used for other devices and systems described herein. The user interface features can be presented on a device with a touch screen wherein interaction with the touch screen provides input to the wearable augmented reality device.

In some implementations, the wearer, clinician, doctor, or other user can use the interface features to control aspects of the vision testing and/or therapy. This can be done, for example, to change the amount of prism correction applied, the amount of lateral shift of the images, to modify characteristics of enhanced images, or to otherwise configure testing or treatment of convergence deficiencies.

FIG. 12 illustrates an example method 1200 for treating convergence deficiencies, such as those caused by strabismus and/or amblyopia. For ease of description, the method 1200 will be described as being performed by an ophthalmic system, such as any of the augmented reality devices described herein. However, it is to be understood that any component or subpart of the various augmented reality devices disclosed herein or other similar devices can be used to perform any step, combination of steps, or portions of a step in the method 1200. The method 1200 includes a process of "re-training" a lazy eye or misaligned eyes by occluding or de-emphasizing the stronger eye. It should be appreciated that many treatment protocols may be devised based on a user's particular prescription, and the exact parameters and/or techniques may vary.

At block 1202, the ophthalmic system determines a difference in the focus and/or convergence points of both eyes. As discussed herein, this difference may be determined based on user input or based on a prescription test performed by the ophthalmic system. Eye tracking and/or gaze detection can also be used. The ophthalmic system can be configured, for example, to perform any of the methods described herein for determining focus points and/or convergence points.

At block 1204, the ophthalmic system selects a treatment protocol to help treat the wearer's visual defect. In some embodiments, the treatment protocol may be devised by a doctor or clinician or the treatment protocol may be devised at an external location and downloaded onto the ophthalmic system. The treatment protocol may comprise various parameters of the treatment protocol. For example, the treatment protocol may involve a frequency at which the treatment is administered. The treatment protocol may include information on the type of images to be presented to the wearer and/or differences in the two displays or images shown to each eye. For example, the treatment protocol can be based on a dichoptic presentation where images of differing characteristics are displayed to the wearer (e.g., different images or the same image with the version of the image shown to the left and/or right eyes altered). In some implementations, the image shown to the weaker eye can be enhanced and/or the image shown to the stronger eye can be diminished. For example, the image shown to the weaker eye can be altered to be made more interesting or compelling to the wearer (e.g., brightened, color-enhanced, three-dimensionally enhanced, sharpened focus, higher resolution, enhanced contrast, moving, higher refresh rate, etc.) Similarly, the image shown to the stronger eye can be altered to be less interesting or less compelling to the wearer (e.g., darkened, muted colors, flattened, blurred, lower resolution, lower contrast, static, lower refresh rate, etc.). In various implementations, only the images shown to the weaker eye are altered while the images shown to the stronger eye are not altered. In various implementations, only the images shown to the stronger eye are altered while the images shown to the weaker eye are not altered. In various implementations, the images shown both to the weaker eye and to the stronger eye are altered. The treatment protocol may include information on the duration of the protocol. The treatment protocol may employ interactive virtual objects, thereby making the "treatment" more enjoyable to the user and increasing user compliance to therapy regimen. The treatment protocol may employ dynamic images (e.g., movies, games, etc.) to make the treatment more enjoyable, thereby increasing compliance.

At block 1206, the ophthalmic system may detect or determine, based at least in part on a scheduler attached to the treatment protocol, a time or time window at which to start the treatment protocol. For example, the treatment protocol may be programmed such that re-training of the eye is to be performed daily at 10 PM or somewhere between 8 AM and 9 AM. The treatment protocol may only be prescribed once every week, for example. The treatment protocol can involve more treatment sessions such as at least twice a week, at least five times a week, every day and/or multiple times of day, such as at least, one, two, three, four, or five times a day. In some embodiments, the treatment protocol may be programmed in response to detecting that the eyes are becoming more or less misaligned. In various embodiments, the treatment protocol may be programmed to occur when the eyes have recovered from the previous treatment protocol.

At block 1208, the ophthalmic system alters the field of view of one or both eyes. This can include, for example, partially or fully occluding the eye(s). In some embodiments, the ophthalmic system may present different images to each eye, sometimes in different locations within the field of view, to either strengthen a weaker eye or promote proper vergence for image fusion within the brain. It should be appreciated that this is simply one example technique, and many other techniques may be used to strengthen or re-train the muscles of the eyes. The occlusion may be a partial or complete occlusion. Full or partial defocus, blurring, attenuation, or other alteration to images presented to the wearer may be used as well.

In some embodiments, the ophthalmic system may skip block 1208. For example, in some treatment protocols, the respective fields of view of the stronger eye and the weaker eye are not altered. The ophthalmic system may present images of different visual characteristics to the wearer's eyes to encourage the weaker eye to gain strength.

As described herein, the content shown to the respective eyes can differ as well, whether or not the field of view of one or both of the eyes is altered. For example, less intriguing content can be shown to the weaker eye. This may be accomplished by projecting images to the weaker eye that are brighter, higher resolution, more complete, moving, higher contrast, three-dimensional, color-enhanced, from a plurality of depth planes, etc. As another example, less intriguing content can be shown to the stronger eye. This may be accomplished by projecting images to the stronger eye that are duller, lower resolution, missing portions, static, lower contrast, flattened, color-muted, from a single depth plane, etc. Intriguing content can be projected to the weaker eye at the same time as less intriguing content can be projected to the stronger eye, thereby encouraging the weaker eye to gain strength.

At block 1210, the ophthalmic system projects stimulatory images attracting the attention of the weaker eye. These stimulatory images may be presented at prescribed locations and/or with enhanced visual characteristics—color saturation, contrast, resolution, depth cues, three-dimensional effects, brightness, intensity, focus, etc., thereby encouraging the eyes to focus and/or converge at a targeted location and/or encouraging the visual content from the weaker eye to strengthen it. The virtual images can be moved over time and at a rate designated by the treatment protocol to draw the eyes together at points of vergence across multiple depth planes. When the eyes align at a common point of vergence, the images from each eye fuse and the brain sees one image instead of two. This may be achieved in the form of a game, for example.

In various embodiments, for example, the ophthalmic system can be configured to simultaneously present images to both eyes (dichoptic) for treatment or therapeutic purposes. The images presented to respective eyes can differ in visual characteristics. This difference can increase performance of a weaker eye over time. For example, to provide a stereoscopic image to the wearer, left and right images can be presented to the wearer. During treatment, the image corresponding to the weaker eye can be enhanced relative to the stronger eye. Enhancement of the image can include, for example and without limitation, increasing brightness of the image, increasing contrast of the image, increasing color saturation of the image, increasing intensity of the image, increasing three-dimensional effects of the image, adding content to the image, etc. Similarly, the image corresponding to the stronger eye can be diminished. Diminishment of the image can include, for example and without limitation, decreasing color saturation of the image, attenuating or decreasing intensity of the image, flattening the image, blurring the image, de-focusing the image, shadowing the image, partially or completely occluding the image, etc. In certain implementations, de-focusing the image can be accomplished by presenting images to the respective eyes from different depth planes. For example, multiple waveguides and associated lenses or other elements with optical power can be used to project images from different depth planes. In some embodiments, treatment can include enhancing images to the weaker eye and diminishing images to the stronger eye. In certain embodiments, treatment can include enhancing images to the weaker eye while not altering images to the stronger eye. In various embodiments, treatment can include diminishing images to the stronger eye while not altering images to the weaker eye. The enhancement and/or diminishment of images can be applied gradually and/or intermittently. For example, the quality of an image can be gradually enhanced or diminished every 30-60 seconds and/or when the ophthalmic system the eyes become more misaligned. As another example, an image can be enhanced or diminished for a time period and then that effect can be removed for a second time period. This can be alternated over the treatment period.

Treatment can also include, in some embodiments, varying depth planes from which images are presented. This can be similar to a Brock string where multiple depth planes are used to re-train eyes with convergence deficiencies. Images are projected from various depth planes, thereby allowing the eyes to converge and focus on images at varying depths. Varying depth planes can also be used to provide treatment similar to pencil pushups. This treatment includes presenting an image at a first depth plane (e.g., about 1 foot away or farther) and then moving the image closer to the wearer to a second depth plane. Moving the image can include gradually moving the depth plane closer to the wearer from the first depth plane to the second depth plane. While the image is being presented at this closer depth plane, the depth of the image can be adjusted so that the wearer can practice focusing on the image in a region where it is difficult to focus (e.g., the wearer has difficulties converging on the image). This treatment also includes providing an image at a third depth plane that is farther away than the first and second depth planes. While the image is being presented at the second depth plane, the wearer can alternate between focusing on the image at the second depth plane and the image being presented at the third depth plane. This can strengthen eye muscles, for example. These methods can be combined with enhancement and/or diminishment of images during treatment.

Treatment can include, in some embodiments, selective occlusion of one or both eyes. This can be done to present visually stimulating images at a targeted portion of the retina to increase effectiveness of the treatment. In some embodiments, the ophthalmic system is configured to use selective occlusion to block portions of objects seen by the wearer using, for example, spatial light modulators, shutters, or the like. Spatial light modulators can as described herein, for example, can be used. Adaptive optics, may also be used to redirect the light. Selective occlusion also includes intermittently occluding images in an eye. This can be done to alternate images to the eyes (e.g., alternate between presenting an image to the left eye and then to the right eye).

Treatment can include, in some embodiments, minor adjustments to a compensating prism correction to gradually influence convergence of the eyes. For example, the amount of compensating prism correction and/or lateral image shift can be reduced during treatment to influence a weaker eye to converge to a targeted point. The amount of compensating prism correction and/or lateral image shift can be reduced over time during a single treatment or over the course of multiple treatments.

At block 1212, the system detects the end of the prescribed time for the treatment protocol or possibly by detecting normal characteristics in the function of the eye for accommodation, vergence, etc. At such time, the ophthalmic system discontinues treatment at block 1214. This can include terminating occlusion or de-emphasis of the eye of the wearer, if occlusion or de-emphasis had been applied. In some embodiments, the wearer may manually administer the treatment protocol based on the wearer's schedule. Similarly, many other such treatment protocols may be envisioned.

In some embodiments, at block 1212, the ophthalmic system determines that the treatment should be discontinued by tracking performance of the wearer during treatment. When the wearer shows signs of fatigue or a lack of compliance, the ophthalmic system discontinues treatment at block 1214. For example, the ophthalmic system can include an eye tracking system that is configured to detect gaze of the wearer. The eye tracking system may detect that the wearer's performance during treatment (e.g., the wearer's ability to successfully focus on the images being presented) has deteriorated over time. This may indicate that the wearer has tired and further training or treatment would have limited benefits. In some embodiments, the ophthalmic system can track the performance of the wearer over time to determine whether the convergence deficiencies of the wearer are decreasing over time (e.g., during a single treatment and/or over multiple treatment sessions).

In some embodiments, at block 1212, the ophthalmic system receives user input indicating that the treatment should be discontinued. When such user input is received, the ophthalmic system discontinues treatment at block 1214.

In some embodiments, at block 1212, the ophthalmic system automatically detects performance of the user during the administered treatment protocol. In block 1212, the ophthalmic system can be configured to return to block 1204 to update or adjust the treatment protocol based on the detected performance of the wearer during the administered treatment protocol. For example, if the angle of convergence of the weaker eye does not improve during treatment, the ophthalmic system can adjust the treatment protocol parameters and proceed with the method 1200 starting again at block 1204. In this way, the ophthalmic system can use the wearer's performance during testing as feedback to make adjustments to the treatment protocol and/or to determine when to terminate the treatment.

In various implementations, the ophthalmic system can be configured to terminate the treatment protocol prior to finishing. For example, if the ophthalmic system detects fatigue in the eye (e.g., the angle of convergence gets worse for weak eye), the ophthalmic system can be configured to terminate the treatment protocol at block 1212 by proceeding to block 1214.

Similar to strabismus, amblyopia or "lazy eye" is a condition in which one of the eyes is weaker than the other. This may be caused by the brain's preference to favor the inputs the stronger eye over the weaker. In some embodiments, the ophthalmic system may be programmed to perform a method similar to the method 1200 described with reference to FIG. 12 to enhance the visual stimulus to, and thereby gradually strengthen, the weaker eye and/or to reproduce the effects of an eye patch by selectively dimming an intensity of light or decreasing the level of visual stimulus entering the stronger eye. Other treatment and training systems and techniques as described above, for example, with reference to Strabismus may also be employed.

In various embodiments, to reduce distraction the view of the world in front of the wearer's eyes through the augmented reality device is blocked or otherwise not visible during examination and/or treatment. A spatial light monitor that adjusts intensity, such as a liquid crystal spatial light modulator or shutter, for example, may be used. This can occur, for example, when images are presented to the viewer, although this approach is not necessary.

Although the system has been described as an augmented reality device, in other embodiments the system may be a virtual reality device. In either case, the system may be an ophthalmic system provided by the physician or clinician for testing at a medical facility or optometrist office or elsewhere. In other embodiments, the system may belong to the wearer and may be employed for other purposes such as entertainment (e.g., games and movies) and/or work activities. As described above, one benefit of implementing treatment on the wearer's system is that the examination can be conveniently undertaken multiple times (at least 2, 3, 4, 5, 6, 8, 10, 12, 16, 18, 24, or more times a year) at the wearer's discretion. Likewise, examination can be performed with or without a medical professional, such as optometrist, ophthalmologist, nurse, technician, medical assistant, etc.

Higher Order Aberrations

Other common eye-related ailments include high order refractive errors, which may include any wavefront curvature corrections that cannot be made with prism and/or lens corrections. These higher order aberrations may account for 10% of all refractive errors. These higher order refractive errors may be the results of irregularly shaped optical surfaces in the eye, and are particularly common after refractive surgeries. For example, shape irregularities in the in the cornea and/or crystalline lens of the eye may introduce higher order refractive errors to light that passes through the eye to the retina. Such higher order aberrations may potentially be reduced with appropriate refractive correction.

Various implementations of the ophthalmic systems described herein may be applicable for providing correction to wavefronts for these higher order aberrations. It should be appreciated that almost all wavefront corrections, up to and including all aberrations described by Zernike modes (e.g., astigmatism, coma, trefoil, spherical aberrations, quatrefoil, etc.) may potentially be made utilizing the ophthalmic device described herein.

In some implementations, the ophthalmic system may also be configured to correct microscopic defects in the cornea, crystalline lens and other transmissive media of the eye. These defects can generate complex refraction, reflection, and scattering patterns that have the effect of visual quality impairment.

In various embodiments, the ophthalmic system may detect patterns in the projected light caused by these defects through, for example, an eye-tracking system or other camera or imaging system. This information may be used by the ophthalmic system to selectively filter out incoming rays of light onto the user's eye that would interact with these defects of the eye, thus blocking optical pathways that contribute to impaired visual quality.

The ophthalmic system may, for example, be a patient-worn ophthalmic device as illustrated in FIGS. 3A-3D and 5, and as described above in connection with correcting for myopia, hyperopia, astigmatism, and other refractive errors. Accordingly, it will be understood that features discussed in connection with the description included above related to the ophthalmic device for correcting for vision defects such as myopia, hyperopia, and astigmatism applies equally in relation to correcting for higher order aberrations. In particular, the ophthalmic device may be configured to provide optical correction to reduce or correct for refractive error, including higher order aberrations. The device, for example, may include adaptive optics or variable focus elements that introduce wavefront correction and can be used to introduce, not only sphere and cylinder to offset defocus and astigmatism, but may also be used to reduce higher order aberrations resulting from the wavefront shape.

As describe above, the ophthalmic device may include an augmented (or virtual) reality display device (62) that includes in a display lens (106) and a light source configured to project light (38) that is directed into the eyes of a user to form images in the eye of the user for the user's viewing. In various embodiments, this display device (62) comprises a waveguide stack (178) that receives light from a fiber scanning display disposed at the edge of the waveguide stack (178) and couples the light out of the waveguide from the backside thereof to the wearer's eyes. In the case where the display device (62) is an augmented reality display device, the ophthalmic device may also direct ambient light from the surrounding world to the eyes of the user through display lens (106), e.g., light from in front of the user. This light may, for example, be transmitted through the waveguide stack (178) to the wearer's eye. As discussed above, the display device (62) may also comprise one or more adaptable optics or variable focus elements (VFEs). As described above, the adaptable optics may be an optical element that can be dynamically altered so as to alter the wavefront incident thereon. For example, the adaptable optic may be a reflective optical element such as a deformable mirror or a transmissive optical element such as a dynamic lens, such as described above in FIGS. 10B-10E.

In some embodiments, the projected light (38) forming an image generated by the ophthalmic system may be incident on the one or more adaptable optics or VFEs as described herein. The adaptable optics may be a reflective optical element such as a deformable mirror or a transmissive optical element such as a dynamic lens (e.g., a liquid crystal lens, an electro-active lens, a conventional refractive lens with moving elements, a mechanical-deformation-based lens, an electrowetting lens, an elastomeric lens, or a plurality of fluids with different refractive indices). The adaptable optics may receive the light having an incident wavefront from a fiber scanning display. The wavefront may be modified to compensate for higher order aberrations by the adaptable optic, as described herein. This corrected or compensated wavefront may then pass through a transmissive beamsplitter and be directed into the eyes of the user.

In some embodiments, alternatively or in combination, adaptable optics comprises a spatial light modular configure to modify phase on a pixel by pixel basis. Optical correction can therefore be imparted on the wavefronts. In various embodiment therefore, the ophthalmic device may be configured to drive the light modulator to compensate for chromatic aberrations.

In one or more embodiments, the ophthalmic system may comprise one or more sensors or subsystems configured to determine higher order aberrations in one or more eyes of the user. In one implementation, the ophthalmic system may utilize wavefront aberrometry technology such as described herein to evaluate refractive defects in the eye. In some embodiments, for example, the ophthalmic device may include cameras (24) and light sources (26), and be configured to be utilized an aberrometer. For example, as described below in reference to aberrometry technology. In some embodiments, the cameras (24) are infrared cameras a. The cameras (24) may be operatively coupled to the local processing module (70) to detect higher order refractive defects in the eye.

Similarly, one or more camera or imaging system may be employed to identify regions of the eye, for example, the cornea, crystalline lens and other transmissive media of the eye, that have microscopic defects that generate complex refraction, reflection, and scattering patterns that reduce the quality of vision. In response, the display can be driven so as not to direct light to said regions with defect.

Additionally, in some embodiments, the ophthalmic device may include one or more transmitters and receivers to allow transmission and reception of data between the ophthalmic device and the remote processing module (72) and/or remote data repository (74). The transmitter and receiver may be combined into a transceiver. In some embodiments the remote processing module (72) and/or remote data repository (74) may be part of a third party server and database that enable a third party (e.g., a doctor or other medical administrator) to transmit data, such as for example, an optical prescription, to the ophthalmic device.

In some embodiments, the various components of the ophthalmic device may be operatively coupled to a local processing module (70). Local processing module (70) may be operatively coupled to a digital memory, and comprise instructions, that when executed, cause the ophthalmic device to correct for higher order refractive aberrations in the eye.

In some embodiments, the ophthalmic system may be an augmented reality system that corrects for higher order refractive errors. As described above, the ophthalmic system may be an augmented reality head mounted display system configured provide wavefront correction to ambient light from the world in front of the user, as well as providing wavefront correction to AR image content generated by the ophthalmic system. Alternatively, the ophthalmic system may be a virtual reality head mounted display system configured to produce VR image content generated by the ophthalmic system having a corrected wavefront and provided to the user while the user's eyes are covered from ambient light in front of the user by the VR head mounted display system. As described previously, a VR head mounted display system may include outward facing cameras configured to capture ambient light from the world in front of the user and generate corrected wavefronts of these images.

In some embodiments, the process flow for correcting for higher order aberrations may be similar to process flow 1000 of FIG. 10A described for correcting for myopia, hyperopia, or astigmatism. In some embodiments, process flow 1000 may be performed by patient-worn ophthalmic devices, such as those described in connection with FIGS. 3A-3D. The process flow 1000 can be implemented by the local processing module (70), for example, by the remote processing module (72) executed by logic devices in the local processing module (70) operably connected to the remote data repository (74). Adaptive optics or VFEs such as electrically reconfigurable mirrors or lenses such as lenses located as shown in FIGS. 10B-10E may be used to provide refractive correction based on the user's optical prescription.

At 1002, the ophthalmic system determines a user's optical prescription, e.g., the higher order aberrations due to irregularly shaped optical surfaces in the eye (e.g., shape irregularities in the cornea and/or crystalline lens of the eye).

As described above, the ophthalmic device may include a user interface whereby the user inputs an optical prescription or the ophthalmic system may go through an eye-prescription configurator program to determine higher order refractive errors of the eye. For example, the ophthalmic system may include an aberrometer, as described herein. In some embodiments, the ophthalmic system may be configured to receive an optical prescription from a third party. For example, a doctor may be able to send a user optical prescription wirelessly (e.g., over the internet, Blue-tooth connection, etc.), which is received by a receiver or transceiver and stored in the digital memory of the local processing module (70).

In some embodiments, at 1002, the ophthalmic system may detect patterns in light projected by the ophthalmic system that is caused by the higher order refractive defects in the eye. For example, the light source (26) may be configured to project infrared light into the eye and the camera (24) may detect the infrared light reflected from the eye due to higher order refractive defects in the eye. Based on the detected reflected or scattered light, the ophthalmic device may detect a pattern that corresponds to higher order aberrations.

At 1004, the ophthalmic system retrieves a mapping table to determine an appropriate image modification program to correct for higher order refractive errors. In some embodiments, the mapping table comprises an association of different optical prescriptions to different image modification programs. For example, for a given optical prescription of the user, the mapping table may list an image modification program configured to compensate for the higher order aberrations as defined by the optical prescription.

In one embodiment, an image modification program defines modifications to the incident wavefront (e.g., modifications to the phase) to generate a compensating wavefront. In another embodiment, the image modification program defines modification to one or more 2D (e.g., modification to the intensity pattern) images generated by the ophthalmic system and presented to the eye of the user. In some embodiments, each 2D image may be a 2D representation of an image at a different focal depth providing the user a 3D perception of the images. In one or more embodiments, the ophthalmic system may be pre-coded with such programs, or these programs may be downloaded in order to perform image modulation based on the prescription. See, for example, the description below in connection with phoropter technology. In some embodiments, the remote processing module (72) may be executed to retrieve or look up the mapping stored in the remote data repository (74).

As described above, the image modification programs may include parameters to be applied to the VFE or adaptable optics of the ophthalmic system based on the desired wavefront correction. The parameters may define the modifications to be applied to the shape and/or characteristics of the adaptable optics, thereby altering the wavefront to correct for higher order refractive errors. These parameters and corresponding set of signals may be based on the optical prescription and/or detected aberration patterns of defects. For example, to correct for higher order refractive errors, the image modification program may have a set of parameters configured to encode a compensating wavefront curvature into the optics of the ophthalmic system (e.g., the VFE or adaptable optics of display device (62)). The compensating wavefront curvature may be such that the wavefront of an image that reaches the retina of the eye is corrected to account for refractive error in the shape of the optical surfaces of the eye, thereby removing the high order aberrations caused by the eye.

Without subscribing to any scientific theory, the eye of a user may experience different higher order refractive errors and/or need for optical correction depending on the focal depth that the eyes are accommodating. Accordingly, in one or more embodiments the image modification program may comprise an association of the distances of accommodation of the eyes for a plurality of different depth planes (e.g., 2 or more, 3 or more, 4 or more, 5 or more, 6 or more, or more depth planes) and corresponding parameters to compensate for higher order refractive errors associated with accommodating at different focal depths. For example, the ophthalmic system may determine at least one of the user's eyes impart first higher order refractive error to an incident wavefront while accommodating at one focal depth, while the user's eye imparts a second refractive error (e.g., requiring a different spherical wavefront) for another focal depth. Accordingly, different compensating wavefronts (e.g., based on different optical prescriptions) may be associated with different focal depths of accommodation, depending on different higher order aberrations experienced by the user at different focal depths.

In some embodiments, encoding a corrected wavefront comprises modifying the wavefronts of ambient light passed to the user from the surrounding world, e.g., in front of the user and ophthalmic system. Similarly, encoding a corrected wavefront may comprise modifying the wavefront the image generated by the ophthalmic device and projected by the display device to the user. For example, as described above, an electrical signal may be applied to electrodes coupled to the adaptable optics that alters the shape or optical characteristics of the adaptable optics. This in turn may alter the wavefront that incident on the adaptable optics. In some embodiments, the wavefront of the ambient light and any projected images may be both modified by either a single VFE or adaptable optics or independently by different VFE or adaptable optics. In some embodiments, where the ophthalmic system is a VR head mounted display, outward facing cameras may obtain images of ambient light in front of the user, the wavefront of which may be altered as described herein.

In some embodiments, where the ophthalmic system detects patterns in reflected light that is indicative of refractive errors, the image modification program may be configured to selectively filter out rays of light projected into a user's eye that interact with the defects of the eye, thus blocking optical pathways that contribute to impaired visual quality. For example, based on the correlation of the mapping of the eye with the high order aberrations, the ophthalmic system may identify one or more rays of light that may interact with the defects in the eye, resulting in the high order aberrations. Once identified, the ophthalmic system may determine to filter these rays of light from the wavefront incident on the optics. Accordingly, since those rays of light do not interact with the defects, the high order aberrations do not impair the visual quality of images presented to the user by the ophthalmic system.

In some embodiments, the remaining steps of process flow 1000 may be carried out in the same manner as described above for correcting for myopia, hyperopia, and astigmatism. Thus, at 1006, the ophthalmic system selects the appropriate image modification program to apply to the images projected to the user by the display of the ophthalmic device. For example, the ophthalmic system may select an image modification program based on the mapping information. In this embodiment, the image modification program may alter a portion of the incident wavefront to compensate for a portion of the eye having refractive defects. At 1008, the ophthalmic system may apply the image modification program to correct the wavefront of the projected images. At 1010, the ophthalmic system may project the corrected wavefront of the image to the user through the display of the ophthalmic system. In various embodiments, the ophthalmic system may automatically apply the high order refractive error correction to an incident wavefront based on information stored remotely (e.g., external to the ophthalmic device), for example, at remote data repository (74).

In some embodiments, where the ophthalmic device is an augmented reality head-mounted display system, wavefront correction may be applied to an image to be presented to the wearer by the ophthalmic device while imaging objects located in front of the head mounted display and the user. For example, AR image content presented by the ophthalmic system may be modified and projected in combination with ambient light. In some embodiments, the ambient light passing from the outside world through the lens 106 may also be modified by the appropriate program to provide optical correction for a wearer viewing the outside world through the lens 106. In another embodiment, in the case of a VR head mounted display system that is opaque to the world in front of the user, the modified image may be a modification of a VR image provided by the ophthalmic system and the display therein for visual representation, for example, a VR image content.

In various embodiments, the process flow 1000 may be implemented as a dynamic vision correction system as described above. For example, the adaptable optics can be driven by electrical signals that change the shape and/or characteristics of the adaptable optics. The altered characteristics of the adaptable optics may then change the shape of a wavefront incident on the adaptable optics to produce a corrected wavefront. This wavefront correction by the ophthalmic system may be changed in real-time as the optical prescription of the user changes over time. For example, the refractive defects of a user's eye may change as the user ages. In some embodiments, at 1010 the ophthalmic system may implement dynamic vision correction by initiating an eye-prescription configurator program. At 1010, the ophthalmic system may be configured return to 1002 and manually and interactively determine the user's prescription at various points over time, in some embodiments, without user activation. Thus, the ophthalmic system may dynamically identify a first optical prescription at a first time and adjust the correction for refractive defects based on that prescription, and identify a second optical prescription at a second time and adjust the correction for refractive defects based on that second prescription.

Chromatic Aberration

In various embodiments, the ophthalmic system may be used to compensate for chromatic aberrations. Chromatic aberrations are errors resulting from colors (e.g., wavelengths) of an image interacting differently with, for example, the optics of the ophthalmic system or the crystalline lens of an eye of the user. These chromatic aberrations result because a lens may have slight variations in the index of refraction for different wavelengths of light.

There are two types of chromatic aberrations, longitudinal chromatic aberrations and lateral chromatic aberrations. Longitudinal chromatic aberrations occur when different wavelengths of light focus to different focal points along the optical axis. Thus, each color of an image may be focused to a different focal depth. Lateral chromatic aberrations occur when different wavelengths of light are focused to a different position on the focal plane of an optical system. Thus, colors of an image are shifted or displaced relative to each other, for example, laterally along the focal plane and perpendicular to the optical axis. Thus, longitudinal chromatic aberrations may cause a discoloration or fringing throughout or anywhere in an image whereas lateral chromatic aberrations may not occur at the center of an image.

In one or more embodiments, the ophthalmic system may be configured to compensate for longitudinal chromatic aberrations by projecting light of different wavelengths (e.g., different colors) at different focal depths. An image to be projected by the ophthalmic system and viewed by a user may comprise multiple colors, thus, projecting light of different wavelengths at different focal depths may compensate for longitudinal chromatic aberrations in viewing said image. As described herein, in various embodiments, the ophthalmic device can function as a solid state variable focus lens with an adjustable focus (e.g., adaptable optics or variable focus element (VFE)). As described above, for example, in correcting for myopia, hyperopia, or astigmatism, the ophthalmic system may be equipped with one or more adaptable optics or VFEs. The adaptable optic may be dynamically altered for a given color, for example by applying electrical signals thereto to change the shape of a wavefront that is incident thereon. By altering the adaptable optic's shape or other characteristics for a given color, the wavefront is changed in relation to that color, for example to vary the focus of the wavefront as described herein to compensate for chromatic aberrations.

In other embodiments, alternatively or in combination, the ophthalmic system can be configured to project light of different wavelengths at different angles to compensate for lateral chromatic aberrations. As described herein, the display may comprise a fiber scanning device that oscillates to create a 2D image pattern. To reduce lateral chromatic aberration, the beam that is projected from the display onto the retina to form the image on the retina for one color can be shifted. For example, the angle of the fiber can be shifted or offset. The amount that this angle is shifted is different for different color components. Additionally or alternatively, by altering the angle of the beam projected onto the eye (e.g., by offsetting the angle of the fiber scanning device or by providing an angular offset to the adaptable optic's shape), the wavefront can be changed for a given color, for example to vary the angle of incidence of the wavefront to compensate for lateral chromatic aberrations. In various embodiments the light is collimated but the angle of the beam changes as the beam is scanned to write the image onto the retina. In some embodiments, changes to the angle of the beam is constant while scanned to write the image onto the retina. In other embodiments, changes to the angle of the beam may be varied while the beam is scanned to write the image.

As described above, the ophthalmic device may include an augmented (or virtual) reality display device (62) that includes a display lens (106) and a light source configured to project light (38) that is directed into the eyes of a user to form images in the eye of the user for the user's viewing. In various embodiments, this display device comprises a waveguide stack that receives light from a fiber scanning display disposed at the edge of the waveguide and couples the light out of the waveguide from the backside thereof to the wearer's eyes. In the case where the display device is an augmented reality display device, the ophthalmic device may also direct ambient light from the surrounding world, e.g., light from in front of the user, to the eyes of the user through display lens (106). This light may, for example, be transmitted through the waveguide stack to the wearer's eye. As discussed above, the display device (62) may also comprise one or more adaptable optics or variable focus elements (VFEs). As described above, the adaptable optics may be an optical element that can be dynamically altered so as to alter the wavefront incident thereon. For example, the adaptable optic may be a reflective optical element such as a deformable mirror or a transmissive optical element such as a dynamic lens, such as described above in FIGS. 10B-10E. Spatial light modulators that modulate the phase can also be employed. Such phase modulators may operate in transmission or reflection. A liquid crystal spatial light modulator may, for example, be employed.

In some embodiments, the ophthalmic system may be configured to compensate for chromatic aberrations based on a predetermined optical prescription of the user, chromatic aberrations due to the optics of embodiments of the ophthalmic system described herein, or both. For example, the light passed through the eye of the user may impart a chromatic aberration to the light received at the retina. The chromatic aberrations due to the eye may be determined based on an optical prescription or an eye-prescription configurator program executed by the ophthalmic system, as described below in reference to FIG. 10A. Similarly, light passed through the optics of the ophthalmic system may also impart some chromatic aberrations onto the light incident on the eye and eventually received at the retina. Chromatic aberrations due to the system may be known based on the specifications and manufacturing requirements of the system. The ophthalmic system may be configured to utilize these pre-determined aberrations and compensate for them when projecting an image to the eye of the wearer.

When the system compensates for chromatic aberrations, not all the chromatic aberration need be removed. For example, as described in reference to light therapy herein, blue light may be especially damaging to retinal cells. Thus, the ophthalmic system may be configured to control the chromatic aberration correction to reduce the amount of blue light incident on the retinal cells of the eye. In other embodiments, alternatively or in combination, some chromatic aberrations may contribute to creating a realistic focus of depth cue for a given user. Thus, the compensation of chromatic aberration may be controlled to permit some aberrations while correcting others to provide optimal vision quality. The system, however, does reduce the effects of chromatic aberrations as viewed by a wearer of the ophthalmic system.

In some embodiments, an ophthalmic system may be configured to correct for chromatic aberrations may be similar to the ophthalmic system described above for correcting for myopia, hyperopia, and/or astigmatism. In some embodiments, the ophthalmic system may be configured to correct for chromatic aberrations along with myopia, hyperopia, astigmatism, or other refractive errors.

As discussed above, for example, the ophthalmic system may be a patient-worn ophthalmic device as illustrated in FIGS. 3A-3D and 5 that may be implemented to compensate for chromatic aberrations. The ophthalmic device may include a display device (62) that includes a light source (18) configured to project light (38) that is directed into the eyes of a user in a display lens (106) of the display device (62). The ophthalmic device may also direct ambient light from the surrounding world to the eyes of the user through display lens (106), e.g., light from in front of the user.

In various embodiments, the ophthalmic device includes outward facing cameras configured to capture ambient light from the environment surrounding the user. For example, the ophthalmic device may include one or more wide-field-of-view machine vision cameras (16) operatively coupled to a local processing module (70). These cameras may be configured to obtain images of the environment around the user, for example, an image of the environment in front of the ophthalmic device and user. In one embodiment these cameras (16) are dual capture visible light/infrared light cameras. Images taken by cameras (16) may be stored in a digital memory of the ophthalmic device and retrieved for subsequent processing.

In various embodiments, the ophthalmic device may comprise a biofeedback system, as described herein, configured to determine a comfort level of the user in viewing an object or image. For example, if a user's eyes are shifting, changing accommodation, changing in pupil size, changing vergence, etc., these may be indicators that the user is unable to comfortably view an object or image. Instability or oscillation in accommodation or behaviors associated with accommodation may be a sign the user is struggling with focusing on an object or image. Accordingly, the biofeedback system may receive real-time inputs relating to the state of the user's eye.

The light source (18) may be configured to project light (38) into the eyes of a user to form an image in the eye of the user. Accordingly, the image may include image content displayed by the ophthalmic device and projected in to the eyes of the user through display lens (106), for example, based on images stored in the digital memory of the local processing module (70). In one implementation, the images stored in the digital memory may be images obtained by outward facing cameras (e.g., cameras (16)). In various embodiments, images formed on the retina may include images formed from ambient light from objects in front of the user that reach the eyes of the user through display lens (106). In various embodiments, the images on the retina may include a plurality of color components. The color components, for example, may be red, green, or blue components. These color components may include portions of the image having the same color or all portions of the same color. For example, an image may comprise various portions having the color blue (e.g., a first color component) and various other portions having the color red (e.g., a second color component). While the color components are described as being red, green, or blue, it will be understood that any color of an image may be applicable and the number of components need not be limited to three. There may be any number of color components, based on the colors of the image. In other embodiments, the image may be monochromatic image, comprising a single color component.

The display device (62) also comprises one or more variable focus elements (VFEs) or adaptable optics. As described above, the VFEs or adaptable optics are configured to be dynamically altered so as to alter the wavefront incident thereon. For example, the adaptable optic may be a reflective optical element such as a deformable mirror or a transmissive optical element such as a dynamic lens, such as described above in FIGS. 10B-10D. As described above in FIG. 10E, the VFEs or adaptable optics may be included in the display lens (106) or located between the display lens (106) and the light source. The VFEs or adaptable optics may also be integrated into a waveguide stack or light source (18). Furthermore, the VFEs or adaptable optics may be positioned between the waveguide stack and the world in front of the ophthalmic device and user. The VFEs or adaptable optics may also be positioned between the waveguide stack and the eye of the user. In another embodiment, the adaptable optics may be positioned between waveguides of the waveguide stack.

In one embodiment, the display device may comprise a waveguide stack, for example, the waveguide stack (178) described above in connection with FIG. 10D. The stacked waveguide assembly (178) comprises transmissive beamsplitter substrates, each of which is configured to project light at a different focal plane or as if originating from a different focal plane. The waveguide stack (178) may comprise a plurality of waveguides (182, 184, 186, 188, 190) and a plurality of lenses (198, 196, 194, 192) configured to selectively send image information to the eye with various levels of wavefront curvature for each waveguide level indicative of focal distance to be perceived for that waveguide level. A plurality of displays (200, 202, 204, 206, 208), or in another embodiment a single multiplexed display or reduced number of multiplexed displays, may be utilized to inject light, e.g., collimated light with image information into the waveguides (182, 184, 186, 188, 190), each of which may be configured to distribute incoming light substantially equally across the length of each waveguide, for exit down toward the eye.

The waveguide (182) nearest the eye may be configured to deliver collimated light, as injected into such waveguide (182), to the eye, which may be representative of the optical infinity focal plane. As described above in more detail, the other waveguides may be configured to represent focal planes closer than infinity at a range of diopters, giving the user 3D perception of images generated by the ophthalmic system as different image content from different waveguides will appear to originate from different depths or distances from the user. The different image content from different waveguides may be configured to be different color components of the image. Thus, each color component (e.g., red, green, blue) may appear to originate from a different focal depth.

For example, the next waveguide up (184) ca be configured to send out collimated light of a first color component which passes through the first lens (192; e.g., a negative lens) before it can reach the eye (58); such first lens (192) may be configured to create a slight convex wavefront curvature so that the eye/brain interprets light of the first color component coming from that next waveguide (184) as coming from a first focal plane closer inward toward the person from optical infinity. Similarly, the third waveguide (186) passes its output light of a second color component through both the first (192) and second (194) lenses before reaching the eye (58); the combined optical power of the first (192) and second (194) lenses may be configured to create another incremental amount of wavefront divergence so that the eye/brain interprets light of the second color component coming from that third waveguide (186) as coming from a second focal plane even closer inward toward the person from optical infinity than was light from the next waveguide (184).

In some embodiments, the number of waveguides may correspond to the number of color components having its focal depth varied to compensate for chromatic aberrations. For example, where color components are red, green, and blue, the waveguide stack (178) may comprise three waveguides, one for each color component. However, in various embodiments, the waveguide stack may include other waveguides beyond just these three. For example, three waveguides, one for each color component may be included for each depth plane. Additional waveguides may also be added. Also, less waveguides may be employed.

As described above, the adaptive optics may be adjusted to correct for the chromatic aberration. In particular, the adaptive optics can be adjusted to provide different optical power when each of the color components is emitted. For example, at a first time a red light source would inject light into a corresponding waveguide, and the adaptive optics could be adjusted to provide a first optical power to the adaptive optics so the red light is focused on the retina. At a second time a green light source would inject light into a corresponding waveguide, and the adaptive optics could be adjusted to provide second optical power, different than the first optical power, to the adaptive optics so the green light is focused on the retina. At a third time a blue light source would inject light into a corresponding waveguide, and the adaptive optics could be adjusted to provide third optical power, different than the first and second optical powers, the adaptive optics so the blue light is focused on the retina. According, the focal depth of each color component of an image may be selectively altered to reduce chromatic aberration thereby reducing longitudinal chromatic aberration.

In various embodiments therefore, the display device (62) comprises adaptable optics or VFEs, for example, similar to VFE (1020) described in FIGS. 10B and 10C. In some embodiments, the VFEs or adaptable optics may be altered as to modify the phase and/or focus of the wavefront of a given color component of an image incident thereon. As described above, the shape of the VFE (1020) may be modified, thus varying the phase, wavefront shape, and possibly the focus of the light incident thereon. Thus, the shape of the VFE may be modified to adjust the focal depth of a given color component of the wavefront incident thereon. For example, where the VFE or adaptable optic is an adaptive optic lens VFE (1020), the VFE (1020) can be coupled to a set of electrodes (1022) that are then selectively controlled in order to modify the shape or index of the material comprising the lens, and consequently change the focus of the light. The adaptive optics lens may comprise, for example, elastomeric material having a shape that can be manipulated by applying voltage or electric field. The electrodes (1022) may thus be controlled in a manner such that the shape of the VFE (1020) complements the chromatic aberrations such that the image may be appropriately viewed by the user's eye. For example, a first color component may be project and the adaptable optic may be modified to have a first focal depth, and a second color component may be project and the adaptable optic may have a second focal depth. The adaptable optic may be changed in real-time at a high enough rate to be unperceivable to the user, thereby variably altering the incident wavefront to correct of chromatic aberrations.

In some embodiments, the shape of the VFE or adaptable optics may be selectively modified so as to vary the position of different images of different color components. The positions may be varied as to substantially align the different images. In some embodiments, the shape of the VFE or adaptable optics may be selectively driven so as to modify the wavefront of the light forming an image so as to change the angle of incidence at which light of different color components is projected onto the eye. Thus, a first color component may be shifted from a first position to a second position on the focal plane. The second position may be configured to correct for lateral chromatic aberrations, such that the first color component is focused at approximately the same position as at least a second color component on the focal plane. In some embodiments, the position of the second component is focused on the fovea of the eye.

In yet another embodiment, alternatively or in combination, light source (18) of the ophthalmic device may comprise a fiber scanner, or other light generating source, that is configured to vary focus in a raster pattern across the retina. The fiber scanner may be configured to generate a raster pattern of a plurality of color components, where each color component projects a color component of the image and are focused at a different focal depth. For example, the longitudinal position of the fiber can be translated to change the focus. Accordingly, the ophthalmic device may be configured to compensate for longitudinal chromatic aberrations.

In some embodiments, the ophthalmic device may include one or more transmitters and receivers to allow for the transmission and reception of data between the ophthalmic device and the remote processing module (72) and/or remote data repository (74). The transmitter and receiver may be combined into a transceiver. In some embodiments the remote processing module (72) and/or remote data repository (74) may be part of a third party server and database that enable a third party (e.g., a doctor or other medical administrator) to transmit data, such as for example, an optical prescription, to the ophthalmic device.

In various embodiments, the ophthalmic device may comprise a feedback mechanism (e.g., a user interface) that may be configured to determine an optical prescription. In some embodiments, for a color component, the user may be able to manually adjust the focus of the variable focus lenses by providing input to the system, for example, to increase or decrease a power of the optics, or the focus of the images being presented to the user. The user input may cause the one or more adaptable optics to change shape thereby altering the focus of the wavefront to cause the associated light and image to focus on the retina. The user can perform this process for each of the color components. In another embodiments, the system may be configured to automatically or interactively determine an optical prescription of a user (e.g., by employing phoropter technology as described herein) and incorporate the optical prescription in the optical sub-parts of the ophthalmic system. For example, the ophthalmic system may objectively determine a prescription based on a biofeedback system, as described herein. The system can perform this process for each of the color components.

In one or more embodiments, the ophthalmic system may comprise one or more sensors configured to assess whether the user can view an image comfortably, e.g., when the user is struggling to focus on the image. For example, the ophthalmic system may utilize gaze orientation, head position, fluctuations or changes in accommodation and/or vergence, and/or eye movement, possible pupil size, and possible shape of the natural lens to determine whether the user can view an image comfortably as described herein. Inwardly facing cameras or other instrumentation, e.g., SLO, may be used to monitor eye to make this assessment.

For example, the display device (62) may include gyroscopic sensors configured to determine head position or head movement of the user (e.g., straight, tilted down, looking up, etc.). Movement of the user's head may be indicative of a user searching for a better viewing angle of the image. In some embodiments, the display device (62) may comprise a sensor assembly (39) having accelerometer, gyroscope, and/or other types of orientation and/or movement sensors various of which are discussed elsewhere herein. The sensor assembly (39) may be configured to detect movement imparted onto and orientation of the display device (62) due to movement of the user's head. The display device (62) may also include processor (32) (e.g., a head pose processor) operably coupled to the sensor assembly (39) and configured to execute digital and/or analog processing to derive head positions from movement detected by the sensor assembly (39). In one embodiment, sensor assembly (39) may generate movement data stored in a digital memory. In some embodiments, the movement data may be used to reduce noise while diagnosing visual defects (e.g., detecting a head movement during a test may be indicative of a faulty test and result). The processor (32) may retrieve this movement data and execute processing logic to determine one or more head positions.

In another embodiment, the display device may include an eye tracking system configured to monitor movement of the user's eyes. For example, as described above, the eye tracking module may be configured to determine changes in gaze orientation as the eyes move about and/or changes in convergence point of the eyes. In some embodiments, the eye tracking module may be configured to monitor for fluctuations in accommodation and accommodation reflect (e.g., fluctuations in accommodation and vergence). Such movement may also be indicative of a user searching for a better viewing angle or focus of the image. As described above, the eye tracking system may comprise inward facing cameras, for example, cameras (24), to track the each eye, which can be operatively coupled to the local processing module (70). The local processing module (70) may include software that, when executed, may be configured to determine the convergence point of the eyes, as described above in reference to FIG. 6 and/or the direction of the eyes.

In some embodiments, the various components of the ophthalmic device may be operatively coupled to a local processing module (70). Local processing module (70) may be operatively coupled to a digital memory, and comprise instructions, that when executed, cause the ophthalmic device to compensate for chromatic aberrations.

In some embodiments, the local processing module (70) may include instructions that when executed are configured to compensate for chromatic aberrations. In some embodiments, this compensation need not be implemented by the optics of display device (62). For example, an image projected by the ophthalmic system may be modified in a digital memory of local processing module (70) or remote from the ophthalmic system and executed by the local processing module (70). The ophthalmic system may generate a 2D image to be presented to the eye of a user, and the system may be configured to modify this image prior to projecting the image to compensate for chromatic aberrations. For example, the pattern or collection of pixels that form the image can be modified to counter, offset, or reduce effects of errors introduced by the eye or the optics of the ophthalmic system. For example, the pattern can be shifted laterally or radially. The modified pattern of one color component may be combined or superimposed onto the modified (e.g., shifted) or unmodified pattern for the other color component and presented to the eye of the user by the ophthalmic device through the display device (62). The light field of a generated image (e.g., the angle, wavelength, and intensity) may also be modified to account for chromatic aberrations. In one embodiment, for example, the blue color component is shifted in one direction when presented by the display, the red color component is shifted in another direction when presented by the display and the green color component is not shifted when presented by the display. The eye will see all three color components, ideally superimposed. Similarly, the, the angle of an incident light ray may be changed based on the lateral chromatic aberration to shift light corresponding to a color component of the image.

In some embodiments, the local processing module (70) may include instructions to vary the intensity of a color component based on chromatic aberrations. For example, an image may comprise a first color component corresponding to a first focal depth and a second color component corresponding to a second focal depth, the second focal depth may correspond to the retina of the eye (e.g., the focal point of the eye). The intensity projected by light source (18) of the first color component may be altered relative to the second color component to reduce the effects of chromatic aberrations. Thus, the un-aberrated second color component may be made to appear more dominate relative to the first color component that contributes to impaired vision. For example, if the eye of the user causes red color components to focus behind the retina (e.g., focal plane of the eye), the user may perceives a bigger area of red than intended. In response, the ophthalmic device may reduce the intensity of the red component to improve vision quality. In another implementation, if a blue component is focused or converges in front of the retina, then the user perceives less blue than intended. In response, the ophthalmic device may increase the intensity of the blue component to compensate for chromatic aberrations.

In some embodiments, the ophthalmic system may be an augmented reality system that corrects for chromatic aberrations. As described above, the ophthalmic system may be an augmented reality head mounted display system configured to provide wavefront correction to ambient light from the world in front of the user, as well as providing wavefront correction to AR image content displayed by the ophthalmic system. The system, as discussed above, may comprise an outward facing camera. Images from the outward facing-camera can be re-rendered on the display for the users viewing. The techniques described above for correcting for chromatic aberration may be applied to these images projected into the eye. Similarly, the AR head mounted display may also compensate for chromatic aberrations of other image content that is also displayed by the ophthalmic system and projected to the user. Image content from the outward facingcamera can be combined with other image content and projected into the eye of the viewer. The head mounted display may be configured to compensate for chromatic aberrations in any projected image in a manner as described above.

Similarly, the ophthalmic system may be a VR head mounted display system configured to produce VR image content compensating for chromatic aberrations. The VR image content may be generated by the ophthalmic system and provided to the user while the user's eyes are covered from ambient light in front of the user by the VR head mounted display system (e.g., opaque). As described above, a VR head mounted display system may include outward facing cameras (e.g., cameras (16)) configured to capture ambient light from the world in front of the user and generate images based on the ambient light. The VR head mounted display may be configured to compensate for chromatic aberrations in any projected image in a manner that is substantially similar to that described above.

In some embodiments, process flow 1000 of FIG. 10A may be implemented to compensate for chromatic aberrations. In some embodiments, process flow 1000 may be performed by patient-worn ophthalmic devices, such as those described in connection with FIGS. 3A-3D. The process flow 1000 can be implemented by the local processing module (70), for example, by the remote processing module (72) executed by logic devices in the local processing module (70) operably connected to the remote data repository (74). Adaptive optics such as electrically reconfigurable lenses such as lenses located as shown in FIGS. 10B-10E may be used to provide refractive correction based on the user's optical prescription.

At 1002, the ophthalmic system determines an optical prescription, e.g., the chromatic aberrations due to irregularly shaped optical surfaces in the eye (e.g., shape irregularities in the cornea, crystalline lens, and/or iris of the eye). The optical prescription may comprise a prescription for longitudinal chromatic aberrations and/or lateral chromatic aberrations. As described above, the ophthalmic device may include a user interface whereby the user inputs an optical prescription or the ophthalmic system may go through an eye-prescription configurator program to determine chromatic aberrations of the eye. In some embodiments, as described herein, the ophthalmic system may be configured to objectively monitor and dynamically (e.g., in real-time) the user's optical prescription based on inputs received from the biofeedback system.

For example, the ophthalmic device may be pre-programmed with discrete granular steps in adjusting focus or altering wavefronts, or varying the angle of incidence of an eye-exam image presented to the user by the ophthalmic system through the display device (62). The eye-exam image may be any image, including conventional eye examination templates, including letters, numbers, graphics, pictures, drawings, designs, etc. In some embodiments, the eye-exam image may include a plurality of color components. In other embodiments, the eye-exam image may be monochromatic comprising a single color component. Adjusting the focus may include adjusting the focus of one or more color components of an image. The user may then specify a desired correction, which may define an optical prescription, to the ophthalmic system through an appropriate feedback mechanism (e.g., a user interface). Or, in another embodiment, the user may have the option of incrementally increasing or decreasing a prescription (e.g., changing the focus and/or wavefront) until the user arrives at a comfortable viewing prescription. See, for example, the description herein connection with phoropter technology. In some embodiments, the ophthalmic system may automatically incrementally increase or decrease a prescription based on the user input into the feedback mechanism.

The ophthalmic system may be configured to present a first monochromatic image of a first color component. The system may then incrementally change the focus depth of the first color component. The user may input into the user interface or feedback component whether the viewing of the first monochromatic image has improved or not through each incremental change, and then, after receiving said input, the ophthalmic system automatically change the focus of the first color component to the next focal depth for user input. Once the system has determined the desired focal depth of the first color component, the ophthalmic system may then repeat the process for one or more other color components. In some embodiments, the color components are red, green, and blue. Once the ophthalmic system performs the eye-exam for each color component, the ophthalmic system may define an optical prescription for longitudinal chromatic aberration.

The ophthalmic system may be configured to follow a similar procedure to determine a lateral chromatic aberration prescription. For example, the focus point of the first monochromatic image may be incrementally shifted (e.g., laterally or radially) about the focal plane, either automatically or by user input, to determine a preferred viewing position of the user. For example, the focus point of the first monochromatic image may be shifted about the retina with respect to the fovea of the eye. In particular, the angle at which the beam is incident on the eye may be adjusted to account for the lateral chromatic image. In some embodiments, the incident beam may be substantially collimated. The offset of the angle may be different for different locations on the image. The process may be carried out for each color component and the inputs from the user or as objectively determined by the ophthalmic system may be stored, thereby defining a lateral chromatic aberration prescription.

In some embodiments, at 1002, the ophthalmic system may be configured to assess whether the user can view an image comfortably and increase or decrease the prescription based thereon. In some embodiments, the ophthalmic system may utilize a biofeedback system configured to objectively monitor, in real-time, whether the user can view an image comfortably, and increase or decrease the prescription based on the monitoring. For example, the ophthalmic system may include an eye-tracking system to monitor for changes in eye position, movement of an eye, fluctuations in accommodation, or changes in vergence of the eyes, pupil size, as described herein. Similarly, sensor assembly (39) may be utilized to monitor head position. Changes in head position, eye position and/or movement of the eye may be indicative that the user is not able to comfortably move the image. For example, the image may be blurry and the user may be searching for a comfortable viewing angle or position. Thus, the ophthalmic system may determine the user is able to view the image of a color component comfortably, and if not, automatically and incrementally adjust (e.g., increase or decrease) the prescription of the user.

Another method to determine whether correction and/or the image is in focus is using an autorefractor. Autorefractor systems for the ophthalmic devices similar to those describe herein can be used to assess the level refractive error and focus. For example the ophthalmic system may independently project one or more color components of light into the eye. The system, through inward facing cameras, may determine that if the image is focused on the fovea of the retina, then that color component is in focus. If the color component is not in focus, then the ophthalmic system may adjust the prescription to bring the color component in focus on the fovea. Other methods for objectively determining a prescription includes objectively measuring someone's refractive error through, for example, phoropter, SLO, autorefractor, etc. as described herein. These technologies may be included as part of the biofeedback system configured to, in real-time, evaluate and adjust a user's prescription.

In some embodiments, the ophthalmic system may be configured to receive an optical prescription from a third party. For example, a doctor may be able to send a user optical prescription wirelessly (e.g., over the internet, Bluetooth connection, etc.), which is received by a receiver or transceiver and stored in the digital memory of the local processing module (72).

At 1004, the ophthalmic system retrieves a mapping table to determine an appropriate image modification program to compensate for chromatic aberrations. The mapping and image modification program may be similar to that described above for correcting for myopia, hyperopia, and astigmatism. In various embodiments, the mapping may associate an optical prescription with image modification programs defining parameters for driving or encoding the optics of the ophthalmic system to compensate for chromatic aberrations. In another embodiment, the mapping may associate an optical prescription with an image modification program defining modifications to be applied by the local processing module (70) to an image stored in the digital memory, for example, by software modification. Accordingly, a given prescription may be mapped or associated with a given image modification program to compensate for said prescription.

For example, as described above, the longitudinal chromatic aberration prescription may be associated with an image modification program comprising parameters to drive the waveguide stack. The parameters may define waveguides and/or reconfigurable elements, for example, dynamic lenses associated with the waveguides based on the desired the optical power or wavefront curvature to be applied by a given waveguide to an incident wavefront of a color component, so as to compensate for the chromatic aberrations. In such an embodiment, the parameters may selectively address specific dynamic lenses at each waveguide to compensate for the aberrations, as described above.

In another embodiment, the image modification program may include parameters to be applied to the adaptable optics or VFE of the ophthalmic system based on the desired compensating wavefront. The parameters may define the modifications to be applied to the shape and/or characteristics of the adaptable optics, thereby altering the wavefront to compensate for chromatic aberrations. These parameters may correspond to a set of signals that may be based on the optical prescription. For example, the image modification program may have a set of parameters configured to encode a compensating wavefront curvature into the optics of the ophthalmic system (e.g., the VFE or adaptable optics of display device (62)). The compensating wavefront curvature may be such that the wavefront of an image that reaches the retina of the eye is corrected to account for chromatic aberrations in the shape of the optical surfaces of the eye and/or optical system of the ophthalmic system, thereby reducing chromatic aberrations.

In yet another embodiment, the image modification program may define parameters for modifying a 2D image of generated by the ophthalmic system to compensate for chromatic aberrations, as described above. For example, for a given optical prescription, the parameters may define an increase or decrease in intensity to be applied to one or more color components to reduce the effects of chromatic aberrations (e.g., fringe discoloration). The intensity may be defined in luma and may be in part based on the color component and the focal depth of an uncompensated color component, as described above.

While some exemplary embodiments are described above, it will be understood that other configurations for compensating for chromatic aberrations are possible, and that other methods and approaches described throughout this disclosure may be utilized to compensate for chromatic aberrations.

In some embodiments, the remaining steps of process flow 1000 may be carried out in a manner similar to that described above for correcting for myopia, hyperopia, and astigmatism. Thus, at 1006, the ophthalmic system selects the appropriate image modification program to apply to the images projected to the user by the display of the ophthalmic device. For example, the ophthalmic system may select an image modification program based on the association of the optical prescription and the desired compensating image modification program. In this embodiment, the image modification program may change the focal depth of one or more color components of an image to compensate for longitudinal chromatic aberrations. In another embodiment, alternatively or in combination, the image modification program may change the angle at which light of one or more color components of an image is projected to compensate for lateral chromatic aberrations.

At 1008, the ophthalmic system may apply the image modification program to compensate for chromatic aberrations of the projected images.

At 1010, the ophthalmic system may project the corrected wavefront of the image to the user through the display of the ophthalmic system. For example, the ophthalmic system may compensate for chromatic aberrations by modifying the wavefront to be presented to the user by the ophthalmic system. As described above, in one embodiment, the ophthalmic system may vary the focal depth of one or more color components of the incident wavefront to generate a compensating wavefront. Similarly, the ophthalmic system may produce a shifted image for one or more a color components based on a varied angle of incidence for that color component to compensate for lateral chromatic aberrations. In either case, the image content may be obtained by front facing cameras (e.g., cameras (16)), which may be included in both an augmented reality head mounted display system or a virtual reality head mounted display system. The image content can also be form other source and comprise other content.

In various embodiments, the ophthalmic system may automatically apply the chromatic aberration compensation to an incident wavefront based on information stored remotely (e.g., external to the ophthalmic device), for example, at remote data repository (74). As described above, the corrected wavefront may be projected to the eye of the user by the ophthalmic system via display device (62) combined or superimposed onto the image on which the corrected wavefront is based.

In various embodiments, the process flow 1000 may be implemented as a dynamic vision correction system as described above. For example, the adaptable optics can be driven by electrical signals that change the shape and/or characteristics of the adaptable optics. The altered characteristics of the adaptable optics may then change the shape of a wavefront incident on the adaptable optics to produce a compensating wavefront. This wavefront compensation by the ophthalmic system may be changed in real-time as the optical prescription of the user changes over time. For example, the chromatic aberration errors of a user's eye may change as the user ages. In some embodiments, at 1010 the ophthalmic system may implement dynamic vision correction by initiating an eye-prescription configurator program. At 1010, the ophthalmic system may be configured to return to 1002 and manually and interactively (or automatically) determine the user's prescription at various points over time, in some embodiments, with or without user initiation, for example at 1002 of FIG. 10A. Thus, the ophthalmic system may dynamically identify a first optical prescription at a first time and adjust the correction for refractive defects based on that prescription, and identify a second optical prescription at a second time and adjust the correction for refractive defects based on that second prescription. The historical data regarding the different correction over time can also be store and used to determine if the user has a health condition or abnormality.

Phoropter

Figure 14:
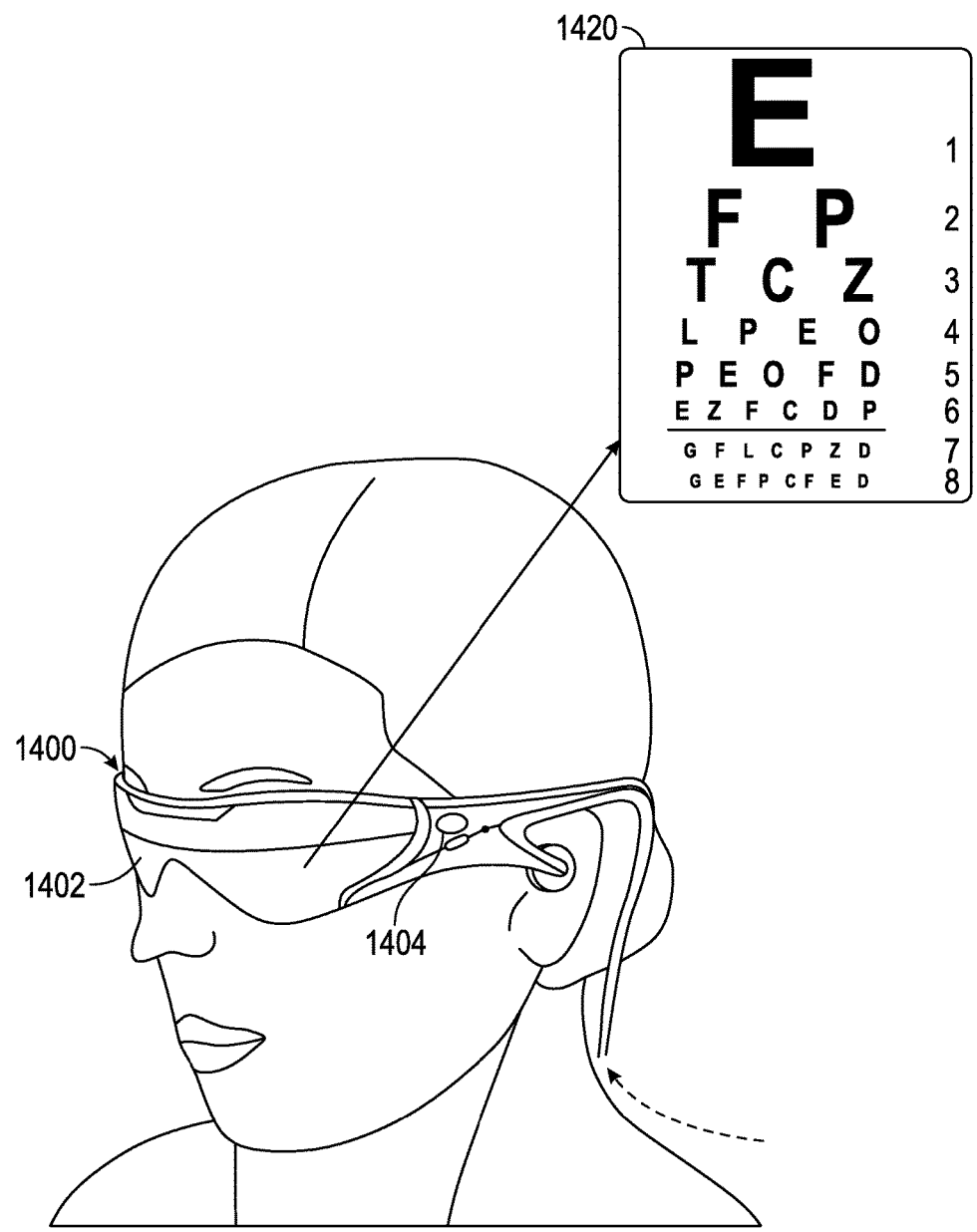
FIG. 14 illustrates an example of a wearable augmented reality device configured to function as a phoropter or refractor.

Referring now to FIG. 14, in one or more embodiments, a wearable augmented reality device 1400 can be used as an ophthalmic system to function as a phoropter or refractor to determine a suitable refraction that corrects or improves the vision of a wearer or a patient. The results of this test can be used, for example, to determine a wearer's or patient's optical prescription (e.g., for corrective lenses in glasses or contact lenses or for use in an augmented reality device). It should be appreciated that such a system may be used to administer an eye exam, and this exam may typically be administered at a doctor's or clinician's office. In one or more embodiments, the patient's individual ophthalmic system may be used, possibly with doctor supervision, or the doctor's office may have its own version of the ophthalmic system that may be used for diagnostic purposes. Although FIG. 14 is discussed in connection with augmented reality, similar features can be included in a virtual reality device such as virtual reality eyewear as well.

A typical phoropter is used by eye care professionals for eye examination and to determine a patient's refractive error and therefore corrective refractions to compensate for any ocular anomalies. Using this information, the eye care professional can determine an optical prescription of the patient's eyes to improve or correct the patient's vision. The phoropter typically comprises different lenses that may be tested, and usually involves presenting an eye test chart of alphabets of varying sizes to test the patient's vision. The patient looks at the eye test chart and lenses of different refractive powers are placed in front of the patient's eyes to determine whether the patient's vision has improved. The traditional set up tends to be bulky, and requires the doctor to individually select a next step size in the lens. The clinician typically asks the patient's feedback on image clarity, and changes the lenses accordingly.

In contrast, some embodiments of the wearable augmented (or virtual) reality device 1400 may be used to perform much of these same functions without a bulky phoropter setup. The wearable augmented (or virtual) reality device 1400 includes an augmented (or virtual) reality display platform 1402 configured to project an image to the eye of a wearer. The display platform 1402 can be configured similarly to the display lens 106, as described herein, for example, with reference to FIG. 5. In some implementations, such as for augmented reality devices, the display platform 1402 can also be configured to pass light from the world or environment through the display platform 1402 (e.g., through a lens in the front thereof) to the eye of the wearer. In this way, the wearer can see images projected with the display platform 1402 superimposed with what the wearer can see in the world. In some embodiments, rather than a physical eye test chart, a virtual eye test chart 1420 may be projected to the wearer using the display platform 1402. To provide functionality similar to a phoropter, the focus of the image can be varied. The wearable augmented (or virtual) reality device 1400 can be configured to administer or provide an eye exam by automatically providing incremental changes in an optical prescription by varying the focus of the image. Similarly, an eye exam can be administered by varying the refractive power of adaptive optics elements in the display platform 1402.

As described herein, the augmented reality device 1400 can include adaptive optics that are configured to change their optical properties. The adaptive optics or variable focus elements (VFE) can provide a variable optical correction, such as sphere, cylinder and axis, or higher order aberration correction. The adaptive optics elements can include deformable mirrors that are configured to change the shape of the reflective surface to direct light to targeted locations. The adaptive optics elements can include optics configured to change an index of refraction to selectively direct light to targeted locations (e.g., liquid crystals). The adaptive optics can include one or more light modulators configured to selectively direct light using a plurality of pixels. The adaptive optics can include acousto-optic modulated mirrors that are configured to time-multiplex incident light to selectively direct incident light.

In certain implementations, the display platform 1402 includes a plurality of waveguides. The plurality of waveguides can be structured in a parallel or in a serial fashion. The waveguides can be configured to project and receive light. The received light can be imaged or otherwise detected. This may be utilized in an eye exam where the waveguides are configured to image the retina of the wearer to monitor images formed at the retina. Individual waveguides can correspond to different depth planes. To determine the accommodative state of the eye, a reflex from the retina (e.g., the reflex from an image projected into the eye of the wearer) can be measured using the waveguides. This can result in a rapid measurement of the accommodative state of the eye. For example, a sequence of point source images (e.g., outside of the visible wavelength band) can be projected from various depths from the waveguides into the eye of the wearer and the waveguides can simultaneously measure the reflex from the retina. The augmented (or virtual) reality device 1400 can be configured to determine in real time the accommodative state of the eye by determining which depth plane corresponds to the brightest, smallest, or best focused image based on the reflex that is the most collimated. In effect, the waveguide stack can act as a set of tuned autocollimators with each waveguide corresponding to a particular focal and/or accommodative state. To do so, the augmented (or virtual) reality device 1400 can be configured to project a beam of light from an optical source into the eyes of the wearer. A portion of the projected beam can be reflected, scattered, and/or diffracted by various anatomical features of the eye of the wearer and received by one or more imaging devices. An electronic hardware processor can be used to analyze light received from the eye of the wearer to examine the various structures of the wearer's eye. This can result in a determination or approximation of the accommodative state of the eye, which may include the shape of the lens, the pupil constriction state, the vergence, dynamic accommodation, etc.

In some embodiments, refractive correction can be provided by the augmented or virtual reality device 1400 using adaptive optics wherein light is injected into waveguides using deformable mirrors and/or refractive lenses. Refractive correction can also be provided using a spatial light modulator (e.g., an optical component comprising an array of elements configured to change a phase of incident light). In certain embodiments, refractive correction can be provided using light from a fiber or other light source such as a scanning source (e.g., a fiber scanning device) that is directed to a deformable mirror that couples the light into a free-space optical beamsplitter to selectively direct light to targeted locations. By altering the shape, refractive index, or phase of the adaptable optical element, properties of wavefront, such as the phase projected by the augmented reality device 1400 can be altered to provide refractive correction designed to reduce or compensate for the refractive error of the wearer's eye.

In some embodiments, an adaptive optical modulated mirror can be configured to selectively direct light into one of a plurality of waveguides. Each of the waveguides can include optical elements (e.g., lenses, mirrors, etc.) configurable to provide a particular optical power. For example, an augmented reality or virtual reality device 1400 can include 10 waveguide stacks where each stack can apply about 0.5 D optical power. By selectively directing light into one of the waveguides and turning the light through a plurality of other waveguides, subsets of the waveguides and associated optical power can be provided to the wavefront. A targeted refractive power/correction (e.g., of sphere) may be achieved. In some embodiments, the waveguide stacks are used in conjunction with adaptive optics elements to correct for astigmatism and/or higher order optical aberrations.

In some embodiments, the augmented reality device 1400 uses pure adaptive optics to achieve a refractive correction. For example, the augmented reality device 1400 can include a plurality of lenses and mirrors. For example, an adaptive optical lens that is transmissive can be employed to correct light projected by a light source of the display as well as correct ambient light form the world in front of the eyewear. In some such embodiments, a plurality of waveguides need not be employed as adaptive optical elements but can be time-multiplexed to enable scanning of different colors (e.g., red, green, and blue) as well as depth planes. In certain implementations, the colors can be scanned for an individual depth plane prior to proceeding to the next depth plane. In some embodiments, a beamsplitter may be employed to couple in light from the light source although other configurations are possible. In some embodiment, a plurality of light guides may be included with the adaptive optical lens. Multiple colors or depth planes can be scanned simultaneously in some embodiments. Transmissive spatial light modulators that modulate the phase may also be used to alter the wavefront shape and provide refractive correction. Adaptive optical mirrors may also be employed. In some embodiments, reflectors may be used to tailor the optical path as desired. A beamsplitter may also be employed, in certain embodiments, to couple in light from the light source.

In some implementations, to conduct an eye exam, the user/wearer may be presented with a variety of images of varying sizes, and the user/wearer may provide input as to the clarity of the image through a user interface 1404 of the ophthalmic system. In some embodiments, the ophthalmic system is configured to automatically determine the clarity of the image based at least in part on detecting whether the image is focused on the retina of the wearer. This can be done by imaging the retina of the user and measuring, analyzing, and/or observing the reflex from the retina of the projected image. Rather than physically changing lenses, as in a typical phoropter, if the user/wearer indicates that a particular image is not clear, or that the image is not comfortably seen, the focus of the image may be automatically varied, (e.g., through the VFE or adaptable optics such as discussed herein) to provide incremental changes in the corresponding or equivalent optical prescription. Thus, eye exams may be conducted seamlessly through the ophthalmic system locally or remotely. For example, a clinician or doctor can administer the eye exam remotely, such as, by way of example and without limitation, over a phone, using video conferencing, over a networked communication program, or the like. It should also be appreciated that, in some implementations, the eye exams may be conducted with or without direct interaction from a clinician or with less or minimal effort and time of the clinician.

In some embodiments, adjustments to the optical prescription may be automatically performed by the ophthalmic system based on physical changes of the eye while attempting accommodation and/or vergence. For example, the ophthalmic system may be programmed to detect certain patterns of eye behavior that are symptomatic of weakening eyes. Based at least in part on the tracked eye behavior, eye adjustments may be automatically made by the ophthalmic system. The system may for example, upon detecting that the wearer struggles to accommodate, initiate a phoropter examination such as described herein or the system may alert the wearer or clinician that the wearer is struggling to accommodate. In some embodiments, the system detects that the wearer struggles to accommodate by detecting microfluctuations in accommodation (e.g., small and/or rapid changes in lens shape, vergence, pupil size, etc.). In certain implementations, accommodative struggles can be detected by monitoring the focus state of an image projected onto the retina of the wearer, as described herein. If the reflex from the retina is fluctuating, the system can be configured to determine that the wearer is struggling to accommodate. The system might present the wearer with images, and test different optical corrections asking the users to provide feedback as to whether the optical correction improves the images. In some implementations, rather than asking for the wearers to provide feedback, or in addition to asking for feedback, the system can be configured to determine if the image is in focus by observing, measuring, and/or analyzing the image on the retina of the wearer. As discussed above, adaptive optics or one or more VFE may be used to implement the different test corrections during the examination. In some embodiments, the system can be used to determine a phoria of the wearer by presenting images to eyes of the wearer one eye at a time. In certain implementations, the system can be used to monitor vergence of the wearer on a target. If the wearer is exophoric when attempting to focus on a close image (e.g., an image projected from a near depth plane), the system can be configured to determine that the wearer may be presbyotic or fatigued and/or whether the wearer may have strabismus or amblyopia. The system can also be configured to administer a variety of tests of visual field by providing images from a variety of different depth planes.

In some embodiments, the display platform 1402 includes a fiber scanning device, such as, for example, discussed herein. In various embodiments, the fiber scanning device can be configured to provide different depth planes from which the image or portions of the image can be projected. In some embodiments, the display platform 1402 includes a waveguide stack, as described herein. The waveguide stack can be configured to provide different depth planes from which the image or portions of the image can be projected. In certain implementations, the waveguide stack includes one or more lenses in the stack, as described herein. In some embodiments, the display platform 1402 includes adaptable optics elements configured to project light with different focal planes. In certain implementations, the adaptable optics elements include variable focus elements (VFEs), as described herein. In some embodiments, the device 1400 can be configured to vary the focus of the projected image by changing an optical path of one or more elements of the display platform 1402. In certain implementations, the device 1400 is configured to vary the optical path length through the use of a fiber light source. For example, the fiber light source can be configured to vary the focus (e.g., the focal point) of the projected image by varying the fiber length (e.g., transmitting light from fibers of different lengths) and/or position (e.g., by mechanically moving a fiber). In certain implementations, the device 1400 is configured to vary the focus of the projected image by varying a microelectromechanical system (MEMS). For example, the device 1400 can include micro-optics implemented using MEMS that include diffractive, refractive, and/or reflective optics elements that can be used to vary the focus of the image. Other types of variable focus elements or adaptive optical elements may be employed.

The image provided by the ophthalmic system can be a stored image. The wearable augmented (or virtual) reality device 1400 can include a data store that includes one or more stored images suitable for conducting an eye exam or for determining an optical prescription for a wearer. The stored image may be letters, number, symbols etc. such as used in eye charts. The image may be presented to the viewer at the desired depth plane, such as at infinity or an otherwise large distance, e.g., at least 20, 40, 60, 80, or 100 feet away. As described herein, the stored image can be processed to produce corrected wavefronts for projecting to the wearer. The corrected wavefronts can be configured to account for an optical prescription or anomaly of the wearer's eye. In some embodiments, adaptable optics in the display platform are used to provide adjustments to the image that the wearer sees to account for the optical prescription. In certain implementations, a combination of adaptable optics and/or software is used to provide the appropriate optical correction to adjust projected images to account for anomalies in the wearer's eye(s). The software may, for example, alter the intensity pattern comprising the image, for example, to compensate for distortion or fisheye wherein straight lines appear curved. For example, to compensate for pincushion distortion, some barrel distortion may be introduced into the intensity pattern that comprises the images. Similarly, to compensate for barrel distortion, some pin cushion distortion may be introduced into the intensity pattern that comprises the images. Other types of modifications to the intensity pattern that makes up the image may be introduced by software that is used to drive a spatial light modulator or light source to produce the desired intensity pattern. In some embodiment, the wearable augmented or virtual reality device 1400 can be configured to use the display platform 1402 to project images of varying size to the wearer or images from varying depth planes to the wearer. In some implementations, the image can include letters or shapes of varying sizes and/or projected from varying depth planes. In various implementations, the size and/or depth planes of the letters and/or shapes projected to the wearer can be varied during the eye exam. In some embodiments, the system can be configured to administer a brightness or glare test that include objective measurements of functional visual acuity in different brightness and glare conditions. In various embodiments, the system can be configured to administer a brightness acuity test to determine the functional visual acuity in various bright light conditions. For example, the system can be configured to simulate three or more bright-light conditions: 1) high-direct overhead sunlight; 2) medium-partly cloudy day; and 3) low-bright overhead commercial lighting. The visual acuity measurements can be similar to those that would be measured in these three conditions using a standard eye chart (e.g. the eye chart 1420). The result of such a test may be an assessment of functional visual acuity. Such tests can be used to test for sensitivity to bright light, photophobia, impaired scotopic vision, and the like. In some embodiments, the system can be configured to test individual colors. For example, the ophthalmic system can be configured to determine refractive errors for individual colors (e.g., red, green, blue, yellow, etc.). In some embodiments, the system can be configured to test a variety of depth planes. For example, the ophthalmic system can be configured to determine refractive errors for individual depth planes. This can result in an optical prescription that changes based at least in part on depth plane. Refractive correction for presbyopia may also be determined.

In some embodiments, the wearable augmented (or virtual reality) device 1400 can include one or more outward facing cameras. In certain implementations, the one or more outward facing cameras can be similar to the cameras 16 described herein with reference to FIG. 5. The outward facing cameras in an augmented reality display device can be configured to capture images the surrounding environment to determine, for example, where to superimpose a test image such as letters or symbols. For example, the augmented reality device might superimpose an image of an eye chart, such as a standard Snellen chart or other visual acuity chart over an area in the field of view of the wearer corresponding to the wall of the optometrist's office. In another example, the outward facing cameras can be configured to capture images of an eye chart, such as a standard Snellen chart or other visual acuity chart that is actually on the wall of the optometrist's office. The wearable augmented or virtual reality device 1400 can then be configured to modify the captured image based at least in part on the desired depth plane for presenting the image. For example, the acquired image can be projected by the display platform 1402 at infinite accommodation. Then, through a user interface 1404, the light from image can be manipulated to provide functionality similar to changing a lens with a typical phoropter. For example, sphere, cylinder, or higher order aberration correction can be introduced. If cylinder is to be added, the appropriate axis can also be determined. In this way, an eye exam can be conducted to determine an optical prescription of the wearer. In some embodiments, the system is configured to objectively measure or estimate an optical prescription through observation, measurement, and/or analysis of the manipulated image, determining whether it is in focus on the retina of the wearer, as described elsewhere herein.

The wearable augmented reality device 1400 can include one or more user interface features 1404 configured to allow a wearer or other person to provide input to the device. The user interface features 1404 can be integrated with the device 1400, as illustrated in FIG. 14. In some implementations, the user interface features 1404 are provided by a device or component that is not physically integrated with the device 1400. For example, the user interface features 1404 can be provided by a device or system that is in communication with the device 1400. This can be a smartphone, computer, tablet, or other computational device that is in wired or wireless communication with the device 1400. In some embodiments, the user interface features 1404 can be provided by a combination of different devices and systems linked to the device, e.g., through wired or wireless communication networks or through components that are physically linked to the device or integrated with the device. A touch screen, voice recognition system, or virtual touch screen are some examples of interfaces. Accordingly, the user interface features 1404 can include capacitive features sensitive to touch, keyboards, buttons, microphones, photodetectors, cameras, and/or a variety of software-implemented features provided by a graphical user interface. The user interface features 1404 can be presented on a device with a touch screen wherein interaction with the touch screen provides input to the wearable augmented or virtual reality device 1400. In various embodiments, a virtual touch screen is provided through the images projected to the user's eyes and sensors to sense the users moving body, e.g., finger. In some embodiments, the user interface features 1404 include gesture detection components to allow a wearer to provide user input through gestures. In some embodiments, the user interface features 1404 include gaze detection components to allow a wearer to provide user input through gaze of the eyes (e.g., this can include selecting a button or other element when the wearer fixates on the button for a time or when the wearer blinks when fixated on the button). Such user interface systems can be employed for other devices and systems described herein.

In the ophthalmic system, the user interface features 1404 can be used by the wearer to provide feedback regarding the quality of the image as perceived by the wearer. The wearer can provide feedback through the user interface features 1404 regarding whether the wearer can comfortably view the image being projected to the user for example as changes to the applied refractive power (e.g., incremental values of sphere, cylinder, and axis and/or higher order aberration correction) are provided incrementally. In this manner, an appropriate optical prescription for the wearer can be determined.

In some implementations, the clinician or doctor can also use the interface features 1404 to vary the focus and/or the depth plane from which the image is being projected to the wearer or the size of the image being projected. Such changes can be used to incrementally if desired.

Figure 15:
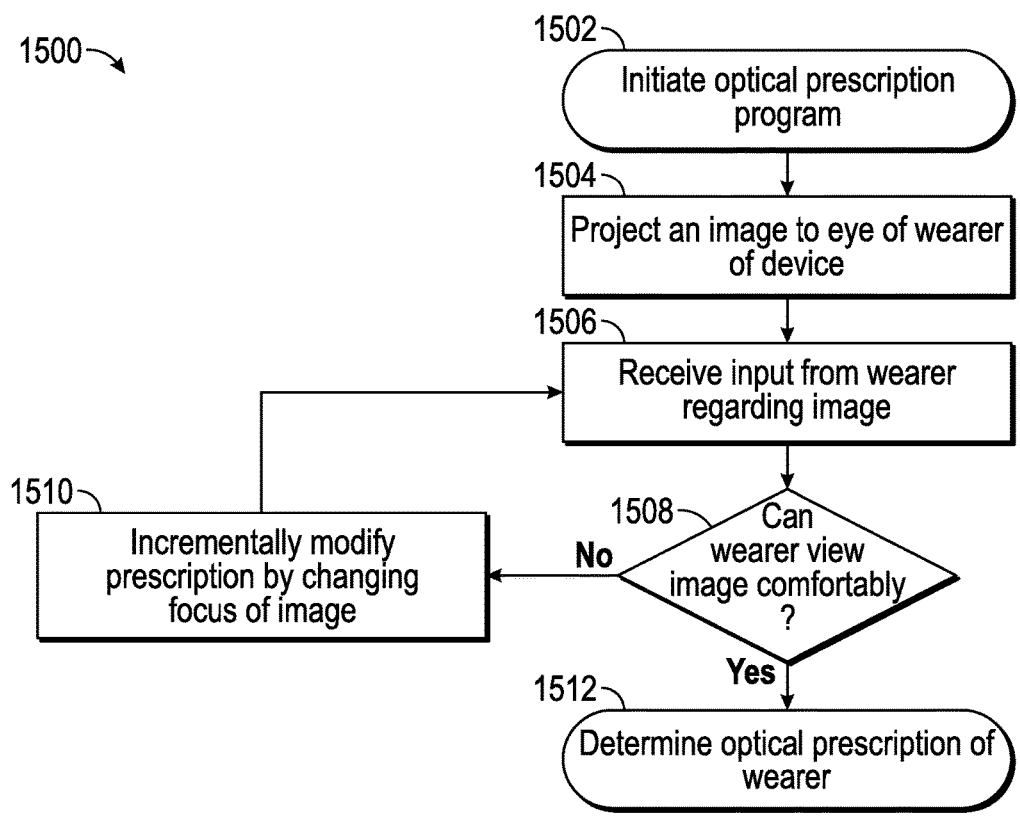
FIG. 15 illustrates an example method for determining an optical prescription of a wearer of an augmented or virtual reality device configured for use as a virtual phoropter.

FIG. 15 illustrates an example method 1500 for determining an optical prescription of a wearer of an augmented (or virtual) reality device configured for use as a virtual phoropter. For ease of description, the method 1500 will be described as being performed by an ophthalmic system, such as the augmented (or virtual) device 1400 described herein with reference to FIG. 14. However, it is to be understood that any component or subpart of the various augmented reality (or virtual) devices disclosed herein or other similar devices can be used to perform any step, combination of steps, or portions of a step in the method 1500.

At block 1502, the ophthalmic device initiates an eye test program. The eye test program can be a stored process or sequence of functions provided by the ophthalmic device. Initiating the eye test program can include determining or retrieving a starting optical prescription, such as for a wearer that has previously undergone an eye test or other eye exam. In some implementations, the eye test program can integrate information about ocular anomalies of the wearer's eye(s), where the information about the ocular anomalies can be entered by the wearer or clinician, determined from a previous eye test program, or retrieved from a data store (e.g., a data store that is part of the ophthalmic system or a networked data store). Initiating the eye test program can include determining the image or sequences of potential images to be projected to the wearer. Initiating the eye test program can include determining whether a clinician or doctor is administering the eye exam or whether the examination is being self-administered by the wearer. In some embodiments, the ophthalmic device initiates the eye test program in response to input received from the wearer or a clinician.

At block 1504, the ophthalmic system projects an image to the wearer's eyes. For example, the ophthalmic system can project an alphabet, letters, and/or shapes of a targeted size to the wearer. The image can be a stored image or the image can be acquired by the ophthalmic system. The image can include elements configured to aid in determining visual acuity of the wearer, wherein the visual acuity elements comprise, for example and without limitation, icons, symbols, letters, shapes, or the like. The visual acuity elements of the image can have a variety of sizes within the image and/or the size of the visual acuity elements can be varied by the ophthalmic system.

At block 1506, the ophthalmic system receives user input regarding the image. The user input may indicate whether the wearer is able to view the image clearly or not. In one or more embodiments, the ophthalmic system may begin by projecting relatively small letters that increase in size until the received user input indicates that the wearer can see the projected image clearly. In some embodiments, the ophthalmic system is configured to present an eye chart, such as a conventional eye chart like the Snellen chart. In such embodiments, the received user input can include which portion or portions of the projected chart the wearer can see clearly.

At block 1508, the ophthalmic system determines whether the user can comfortably view the image (e.g., a projected eye chart). In some embodiments, the system is configured to receive user input through a user interface as to whether the user can comfortably view the image. As described above, examples of such a user interface may include a voice recognition system, a touch screen, or a virtual touch system.

In some embodiments, the user input received in block 1506 is automatically determined through analysis of physical and/or optical characteristics of the wearer. For example, the user input that is automatically determined includes analysis of whether the image is in focus by observing, measuring, and/or analyzing the retina of the wearer. As described herein, by measuring the reflex from the retina, the ophthalmic system can be configured to assess the quality or degree of focus of the image formed by the wearer's eye. In some embodiments, the ophthalmic system can be configured to project a pair of spots into the eye of the wearer. The reflex of these projected spots can be measured and analyze to determine the quality of focus of the image. For example, where the images of the projected spots on the retina are aligned, the ophthalmic system may determine that the wearer is focusing on the projected image or that the wearer is accommodating properly at the targeted location.

In some embodiments, the ophthalmic system is configured to determine that the wearer can comfortably view the image based at least in part on detection of relaxed accommodation and/or vergence. As described herein, the ophthalmic system can include eye detection and/or tracking components configured monitor the eye. Such components may be able to detect accommodation, vergence, and/or pupil size of the wearer. Lens accommodation may be detected, for example, with an OCT (as described in greater detail elsewhere herein) that images the lens or an autorefractor (as described in greater detail elsewhere herein) that measures a size of an image on the retina. Vergence and pupil size can be measured with one or more inward facing cameras. In some embodiments, the ophthalmic system monitors the fluctuations of the eye when the user is trying to focus on a targeted object or image. For example, when an eye focuses on a stationary stimulus, the power of the lens of the eye changes rapidly and continuously. When a person struggles to focus on a stationary object, these fluctuations can increase. This increase in fluctuation can be measured and/or observed by the ophthalmic system to determine that the wearer is not focusing on the targeted image or object. In some embodiments, the ophthalmic system can be configured to monitor these fluctuations and move the projected image (e.g., change the depth plane from which it is being projected) until the wearer successfully focuses on the object. For example, the ophthalmic system can project the image from a depth plane that is relatively near the wearer and push the image back (e.g., increase the distance between the wearer and the depth plane) until the ophthalmic system determines that the wearer is accurately focusing on the image.

Monitoring of the accommodation reflex of the eye can be employed by the ophthalmic system to determine if the wearer is not comfortable with the current prescription or if the wearer needs optical correction. An imaging system such as OCT, which can show the front and rear surfaces of the natural lens of the eye, can be used to determine whether the wearer is accommodating. For close objects, the convexity of the lens is expected to increase. OCT or other imaging system such as described herein (e.g., ophthalmoscope, SLO, confocal microscope, etc.) can also possibly monitor changes in curvature of the lens surface and/or movement of the lens or change in the shape of the lens or structural features of the eye to determine whether a wearer is accommodating, examples of which are described elsewhere herein. Additionally, an autorefractor can be used to determine whether the wearer is accommodating by monitoring the size of an image projected through the lens onto the retina, examples of which are described elsewhere herein. Such methods of monitoring accommodation can be used to determine whether the wearer is accommodating, which can be useful in assessing whether the wearer need optical correction.

Vergence can be employed to assist in determining if an optical correction is needed as well, where vergence is monitored to test accommodation reflex. Using inward facing cameras and processing electronics, the ophthalmic system can be configured to track changes in the line of sight of the left and right eyes and to determine the vergence. Such vergence information can be used to determine whether the wearer's eye is responding as expected to images presented at various depth planes. For example, if both eyes are substantially parallel and not converging when an image at a relatively close depth plane is being presented, the ophthalmic system can be configured to interpret this result as indicating that the wearer is not seeing the image comfortably or that the wearer has a vision defect. The vergence for different depth planes can be determine and whether the eyes match the proper vergence for a particular depth plane can be assessed. Likewise, potentially if vergence is observed to be inward for a depth plane that is at infinity, the wearer may need optical correction.

As another example, the ophthalmic system can test accommodation reflex by determining a size of the wearer's pupil or a change in the size of the wearer's pupil when an image is projected to the wearer. The ophthalmic system can be configured to track changes in the pupil size using an inwardly facing camera that images the eye and in particular the iris. This information can be used to determine whether the wearer's eye is responding as expected to images presented at various depth planes. For example, the size of the pupil is expected to constrict when looking at a closer object (compared to an object that is farther away). Thus, the ophthalmic system can be configured to present an image from a close depth plane and to track the response of the wearer's pupil. If the pupil does not constrict, or constrict sufficiently, the ophthalmic system can be configured to interpret this result as indicating that the wearer is not seeing the image comfortably.

Accordingly, to determine the comfort of the wearer in viewing an image, the ophthalmic system can determine the accommodation, vergence, and/or pupil size of a wearer as part of an examination of the accommodation reflex, when a particular image is projected to the user. Similarly, the comfort of the wearer can be determined when the image is projected through a variety of depth planes. In some embodiments, the ophthalmic system can compare the measured accommodation, vergence, and/or pupil size to an expected accommodation, vergence, and/or pupil size. If one or more of the measured characteristics are within a targeted range of the one or more expected characteristics, then the ophthalmic system can determine that the wearer is comfortably or correctly seeing the image (e.g., the wearer is seeing the image with expected, adequate, or normal visual acuity). If one or more of the measured characteristics are outside of the targeted range of the one or more expected characteristics, then the ophthalmic system can determine that the wearer is not comfortably or correctly seeing the image (e.g., the wearer is seeing the image with impaired visual acuity). In some embodiments, the ophthalmic system combines information regarding the measured characteristics with the information received or determined from the user input in block 1506 to determine whether the wearer comfortably sees the projected image. For example, when viewing an image from a relatively close depth plane, the wearer's eyes are expected to converge or move towards one another, the pupils are expected to constrict, and the convexity of the lens is expected to increase. Deviation from one or more of these expectations can be interpreted as indicating that the user is not seeing the projected image comfortably or correctly (e.g., the wearer is seeing the image with impaired visual acuity).

If the ophthalmic system determines that the wearer is unable to comfortably view the image, for example, either by receiving input from the user through the user interface or by assessing the user's accommodation and/or vergence, the ophthalmic system proceeds to block 1510 to change the focus to incrementally increase the prescription (e.g., add or subtract more positive or negative sphere to get more a more positive or negative spherical wavefront). The system can also test for astigmatism and thus incrementally change the axis and cylinder. The ophthalmic system then returns to block 1506 to receive or determine user input to again determine whether the user can comfortably or comfortably view the image (e.g., with normal visual acuity). This loop can be repeated until the user comfortably sees the image.

In some embodiments, the ophthalmic system is configured to adjust the optical correction at block 1510 based at least in part on feedback received at block 1506 from the user input and/or objective assessment determined at block 1508 or as described elsewhere herein. In some embodiments, the ophthalmic system is configured to adjust the optical correction at block 1510 based at least in part on measurements of the accommodation, vergence, accommodation reflex, and/or pupil size of the wearer when viewing the projected image. Thus, in certain implementations, the ophthalmic system can be configured to conduct the eye examination using subjective and objective tests to determine an optical prescription for the wearer.

In some embodiments, a subjective element of the eye examination can include projecting an image and then projecting the image with a diopter change (e.g., ±0.01 D, ±0.1 D, ±0.125 D, ±0.25 D, ±0.5 D, ±1.0 D, or a substantially continuous change in diopter power such as through an adaptable optics element, etc.) and receiving user input regarding whether the image quality changed. In certain implementations, the ophthalmic system can also be configured to determine changes in the wearer's eyes (e.g., accommodation, vergence, pupil size, etc.) when the diopter is changed. This objective test data can be combined with the subjective response of the wearer to determine if the change in diopter results in a change in visual quality for the wearer.

If the ophthalmic system determines that the wearer is able to view the image comfortably, the ophthalmic system proceeds to block 1512 to determine the prescription of the wearer's eyes. It should be appreciated that, in some implementations, the same process may be repeated for both eyes (e.g., both eyes can be treated together applying the same correction to each eye or individually applying different correction to the left and right eyes). In some embodiments, this can be used to treat anisometropia where two different optical prescriptions are applied to the respective two eyes of the wearer. In some embodiments, the ophthalmic system can be configured to dynamically switch between optical prescriptions depending on what is being viewed by the wearer and/or what activities are being performed by the wearer. For example, lenses for anisometropia can be fatiguing for a wearer when primarily viewing images that are near or that are primarily far when compared to when a wearer is viewing images that are a mix of near, mid, and far ranges. Accordingly, the ophthalmic system can be configured to dynamically change the optical prescription applied in real time based at least in part on known optical prescriptions for treating a wearer's anisometropia, myopia, or hyperopia.

The method 1500 can be used to provide information to an augmented (or virtual) reality device, such as the device 1400 described herein with reference to FIG. 14 or other similar devices described herein. Thus, the augmented (or virtual) reality device can be configured to change the focus or other aspects of images being projected based on the optical prescription of the wearer as described herein. In some embodiments, the same wearable augmented (or virtual) reality device that the wearer uses for entertainment, work, or other purposes can be used to perform the eye examinations described herein.

The method 1500 can be used to determine optical prescriptions, optical correction, or refractive correction for different depths. For example, there can be a first optical prescription for a far depth plane, a second optical prescription for a mid-depth (intermediate) plane, and a third optical prescription for a near depth plane or far and near, far and intermediate, near and intermediate.

The method 1500 and system can be used to correct or improve a wearer's vision where the wearer suffers from presbyopia. Different optical corrections can be applied to different depth planes and the associated content projected from those depth planes. Or the wearable augmented reality devices can be configured to switch between providing the prescriptions for far distance (if any) and near distance based on the sensed orientation of the users, e.g., the user's head or eye. As described herein, orientation sensors or other sensors can be used to determine the orientation of the user's head or eye.

The method 1500 can be performed in real time to automatically determine an optical prescription of a wearer. This information can be stored in the ophthalmic system and used for future tests. For example, the ophthalmic system can be configured to update the wearer's current optical prescription for the wearer based on the examinations. For example, the ophthalmic system can be configured to monitor the eye and record the eye behavior of the wearer over time. Based at least in part on this information, the ophthalmic system can dynamically adjust the optical prescription of the wearer over time. For example, the ophthalmic system can measure the behavior of the eye when presenting an image at a known depth. The ophthalmic system can determine deviation from the expected eye response to the image to determine if the eye is behaving as expected. The ophthalmic system can be configured to initiate an examination and/or update the wearer's optical prescription or to initiate or schedule an updated eye examination if the ophthalmic system determines that the determined deviation is outside of a range, e.g., targeted, acceptable range of the expected behavior.

In some embodiments, the ophthalmic system can be configured to determine the optical prescription obtrusively. For example, this may occur where the ophthalmic system does not provide alternative functionality to the wearer while the eye examination is being conducted. In other words, this may occur where the wearer is requested to focus solely on the eye examination.

In some embodiments, the ophthalmic system can be configured to determine the optical prescription unobtrusively. For example, this may occur where the ophthalmic system is configured to acquire measurements of the wearer's eye behavior while the wearer is doing other things (e.g., watching movies, reading text, looking at images, etc.). The ophthalmic system can be configured to measure characteristics of the wearer's eyes while the wearer is performing these other activities, to compare measured characteristics of the wearer's eyes, to determine deviations from expected characteristics of the wearer's eyes. In some embodiments, the system can be configured to determine the optical prescription based at least in part on these determined deviations. In some embodiments the expected characteristics of the wearer's eyes can be based at least in part on the depth planes and image properties being projected to the wearer. In some embodiments, when such deviations are detected, the system could ask the user to undergo an examination applied by the system or confirm a test optical correction as sufficient or insufficient. In some implementations, the ophthalmic system can be configured to track physical changes in the wearer's eyes while attempting accommodation and vergence while performing these other activities. In some embodiments, this information can be compared to measurements acquired while not attempting accommodation and vergence to determine the optical prescription.

In some embodiments, the ophthalmic system can be configured to objectively measure an optical prescription of a wearer. In various implementations, this may be accomplished without receiving feedback from the wearer regarding image quality. In certain implementations, this may be accomplished without projecting images of varying sizes to the user. For example, the ophthalmic system can be configured to project an image from a virtual infinite depth (e.g., the ophthalmic system puts the image at infinity). The ophthalmic system then measures the accommodation reflex, accommodation, vergence, and/or pupil size of the wearer. Based at least in part on the accommodation, vergence, and/or pupil size of the wearer and the deviation of the wearer's accommodation, vergence, and/or pupil size from what is expected, the ophthalmic system can objectively determine the wearer's optical prescription. For example, if the wearer's eyes are accommodating at +1 D when the image is being put at infinity, the ophthalmic system can objectively determine the optical prescription.

In some embodiments, the ophthalmic system can be calibrated to determine the proper diopter and/or account for the proper diopter correction based at least in part on the configuration of the display platform. For example, when adjusting the depth plane of an image being projected to a wearer, the ophthalmic system can be configured to be calibrated to correctly correlate the change in depth plane to a change in diopter or refractive power. In some embodiments, during calibration, the iris of the wearer is analyzed. The iris can be used to uniquely identify a patient and this unique identification can be used to access associated patient records to correlate the person and their medical records/prescriptions, etc.

In various embodiments, to reduce distraction, the view of the world in front of the wearer's eyes through the augmented reality device is blocked or otherwise not visible during the examination. This can occur, for example, when images are presented to the viewer, although this approach is not necessary.

Although the system shown in FIG. 14 has been described as an augmented reality device, in other embodiments the system may be a virtual reality device. In either case, the system may be a system provided by the physician or clinician for testing at a medical facility or optometrist office or elsewhere. In other embodiments, the system may belong to the user and may be employed for other purposes such as entertainment (e.g., games and movies) and/or work activities. As described above, one benefit of implementing the examination on the user's system is that the examination can be conveniently undertaken multiple times (at least 2, 3, 4, 5, 6, 8, 10, 12, 16, 18, 24, or more times) throughout the year. In some embodiments, the frequency and/or schedule of examinations can be based at least in part on the rate of deterioration of the vision of the wearer. If the rate of deterioration increases, for example, the frequency of examinations can increase. Likewise, the examination can be performed with or without a medical professional, such as optometrist, ophthalmologist, nurse, technician, medical assistant etc.

Red Reflex

The ophthalmic system may also administer a reflex test of the wearer's eye to detect various abnormalities. A reflex test may comprise the steps of shining or projecting light into a patient's eye such that at least a portion of the light reflects from a portion of the eye, and observing a reflection of the light to detect abnormalities. For example, red reflex testing allows for the detection of abnormalities of the retina based on observing the typically red light reflected from the retina. Red reflex testing can allow for detection of cataracts, cancer of the eye, retinoblastoma, detached retina, glaucoma, strabismus, amblyopia, and aberrations of the eye, including low order and high order aberrations. Corneal reflex testing, or Hirschberg testing, refers to detecting the light reflected by the cornea, and may be used to detect strabismus, misalignment, asymmetry, or other conditions of the cornea, such as corneal scarring. In some embodiments, reflex testing may utilize visible light of a single color, multiple colors, white light, and/or infrared light to detect abnormalities.

In some embodiments, the ophthalmic system may be a user display device 62 such as shown in FIG. 5, which includes a light source such as a projecting subsystem 18 configured to project light 38 into the eye 20 of a wearer. The user device 62 may include a display lens 106 which may be mounted to a user's head or eyes by a housing or frame 108. The display lens 106 may comprise one or more transparent mirrors or reflective features positioned by the housing 108 in front of the user's eyes 20 and configured to reflect projected light 38 into the eyes 20 (and also potentially facilitate beam shaping). These reflective surfaces may be partially transmissive to also allow for transmission of at least some light from the local environment, e.g., from in front of the wearer. FIG. 10D also includes another view of an embodiment of a display device comprising a plurality of displays 200, 202, 204, 206, 208 that may be utilized to inject light into a plurality of respective waveguides 182, 184, 186, 188, 190, each of which may be configured, as described above, to distribute incoming light across the length of each waveguide, for exit down toward the eye. Waveguides may project light to the eye from different depth planes. The displays 200, 202, 204, 206, 208 may comprise fiber scanning devices (FSDs) to form the image. Such devices can be configured to project light onto a portion of the retina through a wave guide stack 178. The system may further include one or more fiber scanning displays and/or adaptable optics elements, such as variable focus elements, configured to project light to particular portions of the eye. In some embodiments, the ophthalmic system may comprise a separate light source in addition to the display device 62 for projecting light into the eye so as to form the reflex.

The system can then detect the reflection from the eye of the wearer. For example, the system may include one or more cameras such as eye tracking cameras 24 or similar detection methods to receive a portion of the light reflected from the retina, cornea, or other structure of the wearer's eye. The cameras 24 may detect the color and/or intensity of the reflection, the shape, position, and/or size of the reflection, or any other detectable quality of the reflected light. In some embodiments, the cameras 24 may capture images of the reflection for immediate or later analysis. Where testing is performed on both the left and the right eye of a wearer, the cameras 24 and/or other components of the device 62 may compare any qualities of the reflection for the two eyes so as to detect any asymmetry or other difference between the two eyes of the wearer. In some embodiments, the system may be configured to administer an alternating or unilateral cover test to detect ocular deviation. In a cover test, one eye may be occluded, or both eyes may be alternately occluded, to detect motion of each eye when it is occluded or uncovered and/or when the other eye is occluded or uncovered. The ophthalmic system may occlude an eye of the wearer using a spatial light modulator as described elsewhere herein, and/or by providing an image to only one eye or a portion thereof. In various embodiments, testing of the left and right eyes may be performed simultaneously or at different times, and may involve one camera 24 or multiple cameras 24. In some embodiments, the camera and/or light source may include one or more light pipes. Light from the light source may propagate through the light pipe to the eye or wave guide stack 178. Similarly, light collected by a light pipe or wave guide stack 178 may propagate through the light pipe to one or more cameras.

In some embodiments, reflex testing may be performed along the normal line of sight of a wearer's eye. That is, the light source, camera 24, and or light collected from a common point such as a wave guide or light guide, may be aligned generally along the normal line of sight (i.e., within a maximum angle such as ±5 or ±10 degrees of the normal line of sight) of an eye such that at least some of the projected and reflected light travel substantially along the optical axis of the eye. In some embodiments, testing may not be confined to the optical axis and/or normal line of sight. In such embodiments, the light source may be positioned so as to project light into the wearer's eye at a first angle, and the camera 24 may be positioned at a second different location off the normal line of sight where it can receive the reflected light. In some embodiments, the reflex testing may include multiple projections of light from different first angles, either simultaneously or separated in time.

Red reflex testing generally involves macroscopic imaging of the retina of a patient's eye. The camera might focus generally on the eye, and may be focused on the retina or the cornea, for example. The camera need not zoom in on the retina, as reflex testing does not require the camera to resolve features on the retina. Light can be projected into both eyes of the patient, and the reflections from the retina can be imaged or observed. A normal outcome may be observed if the red color reflected is the same or similar for both eyes, and if the size, location, and shape of the reflection is the same or similar for both eyes. If an eye reflects a color other than red, such as grey or white, the presence of cataracts, retinoblastoma, or other abnormalities may be indicated. Different sizes or shapes of reflecting regions between the two eyes may indicate other abnormalities such as refractive errors, misalignment, strabismus, unequal refraction, or other conditions. Refractive errors may be observed as linear or crescent-shaped regions of the retina that do not display a red reflex. For example, hyperopia may result in an upward-facing crescent, while myopia may result in a downward-facing crescent.

Observation of the retina may be facilitated by the application of mydriatic agents to induce pupil dilation and avoid pupil contraction in response to the projected light. Mydriatic agents may be various mydriasis-inducing drugs such as tropicamide or the like, and are well known for use in optical examinations. Other solutions for reducing pupil contraction or inducing dilation may be used. This solution may be delivered by a port on the ophthalmic display such as described elsewhere herein. In some embodiments, observation of the retina may be performed without mydriatic agents by using a short flash of light, rather than a steady light source. If a short flash of light is applied while the pupil is not contracted (e.g., due to being in a darkened room), the reflected light from the retina may be observed briefly before the pupil has contracted in response to the light. This phenomenon causes the red-eye effect commonly seen in photography. Accordingly, the light source may be configured to deliver a brief flash of light, and inward-facing cameras may be configured to capture an image of the reflected light after an appropriate time delay.

For purposes of red reflex testing, reflected light is frequently applied and viewed at distances between approximately 8 inches and 4 feet from the eye of the patient. If testing is performed with a closer head-mounted ophthalmic device, it may be impractical to mount illuminating or receiving devices at far distances from the eye. Thus, optical elements within the device may be used. For example, the ophthalmic system may include one or more lenses, such as negative power lenses, allowing projection of light that appears to be from a more distant depth plane. Similarly, lenses may be configured to form a virtual image corresponding to an ordinary reflex test viewing distance which may be detected by a camera 24 disposed within the head-mounted ophthalmic system. In some embodiments, a light source and/or image sensor may be mounted on a portion of the head-mounted ophthalmic system such as an ear frame, and mirrors may be used to create a longer projection and/or viewing distance.

Corneal reflex testing, such as the Hirschberg test, may use a fixation target for the wearer. For example, the wearer may be given a fixation target at the center of the field of view. In some embodiments, the fixation target may be located away from the center of the field of view. The fixation target may additionally be projected at multiple depth planes, such as by use of a wave guide stack 178. The depth of the fixation target may be varied during testing, such as by presenting a first fixation target at a first depth plane or location at a first time, followed by additional fixation targets at different depth planes or locations, so as to cause the wearer's eye to accommodate. The fixation target may be a small image, such as a dot or a recognizable picture, a dark spot in an image, or the like. Once the wearer's gaze is fixed on the fixation target, a difference in location of the corneal light reflection between the two eyes of the wearer may indicate the presence of strabismus. In some embodiments, the projected light may be tailored for reflection from the cornea, rather than reflection from other structures of the eye. For example, the light may be of lower intensity than the light used for red reflex testing so as to avoid generating a strong reflection from the retina. Moreover, corneal reflex testing may be performed without the use of mydriatic agents. In the absence of a mydriatic agent, the pupil may contract in response to the projected light, further reducing any retinal reflection that may interfere with the observation of the corneal reflex. In some embodiments, the system may use cover testing by occluding, defocusing, blurring, and/or de-emphasizing one eye of the wearer while leaving the other eye uncovered. Occlusion of one eye may be simulated by projecting the fixation target to the other eye only.

In some embodiments, results of various reflex tests may be imaged, such as by cameras 24, and stored for analysis. Once stored, the test results may be compared with known, published, or otherwise available data from normal and/or abnormal results of reflex testing. For example, an image of the red light reflected from a patient's retina may be compared with an image of the red light reflected from a normal retina (that is, a retina not exhibiting characteristics of any detectable abnormality) to determine if any abnormality is present. If a portion of a patient's eye does not appear consistent with a normal eye condition, the test data may further be compared with imaging data of various known abnormalities so as to accurately diagnose the abnormality of the patient's eye.

Intraocular Pressure

In one or more embodiments, the augmented reality or virtual reality ophthalmic system may be configured to measure intraocular pressure of the user's eye. Referring back to FIG. 5, this embodiment may be implemented by configuring the ophthalmic system 62 with one or more additional components along with necessary circuitry and processing power. In one or more embodiments the ophthalmic system may be designed to include the additional components/sensor(s), or in other embodiments, the additional components may be add-ons to the ophthalmic system.

Intraocular pressure (IOP) is typically governed by the amount of aqueous fluid pressure inside the eye. While some variation in IOP is normal (e.g., between day and night), higher IOP levels or significant differences between IOPs of the left and right eye can be an indication of other physiological issues liked glaucoma, iritis, retinal detachment, uveitis and corneal thickening. IOP typically is normally between approximately 10 and 21 mm Hg, with an average of about 15 or 16 mm Hg, varying by approximately 3.5 mm Hg over the course of a day.

In some embodiments, the ophthalmic system may use tonometry to determine IOP. The system may use contact tonometry by applying contact force to flatten a constant area of the cornea and infer the IOP from the applied force and consequent response. In some embodiments, the system may use non-contact tonometry by applying a rapid pulse of air, acoustic pressure, or other indirectly applied force to flatten the cornea and detect corneal applanation via an electro-optical system. The system may also include an optical coherency tomography (OCT), such as the OCT system describe herein and use this OCT system to measure an ocular reaction using 3D imaging. Compression may be determined by measurement of changes in the curvature of the cornea or movement of the apical corneal interface in relation to posterior interfaces such as the retina.

The ophthalmic system 62 as described may be configured to measure intraocular pressure using optical or ultrasonic measurement technology. In some embodiments, the system 62 may apply a force to induce compression of the cornea and use optical or ultrasonic detection methods to monitor the response to determine the pressure within the eye. Force may be applied by mechanical compression, a burst of air, and/or acoustic waves such as ultrasound. In other embodiments, the system may use optical, ultrasonic, and/or photoacoustic detection methods to determine the pressure within the eye without applying a force to the eyes. For example, ultrasound or acoustic waves can be used to perturb the surface of the cornea. Imaging methods, including ultrasound imaging can be used to measure the resultant change in shape, e.g., applanation of the cornea. In some embodiments, 3D optical imaging and/or ultrasound may be used to determine a density of the fluid within the eye, which may be used to calculate the intraocular pressure based on known properties of the fluid. Such ultrasound systems are described elsewhere herein, for example, with reference to FIG. 24A. 3D optical imaging systems may be capable of determining a density or change in density of the fluid based on known light absorption and/or reflection properties. The system may further include a temperature sensor, such as a non-contact infrared thermometer or other suitable temperature sensor, to detect temperature changes in the eye that may affect the reliability of any of the measurements described above.

The system may further include a sensor and processor 32 configured to determine the intraocular pressure of an eye 20. The sensor may be any type of monitoring device including a light sensor, a 2D imaging head, an interferometry 3D imaging head, and/or other sensors. In some embodiments, the ophthalmic system may use ultrasound or photoacoustic ultrasound for imaging instead of or in addition to the optical sensing technologies described above. For example, ultrasound or optical time-of-flight measurements may be taken to determine any change in one or more properties of the cornea of the wearer's eye due to an applied force. Ultrasound time-of-flight measurements may further be used to determine an intraocular pressure of the eye without applying a force to the eye, as the density of the fluid within the eye is dependent on the intraocular pressure and affects the speed of ultrasound waves within the eye. Decreased time-of-flight may indicate a higher fluid density, which may be correlated with higher intraocular pressure. In some embodiments, intraocular pressure may be determined based on the shape (e.g., applanation), tension, or other characteristic of the exterior surface of the eye. The sensors described above may comprise any cameras 16 or 24 of the ophthalmic system 62, or may be additional elements. For example, in embodiments using ultrasound or photoacoustic ultrasound imaging, the sensors may comprise one or more ultrasound transducers configured to generate an electrical signal based on detected ultrasound waves. Similarly, the sensors may comprise cameras configured to detect visible or infrared light as appropriate in embodiments using visible light or infrared imaging or optical sensors.

Figure 16A:
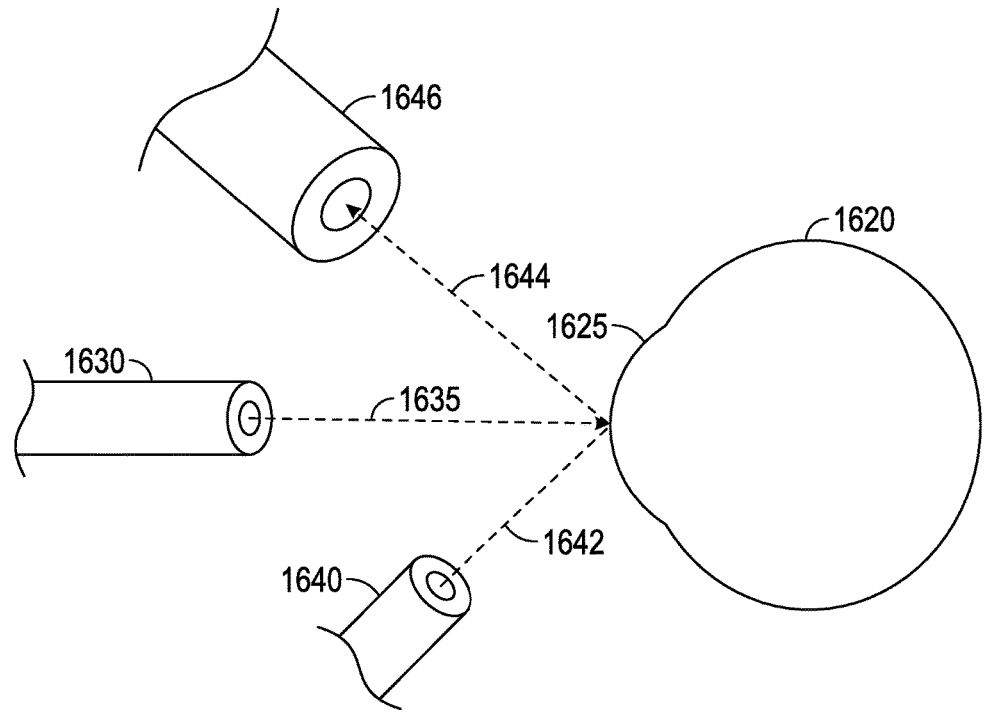
FIG. 16A schematically illustrates an example configuration of a system for determining an intraocular pressure of an eye.

In some embodiments, a light source such as a fiber scanning display (FSD) 18 or a separate light source element may project beams of light 38 into the user's eyes, as described elsewhere herein. The light source may further include an adaptable optics element 316b, variable focus element 316a, waveguide stack 178, and/or one or more lenses, also as described elsewhere herein herein and depicted in FIG. 10E. The light source may further be configured to project light into the wearer's eye from different depth planes. In embodiments in which the light source comprises a fiber scanning display, the fiber length of the display may be variable. The light source may be a display or a separate light source. In one or more embodiments, a set of parameters associated with backscattered or reflected light may be measured by the FSD or other light monitoring device or photo-detectors (as described herein, a FSD may be used to collect light). The pattern of backscattering or reflection of the emitted light may be an indicator of the intraocular pressure of the eye, especially when compared to previous measurements. For example, as shown in FIG. 16A, a light emitter 1640 may emit a beam of light 1642 in the direction of the cornea 1625 of a wearer's eye 1620. A portion of the beam may be reflected as a reflected beam 1644, which may enter a light detector 1646. The remainder of the incident light beam 1642 may be scattered elsewhere. A compression inducing device, such as an air tube 1630, may induce applanation in the cornea 1625, such as by emitting an air jet or pulse 1635. Lower IOP will result in greater applanation, creating a larger and flatter reflective surface, resulting in more of the incident light beam 1642 being reflected to the light detector 1646. Thus, a smaller number of reflected light rays to the light detector may be an indication of high IOP, in one or more embodiments. A greater number of reflected light rays to the light detector may be an indication of low or normal IOP, as lower IOP results in more significant applanation, causing more light rays to be reflected. Other configurations are also possible. Additionally, a wavelength of the light projected into the eye may be changed to provide depth information. For example, infrared wavelengths may penetrate deeper into the eye.

In some embodiments, optical sensing may include analysis of one or more Purkinje images of the wearer's eye. For example, the sensor may be configured to detect the first Purkinje image produced by the reflection of light from the outermost surface of the cornea, also called the P1 image, cornea reflection, or glint. The sensor and processor may analyze the presence, shape, location, intensity, or other detectable characteristic of the glint. Based on glint analysis, vergence, accommodation, curvature, applanation, or other characteristics of the eye may be observed. Repeated measurements may allow for detection of changes in any of the characteristics listed above. In some embodiments, the glint analysis may include measurement of glint characteristics during induced changes in accommodation or vergence to increase the accuracy and reliability of IOP measurements based on the detected glint characteristics, for example, as a noise filter.

The processor 32 of the ophthalmic system shown in FIG. 5 can be configured to determine an intraocular pressure based on the output of any of the sensors described above. For example, the processor may compare output data from one or more sensors with a correlation database that correlates detected parameters with known IOP values. Correlation databases may be stored locally in a memory circuit of the ophthalmic system, or may be stored remotely and accessed via wireless communication. The processor 32 may further be configured to detect the presence of ocular hypertension based on the determined intraocular pressure, as well as other information such as a threshold pressure defining ocular hypertension or other medical information. The threshold pressure values and any other relevant information may be stored locally or remotely, as described above for correlation databases.

In addition, the ocular pulse of an eye may be monitored based on detection of IOP as described above. An ocular pulse occurs due to pulsatile ocular blood flow into the choroid, or vascular layer of the eye. The IOP of an eye changes slightly each time blood is pumped into the eye. Thus, an oscillation of the IOP may be observed matching the rate of the ocular pulse, which may be the same or substantially the same as the heart rate of the wearer. In addition, there may be a systolic and diastolic IOP which may be correlated with the systolic and diastolic states of the cardiac cycle. Thus, increased IOP may be correlated with increased blood pressure. Further, the ocular pulse amplitude (OPA), the measured difference in IOP between the systolic and diastolic cardiac states, may be used as a diagnostic screening tool for carotid artery stenosis. Low OPA may indicate the presence of carotid artery stenosis, with lower amplitudes indicating more severe stenosis. OPA may also be positively or negatively correlated with the presence of glaucomatous damage, the axial length of the eye, and/or other ocular characteristics or hemodynamics. OPA may be measured repeatedly over a period of days, months, or years, with upward or downward trends in OPA indicating similar trends in the blood pressure of the wearer.

Figure 16B:
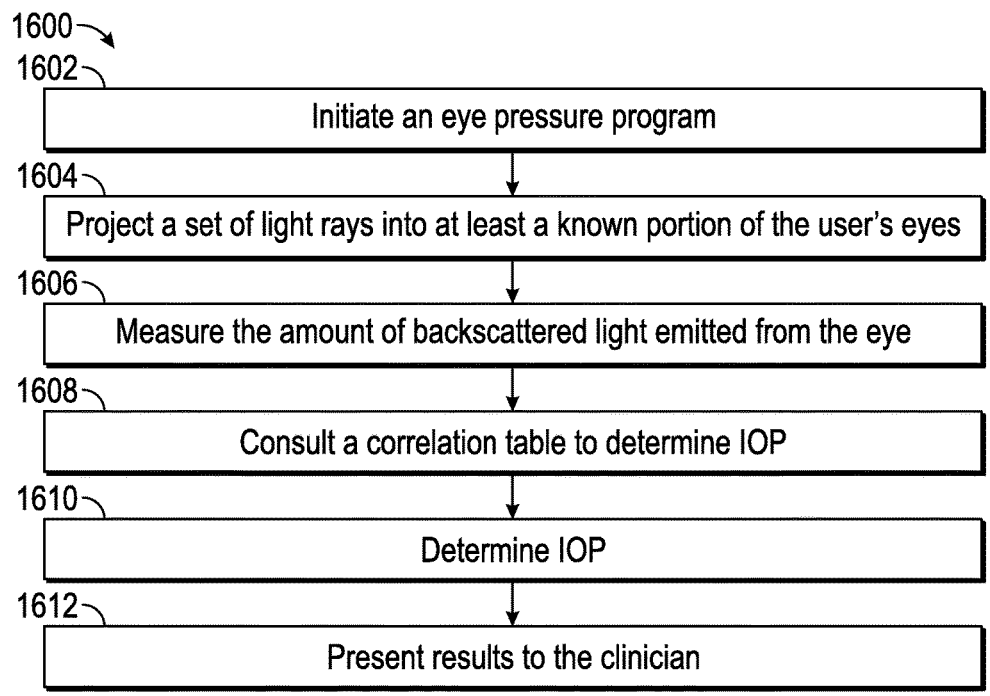
FIG. 16B illustrates an example process flow for determining intraocular pressure according to some embodiments.

Referring now to FIG. 16B, an example process flow 1600 for determining IOP is disclosed. At 1602, an eye pressure test program is initiated. At 1604, light is projected into a known portion of the user's eye(s). At 1606, the pattern or amount of backscattered or reflected light emitted in response to the projected light is measured. As noted above, this may be performed by the FSD itself, in some embodiments, or through a separate light measuring module. In some embodiments, 2D or 3D imaging may be used instead of or in addition to detecting the amount of backscattered or reflected light, as described above. As describe herein, optical imaging, OCT imaging, etc. of the eye, for example, of the cornea may be used to determine applanation or change in surface shape. Ultrasound and/or photoacoustic ultrasound may be used, for example, to image the shape of the eye to determine the extent of applanation of the eye. In some embodiments, applanation may be detected by interferometry. An interferometer, for example, can detect small changes in distance. Accordingly, an interferometer could be used to detect changes in the position of a surface on the eye such as the cornea.

At 1608, the system may consult a correlation database. The correlation database may be a predefined database that correlates the pattern or amount of backscattered light from eye tissue with known IOP values. In some embodiments, the correlation table may correlate other qualities, such as applanation or other eye shape data, with corresponding IOP values. At 1610, the results may be presented to a user or clinician administering the eye pressure test. In some embodiments, the results may be analyzed locally at the ophthalmic device. In other embodiments, the results may be transmitted to a remote location for analysis, determination of IOP and/or diagnosis of ocular hypertension.

Intraocular pressure testing as described above may be performed in discrete tests on demand, or may be performed periodically and/or repeatedly over time. Repeated analysis may allow for the tracking of cyclic variations or long-term progression of IOP in a wearer. Thus, IOP testing functions may be incorporated into a device worn only for ophthalmic diagnosis, or may be a part of a device worn regularly, such as for entertainment, work, or other purpose(s), so that examinations may be performed automatically at regular intervals and/or at various times of day, week, month, year, etc. In some embodiments, therefore, the intraocular pressure is measured by the device at least 2 times, 3 times, 4 times, 6 times, 8 times, 10 times 12 times, 16 times, 18 times a year or more. In some embodiments, the intraocular pressure is measured by the device at least 2 times, 3 times, 4 times, 6 times, 7 times, 8 times, 10 times 12 times, 14 times, 16 times, a week or more. In some embodiments, the intraocular pressure is measured by the device at least 1 time, 2 times, 3 times, 4 times, 6 times, 7 times, 8 times, 10 times 12 times, 14 times, 16 times, a day or more. Repeated and/or periodic testing within a day may provide a measurement of a wearer's daily variation in IOP. Repeated and/or periodic testing over longer periods of time, such as weeks, months, years, etc., may allow long-term decreases or increases in IOP to be tracked, for example, to detect increasing IOP before ocular hypertension occurs, or to monitor the effectiveness of treatment for diagnosed ocular hypertension. In some embodiments, the frequency of regularly scheduled tests may be automatically adjusted based on trending increase or decrease of intraocular pressure testing results. The system may also be configured to alert the wearer and/or a clinician when abnormally high IOP or other anomaly is detected.

Pinhole Occluder

In one or more embodiments, the ophthalmic system may be used for a visual acuity test, similar to visual acuity tests administered through a pinhole occluding device. Pinhole occluding devices focus light and remove the effects of refractive errors (e.g., such as myopia, hyperopia, etc.). Because, with a center-hole pinhole occluder, light passes only through the center of the eye's lens, any defects in the shape of the lens have little or no effect. In some implementations, a pinhole occluding device may be used to identify visual defects caused by refractive error from visual defects caused by other errors. For example, the pinhole occluding device can compensate for mydriatic patient's inability to contract the iris.

In one or more embodiments, the ophthalmic system may provide a version of the pinhole occluder. For example, the ophthalmic system may occlude the field of view for one or both eyes such that peripheral viewing is occluded, but central view (i.e., through the pinhole) is maintained. Accordingly, in various embodiments, the ophthalmic system may occlude, obstruct, de-focus, deemphasize, or block some or a portion of the light rays that contribute to forming an image from entering the eye of a user.

In one implementation and without subscribing to any scientific theory, the ophthalmic system may utilize the pinhole occluder device to provide a means for diagnosing defects in the eye. The ophthalmic system may be configured to occlude the field of view for one or both eyes such that peripheral viewing is occluded, while the central view (i.e., through the pinhole) is maintained. For example, if vision is improved by using a pinhole occluding device with the ophthalmic system, this may be indicative of a refractive error in the peripheral regions or peripheral cataract. Or, if vision is worsened by using the pinhole occluding device, this may be indicative of macular degeneration, or central lens defects. If there is no change in vision quality, then the eye may be normal, or may suffer from amblyopia ("lazy eye") as discussed above. Accordingly, the ophthalmic system may be configured to automatically or interactively obtain information regarding the health state or condition of a user and/or of the user's abnormalities.

In another implementation and without subscribing to any scientific theory, the ophthalmic system may be configured to correct for vision defects of the user by utilizing a pinhole occluder device. For example, if a user having refractive errors at the peripheral of the eye, the ophthalmic system may occlude the field of view for one or both eyes such that peripheral viewing is occluded, but central view (i.e., through the pinhole) is maintained. Thus, the light rays from the peripheral are occluded and do not interact with the refractive errors of the user's eye, thus the user's vision may be improved. Similarly, the pinhole occluder may correct for other vision defects not limited to refractive errors, for example, scotomas (e.g., blind spots) in eccentric (non-foveal part of the eye) vision among others. In another implementation, the ophthalmic device may be configured to apply multiple pinholes to the display device, which each individually function as aperture or field-stops (e.g., occluding extraneous light rays). Such configurations may result in improved focusing of an image by the eye. For example, and without subscribing to any scientific theory, employing multiple pinholes allows light to be passed through the pinhole and propagate through a small area of the lens of the eye. Because light passes only through the small area of the eye's lens, defects in the shape of the lens may have reduced effect. Thus, while more light is passed through the multiple pinholes, the rays do not interact with surface defects in the eye.

In some embodiments, the ophthalmic system may be an augmented reality system that corrects for vision defects. As described above, the ophthalmic system may be an augmented reality head mounted display system configured to apply a pinhole occluder device to ambient light from the world in front of the user, as well as applying the pinhole occluder device to AR image content generated by the ophthalmic system. Alternatively, the ophthalmic system may be a VR head mounted display system configured to produce VR image content generated by the ophthalmic system, apply a pinhole occluder, and provide the VR content to the user while the user's eyes are covered from ambient light in front of the user by the VR head mounted display system. As described previously, a VR head mounted display system may include front facing cameras (e.g., cameras (16) of FIG. 5) configured to capture ambient light from the world in front of the user, and generate and project corrected wavefronts of these images into the eye of the wearer.

In various embodiments, the ophthalmic system may be a patient-worn ophthalmic device as illustrated in FIGS. 3A-3D and 5 and as described above in connection with correcting for myopia, hyperopia, astigmatism, and other refractive errors. Accordingly, it will be understood that the description and components described above related to ophthalmic devices disclosed herein for correcting for vision defects applies equally here.

For example, as described above, the ophthalmic device may include an augmented (or virtual) reality display device (62) that includes a display lens (106) and a light source (18) configured to project light (38) that is directed into the eyes of a user to form images in the eye of the user for the user's viewing. In various embodiments, this display device (62) comprises a waveguide stack (178) that received light from a fiber scanning display disposed at the edge of the waveguide stack (178) and couples the light out of the waveguide from the backside thereof to the wearer's eyes. In the case where the display device (62) is an augmented reality display device, the ophthalmic device may also direct ambient light from the surrounding world, e.g., light from in front of the user, to the eyes of the user through display lens (106). This light may, for example, be transmitted through the waveguide stack to the wearer's eye. As discussed above, the display device (62) may also comprise one or more adaptable optics or variable focus elements (VFEs) (e.g., VFEs 316a and 316b). As described above, the adaptable optics may be an optical element that can be dynamically altered so as to alter the wavefront incident thereon. For example, the adaptable optic may be a reflective optical element such as a deformable mirror or a reconfigurable transmissive optical element such as a dynamic lens, such as described above in FIGS. 10B-10E.

In one or more embodiments, the ophthalmic system disclosed herein may include a pinhole occluder, as described below in accordance with FIGS. 17A and B. In various embodiments, a pinhole occluder may be incorporated into an ophthalmic system, for example, as a part of display device (62). Or, in some embodiments, a pinhole occlude may be a separate component that may be positioned onto the ophthalmic system, for example, mechanically attached thereto.

It should be appreciated that the peripheral field of vision (e.g., FIG. 17B), the central viewing (e.g., FIG. 17C) or any target region may be occluded either by digital means or physical means. For example, physical means may include a mechanical opaque filter configured to include a pinhole disposed at a desired location. In some embodiments, one or more spatial light modulator (e.g., FIGS. 10B and 10C) may be encoded to generate a pinhole occluder, which may be adjusted based on the desired location of the pinhole.

In some embodiments, the ophthalmic system may occlude portions of a scene digitally. For example, local processing module (70) may retrieve an image stored in a digital memory and/or remote data repository (74) to be presented to the user through the display device (62). The ophthalmic system may include local processing module (70) configured to perform instructions to modify the image so as to mimic a pinhole occlude in the 2D image generated by the ophthalmic device.

In another implementation, the scene may be digitally occluded by de-focusing one or more regions of the image and focusing other regions of the image. The focused regions may correspond to a pinhole, while the out-of-focus regions may correspond to an occluded region. In some embodiments, the ophthalmic device may utilize a waveguide stack (178) (e.g., FIG. 10D) to present one or more regions of the image in focus surrounded by out-of-focus regions by selectively addressing waveguides to project light at various focal depths as described in FIG. 10D. In some embodiments portions of the image corresponding to the small region to be viewed may be presented at a first depth plan with the wearer is focused. Conversely, other image content outside that small region may be presented at a second depth plane. This image content on the second depth plane may be purposely blurred or may be blurred when the view is focused on the image content of the first depth plane or both.

In another implementation, the scene may be occluded to present one or more regions of the image with enhanced chroma (e.g., color) or luma (e.g., intensity). For example, a selected region to represent a pinhole may be enhanced by applying more power to the light source (18) or increasing the output of the light source (18), while surrounding regions remain unchanged or experience a decrease in chroma or luma.

Without subscribing to any scientific theory, by increasing the chroma and/or luma of the selected regions relative to the remaining regions, the selected regions may be become more dominate. For example, the ophthalmic system may enhance the chroma and/or luma of a central region of the image. This may cause the central region to appear brighter and more prominent as compared to peripheral regions of the image, thus viewed more clearly by the user. The regions of the image that are enhanced may correspond to regions of the eye identified as having visual defects. Thus, light rays passed through the regions of the eye that do not have defects are more dominant and easier to view than the regions of the eye having vision defects.

FIG. 17A depicts an illustration of a scene (1720) viewed by eyes of a user through an ophthalmic device, for example display lens (106) of FIG. 5, in accordance with various embodiments disclosed herein. The scene may be an image displayed by the ophthalmic device. Or, the scene may be ambient light passed to the user from in front of the user and the ophthalmic device. Or, the scene may be a combination of the ambient light and images displayed by the ophthalmic device. As illustrated, scene (1720) may comprise a person (1721) located at approximately the center of the scene, a tree (1722) located off from the center of the scene, and sun (1723) located along the peripheral of the scene (1720). It will be understood that scene (1720) is for illustration purposes only, and that any scene may be used, including but not limited to, a scene comprising ambient light form the surrounding world form, VR image content and/or AR image content, as described herein.

FIG. 17B illustrates a scenario where the ophthalmic system is configured to occlude the peripheral viewing regions of the scene, but central regions (e.g., as viewed through the pinhole) are maintained. In such an implementation, the pinhole occluder operates as an aperture or field stop that stops down light from the peripheral. For example, the ophthalmic system may implement an occluder (1730a) having a pinhole (1735a) located along the line of sight optical axis of the eye. The occluder (1730a) may be positioned such that light rays from person (1721) pass through the display lens 106 and are viewed by the eye. In contrast, light rays from tree (1722) and sun (1723), respectively, are occluded. In some embodiments, the occluder may comprise one or more spatial light modulators such as liquid crystal spatial light modulators that control the intensity of light transmitted through or reflected from a plurality of separate electrically reconfigurable pixels. In addition to being implemented physically, the occluder (1730a) may be implemented digitally as described herein. For example, image content presented on a display may be limited to a small region as if having been occluded. Similarly, the image that can be viewed on a display can be limited to a small portion of the display by altering the pixels outside said small portion such that said image less discernable than in said small portion of said display. The processing electronics that control the display such as the fiber scanning display can implement such modification to the image content.

In various embodiments the region 1730a that light passes through, e.g., the pinhole, may be circular, square, oval, rectangular or any other shape. For example, the region 1730a may have lateral dimension (e.g., diameter, width, length, etc.) between about 0.5 mm and 2.0 mm. Accordingly, the "pinhole" should not be limited to sizes less than one millimeter, as other dimensions are possible. For example, a pinhole having smaller dimensions may provide vision acuity testing while a pinhole of larger dimensions may provide for testing for reduced vision via decreases in retinal illumination.

FIG. 17C illustrates another embodiment, where the central region may be occluded while one or more portions of the peripheral region is passed to the eye to test peripheral vision. For example, the ophthalmic system may apply an occluder (1730b) having a pinhole (1735b) located off of the line of sight or optical axis of eye along the peripheral of view of scene (1720). Occluder (1730b) may be positioned similarly as occluder (1730a). For example, the occluder (1730b) may be positioned such that light rays from sun (1723) pass through the lens display (106) and are viewed by eye. Whereas, light rays from person (1721) and tree (1722), respectively, are occluded. Similar to that depicted in FIG. 17C (not shown), any area of the eye except specific targeted regions may be occluded to test for those targeted areas. In such embodiments, referring to scene (1720), from tree (1723) located off the normal line of sight of the eye and/or the center axis pass through the ophthalmic system, while light rays and from the person and sun, respectively, are occluded.

In some embodiments, diagnosing refractive errors may comprise testing different regions of the eye by measuring the user's response to various stimuli at the different regions and comparing the results, for example, in a test implemented similar to visual field testing as described herein. Similar to the small dot that is moved around the visual field of the user, the pinhole may be moved around the visual field to diagnose or test various parts of the eye. The ophthalmic system may comprise a spatial light modulator, as described above, configured to project a raster pattern comprising a pinhole occluder. Although the pinhole can be rastered, in other embodiments, the pinhole can be moved about other than in a raster, such as randomly. In one or more embodiments, the ophthalmic device may have a feedback mechanism (e.g., user interface controls) to adjust the pinhole occluder. The user may input a response (e.g., improved or worsened vision) based on the occluding of an image. The ophthalmic system may analyze the user inputs through a pinhole occluding test program (e.g., described below in FIG. 17D), executed by the local processing module (70). The pinhole occluding test program may be pre-coded (e.g., stored in a digital memory of local processing module (70)) or downloaded onto the ophthalmic system from a remote data repository (74).

Thus, for example, if the user indicates that vision improved when applying a pinhole occluder (e.g., occluding the center, peripheral, or any other region of the eye), this may be an indicative of a refractive error in that region or peripheral cataract where the region is the center of the eye. Or, if the user indicates that vision worsened when applying a pinhole occluder, this may be indicative of macular degeneration, or central lens defects. If the user indicates that there is no change in vision quality, then the eye may be normal, or may suffer from amblyopia ("lazy eye") as discussed above. It should be appreciated that the system may analyze the results through a pinhole occluding test program (e.g., FIG. 17D). The pinhole occluding test program that may be pre-coded or downloaded onto the ophthalmic system. Similar to the approaches discussed above, different regions of the eye may be tested by measuring the user's response to various stimuli at the different regions and comparing the results.

Additionally, in one or more embodiments, the ophthalmic system may enable a user to manually adjust a focus dial to determine one or more refractive errors. A virtual phoropter, similar to the one discussed herein, may apply various optical powers in sequence, allowing the user to indicate which version is clearer. This, in turn, may determine the user's prescription from the series of user responses. In other embodiments, a Scheiner double pinhole alignment examination or Shack-Hartmann grid alignment examination may be similarly administered through the ophthalmic device. Any of these systems may be used in conjunction with pinhole occlusion.

In one or more embodiments, the ophthalmic device configured to operate as a pinhole occluder may include any of the features and components of systems devices, and methods described herein. For example, the ophthalmic system may comprise one or more sensors configured to detect real-time information of the world surrounding the user. For example, the ophthalmic system may include a plurality outward facing cameras to capture an intensity image of ambient light from the surrounding world in real-time. For example, the ophthalmic device may include one or more wide-field-of-view machine vision cameras (16) operatively coupled to local processing module (70). These cameras may be configured to image the environment around the user and detect an amount of light. In one embodiment these cameras (16) are dual capture visible light/infrared light cameras. Images taken by cameras (16) may be stored in a digital memory of the ophthalmic device and retrieved for subsequent processing and re-rendering in display device (62).

In some embodiments, images of ambient light of the world surrounding the user from in front of the user captured by the outward facing cameras may be re-rendered in the display device (62) and occluded according to the description here. For example, the re-rendered images may be digitally occluded, as described above, but increasing the clarity and/or focus of a region (e.g., the pinhole) and blurring or defocusing other regions. Similarly, the chroma and or luma of the area representing the pinhole may be enhanced so that the brightness is increased or there is stronger contrast. The re-rendered image may then be projected to the user by the display device (62). These embodiments, may be utilized to diagnose and, in some embodiments, be a therapeutic tool for, macular degeneration, color blindness, etc., as described elsewhere in reference to macular degeneration.

In one or more embodiments, the ophthalmic system may comprise one or more sensors configured to detect real-time information related to at least one of user's eye. In one or more embodiments, as described above, the ophthalmic system may comprise one or more sensors configured to detect an orientation of a user's gaze. In another embodiment, in the alternative or in combination, the user's gaze may be estimated or detected based on tracking one or more eyes of the user through an eye tracking system, as described above. For example, the user's gaze may be estimated or detected based on a user's head position, head pose, or orientation, e.g., forward tilt, as well as based on the angle of convergence triangulated through imaging the eye and imaging the surrounding world, as described above.

In some embodiments, the ophthalmic device may comprise gyroscopic sensors configured to determine a gaze orientation based on head positions or head movement of the user (e.g., straight, tilted down, looking up, etc.). In some embodiments, the display device (62) may comprise a sensor assembly (39) having accelerometer, gyroscope, and/or other types of orientation and/or movement sensors several of which are discussed elsewhere herein. The sensor assembly (39) may be configured to detect movement imparted onto and orientation of the display device (62) due to movement of the user's head. The display device (62) may also include processor (32) (e.g., a head pose processor) operably coupled to the sensor assembly (39) and configured to execute digital and/or analog processing to derive head positions from movement detected by the sensor assembly (39). In one embodiment, sensor assembly (39) may generate movement data stored in a digital memory. The processor (32) may retrieve this movement data and execute processing logic to determine one or more head positions. In some embodiments, the head movement data may be used to reduce noise while diagnosing visual defects (e.g., detecting a head movement during a test may be indicative of a faulty test and result).

In one or more embodiments, real-time information related to the user's eyes may also be based on tracking eye movement through an eye tracking system. As described above, in various embodiments, the ophthalmic system may utilize inward facing cameras (24) (e.g., infrared cameras) to track an eye, which can be operatively coupled to the local processing module (70). The local processing module (70) may include software that, when executed, may be configured to determine the convergence point of the eyes, as described above in reference to FIGS. 5 and 6 and/or the direction of the eyes. From this determination, the ophthalmic system may also execute logic devices to determine a focus location or depth based on the eye tracking.

As described above, in some embodiments, the ophthalmic system may utilize an eye-tracking system to triangulate the user's convergence point and the angle of convergence. For example, while the user's head position may remain unchanged, the user's eyes may move which may be tracked by the eye-tracking system. For example, as a user glances downward, for example, to look at a book, the system may monitor the eye movement and determine that the convergence point has moved inward and downward and that the associated convergence angle has increased. In some embodiments, an increase in the convergence angle may be indicative of the eye focusing on an object located at a near-field focal depth (e.g., a book).

In another embodiment, the system may track the eye movement based on glint detection or Purkinje fringes, as described above and elsewhere herein. For example, the camera (24) tracks the position of a glint with respect to features of the eye (e.g., edge of the eye, intersection of the eye with an eye lid, pupil, etc.).

In various embodiments, the ophthalmic device may comprise a biofeedback system, as described herein, configured to determine a comfort level of the user in viewing an object or image. For example, if a user's eyes are shifting, unstable, oscillating, changing (e.g., in an unsteady or random manner) accommodation, etc., these may be indicators that the user is unable to comfortably view the object. Instability or oscillation in accommodation or behaviors associated with accommodation may be a sign the user is struggling with focusing on an object or image. Accordingly, the biofeedback system may receive real-time inputs relating to the state of the user's eye, e.g., abnormal or unsteady fluctuations in the accommodation and/or behaviors associated with accommodation.

Figure 17D:
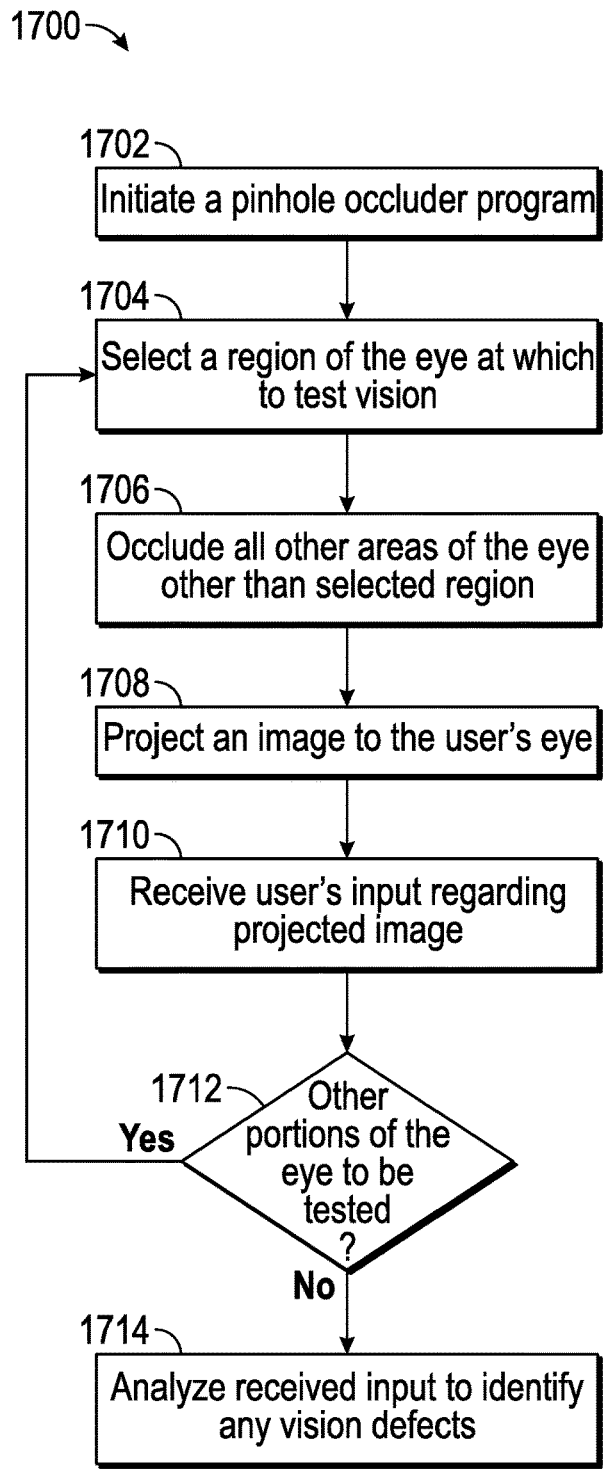
FIG. 17D illustrates an example process flow for administering a pinhole occluding test according to some embodiments.

Referring now to FIG. 17D, an example process flow 1700 is illustrated for diagnosing vision defects utilizing a pinhole occluder program. In some embodiments, process flow 1000 may be performed by patient-worn ophthalmic devices, such as those described in connection with FIGS. 3A-3D. The process flow 1700 can be implemented by the local processing module (70), for example, by executing logic devices to perform instructions stored in a digital memory operatively connected to the local processing module. Process flow 1700 may be performed by an ophthalmic device as describe herein comprising, for example, adaptive optics, VFEs, and/or waveguide stacks as shown in FIGS. 10B-10E. The ophthalmic device may include a light source having a fiber scanning projector, as described above.

At 1702, a pinhole occluding program is initiated. At 1704, a region of the eye is selected. For example, the region maybe selected automatically by the ophthalmic system performing the occluding program. In some embodiments, the program may select a central viewing region of the eye, a peripheral region of the eye, or any target region of the eye, which may be located based on tracking the eye using inward facing cameras (e.g., cameras (24)). The program may define one or more of regions of the eye to locate a pinhole thereby testing multiple areas of the eye. Based on the number of positions and the step size between each, the program may be configured to test the majority of the eye. In other embodiments, alternatively or in combination, the region may be manually selected by the user through a user interface of the ophthalmic device.

At 1706, all other regions of the eye except the selected region may be occluded, as described above. For example, the local processing module (70) may be operatively coupled to one or more mechanical opaque filters. The local processing module (70) may execute instructions to cause the filters to position a pinhole or other transparent region at the determined location. The local processing module (70) may execute instructions to occlude the regions not selected by the program. In various embodiments, alternatively or in combination, the local processing module (70) may be operatively coupled to one or more spatial light modulator to effect the occluding of the other region or regions, as described herein.

At 1708, a stimulus (e.g., an image, a virtual phoropter, etc.) is presented to the user. For example, the ophthalmic system may project light (38) to the eye of the user through display device (62) to produce an image visible to the user. In another embodiment, the image may be based in part on ambient light passed to the user through display device (62) from in front of the user. In yet another embodiment, the image may be an image obtained by outward facing cameras (e.g., cameras (16)) imaging ambient light from in front of the user and then displayed by the ophthalmic device to the user.

At 1710, the ophthalmic system receives input from the user regarding the image presented to the user by the ophthalmic device via the feedback mechanism. For example, a user may be able to indicate that the image is viewable or not, clear, in focus, or not, etc. Based on the user input, the ophthalmic system may be able to determine the health or condition corresponding to the selected region of the eye. As describe above, for example, if the user input is that the stimuli has improved due to implementing the occluding program, this may be indicative of a refractive error or cataract outside of selected region of the eye. Or, if user input is that the stimuli is worsened by using the occluding program, this may be indicative of macular degeneration, or lens defects at the selected region of the eye. If there is no change, then that portion of the eye may be normal, or may suffer from amblyopia ("lazy eye") as discussed above.

In some embodiments, the ophthalmic system may comprise an inward facing camera configured to provide inputs related to vision quality. The inward facing camera may be coupled to a light source that projects light through the pinhole occluder and into the eye. The projected light may be received by the retina, being at least partially occluded. The ophthalmic system may store or be provided with an expected pattern of light to be returned, e.g., a normal return pattern based on a healthy eye. The inward facing camera may detect a pattern of light reflected from the retina, and the ophthalmic system may compare the reflected light pattern against the expected healthy pattern. From this, the system may be able to objectively determine vision quality without requiring user input. For example, light projected through the center of the pupil incident on the fovea should be reflected straight back unaffected. However, if the eye has a refractive error, then the reflected pattern detected by the camera will be refracted based on this error resulting in an abnormal reflection pattern.

In some embodiments, the input from the user may be stored in the digital memory of the local processing module (70) for subsequent access, retrieval, or processing. The user input may be associated with the selected region of the eye, which may also be stored in the digital memory. In another embodiment, the local processing module (70) may be operatively coupled to remote processing module (72) and remote data repository (74), where the input and regions may also be stored and associated.

At 1712, the ophthalmic system determines whether other regions are to be similarly tested. If yes, steps 1704-1710 are repeated. For example, the ophthalmic system may scan across multiple regions of the eye, so as to test and receive inputs 1710 related to the entire surface of the eye. The number of regions of the eye (e.g., a step size between each test), which region has been tested, and which regions remain to be tested, along with the order of the testing, may be stored in the digital memory of local processing module (70) and/or remote data repository (74). For example, the optical prescription of each region may be defined by the received inputs at 1710, and these regions may be mapped to the anatomy of the eye based on imaging the eye by inward facing cameras (e.g., cameras (24)). The number of regions may be any number, for example, one (e.g., center, peripheral, or there between), two regions (e.g., center and a single peripheral) or more regions. The local processing module (70) may retrieve this information so as to determine which region is to be tested next or if any regions remain to be tested. Thus, the ophthalmic system may carry out steps 1704-1710 for each of the multiple regions of the eye.

After all the regions are tested, the ophthalmic system, at 1714, analyzes the received inputs for each region to determine any vision discrepancies. For example, inputs for each region of the eye may be indicative that a particular region suffers from refractive errors, cataracts, macular degeneration, central lens defects, amblyopia, etc., as described above and throughout this disclosure. This may be performed, for example, by comparing the user's responses to historical data (for example, from previous testing performed by the ophthalmic device) about the user, in one or more embodiments. This may be an indication that the user's vision is deteriorating. Or, in other embodiments, the data may be compared to standard data, or typical responses of individuals of a particular age group. Similarly many such approaches and corresponding algorithms may be used to analyze the received data. Pattern recognition may be use in various embodiments. The received data may be stored in the digital memory, and the local processing module (70) may execute instructions to perform algorithms to analyze the received data.

Figure 17E:
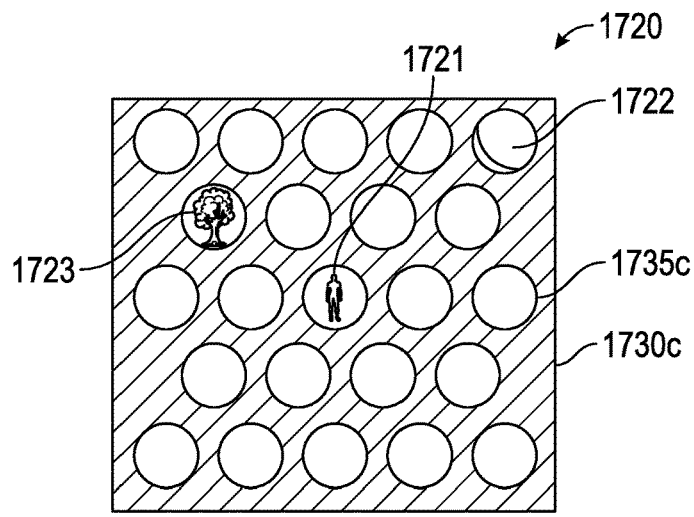
FIG. 17E illustrates an example pinhole occluder comprising multiple pinholes according to some embodiments.
Figure 17F:
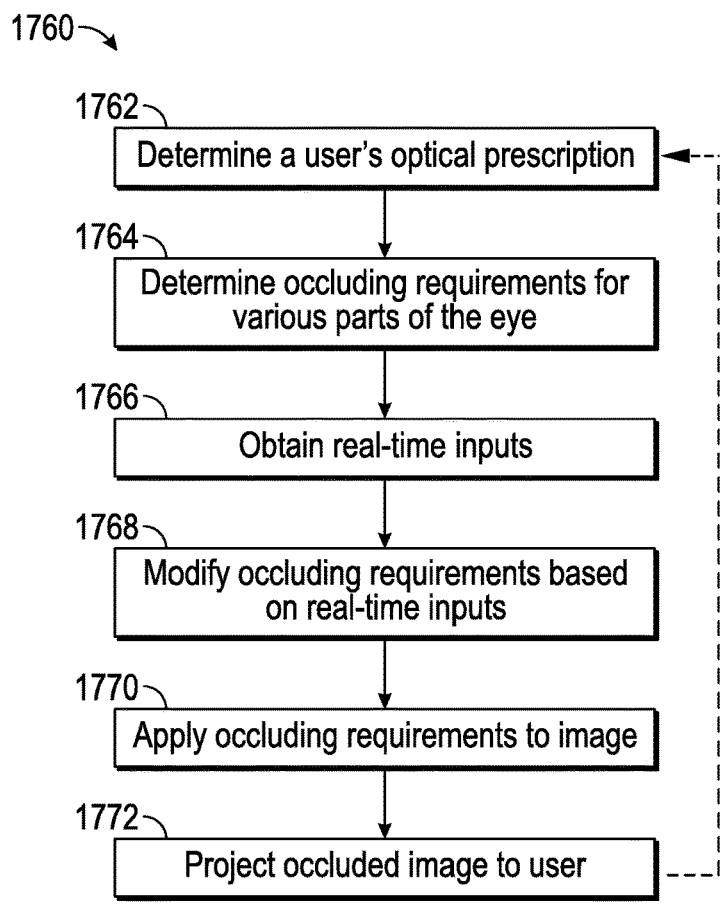
FIG. 17F illustrates an example process flow of correcting vision defects utilizing pinhole occluders according to some embodiments.

FIG. 17F is an exemplary process flow for correcting vision defects. In some implementations, the ophthalmic system may be configured to apply a pinhole occluder to the display device (62) to correct for vision defects of the user. For example, if a user having refractive errors in one or more regions of an eye views the world through pinhole occluder, the user's vision may be improved. In another implementation, the ophthalmic device may be configured to apply multiple pinholes (e.g., pinhole glasses, stenopeic glasses, etc.) to the display device, which may or may not function at least partially as field stops (e.g., occluding extraneous light rays), as described above. Without subscribing to any scientific theory, such configurations may result in improved focusing of an image by the eye. The size and number of holes may be adjusted and determined, for example, based on the visual defects of the user and/or by trying different configurations or otherwise determined. FIG. 17E schematically illustrates such a configuration as viewed through the multiple pinhole occluder. The user may view scene (1720) through display device (62) and occluder (1730*c*) having multiple pinholes (1735*c*). Without subscribing to any particular scientific theory, in some cases this may stop down light rays that interact with vision defects in the eye of the wearer, thereby improving vision.

Referring now to FIG. 17F, an example process flow for therapeutically correcting vision defects (e.g., refractive errors, cataracts, macular degeneration, central lens defects, etc.) by using a pinhole occluder is briefly discussed. The process flow 1760 is directed to modifying an image presented to the user based on a prescription of the user. In some embodiments, process flow 1760 may be performed by patient-worn ophthalmic devices, such as those described in connection with FIGS. 3A-3D. The process flow 1760 can be implemented by the local processing module (70) configured to execute logic devices in the local processing module (70).

At 1762, the ophthalmic system may determine, retrieve, or receive an optical prescription of a user. As described above, the ophthalmic device may include a user interface whereby the user inputs an optical prescription or the ophthalmic system may go through an eye-prescription configurator program to determine vision defects. For example, the process flow 1700 may be one input used to define an optical prescription. Other methods of determining vision defects are possible, for example, as described throughout this disclosure. In some embodiments, the ophthalmic system may be configured to receive an optical prescription from a third party. For example, a doctor may be able to send a user optical prescription wirelessly (e.g., over the internet, Bluetooth connection, etc.), which is received by a receiver or transceiver and stored in the digital memory of the local processing module (72).

In another embodiment, the ophthalmic system may automatically (and possibly incrementally) change the user's prescription based on feedback from the eye tracking system. As described above, the system may determine a user is struggling to view an object or image. For example, as described above, if a user's eyes are shifting, unstable, oscillating, changing (e.g., in an unsteady or random manner) accommodation, etc., as measured, for example, by monitoring the vergence, pupil size, and lens shape or movement as described herein, these may be indicators that the user is unable to comfortably view the object. In response, the system may initiate an eye prescription configurator program.

In some embodiments, the ophthalmic system may be configured to receive an optical prescription from a third party. For example, a doctor may be able to send a user optical prescription wirelessly (e.g., over the internet, Bluetooth connection, etc.), which is received by a receiver or transceiver and stored in the digital memory of the local processing module (70).

At 1764, the ophthalmic system determines occluding requirements of the eye. Occluding requirements may refer to the number of pinholes, the arrangement of the pinholes, or the size of the pinholes. In various embodiments, the occluding requirements may be based on the optical prescription of the user. For example, in some embodiments the local processing module (70) may retrieve, from a digital memory, a correlation of the vision discrepancies and defect regions of the eyes from step 1714 of FIG. 17D. Based on this information, the local processing module (70) may execute instructions to determine where one or more pinholes should be placed and the size of the pinholes to correct for these discrepancies.

At 1766, the ophthalmic system may obtain inputs from the user's eye and/or the ambient light from the world surrounding the user (e.g., "real-time information") and the ophthalmic system via outward facing cameras. The ophthalmic system may, for example, receive these inputs from one or more sensors configured to detect an intensity of ambient light from the surrounding world in real-time. These sensors may comprise, for example, the sensor assembly (39), the eye tracking system, and/or the outward facing cameras (e.g., cameras (16)). These inputs may be stored in the digital memory of the local processing module (70) for subsequent retrieval and processing operations.

In another embodiment, gaze orientation may be an example of the obtained inputs. Gaze orientation may be determined by sensor assembly (39) and/or eye tracking system. The sensors may determine that whether the gaze orientation of a user has changed relative to a pervious orientation. For example, the eye tracking system may monitor eye movements. For example, if the wearer's head is tilted forward and downward, and/or the wearer's eyes are tilted downward, the wearer may be looking at an object such as a book or may be looking at projected image content corresponding to images placed in a location (lower part of field of view) typically associate with nearby objects. The gaze may also be used to determine the vergence of the eyes, how the lines of sight of the pair of eyes converge on a location and how far that location is with respect to the wearer. By monitoring the vergence (e.g., as described in FIG. 6), the gaze orientation at which the viewer is intending to view an object may be determined.

Another example of input at 1766 may be ambient light from the environment surrounding the user. In this respect, the ophthalmic system may also include outward facing cameras (e.g., cameras (16)) to measure the surrounding ambient light intensity. In another embodiment, the local processing module (70) may be configured to determine a time of date, which may be indicative of a light intensity value (e.g., light levels may be lower during the evening as compared to during the day).

At 1768, the ophthalmic system may modify the occluding requirements based on the obtained inputs from 1766. For example, the local processing module (70) may retrieve one or more inputs stored in 1766 from the digital memory and adjust the size, shape, and arrangement of the pinhole occluder.

In some embodiments, ambient light levels detected by outward facing cameras may be retrieved by the local processing module (70) and utilized as an input to determine whether to adjust an aperture stop of the optics of display device (62). For example, where the ophthalmic system detects low levels of ambient light in front of the user using outward facing cameras, the local processing module (70) may execute instructions to increase the aperture stop of the display lens (106), thereby increasing the intensity of the light projected to the user by the ophthalmic system. Conversely, where the system detects high levels of ambient light in front of the user, the local processing module (70) may cause the aperture stop to be decreased, to stop down the light projected to the user.

In various embodiments, the ophthalmic system may be configured to modify the pinhole occluder requirements (e.g., the size, shape, arrangement, etc. of the pinholes) based on other inputs from the surround world. For example, the ophthalmic device may be configured to determine that the user is viewing an object by, for example, utilizing the sensor assembly (39), eye tracking system, or outward facing cameras (e.g., cameras (16)) to detect near-field accommodation of the eyes, as described above. When viewing an object in the near-field, the user may require higher intensity or more light from the object being viewed and less from the surrounding environment. If the user has a dead or weak spot in the central viewing region of the eye, the ophthalmic system may be configured to apply a central pinhole to stop down peripheral ambient light from the surrounding world in front of the user, while increasing the contrast of the light from the viewed object. In another embodiment, if the occluding requirements include multiple pinholes, the pinhole occluder may be configured to defocus the peripheral region, for example, of the image content projected into the eye by the display device.

At 1770, the occluding characteristics may be applied to one or more images to be projected to the user's eyes. In some embodiments, the digital memory or remote data repository (74) may be configured to store image content (e.g., AR and/or VR image content, as described above). The local processing module (70), either independently or in communication with remote processing module (72), may be configured to retrieve this image content and execute instructions to generate a pinhole occluder to occlude the image displayed to the user by the ophthalmic system and/or ambient light passed to the user from in front of the ophthalmic system based on the occluding requirements.

At 1772, the occluded images are projected to the user such that the user views the images comfortably. For example, the ophthalmic system may project light (38) to the user to form an image in the eye of the user. The image may be an occluded image based on a physical or mechanical pinhole occluder such as one or more spatial light modulators to occlude an unmodified image. In another embodiment, alternatively or in combination, the 2D image generated by the ophthalmic system may be occluded digitally by not showing portions of the image that are to be blocked based on software executed in the local processing module (70) and then displayed through display device (62).

In some embodiments, at 1772 the ophthalmic system may implement dynamic vision correction by initiating an eye-prescription configurator program. At 1772, the ophthalmic system can be configured to return to block 1762 and manually and interactively determine the user's prescription at each interval, in some embodiments, without user activation. For example, the ophthalmic system may monitor the viewing comfort of the user, and automatically and possibly incrementally adjust the prescription and/or vision correction where the user is unable to comfortably view images presented them. For example, as described above, the ophthalmic system may utilize the eye tracking system (e.g., cameras (24)) to determine whether a user is struggling to view an image based in part on shifting, instability, oscillating, abnormal, and/or involuntary fluctuations in eye movement, pupil size, vergence, accommodation, and/or gaze orientation. Where struggle is determined, the ophthalmic system may initiate an eye-prescription configuration program to determine a new optical prescription and/or adjust the vision correction (e.g., modify the pinhole occluder requirements). In some embodiments, when struggle is determined, the ophthalmic system may alert the user of such or the ophthalmic system may perform other types of tests such as described herein.

In some embodiments, where the ophthalmic device is an augmented reality head-mounted display system, pinhole occlusion may be applied to an image to be presented to the wearer while imaging objects located in front of the head mounted display and the user. For example, AR image content presented by the ophthalmic system may be occluded and projected in combination with ambient light. In some embodiments, AR image content may include the ambient light passing from the outside world through the lens (106), and such ambient light may also be occluded to provide optical compensation for a wearer viewing the outside world through the lens (106). In another embodiment, in the case of a VR head mounted display system that is opaque to the world in front of the user, the occluded image may be an occlusion one or more regions of a VR image provided by the ophthalmic system and the display therein for visual representation, for example, a VR image content.

Initial W4LT Test

Another test that may be administered through the ophthalmic systems described herein is the Worth Four Light Test or Worth Four Dot Test (either referred hereinafter as "W4LT"). W4LT assesses a patient's degree of binocular vision and binocular single vision. Binocular vision involves an image being projected by each eye simultaneously into a single image in the forward field. The W4LT can detect the suppression of either the right or the left eye. Suppression may occur during the binocular vision when the brain does not process information received from either of the eyes. This is a common adaptation to strabismus, amblyopia (discussed above), and aniseikonia (each eye perceives an image as a different size).

Traditionally, with W4LT testing, the patient wears red-green goggles (usually a red lens over the right eye and a green lens over the left eye). The test can be performed either close to the patient or far away from the patient, and both provide different assessments of the patient's vision. When performed at a far distance, the W4LT instrument is composed of a wall-mounted box with four lights arranged in a diamond configuration with a red light at the top, two green lights at either side, and a white light at the bottom. When performed at a near distance, the same configuration of lights is arranged in a hand held instrument similar to a flashlight.

Because the red filter blocks the green light and the green filter blocks the red light, it is possible to determine if the patient is using both eyes simultaneously in a coordinated manner. With both eyes open, a patient with normal binocular vision will perceive four lights. If the patient either closes or suppresses an eye, they will see either two or three lights. If the patient does not fuse the images of the two eyes they will see five lights (diplopia, commonly known as double vision).

The ophthalmic system may be programmed to administer the W4LT test by providing depth cues with near-field glasses by presenting each eye with an independent image that is to be converged at a distance. These images can be colored dots similar to the W4LT test or any other suitable pair of images. For example, the pair of images can include colored dots, colored symbols, polarized images, colored features, polarized features, colored icons, polarized icons, colored objects, polarized objects, or the like. The responses of the user may be recorded, and analyzed to determine if the user has any vision defects. The results can be reported back to the clinician or patient.

In some embodiments, a wearable augmented reality device can be used as an ophthalmic system to administer a vision test by projecting independent left and right images to left and right eyes of the wearer. This vision test can be W4LT or other similar vision testing program. The ophthalmic device can use the results of the vision test to identify vision defects. For example, the ophthalmic device can use the results of the vision test to assess the wearer's degree of binocular vision and binocular single vision (e.g., whether the wearer suffers from diplopia or double vision). As another example, the ophthalmic device can use the results of the vision test to determine suppression of either the right or left eye of the wearer. The augmented reality device can be configured to present different images to the left and right eyes, to receive user input regarding what is perceived by the wearer when the images are presented, and to determine a vision defect based on the received user input. The augmented reality device can be configured to present different images to the left and right eyes, to automatically assess what is perceived by the wearer when the images are presented, and to determine a vision defect based on the automatic assessment. It should be appreciated that such a system may be used to test and/or treat the eyes of the wearer, and this may typically occur at a doctor's or clinician's office. In one or more embodiments, the patient's individual ophthalmic system may be used, possibly with doctor supervision, or the doctor's office may have its own version of the ophthalmic system that may be used for testing and/or treatment. In some embodiments, the eyewear perform tests periodically (or aperiodically), but a number of times over a period of one or more days, months, or years and record the results. In some embodiments, the eyewear alerts the wearer to let the wearer know that it may be an appropriate time to perform a test. The system can monitor historical changes in the test results and thereby identify any problem such as deterioration in vision or other heath problem.

The wearable augmented reality device includes an augmented reality display platform configured to project images into respective left and right eyes of the wearer. The display platform can be configured similarly to the display lens 106, as described herein in greater detail with reference to FIG. 5. The display platform can include left and right displays respectively for the left and right eyes of the wearer. In some implementations, the display platform can also be configured to pass light from the world or environment beyond the eyewear through the display platform (e.g., a lens and/or adaptive optics elements in the front thereof) to the eye of the wearer. In this way, the wearer can see images projected with the display platform superimposed with what the wearer can see in the world.

In some embodiments, the wearable augmented reality device includes the display platform described above and at least one light source configured to project light into the eye of the wearer. The at least one light source can be configured to project light into the eye of the wearer to form an image in the eye. In some embodiments, the at least one light source includes a fiber scanning display, as described in greater detail elsewhere herein. The fiber scanning display in conjunction with adaptable optics, for example varifocal optical element, can be configured to display or transmit light from one or more depth planes and/or to vary the depth plane. In some embodiments, a test can be performed by projecting images from a distant depth plane (e.g., about 6 m from the wearer) and/or from a near depth plane (e.g., about 0.33 m from the wearer).

In some embodiments, the display platform includes a waveguide stack, as described in greater detail elsewhere herein. The waveguide stack can be configured to project light from different focal planes. In certain implementations, the waveguide stack includes one or more lenses in the stack, as described in greater detail elsewhere herein. The waveguide stack can be configured to display or transmit images from one or more depth planes. In some embodiments, the display platform includes adaptable optics elements configured to project light or images from different depth planes. In certain implementations, the adaptable optics elements include variable focus elements (VFEs), as described in greater detail elsewhere herein.

The wearable augmented reality device can include one or more user interface features configured to allow a wearer or other person to provide input to the device. The user interface features can be integrated with the device. In some implementations, the user interface features are provided by a device or component that is not physically integrated with the device. For example, the user interface features can be provided by a device or system that is in communication with the device. This can be a smartphone, computer, tablet, or other computational device that is in wired or wireless communication with the device. In some embodiments, the user interface features can be provided by a combination of different devices and systems linked to the device, e.g., through wired or wireless communication networks or through components that are physically linked to the device or integrated with the device. In various embodiments, the user interface comprises voice recognition or a virtual touch display. The user interface features can also be presented on a device with a touch screen wherein interaction with the touch screen provides input to the wearable augmented reality device. Accordingly, the user interface features can include capacitive features sensitive to touch, keyboards, buttons, microphones, cameras, motion sensors, photodetectors, or a variety of software-implemented features provided by a graphical user interface. In some embodiments, the user interface includes one or more features or sensors configured to capture gestures of the wearer to provide input. In various embodiments, a virtual touch screen is provided through the images projected to the user's eyes and sensors to sense the users moving body, e.g., finger. In some embodiments, the user interface features include gesture detection components to allow a wearer to provide user input through gestures. In some embodiments, the user interface features include gaze detection components to allow a wearer to provide user input through gaze of the eyes (e.g., this can include selecting a button or other element when the wearer fixates on the button for a time or when the wearer blinks when fixated on the button). Such user interface systems can be employed for other devices and systems described herein.

In some implementations, the wearer, clinician or doctor can use the interface features to control aspects of the W4LT. This can be done, for example, to change the depth plane of the projected images, to modify characteristics of the projected images, or to otherwise configure testing of binocular vision.

FIG. 18 illustrates an example method 1800 of administering a Worth Four Light Test or Worth Four Dot Test to assess the wearer's degree of binocular single vision. For ease of description, the method 1800 will be described as being performed by an ophthalmic system, such as any of the augmented reality devices described herein. However, it is to be understood that any component or subpart of the various augmented reality devices disclosed herein or other similar devices can be used to perform any step, combination of steps, or portions of a step in the method 1800.

At block 1802, the ophthalmic device initiates a W4LT program. The W4LT program can be a stored process or sequence of functions provided by the ophthalmic system. Initiating the W4LT program can include determining or retrieving a starting depth plane or sequence of depth planes for the projected images. In some implementations, the W4LT program can integrate information about ocular anomalies of the wearer's eye(s), where the information about the ocular anomalies can be entered by the wearer or clinician, determined from a previous eye test program, or retrieved from a data store (e.g., a data store that is part of the ophthalmic system or a networked data store). Initiating the W4LT program can include determining the image or sequences of potential images to be projected to the wearer. Initiating the W4LT program can include determining whether a clinician or doctor is administering the eye exam or whether the examination is being self-administered by the wearer. In some embodiments, the ophthalmic system initiates the W4LT program in response to input received from the wearer or a clinician. In some cases, the system initiates the W4LT test based on a predetermined protocol or because the system senses deterioration in eyesight.

At block 1804, the ophthalmic system presents a virtual image to one of the eyes (e.g., a set of colored dots to the right eye), and at block 1806, the ophthalmic system presents another virtual image to the other eye (e.g., a complementary set of colored dots to the left eye). For example, the ophthalmic system can project a left image to the left eye using a left display and a right image to the right eye using a right display. The right image and left image can include elements that are coincidental (e.g., that would be aligned when viewed by a person with normal binocular single vision). The right image and left image can include elements that are unique and misaligned (e.g., that would be perceived as being in different locations by a person with normal binocular single vision). The right image and left images can include colored dots, colored features, colored objects, colored icons, or other similar elements. Similarly, the right display and the left display can be configured to project polarized images (e.g., dots, features, objects, icons, etc.). The ophthalmic system can be configured to project independent images to the respective eyes of the wearer, wherein the independent images are configured to be viewed differently and distinctly by people with binocular singular vision, diplopia, and/or suppression of one eye. In some embodiments, the ophthalmic system can be configured to project independent images to the respective eyes of the wearer wherein the images are projected from different depth planes.

At block 1808, the system may receive input from the user regarding a convergence of both images, through some kind of user interface such as the user interfaces described herein. In some embodiments, the ophthalmic system can be configured to present a number of options for selection by the wearer. The options can correspond to different images that correspond to results of viewing the projected images by persons with regular vision or with vision defects. For example, if the images presented to the wearer correspond to the 4 dots of the W4LT, images can appear to the wearer that have 4 dots, 5 dots, 3 dots, 2 dots, etc. depending on the state of their health, e.g., the heath of their eye and optical pathway. The ophthalmic system can receive user input indicating which of the presented images corresponds to what the wearer perceived when viewing the projected images. In some embodiments, the ophthalmic system can receive other indicators from the wearer indicative of what the wearer perceived. The indicators can include words, colors, numbers, sizes, locations, etc. corresponding to the image the wearer perceived.

In some embodiments, the ophthalmic system is configured to objectively determine convergence of both images. For example, the system can be configured to monitor the image projected onto the retina. By comparing the projected images on the retina, the system can be configured to match them and to determine whether the images are aligned on the same section of the retina. Where the images are aligned, the system can automatically determine that the wearer has normal or correct vision. Where the images are misaligned, the system can automatically determine that the wearer has double vision. In some implementations, the system is configured to monitor the alignment of images in the eyes of the wearer. If the system determines that the images are misaligned, the system can generate an alert or initiate an eye test.

At block 1810, the ophthalmic system analyzes the received input and identifies vision defects of the user. In some embodiments, the ophthalmic system is configured to identify a degree of binocular vision or binocular single vision. In some embodiments, the ophthalmic system is configured to identify a degree of diplopia, esotropia, exotropia, hypotropia, hypertropia, etc. In some embodiments, the ophthalmic system is configured to identify suppression of the right or left eye. The ophthalmic system can be configured to compare the received input with the projected images to determine the vision defects. The ophthalmic system can be configured to compare the alignment of images on the retina of the wearer to automatically determine vision defects. The ophthalmic system can be configured to compare the received input with the depth plane information for the projected images to determine the vision defects.

In some embodiments, the ophthalmic system is configured to initiate testing, returning from block 1810 to 1802, when the system determines that the wearer is struggling to focus or experiencing vision troubles. This is represented by the dotted line from 1810 to 1802.

In various embodiments, to reduce distraction, the view of the world in front of the wearer's eyes through the augmented reality device is blocked or otherwise not visible during the examination. This can occur, for example, when images are presented to the viewer, although this approach is not necessary. In some embodiments, to block ambient light from the outside world in front of the lens from reaching the eye, the system may include one or more spatial light modulator, such as liquid crystal arrays that can be switched so as to block varying amounts light.

Although the system has been described as an augmented reality device, in other embodiments the system may be a virtual reality device. In either case, the ophthalmic system may be a device provided by the physician or clinician for testing at a medical facility or optometrist office or elsewhere. In other embodiments, the ophthalmic system may belong to the wearer and may be employed for other purposes such as entertainment (e.g., games and movies) and/or work activities. As described above, one benefit of implementing the examination on the wearer's system is that the examination can be conveniently undertaken multiple times (at least 2, 3, 4, 5, 6, 8, 10, 12, 16, 18, 24, or more times) throughout the year. The system can also record historical data relating to previous tests and evaluate the change in data over time. In some embodiments, the frequency or schedule of examination can be altered based on results and/or trends of test results. For example, if the test results indicate that vision defects are deteriorating or that the wearer is struggling more to focus on an image (e.g., accommodation fluctuations, vergence fluctuations, squinting in one eye, etc.), the frequency or schedule of the procedure can be altered to increase the frequency of procedures and/or shorten the time between procedures. Likewise, the examination can be performed with or without a medical professional, such as optometrist, ophthalmologist, nurse, technician, medical assistant etc.

Retinoscopy

The wearable augmented reality (or virtual reality) devices described herein can be used as an ophthalmic system to function as a retinoscope to determine vision defects of a wearer or a patient. In particular, the augmented (or virtual) reality device can be used to detect myopia, hyperopia, astigmatisms, and/or other vision defects when operating as a retinoscope. The augmented (or virtual) reality device can be configured to determine, for example, a refractive error of an eye of a patient by using retinoscopy techniques, such as neutralization. Neutralization includes adjusting refractive power in front of an eye until a light beam or spot swept across the eye forms an image at the retina that substantially ceases to move across the retina. The augmented (or virtual) reality instrument may be configured to provide beams with differing optical correction until neutralization is achieved. The augmented (or virtual) reality device can thus be configured to determine an optical prescription to correct identified vision defects. It should be appreciated that such a device may be used to administer an eye exam, and this exam may typically be administered at a doctor's or clinician's office or at a home by the wearer automatically. In one or more embodiments, the patient's individual ophthalmic system may be used, possibly with doctor supervision, or the doctor's office may have its own version of the ophthalmic system that may be used for diagnostic purposes. In various embodiments, this augmented (or virtual) reality device can be configured similarly to the devices disclosed herein.

In some embodiments, the wearable augmented (or virtual) reality device may be used to perform retinoscopy to identify vision defects using light that is swept across a wearer's eye. Examples of devices that can be configured to perform retinoscopy are described herein and include, for example and without limitation, the devices described herein with reference to FIGS. 5, 10D, 10E, 22A, and 22C. The wearable augmented (or virtual) reality device includes an augmented reality display platform configured to project a beam of light into the eye of a wearer. The display platform can be configured similarly to the display lens 106, as described herein with reference to FIG. 5, or other display systems or platforms described herein (e.g., display systems 62, 2062, 2262, 2362 2462, 2662 respectively described herein with reference to FIGS. 5, 20A, 22A, 23B, 24A, 24C, and/or display platform 1402 in FIG. 14). In some implementations, such as for augmented reality devices, the display platform can also be configured to pass light from the world or environment through the display platform (e.g., a lens in the front thereof) to the eye of the wearer. In this way, the wearer can see objects in the world in front of the wearer and can potentially fixate on distant or near objects depending, for example, on the type of retinoscopy test. The focus of the beam projected into the eye can be varied or otherwise provided with optical correction. As such, the wearable augmented reality device can be configured to perform retinoscopy to measure refractive error of an eye of a wearer.

In some embodiments, the wearable augmented reality device includes the display platform described above and at least one light source configured to project light into the eye of the wearer. Example light sources suitable for this purpose are described in greater detail herein, such as light source 2268 described herein with reference to FIG. 22A and/or the light source described herein with reference to FIG. 22C. This light source, which may include wave guides, may augment the display light source and corresponding wave guides (e.g., wave guide stack) employed to project images into the wearers eye to provide augmented reality or virtual reality content. The at least one light source used for retinoscopy can be configured to provide a light beam that is swept across the eye of the wearer. In some embodiments, the wearable augmented reality device also includes a sensor configured to measure light reflected from a retina in response to the light beam from the at least one light source being swept across the eye of the wearer. In various embodiments, the sensor images the eye. This sensor may comprise an eye tracking sensor or other inward facing optical sensor or camera that is configured to be directed to the eye, for example, to image the eye. The wearable augmented reality device can be configured to perform retinoscopy to measure refractive error of the eye of the wearer. For example, the augmented reality device can be configured to sweep the light beam across the eye of the wearer in one or more directions, to detect, measure, or image the reflection, or reflex, from the back of the eye of the wearer (e.g., the retina, the ocular fundus, etc.), and to determine vision defects through observation or measurement of the reflex. Optical correction can be introduced to the light beam and the reflex can be observed to determine when such optical correction is sufficient to offset the wearer's refractive error.

The at least one light source can be configured to provide a light beam that is moved across or around an eye of the wearer of the augmented reality device. In certain implementations, the at least one light source provides a relatively narrow beam or strip of light that is moved across the eye. The beam of light may have a cross-section orthogonal the direction of its optical path that is elongate, wherein this cross-section is longer in one direction than a perpendicular direction. Accordingly, the beam comprises a strip in certain embodiments. The light provided by the at least one light source can be configured to be moved in one or more directions. When the light provided by the at least one light source is a relatively narrow beam or strip of light, the orientation of the beam or strip of light can be changed. Thus, the at least one light source can be configured to provide light that can be used to identify myopia, hyperopia, astigmatism, pigment, age-related macular degeneration, and other vision defects.

The sensor can be configured to sense light reflected from the back of the eye or retina of the wearer (e.g., retinoscopic reflex, ret reflex, or reflex) of the augmented reality device, and in various embodiments form an image the eye. Accordingly, the sensor can be an image sensor or camera, one or more photodetectors, or other device that can provide a signal in response to detected light and possibly an image of the eye. In some embodiments, the sensor can include one or more filters tailored to preferentially pass (e.g., bandpass filters tuned to pass bands of wavelengths that are expected for the reflex) the reflex from the eye of the wearer and to preferentially block light in other wavelength bands. The filters can be physical filters and/or filters applied in signal or image processing software.

The at least one light source and the sensor (e.g., camera) can be coupled to a control system that is configured to process information about the characteristics, direction, orientation, and/or position of the light provided by the at least one light source and to process information about the characteristics, direction, orientation, and/or position of the light detected by the sensor. From this information, the control system can be configured to determine one or more vision defects of the eye of the wearer. In some embodiments, the control system can be configured to modify the light provided by the at least one light source (e.g., the direction, orientation, as well as optical correction provide to the beam etc.) based at least in part on analysis of the light detected by the sensor. In some embodiments, the control system is configured to perform a pre-defined routine to determine vision defects. In some embodiments, the control system can adapt a retinoscopy routine based on results of analysis of the light detected by the sensor at any point during the routine.

The augmented reality system can be configured to project images to the wearer. As described herein, the augmented reality system can provide images to the wearer corresponding to different depth planes, both far and near. Accordingly, the wearer can fixate on the display, looking at images that simulate far and near objects. In this manner, the wearer can have either relaxed accommodation or may exhibit accommodation depending on the test.

The augmented reality system can thus be configured to provide static and/or dynamic retinoscopy. For static retinoscopy, for example, the augmented reality device can be configured to determine refractive errors when the wearer has relaxed accommodation. For dynamic retinoscopy, for example, the augmented reality device can be configured to perform retinoscopy while the wearer accommodates at different distances. This can be accomplished by providing virtual images or objects on which the wearer focuses while performing retinoscopy. The distance to the image or object can be changed while accommodation of the eye is tracked through the methods and systems described herein. Distance to the image can be changed by varying the depth plane of the display device, for example in a manner such as described herein. For example, lenses associated with a waveguide stack through which light is projected to form an image may have an optical power that provides for a specific focal length and associated depth plane. Illustrative and non-limiting examples of this configuration are provided herein in the description of waveguide stacks and lenses with reference to FIGS. 10D and 10E. The distance from the eye to the depth plan can thus be known. In some cases, such lenses or other optical element that project the beam, have variable optical power that can be selected or adjusted, for example, by applying an electrical signal thereto. Accordingly the depth planes can be changed or adjusted as desired in such cases. Alternatively, or in addition, distance to an object can also be changed by placing an actual object in the world in front of the wearer and within the field of view of the wearer that is seen through the display platform of the augmented reality device, as described herein. Either of these approaches can be used to determine, for example, the wearer's accommodative response to changes in target distance. These approaches can also be used to determine, for example, the eye's near point. This can be compared to static retinoscopy that determines, among other things, the eye's far point.

In some embodiments, the at least one light source includes a fiber scanning display, as described herein. In some embodiments, the at least one light source includes a fiber scanning display and a light generating source. The fiber scanning display can be configured to provide different depth planes from which the light beam, can be projected. The fiber scanning device can thus provide different amounts of sphere to determine a suitable optical correction for the wearer. In various embodiments, the fiber scanning display can be configured to send or transmit light towards an eye of the wearer and to collect or receive light reflected from the eye. The fiber scanning display can be configured to sweep or move the light across or around the eye of the wearer. The fiber scanning display can be configured to display or transmit light from one or more depth planes. In certain implementations, the fiber scanning display can be configured to have one or more fibers for generating or distributing light and for receiving light reflected from the eye of the wearer. In various implementations, one or more fibers of the fiber scanning display are configured to generate or distribute light and one or more different fibers are configured to receive light reflected from the eye of the wearer. The fiber scanning display can include multi-mode fiber in some embodiments. An example of this is described herein with reference to multicore fiber 362 illustrated in FIG. 28B.

In some embodiments, the display platform includes a waveguide stack, as described above and elsewhere herein. The waveguide stack can be configured to project light from different focal planes. In certain implementations, the waveguide stack includes one or more lenses or other elements (e.g., reflective, diffractive, etc.) with optical power in the stack, as described herein.

In some embodiments, the display platform includes adaptable optics elements configured to project light to different or targeted portions of the eye of the wearer. In certain implementations, the adaptable optics elements include variable focus elements (VFEs), as described above and elsewhere herein. Illustrative and non-limiting examples of this are described herein with reference to FIGS. 10B, 10C, and/or 10E. In some embodiments, the variable focus elements include a membrane mirror. The membrane mirror can include one or more electrodes on the mirror and a control system that is configured to control the one or more electrodes to modify a shape of the membrane mirror. Other types of adaptable optics and VFEs may be employed. The adaptable optics or VFEs can provide optical correction such as different amounts and directions of sphere and/or cylinder (and axes) that can be tested via neutralization using retinoscopy.

In some embodiments, the wearable augmented reality device includes a camera that is part of the display platform. The camera may be coupled to the waveguides that provide different depth planes. Accordingly, in certain implementations, the ophthalmic system can be configured to project light from a first depth plane and to measure the reflex at a second depth plane different from the first. Illustrative and non-limiting examples of such an image acquisition system are described herein with reference to FIG. 22C.

The wearable augmented reality device can include one or more user interface features configured to allow a wearer or other person to provide input to the device. The user interface features can be integrated with the device. In some implementations, the user interface features are provided by a device or component that is not physically integrated with the device. For example, the user interface features can be provided by a device or system that is in communication with the device. This can be a smartphone, computer, tablet, or other computational device that is in wired or wireless communication with the device. In some embodiments, the user interface features can be provided by a combination of different devices and systems linked to the device, e.g., through wired or wireless communication networks or through components that are physically linked to the device or integrated with the device. The user interface features can be presented on a device with a touch screen wherein interaction with the touch screen provides input to the wearable augmented reality device. Voice recognition systems as well as virtual touch capability may be included in addition or as an alternative. Accordingly, the user interface features can include capacitive features sensitive to touch, keyboards, buttons, microphones, photodetectors, cameras or tracking sensors for tracking gestures such as pointing by the wearer or a variety of software-implemented features provided by a graphical user interface. In various embodiments, a virtual touch screen is provided through the images projected to the user's eyes and sensors to sense the users moving body, e.g., finger. In some embodiments, the user interface features include gesture detection components to allow a wearer to provide user input through gestures. In some embodiments, the user interface features include gaze detection components to allow a wearer to provide user input through gaze of the eyes (e.g., this can include selecting a button or other element when the wearer fixates on the button for a time or when the wearer blinks when fixated on the button). Such user interface systems can be employed for other devices and systems described herein.

In some implementations, the wearer, clinician or doctor can use the interface features to control aspects of the retinoscopy test. This can be done, for example, to change the characteristics of the image or light being provided and/or the depth plane from which the light or image is being projected. This can be used to alter the light and optical correction being provided to the wearer to determine an appropriate optical prescription for the wearer.

In some embodiments, the ophthalmic device (e.g., augmented or virtual reality device) may be configured to provide both static and dynamic retinoscopy. Since the focus of images can be dynamically modified through adaptable optics elements (e.g., VFEs) of the ophthalmic device, both types of retinoscopy may be performed with the same device. It should be appreciated that the ophthalmic device may also provide a static or swept path of light to the retina. This may be a light beam projected by a light source such as a FSD (fiber scanning display) or a light generating source of the ophthalmic device. In some implementations, the ophthalmic device may comprise an additional a component that is configured to sweep light across the retina or otherwise move light on the retina. The augmented reality device can be used to perform retinoscopy and objectively determine refractive errors, which may be advantageous over other instruments that use subjective feedback from patients to determine refractive errors.

To provide static retinoscopy, the augmented reality device is used when the accommodation of the eye of the wearer is relaxed. This can be accomplished, for example, through the use of cyclopegic drops in the eye of the wearer. A light spot or beam can be provided and moved across the eye of the wearer. Lenses and/or refractive corrections or other components that can alter the shape of the wavefront can be applied to neutralize or compensate for vision defects. Adaptive optics or VFEs including reflective, diffractive, and/or refractive may be employed. In some embodiments, when operating as a static retinoscope, an image provided by the augmented reality device for the view used to fixate can be provided from a depth plane that is far, e.g., effectively at infinity. In some embodiments, when operating as a static retinoscope, the light provided by the augmented reality device that is swept across the eye can be provided from a static depth plane. The depth plane from which the virtual image is projected can be placed between infinity and about 0.1 m. In certain implementations, the augmented reality device includes a spray or other delivery device to deliver eye drops or a spray used to dilate the pupil and/or relax accommodation of the eye of the wearer. For example, the augmented reality device can be configured to spray cycloplegic drops in the eye of the wearer.

To provide dynamic retinoscopy, the augmented reality device can be used when the eye of the wearer is allowed to accommodate. An image can be displayed to the wearer or an object can be provided for the wearer to fixate on. The distance of the image or object can be varied so as to induce accommodation. In some embodiments, the accommodation of the eye of the wearer can be observed and/or measured. Using this technique, accommodation lag or lead may be measured.

The augmented reality devices described herein can be used to switch between static retinoscopy and dynamic retinoscopy. This can be accomplished while the augmented reality device is in use. The augmented reality device can be configured to provide images from a variety of depth planes for the wearer to view, allowing both static and dynamic retinoscopy to be performed. For example, the image provided by the augmented reality device can be dynamically modified to switch between static retinoscopy and dynamic retinoscopy.

As was the case in previous embodiments, input may be received by the wearer to determine diagnosis. In some embodiments, the augmented reality device may also include an eye scanning module configured to measure the response of the retina to the swept light. This response may be recorded and analyzed based on retinoscopy-specific algorithms to provide a diagnosis to the patient. For example, algorithms can be based at least in part on retinoscopy where a light is swept across an eye and the reflex is observed and measured wherein refractive errors are associated with observed or measured characteristics of the reflex. In some implementations, the direction of the reflex movement can be used to determine refractive errors. If, for example, the reflex moves in the same direction as the light that is swept across the eye, or demonstrates "with" movement, the augmented reality device can determine that the eye of the wearer is hyperopic. Similarly, if the reflex moves in the opposite direction as the light that is swept across the eye, or demonstrates "against" movement, the augmented reality device can determine that the eye of the wearer is myopic. If the reflex moves in a direction that is not parallel to the direction that the light is swept across the eye, the augmented reality device can determine that the eye of the wearer is astigmatic. In addition, the direction of movement of the reflex relative to the direction of movement of the light provided to the eye can indicate whether positive or negative refractive power is required to correct the vision defect. For example, "with" movement indicates positive refractive power may be required to correct the refractive error, "against" movement indicates negative refractive power may be required, and oblique movement indicates cylindrical refractive power may be required. As described above, different optical correction (e.g., sphere and/or cylinder with varying axes) can be provided to determine the wearer's prescription and suitable refractive correction.

In some implementations, the speed of the reflex, combined with a virtual working distance of the augmented reality device, may also be used to determine characteristics of a visual defect. For example, the speed of the reflex can be correlated to the ametropia or refractive error of the eye (e.g., faster speeds indicate lower ametropia or smaller refractive errors of the eye).

In some implementations, the width of the reflex may also be used to determine characteristics of a visual defect. For example, the width of the reflex can be correlated to the refractive error of the eye (e.g., wider reflexes indicate lower ametropia or smaller refractive errors of the eye).

In some implementations, the orientation of the reflex relative to the source light beam may also be used to determine characteristics of a visual defect. For example, a rotation of the orientation of the reflex relative to the source light beam can be indicative of astigmatism.

In some implementations, the relative brightness of the reflex may also be used to determine characteristics of a visual defect. For example, the relative brightness of the reflex can be used to determine the refractive error of the eye (e.g., brighter reflexes indicate lower ametropia or smaller refractive errors of the eye).

Any combination of the above characteristics of the reflex may be used as well to determine refractive errors. Similarly, changes in the above characteristics of the reflex may be used, alone or in any combination with one another, to determine whether refractive corrections improve or worsen the determined refractive error, where the refractive corrections are applied by the augmented reality device and/or resulting from the addition or subtraction of refractive optical components or other components that introduce optical correction. In some embodiments, the ophthalmic system can be configured to determine in real time whether refractive corrections improve or worsen the determined refractive error. The ophthalmic system can be configured to measure or monitor accommodation reflex by measuring accommodation, vergence, and/or pupils size and fluctuations in these physical characteristics to assess whether the wearer is able to see an image with normal visual acuity. For example, the accommodation, vergence, and/or pupil size of an eye fluctuate when fixated on a stationary target. These fluctuations increase when the eye is having trouble focusing on the image. Accordingly, the ophthalmic system can be configured to monitor fluctuations in the characteristics of the eye and uses this biofeedback to assess the quality of the image seen by the wearer (e.g., whether the wearer is seeing an object or image with normal visual acuity).

FIG. 19 illustrates an example method 1900 for measuring refractive error of a wearer of an augmented reality device configured as an ophthalmic device to perform retinoscopy. For ease of description, the method 1900 will be described as being performed by an ophthalmic system, such as the augmented reality devices described herein. However, it is to be understood that any component or subpart of the various augmented reality devices disclosed herein or other similar devices can be used to perform any step, combination of steps, or portions of a step in the method 1900.

At block 1902, the ophthalmic system initiates a retinoscopy program. The retinoscopy program can be a stored process or sequence of functions provided by the ophthalmic system. Initiating the retinoscopy program can include determining or retrieving a starting optical prescription, such as for a wearer that has previously undergone a retinoscopy test or other eye exam. In some implementations, the retinoscopy program can integrate information about ocular anomalies of the wearer's eye(s), where the information about the ocular anomalies can be entered by the wearer or clinician, determined from a previous retinoscopy program, or retrieved from a data store (e.g., a data store that is part of the ophthalmic system or a networked data store). Initiating the retinoscopy program can include the light beam to be projected to the wearer. Initiating the retinoscopy program can include determining whether a clinician or doctor is administering the eye exam or whether the examination is being self-administered by the wearer. In some embodiments, the ophthalmic system initiates the retinoscopy program in response to input received from the wearer or a clinician.

At block 1904, a beam of light is swept through the wearer's eye. The light can be, for example, a beam, e.g., a spot projected into the eye. The light may be configured to be collimated, converging, diverging. The light can be swept across the eye or otherwise moved around the eye. The beam of light can be provided with optical correction to be tested, e.g., sphere and/or cylinder (with varying axes), to determine focus error and astigmatism.

At block 1906, an eye scanning component of the ophthalmic system is configured to measure a response of the wearer's eye in response to the swept light, e.g., reflex from the wearer's eye. The eye scanning component can be a camera or other sensor described herein. The eye scanning component can be configured to analyze the measurements of the reflex to determine refractive errors. For example, the component (e.g., camera) can include analysis modules that are configured for a pattern recognition measurement, response pattern identification, sensor measurement, reflex tracking, brightness measurements, speed tracking, orientation determination, or the like. The retinoscope program may be precoded with pattern recognition algorithms to identify patterns and/or to analyze a given pattern. The retinoscope program may be precoded with previous images from the wearer to identify changes in a historical analysis.

At block 1908, the wearer's eyes' response may be compared against a correlation table that holds corresponding response values of various vision defects. For example, at block 1908, the ophthalmic system compares the information measured in block 1906 with a correlation table or other data corresponding to expected values of measurements for various vision defects. The comparison can be used to determine refractive errors based on the characteristics of the reflex measured in block 1906.

At block 1910, the values are compared in order to determine any vision defects. Examples of characteristics and their relationship with vision defects are described herein above. For example, the direction, speed, brightness, and/or width of the reflex can be used to determine refractive error. The shape of the reflex can be used to determine other vision defects such as astigmatism. In some embodiments, testing can be initiated if the wearer is struggling to focus or when problems with their vision occur, as represented by the dotted line from block 1910 to block 1902.

In various embodiments, to reduce distraction the view of the world in front of the wearer's eyes through the augmented reality device is blocked or otherwise not visible during retinoscopy. This can occur, for example, when images are presented to the wearer, although this approach is not necessary. In some embodiments, eye tracking can be employed to monitor whether the wearer is distracted. The system can be configured to dynamically filter out distractions based on the results of monitoring an eye tracking system.

Although the system has been described as an augmented reality device, in other embodiments the system may be a virtual reality device. In either case, the system may be a system provide by the physician or clinician for testing at a medical facility or optometrist office or elsewhere. In other embodiments, the system may belong to the wearer and may be employed for other purposes such as entertainment (e.g., games and movies) and/or work activities. As described above, one benefit of implementing retinoscopy on the wearer's system is that the procedure can be conveniently undertaken multiple times (at least 2, 3, 4, 5, 6, 8, 10, 12, 16, 18, 24, or more times) throughout the year. In some embodiments, the frequency or schedule of the procedure can be altered based on results and/or trends of retinoscopy test results. For example, if the test results indicate that vision defects are deteriorating or if the system detects the wearer is struggling with their vision (e.g., through analysis of accommodation fluctuations, vergence fluctuations, etc.), the frequency or schedule of the procedure can be altered to increase the frequency of procedures and/or shorten the time between procedures. Likewise, the procedure can be performed with or without a medical professional, such as optometrist, ophthalmologist, nurse, technician, medical assistant etc.

Photo-Refraction

As described herein, augmented reality devices can include an optical scanning or optical sensing module configured to allow the device to scan an anterior and/or interior portion of the eye using known visible and non-visible light spectrum techniques. One such technique includes photo-refraction, which includes imaging a fundus reflex from the eye(s) of a wearer of an augmented reality device. The image of the fundus reflex can be used to determine a variety of refractive errors. Such techniques may be advantageous with screening non-communicative persons because feedback from the wearer is not required and errors can be objectively measured.

The augmented reality device can be configured similar to the augmented reality devices described herein. The augmented reality device can include a display platform configured to project an image to the eyes of a wearer. The display platform can include one or more light sources that are configured to illuminate the eyes of the wearer. The augmented reality device can include inward-facing imaging devices (e.g., cameras) that are configured to generate images of the eyes of the wearer. The display platform can be configured to pass light from the environment through the display platform to the eye of the wearer.

To act as a photo-refraction device, the augmented reality device can be configured to project a fixation image to the eye of the wearer (e.g., centrally located in the wearer's field-of-view). With the eyes of the wearer fixated on the fixation image, the augmented reality device can project a light configured to illuminate the eye of the wearer so that the imaging devices can capture an image of the fundus reflex from the projected light. The image of the fundus reflex can be used to determine one or more refractive errors of the wearer. The depth plane of the projected light can be substantially the same depth plane as the fixation image. In some embodiments, rather than providing a fixation image, the wearer is instructed to focus on a fixation object that is placed at a targeted distance from the wearer. In such embodiments, the depth plane of the projected light can be substantially the same distance as the targeted distance to the fixation object. The imaging device can be configured to image the eye from substantially the same depth plane as the fixation image or object and projected light. In this way, the eye of the wearer is substantially focused at the same depth as the imaging device. In some embodiments, the imaging device can be configured to be at a conjugate plane of the retina of the wearer. Thus, in various embodiments, the effective distance from the eye to the imaging device, the effective distance from the projected light to the eye, and the effective distance from the fixation image or object to the eye can be substantially the same. In some embodiments, the effective distance from the eye to the fixation target, camera, and/or projected light is at least about 0.33 m and/or less than or equal to about 10 m, at least about 0.5 m and/or less than or equal to about 7 m, at least about 1 m and/or less than or equal to about 5 m, or at least about 2 m and/or less than or equal to about 3 m (e.g., about 2.4 m).

In some embodiments, the light source can provide the projected light along an optical axis that differs from the optical axis from the eye of the wearer to the imaging device. When the light source provides projected light at an off-axis position, the image of the fundus reflex captured by the imaging device can be correlated to a refractive error. For emmetropic eyes, the fundus reflex will generally fill the retina. For myopic eyes, the fundus reflex forms a crescent shape with the crescent on the same side of the retina as the off-axis projected light. For hyperopic eyes, the fundus reflex forms a crescent shape with the crescent on the opposite side of the retina as the off-axis projected light. The photo-refraction device can also be configured to detect anisometropia, fragmented retinal power, lens obstructions (e.g., cataracts, tumors, etc.), strabismus, and the like. In some embodiments, the augmented reality device is configured to compare images acquired of the eye of the wearer to stored images of eyes with different refractive errors to determine refractive errors, if any, in the eye of the wearer. In some embodiments, the augmented reality device is configured to perform pattern recognition to identify and/or determine refractive errors, if any, of the wearer.

The augmented reality device can be configured to determine the amount of refractive correction appropriate to correct detected refractive errors. For example, the characteristics of the fundus reflex can be used to determine the amount of refractive error in the eye. Accordingly, the augmented reality device can be used to automatically determine a refractive correction based at least in part on the measurements described herein. For example, there is a relationship between the size of the crescent and the amount of the wearer's refractive error. Generally, the size of the crescent is related to the effective distance between the wearer's eyes and the imaging device, the diameter of the pupils of the wearer, and the amount of the wearer's refractive error. Thus, the augmented reality device can be configured to determine the refractive error of the eye being measured by controlling or knowing the depth plane of the imaging device, by measuring the pupil size of the wearer, and/or by determining the characteristics of the fundus reflex (e.g., the size of the crescent).

In some embodiments, the sensitivity of the augmented reality device to refractive errors when operating as a photo-refractor is increased with increased pupil size. To increase sensitivity, it may be advantageous to allow or cause the pupils of the wearer to dilate. Similarly, to increase sensitivity, it may be advantageous to have the wearer fixate on a target at infinity. In various implementations, the target can be generated by the augmented reality device. In some implementations, the augmented reality device can be configured to occlude ambient light.

In some embodiments, the augmented reality device can use the described photo-refraction functionality to track performance or behavior of the eye of the wearer. This can be used to provide feedback to one or more testing protocols and/or corrective protocols. The feedback can be used to assess performance of the wearer, improvements or degradations in the vision of the wearer, track fatigue of the wearer, and the like.

For example, in various embodiments, the photo-refraction system can be used to see if refractive correction sufficiently compensates for refractive error, to see if the natural crystalline lens is focusing the image on the retina, and/or if the eye is correctly accommodating, e.g., for closer objects. This system can thus monitor accommodation and whether the wearer is struggling to accommodate or is accommodating successfully. This system can assist in evaluation an optical correction and/or let the wear know if his/her vision is deteriorating and might benefit from optical correction or further testing for refractive error or otherwise.

Slit Lamp

Various embodiments of an augmented reality/virtual reality device described herein can be configured as a slit-lamp ophthalmic diagnostic device. For a discussion of slit lamp instruments see https://en.wikipedia.org/wiki/Slit_lamp. The augmented reality/virtual reality device can comprise a head mounted display with inward facing cameras that is configured to provide images of a wearer's eye. Such a device may, for example, comprise a frame 64, a display system 62 that is positioned forward of the wearer's eyes, and a hardware electronic processing system 70, such as shown in in FIGS. 3A-3C and FIG. 5. This device may also include a light source and an outward facing camera. Such a device may be worn by the user and used to obtain images and perform diagnostic tests on the user's eyes. In particular, such an ophthalmic device may comprise a bright optical source that illuminates an aperture (e.g., a slit) and generates a thin illuminating beam. The generated thin illuminating beam can be conditioned by one or more lenses and filters and directed into the eye of a user. In some embodiments, the dimensions of the aperture (e.g., length and/or width of the slit) can be adjusted to change the dimensions of the beam of light. Additionally, in some embodiments, the angle of incidence and/or the brightness of the thin illuminating beam on the eye can also be adjusted in various embodiments of the slit lamp diagnostic device. The light reflected from the eye can be received by a receiving system (e.g., a camera, a microscope and/or a lens system) to examine various anatomical structures of the wearer's eye including but not limited to eyelid, tear ducts, cornea, sclera, conjunctiva, iris, lens, retina, etc. onto which the thin beam of light is incident. In various embodiments, this thin beam of light comprises a thin sheet of light at the location the beam is incident on the eye.

Different anatomical structures of the wearer's eye or perspective thereof can be examined by altering, the direction of the illuminating beam, the viewing direction, the amount of defocus of the illuminating beam and/or the depth of focus of the illuminating beam, (See https://en.wikipedia.org/wiki/Slit_lamp for additional information). Depending upon the observation desired and depending upon the opacity of the wearer's eye, methods other than direct focal examination may also be used. More particularly, light may be provided at various angles and of various widths ranging from narrow to wide.

Figure 20A:
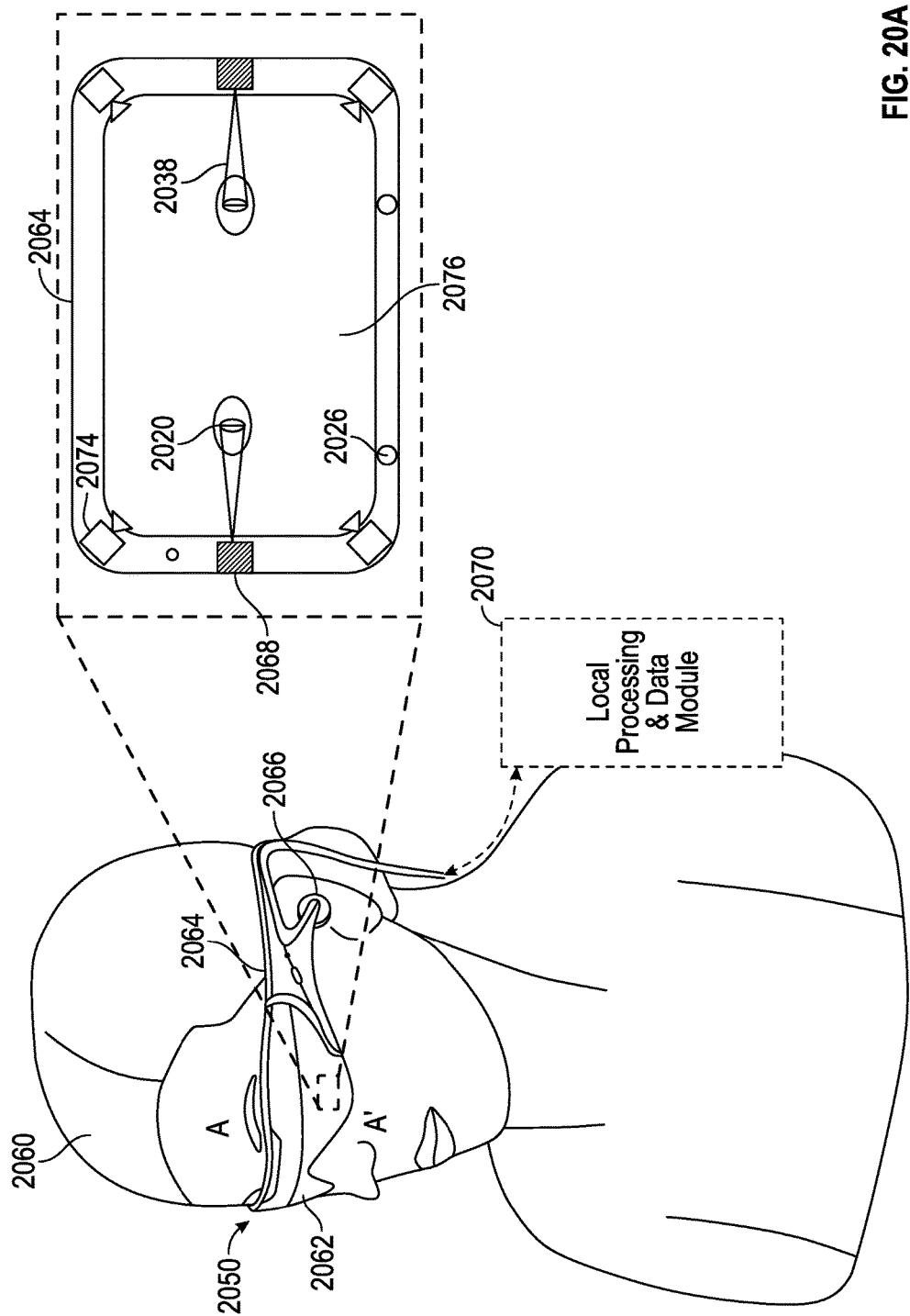
FIG. 20A illustrates a patient worn ophthalmic device configured as a slit lamp diagnostic tool.

FIG. 20A schematically depicts a wearable augmented reality device/virtual reality device 2050 that is configured as a slit-lamp ophthalmic diagnostic device. The device 2050 can be configured to periodically (e.g., hourly, daily, weekly, bi-weekly, monthly, bi-annually, annually, etc.) perform a slit lamp exam of the eye. The device 2050 can be configured to detect symptoms of vision impairments in the user's eye 2020 and perform a slit lamp exam of the eye when such symptoms are detected. In various embodiments, the device 2050 can be configured to perform a slit lamp examination of the eye at irregular time intervals. For example, the device 2050 can be configured to perform a slit lamp examination of the eye a few times an hour, a few times a week, a few times a month, a few times a year, etc. Accordingly, such test can be completed 1, 2, 3, 4, 5, 6, 8, 10, 12, 16, 24 or more times a year. Such a test may be performed more often if a user has a health problem. The device 2050 can also be configured to be used in a doctor's office or a hospital as a slit-lamp diagnostic tool. In contrast to a traditional table/bench top slit lamp device, the ophthalmic device 2050 can be worn by a user 2060. The wearable slit lamp device 2050 can be light-weight, compact and less bulky than a traditional table/bench top slit lamp device.

The wearable device 2050 includes a frame 2064 attached to a display system 2062. The display system 2062 can be configured to be positioned forward of the eyes of the wearer 2060. The display system 2062 of various embodiments of the ophthalmic device 2050 can comprise a display lens 2076 mounted in a frame 2064. In some embodiments, the display lens 2076 can be a unitary lens comprising two ocular zones, each ocular zone positioned in front of the wearer's eyes 2020. In some embodiments, the display system 2062 can comprise two display lenses mounted in the frame 2064, each display lens comprising an ocular zone that is positioned in the front of each of the wearer's eyes 2062.

The wearable device 2050 can be configured to project an illuminating beam 2038 from an optical source 2068 into the eyes 2020 of the wearer 2060. In some embodiments, the optical source 2068 can be a part of the illuminating system of the wearable augmented reality device/virtual reality device 2050 that is configured to provide illumination to the display lens 2076 and/or to the eyes of the wearer. In some such embodiments, the illuminating beam 2038 can be projected from the display lens 2076 to the eye of the user. In some embodiments, the optical source 2068 can be an auxiliary optical source disposed on a side of the display system 2062. In such embodiments, the wearable augmented reality device/virtual reality device 2050 can include optical components, such as, for example, deflectors, reflectors, beam splitters, diffractive optical elements lenses, etc. to direct the illuminating beam 2038 towards the wearer's eye 2020.

A portion of the projected illuminating beam 2038 can be reflected, scattered and/or diffracted by various anatomical features of the eyes of the user 2060 and received by one or more imaging devices 2074. An electronic hardware processor 2070 can be used to analyze light received from the eyes of the user 2060 to examine the various structures of the wearer's eye.

The illuminating beam 2038 can have a brightness that is sufficient to be detected by the one or more imaging devices 2074. In various embodiments, the imaging device 2074 can be inward facing. A cross-sectional shape of the illuminating beam 2038 can be configured such that a dimension of the cross-sectional shape along a superior-inferior axis of the wearer's face and eye 2020 is greater than a dimension of the cross-sectional shape along a nasal-temporal axis of the wearer's face and eye 2020. For example, the illuminating beam can have a rectangular cross-sectional shape having a length measured along the superior-inferior axis of the wearer's face and eyes 2020 greater than the width along the nasal-temporal axis of the wearer's face and eyes 2020. As another example, the illuminating beam can have an elliptical cross-section having a major axis oriented along the superior-inferior axis of the wearer's eye 2020 and the minor axis oriented along the nasal-temporal axis of the wearer's eye 2020.

The aspect ratio describing the proportionality of the height of the cross-sectional shape of the illuminating beam 2038 measured along the superior-inferior axis of the wearer's face and eye 2020 and the width of the cross-sectional shape of the illuminating beam 2038 measured along the temporal-nasal axis of the wearer's face and eyes 2020 can be, for example, between 1.1:1 and 1.5:1; between 1.25:1 and 1.9:1; between 1.51:1 and 2.6:1; between about 2:1 and 2.75:1; between about 2.49:1 and about 3.26:1; between about 3.01:1 and about 5.2:1; between about 5.01:1 and about 10:1 or aspect ratios in any of the sub-ranges of the ranges mentioned above. Accordingly, the beam of light may comprises a thin sheet at the location the beam is incident on the eye.

In various embodiments, the display system 2062 can be configured similar to the display system depicted in FIG. 5 and can include one or more features of the display system described with reference to FIG. 5. For example, the display system 2062 can comprise one or more optical sources 2026 (e.g., infrared or visible lasers/light emitting diodes and one or more imaging devices 2024 (e.g., infrared and/or visible cameras) that are configured to track the eyes 2020 of the user 2060. In various embodiments, the optical source 2068 can comprise the eye tracking optical sources 2026. In various embodiments, the one or more imaging devices 2074 can comprise the eye tracking imaging devices 2024.

As depicted in FIG. 20A, the one or more imaging devices 2074 can be disposed around the periphery of the display system 2062 and configured to receive light from the wearer's eyes 2020. In some embodiments, the one or more imaging devices 2074 can comprise cameras having optical and mechanical features similar to the wide-field-of-view machine vision cameras 16 that are configured to image the environment around the user and described above with reference to FIG. 5. In various embodiments, the one or more imaging devices 2074 and the optical source 2068 can be integrated in a single device as discussed below.

As depicted in FIG. 20A, the optical source 2068 can be disposed around the periphery of the display system 2062. In various embodiments, the optical source 2068 can comprise one or more light emitting diodes that are disposed around the periphery of the display system 2062 and configured to project an illuminating beam 2038 onto the wearer's eyes 2020 using optical systems comprising lenses, prisms, beam splitters, mirrors and/or other optical components. In some embodiments, the optical source 2068 can have structural and functional properties that are similar to the projection system 18 described with reference to FIG. 5.

In various embodiments, the optical source 2068 can be similar to the fiber scanning device (FSD) described above. In such embodiments, the fiber scanning device can be integrated with one or more optical components (e.g., lenses, reflective elements, light guides with diffractive optical elements) and light from the fiber scanning device can be directed towards the wearer's eye 2020. In some embodiments, the display lens 2076 can comprise a plurality of waveguides having optical and structural features similar to the stacked waveguide assembly 178 of FIG. 10D. In some such embodiments, the optical source 2068 comprising a FSD can be configured to inject light into one or more of the plurality of waveguides such that light from the FSD propagates through the one or more of the plurality of waveguides. Diffracting optical elements or other optical components integrated with the plurality of waveguides can be used to direct light out of the plurality of waveguides the wearer's eye 2020.

An optical source 2068 comprising a FSD can project light in various patterns (e.g., raster scan, spiral scan, Lissajous patterns, etc.). In some embodiments of the optical source 2068 can include one or more optical fibers similar to the FSD. In such embodiments, the one or more optical fibers can be configured to direct light from a light source to the display lens 2076. The scanning fiber may be driven to scan in a pattern so as to produce the beam at the eye that is a thin sheet or that has with a cross-sectional shape longer along the superior-inferior direction than along the nasal temporal direction or thin sheet. The one or more optical fibers of the optical source 2068 such as comprising the FSD can be configured to receive light from the wearer's eye 2020 to the imaging device 2074. Alternatively other fibers that may or may not scan with the fiber scanning display fiber may be used to collect the reflected light and image the eye.

The illuminating beam 2038 projected from the optical source 2068 can be directed to be incident at a particular location of the wearer's eye 2020. For example, illuminating beam 2038 can be incident at a desired location of the wearer's eye 2020 such that a center of the illuminating beam 2038 is incident at an angle between 0 degrees and about ±90 degrees with respect to a normal to the surface of the wearer's eye at the desired location. For example, the center of the illuminating beam 2038 can be scanned in an angular range that spans 180 degrees with respect to an axis that is perpendicular (or normal) to a surface of the eye. As another example, the center of the illuminating beam 2038 can be scanned in an angular range that spans 180 degrees with respect to an axis intersecting the eye and passing through the pupil. In various embodiments, the center of the illuminating beam 2038 can be scanned across the entire surface of the user's cornea, fundus and/or lens so as to image and/or examine various regions of the eye. The system 2050 can be configured to image the eye in a variety of directions that are oriented at a variety of angles with respect to an axis intersecting the eye and passing through the pupil. The system 2050 can be configured to image the eye along an axis intersecting the eye and passing through the pupil.

In various embodiments, the optical source 2068 can comprise a scanning laser device that outputs an illumination beam having a spot size between about 1 micron and about 1.0 mm. For example, the illumination beam can have a spot size between about 1-3 microns, between about 2-10 microns, between about 5-25 microns, between about 10-30 microns, between about 20-100 microns, between about 50-200 microns, between about 75-250 microns, between about 100-300 microns, between about 225-500 microns, between about 375-600 microns, between about 500-750 microns, between about 650-850 microns, between about 725 microns-1 mm, or any values in these ranges or sub-ranges. The scanning laser device can be configured to scan across a desired area of the eye in a desired scan pattern. For example, the desired scan pattern can have a length along the superior-inferior axis of the wearer's face that is longer than a length along the nasal-temporal axis of the wearer's face. The scanning laser device can be configured to scan at a speed between about 1 kHz and about 5 MHz to generate the desired scan pattern. Accordingly, the desired scan pattern generated at the desired area of the eye can be considered to comprise a plurality of pixels that are illuminated serially (e.g., one at a time) over the scan period. In some such embodiments, the one or more imaging device 2074 can include a photodetector that is configured to receive back scattered or back reflected light from each of the plurality of pixels. The intensity of the light received by the photodetector can be correlated to the scan angle and/or position of the illumination beam to generate a two-dimensional image of the desired area.

The light projected from the optical source 2068 can be focused at different focal distances in the wearer's eye 2020. For example, the focus of the projected light can coincide with the cornea, the iris, the natural lens, the vitreous or the retina. In various embodiments, one or more adaptable optical elements or variable focusing elements (VFEs) can be optionally used to change the angle of incidence of the light projected from the optical source 2068 and/or the focal plane at which the light projected from the optical source 2068 is focused or appears to originate, as discussed above with reference to FIGS. 10B, 10C and 10D. For example, light output from the optical source 2068 can be modified using optical systems comprising lenses, prisms and/or mirrors (e.g., optical element 1024 of FIG. 10C) such that the depth at which the illuminating beam 2038 is focused in the eye and/or the direction of the illuminating beam 2038 on the eye 2020 of the user 2060 can be varied.

In various embodiments, the VFEs can include deformable mirror devices. For example, the VFEs can comprise one or more electrodes coupled to a membrane mirror. A control system can be configured to selectively control the one or more electrodes to modify a shape of the membrane mirror. Accordingly, the wavefront of the light emitted from the stacked waveguide assembly can be modified by the modifying the shape of the membrane mirror. Embodiments of the wearable device 2650 that do not include an optical source comprising a scanning laser device or a fiber scanning device can include deformable mirror devices to steer the beam and/or to vary the depth at which the beam is focused within the user's eye. In various embodiments, the VFE's can comprise deformable lenses. In various embodiments, the VFE's can comprise deformable lenses. The deformable lenses can comprise an elastomeric material that can be deformed by application of electrostatic energy to create lenses or lenticular surfaces with different curvatures. In some embodiments, the VFE's can comprise lenses that can be deformed with activation of electrodes. Some lenses can vary refractive index with application of voltage to electrodes (e.g., liquid crystal lenses). In various embodiments, the device 2050 can comprise spatial light modulators that modulate the phase. Embodiments of the wearable device 2650 that include an optical source comprising a scanning laser device or a fiber scanning device can include deformable lenses and/or spatial light modulators that modulate phase to steer the beam and/or to vary the depth at which the beam is focused within the user's eye.

The display lens 2076 can also comprise a plurality of stacked waveguides configured to receive light output from the optical source 2068. The plurality of stacked waveguides can have structural and functional properties that are similar to the stacked waveguide assembly 178 illustrated in FIG. 10D and described with reference to FIG. 10D. In various embodiments, the plurality of stacked waveguides can comprise diffractive optical elements that are configured to in-couple light output from the optical source 2068 into one or more of the stacked waveguides. The plurality of stacked waveguides can further comprise diffractive optical elements that are configured to out-couple light propagating in one or more of the stacked waveguides. In various embodiments, the diffractive optical element that are configured to in-couple and out-couple light from the optical source 2068 into or out of the plurality of stacked waveguides can be configured to modify the focal plane and/or the direction of the illuminating beam 2038 on the eye 2020 of the wearer 2060. In various embodiments, the plurality of stacked waveguides can include one or more lensing layers. For example, a lensing layer can be coupled with waveguides of the stacked waveguide assembly as depicted in FIG. 10D.

In various embodiments, the lensing layer can be static such that the focal length and/or other optical properties of the lensing layer are fixed. In such embodiments, light from the optical source 2068 can be coupled in to the waveguide of the plurality of the stacked waveguide assembly that is coupled with lensing layer having optical and mechanical properties that would generate an output light beam having the desired direction and which would be focused or defocused at a desired position of the wearer's eye 2020.

In various embodiments, the lensing layer or other adaptive optics included in the waveguide stack can be dynamic such that the focal length and/or other optical properties of the lensing layer can be varied by application or electrical, magnetic, optical and/or mechanical force. In such embodiments, light from the optical source 2068 can be coupled into one or more of the waveguides of the plurality of the stacked waveguide assembly and the optical and/or mechanical properties of one or more lenses, lensing layers, or adaptive optical element can be modified to generate an output light beam having the desired direction and which would be focused at a desired position of the wearer's eye 2020. Accordingly, the focus of the slit beam on the eye can be altered, for example, by adjusting the adaptable optics or variable focus element.

As discussed above, the illuminating beam 2038 can have a width between about 25 microns and about 1 mm. In some embodiments, the illuminating beam 2038 can have a width less than about 25 microns. For example, the illuminating beam 2038 can have a width between about 1-24 microns (e.g., between 1-3 microns, between 2-10 microns, between 3-15 microns, between 8-24 microns). Without subscribing to any theory, the width of the illuminating beam 2038 can be a maximum distance along the temporal-nasal direction of the wearer's face and eyes 2020 of the cross-sectional shape of the illuminating at the focal plane. For example, the width of the illuminating beam 2038 can be between about 25 microns and about 1 mm, between about 40 microns and about 950 microns, between about 60 microns and about 900 microns, between about 80 microns and about 850 microns, between about 100 microns and about 800 microns, between about 140 microns and about 750 microns, between about 180 microns and about 700 microns, between about 220 microns and about 650 microns, between about 280 microns and about 600 microns, between about 325 microns and about 550 microns, between about 375 microns and about 500 microns, between about 400 microns and about 450 microns, or a width having a value in any ranges or sub-ranges between any of these values.

In various embodiments the camera includes a lens or other imaging optics. This lens or other imaging optics may provide a magnified view of the eye. This lens or other imaging optics may comprise adaptable optics or a variable focus optical element configured to be altered, for example, to change the focus.

Accordingly, the FSD of the ophthalmic device may be used to provide a narrow (or wide beam) of light using the systems and methods discussed above to illuminate an anterior or posterior portion of the eye. It should be appreciated that a focus of the light beams may be varied by one of the many way discussed in U.S. patent application Ser. No. 14/555,585, incorporated by reference above. Similar to above, an eye scanning module may be used to scan the reaction (e.g., reflection pattern, diffraction pattern, scatter pattern) of the user's eye and analyze it to determine if there are any vision defects. In various embodiments, a pattern matching algorithm may be used on image of the illuminated portions of the eye to determine any abnormalities.

The device 2050 comprising a fiber scanning device is adapted to form, shape and steer an optical beam. Accordingly, the device 2050 can produce a beam 2038 with an arbitrary width, pupil location, direction and focus point and thus can be configured to reproduce the functionality of slit-lamp diagnostic instrument. The diffractive optical elements coupled to the waveguides of the stacked waveguide assembly can be configured to produce a number of different output beams, each with a different set of beam parameters. The various beam parameters can be further modified by additional dynamic optical elements that can be coupled with the waveguides of the stacked waveguide assembly. Furthermore, the waveguides of the stacked waveguide assembly can be configured to be bi-directional that can project an optical beam as well as collect and image the light that is backscattered from the eye.

Figure 20B:
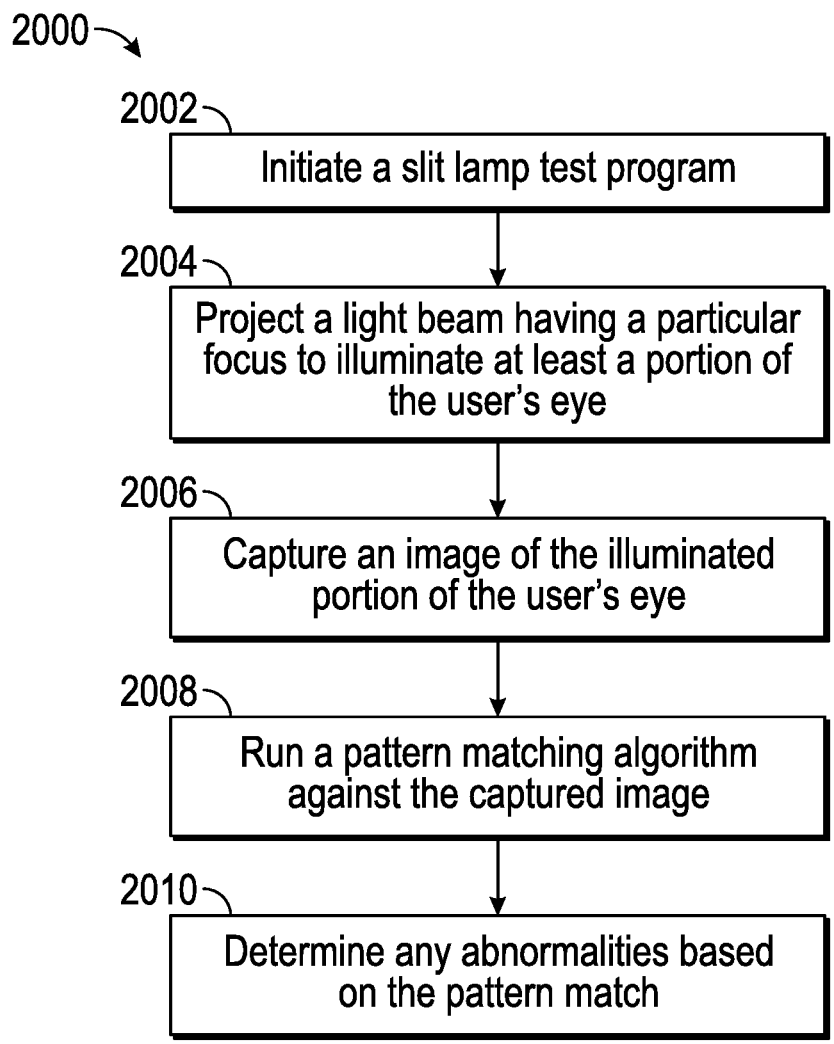
FIG. 20B illustrates an example process flow for administering a slit lamp test.

FIG. 20B illustrates an example flowchart 2000 of a method of performing a slit lamp exam using the augmented reality/virtual reality device 2050. The method of performing the slit lamp exam can be executed by the electronic hardware processor 2070. The method of performing the slit lamp exam can be executed in accordance with a schedule or when the device 2050 detects that the user 2060 is having vision impairments. Referring now to FIG. 20B, at block 2002, a slit lamp program may be initiated. At block 2004, a beam of light (i.e., generated by the optical source 2068 such as by a FSD, a scanning laser, or other display or auxiliary light source) of a particular focus may be projected to at least one portion of the user's eye 2020. The portion of the user's eye 2020 may be illuminated as a result. At block 2006, an image of the illuminated portion of the user's eye 2020 may be captured by the imaging system 2072. It should be appreciated that this function may be performed, for example, by the eye tracking cameras, or a specialized camera designed for this purpose. At block 2008, a pattern matching algorithm may be run against the captured image. The pattern matching algorithm may be executed by the electronic hardware processor 2070. In some embodiments, the captured image from the imaging system 2072 can be transferred to the electronic hardware processor 2070 using wired or wireless technology. The pattern matching algorithm may have several known patterns of eye images that are indicative of various eye abnormalities. In various embodiments, the images captured by the device 2050 can be compared to images of the user's eye 2020 obtained during previous ophthalmoscopic exams for historical analysis. Such comparisons can be useful to track the progression of certain diseases of the eye over time. If the captured image matches any of those known patterns, the ophthalmic system may determine the appropriate abnormality as shown in block 2010.

In various embodiments, the electronic hardware processor 2070 can be configured to generate a three-dimensional map of the wearer's eye based on the light received by one or more imaging devices 2074. For example, the obtained images can be combined and stitched using image processing methods to create a three-dimensional topographic map of one or more regions of the eye. Creating three-dimensional map of the eye based on the images obtained by the device 2050 can be facilitated by different capabilities of the device 2050 discussed above including but not limited to changing the position and intensity (luma) of the light source, changing the wavelength and/or color (chroma) of the light source and/or changing the position/lens/filter of the one or more imaging devices.

Color Blindness

Figure 21A:
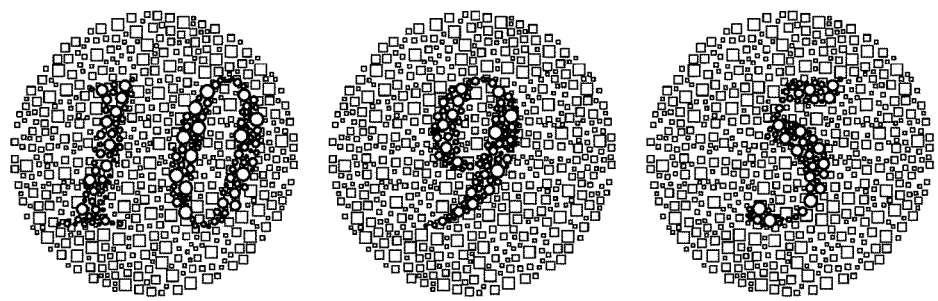
FIG. 21A illustrates a schematic view of various color plates.

The ophthalmic device may also administer a color test to test a patient's deficiencies in detecting specific colors, in one or more embodiments. For example, the device may administer the Ishihara color test, which is designed to test for red-green color perception deficiencies. The test includes showing a series of colored plates ("Ishihara plates"), similar to the one shown in FIG. 21A, to the wearer. As shown in FIG. 21A, the color plate contains a circle of dots which appear to be randomized in size and randomized or uniform in color. Within each circle are patterns of dots which form a number or shape. In some circles, the number or shape is clearly visible only for viewers with normal color vision, but difficult or impossible to see for viewers who have a red-green perception deficiency. In other circles, the number or shape is only visible for viewers with a red-green defect. In some embodiments, color plates may be selected and/or modified based on known conditions and/or previous responses of the wearer. Colors or other stimuli may be changed incrementally to determine the bounds of a wearer's color perception deficiency. That is, hues may change from a first color to a second color through a plurality of hues. For example, a wearer with a detected red-green deficiency may be presented with plates gradually changing the red color to orange or purple, and the wearer's response to each incremental change may be recorded.

In one or more embodiments, the ophthalmic device may be programmed in a manner similar to the above process flows to administer the Ishihara color test by providing virtual images of each of the color plates, and receiving user input regarding the color plate. Referring to FIG. 5, virtual images of the color plates may be provided by a display 106 or other light-emitting module 27. The color plates may be projected in an augmented reality display device 62, with light from the world forming the background surrounding the color plate. In some embodiments, the device may provide a background in addition to the color plate, so as to enhance the visibility of the color plate. For example, the background may be a solid color or a dark background. A dark background approximating black is not projected, but is the result of a lack of illumination. Thus, a dark background may be generated by using one more spatial light modulators (SLMs), e.g., a stack of two or more SLMs, that can be used to attenuate light rays, such that the region surrounding the color plate appears black, nearly black, grey, or otherwise darkened to the wearer. Various SLMs may be used, such as liquid crystal display panels, MEMS shutter displays, DLP DMD arrays, or the like. One way to selectively attenuate for a darkfield perception is to block all of the light coming from one angle, while allowing light from other angles to be transmitted. In some embodiments, multiple SLMs may be used to block more angles of light.

Figure 21B:
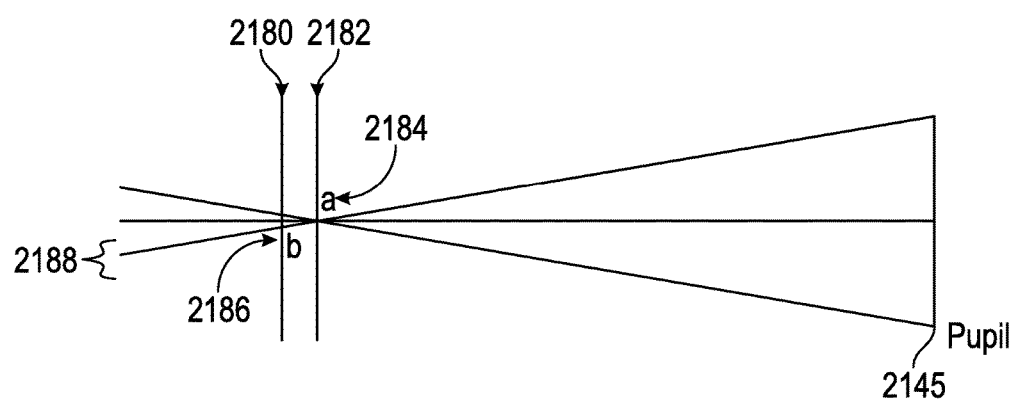
FIG. 21B schematically illustrates an example system for generating a dark background in an augmented reality system.

For example, FIG. 21B depicts an embodiment including two SLMs 2180 and 2182, which may be liquid crystal display panels, MEMS shutter displays, DLP DMD arrays, or the like, which may be independently controlled to block or transmit different rays. For example, if the second panel 2182 blocks or attenuates transmission of rays at point "a" 2184, all of the depicted rays will be blocked. But if only the first panel 2180 blocks or attenuates transmission of rays at point "b" 2186, then only the lower incoming ray 2188 will be block or attenuated, while the rest will be transmitted toward the pupil 2145. Additional numbers of SLMs beyond two provides more opportunities to more precisely control which beams are selectively attenuated. Thus, a relatively dark background may be provided against which to display color plates, as described above.

The ophthalmic system may automatically determine whether the user has a red-green vision defect or other defects based on the input received from the wearer in response to the color test. The user input regarding the color plate may be produced and/or received by any suitable method for a user to input a description of a number, letter, shape, or other image characteristic. For example, the input may be received through a user interface such as a keyboard, number pad, or touch screen having keys or virtual buttons corresponding to the numbers utilized in the Ishihara plates. In some embodiments, the system may be configured to receive a spoken input from the wearer, and to determine the wearer's response to the test using voice recognition. A user interface may further have an option for the wearer to indicate that no number or shape was observed.

In some embodiments, the wearer may provide input through the ophthalmic device, for example, by selecting a virtual button projected by a FSD or other display element of the ophthalmic device. Instead or in addition, the ophthalmic device may be further configured to determine if the wearer saw the number or shape in the projected Ishihara plate without conscious input from the wearer. For example, the system may detect a fixation of the gaze of the wearer on the location of the number or shape in the Ishihara plate for a sufficiently long period of time to be an indication that the number or shape was seen, while an extended period of scanning of the image by the wearer may indicate an inability to see the number or shape. For example, the system may track the wearer's gaze for a period of up to one second, five seconds, ten seconds, or longer.

In various embodiments, the system may use patterns and/or images other than Ishihara plates that test a wearer's ability to detect different colors. For example, the ophthalmic device may be configured to function as an RGB anomaloscope. A test based on color matching of two images and/or light sources is used to provide color detection testing. One source or image can have a fixed control color, while the other source or image is adjustable by the viewer (e.g., a fixed-spectral image that can be adjusted in brightness). The viewer may be presented with a variety of control colors, and attempts to match the adjustable image to the control image, or determine that a match cannot be made.

The ophthalmic device may perform this function by projecting multiple colored light beams or images onto the retina. As discussed above, the light source may be the FSD (or DLP, etc.) or a separate light source 27 configured for this very purpose. For example, multiple FSDs may be used to project light, each FSD projecting light of a different color as needed by the RGB anomaloscope. Alternatively, a light source that produces multiple colors may be used. The images may be projected using the display, for example, through one or more waveguides as described elsewhere herein.

In some embodiments, a traditional split image may be displayed. In other embodiments, a full-field image may be displayed. In other embodiments, an opaque back screen may be added digitally or mechanically, for example, using electronics and/or a shutter and/or a movable baffle. As discussed above, this may be administered by a clinician or doctor, or may simply be used by the user, in other embodiments. The ophthalmic system may determine one or more vision defects by receiving input regarding each image (e.g., whether there is a match or a lack of match). As described above with reference to Ishihara color testing, user input may be provided via a user interface such as a keyboard, touch pad, voice recognition or other input device, and/or may be provided through a virtual user interface projected within the ophthalmic device. Based on the received input, the ophthalmic system may provide a diagnosis or evaluation of the RGB anomaloscope test.

In various embodiments, the ophthalmic system may be configured to administer color testing repeatedly and/or periodically. For example, the system may test a wearer's color perception periodically, such as several times per day or one or more times per week, month, or year, and compare the results over time. The ophthalmic system may, for example, test more than once a year, twice a year, three times a year, four times a year, six times a year, 8 times a year, 10 times a year, 12 times a year, 16 times a year, 18 times a year, or more. Additionally, the ophthalmic system may, for example, test more than once a week, twice a week, three times a week, four times a week, six times a week, 8 times a week, 10 times a week, 12 times a week, 14 times a week, 18 times a year, or more. Additionally, the ophthalmic system may, for example, test more than once a day, twice a week, three times a week, four times a week, five times a day, six times a week or more. In some embodiments, the frequency of regularly scheduled tests may be automatically adjusted based on trending color blindness testing results and/or based on a detection that the wearer is having difficulty distinguishing colors. In such cases, the system may be able to better detect the severity or time-variation of a wearer's color detection deficiency by testing the wearer's color vision at various times of day and in various light conditions. Similarly the system may be able to obtain more complete and/or accurate results by testing a wearer's color vision repeatedly at different depth planes, degrees of accommodation, and/or areas of the retina. Accordingly, the system may be able to vary the depth plane, accommodation, and/or area of the retina when administering a color vision test. Repeated testing over longer time periods, such as months or years, may allow for the tracking of any improvement or degeneration of a wearer's color detection deficiency, such as due to macular degeneration or any other progressive conditions.

The ophthalmic system may be configured for therapeutic functions such as compensating for color detection deficiencies of the wearer. In some embodiments, the system may be configured for both detection (as described above) and therapeutic functions. Therapeutic functions may include modifying color, intensity, and/or other qualities of images and/or light from the world entering the eye of the user. For example, the system may function as a color enhancer by increasing the intensity of light in a portion of an image containing a color of reduced detection. In some embodiments, the system may shift the color of such a region, such as by changing the wavelength of the light or adding light of a different wavelength, so as to present light of a color that the wearer is better able to detect. Color shifting may be accomplished through a multi-notch optical filter capable of notch filtering out the spectral overlap between different photopigments. For example, in some cases of color blindness, the absorptance spectra of the red and green cones may overlap more than normal, causing difficulty in distinguishing red and green. A multi-notch filter may be used to filter out some of the wavelengths of light between red and green (e.g., those wavelengths with relatively high absorptance for both red and green cones) so that the wavelengths that reach the eye are more easily discernable as red or green. In embodiments comprising an augmented reality device, the system may similarly modify the wearer's view of light from the world. The augmented reality system may detect the colors of light entering the device in real time or near real time, and may modify portions of the light or project additional light to correct for the wearer's color detection deficiency. For example, the system may use outward-facing cameras to image the world and color sensors determine the colors of objects. The system may project additional light of same or different color to augment the intensity in areas of reduced detection ability so as to at least partially mitigate the color detection deficiency of the wearer. The system may further incorporate a labeling function, wherein the name of a known deficient color may be augmented over a region of the outside light determined to be of that color. In some embodiments, superposition may be used to enhance color in a portion of the display by projecting light of a desired amplitude, such as by adding a tint to the image.

A similar method may be used in a virtual reality system. The virtual reality system may have a forward and outward looking camera that images the world in front of the wearer and determines the colors of objects. The virtual reality system may reproduce to the wearer an image of the world based on the output of the outward-facing cameras, with some modifications of color and/or brightness and/or other parameters as described above. For example, the virtual reality system may increase the intensity of the image in areas of reduced detection ability so as to at least partially mitigate the color detection deficiency of the wearer.

Ophthalmoscope/Funduscope

Figure 22A:
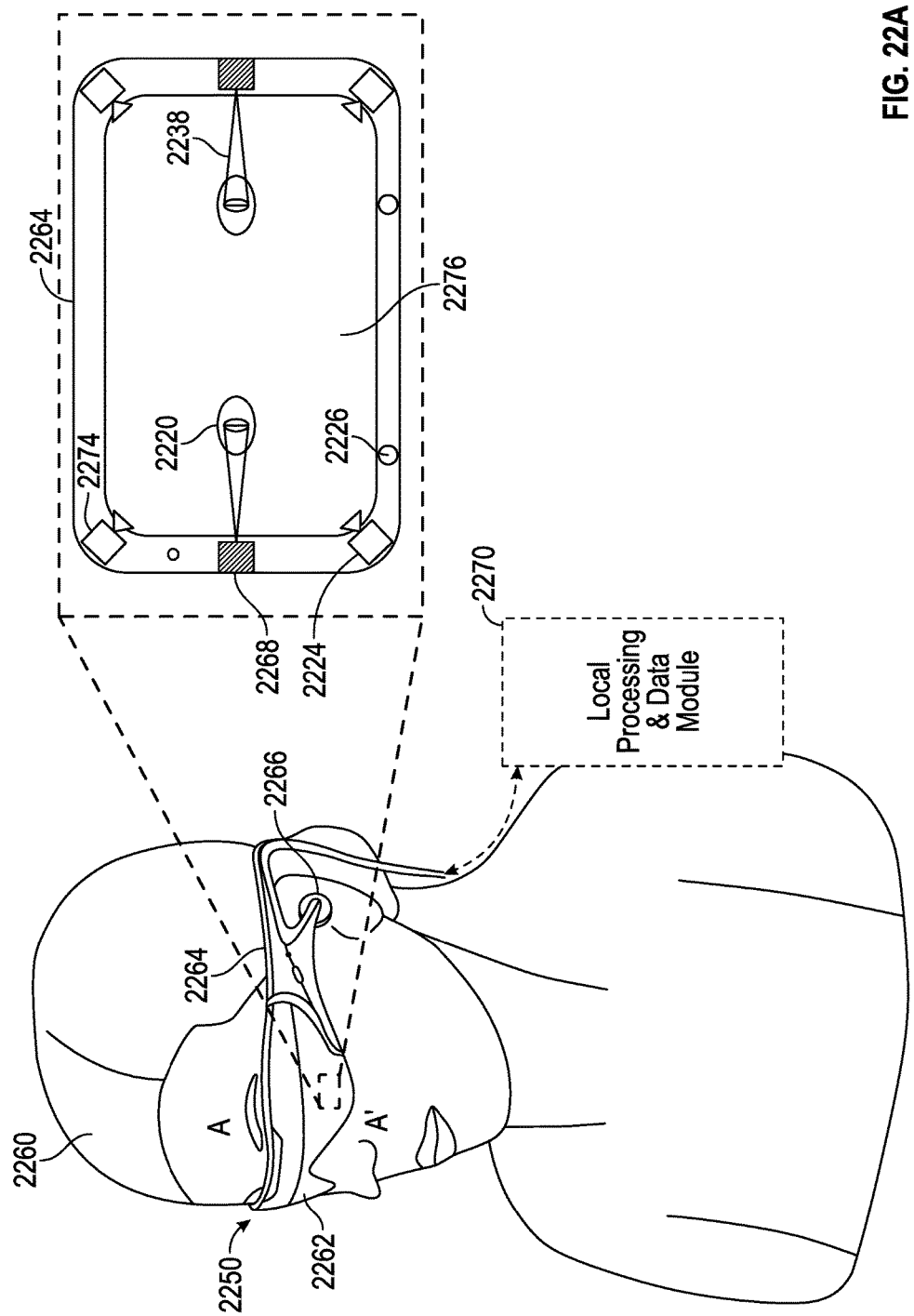
FIG. 22A schematically illustrates an augmented reality/virtual reality eyewear configured as an ophthalmoscope/funduscope.

Various embodiments of an augmented reality/virtual reality device that can be worn by a user 2260 as described herein can be configured to function as an ophthalmoscope/funduscope. FIG. 22A schematically depicts an wearable device 2250 that is configured as an ophthalmoscope/funduscope. The device 2250 includes a frame 2264 attached to a display system 2262. The display system 2262 can be configured to be positioned forward of the eyes 2220 of the user 2260. The device 2250 can be configured to project a beam of light 2238 from an optical source 2268 into the eyes 2220 of the user 2260. A portion of the projected beam 2238 can be reflected, scattered and/or diffracted by various anatomical features of the eyes 2220 of the user 2260 and received by one or more imaging devices 2274. An electronic hardware processor 2270 can be used to analyze light received from the eyes 2220 of the user 2260 to examine the various structures of the user's eye 2220.

In various embodiments of the ophthalmic system 2250, the frame 2264 can be structurally and/or functionally similar to the frame 64 of FIGS. 3A-3C. In various embodiments of the ophthalmic system 2250, the display system 2262 can be structurally and/or functionally similar to the display system 62 of FIGS. 3A-3C and FIG. 5. In various embodiments of the ophthalmic system 2250, the electronic hardware processor 2270 can be similar to the local processing and data module 70 of FIGS. 3A-3C.

The wearable device 2250 configured as an ophthalmoscope can be used to examine various parts of the user's eye 2220 including but not limited to the fundus of the eye 2220. The fundus comprises the retina, optic disc, macula, fovea and posterior pole of the eye, and other structures. The wearable device 2250 can be configured such that a clinician can view various features of the user's eye and detect any abnormalities by viewing the output of the one or more imaging devices 2274. For example, the eye's fundus is one of the parts of the human body where microcirculation can be observed. Accordingly, an examination of the fundus by the wearable device 2250 may advantageously be used to not only detect eye-related health conditions, but other health conditions of the body as well (e.g., brain abnormalities, heart abnormalities, etc.).

The display system 2262 of various embodiments of the device 2250 can comprise a display lens 2276 mounted in the frame 2264. In some embodiments, the display lens 2276 can be a unitary lens comprising two ocular zones, each ocular zone positioned in front of the user's eyes 2220. In some embodiments, the display system 2262 can comprise two display lenses mounted in the frame 2264, each display lens comprising an ocular zone that is positioned in the front of each of the user's eyes 2220.

In some embodiments, the optical source 2268 can be a part of the illuminating system of the wearable device 2250 that is configured to provide illumination to the display lens 2276 and/or to the eyes of the user. In some such embodiments, the beam 2238 can be projected from the display lens 2276 into the eye 2220 of the user 2260. For example, the optical source 2268 can comprise a fiber scanning device (FSD) and the display lens can comprise a plurality of waveguides. Light from the FSD can be injected into one or more of the plurality of waveguides and emitted from the one or more of the plurality of waveguides into the eye 2220 of the user to perform ophthalmoscopic/funduscopic functions.

In some embodiments, the optical source 2268 can be an auxiliary optical source disposed on a side of the display system 2262. In such embodiments, the wearable system 2250 can include optical components, such as, for example, lenses or other refractive components, reflective surfaces, deflectors, reflectors, beam splitters, diffractive optical elements, waveguides, or other optical components, etc. to direct the beam 2038 towards the wearer's eye 2220. For example, in certain embodiments, the ophthalmic system 2250 can comprise an additional FSD and the display lens can comprise additional waveguides (e.g., an additional stack of waveguides). Light from the additional FSD can be injected into one or more additional waveguides and emitted from the one or more waveguides into the eye 2220 of the user to perform ophthalmoscopic/funduscopic functions.

In various embodiments, the optical source 2268 can comprise a scanning laser device that outputs an illumination beam having a spot size between about 1 micron and about 1.0 mm. For example, the illumination beam can have a spot size between about 1-3 microns, between about 2-10 microns, between about 5-25 microns, between about 10-30 microns, between about 20-100 microns, between about 50-200 microns, between about 75-250 microns, between about 100-300 microns, between about 225-500 microns, between about 375-600 microns, between about 500-750 microns, between about 650-850 microns, between about 725 microns-1 mm, or any values in these ranges or subranges. The scanning laser device can be configured to scan across a desired area of the eye in a desired scan pattern. The scanning laser device can be configured to scan at a speed between about 1 kHz and about 5 MHz to generate the desired scan pattern. Accordingly, the desired scan pattern generated at the desired area of the eye can be considered to comprise a plurality of pixels that are illuminated serially (e.g., one at a time) over the scan period. In some such embodiments, the one or more imaging device 2274 can include a photodetector that is configured to receive back scattered or back reflected light from each of the plurality of pixels. The intensity of the light received by the photodetector can be correlated to the scan angle and/or position of the illumination beam to generate a two-dimensional image of the desired area.

In various embodiments the wearable ophthalmic system 2250 can comprise a concave mirror with a hole in the center through which light received from the eye 2220 can be directed towards the one or more imaging devices 2274. In such embodiments, the beam of light 2238 can be reflected into the eye of the user by the concave mirror. In various embodiments, a lens can be rotated into the opening in the mirror to neutralize the refracting power of the eye, thereby making the image of the fundus clearer. Accordingly, in some embodiments, the wearable ophthalmic system 2250 can comprise one or more optical components that are configured to direct the beam of light 2238 from the optical source 2268 into the eye of the user and direct light received from the eye 2220 of the user 2260 towards the one or more imaging devices 2274. The optical components can comprise reflective optical elements, beam splitters, diffractive optical elements, refractive optical elements, light guides with redirecting elements, etc.

As discussed above, the system 2250 configured for non-health applications (e.g., for entertainment such as watching movies or videos, playing games, for work, etc.) can also be used to provide funduscope-like applications. The system 2250 can be configured to periodically (e.g., hourly, daily, weekly, bi-weekly, monthly, bi-annually, annually, etc.) perform an ophthalmoscopic/funduscopic examination. In various embodiments, the system 2250 can be configured to perform an ophthalmoscopic/funduscopic examination of the eye 2220 at irregular time intervals. For example, the system 2250 can be configured to perform an ophthalmoscopic/funduscopic examination a few times an hour, a few times a week, a few times a month, a few times a year, etc. Accordingly, such a test can be completed 1, 2, 3, 4, 5, 6, 8, 10, 12, 16, 24 or more times a year. Such a test may be performed more often if a user has a health problem or when the system 2250 detects symptoms of visual impairments (e.g., the system 2250 detects that the user 2260 is having difficulty in focusing at objects). The system 2250 can also be configured to be used in a doctor's office or a hospital as an ophthalmoscopic/funduscopic examination. In contrast to a traditional table/bench top ophthalmoscope/funduscope, the ophthalmic system 2250 can be worn by a user 2060. The wearable ophthalmoscope/funduscope device 2050 can be lightweight, compact and less bulky than a traditional table/bench top ophthalmoscope/funduscope device.

The projection beam 2238 can have a brightness that is sufficient to be detected by the one or more imaging devices 2274. In various embodiments, the projection beam 2238 can be configured to illuminate a circular portion of the eye having a diameter between about 1 micron and about 25 mm. For example, the circular portion of the eye illuminated by the projection beam 2238 can have a diameter that is substantially equal to (e.g., within about ±10% (or smaller)

of) the diameter of the retina measured from the fovea of an average eye. As another example, the circular portion of the eye illuminated by the projection beam 2238 can have a diameter that is between about 1 micron and about 25 microns, between about 25 microns and about 100 microns, about 50 microns and about 250 microns, about 100 microns and about 500 microns, about 200 microns and about 750 microns, about 350 microns and about 800 microns, about 500 microns and about 1.0 mm, about 600 microns and about 1.5 mm, about 1.0 mm and about 2.0 mm, about 2.7 mm and about 25 mm; between about 3.0 mm and about 22 mm; between about 3.5 mm and about 20 mm; between about 4.0 mm and about 18 mm; between about 4.5 mm and about 15 mm; between about 5.0 mm and about 12.5 mm; between about 5.5 mm and about 11.0 mm; between about 7.5 mm and about 10 mm; or a value in any of these ranges or sub-ranges. In various embodiments, the projection beam 2238 can be configured to illuminate an area of the eye having a dimension between about 1 micron and about 25 mm. For example, the dimension of the area illuminated by the projection beam can be greater than or equal to about 1 micron and less than or equal to about 3 microns, greater than or equal to about 2 microns and less than or equal to about 5 microns, greater than or equal to about 5 microns and less than or equal to about 10 microns, greater than or equal to about 10 microns and less than or equal to about 15 microns, greater than or equal to about 12 microns and less than or equal to about 25 microns, greater than about 25 microns and less than or equal to about 25 mm, greater than about 50 microns and less than or equal to about 20 mm, greater than about 100 microns and less than or equal to about 15 mm, greater than about 250 microns and less than or equal to about 10 mm, greater than about 500 microns and less than or equal to about 5 mm, greater than about 1.0 mm and less than or equal to about 2.5 mm, or a value in any of these ranges or sub-ranges.

In various embodiments, the projection beam 2238 can be directed (e.g., focused) towards a desired location. A scanning fiber device, scanning laser device and/or adaptive optics may be used to direct the beam to the particular location. For example, the projection beam 2238 can be directed at the cornea; directed at the iris; directed at the lens; directed at the vitreous or directed at the retina to examine other parts of the eyes in addition to the fundus. In order to examine different parts of the eye, the projection beam 2238 can be focused at varying depths in the eye that can be achieved by varying the scan angle of the scanning fiber device, varying the focal length of the adaptive optical elements that are used to focus the projection beam 2238 and/or by varying the zoom of the one or more imaging devices 2274.

Various embodiments of the device 2250 illustrated in FIG. 22A can be configured to capture images from various depths in the eye of the user 2260. In some such embodiments of the device 2250, the one or more imaging devices 2274 can include an imaging camera configured to capture light emitted from different depths in the user's eye 2260. For example, the focal length of the lens of the imaging camera can be varied to capture light emitted from different depths in the user's eye 2260. Some embodiments of the device 2250 configured to capture light emitted from different depths in the user's eye 2260 can include a plurality of imaging cameras that are focused at structures in the user's eye 2260 that are located at different depths in the user's eye 2260. Light emitted from a particular depth in the user's eye 2260 can be captured by the imaging cameras that are focused to view structures in the user's eye 2260 at that particular depth. Embodiments of the device 2250 comprising a plurality of imaging cameras that are focused at structures in the user's eye 2260 can be used to collect light emitted from different depths in the user's eyes 2220 simultaneously.

A scanning optical source (e.g., a fiber scanning device) that is configured to inject light into a stacked waveguide assembly including a plurality of lens systems (e.g., lenses or diffracting optical elements having an overall negative optical power) and output coupling elements that are configured to emit light from the waveguide such that the emitted light appears to originate for a different depth plane can be used to collect light from different depths in the user's eyes 2220 simultaneously. FIG. 22C is a schematic partial illustration of an embodiment comprising a stacked waveguide assembly that comprises a plurality of waveguides (e.g., 22005*a*, 22005 and 22005*c*) and a first plurality of scanning fiber devices (e.g., 22003*a* and 22003*b*) configured to inject light from one or more optical sources into one of the plurality of waveguides. A lensing layer 22007 can be coupled with each of the plurality of waveguides. The lensing layer 22007 can include lens elements that provide a net negative optical power such that the user perceives light emitted from the different waveguides to originate from a different depth layer. A lensing layer 22009 can be coupled with each of the plurality of waveguides to image the light output from different depths in the eye. The lensing layer 22009 coupled with waveguides that are configured to image cornea, iris or the lens can comprise lens elements that provide a net positive optical power. The lensing layer 22009 coupled with waveguides that are configured to image the retina may include lens elements that provide a net negative optical power to compensate for the optical power provided by the cornea and the lens.

In some embodiments, the lensing layers 22007 and 22009 can comprise static lens elements with fixed focal length and/or optical power. In some embodiments, the lensing layers 22007 and 22009 can comprise dynamic lens elements with variable focal length and/or optical power. For example, the lensing layers 22007 and 22009 can comprise variable focusing elements and/or adaptive optics having variable focal length and/or optical power as described herein.

In accordance with the principle of reciprocity of light, light emitted from different depths in the user's eye 2220 can be collected by various waveguides of the stacked waveguide assembly and coupled into a second plurality of scanning fiber devices (e.g., 22010*a* and 22010*b*). Each of the second plurality of scanning fiber devices (e.g., 22010*a* and 22010*b*) is associated with a waveguide of the stacked waveguide assembly and configured to direct the received light towards a detector. In various embodiments, the first plurality of scanning fiber devices can be configured to emit light into the associated waveguide as well as collect light from the associated waveguide. Accordingly, the need for the second plurality of scanning fiber devices can be eliminated in such embodiments. Furthermore, in embodiments wherein the first plurality of scanning fiber devices are configured to emit light as well as collect light, a fiber coupler/splitter can be coupled with each of the first plurality of scanning fiber devices to separate the optical path from the optical source and the optical path towards the detector. The lensing layers (e.g., 22009*a* and 22009*b*) comprising lens elements with positive optical power can be configured to compensate the effect of the lens elements with negative optical power on the received light. In various embodiments, the lens elements with positive optical power can be disposed at the output of the waveguides instead of being integrated with the stacked waveguide assembly as shown in FIG. 22C The first and/or the second plurality of fiber scanning devices can each comprise single core fibers or multicore fibers. The implementation of the system discussed above can also be configured to simultaneously emit multiple wavelengths of light and/or receive multiple wavelengths of light. The implementation of the system discussed above can be integrated with other ophthalmic devices described herein including but not limited to eyewear configured as a slit-lamp diagnostic tool, eyewear configured as a confocal microscope, eyewear configured as a scanning laser opthalmoscope, eyewear configured as a two-photon microscope, eyewear configured as an OCT system, etc.

In various embodiments, the optical source 2268 can be configured to generate a white light. Accordingly, in such embodiments, the projection beam 2238 can comprise a white light. In some embodiments, the optical source 2268 can be configured to generate a colored light comprising a range of wavelengths of the visible spectral region. For example, the optical source 2268 can generate a light of any color having wavelengths in the range between about 440 nm and about 510 nm; between about 460 nm and about 550 nm; between about 490 nm and about 560 nm; between about 530 nm and about 610 nm; between about 550 nm and about 620 nm; or a value in any of these ranges or sub-ranges.

In some embodiments, the optical source 2268 can be configured to generate an infrared light comprising one or more wavelengths in a range of wavelengths in the infrared spectrum of light. For example, the projection beam 2238 can comprise one or more wavelengths in the near infrared spectrum of light; in the mid infrared spectrum of light and/or in the far infrared spectrum of light. As another example, the projection beam 2238 can comprise one or more wavelengths between about 700 nm and about 1.5 µm; between about 1.0 µm and about 2.3 µm; between about 1.8 µm and about 3.2 µm; between about 2.4 µm and about 5.8 µm; between about 3.2 µm and about 7.0 µm; and/or between about 6.0 µm and about 13.0 µm. The penetration depth of the projection beam 2238 in the eye 2220 of the wearer 2260 can depend on the wavelengths included in the projection beam 2238. Accordingly, varying the wavelengths included in the projection beam 2238 advantageously can allow imaging of structure and anatomical features at different depths in the eye 2220 of the user 2260.

Embodiments of the system 2250 including an optical source 2268 configured to generate visible/infrared light can be configured for use in fluorescence ophthalmology. For example, fluorescent dye can be applied to the user's eyes 2220 and the fluorescence resulting after illuminating the fluorescent dye with radiation from the optical source 2268 can be analyzed to obtain information about the health of the user's eyes 2220. In various embodiments, the fluorescent dye can be delivered by a fluid delivery system integrated with the system 2250. For example, the fluorescent dye can be delivered by a dispensing module similar to the medication dispensing module (21) described with reference to and illustrated in FIG. 5. The system 2250 configured for use in fluorescence ophthalmology can be useful to detect and/or diagnose various ophthalmic diseases and conditions. For example, a corneal ulcer stained with a fluorescent dye appears green when viewed under cobalt-blue light. Accordingly, corneal ulcers can be detected when a fluorescent dye (e.g., fluorescein) is applied to the cornea and illuminated by beam 2238 having wavelength similar to wavelength of cobalt-blue light.

Various embodiments of the one or more imaging devices 2274 can include one or more wavelength filters configured such that the imaging devices 2274 can selectively receive light at one or more desired wavelength ranges from the eye 2220 of the wearer 2260 while attenuating or filtering out other wavelengths. For example, the imaging devices 2274 can include one or more wavelength filters configured such that the imaging devices 2274 can selectively receive light in visible spectral range, near infrared spectral range, mid infrared spectral range and/or far infrared spectral ranges. As another example, the imaging devices 2274 can include one or more wavelength filters configured such that the imaging devices 2274 can selective receive light between about 440 nm and about 12.0 µm; between about 500 nm and about 10.0 µm; between about 550 nm and about 8.5 µm; between about 600 nm and about 5.0 µm; between about 650 nm and about 3.0 µm; between about 1.0 µm and about 2.5 µm or any values in the above-identified ranges and sub-ranges while attenuating or filtering out wavelengths outside of the selected range.

As depicted in FIG. 22A, the one or more imaging devices 2274 can be disposed around the periphery of the display system 2262 and configured to receive light from the user's eyes 2220. In various embodiments, the one or more imaging devices 2274 can comprise cameras similar to the infrared cameras 2224 that are configured to track the user's eyes 2220 and described above with reference to FIG. 5. In some embodiments, the one or more imaging devices 2274 can comprise cameras similar to the wide-field-of-view machine vision cameras 16 that are configured to image the environment around the user and described above with reference to FIG. 5. In various embodiments, the one or more imaging devices 2274 and the optical source 2268 can be integrated in a single device as discussed below.

As depicted in FIG. 22A, the optical source 2268 can be disposed around the periphery of the display system 2262. In various embodiments, the optical source 2268 can comprise one or more light emitting diodes that are disposed around the periphery of the display system 2262 and configured to project the beam 2238 into the user's eyes 2220. Some embodiments may use one or more optical systems comprising lenses, prisms, beam splitters, mirrors, light guides (with or without diffractive optical elements), diffractive optical components, prismatic components and/or other optical components to direct the beam 2238 into the user's eyes 2220. In some embodiments, the optical source 2268 can have similar characteristics as the projection system 18 described with reference to FIG. 5.

As discussed above, in various embodiments, the optical source 2268 can be similar to the fiber scanning device (FSD) described above. In such embodiments the optical source 2268 can include one or more optical fibers similar configured to transmit light from a light emitter (e.g., laser/LED) towards the eyes 2220 of the user 2260. In such embodiments, the fiber scanning device can be integrated with one or more optical components (e.g., reflective elements, refractive elements, diffractive optical elements, light guides with diffractive optical elements and/or other optical components) and light from the fiber scanning device can be directed towards the user's eye 2020. In some embodiments, the display lens 2276 can comprise a plurality of waveguides having optical and structural features similar to the stacked waveguide assembly 178 of FIG. 10D. In such embodiments, the optical source 2268 comprising a FSD can be configured to inject light into one or more of the plurality of waveguides such that light from the FSD propagates through the one or more of the plurality of waveguides. Diffracting optical elements or other optical components integrated with the plurality of waveguides can be used to direct light out of the plurality of waveguides the user's eye 2020.

An optical source 2268 configured as a FSD can scan in a variety of pattern (e.g., raster scan, spiral scan, Lissajous patterns, etc.) and speeds. The projected light pattern of the beam 2238 can depend on the scan pattern of the FSD, the scanning speed of the FSD and/or the speed of the one or more imaging devices 2274. In some embodiments of the optical source 2268 configured similar to the FSD, the optical fibers that are configured to transmit light from the optical source may also be used to receive light from the user's eye 2220.

The projection beam 2238 projected from the optical source 2268 can be directed to be incident at a particular location of the wearer's eye 2220. For example, projection beam 2238 can be incident at a desired location of the wearer's eye 2220 such that a center of the projection beam 2238 is incident at an angle between 0 degrees and about ±90 degrees with respect to a normal to the surface of the wearer's eye at the desired location. For example, the center of the projection beam 2238 can be scanned in an angular range that spans 180 degrees with respect to an axis that is perpendicular (or normal) to a surface of the eye. As another example, the center of the projection beam 2238 can be scanned in an angular range that spans 180 degrees with respect to an axis intersecting the eye and passing through the pupil. The projection beam 2238 can be configured to illuminate the entire back hemisphere of the user's eye 2220. As another example, the projection beam 2238 from the optical source 2268 can be incident at a desired location of the user's eye 2220 at an angle with respect to the user's line of sight. The light projected from the optical source 2268 can be focused at different focal distances in the user's eye 2220. For example, the focal plane of the projected light can coincide with the cornea, the iris, the natural lens, the vitreous, the fovea or the retina.

In various embodiments, adaptive optics or variable focusing elements (VFEs) can be optionally used to change the angle of incidence of the light projected from the optical source 2268 and/or the focal plane at which the light projected from the optical source 2268 is focused, as discussed above with reference to FIGS. 10B, 10C and 10D. For example, light output from the optical source 2268 can be modified using optical systems comprising lenses, prisms and/or mirrors (e.g., optical element 1024 of FIG. 10C) such that the depth at which the beam of light 2238 is focused in the user's eye 2220 and/or the direction of the beam 2238 on the eye 2220 of the user 2260 can be selected. Adaptive optics can be used to control/shape the wavefront of the beam of light 2238, control the direction of the beam of light 2238, convergence or divergence of the beam of light 2238, and/or remove optical aberrations from the light received from the eye.

In various embodiments, the VFEs can include deformable mirror devices. For example, the VFEs can comprise one or more electrodes coupled to a membrane mirror. A control system can be configured to selectively control the one or more electrodes to modify a shape of the membrane mirror. Accordingly, the wavefront of the light emitted from the stacked waveguide assembly can be modified by the modifying the shape of the membrane mirror. Embodiments of the wearable device 2650 that do not include an optical source comprising a scanning laser device or a fiber scanning device can include deformable mirror devices to steer the beam and/or to vary the depth at which the beam is focused within the user's eye. In various embodiments, the VFE's can comprise deformable lenses. The deformable lenses can comprise an elastomeric material that can be deformed by application of electrostatic energy to create lenses or lenticular surfaces with different curvatures. In some embodiments, the VFE's can comprise lenses that can be deformed with activation of electrodes. Some lenses can vary refractive index with application of voltage to electrodes (e.g., liquid crystal lenses). In various embodiments, the device 2250 can comprise spatial light modulators that modulate the phase. Embodiments of the wearable device 2650 that include an optical source comprising a scanning laser device or a fiber scanning device can include deformable lenses and/or spatial light modulators that modulate phase to steer the beam and/or to vary the depth at which the beam is focused within the user's eye.

The display lens 2276 can comprise or be integrated with a plurality of stacked waveguides configured to receive light output from the optical source 2268. The plurality of stacked waveguides can have characteristics that are similar to the stacked waveguide assembly 178 illustrated in FIG. 10D and described with reference to FIG. 10D. In various embodiments, the plurality of stacked waveguides can comprise diffractive optical elements that are configured to in-couple light output from the optical source 2268 into one or more of the stacked waveguides. The plurality of stacked waveguides can further comprise diffractive optical elements that are configured to out-couple light propagating in one or more of the stacked waveguides. In various embodiments, the diffractive optical elements that are configured to in-couple and out-couple light from the optical source 2268 into or out of the plurality of stacked waveguides can be configured to modify the focal plane and/or the direction of the illuminating beam 2238 on the eye 2220 of the user 2260. In various embodiments, the plurality of stacked waveguides can include one or more lensing layers. For example, a lensing layer can be coupled with each waveguide of the stacked waveguide assembly as depicted in FIG. 10D. In various embodiments, the light source used to provide illumination for the ophthlamoscope/funduscope may comprise such waveguide configurations. In some embodiments, this waveguide assembly and/or the fiber scanning display or other light source coupling light into the waveguide assembly may comprise the same components that are used to project images into the eye for the augmented reality or virtual reality. In some embodiments, this waveguide assembly and/or the fiber scanning display or other light source coupling light into the waveguide assembly may be integrated with similar components that are used to project images into the eye for the augmented reality or virtual reality. For example, additional waveguides may be added to the waveguide assembly to provide illumination to the eye and or to collect light from the eye to provide the ophthalmoscope/funduscope imaging. Similarly, additional light sources such as FSD may be added to inject light into waveguides of the waveguide assembly to provide illumination to the eye and or to collect light from the eye to provide the ophthalmoscope/funduscope imaging.

In various embodiments, the lensing layer can be static such that the focal length and/or other optical properties of the lensing layer are fixed. In such embodiments, light from the optical source 2268 can be coupled in to the waveguide of the plurality of the stacked waveguide assembly that is coupled with lensing layer having characteristics that would generate an output light beam having the desired direction and which would be focused at a desired location of the user's eye 2220.

In various embodiments, the lensing layer can be dynamic such that the focal length and/or other optical properties of the lensing layer can be varied by application of an electrical signal. In such embodiments, light from the optical source 2268 can be coupled into one or more of the waveguides of the plurality of the stacked waveguide assembly and the characteristics of one or more lensing layers can be modified to generate an output light beam having the desired direction and which would be incident at a desired position of the user's eye 2220.

The system 2250 comprising a fiber scanning device and/or a scanning device discussed above is adapted to form, shape and steer an optical beam. Accordingly, the system 2250 can produce a beam 2238 with an arbitrary width, pupil location, direction and focus point and thus can be configured to reproduce the functionality of an ophthalmoscope or funduscope. The diffractive optical elements coupled to the waveguides of the stacked waveguide assembly can be configured to produce a number of different output beams, each with a different set of beam parameters. The various beam parameters can be modified by additional dynamic optical elements that can be coupled with the waveguides of the stacked waveguide assembly. Furthermore, the waveguides of the stacked waveguide assembly can be configured to be bi-directional that can project an optical beam as well as collect and image the light that is backscattered from the eye.

Accordingly, the FSD of the ophthalmic device (or other light source) may be configured to project a light beam to the anterior or posterior portion of the eye and capture an image of the user's eye using the systems and methods discussed above. It should be appreciated that a focus of the light beams may be varied by one of the many way discussed in U.S. patent application Ser. No. 14/555,585, incorporated by reference above. Similar to above, an eye scanning module may be used to scan the light from the eye (e.g., reflection pattern, diffraction pattern, scatter pattern) of the user's eye and analyze it to determine if there are any vision defects. As in the case of other embodiments described above and elsewhere herein, the ophthalmic system may receive input from the user, or analyze the captured image and run it through various pattern matching algorithms to determine any abnormalities. In various embodiments, the images captured by the system 2250 can be compared to images of the user's eye 2220 obtained during previous ophthalmoscopic exams for historical analysis. Such comparisons can be useful to track the progression of certain diseases of the eye over time.

Figure 22B:
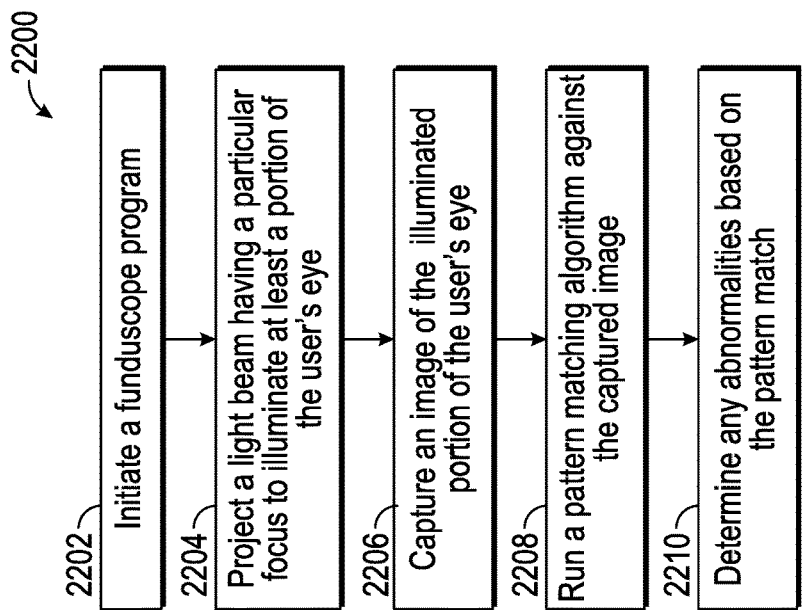
FIG. 22B illustrates an example process flow of using the health system as a funduscope, according to some embodiments.
Figure 22C:
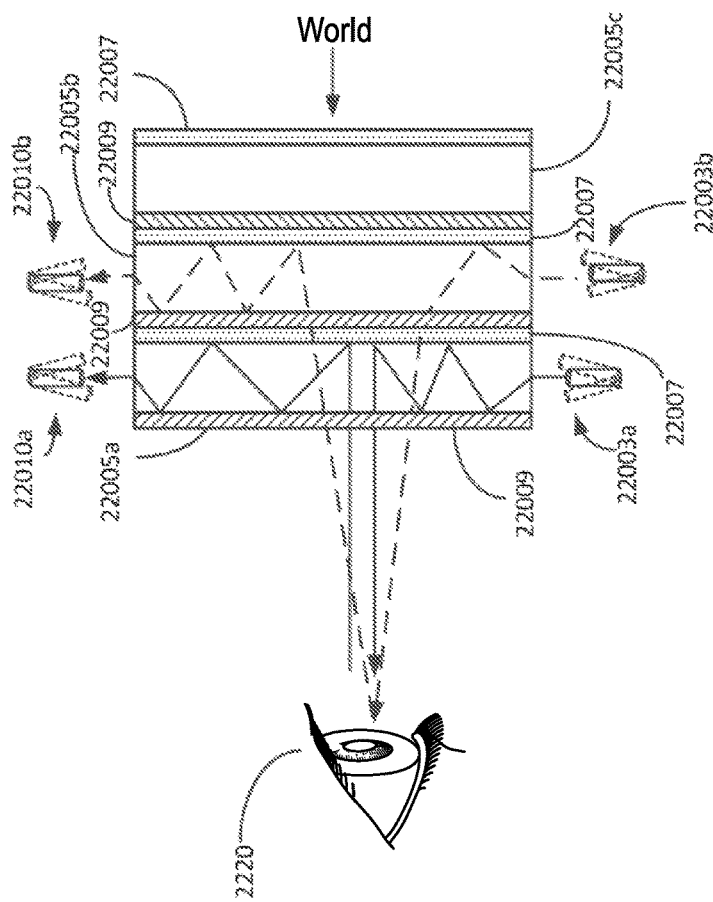
FIG. 22C is a schematic partial illustration of an embodiment configured to provide illumination to structures at various depths in the eye as well as image the structures at different depths in the eye.

FIG. 22B illustrates an example flowchart 2200 of a method of examining the eye (e.g., fundus or retina) using the ophthalmic system 2250. The method of examining the eye can be executed by the electronic hardware processor 2270 in conjunction with the optical system 2250. The system 2250 can be configured to initiate an ophthalmoscopic/funduscopic examination of the eye if it detects that the user 2260 is having difficulty in focusing or has some other visual impairments. Referring now to FIG. 22B, at block 2202, a funduscope program may be initiated. At block 2204, a beam of light of a particular focus may be projected to at least one portion of the user's eye using the optical source 2268. As discussed above, the optical source 2268 can include the fiber scanning device or an alternate optical source, such as, for example, infrared sources configured to track the user's eye. The portion of the user's eye may be illuminated as a result. At block 2206, the system may capture an image of the illuminated portion of the user's eye. It should be appreciated that this function may be performed by the eye tracking cameras, FSD, or a specialized camera designed for this purpose as discussed above. At block 2208, a pattern matching algorithm can be used to compare the captured image with several known images that are indicative of various eye abnormalities. In various embodiments, the images obtained/captured by the system 2250 can be processed using a color matching algorithm wherein the color of one or more portions of the obtained/captured images can be compared with the color of those one or more portions with previously obtained/captured images or some stored images. The several known images may be stored in a library that is accessible by the electronic hardware processor 2270. For example, the images obtained/captured by the system 2250 can be stored in an electronic medical record (EMR) associated with the user 2260 for historical analysis.

The images obtained/captured by the system 2250 can be analyzed using image processing algorithms, such as, for example, pattern matching algorithm, color matching, etc. determine any abnormalities. For example, the images can be analyzed to determine if the optic disc is swollen or appears to have blurred edges/margins. As another example, the images can be analyzed to measure a size of the optic disc and/or optic cup. The measured sizes of the optic disc and/or cup can be used to obtain a cup-to-disc ratio which is calculated as a ratio between the diameter of the cup portion of the optic disc and the total diameter of the optic disc. A higher value of the cup to disc ratio can be indicative of glaucoma. As yet another example, the images can be analyzed to determine the color of the fundus. A darker colored fundus may be indicative of retinitis pigmentosa. In contrast, a pale colored fundus may be seen in users with arterial occlusion. The images obtained by the ophthalmoscope may be analyzed to detect other abnormalities such as, for example, hemorrhages or exudates. A green filter (that attenuates red light substantially) may advantageously make it easier to detect hemorrhages or exudates. Users with hypertensive retinopathy can exhibit hard exudates, hemorrhages (rarely papilloedema) and/or retinal oedema which can be detected from the images obtained by the system 2250. Some users with diabetic retinopathy can exhibit dot and blot hemorrhages and/or hard exudates which can be detected from the images obtained by the system 2250. Some users with diabetic retinopathy can also exhibit cotton wool spots or soft exudates.

As described above, in addition to looking for common eye defects, the micro capillaries of the eye may be indicative of other health issues as well. The conditions of the retina or retinal vessels can be indicative of certain vascular diseases or other diseases. For example, the blood vessels in each of the four quadrants of obtained images can be examined to determine the conditions of arteries are usually thinner and cross veins, determine the number of vessels, determine whether the vessels are straight or tortuous, determine the color and width of the vessels, determine the light reflex and points of crossing. These determinations may provide an indication of the user's health. For example, arteriolar changes, arteriolar vasoconstriction/narrowing, changes in arteriolar wall (arteriosclerosis), etc. can be indicative of hypertensive retinopathy. As another example, manifestations of copper wire arterioles and silver wire arterioles, and "arterio-venular (AV) nicking/nipping", due to venous constriction and banking can also be indicative of hypertensive retinopathy. New vessel formation around optic disc and/or microaneurysms may be indicative of diabetic retinopathy.

As discussed above, in various embodiments, pattern matching algorithm may be configured to compare the captured image with a library of known patterns that are indicative of different types of diseases and/or abnormalities that may affect the health of the eye. If the captured image includes patterns that match any of the known patterns, the ophthalmic system 2250 may be configured to determine the corresponding abnormality or disease progression as shown in block 2210. The results of the pattern matching algorithm and/or the captured image may subsequently be displayed to the clinician and/or the user, in one or more embodiments.

Confocal Microscopy/Two-photon Microscopy/SLO

Various embodiments of an augmented reality/virtual reality system that can be worn by a user as described herein can be configured to perform confocal microscopy. FIG. 24C schematically depicts a wearable device 2650 that can be configured to perform confocal microscopy. The device 2650 includes a frame 2664 attached to a display system 2662. The display system 2662 can be configured to be positioned forward of the eyes 2620 of the user 2660. The device 2650 can be configured to project a beam of light 2638 from a light source 2668 into the eyes 2620 of the user 2660. A portion of the projected beam 2638 can be reflected, scattered and/or diffracted by various anatomical features of the eyes 2620 of the user 2660 and received by one or more imaging devices 2674. An electronic hardware processor 2670 can be used to analyze light received from the eyes 2620 of the user 2660 to examine the various structures of the user's eye 2620.

In various embodiments of the ophthalmic system 2650, the frame 2664 can have characteristics similar to the frame 64 of FIGS. 3A-3C. In various embodiments of the ophthalmic system 2650, the display system 2662 can have characteristics similar to the display system 62 of FIGS. 3A-3C and FIG. 5. In various embodiments of the ophthalmic system 2650, the electronic hardware processor 2670 can be similar to the local processing and data module 70 of FIGS. 3A-3C.

The display system 2662 of various embodiments of the ophthalmic system 2650 can comprise a display lens 2676 mounted in the frame 2664 through which the wearer can view the world. In some embodiments, the display lens 2676 can be a unitary lens comprising two ocular zones, each ocular zone positioned in front of the user's eyes 2620. In some embodiments, the display system 2662 can comprise two display lenses mounted in the frame 2664, each display lens comprising an ocular zone that is positioned in the front of each of the user's eyes 2620.

The optical source 2668 can comprise a light emitter including one or more lasers, one or more LEDs, one or more flashlamps and/or one or more superluminescent diodes. In some embodiments, the optical source 2668 can be a part of the illuminating system of the wearable device 2650 that is configured to provide illumination to the display lens 2676 and/or to the eyes 2620 of the user 2660. In some such embodiments, the beam 2638 can be projected from the display lens 2676 into the eye 2620 of the user 2660. For example, the optical source 2668 can comprise a fiber scanning device (FSD) and the display lens can comprise a plurality of waveguides having characteristics similar to the waveguide stack 178 described above with reference to FIG. 10D. Light from the FSD can be injected into one or more of the plurality of waveguides and emitted from the one or more of the plurality of waveguides into the eye 2620 of the user to perform confocal microscopy. The plurality of waveguides of the display lens can be coupled with adaptive focusing elements that can change characteristics of the wavefront emitted from the plurality of waveguides.

In some embodiments, the optical source 2668 can be an auxiliary optical source disposed on a side of the display system 2662. In such embodiments, the wearable system 2650 can include optical components, such as, for example, lenses or other refractive components, reflective surfaces, deflectors, reflectors, beam splitters, diffractive optical elements, waveguides, or other optical components, etc. to direct the beam 2638 towards the wearer's eye 2620. For example, the optical source 2668 can comprise an additional FSD and the display lens can comprise an additional stack of waveguides. Light from the additional FSD can be injected into one or more waveguides of the additional stack of waveguides and emitted from the one or more waveguides of the additional stack of waveguides into the eye 2620 of the user to perform confocal microscopy. The waveguides in the additional stack of waveguides can be coupled with adaptive focusing elements that can change characteristics of the wavefront emitted from the additional stack of waveguides.

When the device 2650 is configured as a confocal microscope, light output from the optical source 2638 can be directed towards a desired region of the eye 2620 (such as the retina) through a first aperture and focused on the part of the eye through a first lens. In various embodiments, the first lens images the first aperture onto the eye and in particular the region of the eye to be imaged. The first aperture and this region of the eye to be imaged are at conjugate focal planes (of the first lens). Light scattered/reflected/diffracted from the part of the eye is directed through a second lens towards the one or more imaging devices 2674 through a second aperture. The second aperture and the region of the eye to be imaged are at conjugate focal planes (of the second lens). The second aperture can have a dimension such that out-of-focus light from the desired region of the eye is rejected by the second aperture and not incident on the one or more imaging devices 2674.

In various embodiments, a single lens is used as the first lens and the second lens. The single lens may be disposed between the eye and the beamsplitter and the beamsplitter may be in an optical path between the first aperture and the lens and as well as in an optical path between the second aperture and the lens. As described above, the first aperture and the region of the eye to be measured are at conjugate focal planes of the lens. Similarly, the second aperture and the region of the eye to be measured are at conjugate focal planes of the lens.

In various embodiments, the first and the second apertures can coincide such that the device 2650 includes only a single aperture disposed in the confocal plane of the lens configured to direct focused light onto the desired region of the eye 2620 and receive light from desired region of the eye 2620 while rejecting out-of-focus light.

Various embodiments of the device 2650 comprising a fiber scanning device configured as the optical source 2668 and/or configured to receive light from the desired region of the eye 2620 and direct towards the one or more imaging devices 2674 need not include a separate first and/or second aperture. Instead, in some such embodiments, the output aperture of the optical fibers that are included in the fiber scanning device can be configured as the first and/or the second aperture. The first and/or the second aperture can comprise a pinhole. Various embodiments of the device 2650 in which a same fiber of the fiber scanning device is configured to project the illuminating light beam as well as to receive light from the desired region of the eye 2620 and direct towards the one or more imaging devices 2674 as illustrated in FIG. 24D-1 is configured as a confocal microscope by its nature.

As discussed above, various embodiments of the device 2650 configured as an confocal microscope can include a beam splitter and/or a fiber splitter/coupler that is disposed in the optical path to direct light from the optical source 2668 towards the desired region of the user's eye 2620. The beam splitter can be further configured to direct light originating from the desired region of the user's eye 2620 towards the one or more imaging devices 2674. Various embodiments of the device 2650 can comprise one or more scanning mirrors (e.g., horizontal and vertical scanning mirrors), deformable mirror devices, etc. such that light output from the optical source 2668 can be scanned across a region (e.g., retina, cornea, lens, vitreous humor) of the user's eye 2620 confocal microscopy can be performed by the device 2650. The horizontal and vertical scanning mirrors can scan in the lateral directions (x and y) in comparison to the longitudinal direction (z) which can correspond to the optical axis of the system and which may be orthogonal to the lateral directions (x and y). FIG. 24D-2 is a schematic partial illustration of an embodiment of an eyewear comprising an optical source 2668, one or more imaging device 2674, a beam splitter, a lensing system and a scanning mirror. The scanning mirror illustrated in FIG. 24D-2 can comprise a deformable mirror device in some embodiments.

In one or more embodiments of the device 2650 comprising a fiber scanning device (FSD) as the optical source 2668, the FSD can serve as a 3D scanning head configured to scan light across the region of the user's eye 2620. In one or more embodiments light beams of varying wavelengths (i.e., other than visible light spectrum) may be projected (e.g., through FSD or other optical sources) to provide additional 3D resolution.

Figure 24A:
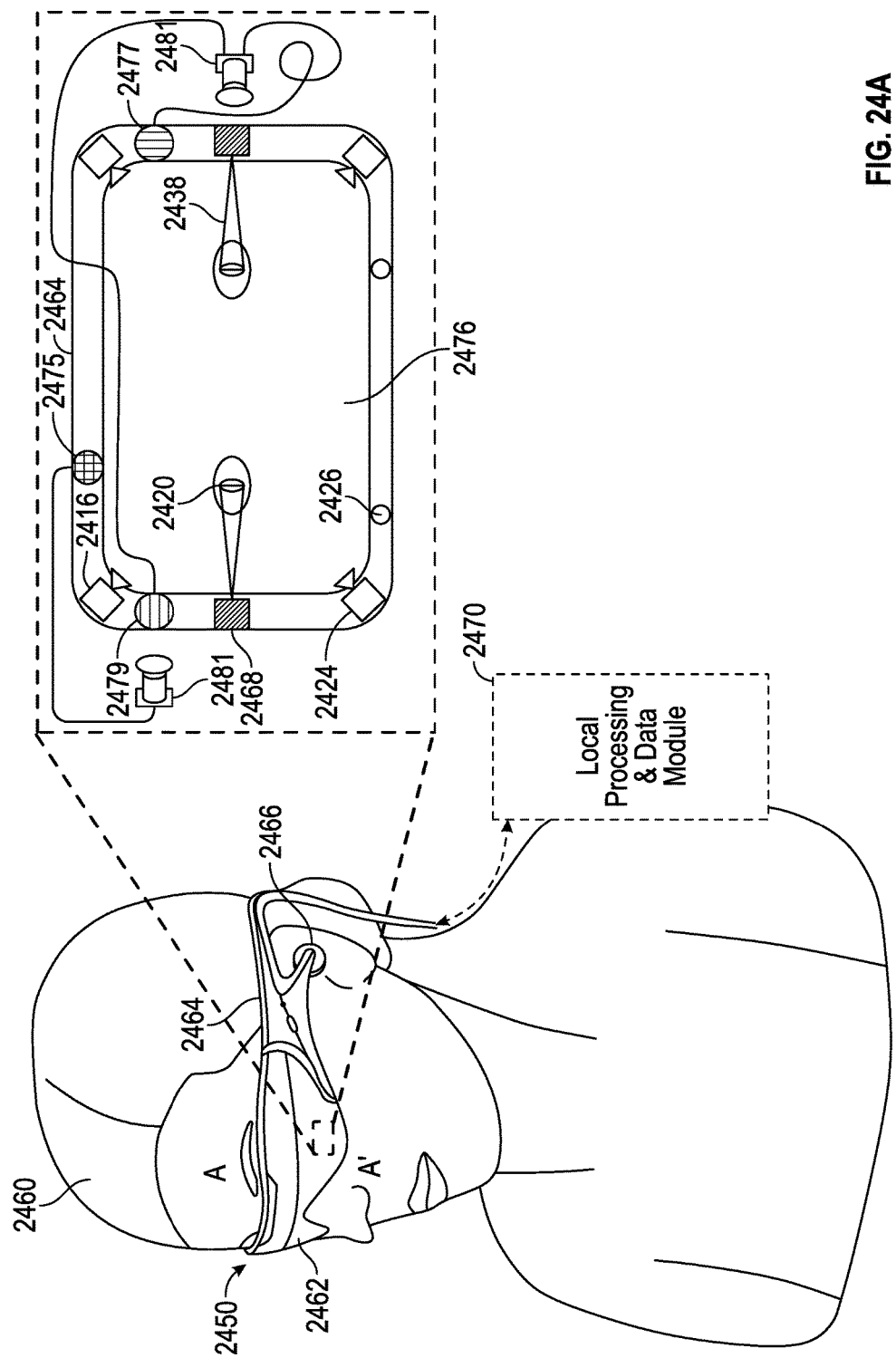
FIG. 24A is a schematic illustration of an augmented reality/virtual reality eyewear comprising one or more ultrasonic probe and one or more ultrasound transmitters and receivers.
Figure 24B:
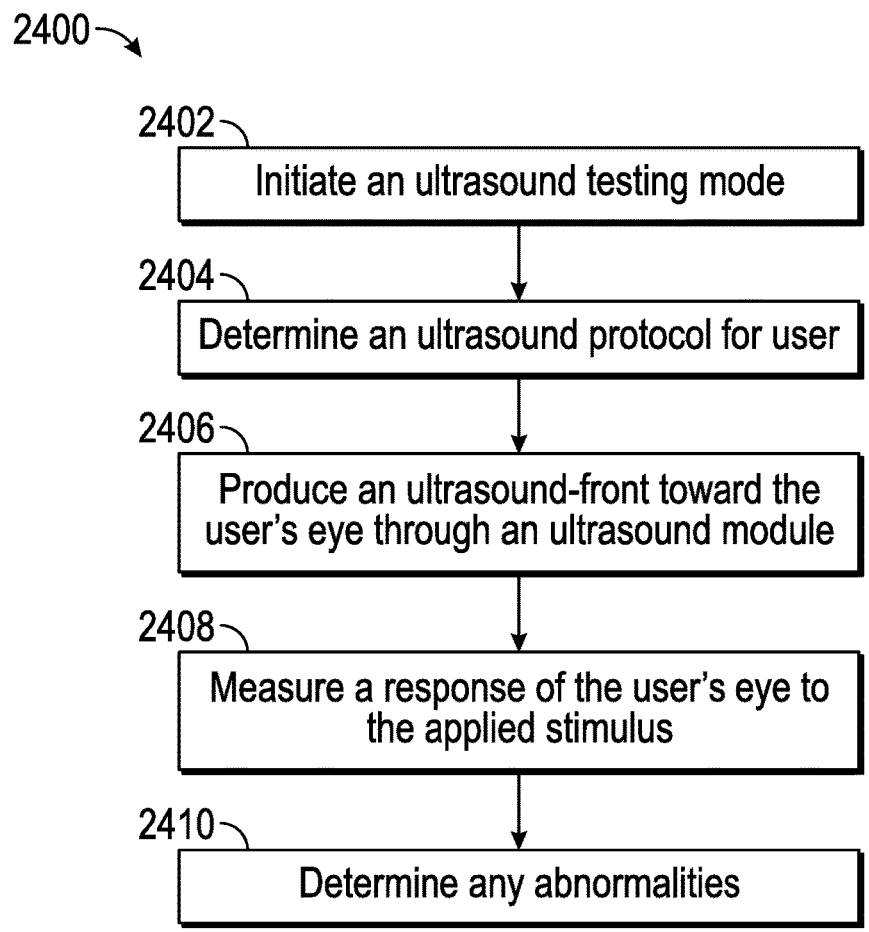
FIG. 24B illustrates an example process flow for using ultrasound through the ophthalmic device, according to some embodiments.
Figure 24C:
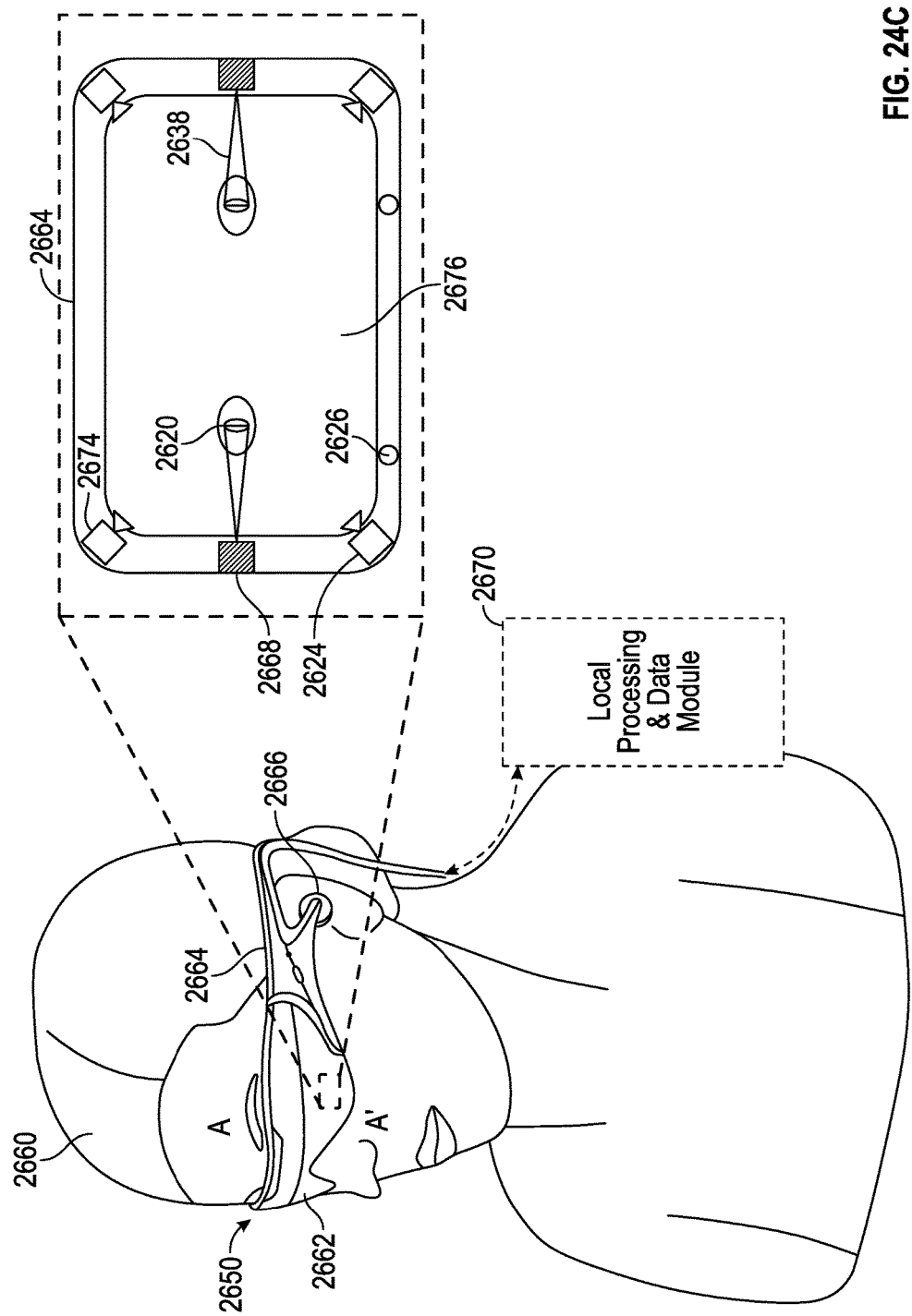
FIG. 24C schematically illustrates an augmented reality/virtual reality eyewear configured to perform confocal microscopy, scanning laser ophthalmoscopy or two-photon microscopy.
Figures 1, 24D:
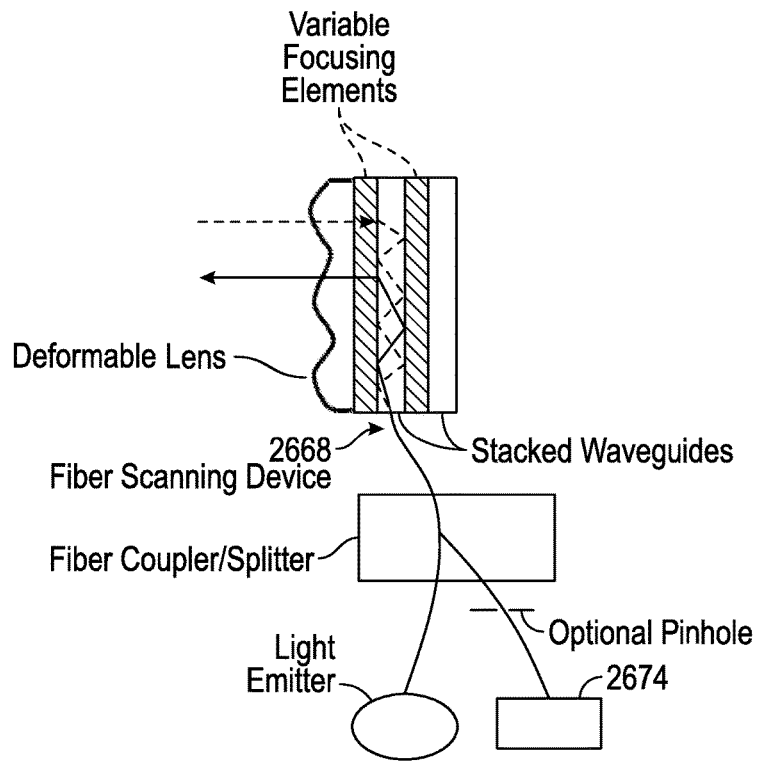
Figures 2, 24D:
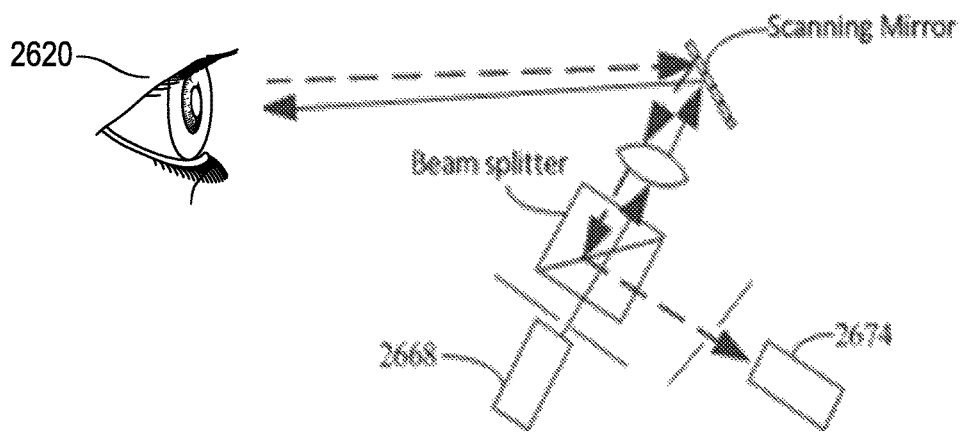

FIG. 24D-1 schematically depicts a partial view of an embodiment of the device 2650 comprising a fiber scanning device that is configured to output the projection beam 2638 as well as receive light from the desired region of the eye 2620 and direct the received light towards the one or more imaging devices 2674. In the illustrated embodiments, the FSD is configured to inject light into one or more waveguides of a stacked waveguide assembly. Light propagating through the waveguide can be out-coupled from the waveguide by diffractive optical elements coupled to the waveguide. The stacked waveguide assembly can further comprise optional variable focusing elements (VFEs) and/or optional adaptable optical elements that are configured to change the wavefront of the light out-coupled from the waveguide. In some embodiments, the stacked waveguide assembly can further comprise a plurality of deformable mirror devices that can scan the projection beam 2638 in horizontal and vertical directions across the region of the user's eye 2620.

The light projected from the optical source 2668 can be focused at different focal distances in the wearer's eye 2620. For example, the focus of the projected light 2638 can coincide with the cornea, the iris, the natural lens, the vitreous or the retina. In various embodiments, one or more adaptable optical elements or variable focusing elements (VFEs) can be optionally used to change the angle of incidence of the light projected from the optical source 2668 and/or the focal plane at which the light projected from the optical source 2668 is focused or appears to originate, as discussed above with reference to FIGS. 10B, 10C and 10D.

For example, light output from the optical source 2668 can be modified using optical systems comprising lenses, prisms and/or mirrors (e.g., optical element 1024 of FIG. 10C) such that the depth in the eye at which the projected beam 2638 is focused and/or the direction of the illuminating beam 2638 on the eye 2620 of the user 2660 can be varied.

In various embodiments, the VFEs can include deformable mirror devices. For example, the VFEs can comprise one or more electrodes coupled to a membrane mirror. A control system can be configured to selectively control the one or more electrodes to modify a shape of the membrane mirror. Accordingly, the wavefront of the light emitted from the stacked waveguide assembly can be modified by the modifying the shape of the membrane mirror. Embodiments of the wearable device 2650 that do not include an optical source comprising a scanning laser device or a fiber scanning device can include deformable mirror devices to steer the beam and/or to vary the depth at which the beam is focused within the user's eye. In various embodiments, the VFE's can comprise deformable lenses. The deformable lenses can comprise an elastomeric material that can be deformed by application of electrostatic energy to create lenses or lenticular surfaces with different curvatures. In some embodiments, the VFE's can comprise lenses that can be deformed with activation of electrodes. Some lenses can vary refractive index with application of voltage to electrodes (e.g., liquid crystal lenses). In various embodiments, the device 2650 can comprise spatial light modulators that modulate the phase. Embodiments of the wearable device 2650 that include an optical source comprising a scanning laser device or a fiber scanning device can include deformable lenses and/or spatial light modulators that modulate phase to steer the beam and/or to vary the depth at which the beam is focused within the user's eye.

In various embodiments, the optical source 2668 can comprise a scanning laser device that outputs an illumination beam having a spot size between about 1 micron and about 1.0 mm. For example, the illumination beam can have a spot size between about 1-3 microns, between about 2-10 microns, between about 5-25 microns, between about 10-30 microns, between about 20-100 microns, between about 50-200 microns, between about 75-250 microns, between about 100-300 microns, between about 225-500 microns, between about 375-600 microns, between about 500-750 microns, between about 650-850 microns, between about 725 microns-1 mm, or any values in these ranges or subranges. The scanning laser device can be configured to scan across a desired area of the eye in a desired scan pattern. The scanning laser device can be configured to scan at a speed between about 1 kHz and about 5 MHz to generate the desired scan pattern. Accordingly, the desired scan pattern generated at the desired area of the eye can be considered to comprise a plurality of pixels that are illuminated serially (e.g., one at a time) over the scan period. In some such embodiments, the one or more imaging devices 2274 can include a photodetector that is configured to receive back scattered or back reflected light from each of the plurality of pixels. The intensity of the light received by the photodetector can be correlated to the scan angle and/or position of the illumination beam to generate a two-dimensional image of the desired area. In various embodiments, a plurality of photodetectors can be disposed about a periphery of the eyewear that are configured to collect the backscattered radiation. In such embodiments, the two-dimensional image of the desired area can be generated by averaging the intensity detected by the plurality of detectors over time.

In various embodiments, the optical source 2668 can be configured to generate a white light or a colored light comprising a range of wavelengths of the visible spectral region. For example, the optical source 2668 can generate a light of any color having wavelengths in the range between about 440 nm and about 510 nm; between about 460 nm and about 550 nm; between about 490 nm and about 560 nm; between about 530 nm and about 610 nm; between about 550 nm and about 620 nm; or a value in any of these ranges or sub-ranges.

In some embodiments, the optical source 2668 can be configured to generate infrared light comprising one or more wavelengths in a range of wavelengths in the infrared spectrum of light. For example, the projection beam 2668 can comprise one or more wavelengths in the near infrared spectrum of light; in the mid infrared spectrum of light and/or in the far infrared spectrum of light. As another example, the projection beam 2668 can comprise one or more wavelengths between about 700 nm and about 1.5 µm; between about 1.0 µm and about 2.3 µm; between about 1.8 µm and about 3.2 µm; between about 2.4 µm and about 5.8 µm; between about 3.2 µm and about 7.0 µm; and/or between about 6.0 µm and about 13.0 µm.

The penetration depth of the projection beam 2668 in the eye 2620 of the wearer 2660 can depend on the wavelengths included in the projection beam 2638. Additionally, the optical path length difference between the projection beam 2638 and the reference beam can also depend on the wavelength. Accordingly, varying the wavelengths included in the projection beam 2638 advantageously can allow imaging of structure and anatomical features at different depths in the eye 2620 of the user 2660.

As depicted in FIG. 24C, the one or more imaging devices 2674 can be disposed around the periphery of the display system 2662 and configured to receive light from the user's eyes 2620. In various embodiments, the one or more imaging devices 2674 can comprise inward facing cameras. For example, the one or more imaging devices 2674 can comprise cameras having characteristics similar to the infrared cameras 2624 that are configured to track the user's eyes 2620 and described above with reference to FIG. 5. In some embodiments, the one or more imaging devices 2674 can comprise cameras similar to the wide-field-of-view machine vision cameras 16 that are configured to image the environment around the user and described above with reference to FIG. 5. The one or more imaging devices 2674 can comprise photodiodes (e.g., silicon-based, Germanium-based for IR light, photomultiplier tubes (PMTs), charge-coupled devices (CCDs), CMOS based sensors, Shack-Hartman wavefront sensors etc.). As discussed above, in various embodiments, the one or more imaging devices 2674 can be integrated with the FSD configured as an optical source 2668. For example, the optical fibers of the FSD can be configured to receive light received from the eye and direct the received light to the one or more imaging devices 2674.

Various embodiments of the one or more imaging devices 2674 can include one or more wavelength filters configured such that the imaging devices 2674 can selectively receive light at one or more desired wavelength ranges from the eye 2620 of the wearer 2660 while attenuating or filtering out other wavelengths. For example, the imaging devices 2674 can include one or more wavelength filters configured such that the imaging devices 2674 can selectively receive light in visible spectral range, near infrared spectral range, mid infrared spectral range and/or far infrared spectral ranges. As another example, the imaging devices 2674 can include one or more wavelength filters configured such that the imaging devices 2674 can selective receive light between about 440 nm and about 12.0 mm; between about 500 nm and about 10.0 mm; between about 550 nm and about 8.5 mm; between about 600 nm and about 5.0 mm; between about 650 nm and about 3.0 mm; between about 1.0 mm and about 2.5 mm or any values in the above-identified ranges and sub-ranges while attenuating or filtering out wavelengths outside of the selected range.

The information and/or images captured by the one or more imaging devices 2674 may be processed in real-time or later. In various embodiments, the system 2650 can include optical sources and detectors that track the movement of the eye. The optical sources and detectors that track the movement of the eye can have characteristics similar to the source 26 and cameras 24 described with reference to FIG. 5. The eye tracking optical sources and detectors may be used to cancel out any effects of eye movement and/or to reduce noise.

As discussed above, the wearable device 2650 may be configured to not only project light associated with visible light (usually done through RGB sources), but may also be configured with other multi-spectral components (e.g., laser sources, infrared sources, LED light etc.) to emit light having a range of wavelengths and spectral compositions. Or, in other embodiments, tunable lasers may be used (e.g., cavity length may change in the laser or diffractive gratings may be modified) that are capable of changing the wavelength of light over time, on a frame-sequential basis, line-sequential basis, pixel by pixel basis, etc.

Multi-spectral light emission may be advantageous for imaging purposes because different parts of the eye may react better to other colors or spectra of light, leading to more accurate imaging techniques. Thus, the wearable device 2650 configured as a confocal microscope may comprise additional components that are configured to emit multi-spectral light.

Figure 24E:
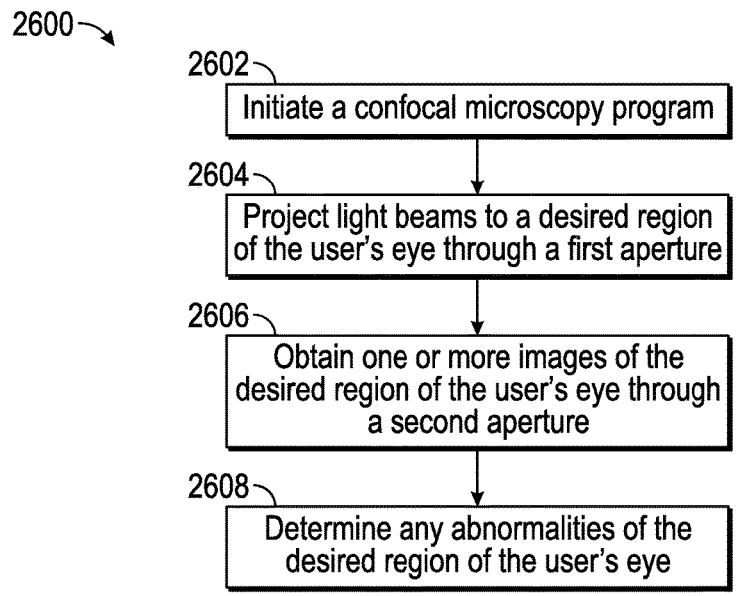
FIG. 24E illustrates an example process flow and system configurations of using the augmented reality/virtual reality eyewear as a confocal microscope.

FIG. 24E illustrates an example flowchart 2600 of a method of examining the eye using the ophthalmic system 2650. The method of examining the eye can be executed by the electronic hardware processor 2670 in conjunction with the optical system 2650. Referring now to FIG. 24E, an example process flow 2600 is provided. At block 2602, a confocal microscopy program may be initiated. At block 2604, one or more beams of light may be directed to a desired region of the user's eyes through a first aperture using the optical source 2654. At block 2606 one or more images of the desired region can be obtained by one or more imaging devices 2674 through a second aperture. At block 2608 the obtained images of the desired region can be analyzed to detect abnormalities of the eye 2620. For example, the obtained images can be compared with stored images accessible by the electronic hardware processor 2670 using pattern matching algorithms to detect abnormalities. The stored images can comprise images of healthy eyes, images that show characteristics of eye affected with particular diseases and/or images of the user's eyes obtained from past examinations. The electronic hardware processor 2670 can be configured to obtain quantitative measurements (e.g., volumetric measurements) of various parts of the obtained images of the user's eye. The quantitative measurements can be transmitted to a clinician for further analysis. As another example, one or more parameters can be extracted from the obtained images to detect abnormalities. The obtained images and/or the quantitative measurements can be used to monitor eye health or disease progression.

Various embodiments of the device 2650 can be configured to perform scanning laser ophthalmoscopy (SLO) which comprises a confocal microscope for diagnostic imaging of the retina or cornea. Embodiments of the device 2650 configured as a scanning laser ophthalmoscope comprise a laser as the light emitter of the optical source 2668. Light from the laser can be focused at a desired region of the eye (e.g., retina). The laser light can be scanned across the desired region and reflected light can be captured through a small aperture (e.g. a pinhole) such that out-of-focus light can be suppressed or eliminated. One or more scanning mirrors can be used to move the laser light across the desired region. In some embodiments, the laser light can be generated by a FSD that can be configured to scan in a variety of patterns (e.g., raster scan, spiral scan, Lissajous patterns, etc.) and speeds. The projected light pattern across the desired regions can depend on the scan pattern of the FSD, the scanning speed of the FSD and/or the speed of the one or more imaging devices. In this manner, SLO can be used to obtain a sharp, high contrast image of the desired region. The image obtained by SLO can have a high degree of spatial sensitivity.

Various embodiments of the device 2650 can be configured to perform adaptive optics scanning laser ophthalmoscopy (AOSLO) that uses adaptive optics to remove optical aberrations of the eye such as of the cornea and lens. In various embodiments, for example, the device 2650 may optionally include one or more adaptive optical elements or VFEs disposed in the optical path from the laser light source 2654 to the eye and from the imaging devices 2674 to the eye. The adaptive optical element or VFE may comprise, for example, such as a deformable mirror and may be configured as described herein. Additionally, an aberrometer such as a Shack-Hartman wavefront sensor, can be disposed to receive light returned from the eye such as describe herein. The aberrometer is configured to measure the aberrations wavefront of the eye as discussed above. Processing electronics can be configured to drive the adaptive optics, e.g., the deformable mirror, so as to alter the wavefronts directed to and from the eye so as to compensate for or reduce the effect of the aberration of the eye on the wavefront. As a result of reduced aberrations introduced by the eye, AOSLO can provide a greater degree of accuracy when compared to SLO.

The systems and methods described above to perform confocal microscopy, scanning laser ophthalmoscopy or adaptive optics scanning laser ophthalmoscopy can also be used to perform multi-photon microscopy or two-photon microscopy (or multi-photon fluorescence or two-photon fluorescence microscopy). For example, a fluorescent dye can be provided to a desired or target region of user's eye. In some embodiments, the fluorescent dye is ejected from a port on the wearable device 2650 and applied to the eye as described herein. The wearable device 2650 can be configured such that one or more drops of fluorescent dyes can be applied or sprayed onto the eye. Fluorescence can be produced in the target region by absorption of two-photons. Two-photon absorption involves the absorption of light of lower energy by a medium and the resultant emission of higher energy light. In certain cases, two-photons of the lower energy light are absorbed and one photon of the higher energy is emitted. The amount of light required to excite fluorescence by the two-photon absorption process can be high. Accordingly, the light emitter of the optical source 2668 in the wearable device 2650 that is configured to perform two-photon microscopy may comprise a high radiance source. The radiance of the light emitter included in a system configured to perform two-photon microscopy can be of the order of $10^{10}$-$10^{12}$ W/cm$^2$ in some embodiments. The light emitter can include a continuous-wave (CW) laser having sufficient power that can provide the radiance levels for performing two-photon microscopy. In some embodiments, the light emitter can include a pulsed laser, such as, for example, a femto-second laser or a pico-second laser. The pulsed laser can be configured to operate at high repetition rates to achieve higher peak power that may assist in increasing two-photon excitation efficiency. In some other embodiments, the light emitter can comprise a mode-locked laser or a fiber laser that is configured to output ultra-fast pulses (e.g., pico-second pulses or femto-second pulses). The light emitted from the laser can have wavelengths between about 700-1600 nm.

In various embodiments of the optical source included in eyewear configured to perform scanning laser ophthalmoscopy, adaptive optics scanning laser ophthalmoscopy and/or multi-photon microscopy can comprise a laser. Light from the laser can be coupled into the fiber scanning device (FSD), which in certain embodiments injects the light into one or more waveguides of the stacked waveguide assembly. Light propagating through the one or more waveguides can be out-coupled by diffractive optical elements or other optical elements in various embodiments. Light output from the waveguides can be shaped by one or more variable focusing elements comprising adaptive optics and directed towards a target region of the user's eye. The FSD, however, need not be used in conjunction with a waveguide stack. In various embodiments, the FSD can be configured to scan in a variety of patterns (e.g., raster scan, spiral scan, Lissajous patterns, etc.) and speeds. The projected light pattern to the target region can depend on the scan pattern of the FSD, the scanning speed of the FSD and/or the speed of the one or more imaging devices. In some embodiments, deformable mirror devices can be employed to steer light output from the waveguides to the target region of the user's eye. The deformable devices can be employed in addition to or instead of scanning the FSD in a variety of directions.

In various embodiments, the optical source included in eyewear configured to perform scanning laser ophthalmoscopy, adaptive optics scanning laser ophthalmoscopy and/or multi-photon microscopy can comprise a scanning laser device that outputs an illumination beam having a spot size between about 1 micron and about 1.0 mm. For example, the illumination beam can have a spot size between about 1-3 microns, between about 2-10 microns, between about 5-25 microns, between about 10-30 microns, between about 20-100 microns, between about 50-200 microns, between about 75-250 microns, between about 100-300 microns, between about 225-500 microns, between about 375-600 microns, between about 500-750 microns, between about 650-850 microns, between about 725 microns-1 mm, or any values in these ranges or sub-ranges. The scanning laser device can be configured to scan across a desired area of the eye in a desired scan pattern. For example, the desired scan pattern can have a length along the superior-inferior axis of the wearer's face that is longer than a length along the nasal-temporal axis of the wearer's face. The scanning laser device can be configured to scan at a speed between about 1 kHz and about 5 MHz to generate the desired scan pattern. Accordingly, the desired scan pattern generated at the desired area of the eye can be considered to comprise a plurality of pixels that are illuminated serially (e.g., one at a time) over the scan period. In some such embodiments, the one or more imaging device 2074 can include a photodetector that is configured to receive back scattered or back reflected light from each of the plurality of pixels. The intensity of the light received by the photodetector can be correlated to the scan angle and/or position of the illumination beam to generate a two-dimensional image of the desired area.

In some embodiments, the light output from the waveguide can be focused at the target region of the user's eye 2620 by the variable focusing elements. Two-photon excitation can be achieved in the focal volume of the target region in which the optical energy is sufficiently high. For example, in various embodiments, two-photon excitation can be excited in a diffraction-limited focal volume of the target region of the user's eye 2620. In various embodiments, the light output from the laser can be focused to a spot size that corresponds to the diffraction-limited spot. Light emitted from the volume of the target region in which two-photon excitation is achieved can be directed towards the one or more imaging devices 2674. As described above, the light output from the waveguides can be scanned horizontally and/or vertically in the target region of the user's eye to construct two-dimensional images of the target region. Additionally, by varying the depth in the eye at which light output from the waveguide is focused, three-dimensional images can be constructed. In various embodiments, the depth in the eye at which light output from the waveguide is focused can be varied based on the scan angle of the fiber scanning device. In some embodiments, the depth in the eye at which the beam 2638 is focused can be varied by varying the wavelength of light. In some other embodiments, the depth in the eye at which the beam 2638 is focused can be varied by scanning the beam along a longitudinal axis of the beam 2638 that is aligned with the direction of propagation of the beam 2638. In various embodiments, the longitudinal axis of the beam 2638 can be aligned with the line of sight of the user 2620.

Since the light received by the one or more imaging devices when the device 2650 is configured as a two-photon microscope is confined to the focal volume, out-of-focus light or any other stray light can be rejected by providing appropriate filters configured for the wavelength of the two-photon emission. Such filters may comprise transmission filters that are configured to substantially transmit light having wavelength corresponding to the emission of the two-photon excitation process while reducing transmission of other wavelengths. Other types of filters or filter configurations the can separate out the wavelength corresponding to the emission of the two-photon excitation process from other wavelengths can be used.

Accordingly, various embodiments the augmented or virtual reality eyewear may comprise a multi-photon microscope or two-photon microscope.

The device 2650 configured as a confocal microscope, a scanning laser ophthalmoscope, adaptive optics scanning laser ophthalmoscope and/or two-photon microscope can be used to visualize retinal topography, deep fundus imaging (i.e., detecting lesions), retinal pigment epithelium (RPE) changes and other age related macular degeneration. The device 2650 configured as a confocal microscope, a scanning laser ophthalmoscope, adaptive optics scanning laser ophthalmoscope and/or two-photon microscope may also be used to provide a multi-spectral image comparison, which can help improve visual discrimination of retinal and subretinal features through spectral and depth enhanced differential visibility.

In various embodiments, the device 2650 configured as a confocal microscope, a scanning laser ophthalmoscope, adaptive optics scanning laser ophthalmoscope and/or two-photon microscope can allow a clinician to view the obtained images of the user's eye in real time. For example, the system can be configured to allow the clinician to read a word that the user is seeing and/or view the scene that the user is seeing. The device 2650 can be configured to allow a clinician to determine in real time which part of the retina the user is using to see. For example, most users normally rely on the foveal region of the retina to see. However, users with macular degeneration may rely on other parts of the retina to see. Various embodiments of augmented reality/virtual reality eyewear described herein, such as, for example, the device 2650 configured as a confocal microscope, a scanning laser ophthalmoscope, adaptive optics scanning laser ophthalmoscope and/or two-photon microscope can be configured to perform micro visual fields testing. A device configured to perform micro visual fields testing comprises placing small targets on the retina that can be viewed by the user and determining the blind spots of the retina based on the user's feedback and/or ability to see the small targets.

Various embodiments of the device 2650 configured as a confocal microscope, a scanning laser ophthalmoscope, adaptive optics scanning laser ophthalmoscope and/or two-photon microscope can be configured to measure refractive error. For example, a size of the image on the back of the retina can be measured by the clinician to determine if it is smaller, larger, out of focus or has some other deficiencies.

Various embodiments of the device 2650 configured as a confocal microscope, a scanning laser ophthalmoscope, adaptive optics scanning laser ophthalmoscope and/or two-photon microscope can be configured to track eye movement of the user 2660 which can be advantageous in providing the ability to view the objects and scenes that the user 2660 is viewing in real-time.

Various embodiments of the device 2650 configured as a confocal microscope, a scanning laser ophthalmoscope, adaptive optics scanning laser ophthalmoscope and/or two-photon microscope can be configured to measure the thickness of the retina, thickness of the macula and/or thickness of individual retinal layers.

For example, scanning laser ophthalmoscopy or confocal scanning laser ophthalmoscopy (cSLO) can be used to scan across the retina in accordance with a scan pattern (e.g., a raster scan). Light from the scanned region of the retina can be received at the one or more imaging devices 2674 to construct a two/three-dimensional image of the retina. For example, sequential cSLO scans captured at increasing depths can be combined to create three-dimensional topographic images of the retina or optic disc. Image stacks can be aligned to create a final composite image to provide retinal thickness, measurements of the macula and other parameters of the retina. In one or more embodiments, an aperture can be positioned in front of the one or more imaging device 2674 to reject out-of-focus light that may add noise or aberrations to the constructed two/three-dimensional image of the retina.

Various embodiments of the device 2650 configured as a confocal microscope, a scanning laser ophthalmoscope, adaptive optics scanning laser ophthalmoscope and/or two-photon microscope can be configured to image the macula of the user 2660. The macula images can be useful to measure thickness of the macula as discussed above. The macula images can also be useful to determine swelling of the macula. This can be advantageous in early detection of glaucoma—which causes structural changes in the macula before functional changes. For example, glaucoma can cause loss of retinal ganglion cells, changes in the inner plexiform layer, thinning of certain retinal layers, etc. These structural changes can be determined from the images of the retina and/or macula.

Various embodiments of the device 2650 configured as a confocal microscope, a scanning laser ophthalmoscope, adaptive optics scanning laser ophthalmoscope and/or two-photon microscope can be configured to image the shape of the front and the back surface and/or thickness of the lens of the user 2660 so as to determine accommodation state based on the shape of the lens and/or measure refractive error. For example, the user 2660 can be made to focus on targets at different depths by projecting the beam 2638 from different depth planes. The changes in the accommodation state of the lens as well as the size and acuity of the images formed on the retina can be imaged to assist in determining refractive errors.

Various embodiments of the device 2650 configured as a confocal microscope, a scanning laser ophthalmoscope, adaptive optics scanning laser ophthalmoscope and/or two-photon microscope can be configured to determine spatial distribution and anisotropy of cone cells around fovea. This can be advantageous in determining if the user is myopic, emmetropic or hypermetropic. For example, myopic users can exhibit decrease in foveal cone packing density for myopia as compared to emmetropic eyes. Changes in cone packing density can also be observed in user's with cone dystrophy and/or retinitis pigmentosa. Macular dystrophy may cause abnormal photoreceptor structure. Accordingly, macular dystrophy can be determined by imaging the photoreceptor structure of the user.

Various embodiments of the device 2650 configured as a confocal microscope, a scanning laser ophthalmoscope, adaptive optics scanning laser ophthalmoscope and/or two-photon microscope can be configured to perform fluorescence microscopy. For example, a fluorescent dye can be injected into the blood vessels of the user and fluorescence microscopy can be used to track blood flow in the fundus or retina in real time. As another example, a fluorescent dye can be injected into the blood vessels of the user and fluorescence microscopy can be used to image individual capillaries in nerve fiber layer, to determine thickness of nerve fiber layer and/or to determine vessel patterns in the fundus of the eye. In various embodiments, the fluorescent dye can be delivered by a fluid delivery system integrated with the system 2650. As described herein, the device may include output ports for delivering fluorescent dyes. Accordingly, fluorescence microscopy can be useful to determine changes in nerve fiber layer thickness or vasculature alterations resulting from retina damage caused by different diseases of the eye, such as, for example, glaucoma, macular dystrophy, etc. As another example, fluorescence microscopy can be used to analyse lipofuscin granule autofluoresence with simultaneous cone structure imaging and cone/retinal pigment cell ratio analysis to track retinal damage from retinal dystrophies. As yet another example, light damage to macula from particular wavelengths can be observed by fluorescence microscopy.

The ophthalmic system 2650 can be configured for non-health applications (e.g., for entertainment such as watching movies or videos, playing games, for work, etc.) as well as a confocal microscope, a scanning laser ophthalmoscope, adaptive optics scanning laser ophthalmoscope and/or two-photon microscope. The system 2650 can be configured to periodically (e.g., hourly, daily, weekly, bi-weekly, monthly, bi-annually, annually, etc.) perform confocal microscopy. In various embodiments, the system 2650 can be configured to perform confocal microscopy of the eye 2620 at irregular time intervals. For example, the system 2650 can be configured to perform confocal microscopy, a scanning laser ophthalmoscopy, adaptive optics scanning laser ophthalmoscopy and/or two-photon microscopy a few times an hour, a few times a week, a few times a month, a few times a year, etc. Accordingly, such an examination can be completed 1, 2, 3, 4, 5, 6, 8, 10, 12, 16, 24 or more times a year. Such an examination may be performed more often if a user has a health problem. The system 2650 can be configured to perform confocal microscopy, a scanning laser ophthalmoscopy, adaptive optics scanning laser ophthalmoscopy and/or two-photon microscopy if the system 2650 detects that the user 2660 is having difficulties with vision or is having difficulties in focusing. The system 2650 can also be configured to be used in a doctor's office or a hospital as a confocal microscope. However, the ophthalmic system 2650 can be worn by a user 2660.

Autorefractor

In one or more embodiments, the ophthalmic device may be configured to function as an autorefractor. An autorefractor provides an objective measurement of a person's refractive error. In contrast to a phoropter which requires subjective responses from the patient, the autorefractor does not rely on responses from the user. A cycloplegic agent (e.g., eye drops) may be used to keep the ciliary muscles in a relaxed position, resulting in a loss of accommodation of the user. This relaxed position of the eye provides for a more consistent view of the retina. The patient may be asked to view an image projected inside the autorefractor device. The image may move in and out of focus across depth planes as the machine takes readings to determine when the image is on the retina. The machine may average the results to determine a prescription.

To this end, the ophthalmic device may use the FSD to provide one or more images at varying depths, and scanning, through an eye-scanning module, to capture images of the retina while the eye is focused at the images of varying depths. As was the case in previous examples, various algorithms may be used to determine when the patient properly focuses on the image, and subsequently determine an optical prescription for the user. The processor of the ophthalmic device may be used to perform a number of objective refractive examinations using visible or infrared light. In one or more embodiments, image quality analysis/contrast peak detection techniques may be used in analysis. Similarly, the Scheiner double pinhole alignment, Shack-Hartmann grid alignment and/or the retinoscopic reflex neutralization may be used as well.

Figure 26A:
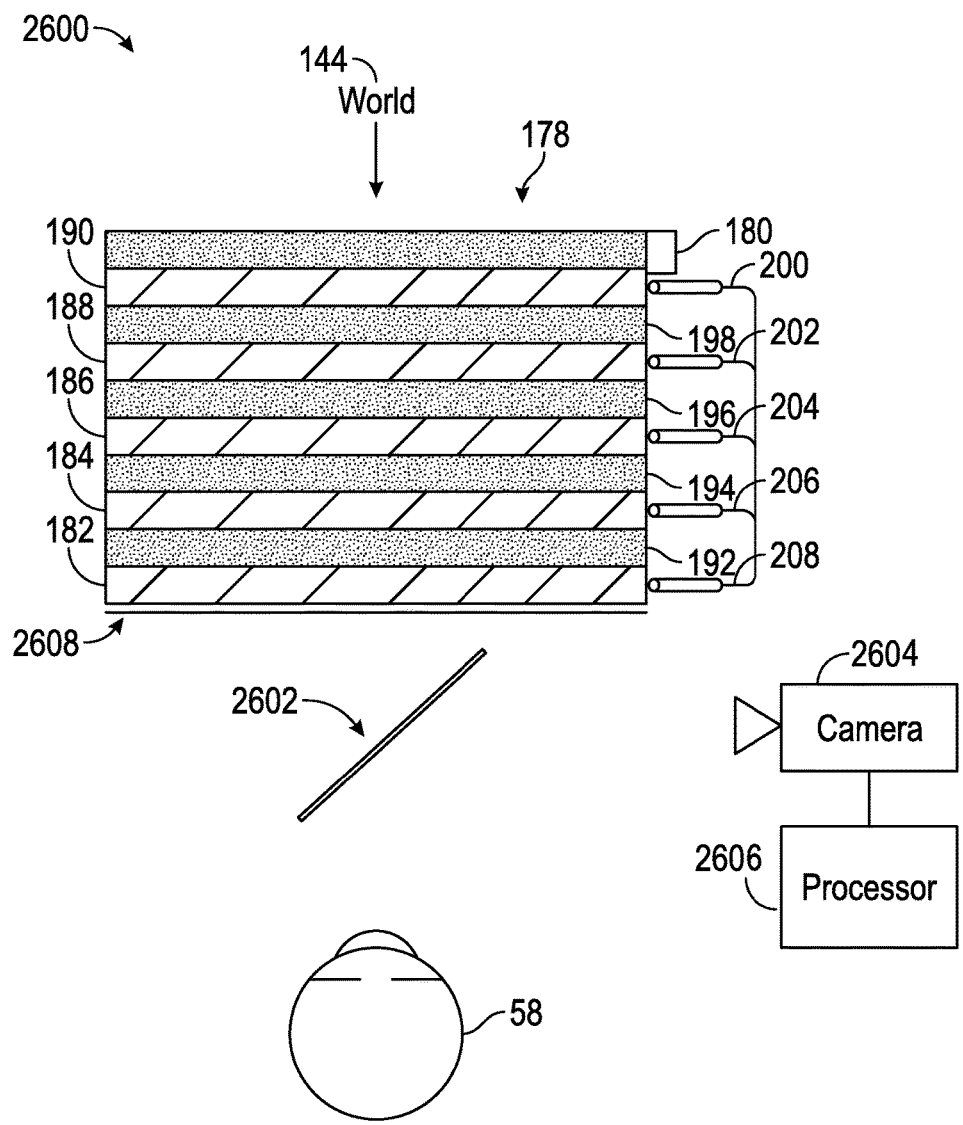

FIG. 26A illustrates an example embodiment of an augmented and/or virtual reality system 2600 configured as an autorefractor. In some embodiments, the system 2600 includes a stacked waveguide assembly 178, an adaptable optics element, such as a variable focus element (VFE) (e.g., a deformable mirror membrane whose shape is controlled by electrical signals applied to a plurality of electrodes) or an optical element that can otherwise alter its optical characteristics in a controlled manner, or any combination of the same. Examples of such are disclosed herein with respect to FIGS. 10A-10D. The system 2600 may also include a beamsplitter 2602, a camera 2604, a processor 2606, and a positive lens 2608. The system 2600 can be head-mounted so as to be aligned with a user's eye 58. Although the autorefractor system 2600 is illustrated for a single eye, it could also be a binocular autorefractor capable of testing the refraction of both eyes of a patient simultaneously. The system 2600 can also include any of the other elements or features described herein. In some cases, the additional elements which are used in autorefractor embodiments but which would not necessarily be required for other functions described herein can be provided as add-on attachments to an augmented and/or virtual reality system.

The stacked waveguide assembly 178 can be used to transmit light with varying amounts of wavefront curvature to the eye 58. For example, the stacked waveguide assembly 178 can transmit light beams to the eye 58 with different amounts of vergence, including light beams with positive vergence or negative vergence, as well as collimated beams.

The stacked waveguide assembly 178 can include multiple waveguides (182, 184, 186, 188, 190) and multiple lenses (192, 194, 196, 198). In some embodiments, the lenses (192, 194, 196, 198) are negative lenses. As shown in FIG. 26A, the waveguides and negative lenses can be arranged in an alternating stacked configuration. The stacked waveguide assembly 178 also includes a plurality of light sources (200, 202, 204, 206, 208). As discussed herein, these light sources can be fiber scanning displays, though other light sources can also be used. Each respective light source can inject light into a corresponding waveguide (182, 184, 186, 188, 190), which distributes the light substantially equally across its length and redirects the light toward the eye 58. In some embodiments, the light sources (200, 202, 204, 206, 208) can inject collimated light into the respective waveguides (182, 184, 186, 188, 190) and each of the waveguides can output collimated beams of light at a range of different output angles. The light provided by the light sources (200, 202, 204, 206, 208) can be in the visible or infrared spectrum.

Figure 26B:
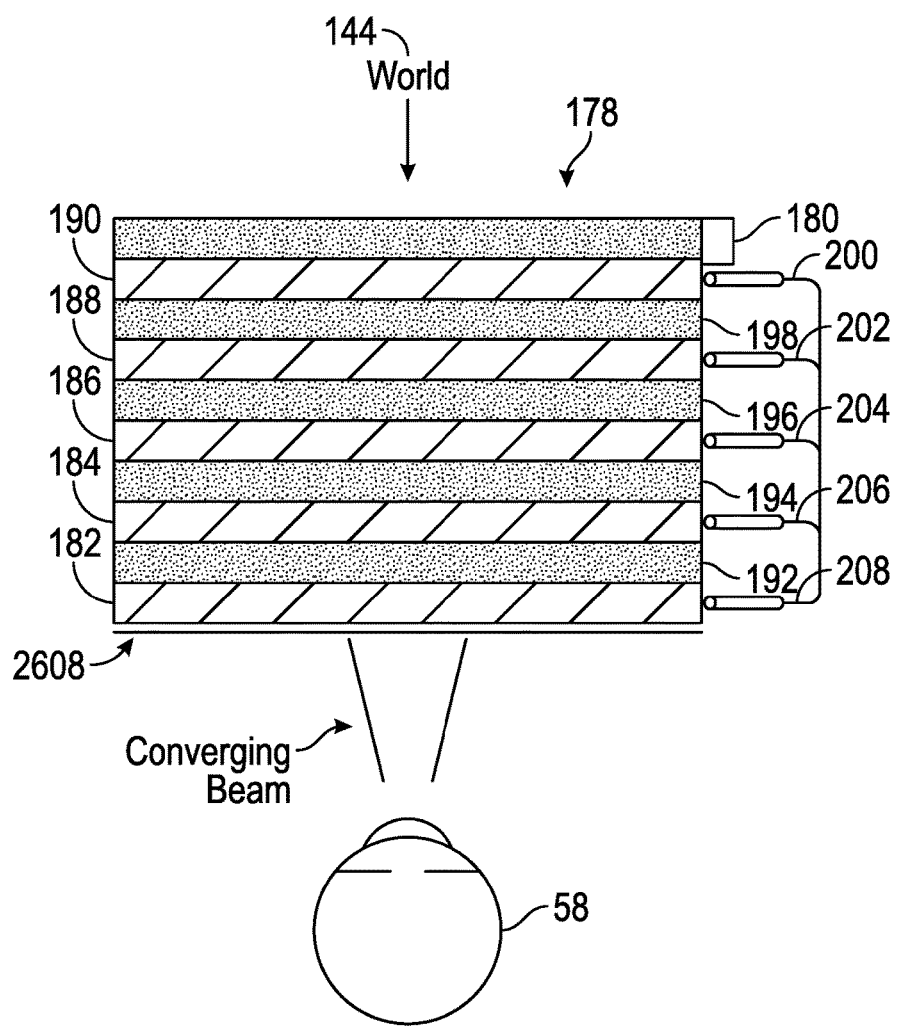

In some embodiments, the first waveguide 182 nearest the eye 58 may be used to deliver light beams with positive vergence to the eye. This may be accomplished by, for example, providing a positive lens 2608 between the first waveguide 182 and the eye 58. The positive lens 2608 can impart a degree of positive vergence to all of the light beams which pass through it. FIG. 26B illustrates an example of a light beam with positive vergence being transmitted to the eye 58. As just discussed, this positive vergence beam can result from light originating at the first waveguide 182.

The remaining waveguides (184, 186, 188, 190) may deliver light beams to the eye 58 with different amounts of vergence. For example, the second waveguide 184 in the stack can be used to provide light beams with a lesser degree of positive vergence than the first waveguide 182 in the stack. This can be accomplished, for example, by transmitting light from the second waveguide 184 through a negative lens 192. The negative lens 192 imparts a degree of negative vergence to the beams of light which pass through it, thus causing such beams to have relatively less positive vergence when compared to those which are output from the first waveguide 182 in the stack.

Figure 26D:
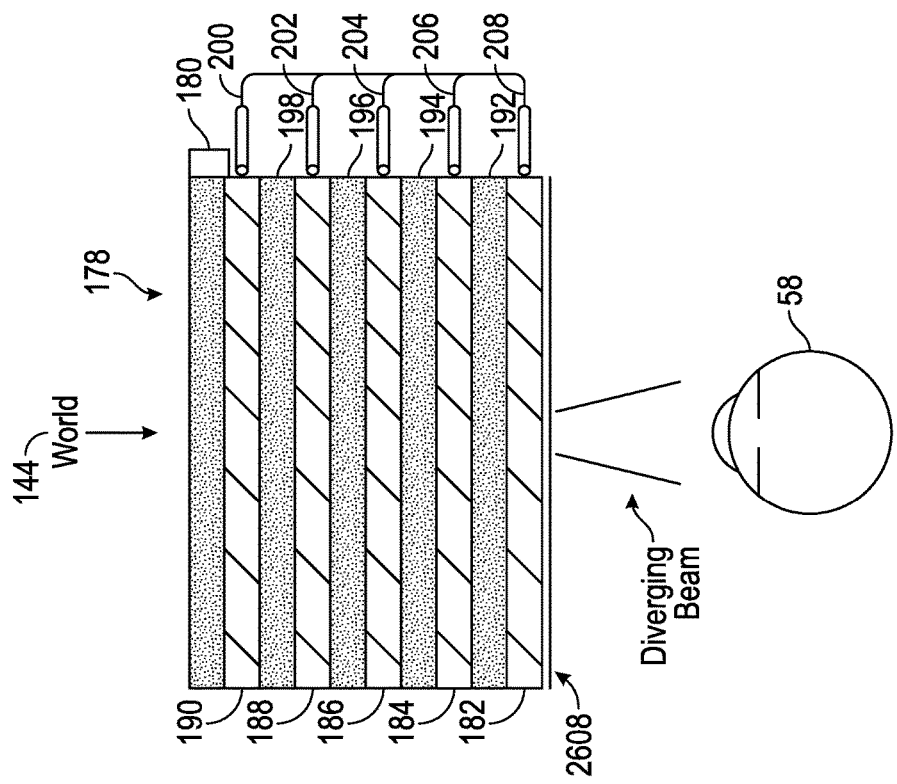
Figure 26C:
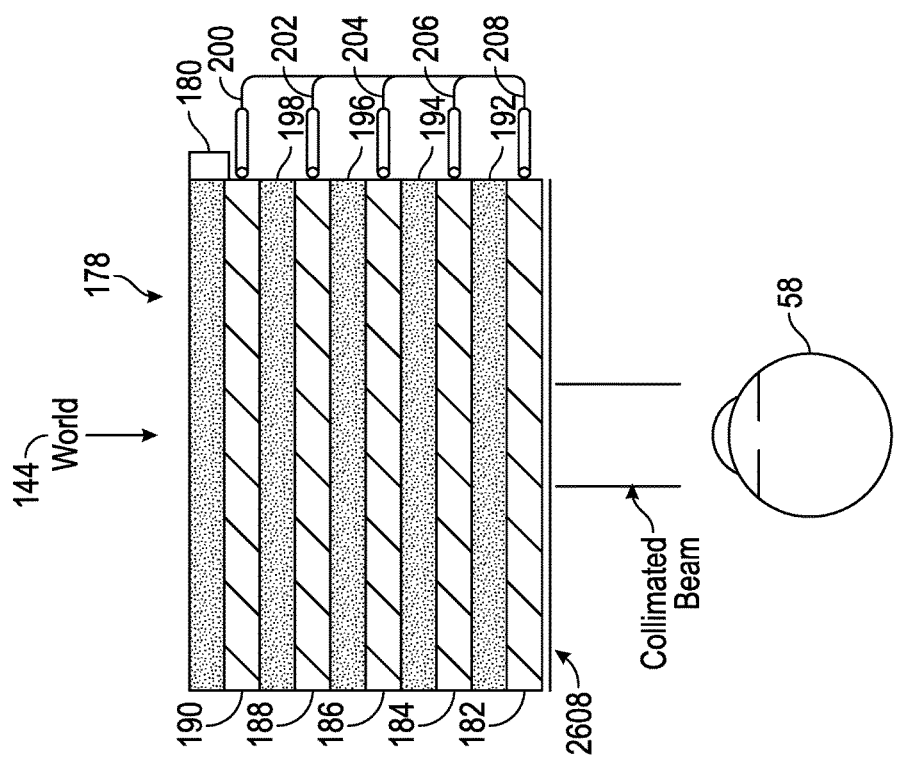

In a similar fashion, the third waveguide 186 in the stack can be used to provide light beams with a lesser degree of positive vergence than those which are output from the second waveguide 184 in the stack. For example, the third waveguide 186 can be used to provide collimated light beams with zero vergence to the eye 58. This can be accomplished by transmitting light from the third waveguide 186 through both the first negative lens 192 and an additional negative lens 194. Each of these negative lenses (192, 194) impart a degree of negative vergence to the beams of light which pass through them, thus causing them to have relatively less positive vergence when compared to those which are output from the first or second waveguides (182, 184) in the stack. FIG. 26C illustrates an example of a collimated light beam with zero vergence being transmitted to the eye 58. As just discussed, this collimated beam can result from light originating at the third waveguide 186.

The fourth waveguide 188 in the stack can be used to provide light beams to the eye 58 with an even lesser degree of positive vergence than those which originate from the first, second, and third waveguides (182, 184, 186) in the stack. For example, the fourth waveguide 188 can be used to provide light beams with a degree of negative vergence to the eye 58. This can be accomplished due to the fact that beams of light which exit from the fourth waveguide 188 travel through one additional negative lens 196 as compared to beams of light which are output from the preceding waveguides in the stack.

Finally, the fifth waveguide 190 in the stack can be used to provide light beams with an even greater degree of negative vergence as compared to those which originate from the fourth waveguide 188. Once again, this can be accomplished by transmitting light beams which are output from the fifth waveguide 190 through yet another negative lens 198 along the optical path to the eye 58. FIG. 26D illustrates an example of a light beam with negative vergence being transmitted to the eye 58. As just discussed, this negative vergence beam can result from light originating at the fifth waveguide 190.

The stacked waveguide assembly 178 can also include a compensating lens layer 180. This lens layer can compensate for the cumulative effect of the negative lenses (192, 194, 196, 198) when the user is viewing light from the outside world 144 on the other side of the stacked waveguide assembly 178. The compensating lens layer 180 can also be designed to compensate for the positive lens 2608 provided between the stacked waveguide assembly 178 and the user's eye 58 (if such a positive lens is present).

As just described, the waveguides in the stacked waveguide assembly 178 can be used to controllably provide beams of light to the eye 58 with a range of different vergences, from beams with positive vergence to collimated beams to beams with negative vergence. Although the embodiment has been described from the perspective that the output beam with the greatest degree of positive vergence originates from the first waveguide 182 while the output beam with the greatest degree of negative vergence originates from the last waveguide 190, this could be reversed by appropriate selection of the lenses (192, 194, 196, 198, 180, 2608). Furthermore, it is not necessarily required that the system be capable of outputting beams with positive vergence, negative divergence, and zero vergence; some systems may only output beams having a subset of these possible vergences. Finally, although the illustrated stacked waveguide assembly 178 includes five waveguides, other embodiments can include additional waveguides in order to provide light beams with a greater range of vergences and/or finer steps between the available vergences. Alternatively, other embodiments could include fewer waveguides in order to simplify the device, reduce cost, etc.

With reference back to FIG. 26A, the beams of light which are output from the stacked waveguide assembly 178 propagate toward the user's eye along the visual axis. In the illustrated embodiment, these beams are transmitted through a beamsplitter 2602 which is provided between the stacked waveguide assembly 178 and the eye 58. The beamsplitter 2602 is aligned with the visual axis of the eye 58 and allows the camera 2604 to view the eye 58. Although the beamsplitter 2602 is illustrated as being located between the stacked waveguide assembly 178 and the eye 58, it could alternatively be located on the opposite side of the stacked waveguide assembly 178 from the eye 58, and the camera 2604 could view the eye 58 through the stacked waveguide assembly 178.

As already discussed, the autorefractor system 2600 can provide imagery to the eye 58 using beams of light with varying degrees of vergence. As this imagery is provided to the eye 58, the camera 2604 can be used to monitor the retina of the eye 58. The camera 2604 can provide retinal images to the processor 2606. The processor 2606 can then perform image processing algorithms on the retinal images to determine when the imagery projected by the autorefractor system 2600 is best focused on the retina of the eye 58. Such image processing algorithms can include, for example, contrast peak detection. (Imagery projected on the retina of the eye 58 will generally have relatively low contrast when the imagery is blurred and peak contrast when the imagery is sharply focused by the eye 58.) The processor 2606 can calculate the refractive power of the eye 58 based on the degree of vergence (whether positive, collimated, or negative) required to allow the eye 58 to focus light on the retina. The processor 2606 can determine image quality in multiple meridians in order to calculate not only spherical power of the eye but also cylindrical power and axis.

The processor 2606 can control the operation of the autorefractor system 2600. In one example embodiment, the control method can include causing one or more of the light sources (200, 202, 204, 206, 208) to project an image toward the eye 58 using beams of light having a first vergence value (whether positive, collimated, or negative). The processor 2606 can then capture an image of the retina of the eye 58 using the camera 2604. The processor 2606 can analyze the captured retinal image to determine a metric of the quality of the image formed on the retina when using beams of light having the first vergence value.

The processor 2606 can then cause one or more of the light sources to project the image toward the eye 58 using beams of light having a second vergence value that is different from the first vergence value. The processor 2606 can then once again capture an image of the retina of the eye 58 using the camera 2604 and analyze the retinal image to determine a metric of the quality of the image formed on the retina when using beams of light having the second vergence value. The processor 2606 can then compare the first image quality metric with the second image quality metric. Based on this comparison, the processor 2606 can select a third vergence value to use when projecting the image toward the eye 58 using any of a variety of optimization algorithms. The processor 2606 can then calculate a third image quality metric indicative of the quality of the image formed on the retina when using beams of light having the third vergence value. This process can be performed iteratively until the image quality metric is maximized or otherwise determined to be sufficient. Finally, the processor 2606 can compute the refractive power of the eye 58 based on the vergence value corresponding to this image quality metric. In addition, the processor 2606 can initiate execution of the phoropter method described herein if the autorefractor system 2600 identifies refractive error(s) above a threshold. The phoropter system can be used as check on the accuracy of the measurements by the autorefractor system 2600, or vice versa. In this way, the autorefractor system 2600 and the phoropter system described herein can be used jointly to characterize a patient's vision.

FIG. 26E illustrates another example embodiment of an augmented and/or virtual reality system 2650 configured as an autorefractor. The autorefractor system 2650 can include all of the features of the autorefractor system 2600 illustrated in FIG. 26A (though the beamsplitter 2602, the camera 2604, and the processor 2606 are not shown for clarity). In addition, the autorefractor system 2650 illustrated in FIG. 26E can include a Scheiner's pinhole disc 2660 located along the optical path of the system before the eye 58. The Scheiner's disc 2660 can be located, for example, between the stacked waveguide assembly 178 and the beamsplitter 2602. This is an opaque disc with two or more small apertures. As illustrated in FIG. 26E, when a collimated beam of light is incident upon the Scheiner's disc 2660, the beam is blocked from being transmitted to the eye except for rays of light which are able to pass through the two apertures. In the case of an emmetropic eye, the rays of light transmitted through each of the two apertures are focused to a common spot on the retina of the eye 58. Thus, a retinal image taken by the camera 2604 would reveal a single spot.

Figure 26G:
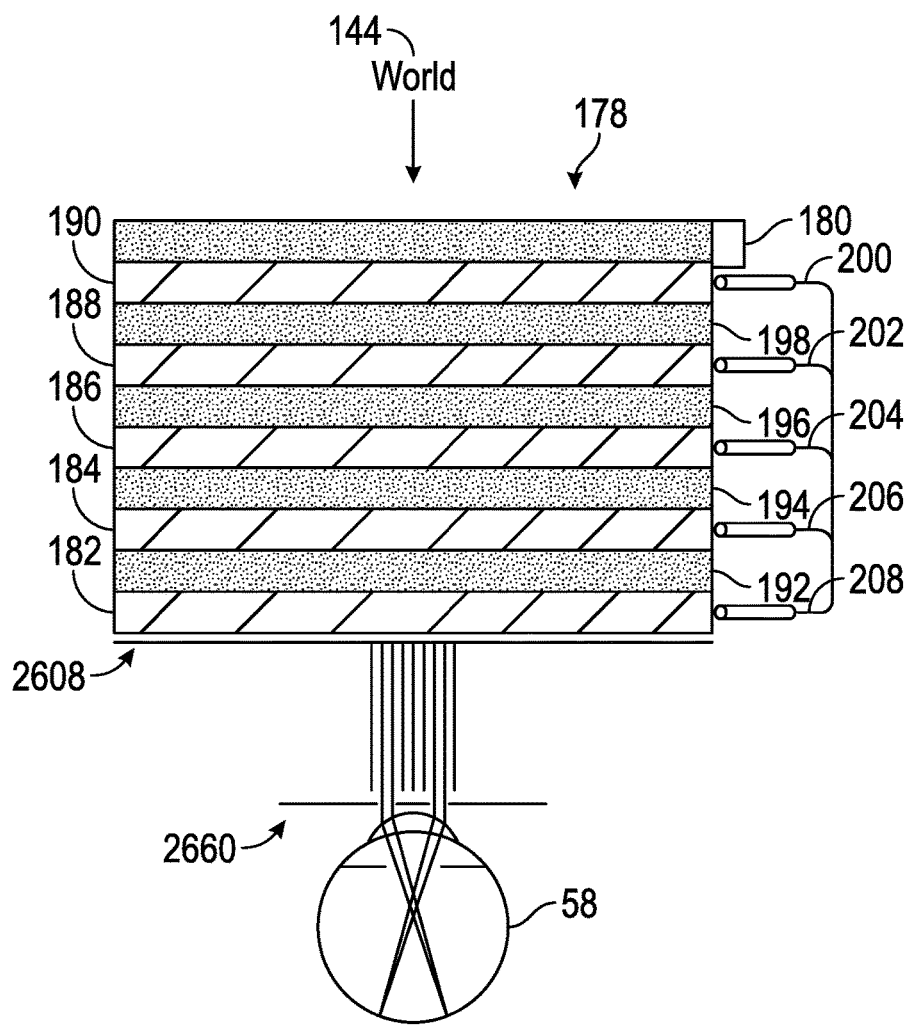

While FIG. 26E illustrates the effect on an emmetropic eye of a collimated beam passing through a Scheiner's disc 2660, FIGS. 26F and 26G respectively show the same effect on a hyperopic eye and on a myopic eye. As seen in FIG. 26F, the optical power of the hyperopic eye is not strong enough to focus the rays of light transmitted through the two apertures of the Scheiner's disc 2660 to a single spot. Thus, a retinal image taken by the camera 2604 would reveal two distinct spots in the case of a collimated beam illuminating a Scheiner's disc in front of a hyperopic eye. As seen in FIG. 26G, the optical power of the myopic eye is too strong, which results in the rays of light transmitted through the two apertures of the Scheiner's disc 2660 being focused in front of the retina. This, too, results in two distinct spots being formed on the retina.

The autorefractor system 2650 can therefore vary the vergence of the beam of light which is incident upon the Scheiner's disc until a single spot is formed on the retina of the eye. The refractive power of the eye 58 can be calculated based on the beam vergence required to form a single spot on the retina.

The processor 2606 can control the operation of the autorefractor system 2650. In one example embodiment, the control method can include causing one or more of the light sources (200, 202, 204, 206, 208) to project a beam of light having a first vergence value (whether positive, collimated, or negative) onto the Scheiner's disc 2660. The processor 2606 can then capture an image of the retina of the eye 58 using the camera 2604. The processor 2606 can analyze the retinal image to determine the number of spots which are evident. If only a single spot is evident, the processor 2606 can calculate the refractive power of the eye 58 based on the first vergence value. Alternatively, if multiple spots are evident, the processor 2606 can select a second vergence value that is different from the first vergence value. The processor 2606 can then cause a beam of light having the second vergence value to be projected onto the Scheiner's disc 2660. The processor 2606 can once again capture an image of the retina of the eye 58 using the camera 2604 and analyze the retinal image to determine the number of spots which are evident. If a single spot is evident, the processor 2606 can calculate the refractive power of the eye 58 based on the second vergence value. Otherwise, the third vergence value can be selected and the process can be iteratively repeated until a single spot is formed on the retina. The processor 2606 can then compute the refractive power of the eye 58 based on that vergence value.

Any of the autorefractor or other diagnostic methods described herein can be used for real-time adjustments while the user is watching content to ensure the content is focused.

In addition, monitoring of the user's refractive error can be performed on a long term basis (e.g., weeks, months, or years) to provide longitudinal monitoring and analysis of the user's refractive error. The frequency of regularly-scheduled tests may be automatically adjusted based on trending of the test results or when the system detects that the user is have difficulties with vision.

OCT

Figure 23A:
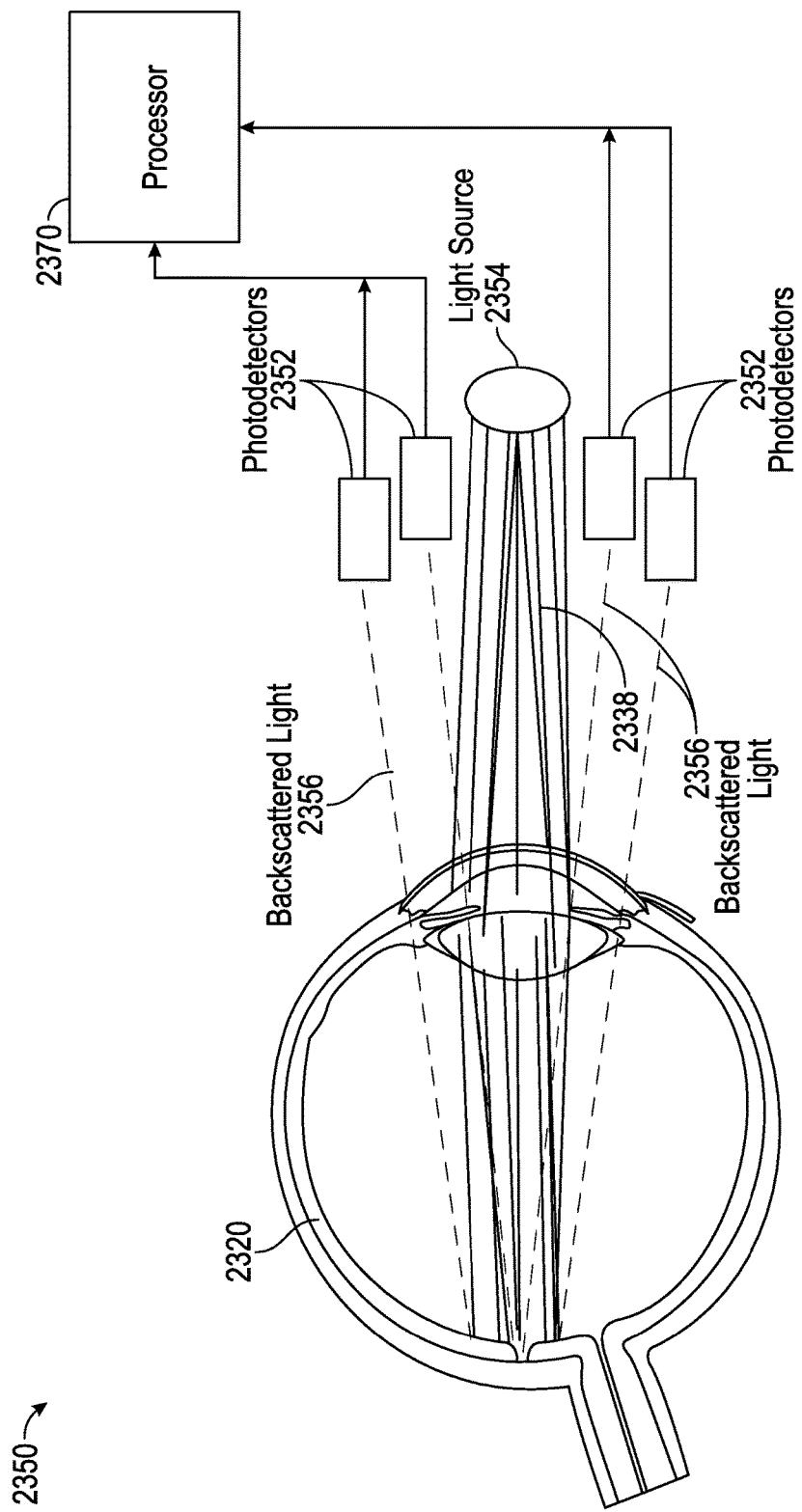
FIG. 23A schematically illustrates a set-up to perform optical coherence tomography (OCT) examination.
Figures 1, 23A:
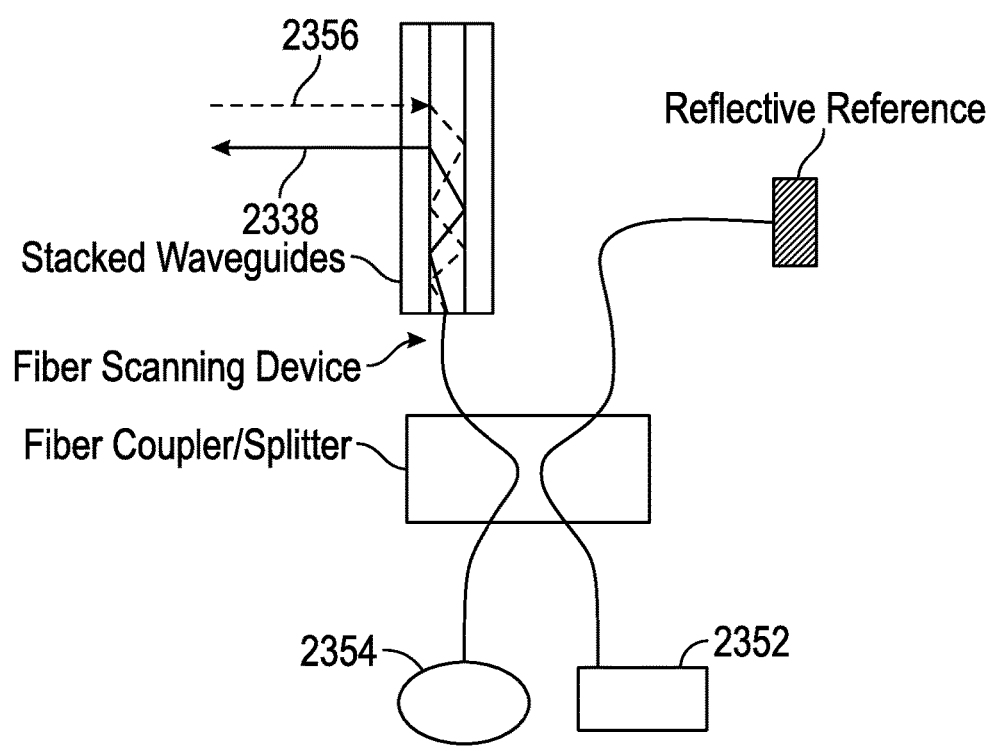
Figure 23B:
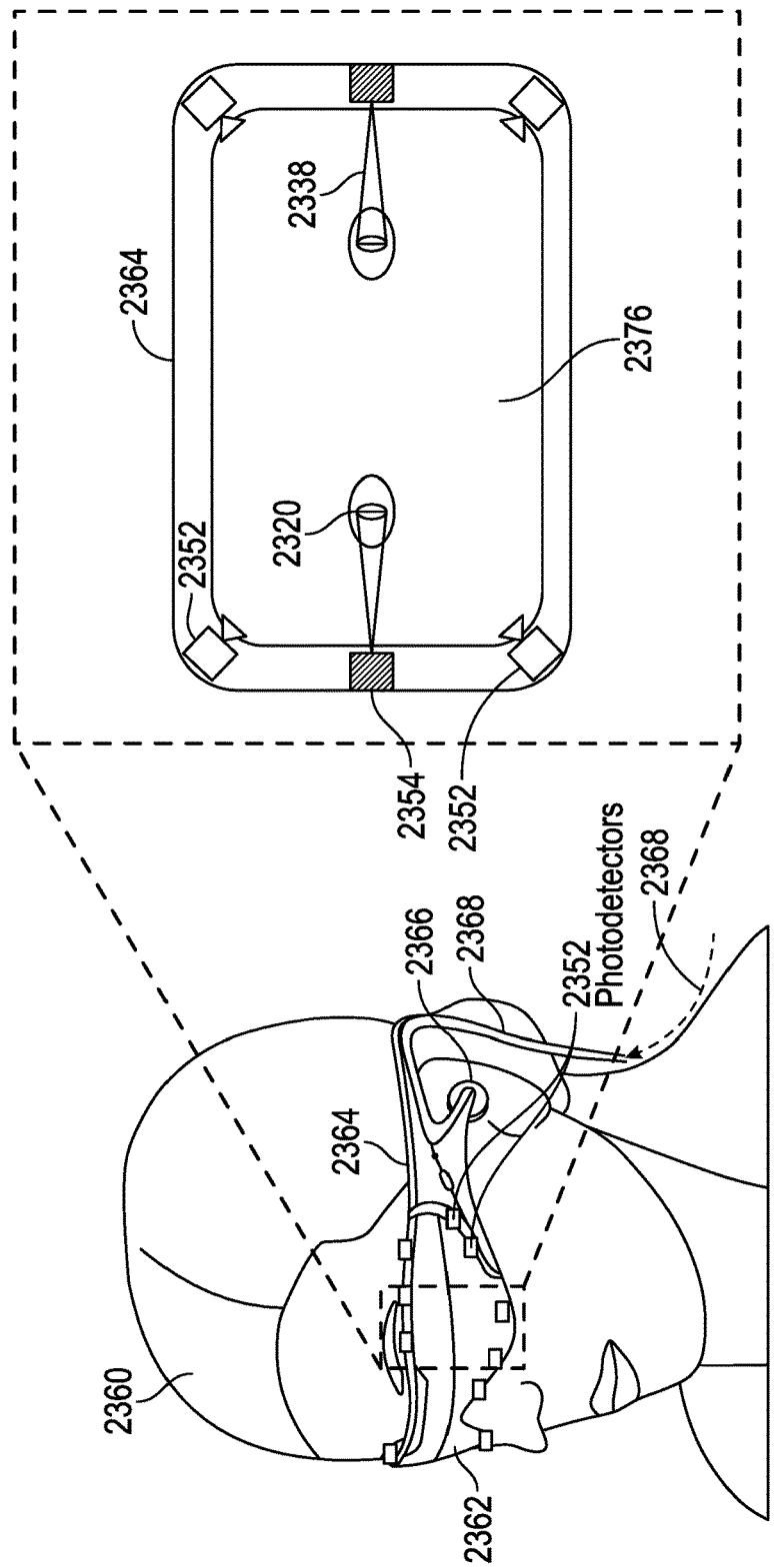
FIG. 23B schematically illustrates an augmented reality/virtual reality eyewear comprising a plurality of photodetectors configured to receive light reflected/back-scattered from the eye.

Various embodiments of the augmented reality/virtual reality wearable device that can be worn by a user as described herein can be configured to function as an optical coherence tomography (OCT) system. FIGS. 23A and 23B schematically depict a wearable device 2350 that can be configured to function as an OCT system. The device 2350 includes a frame 2364 attached to a display system 2362. The display system 2362 can be configured to be positioned forward of the eyes 2320 of the user 2360. The device 2350 can be configured to project a beam of light 2338 from a light source 2354 into the eyes 2320 of the user 2360. A portion of the projected beam 2338 can be reflected, scattered and/or diffracted by various anatomical features of the eyes 2320 of the user 2360 as light rays 2356 and received by one or more imaging devices 2352. An electronic hardware processor 2370 can be used to analyze light received from the eyes 2320 of the user 2360 to examine the various structures of the user's eye 2320.

In various embodiments of the wearable device 2350, the frame 2364 can have characteristics similar to the frame 64 of FIGS. 3A-3C. In various embodiments of the wearable device 2350, the display system 2362 can have characteristics similar to the display system 62 of FIGS. 3A-3C and FIG. 5. In various embodiments of the device 2350, the electronic hardware processor 2370 can be similar to the local processing and data module 70 of FIGS. 3A-3C.

The display system 2362 of various embodiments of the ophthalmic system 2350 can comprise a display lens 2376 mounted in the frame 2364. In some embodiments, the display lens 2376 can be a unitary lens comprising two ocular zones, each ocular zone positioned in front of the user's eyes 2320. In some embodiments, the display system 2362 can comprise two display lenses mounted in the frame 2364, each display lens comprising an ocular zone that is positioned in the front of each of the user's eyes 2320.

The optical source 2354 can comprise one or more LEDs, one or more flashlamps, one or more superluminescent diodes and/or possibly one or more lasers. In various embodiments the light source is an incoherent light source. In some embodiments, the optical source 2354 can be a part of the illuminating system of the device 2350 that is configured to provide illumination to the display lens 2376 and/or to the eyes 2320 of the user 2360. In some such embodiments, the beam 2338 can be projected from the display lens 2376 into the eye 2320 of the user 2360. For example, the optical source 2354 can comprise a fiber scanning device (FSD) and the display lens can comprise a plurality of waveguides having characteristics similar to the waveguide stack 178 described above with reference to FIG. 10D. Light from the FSD can be injected into one or more of the plurality of waveguides and emitted from the one or more of the plurality of waveguides into the eye 2320 of the user to perform OCT functions. The plurality of waveguides of the display lens can be coupled with adaptive focusing elements that can change characteristics of the wavefront emitted from the plurality of waveguides.

In some embodiments, the optical source 2354 can be an auxiliary optical source disposed on a side of the display system 2362. In such embodiments, the wearable device 2350 can include optical components, such as, for example, lenses or other refractive components, reflective surfaces, deflectors, reflectors, beam splitters, diffractive optical elements, waveguides, or other optical components, etc. to direct the beam 2338 towards the wearer's eye 2320. For example, the optical source 2354 can comprise an additional FSD and the display lens can comprise an additional stack of waveguides. Light from the additional FSD can be injected into one or more waveguides of the additional stack of waveguides and emitted from the one or more waveguides of the additional stack of waveguides into the eye 2320 of the user to perform OCT functions. The waveguides in the additional stack of waveguides can be coupled with adaptive focusing elements that can change characteristics of the wavefront emitted from the additional stack of waveguides. As discussed in detail below, the beam 2338 from the optical source 2354 can be incident on a desired region of the wearer's eye 2320. The beam 2338 can be scanned along x-, y- and z-directions across the desired region of the wearer's eye 2320 to two/three-dimensional images of the desired region.

The wearable device 2350 configured as an OCT system can include an interferometer and can obtain sub-surface images of translucent or opaque materials (e.g., various structures in the user's eye 2320, various ophthalmic tissue in the user's eye 2320) at a resolution equivalent to a low-power microscope. The system can be configured to use light imaging reflections from within the tissue to provide cross-sectional images to produce micrometer resolution 3D images. In various embodiments, light from the optical source 2354 can generate the projection optical beam 2338 that is directed at the tissue, and a reference beam that is directed towards a reflective reference such as a mirror or reflective element. A small portion of this light that reflects from the sub-surface features of the tissue to which the projection optical beam 2338 is directed as light rays 2356 is collected and interfered with light reflected from the reflective reference. Interferometry techniques may be used to record the optical path length of received photons, thereby allowing rejection of most photons that scatter multiple times before detection.

In various embodiments, a beam splitter can be disposed in the optical path of light emitted from the optical source 2354 to generate the projection beam 2338 and the reference beam. As shown in FIG. 23A-1, in embodiments of the device 2350 in which the optical source 2354 comprises a FSD, a fiber splitter/coupler can be used to generate the projection beam 2338 and the reference beam and to combine light scattered or back reflected from the various structures in the eye 2320 and the reflected reference beam. In various embodiments, the reflective reference can be a movable reflector. FIG. 23A-1 also shows a light guide with turning features in a wave guide stack that may be used to direct the OCT light beam to the eye and to receive light returned therefrom. This waveguide guide may be included in a waveguide stack such as the waveguide stack configured to project images to the eye as described herein. The inset shows the fiber coupler used to couple light into the reference arm and reflect from the movable reference reflector (e.g. movable mirror) as well as the detector that receives both the light reflected from the reference reflector as well as the light returned (e.g., reflected or backscattered, etc.) from the eye.

As discussed above, in some embodiments an incoherent light source such as an LED (e.g., superluminescent LED) may be used. Such a light source provides the interferometer with a reduced coherence length. As a result, the OCT instrument has a short depth of focus or region from which light is collected to image. This region can be scanned in the longitudinal direction (z), along the direction of the beam, to produce what is referred to as an A scan. Additionally, a small spot size of the beam that is incident on the eye may provide for reduced lateral resolution. Again the beam can be scanned orthogonal to the longitudinal direction, in the lateral directions (x and y), to generate B and C scan and thus create 2D and 3D images showing the tissue and structure of the eye.

The region can be scanned in the longitudinal direction (z direction) by changing the position of the reflective reference, the wavelength of the projection beam 2338 and/or the reference beam or the angle between the projection beam 2338 and the reference beam, which changes the optical path length difference between the projection beam 2338 and the reference beam. Varying the optical path length difference between the projection beam 2338 and the reference beam can advantageously allow the device 2350 configured as an OCT system to build clear 3D images of thick samples by rejecting background signal while collecting light directly reflected from surfaces of interest.

In one or more embodiments of the device 2350, the optical source 2354 can comprise a FSD that can serve as a 3D scanning head configured not only to project light beams but also to receive light beams 2356 backscattered from the eye. In one or more embodiments light beams of varying wavelengths (i.e., other than visible light spectrum) may be projected (e.g., through FSD or other optical sources) to provide additional 3D resolution. The OCT system may comprise a time-domain or frequency domain OCT. In various embodiments, the device 2350 can be configured as a Spectral (Fourier) Domain OCT which can simultaneously receive and measure reflected/backscattered light from the eye comprising a plurality of wavelengths in a spectral range.

In various embodiments, the optical source 2354 can comprise a scanning laser device that outputs an illumination beam having a spot size between about 1 micron and about 1.0 mm. For example, the illumination beam can have a spot size between about 1-3 microns, between about 2-10 microns, between about 5-25 microns, between about 10-30 microns, between about 20-100 microns, between about 50-200 microns, between about 75-250 microns, between about 100-300 microns, between about 225-500 microns, between about 375-600 microns, between about 500-750 microns, between about 650-850 microns, between about 725 microns-1 mm, or any values in these ranges or sub-ranges. The scanning laser device can be configured to scan across a desired area of the eye in a desired scan pattern. The scanning laser device can be configured to scan at a speed between about 1 kHz and about 5 MHz to generate the desired scan pattern. Accordingly, the desired scan pattern generated at the desired area of the eye can be considered to comprise a plurality of pixels that are illuminated serially (e.g., one at a time) over the scan period. In some such embodiments, the one or more imaging device 2352 can include a photodetector that is configured to receive back scattered or back reflected light from each of the plurality of pixels. The intensity of the light received by the photodetector can be correlated to the scan angle and/or position of the illumination beam to generate a two-dimensional image of the desired area.

The light projected from the optical source 2354 can be focused at different focal distances in the wearer's eye 2320. For example, the focus of the projected light can coincide with the cornea, the iris, the natural lens, the vitreous or the retina. In various embodiments, one or more adaptable optical elements or variable focusing elements (VFEs) can be optionally used to change the angle of incidence of the light projected from the optical source 2354 and/or the focal plane at which the light projected from the optical source 2354 is focused or appears to originate, as discussed above with reference to FIGS. 10B, 10C and 10D. For example, light output from the optical source 2354 can be modified using optical systems comprising lenses, prisms and/or mirrors (e.g., optical element 1024 of FIG. 10C) such that the depth at which the beam 2338 is focused in the eye and/or the direction of the beam 2338 on the eye 2320 of the user 2360 can be varied.

In various embodiments, the VFEs can include deformable mirror devices. For example, the VFEs can comprise one or more electrodes coupled to a membrane mirror. A control system can be configured to selectively control the one or more electrodes to modify a shape of the membrane mirror. Accordingly, the wavefront of the light emitted from the stacked waveguide assembly can be modified by the modifying the shape of the membrane mirror. Embodiments of the wearable device 2650 that do not include an optical source comprising a scanning laser device or a fiber scanning device can include deformable mirror devices to steer the beam and/or to vary the depth at which the beam is focused within the user's eye. In various embodiments, the VFE's can comprise deformable lenses. The deformable lenses can comprise an elastomeric material that can be deformed by application of electrostatic energy to create lenses or lenticular surfaces with different curvatures. In some embodiments, the VFE's can comprise lenses that can be deformed with activation of electrodes. Some lenses can vary refractive index with application of voltage to electrodes (e.g., liquid crystal lenses). In various embodiments, the device 2350 can comprise spatial light modulators that modulate the phase. Embodiments of the wearable device 2650 that include an optical source comprising a scanning laser device or a fiber scanning device can include deformable lenses and/or spatial light modulators that modulate phase to steer the beam and/or to vary the depth at which the beam is focused within the user's eye.

In various embodiments, the optical source 2354 can be configured to generate a white light or a colored light comprising a range of wavelengths of the visible spectral region. For example, the optical source 2354 can generate a light of any color having wavelengths in the range between about 440 nm and about 510 nm; between about 460 nm and about 550 nm; between about 490 nm and about 560 nm; between about 530 nm and about 610 nm; between about 550 nm and about 620 nm; or a value in any of these ranges or sub-ranges.

In some embodiments, the optical source 2354 can be configured to generate an infrared light comprising one or more wavelengths in a range of wavelengths in the infrared spectrum of light. For example, the projection beam 2338 can comprise one or more wavelengths in the near infrared spectrum of light; in the mid infrared spectrum of light and/or in the far infrared spectrum of light. As another example, the projection beam 2338 can comprise one or more wavelengths between about 700 nm and about 1.5 μm; between about 1.0 μm and about 2.3 μm; between about 1.8 μm and about 3.2 μm; between about 2.4 μm and about 5.8 μm; between about 3.2 μm and about 7.0 μm; and/or between about 6.0 μm and about 13.0 μm.

The penetration depth of the projection beam 2338 in the eye 2320 of the wearer 2360 can depend on the wavelengths included in the projection beam 2338. Additionally, the optical path length difference between the projection beam 2338 and the reference beam can also depend on the wavelength. Accordingly, varying the wavelengths included in the projection beam 2338 can advantageously allow imaging of structure and anatomical features at different depths in the eye 2320 of the user 2360.

The device 2350 can be configured to image the retina and/or various retinal layers by varying the depth of the projection beam 2338. A measurement of the thickness of the retina and/or various retinal layers can be obtained from these images. The measurements of the thickness of the retina and/or various retinal layers can be used for posterior pole asymmetry analysis (PPAA) that maps retinal thickness across the posterior pole and graphs asymmetry both between hemispheres and between the eyes. Accordingly, the device 2350 can be used to compare thickness of the retina and/or various retinal layers of one of the user's eye 2320 with thickness of the retina and/or various retinal layers for an average healthy eye and/or with thickness of the retina and/or various retinal layers for another of the user's eye 2320.

The device 2350 can be configured to image the macula of the wearer's eye 2320. The macula images can be useful to measure thickness of the macula as discussed above. The macula images can also be useful to determine swelling of the macula. This can be advantageous in early detection of glaucoma—which causes structural changes in the macula before functional changes. For example, glaucoma can cause loss of retinal ganglion cells, changes in the inner plexiform layer, thinning of certain retinal layers, etc. These structural changes can be determined from the images of the retina and/or macula.

The device 2350 can be configured to image the lens of the wearer 2360 so as to determine accommodation state based on the shape of the front and back surface and/or thickness of the lens and/or measure refractive error. For example, the wearer 2360 can be made to focus on targets at different depths by projecting the beam 2338 from different depth planes. The changes in the accommodation state of the lens as well as the size and acuity of the images formed on the retina and/or seen by the wearer 2360 can be imaged to determine refractive errors. Such measurements can be useful in performing phoropter tests, monitoring refractive state of the eye or assisting in performing tests that can correct refractive errors.

Various embodiments of the one or more imaging devices 2352 can include one or more wavelength filters configured such that the imaging devices 2352 can selectively receive light at one or more desired wavelength ranges from the eye 2320 of the wearer 2260 while attenuating or filtering out other wavelengths. For example, the imaging devices 2352 can include one or more wavelength filters configured such that the imaging devices 2352 can selectively receive light in visible spectral range, near infrared spectral range, mid infrared spectral range and/or far infrared spectral ranges. As another example, the imaging devices 2352 can include one or more wavelength filters configured such that the imaging devices 2352 can selectively receive light between about 440 nm and about 12.0 ⌈m; between about 500 nm and about 10.0 ⌐m; between about 550 nm and about 8.5 ⌐m; between about 600 nm and about 5.0 ⌊m; between about 650 nm and about 3.0 ⌊m; between about 1.0 ⌐m and about 2.5 ⌐m or any values in the above-identified ranges and sub-ranges while attenuating or filtering out wavelengths outside of the selected range.

The information and/or images captured by the one or more imaging devices 2352 may be processed in real-time or later. In various embodiments, the device 2350 can include optical sources and detectors that track the movement of the eye. The optical sources and detectors that track the movement of the eye can have characteristics similar to the source 26 and cameras 24 described with reference to FIG. 5. The eye tracking optical sources and detectors may be used to cancel out any effects of eye movement. The wearable device 2350 configured as an OCT system may be used to provide a superior in-vivo-wide-field micro-angiography imaging device, in one or more embodiments.

The wearable device 2350 configured as an OCT system, may be used to visualize retinal topography, deep fundus imaging (i.e., detecting lesions), retinal pigment epithelium (RPE) changes and other age related macular degeneration, visualize retinal vasculature, visualize blood flow in the fundus of the eye, visualize shape and structure of blood vessels in the fundus of the eye, etc. The wearable device 2350 may also be used to provide a multi-spectral image comparison, which can be advantageous in improving visual discrimination of retinal and sub-retinal features through spectral and depth enhanced differential visibility.

For example, the device 2350 can be configured to perform OCT angiography. Accordingly, the device 2350 can be used to visualize blood flow in the retina and/or choroid capillary network. Visualizing blood flow in the retina and/or choroid capillary network can be advantageous in detecting growth of abnormal blood vessels by using the motion of blood as contrast. Visualizing blood flow in the retina and/or choroid capillary network using OCT angiography techniques can image multiple levels of vascular tree in the retina, such as, for example, radial peripapillary capillary level, superficial level and deep plexus level without using fluorescent dyes. The device 2350 can also be used perform multicolor analysis of the retina and/or segmentation of the retinal layers.

As discussed above, the wearable device 2350 may be configured to not only project light associated with visible light (usually done through RGB sources), but may also be configured with other multi-spectral components (e.g., laser sources, infrared sources, LED light etc.) to emit light having a range of wavelengths and spectral compositions. Or, in other embodiments, tunable lasers may be used (e.g., cavity length may change in the laser or diffractive gratings may be modified) that are capable of changing the wavelength of light over time, on a frame-sequential basis, line-sequential basis, pixel by pixel basis, etc.

Multi-spectral light emission may be advantageous for imaging purposes because different parts of the eye may react better to other colors or spectra of light, leading to more accurate imaging techniques. Thus, the wearable device 2350 configured as an OCT system may comprise additional components that enable emission of multi-spectral light. For example, the device 2350 can be configured to perform spectral (Fourier) domain OCT.

In one or more embodiments, the wearable device 2350 may transmit light of different wavelengths from multiple angles to penetrate the soft tissue at the back of the eye. The wearable device 2350 may comprise optical sources that can provide laser tomography, as well as white light tomography. Similarly, ERG (Electroretinography) or EOG (Electrooculography), gaze tracking and computational capabilities may advantageously allow the wearable device 2350 to collect, de-noise and process light returning from the retinal tissue with precision. If for example ERG or gaze tracking detect movement of the eye during measurement, the system may discard or filter the data or process the data differently. Such processing could be to enhance or improve the image.

Other sensors or sensing systems such as accelerometers, motion sensors, headpose tracking devices, etc. may be employed to determine if the user moved and introduced vibration into the measurement and/or captured image.

Figure 23C:
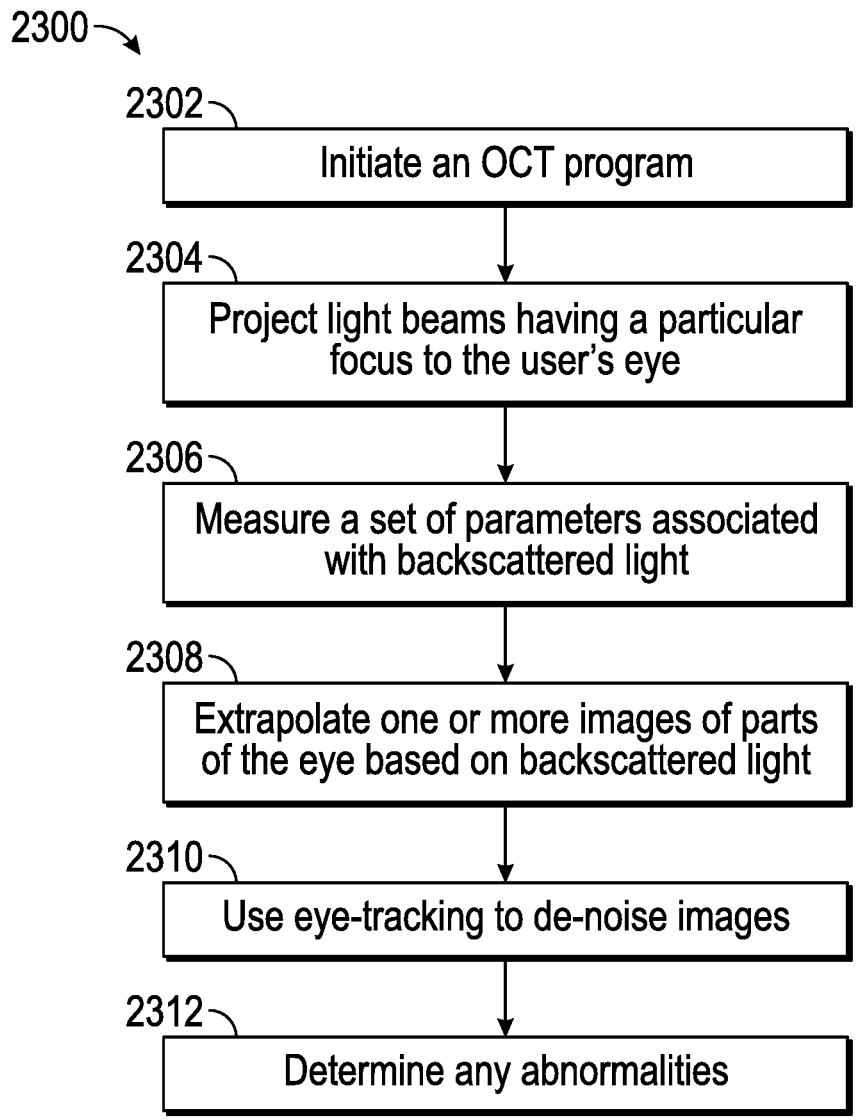
FIG. 23C illustrates an example process flow and system configurations of using the health system as an OCT system, according to some embodiments.

FIG. 23C illustrates an example flowchart 2300 of a method of examining the eye using the wearable device 2350. The method of examining the eye can be executed by the electronic hardware processor 2370 in conjunction with the wearable device 2350. The device 2350 can be configured perform an OCT examination of the eye if the device 2350 detects that the user 2360 is having difficulties with vision or trouble focusing. Referring now to FIG. 23C, an example process flow 2300 is provided. At block 2302, an OCT program may be initiated. At block 2304, one or more beams of light may be projected to a portion of the user's eyes using the optical source 2354. At block 2306 backscattered light 2356 and/or reflected reference beam can be collected by the optical fibers of a FSD that is employed as the optical source 2354 or other imaging devices 2352 (e.g., photodetectors) to measure a set of parameters associated with backscattered light 2356 emitted back from the eye. At block 2308, the system may be configured to extrapolate an image of the portion of the user's eye 2320 based on the measured set of parameters associated with backscattered light 2356. At block 2310, eye movements may be measured and used to de-noise the extrapolated image and to produce a more accurate image. At block 2312, any abnormalities of the eye 2320 may be detected from the obtained images and communicated to a clinician or doctor. For example, the obtained images can be compared with stored images accessible by the electronic hardware processor 2370 using pattern matching algorithms to detect abnormalities. The stored images can comprise images of healthy eyes, images that show characteristics of eye affected with particular diseases and/or images of the user's eyes obtained from past examinations. The electronic hardware processor 2370 can be configured to obtain quantitative measurements (e.g., volumetric measurements) of various parts of the obtained images of the user's eye. The quantitative measurements can be transmitted to a clinician for further analysis. As another example, one or more parameters can be extracted from the obtained images to detect abnormalities. The obtained images and/or the quantitative measurements can be used to monitor eye health or disease progression.

Referring now to FIG. 23A, a schematic of the wearable device 2350 that uses photodetectors 2352 to perform an OCT function is illustrated. As shown in FIG. 23B, a light source 2354 directs a projection beam 2338 into the user's eyes 2320. The light rays pass through the user's cornea and iris and reach the user's retina. It should be appreciated that the angle at which the light source 2354 projects the light may be varied based on the areas of the retina or the eye space that need to imaged. As shown in FIG. 23A, some of the light rays (e.g., visible light, RGB light, IR light, multi-spectral light) that are projected into the eye 2320 are backscattered as light rays 2356 and are captured by photodetectors 2352 that may be positioned at various parts of the wearable device 2350. For example, the photodetectors 2352 may be positioned all around the rim of the wearable device 2350, around the periphery of the frame of the wearable device 2350 or any other suitable configuration, as shown in FIG. 23B. A reference beam generated by the optical source 2354 that is reflected from a reflective reference can also be received at the photodetectors 2352 and interfered with the backscattered light 2356 to obtain an OCT signal.

One or more parameters of the light received by the photodetectors 2352 (e.g., density, angle, intensity, spectral content, etc.) and/or the OCT signal may be communicated by the photodetectors 2352 to a processor 2370 that may use one or more algorithms to extrapolate an image from the data transmitted from the photodetectors. In one or more embodiments, the photodetectors may comprise photo-diodes (e.g., silicon-based, Germanium-based for IR light, photomultiplier tubes (PMTS), charge-coupled devices (CCDs), CMOS based sensors, Shack-Hartman wavefront sensors etc.). In one or more embodiments multi-mode fibers may be used to receive the backscattered light, and channeling them into PMTS or any other type of photodetectors.

Although the backscattered light 2356 is illustrated in FIG. 23A as coming off an angle into the photodetectors 2352 for illustrative purposes, it should be appreciated that the backscattered light 2356 can reflect back at the same angle at which it was emitted. Thus, some embodiments may include beamsplitters to direct the backscattered light into one or more photodetectors (not shown).

It is appreciated that the backscattered light 2356 may come from the retina as shown in FIG. 23A, but the light may also be a Purkinje image (e.g., corneal glint, etc.) reflected off the cornea or any other glint of the eye. Different photodetectors may be more sensitive to different types of light or parameters. For example, some photodetectors may be better at tracking corneal glints; such sensors may be strategically placed to detect the corneal glint or Purkinje image. Or, other photodetectors may be better at differentiating between various angles at which light is backscattered from the retina, and may be placed in a manner such that it is optically conjugate to the retina. Thus, the wearable device 2350 can comprise various photodetectors that are configured to detect different types (or parameters) of the backscattered light 2356.

The wearable device 2350 can be configured for non-health applications (e.g., for entertainment such as watching movies or videos, playing games, for work, etc.) as well as an OCT system. The wearable device 2350 can be configured to periodically (e.g., hourly, daily, weekly, bi-weekly, monthly, bi-annually, annually, etc.) perform an OCT examination or when the device 2350 detects that the user 2360 is having difficulties with vision or trouble focusing. In various embodiments, the system 2350 can be configured to perform an OCT examination of the eye 2320 at irregular time intervals. For example, the wearable device 2350 can be configured to perform an OCT examination a few times an hour, a few times a week, a few times a month, a few times a year, etc. Accordingly, such an examination can be completed 1, 2, 3, 4, 5, 6, 8, 10, 12, 16, 24 or more times a year. Such an examination may be performed more often if a user has a health problem. The system 2350 can also be configured to be used in a doctor's office or a hospital as an OCT examination. In contrast to a traditional table/bench top OCT system, the wearable device 2350 can be worn by a user 2360. The wearable device 2350 configured as an OCT system can be lightweight, compact and less bulky than a traditional table/bench top OCT system.

In certain embodiments, the doctor, nurse, technician or other health care provider controls the system. Alternatively, the user controls the OCT system. In some embodiments, the system is automated and algorithmically controlled. For example the timing parameter such as when the OCT imaging is conducted is determined by the system. The system may determine that testing should be commences based on an indication, for example, from one of the diagnostic tests described, that the health of the eye has diminished or that an indication of a health problem has been detected. Alternatively, the system may simply follow a protocol, such as a schedule to undertake testing periodically or not periodically, such as discussed above.

Various embodiments of the device 2350 can include alarm systems including components that can provide audible, visual, graphic and/or tactile alerts to the user 2360 prior to the commencement of the testing, during testing and/or after completion of the testing. Furthermore, the device 2350 can also include components that can provide audible, visual and/or graphic instructions to the user 2360 prior to the commencement of the testing, during testing and/or after completion of the testing.

Aberrometer

In one or more embodiments the ophthalmic device may function akin to an aberrometer. An aberrometer measures precise irregularities in the eye. These aberrations are very unique aberrations particular to each individual, similar to fingerprints. The device measures a wavefront as it passes through the eyes. In an eye with no aberrations, the wavefront will be flat. In an eye with imperfections, the wavefront will be bent and/or distorted. These microscopic aberrations can distort light as it passed through the cornea and lens and into the retina. The result may have a significant impact on the quality of vision, and may affect depth perception, contrast, color perception, night vision, etc. Identifying these aberrations can help produce more accurate prescription eye wear.

In order to identify refractive error, the aberrometer may send out a band of laser light into the eye. The light passes through the cornea and the lens of the eye and is reflected back by the retina. The reflected light may then be measured by the aberrometer to produce 3D images. The aberrometer is typically used while performing laser vision correction surgery. The map created by the aberrometer directs the delivery of laser light that precisely re-shapes the cornea.

In one or more embodiments, the fiber scanning display (FSD) of the ophthalmic device may be used to produce light in a desired wavefront. As was the case in previous embodiments, the response of the applied stimulus may be measured. It should be appreciated that wavefronts of different frequencies may be applied. Similarly, visible or non-visible light may be projected into the eye, to produce the correct resolution for the resultant 3D image. In one or more embodiments, the captured data may be processed to determine any abnormalities, similar to the process flow shown in FIG. 23C.

Figure 27:
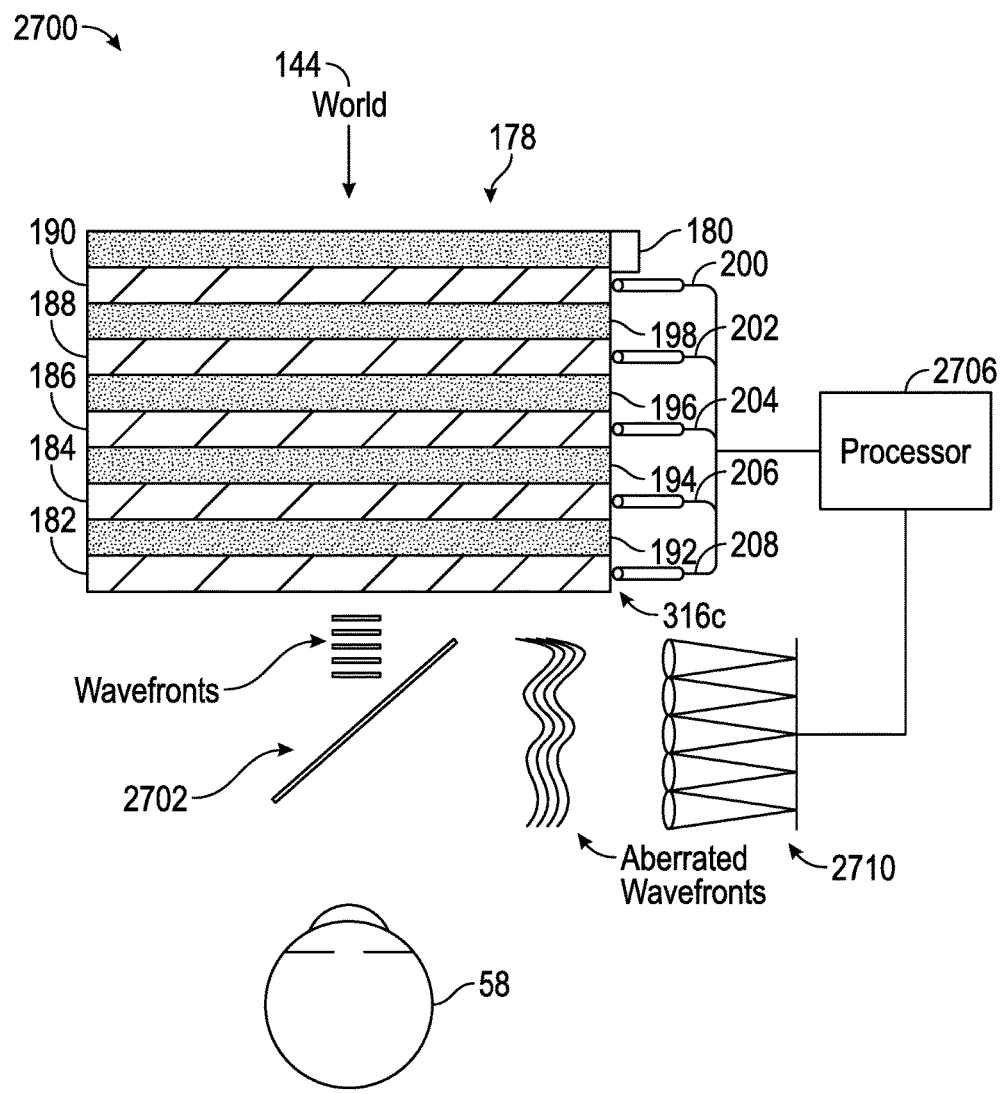
FIG. 27 illustrates an example embodiment of an augmented and/or virtual reality system configured as a wavefront aberrometer.

FIG. 27 illustrates an example embodiment of an augmented and/or virtual reality system 2700 configured as a wavefront aberrometer. In some embodiments, the system 2700 includes a stacked waveguide assembly 178, an adaptable optics element, such as a variable focus element (VFE) (e.g., a deformable mirror membrane whose shape is controlled by electrical signals applied to a plurality of electrodes) or an optical element that can otherwise alter its optical characteristics in a controlled manner, or any combination of the same. Examples of such are disclosed herein with respect to FIGS. 10A-10D. The system 2700 may also include a beamsplitter 2702, a wavefront sensor 2710, and a processor 2706. The system 2700 can be head-mounted so as to be aligned with a user's eye 58. The system 2700 can also include any of the other elements or features described herein. In some cases, the additional elements which are used in wavefront aberrometer embodiments but which would not necessarily be required for other functions described herein can be provided as add-on attachments to an augmented and/or virtual reality system.

The stacked waveguide assembly 178 can include multiple waveguides (182, 184, 186, 188, 190) and multiple lenses (192, 194, 196, 198). In some embodiments, the lenses (192, 194, 196, 198) are negative lenses, though in other embodiments they could be positive lenses. As shown in FIG. 27, the waveguides and negative lenses can be arranged in an alternating stacked configuration. The stacked waveguide assembly 178 also includes a plurality of light sources (200, 202, 204, 206, 208). As discussed herein, these light sources can be fiber scanning displays, though other light sources can also be used. Each respective light source can inject light into a corresponding waveguide (182, 184, 186, 188, 190), which distributes the light substantially equally across its length and redirects the light toward the eye 58. In some embodiments, the light sources (200, 202, 204, 206, 208) can inject collimated light into the respective waveguides (182, 184, 186, 188, 190) and each of the waveguides can output collimated beams of light at a range of different output angles. The light provided by the light sources (200, 202, 204, 206, 208) can be in the visible or infrared spectrum, for example. In other embodiments, still other wavelengths of light could be used.

As discussed herein with respect to other embodiments, the stacked waveguide assembly 178 can be used, whether alone or in conjunction with one or more additional lenses or adaptive optics, to transmit light with varying amounts of wavefront curvature to the eye 58. The wavefront aberrometer system 2700 can likewise use any such arrangement in order to generate wavefronts of lights having desired characteristics.

The stacked waveguide assembly 178 can also include a compensating lens layer 180. This lens layer can compensate for the cumulative effect of the negative lenses (192, 194, 196, 198) when the user is viewing light from the outside world 144 on the other side of the stacked waveguide assembly 178. The compensating lens layer 180 can also be designed to compensate for any other optical elements which may be provided between the stacked waveguide assembly 178 and the user's eye 58.

With reference back to FIG. 27, the wavefronts of light which are output from the stacked waveguide assembly 178 propagate toward the user's eye along the visual axis. In some embodiments, the stacked waveguide assembly 178 outputs a probe beam of light having planar wavefronts, as shown in FIG. 27. The probe beam is transmitted through a beamsplitter 2702 which is provided between the stacked waveguide assembly 178 and the eye 58. The probe beam then enters the eye 58 and is eventually backscattered by the retina. As the probe beam propagates through the eye, its planar wavefronts can be affected by irregularities or imperfections in the optics of the eye 58. Such irregularities or imperfections can cause the wavefronts to likewise become irregular.

Once the backscattered probe beam exits the eye, it is reflected by the beamsplitter 2702 toward a wavefront sensor 2710. As shown in FIG. 27, the wavefronts which exit the eye can become irregular. The specific shape of the aberrated wavefronts is dependent upon the irregularities or imperfections in the eye 58. The system can include a relay lens system that relays the wavefronts at approximately the pupil plane of the eye to the wavefront sensor 2710. The wavefront sensor 2710 is capable of measuring and characterizing the shape of these wavefronts.

The illustrated wavefront sensor 2710 is a Shack-Hartmann type wavefront sensor (though any other type of wavefront sensor can also be used). It includes an array of lenslets which spatially sample the incident wavefronts at many different locations. The wavefront sensor 2710 also includes a detector, such as a CCD or CMOS array, located one focal length away from the lenslet array. Each lenslet focuses a spot of light on the detector. The precise location of each spot on the detector depends upon the local curvature of the wavefront at the location of the corresponding lenslet. The detector therefore creates an image which consists of an array of spots. This image can be analyzed by the processor 2706 to determine the precise location of each spot, which is in turn indicative of the wavefront curvature at the location of the corresponding lenslet. In this way, the processor 2706 can determine the curvature of the wavefront at each spatial location sampled by the lenslet array. Based on the shape of a measured wavefront, the processor can calculate aberrations of the eye, including both lower-order and higher-order aberrations. These aberrations can be represented numerically as, for example, Zernike coefficients.

Once the processor 2706 has determined the aberrations of the eye 58, it can output those measurements in, for example, numerical or graphical form. The measurements can be used to determine a treatment plan for the eye 58, such as a corrective optical prescription. In addition, the measurements of the aberrations of the eye 58 can be used to control an adaptive optical element which can then be used to project optically corrected imagery into the eye 58, thus providing a crisper image to the user. For example, in some embodiments, the processor 2706 can be used to control the shape of the wavefronts output by the stacked waveguide assembly as it projects virtual and/or augmented reality imagery into the eye 58. In this way, the imagery provided to the user can be specially corrected based upon the aberrations of the user's own eye. If the stacked waveguide assembly 178 is only capable of correcting lower-order aberrations of the eye 58, then a different or additional adaptive optical element can also be provided in order to correct for higher-order aberrations. For example, a deformable membrane mirror whose shape is controlled by electrical signals applied to a plurality of electrodes can be used to correct for higher-order aberrations. Such a deformable membrane mirror could be provided in the optical path between the light sources (200, 202, 204, 206, 208) and the waveguides (182, 184, 186, 188, 190). Many other arrangements and/or adaptive optical elements can also be used to correct lower and/or higher-order aberrations of the eye 58 based on measurements from the wavefront sensor 2710.

The augmented and/or virtual reality system 2700 illustrated in FIG. 27 can also be configured as a light field camera or light field microscope that can be used to examine the eye of the wearer. As discussed further herein, this can be done by including a lens that focuses light at or near the lenslet array shown in FIG. 27. One advantage of such a device is that the light field imagery it captures can be computationally re-focused at different planes at any time after the light field is captured. For example, the device could capture a light field image of the wearer's eye. In post-processing, the light field image could be focused on the patient's retina to perform a retinal examination. The same light field image could also be focused on any other anatomy of the eye in post-processing.

Conventional cameras reduce a three-dimensional object to a flat, two-dimensional recording of light intensity, as detected from the object space within the field of view of the camera. This flattening effect is a result of imaging, in which light rays originating at different points on an object within the field of view of the camera are focused by a lens to corresponding points on an image plane. Angular information is lost in this process; for example, the light intensity recorded at a given pixel in a conventional image does not indicate the respective intensity contributions of light rays that originate from the corresponding point in the field of view with different angular orientations. Instead, the intensity measured at each point in the image plane is indicative of the combined intensity of the various light rays that enter the camera with different angular orientations from the corresponding point in the field of view. Thus, various properties, like depth, cannot be determined quantitatively from a conventional image.

The flattening from three dimensions to two dimensions in a conventional camera significantly limits the information content of the image. Perhaps the simplest consequence of this flattening is ambiguity in depth, with objects behind and in front of the focal plane being blurred (out of focus).

One method of obtaining information regarding the respective intensities of light rays with different angular orientations from within the field of view is to provide a wavefront sensor, such as a Shack-Hartman array of lenslets in proximity to a sensor (e.g., a CCD or CMOS sensor), as shown in FIG. 27. Each lenslet samples a spatially localized region of the wavefronts of light that enter the instrument from the field of view, and allows local angular information to be recorded on the sensor. In this way, the sensor can detect the respective intensity of light rays that arrive at each lenslet from different angular directions. This four-dimensional information of light intensity at each position (x, y) for each angle ($\theta x$, $\theta y$) quantifies the light field within the instrument's field of view.

As mentioned above, the system 2700 illustrated in FIG. 27 can be configured as a light field camera or microscope by including a lens in the optical path of the instrument to focus light at approximately the plane of the wavefront sensor 2710. The lens could be placed, for example, between the beamsplitter 2702 and the wavefront sensor 2710, though other locations may also be suitable. The stacked waveguide assembly 178 can be used to provide one or more beams of light that illuminate the eye 58. This light can be back-scattered by the retina toward the beamsplitter 2702. The light can then be focused by a lens. The lens can be positioned and configured such that its focal plane is at or near the wavefront sensor 2710. The wavefront sensor 2710 can then collect the four-dimensional information of light intensity at each position (x, y) for each angle ($\theta x$, $\theta y$). This light field information can be processed by, for example, the processor 2706 to provide an image focused at any desired plane.

Ultrasound

FIG. 24A schematically depicts a wearable device 2450 that can be worn by a user 2460 configured to perform an ultrasonic examination of the eye of the user 2460. The device 2450 includes a frame 2464 attached to a display system 2462. The display system 2462 can be configured to be positioned forward of the eyes 2420 of the user 2460. Various embodiments of the wearable device 2450 can comprise an ultrasonic stimulator module to produce an ultrasound-front that provides a stimulus to the user's eye 2420. The ultrasonic stimulator module can comprise a probe 2481 configured to contact parts of the eye (e.g., upper eyelid, eye orbit, sclera, cornea, etc.). The probe 2481 can be configured to be connected to an ultrasonic transmitter 2477 configured to deliver ultrasonic energy to the eye and an ultrasonic receiver 2479 configured to receive ultrasonic energy reflected and/or scattered from various structures. In some embodiments, the probe 2481 can be configured to be connected to an ultrasonic transceiver 2475 that combines the ultrasonic transmitter and receiver. In some embodiments, the ultrasonic stimulator module can be configured to deliver ultrasonic energy to various parts of the eye without contacting one or more parts of the eye. For example, the ultrasonic stimulator module can comprise an electromagnetic acoustic transducer (EMAT). The ultrasonic stimulator module can comprise one or more ultrasonic transducers that are configured to convert the ultrasonic energy reflected and/or scattered from various structures in the eye to electrical signals. The probe 2481 can be configured to transmit ultrasound to various regions of the eye as well as receive ultrasound reflected from various regions of the eye.

Accordingly, the wearable device 2450 may be configured to measure the response of the applied stimulus and generate images of the various structures of the eye. For example, in various embodiments, the probe 2481 may be moveable so as to scan one or more directions. In some embodiments, for example, the probe 2481 can be scanned in two or three different potentially orthogonal directions (such as x and y or possible x, y and z) to produce a two-dimensional images or three-dimensional. In some embodiments, as another example, the probe 2481 can be moved to transmit and receive ultrasound energy at different angles to produce two-dimensional and/or three-dimensional images. Similarly, the ultrasound sensor that detects the ultrasound energy can be move or scanned. For example, the ultrasound sensor can be scanned in two or three different potentially orthogonal directions (such as x and y or possible x, y and z) to produce a two-dimensional images or three-dimensional. An electronic hardware processor 2470 having characteristics similar to the local processing and data module 70 of FIGS. 3A-3C can be used to analyze ultrasound energy received from the eyes 2420 of the user 2460 to examine the various structures of the user's eye 2420.

The wearable device 2450 may produce more accurate results by reducing noise that can arise due to clinician movement or interference. In some embodiments, the ultrasound energy may be applied continuously for a given period of time to perform the ultrasound examination. Alternately, in some embodiments, the ultrasound energy can be applied in a pre-determined pattern or protocol unique to the user 2460.

The wearable device 2450 can obtain images of various parts of the eye including the lens, the retina and other structures in the eye for diagnostic and therapeutic use. For example, ultrasound energy having low-power (e.g., ultrasound power less than 2 W/cm$^2$) and/or at low frequencies (e.g., ultrasound frequency less than or equal to about 40 kHz) can be used to treat glaucoma and/or reduce intraocular pressure (IOP). As another example, high intensity focused ultrasound (HIFU) having energy of about 2 W/cm$^2$ and a frequency of about 21 MHz can be used to treat glaucoma or reduce intraocular pressure (IOP). As another example, ultrasound energy having power of between a fraction of 1 W/cm$^2$ and about 5 W/cm$^2$ and at frequencies between about 1 MHz and about 5 MHz can be used for cosmetic purposes (e.g., promote collagen production and/or reduce the appearance of bags under the eyes. Ultrasound stimuli can evoke responses in the retina that look qualitatively similar to strong visual responses but with shorter latency. Different ultrasound frequencies including High-frequency ultrasound can be used to accurately identify a variety of ocular pathologies, including retinal detachment. For example, ultrasound frequencies of about 8 MHz can be used to obtain A-scans of the eye. As another example, ultrasound frequencies between about 10 MHz to 15 MHz can be used to obtain B-scans of the eye.

FIG. 24B illustrates an example flowchart 2400 of a method of examining the eye using the device 2450. The method of examining the eye can be executed by the electronic hardware processor 2470 in conjunction with the device 2450. The device 2450 can be configured perform an ultrasound examination of the eye if the device 2450 detects that the user 2460 is having difficulties with vision or trouble focusing. Referring now to FIG. 24B, an example process flow 2400 is disclosed. At block 2402, an ultrasound mode may be initiated. As described earlier, in various embodiments, a separate ultrasound producing component may be coupled to an AR device. For example, ultrasonic energy can be generated by an ultrasonic stimulator module comprising, one or more ultrasonic transducers that is integrated with the augmented reality/virtual reality wearable device 2450 when the ultrasound mode if initiated. At block 2404, an ultrasound protocol is determined for the user. For example, the ultrasound may be delivered continuously, or may follow a particular pattern specific to the user. At block 2406, an ultrasound wavefront or front is delivered to the user's eye. In one or more embodiments, the response of the eye is measured as illustrated in block 2408. For example, the ultrasound waves reflected from various structures in the eye can be received by the transducers in the ultrasonic stimulator module can be converted to electrical signals. This information can be used to create or generate an ultrasound image by the device 2450. Any abnormalities of the eye can be detected from the generated ultrasound image by a clinician or by an electronic processor that can use pattern-matching algorithms to detect abnormalities as illustrated in block 2410.

For example, the obtained ultrasound images can be compared with stored images accessible by the electronic hardware processor 2470 using pattern matching algorithms to detect abnormalities. The stored images can comprise images of healthy eyes, images that show characteristics of eye affected with particular diseases and/or images of the user's eyes obtained from past examinations. The electronic hardware processor 2470 can be configured to obtain quantitative measurements (e.g., volumetric measurements) of various parts of the obtained images of the user's eye. The quantitative measurements can be transmitted to a clinician for further analysis. As another example, one or more parameters can be extracted from the obtained images to detect abnormalities. The obtained images and/or the quantitative measurements can be used to monitor eye health or disease progression.

As illustrated in FIG. 24A, the display system 2462 of the device 2450 can comprise a display lens 2476 mounted in the frame 2464. In some embodiments, the display lens 2476 can be a unitary lens comprising two ocular zones, each ocular zone positioned in front of the users eyes 2420. In some embodiments, the display system 2462 can comprise two display lenses mounted in the frame 2464, each display lens comprising an ocular zone that is positioned in the front of each of the users eyes 2420. The display lens 2476 using illumination from an optical source 2468 can project the generated ultrasonic images to a particular position of the user's eye 2420. The display lens 2476 can include a plurality of waveguides having characteristics similar to the waveguide stack 178 described above with reference to FIG. 10D. In various embodiments, the plurality of waveguides can comprise diffractive optical elements that are configured to in-couple light output from the optical source 2468 into one or more of the plurality of waveguides. The plurality of waveguides can further comprise diffractive optical elements and/or variable focusing elements that are configured to out-couple light propagating therein. The diffractive optical elements and/or variable focusing elements can be configured to modify the focal plane and/or the direction of the light projected from the display lens 2476 such that the projected images appear to originate from different depth planes and different direction. In this manner two/three-dimensional images can be projected to a desired position of the user's eye. This display lens 2476 may be employed to display the results of the ultrasound imaging to the wearer. For example, light can be projected into the eye of the wearer to form images on the retina as described herein so as to present 2D or 3D images corresponding to the ultrasound images.

In various embodiments, the optical source 2468 can comprise a fiber scanning device (FSD) that includes a plurality of optical fibers configured to transmit light from a light emitter (e.g., laser, LED, flash lamp, superluminescent diodes, etc.) to the display lens 2476. In various embodiments, the FSD can be scanned in a variety of patterns (e.g., raster scan, spiral scan, Lissajous patterns, etc.) and speeds. The two/three-dimensional images can also be projected to a desired position of the user's eye based by varying the scan pattern and the scan speed of the FSD. As discussed above, in some embodiments, the two or three-dimensional imaged projected into the eye of the wearer may correspond to ultrasound image obtained using the wearable device (e.g., using the transducers).

In various embodiments, the device 2450 can be configured to perform ultrasonic stenography. For example, the transducer or ultrasound source(s) can be configured to produce high frequency ultrasonic waves that are reflected and not absorbed by different structures in the eye and can be collected by the transducers or sensors or the FSD.

In various embodiments, the system may be configured to perform auscultation. In various embodiments, for example, the system may include transducers or sensor that detect and measure ultrasonic energy originating from the eye or wearer. Such a configuration can be in contrast to a system that includes a transducer to produce ultrasound and direct the ultrasound to the eye or wearer and a sensor to detect the ultrasound that is reflected from the eye or wearer. The ultrasound sensor can be used to detect or "listen" to ultrasonic energy emitted from the wearer such as from blood flow through the vasculature of the eye of the wearer. In various embodiments, the device 2450 can be configured to transmit and/or receive energy in audible frequency range. Detecting ultrasonic energy from the wearer's vasculature can, for example, be used to perform a sound analysis of blood flow in the fundus of the eye.

In various embodiments of the device 2450, the received ultrasound signals from the eye can be analyzed to measure a Doppler shift to measure velocity of blood flowing in the blood vessels of the retina. Traditional velocity measurements with ultrasound are based on the Doppler principle, which states that sound emitted from a moving source or sound reflected from a moving target will lead to a shift in the frequency of the sound. This so-called Doppler shift can be measured directly from the received signal through a continuous wave ultrasound emission also referred to as CW-Doppler or sampled through the emission of several ultrasound pulses also referred to as PW-Doppler.

One of the advantages of ultrasound imaging is its ability to measure blood and tissue velocities with high precision and at a high frame rate. In the diagnostic setting, information of blood velocities can be used to identify abnormal blood flow related to pathology, such as the jet flow pattern resulting from a heart valve leakage. Further, information about tissue velocities can be used to quantify the function of the heart, through the identification of areas of the heart muscle with reduced contractibility. Various embodiment of the device 2450 configured to perform an ultrasound examination, can be capable of detecting ocular murmurs or ocular bruits that can be identified with subarachnoid hemorrhage, stroke, and carotid-cavernous fistula, symptomatic atherothrombic vascular disease. The device 2450 configured to perform an ultrasound examination, can be capable of detecting carotid or renal bruits seen in users with hypertension.

The device 2450 can be configured for non-health applications (e.g., for entertainment such as watching movies or videos, playing games, for work, etc.) as well as an OCT system. The device 2450 can be configured to periodically (e.g., hourly, daily, weekly, bi-weekly, monthly, bi-annually, annually, etc.) perform an ultrasound examination. In various embodiments, the device 2450 can be configured to perform an ultrasound examination of the eye 2420 at irregular time intervals. For example, the device 2450 can be configured to perform an ultrasound examination a few times an hour, a few times a week, a few times a month, a few times a year, etc. Accordingly, such an examination can be completed 1, 2, 3, 4, 5, 6, 8, 10, 12, 16, 24 or more times a year. Such an examination may be performed more often if a user has a health problem or when the device 2450 detects that the user is having difficulty in focusing or having trouble with their vision. The device 2450 can also be configured to be used in a doctor's office or a hospital as an ultrasound examination.

Electrooculography (EOG), Electroencephalography (EEG), and Electroretinography (ERG)

Figure 24F:
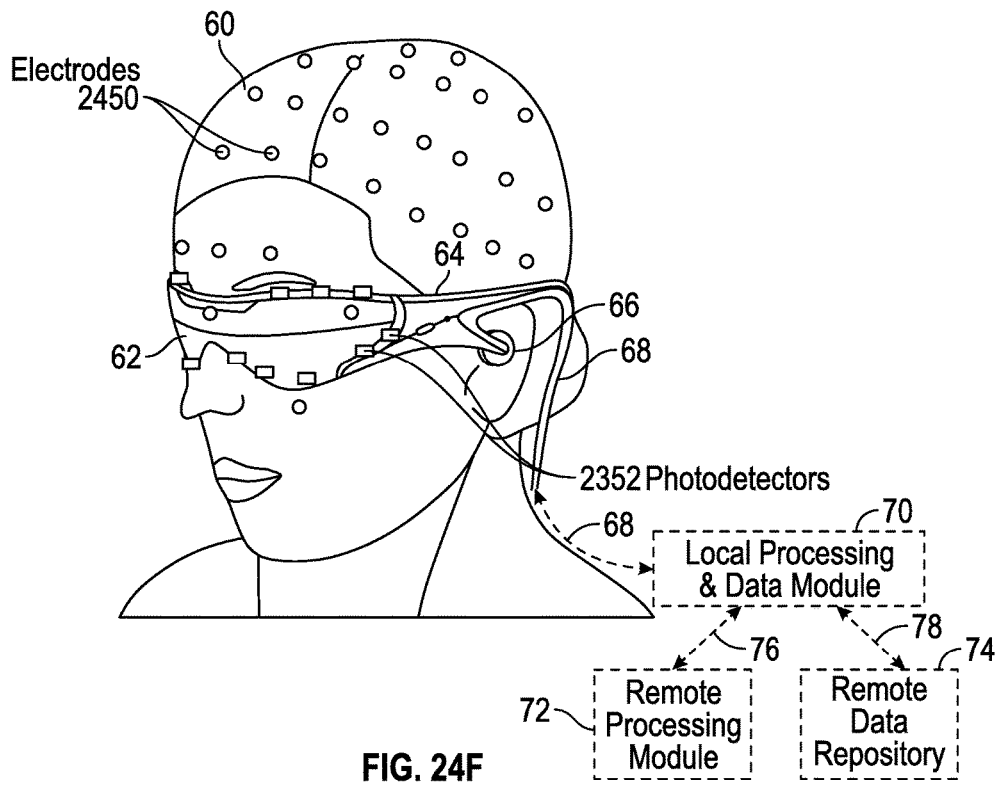
FIG. 24F is a schematic illustration of an augmented reality/virtual reality eyewear comprising electrodes positioned around a user's eye.

In various embodiments, the wearable augmented reality device may be integrated in a system that includes electrodes and electronics configured for EOG (electrooculography), EEG (electroencephalography), and ERG (electroretinography). As shown in FIG. 24F, for example, electrodes (2450) can be positioned around the eye and/or on a person's head. In some embodiments, the electrodes (2450) can be mounted on the augmented reality head mounted eyewear, for example, on the frame of the eyewear. One or more of the electrodes may be disposed on an inner surface of the eyewear. Such electrodes may be positioned, for example, on the portions of the eyewear that supports the lens (e.g., rims) or the temples or earstems, on straps or other support members that support the head mounted assembly on the head. Accordingly, these electrodes may be in contact with the forehead and/or the sides of the head, for example, above the ear. The electrodes may also be in contact with the eye or face or facial tissue around the eye.

The electrodes (2450) can be connected to wires or leads that are supported by the frame or main body of the eyewear and/or may be configured to be in communication via wireless technology to the device. Accordingly, the electrodes (2450) may be in direct contact with a part of the user's body. The electrodes (2450) may also be disposed at a distance from a user's body, have a particular material or a part of a device disposed between the electrode (2450) and the user's body, or be disposed at other locations suitable for measuring electrical potentials.

The electrodes may be electrically connected to and in communication with a local processing and data module (70), a remote processing module (72), and/or a remote data repository (74) in any combination or configurations. A voltage measurement may be measured from the electrodes (2450) and a potential difference for the electrodes (2450) may be determined by the local processing data module (70)

or the remote processing module (72). Alternatively, the potential difference may come straight from a plurality of electrodes (2450). Additional circuitry may or may not be included on the electrodes or between the electrodes and the local processing and data module (70).

The remote processing module (72) may be configured to receive measurements from the electrodes (2450) and/or send control signals to the electrodes directly or via the local processing and data module (70). In some embodiments, the local processing and data module (70) may perform some or all of the transmission of the control signals and the reception of the measurements. Likewise, RF signal conditioning and signal processing of the measurements can happen in whole or in part in the local processing and data module (70) and/or in the remote processing module (72). The measurements and the derived parameters of the electrodes (2450) may be stored in whole or in part in the local processing and data module (70) and/or the remote data repository (74).

Based on the electrical signal measurements from the electrodes (2450), positions of the eye may be determined and thus patterns of the eye may be detected. In one or more embodiments, the ophthalmic device and system may be used and configured for electrooculography (EOG). EOG measures the potential voltage between the cornea and Bruch's membrane, which is located at the back of the eye. One primary application is in recording eye-movement. For EOG, a pair of electrodes can be placed to the left and right of the eye and/or above and below the eye, as illustrated in the example shown in FIG. 24F. In some embodiments, for example, the patient may be placed in a well-illuminated room such that the patient's eyes are dilated. If the eye moves toward an electrode, a potential difference occurs between the electrodes and the position of the eye can be determined, and therefore a measure of eye movement can be determined. These electrodes may be placed on inwardly facing surfaces of the eyewear or head mounted device in various embodiments. In some cases, such electrodes may be mounted on padded surfaces on the eyewear. These padded surfaces can be inwardly facing. Such surface may cause the electrode to contact the face (front or side) such as cheek, forehead or temples. In some cases, the electrodes may be adhered to the face (front or side) such as cheek, forehead or temples, and be connected to the head mounted device by wires or leads. Wireless connection to the electronics is also possible as discussed above. Electronics, for example, in any of the configurations discussed above or otherwise, can be employed to receive and/or process the EOG signals to determine eye movement or other conditions.

In one or more embodiments, the ophthalmic device may also comprise EEG sensors to map brain activity. The electrodes (2450) may be placed around and/or on the user's head to also measure and compare electrical potentials in this region. The electrodes (2450) may be placed on a helmet, hat, cap, net, or other housing, frame or surface or surfaces disposed on or around the head or portions thereof to provide for ease of placement onto a user's head. In some embodiments, for example, straps could be disposed across portions of the head and electrodes mounted on the inner or underside to contact the user's head. The electrodes (2450) may also be connected via wireless or wired technology that is then connected to the ophthalmic device. In certain embodiments, the electrodes (2450) are placed on the back of the wearer's head closer to the optic nerve. Straps, frames, or other flexible or rigid members can provide support for one or more electrodes and maybe disposed on an inner surface those members so as to face and contact the head.

The EEG sensors may detect any abnormal activity or pattern in the brain and report out to the user and/or clinician. This may be especially useful for patients immediately after brain surgery or for at-risk patients. The ophthalmic device may be pre-programmed with an EEG sensing module to analyze data collected by the EEG sensors. Electronics, for example, in any of the configurations discussed above or otherwise, can be employed to receive and/or process the EEG signals and analyze data collected by the EEG sensors.

In one or more embodiments, the ophthalmic device may be configured with electrodes (2450) that are placed around and/or on the user's eyes to measure and compare a resting electrical potential of the retina. Electroretinography (ERG) is the mass electrical response of the retina to photic stimulation, and can measure electric potentials of a variety of different cell types in the retina. Examples include photoreceptors, inner retinal cells, and ganglion cells. For example, the electrodes (2450) can be placed on the cornea such as via contact lenses, inserted between the cornea and the lower eyelid, or the skin near the eye. However, electrodes (2450) can also be placed to record ERG from the skin. The ERG can be placed just above or below the eye, or below the eye next to the lateral canthus. Because the skin electrodes do not contact the eye, attenuation in ERG signal amplitude will likely be present and can be significant. In various embodiments, averaging and other signal processing techniques can be used to increase the signal-to-noise ratio. A patient's eyes may be exposed to stimuli and the electrode that is disposed on the cornea measures electrical responses of cells that sense light in the retina located in the back of an eye. Generally, when light enters the eye, the light is converted into electrical energy by specialized cells in the retina. Stimuli for ERG may be flash or patterns, with or without a background light, or varying colors. Examples include dim flashing (for measuring photopic and/or scotopic rod cell activity), flashing (for measuring cone cell activity), and/or pattern stimuli (for measuring retinal ganglion cell activity). ERG electrodes measure electrical activity associate with this process. Other methods of recording may also be used.

This information may be coupled with optical eye imaging techniques to detect any eye abnormalities. Some such imaging techniques may include those described herein.

These padded surfaces can be inwardly facing. Such surfaces may cause the electrode to contact the eye or orbital or eye sockets, the face (front or side) such as cheek, forehead or temples or elsewhere. In some cases, the electrodes may be adhered to the eye or orbital or eye socket, the face (front or side) such as cheek, forehead or temples, and be connected to the head mounted device by wires. Wireless connection to the electronics is also possible as discussed above. Electronics, for example, in any of the configurations discussed above or otherwise, can be employed to receive and/or process the ERG signals to analyze the signals.

Accordingly, other imaging and diagnostic as well as treatment tools such as descried herein may also be included in the system. The wearable augmented reality device may comprise a virtual reality device and/or an augmented reality device. The electrodes may be included in a system with the augmented or virtual reality system.

Although electrodes are disclosed, other types of sensors may possible be used for EEG, EOG, and/or ERG. The electrodes (2450) may be electrical conductors able to measure electric potentials, and/or may be a specialized set of unique electrodes for particular tests as described above.

Light Therapy

In one or more embodiments, light therapy may be selectively administered to one or more areas of the user's eyes. Light therapy refers to selective administration of light (e.g., multi-spectral light, blue light, IR, etc.) for various applications. In some embodiments, the amount of one or more wavelengths of light that is projected by or transmitted through the display (62; FIGS. 3A-3D) into the eyes of the user may be reduced, or may be increased, depending on application.

In some embodiments, the reduction or increase in the amount of light of one or wavelengths propagating from or through the display to the eyes of the user may be adjusted dynamically, and may occur in real time, based on the wavelengths of light propagating towards the user's eyes from the ambient environment and/or based on the content of images to be displayed to the viewer. In addition or alternatively, the reduction or increase may be determined based on temporal considerations, including the time of day, date, time of year, season, etc. For example, blue light has been found to affect sleep, and the display (62) may be programmed to adjust its output of blue light at night, or depending on temporal proximity to a user's time that the user is anticipated to go to sleep cycle.

As another example, it has been observed that overexposure to blue light is especially damaging to retinal cells. The ophthalmic system may be programmed, in one or more embodiments to detect an overexposure of blue light through one or more sensors, and to selectively filter out the blue light to prevent damage to retinal cells. It will be appreciated that the one or more sensors may be the cameras (16) of FIG. 5. In some other embodiments, the one of the sensors may be dedicated color sensors facing outward from the frame (108). Filtering out the blue light may involve reducing the amount of blue light projected by the display system (62) to the user's eyes and/or by having the display (62) filter out or block blue light propagating through the display (62) from the ambient environment to the user's eyes. It will be appreciated that "blue light" refers to light of one or more wavelengths that are perceived by a viewer as the color blue and reducing blue light refers to reducing the amount of these one or more wavelengths that reaches the eye or eyes of the user.

In some embodiments, reducing the amount the light of a certain color projected by the display system (62) may be accomplished using a wavelength selective filter (e.g. a color filter) disposed in the path of the light to the user's eyes. For example, the filter may be provided at the locations at which the waveguides (182, 184, 186, 188, 190) (FIG. 10D) receive light from the plurality of displays (200, 202, 204, 206, 208). In some embodiments, the filter may be a coating on a surface of the waveguide receiving the blue light from the plurality of displays (200, 202, 204, 206, 208). In some embodiments, the filter may be selectively engaged or disengaged.

In some embodiments, the amount of light of particular wavelengths (e.g., blue light) directed by the display system (62) to the user's eyes may be reduced by reducing the intensity of a light source that generates the light of those waveguides. For example, in some embodiments, the display (62) may be configured to display color images using light sources that output light of wavelengths corresponding to different component colors (e.g. red, green, and blue light). The different component colors, when combined, form a full color image. In some embodiments, the display (62) may be configured to reduce the output of, e.g., the blue light source in cases where blue light is to be reduced. For example, the local processing module (82; FIGS. 3A-3C) and/or remote processing module (72; FIGS. 3A-3D) may be configured to provide instructions for the blue light source to output less blue light (e.g., by reducing power supplied to the light source) than might otherwise be specified to form a full color image. In some embodiments, the amount of light of other wavelengths may similarly be actively reduced as desired using a filter and/or by reducing the emission of light of desired wavelengths from a light source.

It will be appreciated that the reduction of the amount of some wavelengths of light reaching the eyes of the user may be triggered by an analysis of the intensity of those wavelengths of light in the image content to be projected to the user's eyes. The display (62) may be programmed with a threshold value, above which the display (62) is programmed to reduce the output level of selected wavelengths. In some other embodiments, the display (62) may simply be programmed to reduce any output of the particular wavelengths by a set amount. The particular wavelengths and output level may be user selectable or may be programmed by a third party (e.g., a health care provider) as part of a therapy protocol in some embodiments.

In addition to or as an alternative to reducing the output of certain wavelengths by the display (62), in some embodiments, the display (62) may reduce the amount of light of one or more wavelengths that is transmitted through the display (62) from the ambient environment to the user. For example, the display (62) may selectively block or occlude particular portions of the user's field of view to reduce the amount of the one or more wavelengths that reaches the eyes of the viewer from the ambient environment. A method and apparatus for blocking portions of the user's field of view may be found in U.S. Patent Application Publication No. 2015/0205126, which is incorporated by reference herein. In some embodiments, a light sensor, such as the cameras (16; FIG. 5) may be utilized to detect the level and the originating direction or location of light of the one or more wavelengths that are incident on the display (62). This information may then be used to block light from that direction (e.g., by activating switchable elements in the display (62)), to reduce the amount of the light from that direction that reaches the user's eyes. In some embodiments, the blocked portion of the user's field of view may be replaced by images projected to the user's eyes by the display (62). These projected images may be an image of the blocked portion of the user's field of view, but with lower levels of the light of wavelengths to be reduced than that present in the ambient environment.

In contrast to overexposure, some studies have found that underexposure to light in general, or light of certain wavelengths, has a profound effect on patient's circadian rhythms and has been linked to depression, sleeping disorders, and other mental problems. To this end, the ophthalmic system may be similarly programmed to detect an underexposure to light of certain wavelengths, e.g. white light, blue light, or any other spectrum of light through one or more sensors, and selectively administer (e.g., with a periodic regimen, etc.) light into the user's eyes to correct the imbalance. Many other similar applications may be envisioned. As noted above, the underexposed wavelengths of light may be detected using one or more of the cameras (16), or a dedicated color sensor.

The light may be emitted by any light source (e.g., LED, FSDs, multicore fibers, DLP, OLEDs, IR light sources, etc.). For example, augmentation of the one or more wavelengths of light may be accomplished by increasing the light output of a light source for those wavelengths of light (e.g., by increasing the power supplied to a blue-light light source, a red-light light source, etc.). In one or more embodiments, the ophthalmic system, which includes the display (62), may comprise a light-emitting module 27 (e.g., polychromatic polarized light, lasers, light-emitting diodes, fluorescent lamps, dichroic lamps, full spectrum light, etc.) to selectively administer light based on a treatment protocol. The light-emitting module (27) may function as an auxiliary light source to output light of desired wavelengths.

It will be appreciated that various forms of light therapy may be administered through the ophthalmic system. Such light therapy may consist of exposure of the eye (or regions of the eye) to daylight or light associated with specific wavelengths. Depending on the patient's symptoms, location, environment (external parameters such as the time of day, time of year, date, and season), mood, input or any other detected sign of depression or abnormality, the ophthalmic system may determine the appropriate treatment protocol. In some embodiments, it will be appreciated that mood and/or mental abnormalities may be detected by the inward facing cameras (24) and/or EEG sensors, as disclosed herein.

Regarding the treatment protocol, light may be administered for a prescribed amount of time periodically or continuously. In some embodiments, the ophthalmic system may also be configured to determine the wavelength of the light to be administered to achieve a desired result. For example, where a need for cell growth and repair is determined to be present, the ophthalmic system may be configured to administer light of wavelengths corresponding to the color red, which has been determined to promote cell growth and repair. Other treatment parameters may be similarly used in determining an efficacious treatment protocol. For example, the display (62) may be configured to provide full-spectrum light, or blue and/or green light to the user for a set duration and/or at certain times of day (e.g., morning, include before sunrise) to treat depression, seasonal affective disorder, and/or to reset circadian rhythms (e.g., due to jet lag). Advantageously, because the portability of the display (62) may allow it to be worn by the user throughout the day, the user's perceptions of the length of days and the timing and duration of night and daylight may be modified as desired using the system (62). For example, full spectrum and/or blue light may be generated in the morning and/or at night to augment light from the ambient to provide the effects of a day having different lengths or different daylight hours. In one or more embodiments, the ophthalmic system may be stored with a light therapy program to determine an appropriate protocol.

In one or more embodiments, the ophthalmic system may be used to prevent or mitigate age-related macular degeneration (AMD). AMD is a common eye condition that may cause significant visual loss in affected patients. AMD may be affect patients in either a dry form or a wet form. The dry form generally causes gradual vision loss from deterioration of the retina. The wet form involves the growth of abnormal blood vessels under the retina called choroidal neurovascularization (CNV). These abnormal blood vessels can leak fluid and/or blood and may affect visual deterioration.

To this end, the ophthalmic system may comprise one or more components for laser photodynamic therapy to combat AMD and other such related diseases. Laser therapy has proven to be beneficial in treating AMD. The ophthalmic system may be configured to determine a location of macular degeneration, and administer laser treatment or laser photodynamic treatment to the areas most affected by AMD or any other related disease. The laser may be administrated such that the growth of abnormal blood cells is mitigated, and in some cases, the laser may help close or reduce the excess blood cells, in the case of wet form AMD.

In one or more embodiments, photodynamic therapy (PDT) may be used to close abnormal blood vessels caused due to AMD without damaging the overlying retina. The ophthalmic system may comprise a separate module to inject a photo-sensitizing agent (Visudyne) into a vein, which may travel through the bloodstream and collect in the abnormal vessels under the retina.

The ophthalmic system may then be configured to administer a low-energy laser (e.g., through a laser module of the ophthalmic system) to activate the photo-sensitizer. The activated photo-sensitizer results in a chemical reaction that leads to the closure of the leaking blood vessels.

Macular Degeneration

In one or more embodiments, the ophthalmic system may be configured to detect, diagnose and/or compensate for macular deficiencies. Macular deficiencies (e.g., holes, cysts, degeneration, etc.) are damages at the macular and foveal tissue in the retina that create anomalies, dead spots or regions of reduced sensitivity to light or devoid of sensitivity to light in the user's field of view. Common forms of macular deficiency include age-related macular degeneration (AMD), Stargardt disease, Best disease, and other degenerative conditions. Age-related macular degeneration includes "dry" AMD, characterized by atrophy of the retinal pigment epithelial layer, and "wet" AMD, in which vision loss occurs due to complications from abnormal blood vessel growth in the retina. Macular deficiencies may result in anomalies, dead spots or regions of reduced sensitivity to light in various parts of the field of view, as well as loss of contrast or color sensitivity. Frequently, anomalies, dead spots or regions of reduced sensitivity occur near the center of the field of view rather than at the periphery.

The ophthalmic system may be configured to detect or diagnose macular deficiencies by determining the ability of a portion of the retina to detect an image. In some embodiments, the ophthalmic system may be a user display device 62 such as shown in FIG. 5, which includes a projecting subsystem 18 configured to project light 38 into the eye of a wearer to form an image in the eye. The user display device 62 includes a display lens 106 which may be mounted to a user's head or eyes by a housing or frame 108. The display lens 106 may comprise one or more transparent mirrors or reflective features positioned by the housing 108 in front of the user's eyes 20 and configured to reflect projected light 38 into the eyes 20 (and also potentially facilitate beam shaping). These reflective surfaces may be partially transmissive to also allowing for transmission of at least some light from the local environment. FIG. 10D also includes another view of an embodiment of a display device comprising a plurality of displays 200, 202, 204, 206, 208 that may be utilized to inject image information into a plurality of respective waveguides 182, 184, 186, 188, 190, each of which may be configured, as described above, to distribute incoming light across the length of each waveguide, for exit down toward the eye. The displays 200, 202, 204, 206, 208 may comprise fiber scanning devices (FSDs) to form the image. Such devices can be configured to project an image onto a portion of the retina.

The system can then detect a response from the wearer. For example, the image may be a small dot that can be clearly seen if projected to a healthy portion of the retina but likely would not be seen if projected to a deficient portion. In some embodiments, the wearer may be prompted automatically or by another user, such as a medical professional, to indicate if the wearer saw an image. The user may then input the wearer's response through a user interface. In some embodiments, the ophthalmic system may increase accuracy by using eye tracking cameras 24 or similar detection methods to observe if an involuntary reaction occurs in response to the projection of the image, such as a change in focus or gaze or continued eye scanning, without requiring a conscious input. Eye tracking cameras 24 may be inward-facing (i.e., directed toward the user's eye) cameras as illustrated in FIG. 5. In some embodiments, the ophthalmic system may directly prompt the wearer to indicate if the image was observed, such as by a manual input or by consciously directing the wearer's gaze to the image or to a projected virtual button image. A virtual button image may be projected by the display lens 106, and the wearer's selection of the button may be detected by the eye tracking cameras 24 or through gesture recognition.

In some embodiments, the test described above may be repeated at different portions of the retina, or with different images at the same portion of the retina, to detect areas of macular deficiency. For example, a particular portion of the retina where an image can be seen by the wearer may be determined to be healthy, while a portion of the retina where the same image cannot be seen may be determined to be deficient. In another example, an image consisting primarily of longer wavelength visible light, such as red light, may first be projected. An image consisting primarily of shorter wavelength visible light, such as blue light, may then be projected to the same portion of the retina, and any disparity in visibility to the wearer may be indicative of a loss of color sensitivity in the wearer. In some embodiments, a plurality of images differing in contrast, saturation, hue, intensity, periodicity or spatial frequency, or any other characteristic may be presented to the wearer at different locations on the wearer's retina so as to diagnose various sensitivity losses due to macular deficiencies. Images of the wearer's retina may be used in addition to the results of the testing described above to improve the reliability of macular deficiency diagnosis. Such images may be obtained, for example, by an ophthalmoscope or funduscope, optical coherence tomography, or other imaging technology, various of which are discussed herein.

Macular deficiency testing may be performed in discrete tests on demand, or may be performed periodically and/or repeatedly over time. Repeated analysis may allow for the tracking of progressive macular deficiencies, such as age-related or other macular degeneration. Thus, macular deficiency diagnosis functions may be incorporated into a device worn only for ophthalmic diagnosis, or may be a part of a device worn regularly, such as for entertainment, work, or other purpose(s), so that examinations may be performed automatically at regular intervals and/or at various times of day, week, month, year, etc. In some embodiments, the wearer may be notified before an automatic examination is administered, such as by an alert sound and/or a visually displayed message. Results of macular deficiency testing may be evaluated in real time at the device for evaluation and/or diagnosis, or may be transmitted via the cloud or other network to be evaluated remotely. Remote evaluation and/or diagnosis of anomalies or other macular deficiency may be transmitted back to the device to enable the treatment or compensation methods described below. Unique characteristics of the wearer's eye may be recorded by the device and used for identity verification to ensure the security and privacy of the transmitted data. For example, the camera may image the iris and the processor may perform pattern recognition to determine whether the identity of the wearer corresponds to the identity of the person to whom the test results correspond. The system may then display the test results only if the wearer is the person to whom the test results correspond.

The ophthalmic system may help compensate for macular degeneration by directly projecting light into the retina and specifically targeting healthy cells at the periphery of the macula. By changing where light is projected, the device can selectively target healthy cells and improve the user's quality of vision. In one or more embodiments, the light projecting source comprises a fiber scanning device (FSD) such as a fiber scanning display that may be configured to project images via the waveguides into different portions of the user's eyes. The system may comprise other types of displays that can be configured to selectively project light onto different portions of the retina. This technology may be leveraged to selectively project pixels of an image to the healthy retinal cells, and reduce, minimize, or alter the nature of light projected to the damaged areas. For example, pixels projected to the anomaly may be magnified or made brighter. It should also be appreciated that this technique may also require modifications to the projected image data itself, and the processor may alter the nature of the image such that the user does not notice any difference when viewing the image.

In embodiments comprising an augmented reality device, the system may modify the wearer's view of light from the world. The augmented reality system may detect the light entering the device in real time or near real time, and may modify portions of the light or project additional light to correct for the wearer's macular deficiency. For example, the system may use outward-facing cameras to image the world. The system may project additional light so as to project an image of the world to the wearer. Pixels may be selectively projected to healthy retinal cells, while pixels projected to anomalies may be reduced, minimized, magnified, brightened, or otherwise altered in magnification, intensity, hue, saturation, spatial frequency, or other quality. The system may also be used to generally darken bright rooms and/or brighten nighttime views for wearers with difficulty adjusting to changing light conditions due to macular degeneration.

A similar method may be used in a virtual reality system. The virtual reality system may have a forward and outward looking camera that images the world in front of the wearer and determines the colors of objects. The virtual reality system may reproduce to the wearer an image of the world based on the output of the outward-facing cameras, with some modifications of brightness, magnification, color, and/or other parameters as described above. For example, the virtual reality system may selectively project pixels of the image of the world so as to at least partially mitigate the macular deficiencies of the wearer.

In augmented or virtual reality systems, the system may use outward facing camera(s) to provide alerts to a wearer. Alerts may be based on detection of hazardous conditions not visible to a wearer due to a macular deficiency. The system may determine the presence of an invisible hazard based on a correlation of the images from the outward facing camera(s) with known macular deficiency data of the wearer, such as location of anomalies on the retina. When a hazard in a blind spot is detected, such as an incoming object, a hole in the ground, or other condition, the system may alert the wearer. Alerts may include visual, audio, or tactile notifications. In cases of complete blindness, the system may be configured to detect the presence of a desired item (e.g., a chair, a table, a bed, etc.) and provide proximity information to the wearer, such as by audible notification.

Figure 13:
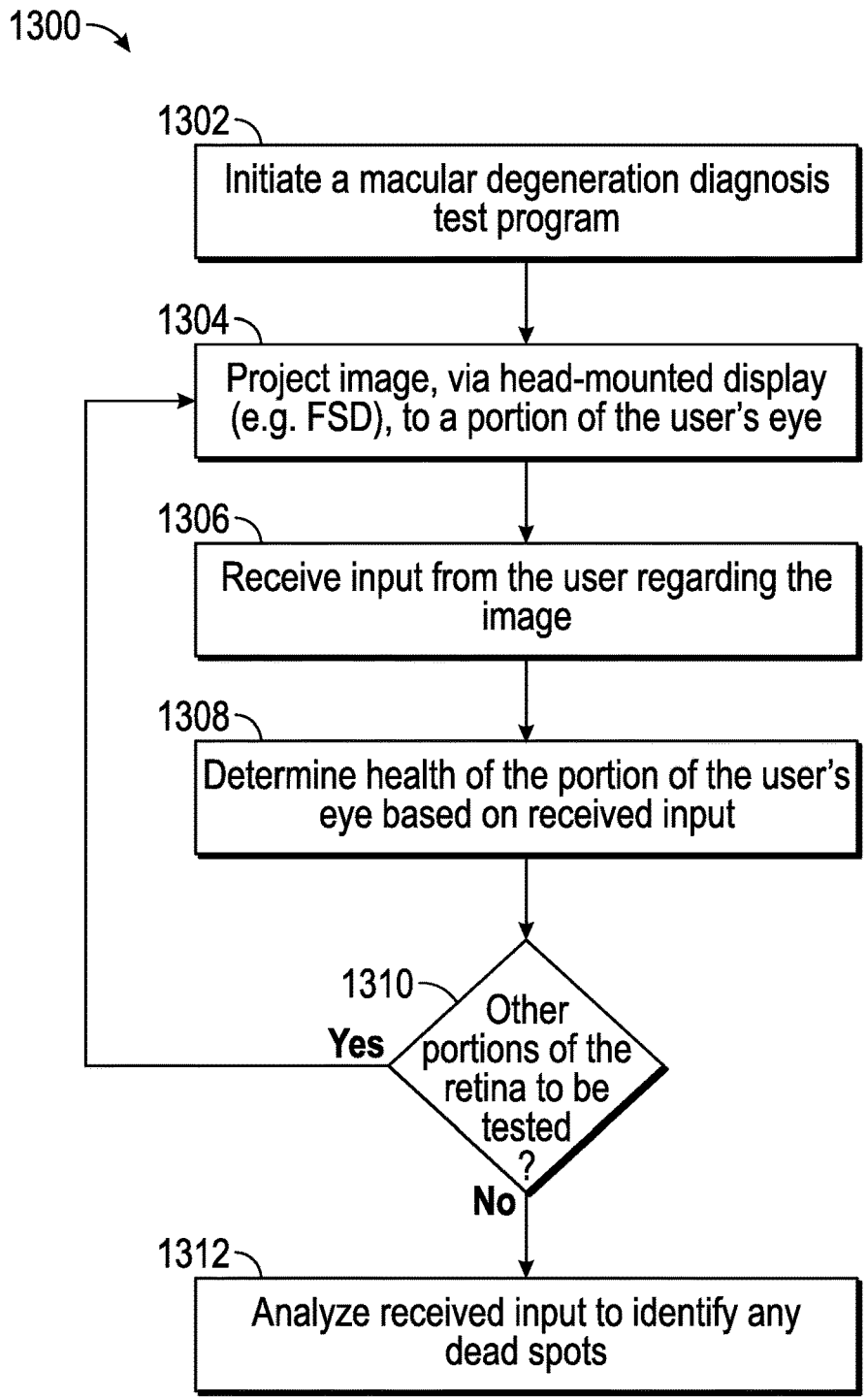
FIG. 13 illustrates an example process flow for detecting dead spots in the macula, according to some embodiments.

In one or more embodiments, the ophthalmic system may diagnose or evaluate the user's eye anatomy to determine a location of macular degeneration. Referring now to FIG. 13, an example process flow 1300 to diagnose, detect, and/or identify any areas of macular degeneration is provided. At 1302, a macular degeneration diagnosis/evaluation program may be initiated. As was the case in many embodiments described above, the program may be pre-coded or downloaded into the ophthalmic system. At 1304, an image is projected, through one or more FSDs, to a particular portion of the user's eye. For example, an image (e.g., a small dot, a small shape, etc.) is directed to the center of the user's eye (e.g., formed at the center of the retina).

At 1306, the system may receive input, through any type of user interface, regarding a quality of the image. For example, the user may be asked to rate a quality of the image from 1 to 10. Or, in another embodiment, the image may be projected with increasing or decreasing visual stimulus, and the user may have to identify when the image appears or disappears from the user's vision, is reduced in visual stimulus, and/or expresses movement. In some embodiments, the system may detect the time required for the wearer to answer, as a wearer taking a long time to answer may be having difficulty seeing the stimulus. Similarly, many such techniques may be used, such as Pelli Robson or sine-wave grating tests. At 1308, based on the received user's input, the system may determine a health of that portion of the user's eye.

At 1310, the system may determine if other portions of the eye need to be similarly diagnosed and/or evaluated. If yes, steps 1304-1308 are repeated. After the various other portions of the eye have been similarly tested, at 1312, the results of the health of the various portions of the user's eye are analyzed, and any anomalies may be identified.

In one or more embodiments, the AR system behaves like a visuscope containing a small graticule target for the measurement of eccentric fixation. The light projecting source (e.g., FSD) may project an image on the patient's retina, and the patient may be asked to look at the center of the target. The position of the foveal reflect relative to the center of the graticular target may indicate whether, and to the extent that, the patient has eccentric fixation. Similarly, a direction and degree of eccentric fixation may be determined through the above process.

If it is determined that the user has one or more anomalies, the ophthalmic system may be configured to project a modified image to the user's eye such that the majority of the image is viewed through healthy peripheral retinal cells, and any pixels projected to the anomalies are adjusted. It should be appreciated that the image to be projected may need to be modified through predetermined algorithms such that the user views the image through the healthy cells, but does not notice any change in the image itself.

Contrast Testing

In one or more embodiments, the ophthalmic system may be configured to test a wearer's contrast sensitivity. Contrast sensitivity testing may be used to assess a wearer's ability to distinguish different luminances in an image. Contrast sensitivity testing may indicate the presence of conditions such as age-related macular degeneration, amblyopia, and/or cataracts.

The ophthalmic system may be configured to administer contrast sensitivity testing by projecting static or changing images. In some embodiments, the ophthalmic system may be a user display device 62 such as shown in FIG. 5, which includes a projecting subsystem 18 configured to project light 38 into the eye of a wearer to form an image in the eye. The user display device 62 includes a display lens 106 which may be mounted to a user's head or eyes by a housing or frame 108. The display lens 106 may comprise one or more transparent mirrors or reflective features positioned by the housing 84 in front of the user's eyes 20 and configured to reflect projected light 38 into the eyes 20 (and also potentially facilitate beam shaping). These reflective surfaces may be partially transmissive to also allowing for transmission of at least some light from the local environment. FIG. 10D also includes another view of an embodiment of a display device comprising a plurality of displays 200, 202, 204, 206, 208 that may be utilized to inject image information into a plurality of respective waveguides 182, 184, 186, 188, 190, each of which may be configured, as described above, to distribute incoming light across the length of each waveguide, for exit down toward the eye. The displays 200, 202, 204, 206, 208 may comprise fiber scanning devices (FSDs) to form the image. Such devices can be configured to project static or changing images of varying contrasts to test a wearer's contrast sensitivity. Such devices may also be configured to simulate foreground and background portions of an image for purposes of contrast sensitivity testing. Foreground and background may be projected from different depth planes, or may be simulate by a single plane. For example, a varying dark foreground plane may be provided in combination with a bright background plane.

The system can then detect a response from the wearer. For example, the image may be a high-contrast image that gradually increases or decreases in contrast. In some embodiments using changing images, the wearer may be prompted automatically or by another user, such as a medical professional, to indicate when the image appears or disappears, and/or to indicate if the wearer can distinguish between images of different luminance. In other embodiments using static images, the user may be prompted to indicate the observed content of the image, such as visible letters, numbers, shapes, or other patterns. The user may then input the wearer's response through a user interface. In some embodiments, the ophthalmic system may increase accuracy by using eye tracking cameras 24 or similar detection methods to observe if an involuntary reaction occurs in response to the projection of the image, such as a change in focus or gaze, or a blink. Eye tracking and/or head pose measurement can further be used for noise filtering in measured data, as well as to ensure that the image is actually projected to the desired part of the retina. Eye tracking cameras 24 may be inward-facing (i.e., directed toward the user's eye) cameras as illustrated in FIG. 5. In some embodiments, the ophthalmic system may directly prompt the wearer to indicate when the image was observed or when the image disappeared, such as by a manual input or by consciously directing the wearer's gaze to the image or to a projected virtual button image. In some embodiments, the wearer may select a virtual button image by looking at a button for a set duration. A virtual button image may be projected by the display lens 106, and the wearer's selection of the button may be detected by the eye tracking cameras 24 or through gesture or voice recognition. In some embodiments, a combination of gaze tracking and gesture recognition may be used to detect a wearer response, e.g., the wearer may indicate a response by looking at a button and blinking one or both eyes to select the button.

In some embodiments, the system may evaluate the wearer's contrast sensitivity using a changing image. An image of relatively high contrast may be projected to the wearer, and the contrast of the image may gradually be reduced. For example, a dark grey image presented against a white background may be gradually lightened until the image becomes white or nearly white. The wearer may be directed to indicate when the image can no longer be discerned due to the similarity to the background color. The test may be repeated multiple times with the same or different images to gain a more accurate estimate of the wearer's contrast sensitivity. For example, an image may change to a different number/letter/shape each time it is lightened, and the wearer may be asked to report the number/letter/shape of the image after each change. Color variation between images and/or glare testing (described in greater detail below) may be incorporated as well.

In some embodiments, the system may evaluate the wearer's contrast sensitivity using a static image. For example, the system may use an image such as a Pelli-Robson contrast sensitivity chart. The Pelli-Robson chart contains multiple rows of capital letters against a white background. The top left letter is printed in black, with each successive row and/or letter being printed in a lighter shade of grey, the bottom row and right letter being printed in a shade close to white. The system may project a Pelli-Robson chart or similar sequence of letters, numbers, shapes, or other patterns of increasing or decreasing contrast. The wearer may be asked to read the sequence of letter or numbers or describe shapes or patterns, providing a response via any of the response methods described above. The system may then determine a contrast sensitivity of the wearer based on the lowest contrast for which the wearer is able to accurately detect the presence of a letter, number, shape, or other pattern.

Similarly, the system may use a sine-wave grating image as a static image for contrast sensitivity testing. A sine-wave grating image includes a series of fuzzy, parallel bars of lighter and darker shades. The bars may vary in width (i.e., spatial frequency) along the axis perpendicular to the bars. A series of sine-wave gratings of various contrast amplitudes (i.e., the difference in light intensity between the darkest and lightest portions of the image) may be shown to the wearer. The wearer may be direct to indicate whether the bars are visible in each image, and if so, which bars are visible. Thus, the system may be able to determine the wearer's contrast sensitivity for various spatial frequencies. In some embodiments, a sine-wave grating test may be combined with glare testing. For example, the device may further comprise at least one inward-facing light source directed at the eyes to simulate glare conditions so as to determine the effect of glare on the contrast sensitivity of the wearer.

Contrast sensitivity testing may be performed in discrete tests on demand, or may be performed periodically and/or repeatedly over time. Repeated analysis may allow for the tracking of progressively decreasing or increasing contrast sensitivity through historical analysis of previous results, as well as for monitoring or detecting abnormalities. Thus, contrast sensitivity testing functions may be incorporated into a device worn only for ophthalmic diagnosis, or may be a part of a device worn regularly, such as for entertainment, work, or other purpose(s), so that examinations may be performed automatically at regular intervals and/or at various times of day, week, month, year, etc. In some embodiments, the frequency of regularly scheduled tests may be automatically adjusted based on trending of the contrast sensitivity testing results. If the system detects that the wearer is experiencing decreased contrast sensitivity, the system may initiate further testing and/or contact a clinician. For example, the system may contact a clinician if it detects that the wearer is having difficulty seeing in dark conditions or exhibiting accommodation/vergence fluctuations associated with struggling to focus. In augmented or virtual reality systems, the system may use outward facing camera(s) to provide alerts to a wearer. Alerts may be based on detection of hazardous conditions not visible to a wearer due to a deficiency in contrast sensitivity. The system may determine the presence of an invisible hazard based on a correlation of the images from the outward facing camera(s) with known contrast sensitivity data of the wearer, such as light conditions in which the wearer has reduced contrast sensitivity. When a hazard is detected that the wearer is unlikely to be able to see, such as an incoming dark object or a hole in the ground during darkened nighttime conditions, the system may alert the wearer. Alerts may include visual, audio, or tactile notifications.

The system may further provide therapeutic functionality based on detected contrast sensitivity deficiency. For example, after detecting/diagnosing a reduced contrast sensitivity, the display device 62 may simulate contrast-enhancing tinted glasses, such as yellow-tinted glasses. Tinting simulation may be accomplished in augmented reality systems by color enhancement or other processing, as described elsewhere herein. In virtual reality systems, an outward-facing camera or cameras may be used to image the world, and a yellow-tint filter may be applied before projecting the image of the world to the wearer through the display device.

Visual Fields

In one or more embodiments, the ophthalmic system may be configured to detect, diagnose and/or compensate for visual field deficiencies. Visual field testing may be used to detect visual deficiencies in the central and/or peripheral vision by analyzing a subject's ability to see stationary and/or moving objects and/or images at various locations of the subject's visual field. Visual field testing may indicate the presence of various conditions, such as scotoma, trauma to the cornea, vitreous tears, traumatically induced cataracts, retinal hemorrhage, retinal detachment, macular degeneration, or intrabulbar hemorrhage (Torsion's syndrome).

The ophthalmic system may be configured to administer visual field testing by determining the ability of a subject to detect an image at various locations within the visual field. In some embodiments, the ophthalmic system may be a user display device 62 such as shown in FIG. 5, which includes a projecting subsystem 18 configured to project light 38 into the eye of a wearer to form an image in the eye. The user display device 62 includes a display lens 106 which may be mounted to a user's head or eyes by a housing or frame 108. The display lens 106 may comprise one or more transparent mirrors or reflective features positioned by the housing 84 in front of the user's eyes 20 and configured to reflect projected light 38 into the eyes 20 (and also potentially facilitate beam shaping). These reflective surfaces may be partially transmissive to also allowing for transmission of at least some light from the local environment. FIG. 10D also includes another view of an embodiment of a display device comprising a plurality of displays 200, 202, 204, 206, 208 that may be utilized to inject image information into a plurality of respective waveguides 182, 184, 186, 188, 190, each of which may be configured, as described above, to distribute incoming light across the length of each waveguide, for exit down toward the eye. The displays 200, 202, 204, 206, 208 may comprise fiber scanning devices (FSDs) to form the image. Such devices can be configured to project a stationary or moving image at a portion of the visual field, such as at the periphery.

The system can then detect a response from the wearer. For example, the image may be a small dot that can be clearly seen if projected in a healthy portion of the visual field but likely would not be seen if projected in a deficient portion. In some embodiments, the wearer may be prompted automatically or by another user, such as a medical professional, to indicate if the wearer saw an image and/or the time at which the wearer observed the image. The user may then input the wearer's response through a user interface. In some embodiments, the ophthalmic system may increase accuracy by using eye tracking cameras 24 or similar detection methods to observe if an involuntary reaction occurs in response to the projection of the image, such as a change in focus or gaze, or a blink. Eye tracking and/or head pose measurement can further be used for noise filtering in measured data, as well as to ensure that the image is actually projected to the desired part of the retina. Eye tracking cameras 24 may be inward-facing (i.e., directed toward the user's eye) cameras as illustrated in FIG. 5. In some embodiments, the ophthalmic system may directly prompt the wearer to indicate if the image was observed, such as by a manual input or by consciously directing the wearer's gaze to the image or to a projected virtual button image. In some embodiments, the system may require verification by the user of a characteristic of the image (e.g., a number, color, letter, shape, etc.) to ensure that the wearer saw the image. A virtual button image may be projected by the display lens 106, and the wearer's selection of the button may be detected by the eye tracking cameras 24 or through gesture recognition. Wearer responses may also be detected by voice recognition. For example, the system may detect a wearer's spoken indication of seeing the image, or of one or more characteristics of the image, as described above.

In some embodiments, the system may be used to evaluate the wearer's visual field perception at the periphery of the field of view. For example, the system may provide a stationary fixation target near the optical axis. While the wearer's gaze is fixed at the fixation target, an image may be projected at an outer portion of the display, outside the wearer's visual field. The image may then be moved inward, toward the fixation target, until it enters the field of view. The wearer may be directed to indicate when the target becomes visible, such as by any of the response methods described above. In some embodiments, the wearer may be directed to describe a characteristic of the image, such as a shape, number of apparent objects, or other feature. The test may be repeated in various quadrants or locations of the periphery of the wearer's visual field, such as at the left, right, top, and/or bottom of the visual field. In embodiments where the ophthalmic system comprises an augmented reality system, a physical object, such as a finger or other suitable object, may be used instead of a projected image, with the display providing the fixation target.

Visual field testing may be performed in discrete tests on demand, or may be performed periodically and/or repeatedly over time. Repeated analysis may allow for the tracking of progression of visual field deficiencies through a historical analysis of previous results. Thus, visual field testing functions may be incorporated into a device worn only for ophthalmic diagnosis, or may be a part of a device worn regularly, such as for entertainment, work, or other purpose(s), so that examinations may be performed automatically at regular intervals and/or at various times of day, week, month, year, etc. In some embodiments, the frequency of regularly scheduled tests may be automatically adjusted based on trending of the visual field testing results.

In augmented or virtual reality systems, the system may use outward facing camera(s) for providing alerts to a wearer. Alerts may be based on detection of hazardous conditions not visible to a wearer due to a visual field deficiency. The system may determine the presence of an invisible hazard based on a correlation of the images from the outward facing camera(s) with known visual field data of the wearer, such as quadrants in which a wearer has reduced peripheral vision. When a hazard in a deficient quadrant is detected, such as an incoming object, a hole in the ground, or other condition, the system may alert the wearer. Alerts may include visual, audio, or tactile notifications.

Laser Photodynamic Therapy

In one or more embodiments, the ophthalmic system may be configured to administer laser therapy to the eye of the wearer to treat various eye conditions. For example, the ophthalmic system may include a laser (e.g. laser (27); FIG. 5), and the eye of the wearer may be subjected to laser light at a selected wavelength and intensity for a particular duration selected to alter eye tissue.

As an example of a condition treatable by the laser therapy, the ophthalmic system may be used to prevent or mitigate age-related macular degeneration (AMD). AMD is a common eye condition that may cause significant visual loss in affected patients. AMD may affect patients in either a dry form or a wet form. The dry form generally causes gradual vision loss from deterioration of the retina. The wet form involves the growth of abnormal blood vessels under the retina called choroidal neurovascularization (CNV). These abnormal blood vessels can leak fluid and/or blood and may affect visual deterioration.

In some embodiments, the ophthalmic system may comprise one or more components for laser photodynamic therapy to combat AMD and/or other such related diseases. Laser therapy has proven to be beneficial in treating AMD. The ophthalmic system may be configured to determine a location of macular degeneration, and administer laser treatment or laser photodynamic treatment to the areas most affected by AMD or any other related disease. In some embodiments, the location of the macular degeneration may be determined by imaging the eye (e.g. using cameras (24); FIG. 5), which may include imaging the retina and tissue surrounding the retina, and/or by visual fields testing to determine the presence and location of choroidal neurovascularization. Once the location of the choroidal neurovascularization is determined, laser light may be selectively applied to that location. The laser may be administrated such that the growth of abnormal blood vessels is mitigated, and in some cases, the laser may help close or reduce the excess blood vessels, in addition to removing or destroying other tissue or blood cells, in the case of wet form AMD.

It will be appreciated that abnormal blood vessel growth may occur in wet AMD (e.g. in the choroid behind the retina, due to Choroidal Neovascularization or CNV). The abnormal blood vessels may leak blood/fluid (including blood cells) onto the central vision area. Advantageously, exposing the abnormal vessels to a laser may cause coagulation at the sites of exposure, thereby reducing the leakage of fluid from the vessels, which in turn may help to keep the macula unobstructed. Causing coagulation using the laser may be referred to as laser photocoagulation. Without being limited by theory, it is believed that the light energy provided by the laser may heat tissue and/or fluid in the blood vessels, which may seal and/or destroy the tissue and/or fluid, including the blood vessels.

The laser photocoagulation may take various forms and treat various conditions. In some embodiments, the photocoagulation treat retinoblastoma. For example, the laser beam may be aimed through the pupil and focused on blood vessels that surround and supply the retinoblastoma tumor, destroying the blood vessels with the heat caused by the beam. As a result, the cancer cells forming the tumor are starved of nutrients and the tumor may be reduced in size or destroyed.

In some embodiments, the laser photocoagulation may be a focal photocoagulation in which specific leaking blood vessels in a small area of the retina, usually near the macula, are identified and sealed. In some other embodiments, the laser photocoagulation may be a scatter (pan-retinal) photocoagulation. Such a scatter treatment may be used to slow the growth of new abnormal blood vessels that have developed over a wider area of the retina. Hundreds of laser burns or exposures may be made on the retina to stop the blood vessels from growing over that relatively wider area.

In one or more embodiments, photodynamic therapy (PDT) may be used to close abnormal blood vessels caused due to AMD without damaging the overlying retina. The ophthalmic system may comprise a separate module to inject a photo-sensitizing agent (Visudyne) into a vein, or the photo-sensitizing agent may be separately injected (e.g. by a medical professional). The photo-sensitizing agent may then travel through the bloodstream and collect in the abnormal vessels under the retina.

The ophthalmic system may then be configured to administer a low-energy laser (e.g., through a laser module of the ophthalmic system) to activate the photo-sensitizer. The activated photo-sensitizer results in a chemical reaction that leads to the closure of the leaking blood vessels.

In one or more embodiments, the ophthalmic system may comprise one or more laser modules to selectively administer laser therapy into the user's eyes. By determining the presence and/or location of the disease or application, an area requiring treatment may be determined, a treatment protocol may be determined, and the laser may be activated such that laser therapy is specifically delivered to particular part(s) of the eye.

In some embodiments, the ophthalmic system may be configured to deliver visual and/or auditory information to the wearer as part of a laser therapy. It will be appreciated that visual information may be displayed on the display (62; FIG. 5) and audible information may be delivered using the speakers (66; FIGS. 3A-3D).

For example, the ophthalmic system may be configured to provide visual and/or auditory instructions to the wearer before exposing the wearer to laser light. In some embodiments, the ophthalmic system is configured to display images to the wearer as part of the laser therapy. It may be desirable in some therapies to orient the eye of the viewer towards a particular direction to, e.g. facilitate access of a particular part of the eye by light from the laser, and/or to keep the eye in a desired orientation. In such embodiments, the ophthalmic system may be configured to orient the eye by displaying an object for the eyes of the wearer to focus on. The object may be maintained at one stable location to facilitate maintaining the eye of the wearer in a particular orientation. In some other embodiments, the displayed object may move to encourage movement of the eye, so that the eye traces out a predetermined pattern. In some embodiments, the ophthalmic system may provide instructions to the wearer after exposure to light from the laser. For example, the ophthalmic system may display instructions and/or provide audible instructions for the wearer to take various actions, e.g. to facilitate recovery after the laser treatment. As examples, the instructions may comprise one or more of shutting the eyelids for a set duration and blinking a set number of times.

Delivery of Medication

In one or more embodiments, as discussed herein, the ophthalmic device may include an augmented or virtual reality system such as the system 62 (FIG. 5) comprising the medication dispensing module (21). The medication dispensing module (21) may be configured to advantageously deliver a prescribed medication to the user or wearer of the display system (62). The dispensing of the medication may be conducted based on a prescribed treatment protocol in some cases.

As an example, the ophthalmic system may be configured to dispense a liquid, such as a saline solution, to the wearer. In some embodiments, the liquid solution may be delivered as a mist (e.g., using outlets 22 in embodiments where one or more outlets is an atomizer), as a spray, as drops, and/or as a stream of liquid. It will be appreciated that the size and shape of the openings in the outlets 22 and/or the speed and pressure of the liquid solution exiting the openings may be selected to output a mist, spray, drops, or stream as desired for a particular application. In one example, the ophthalmic device may be configured to detect whether the eyes of the wearer are dry and to output the liquid out of the outlets 22 upon detecting that the wearer's eyes are indeed dry. For example, the ophthalmic system may be configured to output a mist, and thus a mist may be delivered to patients or wearers suffering from dry eye.

It will be appreciated that the application of a liquid, such as a saline solution, to the eye can aid in the treatment of or alleviate dry eye symptoms associated with various conditions. For example, patients with rheumatoid arthritis may benefit from such a liquid, as corneal and conjunctival drying may be found in such patients. Without being limited by theory, lymphocytic infiltration is believed to destroy the tear-forming glands, thereby causing dryness. As a result, patients may experience blurred vision and/or a foreign body sensation in or around their eyes. In addition, severe drying may cause the cornea to become permanently scarred. The regular application of a liquid, such as a saline solution, to the eye may help to alleviate or prevent dryness, thereby alleviating the effects of dryness noted above. More generally, as discussed herein, the application of the liquid may be used to treat the "keratitis sicca" syndrome, which may also be found in other connective tissue diseases, e.g. Sjögren's syndrome and scleroderma.

In some embodiments, the degree of dryness may be detected using fluorescein dye applied to the eye, e.g., to the cornea. The dye is believed to stain and show green colors in de-epithelialized areas, in which eye tissue has been damaged by dryness. In some embodiments, the ophthalmic system is configured to apply the die to the eye and a camera on the ophthalmic system may be utilized to detect staining of eye tissue, e.g., to detect green colors in the cornea. The amount of stain detected (e.g., the intensity of the green color) may be correlated with and used to determine the amount of liquid applied to the eye, e.g., the amount of saline solution applied to address eye dryness.

In general, in some embodiments, eye dryness may be detected by imaging the eye and detecting indicia of dryness, or of the presence of water. Once a detected parameter reaches a threshold, the ophthalmic system may be configured to apply a liquid to the eye. For example, multispectral imaging and funduscope examinations of the cellular composition and characteristics of the eye may be used. In some other embodiments, eye dryness may be detected by using an inward-facing camera to detect the glint of the eye tissue.

If it is wet, there will be light reflected back, if it is dry the reflection will be less. In some embodiments, a camera and an eye color sensor may be utilized to detect redness in the eye or bloodshot eyes. The level of redness in the eye, or bloodshot eyes, may be interpreted by the ophthalmic system as dryness. In some other embodiments, the degree of blinking may be used to determine that the user's eyes are dry. For example, a rate or frequency of blinking above a threshold may be indicative of dryness or other eye irritation, it may trigger the application of a liquid to the eye. In some embodiments, multiple tests or indicators of dryness may be detected in conjunction with one another to increase the accuracy of a dryness determination.

As disclosed herein, it will be appreciated that the delivery of the medication may be triggered by one or more conditions detected in the environment or the wearer. In some embodiments, the ophthalmic system may include one or more sensors to measure one or more of a temperature of the wearer and/or environment, a duration since an immediately previous delivery of liquid to the eye, an ambient humidity, and a pollen or particulate count. The ophthalmic system may also be programmed with thresholds for various measurements. The ophthalmic system may be further programmed to deliver an appropriate liquid to the eye of the wearer once a particular threshold is exceeded. For example, the presence of foreign objects (e.g., as determined by a pollen or particulate count, or a camera inspection of the eye to detect a foreign object on the eye) over a particular threshold may be considered an eye irritant and a saline or water stream may be applied to the eye to flush the irritants. In some cases, a database, such as a remote database, or a calendar may be consulted to validate or determine the likelihood of the presence of foreign objects. For example, it will be appreciated that pollen from different types of plants may be present at different times of the year and a known sensitivity of the user to a particular type of pollen may cause the threshold for the application of medication to the eye to be lowered at a time of year when that particular type of pollen is known to be present. At other times of the year, the threshold may be raised by the ophthalmic system. In some embodiments, the presence of other irritants, such as chemicals or liquids, e.g., chlorine, may be detected or inferred. For example, the user may be determined, by imaging his/her surroundings and/or detecting a location of user, to be in a chlorinated pool. Upon exiting the pool, the ophthalmic system may be configured to flush the eye to remove chlorinated water. In another example, a treatment protocol may specify the delivery of the liquid a given number of times over a time period and the ophthalmic system may be configured to deliver the liquid at regular time intervals within that time period.

In some embodiments, the liquid may be delivered in conjunction with other types of therapy. For example, phototherapy or laser therapy may benefit from the application of photosensitive liquids, e.g., photosensitive dyes, to the wearer. In some embodiments, ultraviolet-activated riboflavin treatment for myopia may be conducted using Vitamin B2 (riboflavin) which is applied onto the cornea and then ultraviolet A (UVA) light is directed to the eye (e.g., from the ophthalmic system or an external source) for a set duration (e.g., 20 minutes) to strengthen, stiffen and flatten a distorted cornea. The photosensitive liquids may react with the applied light to improve contrast and/or the ability to image features in the eye. For example, a dye may selectively accumulate on or in particular material or structure, e.g., blood vessels, thereby improving the ability of imaging devices (e.g., cameras 24) to image those blood vessels in the eye. As another example, eye diagnostics may benefit from application of a pupil dilating liquid to the eye. The dilation may be utilized to provide a better view into the interior of the eye.

Platform for other Therapies

Advantageously, the proximity of the ophthalmic system to the user allows the ophthalmic system to dispense other types of therapy to the user based on a treatment protocol. Examples of these other types of therapy may include vibration at specific times (e.g., massage the face or skull), sound (e.g., binaural beats, etc.), temperature (e.g., cooling, warming means), to name a few.

To facilitate these other therapies, with reference again to FIG. 5, in some embodiments, the display device may comprise an actuator (30) connected to a terminal part (30*a*) that is configured to contact the wearer, to administer vibration therapy to the wearer. As illustrated, the actuator (30) may be mounted on the frame (108) and the terminal part (30*a*) may be positioned to contact the face or skull of the wearer. The actuator (30) may be configured to move the terminal part (30*a*) back-and-forth to provide vibration to the wearer, e.g., by applying and removing pressure at the point of contact with the wearer. While a single actuator (30) is illustrated, it will be appreciated that the ophthalmic system may include multiple actuators (30), mounted on the frame (108), and/or otherwise attached to the wearer and in electronic communication with the ophthalmic system.

Examples of suitable actuators include piezoelectric actuators, which may advantageously be made small and can generate vibrations in a wide range of frequencies or intervals. Other examples of actuators include eccentric cams, Eccentric Rotating Mass (ERM) vibration motors (such as pager motors), and Linear Resonant Actuators (LNAs). In some embodiments, these actuators may be used to cause vibration of the frame (108), thereby distributing the vibration over the multiple points of contact that the frame (108) makes with the wearer, rather than just at a single point of contact with the actuator. In some embodiments, the actuator (30) may also be configured to move along two or more axes to, e.g., provide a brushing or kneading motion at the point of contact with the wearer.

In some embodiments, one or more actuators (30; FIG. 5) may provide tactile or vibration therapy to the wearer. For example, the actuator (30) may move to provide vibrations at the point of contact with the wearer, and/or may vibrate the frame (108) to provide vibrations to the wearer through the frame (108). As another example, as noted above, the actuator (30) may be configured to brush or move along the surface of the wearer's face or skull. In some embodiments, the ophthalmic system may be configured to have the actuator (30) apply pressure at a particular location for an extended duration to, e.g., provide an acupressure treatment. In some embodiments, the actuator (30) may be configured to vibrate at ultrasonic frequencies to emit ultrasonic sound which provide a non-contact haptic ultrasound treatment.

In some embodiments, the ophthalmic system may be configured to provide temperature therapy to the wearer. With continued reference to FIG. 5, the display device may include a temperature regulator (29) in communication with a heating/cooling outlet (28) via the connector (28*a*). In some embodiments, the temperature regulator (29) may include resistive heating filaments and/or a cooler with cooling coils containing a refrigerant. In some other embodiments, the temperature regulator (29) may be a thermoelectric heater or cooler that makes use of the thermoelectric effect to achieve the desired degree of heating or cooling. The temperature regulator (29) may also include a gas source (e.g., pressurized air), which delivers the gas to the heating/cooling outlet (28) via the connector (28*a*). In such arrangements, the connector (28*a*) may be a channel or tube, and the heating/cooling outlet (28) may be an opening through which the gas exits and is directed to the wearer, e.g., to one or more eyes of the wearer. The temperature regulator (29) heats or cools the gas as desired, e.g. for a particular therapy, before the gas is directed to the viewer.

In some embodiments, the connector (28*a*) may be a thermal pipe which provides and/or removes heat from the frame (108) and the heating/cooling outlet (28) may simply be the point of contact between the connector (28*a*) and the temperature regulator (29). In such arrangements, one or more thermal pipes may also be arranged along the frame (108). Such an arrangement may be utilized to regulate the temperature of the frame (108), which may also allow therapies based on temperature to be applied around the eyes of the wearer. In some embodiments, the temperature regulator (29) may be integrated into the frame (108).

In some embodiments, the ophthalmic system may be configured to conduct a temperature therapy using the heater and/or cooler (29; FIG. 5). For example, as discussed herein, heated and/or cooled streams of air (e.g., through the heating/cooling outlet (28)) may be applied to the wearer, e.g. to one or more eyes of the wearer. As another temperature therapy, the frame (108) may be heated and/or cooled to subject the eyes of the viewer and the neighboring areas to different temperatures as part of a therapy protocol. In one or more embodiments, the ophthalmic device may also comprise EEG sensors (31; FIG. 5) to map brain activity. The EEG sensors (31) may detect any abnormal activity or pattern in the brain and report out to the user and/or clinician. This may be especially useful for patients immediately after brain surgery or for at-risk patients. The ophthalmic device may be pre-programmed with an EEG sensing module to analyze data collected by the EEG sensors (31). While a single EEG (31) sensor is illustrated, it will be appreciated that the ophthalmic device may include multiple EEG sensors contacting the wearer at multiple locations.

In other embodiments, the ophthalmic system may be configured to dispense other types of medication or therapies based on a treatment protocol. Advantageously, the proximity of the ophthalmic system to the wearer allows various other types of therapy to be readily administered to the wearer, including therapies based on, for example, direct physical contact with the wearer, sound, and/or temperature. These other types of therapy may include tactile stimulation, including vibration at specific times (e.g., massage the face or skull), sound (e.g., binaural beats, etc.), temperature (e.g., cooling, warming means), to name a few.

In some embodiments, the ophthalmic system may be configured to administer sound therapy to the user using a speaker, such as the speaker (66; FIGS. 3A-3D). For example, the ophthalmic system may be configured to deliver binaural beats to the ears of the wearer through the speaker (66). A pair of the speakers (66) may be provided, one for each ear of the wearer. As another example of sound therapy, the ophthalmic system may be configured to direct sound waves to the eye of the wearer. For example, in some embodiments, the ophthalmic system may include one or more speakers, or sound transducers, (67; FIG. 5). The speakers (67) may be attached to the frame (108) may be directed towards the eye of the wearer to provide sound stimulation to the eye.

It will be appreciated that these therapies may be applied based on determinations of the wearer's physical and/or mental state. For example, the ophthalmic system may include the EEG sensor (31), which may be utilized to detect the presence of triggers for launching one of these other therapies. In some embodiments, the EEG sensor (31) may be utilized to detect electrical activity in the brain that is indicative of stress. Upon detecting such activity, the ophthalmic system may be configured to apply massage therapy to the wearer with the goal of reducing stress levels.

In some embodiments, the ophthalmic system may be configured to deliver alerts to the wearer (e.g., a patient) as part of the delivery of medication to the wearer or as part of other therapies. It will be appreciated that the alert may be visual or based on other action which may be sensed by the wearer, including sound-based alerts, pressure-based alerts, and/or temperature-based alerts. For example, the alerts may take the form of audio notifications, tapping/pressure on the user by the ophthalmic system, applying heat or removing heat, or directing airstream to the wearer. In one or more embodiments, the patient may receive an alert directing them to keep their eyes open, and/or focus on a visual cue while the medication or any of the above therapies is delivered. In some embodiments, keeping their eye open may be facilitated by displaying an object or image(s) for the wearer to fixate on. In some other embodiments, the alert may instruct or otherwise encourage the wearer to focus on a displayed visual cue. The visual cue may move, and the tracking of that moving cue by the wearer's eyes may be utilized to provide different orientations and/or views of those eyes. It will be appreciated that the display system may set visual alerts at any desired depth plane, thereby allowing the alerts to be clearly seen and/or read without the wearer needing to change accommodation and/or vergence.

As disclosed herein, the ophthalmic device may be an augmented reality head-mounted ophthalmic system or a virtual reality head-mounted ophthalmic system. It will be appreciated that the augmented reality head-mounted ophthalmic system may be configured to pass light from the world into the eye of the wearer wearing the head-mounted ophthalmic system. On the other hand, the virtual reality head-mounted ophthalmic system may be configured to not pass light from the world in front of the head-mounted ophthalmic system into the eye of the wearer wearing the head-mounted ophthalmic system. In such virtual reality systems, light from the outside world would not form an image of the world in the eye of the wearer. Rather, in some embodiments, images of the world seen by a wearer wearing the system are limited to those displayed by the display in the ophthalmic system.

Figure 25:
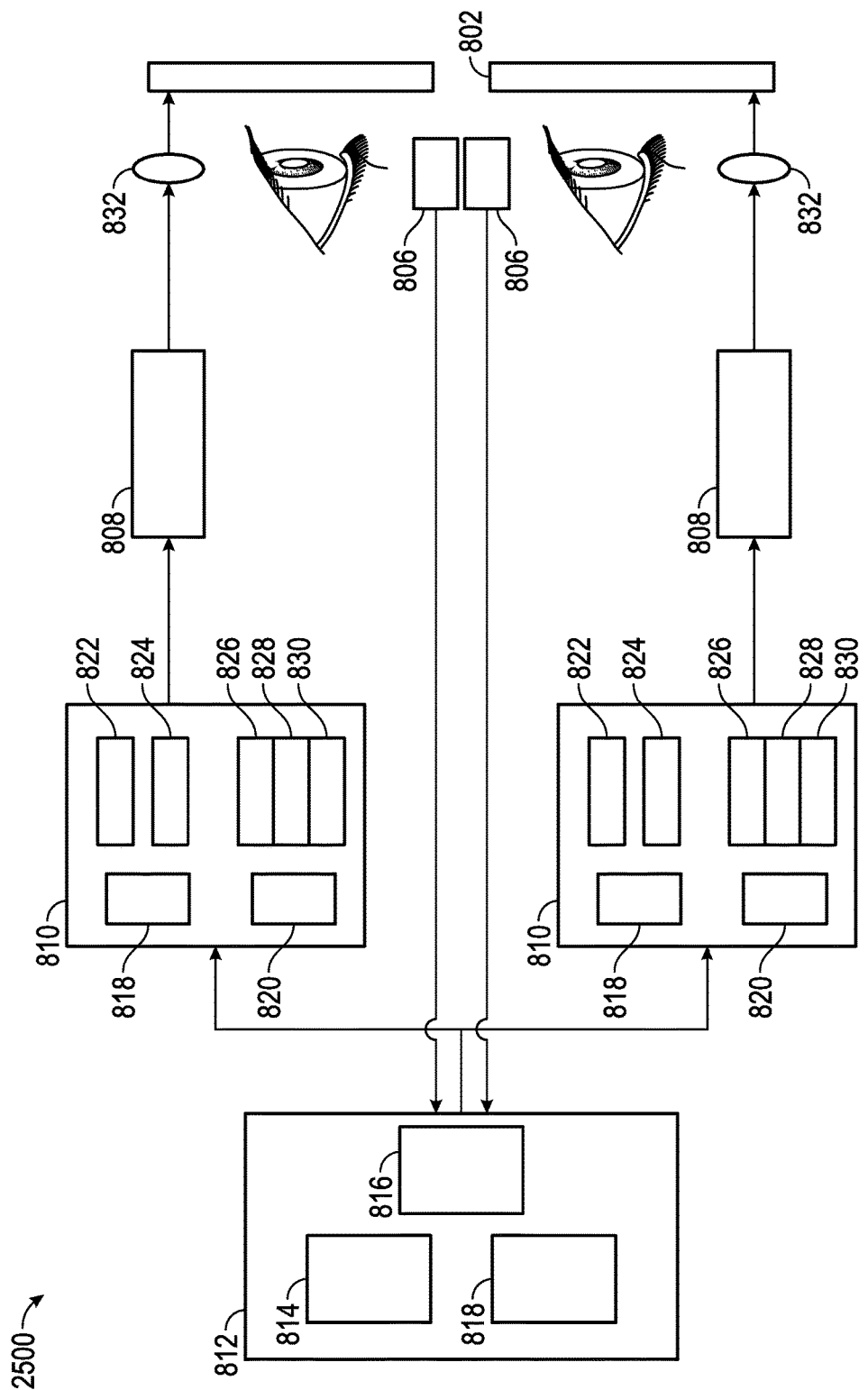
FIG. 25 illustrates a schematic view of an exemplary configuration of an health system.

Referring now to FIG. 25, an exemplary embodiment 2500 of the ophthalmic system is briefly described. It should be appreciated that other embodiments of the ophthalmic system may comprise additional components (e.g., light emitting module, ultrasound module, imaging module, electrodes, etc.) FIG. 25 illustrates a basic structure for the ophthalmic system, but it should be appreciated that other components may be used in conjunction with the ophthalmic system for different applications. The ophthalmic system generally includes an image generating processor 812, at least one FSD (or any other spatial light modulator) 808, display or image processing circuitry 810, a coupling optic 832, and at least one optics assembly that 802. The system may also include an eye-tracking subsystem 808.

As shown in FIG. 25, the display circuitry may comprise circuitry 810 that is in communication with the image generation processor 812, a maxim chip 818, a temperature sensor 820, a piezo-electrical drive/transducer 822, a red laser 826, a blue laser 828, and a green laser 830 and a fiber combiner that combines all three lasers 826, 828 and 830.

The image generating processor is responsible for generating images to be ultimately displayed to the user. The image generating processor may convert an image or video associated with treatment or diagnostic content to a format that can be projected to the user in 3D. For example, in generating 3D content, the virtual content or images may need to be formatted such that portions of a particular image are displayed on a particular depth plane while other are displayed at other depth planes. Or, all of the image may be generated at a particular depth plane. Or, the image generating processor may be programmed to feed slightly different images to right and left eye such that when viewed together, the image appears coherent and comfortable to the user's eyes.

In one or more embodiments, the image generating processor 812 delivers images and/or light to the optics assembly in a time-sequential manner. A first portion of a virtual scene may be delivered first, such that the optics assembly projects the first portion at a first depth plane. Then, the image generating processor 812 may deliver another portion of the same scene such that the optics assembly projects the second portion at a second depth plane and so on.

The image generating processor 812 may further include a memory 814, a CPU 818, a GPU 816, and other circuitry for image generation and processing. The image generating processor may be programmed with the desired virtual content to be presented to the user of the ophthalmic system. It should be appreciated that in some embodiments, the image generating processor may be housed in the wearable ophthalmic system. In other embodiments, the image generating processor and other circuitry may be housed in a belt pack that is coupled to the wearable optics.

The ophthalmic system also includes coupling optics 832 to direct the light from the light modulator (e.g., FSD) to the optics assembly 802. The coupling optics 832 may refer to one more conventional lenses that are used to direct the light into the DOE assembly. The ophthalmic system also includes the eye-tracking subsystem 806 that is configured to track the user's eyes and determine the user's focus.

In one or more embodiments, software blurring may be used to induce blurring as part of a virtual scene. A blurring module may be part of the processing circuitry in one or more embodiments. The blurring module may blur portions of one or more frames of image data being fed into the DOE. In such an embodiment, the blurring module may blur out parts of the frame that are not meant to be rendered at a particular depth frame or blurring may be used to diminish the transitions between depth planes.

Outward Looking Camera

As described herein, in some embodiments, the system may include one or more outward-looking (e.g. forward-looking) cameras to capture image information from the ambient environment, and this image information may subsequently be displayed as images presented to the wearer of system. In some embodiments, the images presented by the system to the wearer may be re-rendered to provide images that are modified relative to images originally captured by the camera. The modification may be performed by a processor, e.g., an image processor, that receives the image information captured by the cameras and processes the image information to include changes that are later communicated to light modulators that generate the displayed image. In some embodiments, the wearer's view of the world and particular features in that view may be modified as desired for diagnostic or therapeutic purposes.

With reference to FIG. 5, the head-mounted health system may include one or more outward-facing cameras 16 (e.g., two outward-facing cameras) to image the world around the wearer. The system may process the image information (e.g., image(s)) captured by the camera(s) 16 to re-render the image information for display to the wearer. In some embodiments, the device may project light from the display device 108 to the wearer's eye so as to project a re-rendered image of the world to wearer.

In some embodiments, in the re-rendering step, the processor may be configured to selectively modify properties of the image that will be displayed to the wearer. For example, the processor may be configured to selectively alter portions of the image based on a distribution of health and unhealthy cells in a retina of the wearer, e.g., so that those portions are projected to healthy retinal cells, while portions of the image projected to unhealthy retinal cells may be reduced, minimized, magnified, brightened, or otherwise altered in magnification, intensity, hue, saturation, spatial frequency, or other quality. Similarly, any desired portion of the image may be modified in magnification, intensity, hue, saturation, spatial frequency, or any other quality as required to mitigate and/or compensate for any known ophthalmic condition of the wearer. The wavefront of the image may also be modified and/or reshaped so as to mitigate focus-related conditions in some embodiments. In other examples, the system may also be used to generally darken bright rooms and/or brighten nighttime views for wearers with difficulty adjusting to changing light conditions, by, e.g., substituting all or portions of the user's view of the world with re-rendered content, which may present a darker or lighter view of the world, as desired. In another example, the system may modify or shift colors to enhance the vision of the wearer, including colorblind wearers. It will be appreciated that the system may include an augmented reality display or a virtual reality display, and that re-rendering image information as disclosed herein may be applied in displaying content on either type of display.

Continuing with FIG. 5, in some embodiments, the health system may have one or more forward and outward looking cameras 16 that image the world around (e.g., in front of) the wearer. The system may be configured to determine various characteristics of the image, such as the intensity, hue, saturation, and/or spatial frequency of regions of the image. The system may process, re-render, and reproduce to the wearer, via the display device 108, an image of the world based on the information captured by the outward-facing cameras 16, with some modifications of brightness, magnification, color, wavefront, and/or other parameters as described above. In some embodiments, the display device may project only a partial image to the eye of the wearer, with the partial image augmenting the light passing through the display to the eye of the wearer to produce the desired modification. For example, the augmented reality system may shift the color of portions of the image based on a known color detection deficiency of the wearer, as described elsewhere herein. In another example, the augmented reality system may enhance the difference in brightness between two or more portions of the image based on a known contrast sensitivity deficiency of the wearer.

In some embodiments, the display may be a light field display, such as described herein.

Example Systems with Transmissive and Reflective Adaptive Optics

In one or more embodiments, the ophthalmic system may be configured to include reflective adaptive optics to provide correction for conditions such as spherical aberrations, astigmatism, and/or higher order aberrations. Some aberrations, such as myopia, hyperopia, and astigmatism, and/or higher order aberrations, may be corrected by a system comprising a transmissive adaptive optics element, such as the system 2900 depicted in FIG. 29A. Treatment of myopia, hyperopia, and astigmatism, and/or higher order aberrations with transmissive adaptive optics is discussed in greater detail elsewhere herein. The system 2900 of FIG. 29A may be incorporated in any of the wearable augmented or virtual reality devices described elsewhere herein.

In an augmented reality device, the system 2900 may include an adaptive optics element such as a transmissive variable focus element 2902 (VFE) located at a pupil conjugate plane 2904 and configured to modify the incoming light approaching the pupil 2906 of the eye to correct for aberrations. In some embodiments, light from the world may be transmitted from the world through the transmissive VFE 2902 to the pupil 2906 of an eye 2908 of the wearer by a series of lenses 2910, 2912, 2914, 2916. The light from the world may enter as a wavefront of collimated light, and each pair of lenses 2910/2912, 2914/2916 may form an afocal telescope, wherein the input and output of the telescope can comprise collimated light. As shown, the transmissive VFE is between the two afocal telescopes. In some embodiments, the system comprises a relay, and the system can be configured to be telecentric. A fiber scanning display 2918 may project additional light to form augmented reality images in the eye 2908. To combine the output beam 2920 of the fiber scanning display 2918 with the light entering the system 2900 from the world, light from the fiber scanning display 2918 may be projected to a beam splitter 2922 such that the corrective VFE 2902 is disposed between the beam splitter 2922 and the eye 2908. Thus, both light from the world and light from a fiber scanning display 2918 may be directed to the eye of the wearer, with the images from both light sources being potentially corrected for the wearer's aberrations such as myopia, hyperopia, and/or astigmatism by the transmissive VFE 2902 or other adaptive optic element.

Figure 29A:
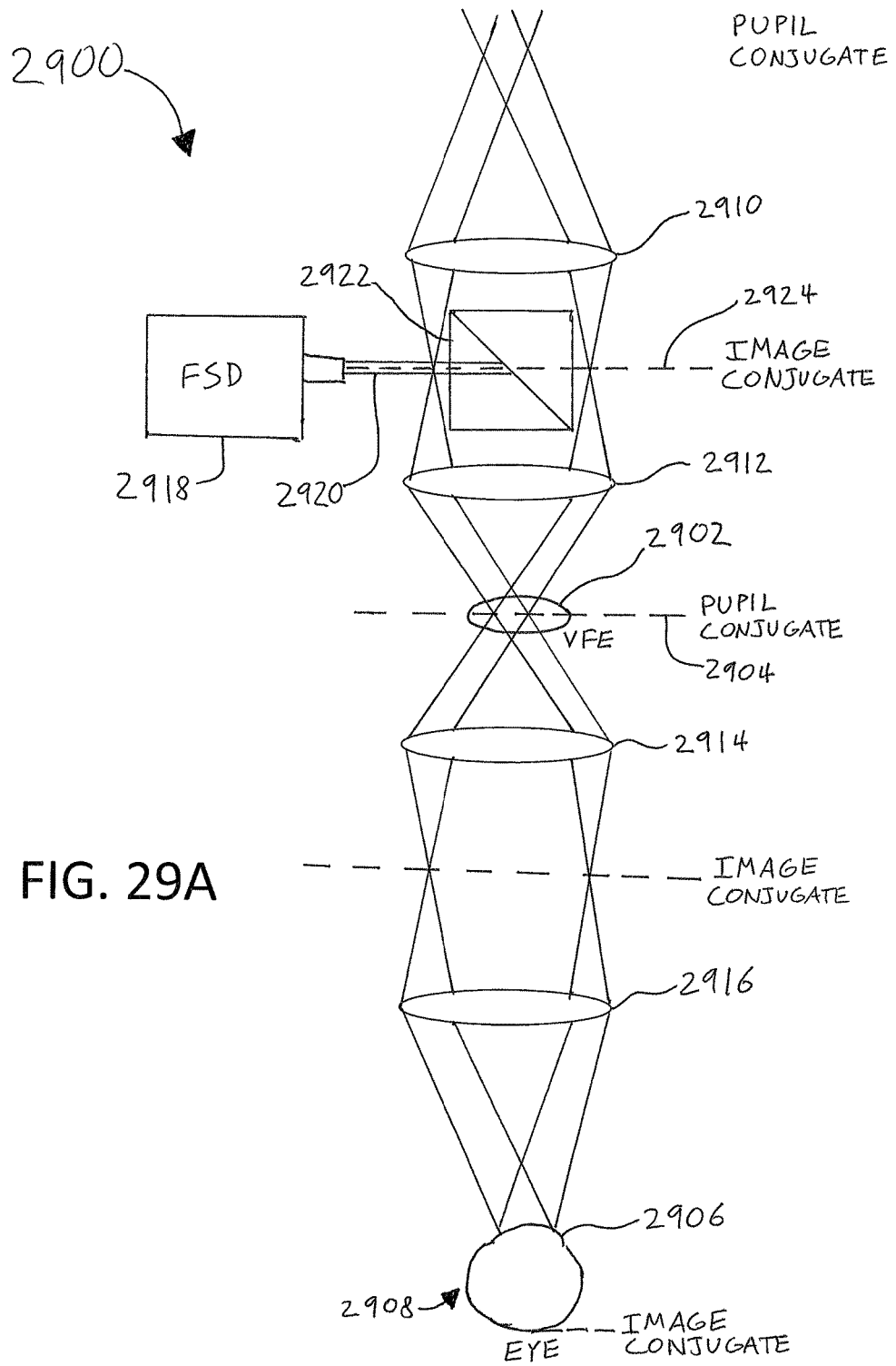
FIG. 29A schematically illustrates an example embodiment of a system with transmissive adaptive optics.

A system such as the reflective system 2901 depicted in FIG. 29B may be able to provide similar correction for wearers with myopia, hyperopia, and astigmatism, and/or higher order aberrations. Rather than a transmissive VFE 2902 as shown in FIG. 29A, embodiments of a reflective system may include a reflective VFE 2926 (e.g., a movable membrane mirror or other deformable mirror). The treatment of myopia, hyperopia, and astigmatism, and/or higher order aberrations with reflective adaptive optics is discussed in greater detail elsewhere herein.

A system incorporating a reflective VFE 2926 (e.g., a movable membrane mirror or other deformable mirror) may comprise many of the same elements as in the system 2900 of FIG. 29A, such as lenses 2910, 2912, 2914, and 2916 which may comprise afocal telescopes. The output beam 2920 of a fiber scanning display 2918 may be combined with light from the world at a beam splitter 2922 located at an image conjugate plane 2924. In some embodiments, the system comprises a relay and can be configured to be telecentric. A second beam splitter 2928 may be included as shown in FIG. 29B. Light from the world may enter beam splitter 2928, where at least a portion is reflected to the reflective VFE 2926, located at a pupil conjugate plane 2904. The reflective VFE 2926 may comprise, for example, a MEMS device or a deformable mirror, for example, such as described herein. The corrected wavefront may then be reflected through lenses 2914, 2916 to enter the eye 2908 of the wearer at the pupil 2906. The correction applied to the wavefront at the reflective VFE 2926 may cause the wavefront to form a normal image of the light from the world and the light from the fiber scanning display 2918 despite the presence of a higher order aberration, as described elsewhere herein.

Variations of these designs are also possible.

CONCLUSION

As discussed herein, the disclosed head-mounted displays may advantageously form part of a user-wearable diagnostic or health system, which may be used for performing health-related diagnostics, monitoring, and therapeutics on the user. In some embodiments, the health-related diagnostics, monitoring, and therapeutics may include ophthalmic diagnostic analyses, monitoring, and therapies. In view of the disclosure herein, however, it will be appreciated that the diagnostic or health system is not limited to ophthalmic applications and may be applied generally to health-related diagnostics, monitoring, and therapeutics.

As discussed herein, a user-wearable diagnostic system is provided. The user-wearable diagnostic system may comprise a frame configured to mount on the user and an augmented reality display attached to the frame and configured to direct images to an eye of the user. A light detector may be attached to the frame and configured to detect light reflected from an eye of the user. The user-wearable diagnostic system also comprises a processor configured to conduct a health analysis of the user based on light detected by the light detector or other detectable parameters. Various details of the above-noted features have been described above, and some of the description is reprised in turn below, as an aid to the reader.

In some embodiments, the frame may correspond to the frame (64) (FIGS. 3A-3D), and the augmented reality display may correspond to the display (62) (FIGS. 3A-3D). The augmented reality display may comprise a waveguide configured to allow a view of the world through the waveguide and to form images by directing light out of the waveguide and into an eye of the user. The waveguide may be part of a stack of waveguides, and each waveguide of the stack may be configured to output light with different amounts of divergence in comparison to one or more other waveguides of the stack of waveguides. In some embodiments, the waveguides and waveguide stack may correspond to the waveguides (182, 184, 186, 188, 190) and stacked waveguide assembly (178), respectively, of FIGS. 10D-10E, 27, and 28A-28G.

It will be appreciated that the display may be configured to both output light to or image information from the user, and to block light from the outside world. In some embodiments, the diagnostic system may be configured to conduct the health analysis by occluding certain areas of a field of vision of the user.

In some embodiments, the processor may correspond to the local processing and data module (70) or the remote processing module (72) (FIGS. 3A-3D). It will be appreciated that the processor may be configured or programmed to conduct any of the health analyses disclosed herein.

In some embodiments, the light detector may be an inwardly-facing (user-facing) image capture device, such as an inwardly-facing camera. The camera may be an infrared camera in some cases. The camera may correspond to the camera (24) of FIG. 5 in some embodiments. Other examples of light detectors include the photodetectors (2352) of FIGS. 23A and 23B.

The processor may be configured to conduct a health analysis using data provided by the light detector, the data being derived from detecting light reflected from one or both eyes of the user. For example, the light detector may be configured to track the movement of the eyes of the user. In some embodiments, the user-wearable diagnostic system may comprise a light source configured to emit light towards the user, and the light detector may be configured to detect all or portions of the emitted light reflected by the user. The light source may be configured to emit light of multiple wavelengths, and the diagnostic system may be configured to change the emitted wavelength based on the features of the user to be imaged. In some applications, the light source may be configured to emit infrared light or non-visible light, which may have advantages in allowing imaging of the eye or surrounding tissue without being seen by the user. The light source may correspond to the light sources (26) of FIG. 5 and/or the light source 2354 of FIGS. 23A and 23B in some embodiments. It will be appreciated that the light source may include a plurality of discrete light emitters that are configured to, e.g., emit light of different wavelengths than other light emitters, and light of different wavelengths may be emitted by selectively powering the light emitters.

In some embodiments, the augmented reality display is a fiber scanning display comprising fibers configured to project light in a pattern to form images in the eye of the user. In some applications, at least some fibers of the fiber scanning display may be used as part of the light detector to receive or capture light to image the eye of the user. Advantageously, light propagation in the fibers may occur in multiple directions and the same fibers of the fiber scanning display may be configured to project light to the eye (e.g., from a spatial light modulator or directly from a light source), and to also receive reflected portions of the light during the health analysis and to direct the light to, e.g., an image sensor. In some embodiments, the fiber scanning display may be configured to change a wavelength of light projected into the eye, e.g., by selectively powering a light emitter that projects light into a scanning fiber which propagates the light to be projected into the eye. Such changes in wavelength and the subsequent reflection and detection of light of those wavelengths may advantageously be used to provide depth information for tissue that the light is reflected from. In some embodiments, the fiber scanning display may correspond to a display utilizing the fibers (352, 362) of FIGS. 28A and 28B.

The processor may be configured to conduct various health analyses based on the receipt of light by the light detector. For example, the light detector may be configured to monitor an eyelid of the user, and the processor may be configured to conduct the health analysis based on this eyelid monitoring. As another example, the light detector may be configured to monitor a pupil of the user, and the processor may be configured to conduct a health analysis based on this pupil monitoring.

In some embodiments, the light detector may be configured to image a fundus of the eye of the user. In some health analyses, the light detector may be configured to image microcirculation in the fundus. As noted herein, microcirculation abnormalities may be indicative of various health concerns, which may be detected using information derived from the microcirculation imaging. For example, the processor may be configured to analyze brain health and heart health based on information from this microcirculation imaging. In another example, the processor may be configured to detect hypertension based on the imaged microcirculation.

In some embodiments, the processor may be configured to conduct the health analysis by detecting, using information captured by the light detector, one or more of: eye movements, eye movement patterns, blinking patterns, eye vergence, fatigue, changes in eye color, depth of focus of the eye, changes in focal distance for the eye, eye fatigue, dry eye, and hypertension. In some embodiments, pattern recognition may be applied to information received from the light detector as part of the health analysis.

In some embodiments, the processor may be configured to conduct the health analysis by detecting an intraocular pressure of the eye. This may be accomplished, for example, by projecting light into the eye and using the light detector to detect the pattern, density, or amount of backscattered light received from the eye.

As discussed herein, the user-wearable health or diagnostic system may provide light to the user's eyes through, e.g., the display (e.g., display (62) (FIGS. 3A-3D)) or another light source (e.g., light emitting module (27) (FIG. 5)). In some embodiments, the processor may be configured to conduct a health analysis by directing the augmented reality display to provide light stimulation to the eye of the user.

As discussed herein, the display may advantageously be configured to display images on different depth planes and/or at different locations within the user's field of view, which allows the display to cause the eyes to focus and converge at a given depth plane and/or in a given direction. In some health analyses, this ability to cause the eyes to focus and converge on different depth planes as desired may be utilized for diagnostic purposes. One or more images may be displayed at varying depths and images of one or both of the eyes focused at these varying depths may be captured for the health analysis. In addition or alternatively, an image may be displayed to cause the eyes to focus and converge in a particular direction and/or depth plane. This may be utilized, for example, to obtain a desired view of the eye without moving the light detector.

In some embodiments, the light detector may comprise a plurality of photodetectors and the photodetectors may be arranged at different angles to the user. Such a configuration may be used to capture different views of the eye, e.g., different simultaneous views, for a health analysis. Examples of such photodetectors include the photodetectors (2352) of FIGS. 23A and 23B.

It will be appreciated that noise and/or visual artifacts may be present in the images captured by the light detector. The diagnostic system may be configured to track eye movements and reduce noise in these images based on the tracked eye movement and/or other body motion such as head movements. For example, movement of the eye may provide different views of the eye, which may be used to determine whether an observed feature is an optical artifact present only in a particular view, or whether the observed feature is indeed present in the eye (and, thus, present in a multiplicity of different image views). It will be appreciated that head movements may be tracked using an accelerometer attached to the head-mounted display system.

As used herein, it will be appreciated that imaging and light detection may occur in visible and non-visible wavelengths. Examples of light of non-visible wavelengths include infrared light.

It will be appreciated that various other sensors may be provided with the user-wearable health or diagnostic system to conduct non-eye diagnostics of the user. An example of such other sensors comprises an EEG sensor. The processor may be configured to utilize data obtained from the EEG sensor to conduct the health analysis by detecting brain activity. In some embodiments, the system is configured to issue an alert triggered by the detection of brain activity. The alert may be issued to one or both of the user and a clinician.

In some other embodiments, the other sensors may comprise one or more sensors selected from the group consisting of temperature sensors, pressure sensors, light sensors, non-invasive blood glucose sensors, and ETCO2 sensors.

The other sensors may also comprise one or more sensors configured to monitor one of more conditions of the ambient environment of the user, and the system may be configured to conduct the health analysis using data collected by the one or more sensors. For example, the one or more sensors may comprise a camera configured to image the ambient environment. The processor may be configured to use information from the camera to identify and analyze food, drug, nutrients and toxins that the user intakes. In some embodiments, the processor may be configured to correlate identified food, drug, nutrients or toxins with other user health data. In some embodiments, the processor may be configured to determine a head pose of the user based on information received from the camera. The camera may correspond to a camera (16) of FIG. 5 in some embodiments.

In some embodiments, the other sensors may comprise one or more of location and orientation sensors. Examples of location and orientation sensors comprise an accelerometer, a GPS sensor, a compass, a gyroscope, an inertial measurement device, and a camera. In some applications, the processor may be configured to conduct the health analysis by determining environmental information based upon a location of the user. The processor may be configured to conduct the health analysis by accessing information characterizing the location. Examples of information characterizing the location comprise one or more of pollen count, demographics, air pollution, environmental toxins, information from smart thermostats lifestyle statistics, or proximity to a health-care provider. In some embodiments, the processor may be configured to access cloud-based databases to obtain information characterizing the location. The information characterizing the location may be combined by the processor with information obtained from one or more sensors of the diagnostic system to arrive at a result for the health analysis.

In some embodiments, the other sensors may comprise a microphone, which may be used to gather information about the ambient environment and/or information about the user's activities. For example, the microphone may capture sounds indicative of chewing by the user and the processor may be configured to determine that the user is indeed chewing food. It will be appreciated that eating of food may be associated with various changes in physiological state and, as such, the timing of food intake may be a useful variable to take into account when diagnosing various the health conditions disclosed herein. The microphone may correspond to the microphone (55) of FIGS. 3A-3D in some embodiments.

The diagnostic system may also include one or more output devices for providing non-optical stimulation to the user. An example of such an output device comprises a speaker, through which the processor may be configured to conduct the health analysis by providing auditory stimulation to the user. As another example, the one or more output devices may comprise a heater and/or a cooler. The speaker may correspond to the speaker (66) of FIGS. 3A-3D in some embodiments and the heater and/or cooler may correspond to the temperature regulator (29) of FIG. 5.

It will be appreciated that the processor is programmable and advantageously allows wide latitude in how the health analyses are conducted. For example, the processor may be configured to perform the health analysis autonomously, without requiring user or clinician input. The health analyses may simply be conducted in the background as the user goes about his/her day in some cases. For example, the diagnostic system may detect a condition (e.g., a mental state and/or a physiological state) which triggers a health analysis. The system may then conduct the health analysis and may provide results of that analysis to the user and/or a clinician. Advantageously, this automatic detection, analysis, and routing of results may provide a biofeedback loop to help address health conditions in real-time, or with little delay. In some other cases, some input from a clinician or a user may be useful to guide the health analysis and the health analysis may thus be performed semi-autonomously. In yet other cases, the diagnostic system performs the health analysis under the control of the clinician. Such control may be advantageous, for example, where the analysis requires a clinician to make a judgment or obtain other data regarding the user that is independent of the parameters that the user-wearable diagnostic system is able to measure. It will be appreciated that, whether the diagnostic system is configured to perform the health analysis autonomously, semi-autonomously, or under the control of a clinician, the system may be configured to provide results of the health analysis to a clinician. The clinician may then review the results, advise the user of additional diagnostics, develop a therapy protocol, etc.

In addition to conducting a one-time health analysis based on current health data, the diagnostic system may be configured to track health data over time. The diagnostic system may be configured to perform health analysis based on this tracked health data. In some embodiments, the diagnostic system may be configured to compare contemporaneous health data with historical health data. The diagnostic system may be configured to send alerts to the user and/or a clinician in response to comparing the contemporaneous health data with the historical health data. In some embodiments, the diagnostic system may be configured to send alerts indicating the commencement of a health analysis.

In some embodiments, the diagnostic system may be configured to compare user health data with data from other users or individuals in the population. For example, the diagnostic system may be configured to compare health data for the user with standard data for individuals of a particular age group.

In some embodiments, as disclosed herein, the diagnostic system may comprise a sound emitter configured to emit sound waves toward the user, and a sound detector attached to the frame and configured to detect sound waves reflected from the user. The light detector, however, may be omitted in some embodiments, or may be retained in other embodiments. The processor may be configured to conduct a health analysis of the user based on information detected by the sound detector alone or in conjunction with other sensors, such as the light sensor. In some embodiments, the sound emitter may be configured to provide ultrasonic stimulation to the eye of the user. In some embodiments, the sound emitter may be configured to emit ultrasonic sound waves, and the sound detector may be configured to detect ultrasonic sound waves reflected from the user.

As disclosed herein, the user-wearable system may be a user-wearable health system for conducting a health therapy protocol on the user, in addition to or as an alternative to, health analyses. The user-wearable health system may comprise a frame configured to mount on the user; an augmented reality display attached to the frame and configured to direct images to an eye of the user; and a processor configured to direct the augmented reality display to conduct a health therapy protocol on the user. It will be appreciated that the processor may be configured or programmed to conduct any of the health therapy protocols disclosed herein.

As noted above, the frame may correspond to the frame (64) (FIGS. 3A-3D), and the augmented reality display may correspond to the display (62) (FIGS. 3A-3D). As also noted above, the augmented reality display may comprise a stack of waveguides that are configured to provide a view of the world and to direct image information to the eye of the user. Also, the processor may correspond to the local processing and data module (70) or the remote processing module (72) (FIGS. 3A-3D).

In some embodiments, the health therapy protocol comprises providing health therapy image information to the user through the augmented reality display. For example, the health therapy image information may comprise health alerts. In providing these health alerts, in some cases, the user-wearable health system may comprise a sensor configured to monitor physiological responses of the user. The processor may receive information from the sensor regarding these physiological responses and may be configured to select the health alerts based on the information received from the sensor, which may be any of the sensors noted herein.

It will be appreciated that the augmented reality display may be configured to display information over multiple depth planes and, as such, the eye of the user may be focused on one of these depth planes. As a result, the user may not readily see an alert that is on a depth plane that is different from the plane that the user's eyes are focused on. To provide alerts that are more readily noticed by the user and which do not require that the user refocus their eyes to different depth plane, in some embodiments, the health system may comprise an image sensor configured to detect a depth of focus of the user's eyes. In addition, the system may be configured to display the health alert on a depth plane corresponding to that depth of focus.

In some cases, the ability of the augmented reality display to project an image at a variable focal plane and/or from different directions in the user's field of view may be utilized as part of the health therapy protocol. In some embodiments, as discussed herein, the augmented reality display may be configured to project an image to the eye to focus the eye in a variable direction or focal plane while the health therapy protocol is conducted.

It will be appreciated that the augmented reality display may have optical power and may be able to modify the path of light incident on the user's eyes. In some embodiments, the health therapy conducted by the health system may comprise modifying the path of light incident on the user's eyes based on a prescription for the eyes of the user.

In some embodiments, the health therapy protocol comprises providing eye stimulation to the user through the augmented reality display. It will be appreciated some users may have relatively weaker and relatively stronger eyes. The processor may be configured to provide increased eye stimulation to the weaker eye in comparison to the stronger eye of the user. In some embodiments, the eye stimulation may comprise health therapy image information that is selectively directed to periphery portions of a retina of the user.

As noted above, the health system may comprise an image sensor configured to detect a depth of focus of the user's eye. In conjunction with providing eye stimulation, the detected depth of focus may be used by the system to provide the eye stimulation on a depth plane corresponding to that detected depth of focus.

In some embodiments, the health therapy protocol comprises providing light therapy to the user through the augmented reality display. For example, the health system may comprise a light sensor configured to detect user exposure to light of different wavelengths, and the system may be configured to administer light to the user based on the wavelengths of light detected by the sensor. In some cases, the system may be configured to reduce the amount of blue light propagating to the eye of the user in response to detecting overexposure to blue light, with overexposure corresponding to an amount of blue light that is above a threshold. The threshold may be set by the user or by clinician, or may be determined by an analysis performed by the health system in some embodiments. In some other cases, rather than addressing overexposure, the system may be configured to administer light of one or more wavelengths to the user in response to detecting underexposure to light of the one or more wavelengths. As discussed herein, exposure to light of different wavelengths at different times or for different durations may affect the circadian rhythm of the user. In some embodiments, the system may be configured to modify the circadian rhythm of the user by administering or reducing an amount of light of one or more wavelengths in light propagating into the eye of the user. Administering or reducing the amount of light of certain wavelengths may involve changing the amount of light of some wavelengths that are outputted by the display and/or changing the amount of some wavelengths of light that are transmitted through the display to the user's eyes.

In addition to circadian rhythm, exposure to light may impact the mental state of the user. In some embodiments, the health system may be configured to modify the mental state of the user by administering or reducing an amount of light of one or more wavelengths in light propagating into the eye of the user. It will be appreciated that administering light involves increasing the amount of light of the one or more wavelengths to propagate into the eye of the user. The administering or reduction of light may be conducted in response to parameters sensed by the health system. For example, the health system may be configured to monitor the user's physical state, environment, mood, or detect signs of depression or mental abnormalities. A light therapy may be selected based upon the results of the detection or monitoring.

In addition to a display for providing image information, the user-wearable system may comprise one or more peripheral output devices for providing non-optical stimulation to the user. For example, the one or more peripheral output devices may comprise a vibrator, and the processor may be configured to conduct a health therapy protocol that comprises instructing the vibrator to provide a massage of the user. In some embodiments, the vibrator may massage the face or skull the user. In some other embodiments, the system may be configured to utilize the vibrator to provide haptic feedback or tactile alerts to the user. The vibrator may correspond to the vibrator (30) of FIG. 5.

In some other embodiments, the one or more peripheral output devices may comprise a speaker. The processor may be configured to provide instructions to the speaker to conduct a health therapy protocol. For example, two or more of the speakers, at least one for each ear, may be provided and binaural beats may be provided to user through the speakers.

As noted herein, the ability of the health system to be worn for extended periods of time and/or periodically over extended durations of time can provide advantages for increasing the efficacy of health therapy protocols. In some embodiments, the health system may be configured to track health data over time. The health system may be further configured to perform an analysis of contemporaneous health data with historical health data and to adjust the treatment protocol based on the analysis.

As discussed herein, the health system may be connected to remote databases. Advantageously, this connection allows existing health therapy protocols to be adjusted and/or new health protocols to be obtained. For example, the system may be configured to download health therapy protocols based on a condition of the user. The remote databases may correspond to the remote data repository (74) of FIGS. 3A-3D.

As discussed herein, the wearable diagnostic system may be worn by a clinician to diagnose a patient. In some embodiments, the wearable diagnostic system may comprise a frame configured to mount on the clinician; an augmented reality display attached to the frame and configured to direct images to an eye of the clinician; an outward-facing image capture device configured to image an eye of a patient; and a processor configured to conduct a health analysis of the patient based on the image of the eye captured by the image capture device. The diagnostic system may be configured to provide a diagnosis using a stimulus-response-measurement analysis process in which a stimulus is applied to the patient to elicit a response, and the response to the stimulus is measured by the diagnostic system. In some embodiments, the outward facing camera is configured to image an interior of an eye of the patient.

It will be appreciated that the user-wearable diagnostic or health system disclosed herein may provide one or more of the following advantages. In some embodiments, the head-mounted display may display images in a manner that follows the natural accommodation-vergence reflex of users. This can facilitate the long-term wearing of the device, by reducing the eyestrain and/or discomfort that conventional augmented or virtual reality systems may induce. The proximity of the head-mounted display to the user, particularly to the user's eyes, and the ability to gather information over an extended duration can facilitate diagnostic testing and treatment on an on-going basis. In some cases, the diagnostic testing and treatment may occur continuously or periodically throughout the time that the user wears the head-mounted display, which may be hours or the majority of a day, over with the span of multiple days, weeks, months or years. Advantageously, the ability to gather diagnostic or therapeutic information over an extended duration can increase the accuracy of the diagnosis and the efficacy of the therapy. In some embodiments, the health or diagnostic system may further improve health analyses by providing a more dynamic analysis, in which data is gathered as the user goes about his/her day performing a variety of actions in a variety of environments, rather than sitting statically or stressed in a clinician's office.

In some embodiments, the head-mounted display system may provide both more information regarding a particular parameter (by detecting this information multiple times over an extended time frame, e.g., of days, weeks, months, or years, as noted above), and a greater variety of information. For example, as disclosed herein, the head-mounted display system may include a plurality of sensors, including sensors that monitor the user and sensors that monitor the ambient environment. It will be appreciated that sensors that monitor the environment may include outward-facing cameras (e.g., cameras 16 (FIG. 5)). In addition, the health or diagnostic system may include location sensors (e.g., GPS sensors) and the ability to electronically communicate with external sources of information, such as the remote data repository (74). In some embodiments, the remote data repository (74) may be a cloud-based database and communication may be conducted through a network, e.g., over the internet. As discussed herein, the system may detect the location of the user and may obtain information characterizing the ambient environment, e.g., from the remote data repository. This information may include, e.g., pollen count, pollution, demographics, environmental toxins, interior climate and air quality conditions, lifestyle statistics, proximity to healthcare providers, etc.

The head-mounted display system may allow any of the types of diagnostic information for and/or results of the various diagnostic analyses disclosed herein to be correlated with other information, e.g., information relating to other physiological parameters of the user, information about the ambient environment, or temporal information such as the time or date. For example, this other information may be analyzed locally by the system or a remote processing unit to determine whether results of the diagnostic analysis vary depending on any of these other pieces of information. In some other embodiments, the occurrence of a particular diagnostic result may be correlated with the occurrence of particular environmental conditions. This correlation may be used to develop therapeutic protocols. If a particular environment and/or object or conditions within the environment is known to trigger an adverse physiological response, the head-mounted display system may be configured to display an alert warning of the likely adverse response and/or recommending that the environment, condition, and/or object be avoided. For example, a camera on the head-mounted display system may be configured to detect restaurant menu items (e.g., by using text recognition to read menus) and may display alerts for items that are known to or have been correlated in the past with causing an adverse physiological reaction in the user. In addition, the system may be configured to recognize items being ingested by the user (e.g., through image recognition, through recognition of identifiers such as words or codes on a food package, etc.) and to correlate subsequent physiological reactions in the user to the food. In another example, the inward-facing camera may detect eye fatigue at the end of a long period of eye strain and may display alerts for ocular stimulus that have been correlated with causing eye strain in the user.

In addition, the local system or remote processing unit may have access to the diagnostic information and/or results for multiple users, and the user's diagnostic results may be compared to that of other users to further validate a link or correlation with any of these other pieces of information.

It will be appreciated that the user-wearable health or diagnostic system disclosed herein may provide a user with access to sensitive personal health information. In addition, any misattribution of user information can adversely impact the efficacy of therapies provided to the user, and the accuracy of future health analysis results for the user, particularly where those health results are derived from an analysis of historical data. Misattribution of personal information may occur when, e.g., the system obtains data for the current user of the system, but associates this information with another user's historical data, e.g. through a system error or an impersonation of a particular user by another user. Consequently, in some embodiments, the user-wearable health or diagnostic system is configured to determine or authenticate the identity of the user before conducting any of the monitoring, diagnostics, or therapies disclosed herein. Such authentication may involve simple password entry or other security information input by the user.

In some other embodiments, in addition to, or in place of the entry of security information by the user, the authentication may be conducted using biometric data. Such biometric data may include, e.g., fingerprint scanning, iris scanning, or pupil scanning.

In some embodiments, an inward-facing camera, such as one or both of the cameras (24; FIG. 5) may be utilized as an iris scanner for iris recognition of one or more eyes of the user. Advantageously, the iris contains unique sets of features that are stable over time and that are unique to each individual. As a result, the sets of features, which may define unique patterns, may be used to identify individuals, often with a greater precision than fingerprints. These sets of features may be captured by the inward-facing camera, e.g., as part of a captured image of the iris, and the health or diagnostic system may analyze the image to detect whether a unique set of iris features matching that of the set of iris features of the user are present. If the user's unique set of iris features is found to be present, then the health or diagnostic system notes the match and the user is determined to indeed be wearing the health or diagnostic system. The system may then proceed to carrying out monitoring, diagnostics, or therapies associated with that user.

In some other embodiments, the inward-facing camera may be used as a retina scanner for one or more eyes of the user. Such a retina scan may include an infrared light emitter (e.g., the light source 2668; FIG. 24C) configured to direct light into the user's eye. It will be appreciated that the pattern of blood vessels in a user's retina is unique and typically does not change over time, and that the blood vessels reflect different amounts of infrared light than surrounding tissue. The unique pattern formed by this differential light reflection may be detected by the camera. If the detected retina pattern is found to match the user's stored retina pattern, then the health or diagnostic system provides a signal indicating a match and the user is determined to indeed be wearing the health or diagnostic system. As above, the system may then proceed to carrying out monitoring, diagnostics, or therapies associated with that user.

In some embodiments, to provide a heightened level of security, multiple authentication protocols may be conducted before carrying out the monitoring, diagnostics, or therapies. For example, both iris and retina scanning may be conducted. Advantageously, the user-wearable health or diagnostic system may already include the necessary ophthalmic hardware (e.g., light sources and eye imagers) to conduct the desired eye-based authentication.

The user-wearable health or diagnostic system disclosed herein can provide various other benefits. For example, the integration of a single display device configured for both health diagnosis and therapy can provide a feedback loop with the user that facilitates the therapy. In some cases, by continually monitoring the user's health and/or environment, real-time alerts may be displayed to facilitate a therapeutic protocol and increase the likelihood that protocols based on behavior modification are successfully implemented.

It will be appreciated that each of the processes, methods, and algorithms described herein and/or depicted in the figures may be embodied in, and fully or partially automated by, code modules executed by one or more physical computing systems, hardware computer processors, application-specific circuitry, and/or electronic hardware configured to execute specific and particular computer instructions. For example, computing systems can include general purpose computers (e.g., servers) programmed with specific computer instructions or special purpose computers, special purpose circuitry, and so forth. A code module may be compiled and linked into an executable program, installed in a dynamic link library, or may be written in an interpreted programming language. In some embodiments, particular operations and methods may be performed by circuitry that is specific to a given function.

Further, certain embodiments of the functionality of the present disclosure are sufficiently mathematically, computationally, or technically complex that application-specific hardware or one or more physical computing devices (utilizing appropriate specialized executable instructions) may be necessary to perform the functionality, for example, due to the volume or complexity of the calculations involved or to provide results substantially in real-time. For example, a video may include many frames, with each frame having millions of pixels, and specifically programmed computer hardware is necessary to process the video data to provide a desired image processing task or application in a commercially reasonable amount of time.

Code modules or any type of data may be stored on any type of non-transitory computer-readable medium, such as physical computer storage including hard drives, solid state memory, random access memory (RAM), read only memory (ROM), optical disc, volatile or non-volatile storage, combinations of the same and/or the like. In some embodiments, the non-transitory computer-readable medium may be part of one or more of the local processing and data module (70), the remote processing module (72), and remote data repository (74). The methods and modules (or data) may also be transmitted as generated data signals (e.g., as part of a carrier wave or other analog or digital propagated signal) on a variety of computer-readable transmission mediums, including wireless-based and wired/cable-based mediums, and may take a variety of forms (e.g., as part of a single or multiplexed analog signal, or as multiple discrete digital packets or frames). The results of the disclosed processes or process steps may be stored, persistently or otherwise, in any type of non-transitory, tangible computer storage or may be communicated via a computer-readable transmission medium.

Any processes, blocks, states, steps, or functionalities in flow diagrams described herein and/or depicted in the attached figures should be understood as potentially representing code modules, segments, or portions of code which include one or more executable instructions for implementing specific functions (e.g., logical or arithmetical) or steps in the process. The various processes, blocks, states, steps, or functionalities can be combined, rearranged, added to, deleted from, modified, or otherwise changed from the illustrative examples provided herein. In some embodiments, additional or different computing systems or code modules may perform some or all of the functionalities described herein. The methods and processes described herein are also not limited to any particular sequence, and the blocks, steps, or states relating thereto can be performed in other sequences that are appropriate, for example, in serial, in parallel, or in some other manner. Tasks or events may be added to or removed from the disclosed example embodiments. Moreover, the separation of various system components in the embodiments described herein is for illustrative purposes and should not be understood as requiring such separation in all embodiments. It should be understood that the described program components, methods, and systems can generally be integrated together in a single computer product or packaged into multiple computer products.

In the foregoing specification, the invention has been described with reference to specific embodiments thereof. It will, however, be evident that various modifications and changes may be made thereto without departing from the broader spirit and scope of the invention. For example, in addition to scanning fiber displays (FSDs), it will be appreciated that the projected light and images for embodiments disclosed herein may be provided by other types of displays. Examples of such other types of displays include liquid crystal displays, micromirror-based displays (e.g., DLP displays), and OLED displays.

In some embodiments, in addition to or as an alternative to the application of liquids to the eye, solid state materials such as powders or powdered medications may also be delivered to the eye by the ophthalmic system.

The specification and drawings are, accordingly, to be regarded in an illustrative rather than restrictive sense.

Indeed, it will be appreciated that the systems and methods of the disclosure each have several innovative aspects, no single one of which is solely responsible or required for the desirable attributes disclosed herein. The various features and processes described above may be used independently of one another, or may be combined in various ways. All possible combinations and subcombinations are intended to fall within the scope of this disclosure.

Certain features that are described in this specification in the context of separate embodiments also can be implemented in combination in a single embodiment. Conversely, various features that are described in the context of a single embodiment also can be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. No single feature or group of features is necessary or indispensable to each and every embodiment.

Headings are used throughout this application as an organizational aid for the reader. These headings may group together examples of methods, apparatuses, and structures that may generally relate to a particular topic noted in the headings. It will be appreciated, however, that while the various features discussed under the heading may relate to a particular topic, the headings should not be understood to indicate that the features discussed under a given heading are limited in applicability only to the topic or topics that listed in the heading. For example, a heading may be labeled "Myopia/Hyperopia/Astigmatism". However, the subject matter included under this heading may equally be applicable to subject matter contained in any other section, such as content under the heading "Presbyopia," "Retinoscopy," "Autorefractor," and other sections. Alternatively, subject matter from other sections may also be applicable to the "Myopia/Hyperopia/Astigmatism" sections.

Indeed, as shown in various figures (e.g., FIG. 5), structures for various health analyses and/or therapies may coexist in the same health system. Moreover, as disclosed herein, the same feature may be applied to facilitate multiple health analyses and/or therapies. For example, structures used for delivering medication may also be utilized for various diagnostics, as disclosed herein. Consequently, health systems according to some embodiments may include various combinations of the structural features disclosed herein, including combinations of features disclosed under different headings. In addition, the health system may be configured to perform various combinations of the health analyses and therapies disclosed herein, including those disclosed under different headings.

It will be appreciated that conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise. Similarly, while operations may be depicted in the drawings in a particular order, it is to be recognized that such operations need not be performed in the particular order shown or in sequential order, or that all illustrated operations be performed, to achieve desirable results. Further, the drawings may schematically depict one more example processes in the form of a flowchart. However, other operations that are not depicted can be incorporated in the example methods and processes that are schematically illustrated. For example, one or more additional operations can be performed before, after, simultaneously, or between any of the illustrated operations. Additionally, the operations may be rearranged or reordered in other embodiments. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products. Additionally, other embodiments are within the scope of the following claims. In some cases, the actions recited in the claims can be performed in a different order and still achieve desirable results.

Accordingly, the claims are not intended to be limited to the embodiments shown herein, but are to be accorded the widest scope consistent with this disclosure, the principles and the novel features disclosed herein.

What is claimed is:

1. A wearable augmented reality device configured to be used by a wearer, said device comprising:
   an augmented reality head-mounted ophthalmic system comprising a wearable augmented reality display platform, said augmented reality head-mounted ophthalmic system configured to pass light from the world into an eye of a wearer wearing the head-mounted system, said wearable augmented reality display platform comprising a display comprising at least one light source, wherein the wearable augmented reality display platform comprises a waveguide stack comprising a plurality of waveguides, each waveguide of the plurality of waveguides comprising:

in-coupling diffractive optical elements configured to in-couple light provided by the light source, and out-coupling diffractive optical elements configured to out-couple in-coupled light to the eye of a wearer of the head-mounted augmented reality display, wherein one or more waveguides of the plurality of waveguides are configured to output the in-coupled light with a different amount of wavefront divergence than one or more other waveguides of the plurality of waveguides, wherein the different amounts of wavefront divergence correspond to different depth planes; and wherein said wearable augmented reality device is configured to selectively modify wearer perception of said light from the world by out-coupling in-coupled light from the waveguide stack to the eye of the wearer based on a color detection deficiency of the wearer.

2. The device of claim 1, wherein said augmented reality head-mounted ophthalmic system further comprises at least one outward-facing camera configured to image said light from the world.

3. The device of claim 2, wherein said outward-facing camera is configured to detect the presence in said light from the world of a color for which the wearer has a detection deficiency.

4. The device of claim 1, wherein said selective modification comprises enhancing the color of light projected from at least a portion of the display.

5. The device of claim 1, wherein said selective modification comprises projecting light from the at least one light source to increase the amplitude of said light in a region of the display comprising a color for which the wearer has a detection deficiency.

6. The device of claim 1, wherein said selective modification comprises changing the color of light in a region of the display.

7. The device of claim 6, wherein changing the color of light in a region of the display comprises using an optical filter.

8. The device of claim 7, wherein changing the color of light in a region of the display comprises using an optical filter to remove spectral overlap between a plurality of photopigments.

9. The device of claim 8, wherein said plurality of photopigments comprise at least one photopigment associated with the detection of red light and at least one photopigment associated with the detection of green light.

10. The device of claim 7, wherein said optical filter comprises a multi-notch filter.

11. The device of claim 1, wherein said selective modification comprises decreasing the visibility of at least a portion of said light from the world through destructive interference.

12. A method of providing augmented reality content for mitigating a color detection deficiency, the method comprising:

passing light from the world into an eye of a wearer of an augmented reality display device, said wearer having a color detection deficiency, said augmented reality display device comprising a light source and a waveguide stack comprising a plurality of waveguides, each waveguide of the plurality of waveguides comprising:
in-coupling diffractive optical elements configured to in-couple light provided by the light source, and
out-coupling diffractive optical elements configured to out-couple in-coupled light to the eye of the wearer of the head-mounted augmented reality display,
wherein one or more waveguides of the plurality of waveguides are configured to output the in-coupled light with a different amount of wavefront divergence than one or more other waveguides of the plurality of waveguides, wherein the different amounts of wavefront divergence correspond to different depth planes;

imaging said light from the world at the display device; and selectively modifying wearer perception of light directed from the waveguide stack to the eye of the wearer based on the color detection deficiency.

13. The method of claim 12, wherein selectively modifying said light comprises projecting light from a light source of the display device into the eye of the wearer.

14. The method of claim 13, wherein selectively modifying said light comprises increasing contrast of light projected from the display device.

15. The method of claim 12, further comprising identifying, within said light from the world, light of a wavelength associated with said color detection deficiency.

16. The method of claim 15, further comprising determining a location within a field of view of the wearer associated with said light of the wavelength associated with said color deficiency.

17. The method of claim 16, wherein selectively modifying said light comprises projecting additional light into the eye of the wearer at said location within the field of view of the wearer.

18. The method of claim 17, wherein said additional light has a wavelength different from at least one wavelength of said light from the world detected at said location.

* * * * *